United States Patent
Carman et al.

(10) Patent No.: US 7,226,791 B2
(45) Date of Patent: Jun. 5, 2007

(54) POLYNUCLEOTIDES ENCODING NOVEL GUANYLATE BINDING PROTEINS (GBP'S)

(75) Inventors: Julie Carman, Lawrenceville, NJ (US); Stephen J. Warner, St. Louis, MO (US); Rolf-Peter Ryseck, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 162 days.

(21) Appl. No.: 10/858,367

(22) Filed: Jun. 1, 2004

(65) Prior Publication Data

US 2005/0026191 A1 Feb. 3, 2005

Related U.S. Application Data

(60) Provisional application No. 60/475,234, filed on Jun. 2, 2003.

(51) Int. Cl.
- C12N 1/20 (2006.01)
- C12N 15/00 (2006.01)
- C12N 5/00 (2006.01)
- C12Q 1/68 (2006.01)
- C12P 21/06 (2006.01)

(52) U.S. Cl. .................. 436/69.1; 435/252.3; 435/6; 435/320.1; 536/23.1

(58) Field of Classification Search ............... 536/23.2, 536/23.1; 435/252.3, 320.1, 69.1, 6
See application file for complete search history.

(56) References Cited

U.S. PATENT DOCUMENTS

2003/0170742 A1 9/2003 Carman et al.

OTHER PUBLICATIONS

Baeuerle, et al., "IκB: A Specific Inhibitor of the NF-κB Transcription Factor", Science, vol. 242, pp. 540-545 (1988).
Nguyen, et al., "Murine GBP-5, a New Member of the Murine Guanylate-Binding Protein Family, Is Coordinately Regulated with Other GBPs *In Vivo* and *In Vitro*", J. of Interferon and Cytokine Res., vol. 22, pp. 899-909 (2002).
Shyun, et al., "Interferon Induction of Fibroblast Proteins with Guanylate Binding Activity", J. of Biol. Chem., vol. 258 (12), pp. 7746-7750 (1983).
Schwemmle, et al., "The Interferon-induced 67-κDa Guanylate-binding (hGBP1) is a GTPase That Converts GTP to GMP", J. of Biol. Chem., vol. 269 (15), pp. 11299-11305 (1994).
Polleux, et al., "Semaphorin 3A is a chemoattractant for cortical apical dendrites", Nature, vol. 404, pp. 567-573 (2000).
Prakash, et al., "Triphosphate structure of guanylate-binding protein 1 and implications for nucleotide binding and GTPase mechanism", EMBO J., vol. 17, pp. 4555-4564 (2000).

(Continued)

Primary Examiner—Maryam Monshipouri
(74) Attorney, Agent, or Firm—Eve L. Frank; John A. Lamerdin

(57) ABSTRACT

The present invention provides polynucleotides encoding human and murine guanylate binding protein polypeptides, fragments and homologues thereof. Also provided are vectors, host cells, antibodies, and recombinant and synthetic methods for producing said polypeptides. The present invention further relates to diagnostic and therapeutic methods for applying the guanylate binding protein polypeptides to the diagnosis, treatment, and/or prevention of various diseases and/or disorders related to these polypeptides, such as rheumatoid arthritis and/or conditions related to aberrant NF-κB activity, guanylate binding activity and GTPase activity. The present invention further relates to screening methods for identifying agonists and antagonists of the polynucleotides and polypeptides of the present invention.

15 Claims, 68 Drawing Sheets

OTHER PUBLICATIONS

Patrone, et al., "Genes expressed during the IFNγ-induced maturation of pre-B cells", Molec. Immunol., vol. 38, pp. 597-606 (2001).

Wynn, et al., "Identification and Characterization of a New Gene Family Induced during Macrophage Activation", J. of Immunol., vol. 147, pp. 4384-4392 (1991).

Vestal, et al., "Rat p67 GBP is Induced by Interferon-γ and Isoprenoid-Modified in Macrophages", Biochem. and Biophysical Res. Commun., vol. 224, pp. 528-534 (1996).

Sun, et al., "Interleukin-10 Gene Transfer Activates Interferon-γ and the Interferon-γ-Inducible Genes *Gpb-1/Mag-1* and *Mig-1* in Mammary Tumors", Int. J. Cancer, vol. 80, pp. 624-629 (1999).

Saunders, et al., "Regulation of Guanylate-Binding Protein Expression in Interferon-γ-Treated Human Epidermal Keratinocytes and Squamous Cell Carcinoma Cells", J. Invest. Dermatology, vol. 112 (6), pp. 977-983 (1999).

Lubeseder-Martellato, et. al., "Guanylate-Binding Protein-1 Expression is Selectively Induced by Inflammatory Cytokines and is an Activation Marker of Endothelial Cells during Inflammatory Diseases", Amer, J. Pathology, vol. 161 (5), pp. 1749-1759 (2002).

Boehm, et al., "Two Families of GTPases Dominate the Complex Cellular Response to IFN-γ", J. of Immunol., vol. 161, pp. 6715-6723 (1998).

Han, et al., "Cloning, expression, and characterization of a novel guanylate-binding protein, GBP3 in murine erythroid progenitor cells". Biochimica et Biophysica Acta, vol. 1384, pp. 373-386 (1998).

Anderson, et al., "Interferon-Induced Guanylate Binding Protein-1 (GBP-1) Mediates an Antiviral Effect against Vesicular Stomatitis Virus and Encephalomyocarditis Virus", Virology, vol. 256, pp. 8-14, 1999.

Guenzi, et al., "The helical domain of GBP-1 mediates the inhibition of endothelial cell proliferation by inflammatory cytokines", EMBO J., vol. 20, pp. 5568-5577 (2001).

Gorbacheva, et al., "The Interferon (IFN)-induced GTPase, mGBP-2", J. Biol.Chem., vol. 277 (8), pp. 6080-6087 (2002).

Fujihara, et al., "A D-Amino Acid Peptide Inhibitor of NF-κB Nuclear Localization is Efficacious in Models of Inflammatory Disease", J. of Immunol., vol. 165, pp. 1004-1012 (2000).

Plaksin, et al., "KBF1 (p50 NF-κB Homodimer) Acts as a Repressor of H-2K$^b$ Gene Expression in Metastic Tumor Cells", J. Exp. Med., vol. 177, pp. 1651-1662 , 1999.

Prakash, et al., "Structure of human guanylate-binding protein 1 representing a unique class of GTP-binding proteins", Nature, vol. 403, pp. 567-571 (2000).

FIG. 1A

```
  1  AAGAAAAAAAGTGGGAGAAATCAGTGCAGCCAAATTCAGAACTAAAGAGAAGAGAATAAA   60

61  GACTCATAACTTTCTCATTGAAGCTGCCTTCTTACCAAGTCCAGAGGATCTCTACTCTGG  120

121  ACAGAGGAACGCCCTGAACATGGCATCAGAGATCCACATGCCAGGCCCAGTGTGCCTCAT  180
  1                  M  A  S  E  I  H  M  P  G  P  V  C  L  I    14

181  TGAGAACACTAAAGGGCATCTGGTGGTGAATTCAGAAGCTCTGGAAATCCTGTCTGCCAT  240
 15   E  N  T  K  G  H  L  V  V  N  S  E  A  L  E  I  L  S  A  I   34

241  TACACAGCCTGTAGTAGTGGTGGCAATTGTGGGCCTCTACCGCACAGGCAAATCCTACCT  300
 35   T  Q  P  V  V  V  V  A  I  V  G  L  Y  R  T  G  K  S  Y  L   54

301  AATGAACAAGCTGGCTGGGAAGAACAAAGGCTTCCCTCTGGGCTGCACAGTGAAGTCTGA  360
 55   M  N  K  L  A  G  K  N  K  G  F  P  L  G  C  T  V  K  S  E   74

361  AACCAAAGGCATCTGGATGTGGTGTGTGCCCCACCCCTCCAAGCCAAACCACACCCTGAT  420
 75   T  K  G  I  W  M  W  C  V  P  H  P  S  K  P  N  H  T  L  I   94

421  CCTTCTGGACACGGAGGGCCTGGGTGATATGGAAAAGAGTGACCCTAAGAGTGACTCGTG  480
 95   L  L  D  T  E  G  L  G  D  M  E  K  S  D  P  K  S  D  S  W  114

481  GATCTTTGCCCTGGCTGTGCTTCTAAGCAGCAGCTTTGTCTACAACAGCATGGGCACCAT  540
115   I  F  A  L  A  V  L  L  S  S  S  F  V  Y  N  S  M  G  T  I  134

541  CAACCACCAGGCCCTGGAGCAGCTGCACTACGTGACTGAGCTAACAGAGCTAATCAGGGC  600
135   N  H  Q  A  L  E  Q  L  H  Y  V  T  E  L  T  E  L  I  R  A  154

601  AAAATCGTGCCCCAGACCTGATGAAGTTGAGGACTCCAGCGAGTTTGTGAGTTTCTTTCC  660
155   K  S  C  P  R  P  D  E  V  E  D  S  S  E  F  V  S  F  F  P  174

661  AGACTTTATTTGGACTGTTCGAGATTTTACCCTGGAGCTGAAGTTAGATGGACACCCCAT  720
175   D  F  I  W  T  V  R  D  F  T  L  E  L  K  L  D  G  H  P  I  194

721  CACAGAAGATGAGTACCTGGAGAATGCCTTGAAGCTGATTTCAGGCAAGAATCCCCAAAT  780
195   T  E  D  E  Y  L  E  N  A  L  K  L  I  S  G  K  N  P  Q  I  214

781  CCAAAATTCTAACAAGCCCAGGGAGTGGATCAGGCATTTCTTTCCAAAACAGAAGTGCTT  840
215   Q  N  S  N  K  P  R  E  W  I  R  H  F  F  P  K  Q  K  C  F  234

841  TGTCTTTGACCGGCCAATAAATGACAAAAAACTCTTACTCCATGTTGAAGAAGTACGAGA  900
235   V  F  D  R  P  I  N  D  K  K  L  L  L  H  V  E  E  V  R  E  254

901  AGACCAACTGGATAGTAATTTCCAGATGCAATCAGAAAATTTCTGTTCTTATATCTTCAC  960
255   D  Q  L  D  S  N  F  Q  M  Q  S  E  N  F  C  S  Y  I  F  T  274
```

FIG. 1B

```
 961  CCATGCAAAGACCAAGACCCTGAGAGAGGGAATCCTTGTCACTGGAAACCGGCTGGGGAT  1020
 275    H  A  K  T  K  T  L  R  E  G  I  L  V  T  G  N  R  L  G  M   294

1021  GCTGGTGGAGACCTACCTGGATGCCATCAACAGTGGAGCGACTCCTTGTCTGGAGAATGC  1080
 295    L  V  E  T  Y  L  D  A  I  N  S  G  A  T  P  C  L  E  N  A   314

1081  AATGGCAGTTCTGGCCCAGTGTGAGAACTCAGCAGCCGTGCAGAGGGCAGCCAACCACTA  1140
 315    M  A  V  L  A  Q  C  E  N  S  A  A  V  Q  R  A  A  N  H  Y   334

1141  CAGCCAGCAGATGGCCCAGCAAGTGAGATTCCCCACAGACACACTCCAGGAGCTGCTGGA  1200
 335    S  Q  Q  M  A  Q  Q  V  R  F  P  T  D  T  L  Q  E  L  L  D   354

1201  CGTGCATGCAGTTTGTGAGAGGGAAGCCATTGCAGTCTTCATGGAGTACTCCTTCAAAGA  1260
 355    V  H  A  V  C  E  R  E  A  I  A  V  F  M  E  Y  S  F  K  D   374

1261  TAAAAGCCAGGAATTTCAGAAGAAGCTTGTGGACACCATGGAGAAAAAGAAGGAAGACTT  1320
 375    K  S  Q  E  F  Q  K  K  L  V  D  T  M  E  K  K  K  E  D  F   394

1321  TGTGCTGCAGAATGAAGAGGCATCTGCCAAATATTGTCAGGCTGAGCTTAAGCGGCTTTC  1380
 395    V  L  Q  N  E  E  A  S  A  K  Y  C  Q  A  E  L  K  R  L  S   414

1381  AGAGCTCTTGACAGAAAGTATTTCAAGAGGAACTTTCTTTGTTCCGGGGGGGCACAATAT  1440
 415    E  L  L  T  E  S  I  S  R  G  T  F  F  V  P  G  G  H  N  I   434

1441  CTACTTAGAAGCAAAAAAGAAGATTGAACAGGACTATACACTAGTGCCCAGAAAAGGAGT  1500
 435    Y  L  E  A  K  K  K  I  E  Q  D  Y  T  L  V  P  R  K  G  V   454

1501  TAAGGCAGACGAGGTCCTCCAGAGCTTCCTGCAGTCACAGGTGGTTATAGAGGAATCCAT  1560
 455    K  A  D  E  V  L  Q  S  F  L  Q  S  Q  V  V  I  E  E  S  I   474

1561  CCTGCAGTCAGACAAAGCCCTCACTGCTGGAGAGAAGGCCATAGCAGCTAAGCAGGCTAA  1620
 475    L  Q  S  D  K  A  L  T  A  G  E  K  A  I  A  A  K  Q  A  K   494

1621  GAAGGAGGCAGCTGAAAAGGAACAGGAGCTGCTAAGACAAAAACAGAAGGAACAGCAGCA  1680
 495    K  E  A  A  E  K  E  Q  E  L  L  R  Q  K  Q  K  E  Q  Q  Q   514

1681  AATGATGGAGGCTCAAGAGAGAAGTTTCCAGGAAAACATAGCTCAACTCAAGAAGAAGAT  1740
 515    M  M  E  A  Q  E  R  S  F  Q  E  N  I  A  Q  L  K  K  K  M   534

1741  GGAGAGGGAAAGGGAAAACTATATGAGAGAACTGAGAAAGATGTTGAGTCACAAGATGAA  1800
 535    E  R  E  R  E  N  Y  M  R  E  L  R  K  M  L  S  H  K  M  K   554

1801  GGTCCTAGAAGAACTGCTTACTGAAGGATTTAAAGAGATATTTGAGTCGTTAAATGAAGA  1860
 555    V  L  E  E  L  L  T  E  G  F  K  E  I  F  E  S  L  N  E  E   574
```

FIG. 1C

```
1861 GATTAATCGACTGAAAGAACAAATTGAAGCAGCTGAAAATGAAGAGCCCTCAGTGTTTTC 1920
 575   I   N   R   L   K   E   Q   I   E   A   A   E   N   E   E   P   S   V   F   S   594

1921 ACAGATTCTTGATGTGGCTGGCAGTATATTTATTGCAGCACTACCTGGGGCTGCTAAGCT 1980
 595   Q   I   L   D   V   A   G   S   I   F   I   A   A   L   P   G   A   A   K   L   614

1981 AGTTGATTTAGGAATGAAAATTCTTAGCTCATTATGTAATAGGCTGAGAAATCCTGGTAA 2040
 615   V   D   L   G   M   K   I   L   S   S   L   C   N   R   L   R   N   P   G   K   634

2041 GAAAATTATAAGCTGAGGTTTCTTTTGTTAAAATGGTATAACGCTGTTGCTCATTTTAAA 2100
 635   K   I   I   S                                                                    638

2101 AGTATATGTGTTATTGCAGTTTCATTTAAGAAGAGTTTAAAATTAAAAAGCAAATTTCAA 2160

2161 AGAATATTATGGCCTGAAGTTCATAAAAACAAACTTAATTTTGACTAAAGTAATAATTAA 2220

2221 TAGAAATGGGGAACAAGTTAGAAGATAAAATTATTCCTAGAAAAGATTTAAGTAAAGCAA 2280

2281 AAGGACAAATGGTAATATAAAGAAATTATTTTCAATTAATGTTATAGTCACAGAGATAAT 2340

2341 TTAAGTTATAATTAGCTCTTGCAAATCAGTGAGAAGAGAGTAACGCCACATATTTTAAAC 2400

2401 AGGCAAAAATATGATAATAAAAATGTTTAATTTTACTGACAATAAAAGTTGTGC   2454
```

FIG. 2A

```
aagcttggta ccgagctcgg atcatcaaca agtttgtaca aaaaagcagg ctccgcggcc      60
gcccccttca ccagatctgc agttgcc atg gaa tct gga ccc aaa atg ttg gcc     114
                               Met Glu Ser Gly Pro Lys Met Leu Ala
                                 1               5 ccc gtt tgc ctg gtg gaa aat aac aat gag cag cta ttg gtg aac cag       162
Pro Val Cys Leu Val Glu Asn Asn Asn Glu Gln Leu Leu Val Asn Gln
 10              15                  20                  25 caa gct ata cag att ctt gaa aag att tct cag cca gtg gtg gtg gcc       210
Gln Ala Ile Gln Ile Leu Glu Lys Ile Ser Gln Pro Val Val Val Ala
                 30                  35                  40 att gta gga ctg tac cgt aca ggg aaa tcc tac ttg atg aac cat ctg       258
Ile Val Gly Leu Tyr Arg Thr Gly Lys Ser Tyr Leu Met Asn His Leu
             45                  50                  55 gca gga cag aat cat ggc ttc cct ctg ggc tcc acg gtg cag tct gaa       306
Ala Gly Gln Asn His Gly Phe Pro Leu Gly Ser Thr Val Gln Ser Glu
         60                  65                  70 acc aag ggc atc tgg atg tgg tgc gtg ccc cac cca tcc aag cca aac       354
Thr Lys Gly Ile Trp Met Trp Cys Val Pro His Pro Ser Lys Pro Asn
     75                  80                  85 cac acc ctg gtc ctt ctg gac acc gaa ggt ctg ggc gat gtg gaa aag       402
His Thr Leu Val Leu Leu Asp Thr Glu Gly Leu Gly Asp Val Glu Lys
 90                  95                 100                 105 ggt gac cct aag aat gac tcc tgg atc ttt gcc ctg gct gtg ctc ctg       450
Gly Asp Pro Lys Asn Asp Ser Trp Ile Phe Ala Leu Ala Val Leu Leu
                110                 115                 120 tgc agc acc ttt gtc tac aac agc atg agc acc atc aac cac cag gcc       498
Cys Ser Thr Phe Val Tyr Asn Ser Met Ser Thr Ile Asn His Gln Ala
            125                 130                 135 ctg gag cag ctg cat tat gtg acg gag ctc aca gaa cta att aag gca       546
Leu Glu Gln Leu His Tyr Val Thr Glu Leu Thr Glu Leu Ile Lys Ala
        140                 145                 150 aag tcc tcc cca agg cct gat gga gta gaa gat tcc aca gag ttt gtg      594
Lys Ser Ser Pro Arg Pro Asp Gly Val Glu Asp Ser Thr Glu Phe Val
    155                 160                 165 agt ttc ttc cca gac ttt ctt tgg aca gta cgg gat ttc act ctg gag      642
Ser Phe Phe Pro Asp Phe Leu Trp Thr Val Arg Asp Phe Thr Leu Glu
170                 175                 180                 185 ctg aag ttg aac ggt cac cct atc aca gaa gat gaa tac ctg gag aat      690
Leu Lys Leu Asn Gly His Pro Ile Thr Glu Asp Glu Tyr Leu Glu Asn
                190                 195                 200 gcc ttg aag ctg att caa ggc aat aat ccc aga gtt caa aca tcc aat      738
Ala Leu Lys Leu Ile Gln Gly Asn Asn Pro Arg Val Gln Thr Ser Asn
            205                 210                 215 ttt ccc agg gag tgc atc agg cgt ttc tta cca aaa cgg aag tgt ttc      786
Phe Pro Arg Glu Cys Ile Arg Arg Phe Leu Pro Lys Arg Lys Cys Phe
        220                 225                 230
```

Figure 2B

```
gtc ttt gac cgg cca aca aat gac aaa gac ctt cta gcc aat att gag      834
Val Phe Asp Arg Pro Thr Asn Asp Lys Asp Leu Leu Ala Asn Ile Glu
    235                 240                 245 aag gtg tca gaa aag caa ctg gat ccc aaa ttc cag gaa caa aca aac      882
Lys Val Ser Glu Lys Gln Leu Asp Pro Lys Phe Gln Glu Gln Thr Asn
250                 255                 260                 265 att ttc tgt tct tac atc ttc act cat gca aga acc aag acc ctc agg      930
Ile Phe Cys Ser Tyr Ile Phe Thr His Ala Arg Thr Lys Thr Leu Arg
                270                 275                 280 gag gga atc aca gtc act ggg aat cgt ctg gga act ctg gca gtg act      978
Glu Gly Ile Thr Val Thr Gly Asn Arg Leu Gly Thr Leu Ala Val Thr
            285                 290                 295 tat gta gag gcc atc aac agt gga gca gtg cct tgt ctg gag aat gca     1026
Tyr Val Glu Ala Ile Asn Ser Gly Ala Val Pro Cys Leu Glu Asn Ala
        300                 305                 310 gtg ata act ctg gcc cag cgt gag aac tca gcg gcc gtg cag agg gca     1074
Val Ile Thr Leu Ala Gln Arg Glu Asn Ser Ala Ala Val Gln Arg Ala
    315                 320                 325 tct gac tac tac agc cag cag atg gcc cag cga gtg aag ttc ccc aca     1122
Ser Asp Tyr Tyr Ser Gln Gln Met Ala Gln Arg Val Lys Phe Pro Thr
330                 335                 340                 345 gac acg ctc cag gag ctg ctg gac gtg cat gcg gcc tgt gag agg gaa     1170
Asp Thr Leu Gln Glu Leu Leu Asp Val His Ala Ala Cys Glu Arg Glu
                350                 355                 360 gcc att gca atc ttc atg gag cac tcc ttc aag gat gaa aat cag gaa     1218
Ala Ile Ala Ile Phe Met Glu His Ser Phe Lys Asp Glu Asn Gln Glu
            365                 370                 375 ttc cag aag aag ttc atg gaa acc aca atg aat aag aag ggg gat ttc     1266
Phe Gln Lys Lys Phe Met Glu Thr Thr Met Asn Lys Lys Gly Asp Phe
        380                 385                 390 ttg ctg cag aat gaa gag tca tct gtt caa tac tgc cag gct aaa ctc     1314
Leu Leu Gln Asn Glu Glu Ser Ser Val Gln Tyr Cys Gln Ala Lys Leu
    395                 400                 405 aat gag ctc tca aag gga cta atg gaa agt atc tca gca gga agt ttc     1362
Asn Glu Leu Ser Lys Gly Leu Met Glu Ser Ile Ser Ala Gly Ser Phe
410                 415                 420                 425 tct gtt cct gga ggg cac aag ctc tac atg gaa aca aag gaa agg att     1410
Ser Val Pro Gly Gly His Lys Leu Tyr Met Glu Thr Lys Glu Arg Ile
                430                 435                 440 gaa cag gac tat tgg caa gtt ccc agg aaa gga gta aag gca aaa gag     1458
Glu Gln Asp Tyr Trp Gln Val Pro Arg Lys Gly Val Lys Ala Lys Glu
            445                 450                 455 gtc ttc cag agg ttc ctg gag tca cag atg gtg ata gag gaa tcc atc     1506
Val Phe Gln Arg Phe Leu Glu Ser Gln Met Val Ile Glu Glu Ser Ile
        460                 465                 470 ttg cag tca gat aaa gcc ctc act gat aga gag aag gca gta gca gtg     1554
Leu Gln Ser Asp Lys Ala Leu Thr Asp Arg Glu Lys Ala Val Ala Val
    475                 480                 485
```

Figure 2C

```
gat cgg gcc aag aag gag gca gct gag aag gaa cag gaa ctt tta aaa      1602
Asp Arg Ala Lys Lys Glu Ala Ala Glu Lys Glu Gln Glu Leu Leu Lys
490             495                 500                 505 cag aaa tta cag gag cag cag caa cag atg gag gct caa gtt aag agt      1650
Gln Lys Leu Gln Glu Gln Gln Gln Gln Met Glu Ala Gln Val Lys Ser
                510                 515                 520 cgc aag gaa aac ata gcc caa ctg aag gag aag ctg cag atg gag aga      1698
Arg Lys Glu Asn Ile Ala Gln Leu Lys Glu Lys Leu Gln Met Glu Arg
                525                 530                 535 gaa cac cta ctg aga gag cag att atg atg ttg gag cac acg cag aag      1746
Glu His Leu Leu Arg Glu Gln Ile Met Met Leu Glu His Thr Gln Lys
                540                 545                 550 gtc caa aat gat tgg ctt cat gaa gga ttt aag aag aag tat gag gag      1794
Val Gln Asn Asp Trp Leu His Glu Gly Phe Lys Lys Lys Tyr Glu Glu
555                 560                 565 atg aat gca gag ata agt caa ttt aaa cgt atg att gat act aca aaa      1842
Met Asn Ala Glu Ile Ser Gln Phe Lys Arg Met Ile Asp Thr Thr Lys
570                 575                 580                 585 aat gat gat act ccc tgg att gca cga acc ttg gac aac ctt gcc gat      1890
Asn Asp Asp Thr Pro Trp Ile Ala Arg Thr Leu Asp Asn Leu Ala Asp
                590                 595                 600 gag cta act gca ata ttg tct gct cct gct aaa tta att ggt cat ggt      1938
Glu Leu Thr Ala Ile Leu Ser Ala Pro Ala Lys Leu Ile Gly His Gly
                605                 610                 615 gtc aaa ggt gtg agc tca ctc ttt aaa aag cat aag ctc ccc ttt aag      1986
Val Lys Gly Val Ser Ser Leu Phe Lys Lys His Lys Leu Pro Phe Lys
                620                 625                 630 ggt ggg cgc gcc gac cca gct ttc ttg tac aaa gtg gtt gat cta gag      2034
Gly Gly Arg Ala Asp Pro Ala Phe Leu Tyr Lys Val Val Asp Leu Glu
                635                 640                 645 ggc ccg cgg ttc gaa caa aaa ctc atc tca gaa gag gat ctg aat atg      2082
Gly Pro Arg Phe Glu Gln Lys Leu Ile Ser Glu Glu Asp Leu Asn Met
650                 655                 660                 665 cat acc ggt cat cat cac cat cac cat tgagtttaaa cccgctgatc a          2130
His Thr Gly His His His His His His
                670
```

FIG. 3A

```
  1 ATGGTATCAGAGATCCACATGACAGGCCCAATGTGCCTCATTGAGAACACTAATGGGCGA   60
  1  M  V  S  E  I  H  M  T  G  P  M  C  L  I  E  N  T  N  G  R   20

61 CTGATGGCGAATCCAGAAGCTCTGAAGATCCTTTCTGCCATTACGCAGCCTGTGGTGGTG  120
 21  L  M  A  N  P  E  A  L  K  I  L  S  A  I  T  Q  P  V  V  V   40

121 GTGGCGACTCGCACAGGAAAATCCTACCTGATTAACAAGCTGGCTCAGAAGAAAAAGGGC  180
 41  V  A  T  R  T  G  K  S  Y  L  I  N  K  L  A  Q  K  K  K  G   60

181 TTCTCTCTGGGCTCCACAGTGCAGTCTCACACTAAAGGAATCTGGATGTGGTGTATGCCC  240
 61  F  S  L  G  S  T  V  Q  S  H  T  K  G  I  W  M  W  C  M  P   80

241 CATCCCAAGAAGCCAGGCCACATCCTAGTTCTGCTGGACACCGAGGGTCTGGGAGATGTA  300
 81  H  P  K  K  P  G  H  I  L  V  L  L  D  T  E  G  L  G  D  V  100

301 GAGAAGGGTGACAACCAGAATGACTCCTGGATCTTCGCCCTGGCCGTCCTCCTGAACAGC  360
101  E  K  G  D  N  Q  N  D  S  W  I  F  A  L  A  V  L  L  N  S  120

361 ACTTCCATGTACAATAGCATAGGAACCATTAACCAGCAGGCCATGGACCAACTGCACTAT  420
121  T  S  M  Y  N  S  I  G  T  I  N  Q  Q  A  M  D  Q  L  H  Y  140

421 GTGACAGAGCTGACACATCGAGTCCAACCAAAATCTTCACCTGATGAGAATGAGAATGAG  480
141  V  T  E  L  T  H  R  V  Q  P  K  S  S  P  D  E  N  E  N  E  160

481 GATTCAGCTGACTTTGAGAGCTTCTTCCCAGACTTTGCAGGTCTAGAGAGCCTGGTGCTG  540
161  D  S  A  D  F  E  S  F  F  P  D  F  A  G  L  E  S  L  V  L  180

541 ACCTATGTCAATGCCATCAGCAGTGGGGATCTACCCTGCATGGAGAACGCAGTCCTGGCC  600
181  T  Y  V  N  A  I  S  S  G  D  L  P  C  M  E  N  A  V  L  A  200

601 TTGGCCCAGATAGAGAACTCAGCCGCAGTGCAAAAGGCTATTGCCCACTATGAAAAGCAG  660
201  L  A  Q  I  E  N  S  A  A  V  Q  K  A  I  A  H  Y  E  K  Q  220

661 ATGGGCCAGAAGGTGCAGCTGCCCACAGAAACCCTCCAGGAGCTGCTGGACCTGCACAGG  720
221  M  G  Q  K  V  Q  L  P  T  E  T  L  Q  E  L  L  D  L  H  R  240

721 GACAGTGAGAGCAAGGCCACTGAAGTTTTCATCAGGAGTTCCTTCAAAGATGTGGACCAT  780
241  D  S  E  S  K  A  T  E  V  F  I  R  S  S  F  K  D  V  D  H  260

781 CTATTTCAAAAGGAGTTAGCGGCCCAGCTAGACAAAAAGCGGGATGACTTTTGTAAACAG  840
261  L  F  Q  K  E  L  A  A  Q  L  D  K  K  R  D  D  F  C  K  Q  280

841 AATCAGGAAGCATCATCAGATCGTTGCTCAGCTTTACTTCAGGTCATTTTCAGTCCTCTA  900
281  N  Q  E  A  S  S  D  R  C  S  A  L  L  Q  V  I  F  S  P  L  300
```

FIG. 3B

```
 901  GAAGAAGAAGTGAAGGCGGGAATTTATTCGAAACCAGGGGGCTATCGTCTCTTTATTCAG   960
 301  E   E   E   V   K   A   G   I   Y   S   K   P   G   G   Y   R   L   F   I   Q    320

961  AAGTTACAAGACCTGGAGAAAAAGTACTATGAGGAACCGAGGAAGGGGATACAGGGAATT  1020
 321  K   L   Q   D   L   E   K   K   Y   Y   E   E   P   R   K   G   I   Q   G   I    340

1021  TCACCACCAAGGACAACAGGGCAAAGGAAAGAATTCCCAGAGGAAAGGATGGCAGGAAGA  1080
 341  S   P   P   R   T   T   G   Q   R   K   E   F   P   E   E   R   M   A   G   R    360

1081  CAAACAGGAACACCTGCTTACAGCCGTCTCCTACTTCTCACTTTGTGTTCTCTGGGTCCT  1140
 361  Q   T   G   T   P   A   Y   S   R   L   L   L   T   L   C   S   L   G   P    380

1141  AAGGCTGAAGAGATTCTGCAGACATACTTGAAATCCAAGGAGTCTATGACTGATGCAATT  1200
 381  K   A   E   E   I   L   Q   T   Y   L   K   S   K   E   S   M   T   D   A   I    400

1201  CTCCAGACAGACCAGACTCTCACAGAAAAAGAAAAGGAGATTGAAGTGGAACGTGTGAAA  1260
 401  L   Q   T   D   Q   T   L   T   E   K   E   K   E   I   E   V   E   R   V   K    420

1261  GCTGAGTCTGCACAGGCTTCAGCAAAAATGTTGCAGCAAATGCAAAGAAAGAATGAGCAG  1320
 421  A   E   S   A   Q   A   S   A   K   M   L   Q   Q   M   Q   R   K   N   E   Q    440

1321  ATGATGGAACAGAAGGAGAGGAGTTATCAGGAACACTTGAAACAACTGACTGAGAAGATG  1380
 441  M   M   E   Q   K   E   R   S   Y   Q   E   H   L   K   Q   L   T   E   K   M    460

1381  GAGAGCGACAGG  1392
 461  E   S   D   R    464
```

FIG. 4A

```
  1  CAGTTTCATTAGGCTCTGAAGCCATTACAAAGGTTGCTTAACTTCTAATTATTTGATCAC   60

61  TGAGGAAAATCCAGAAAGCTACACAACACTGAAGGGGTGAAATAAAAGTCCAGCGATCCA  120

121  GCGAAAGAAAAGAGAAGTGACAGAAACAACTTTACCTGGACTGAAGATAAAAGCACAGAC  180

181  AAGAGAACAATGCCCTGGACATGGCTCCAGAGATCCACATGACAGGCCCAATGTGCCTCA  240
  1                         M  A  P  E  I  H  M  T  G  P  M  C  L  I   14

241  TTGAGAACACTAATGGGGAACTGGTGGCGAATCCAGAAGCTCTGAAAATCCTGTCTGCCA  300
 15   E  N  T  N  G  E  L  V  A  N  P  E  A  L  K  I  L  S  A  I   34

301  TTACACAGCCTGTGGTGGTGGTGGCAATTGTGGGCCTCTACCGCACAGGAAAATCCTACC  360
 35   T  Q  P  V  V  V  V  A  I  V  G  L  Y  R  T  G  K  S  Y  L   54

361  TGATGAACAAGCTAGCTGGGAAGAATAAGGGCTTCTCTCTGGGCTCCACAGTGAAATCTC  420
 55   M  N  K  L  A  G  K  N  K  G  F  S  L  G  S  T  V  K  S  H   74

421  ACACCAAAGGAATCTGGATGTGGTGTGTGCCTCACCCCAAAAAGCCAGAACACACCTTAG  480
 75   T  K  G  I  W  M  W  C  V  P  H  P  K  K  P  E  H  T  L  V   94

481  TCCTGCTTGACACTGAGGGCCTGGGAGATGTAAAGAAGGGTGACAACCAGAATGACTCCT  540
 95   L  L  D  T  E  G  L  G  D  V  K  K  G  D  N  Q  N  D  S  W  114

541  GGATCTTCACCCTGGCCGTCCTCCTGAGCAGCACTCTCGTGTACAATAGCATGGGAACCA  600
115   I  F  T  L  A  V  L  L  S  S  T  L  V  Y  N  S  M  G  T  I  134

601  TCAACCAGCAGGCTATGGACCAACTGTACTATGTGACAGAGCTGACACATCGAATCCGAT  660
135   N  Q  Q  A  M  D  Q  L  Y  Y  V  T  E  L  T  H  R  I  R  S  154

661  CAAAATCCTCACCTGATGAGAATGAGAATGAGGATTCAGCTGACTTTGTGAGCTTCTTCC  720
155   K  S  S  P  D  E  N  E  N  E  D  S  A  D  F  V  S  F  F  P  174

721  CAGATTTTGTGTGGACACTGAGAGATTTCTCCCTGGACTTGGAAGCAGATGGACAACCCC  780
175   D  F  V  W  T  L  R  D  F  S  L  D  L  E  A  D  G  Q  P  L  194

781  TCACACCAGATGAGTACCTGGAGTATTCCCTGAAGCTAACGCAAGGTAACAGGAAGCTTG  840
195   T  P  D  E  Y  L  E  Y  S  L  K  L  T  Q  G  N  R  K  L  A  214

841  CCCAGCTTGAGAAACTACAAGATGAAGAGCTGGACCCTGAATTTGTGCAACAAGTAGCAG  900
215   Q  L  E  K  L  Q  D  E  E  L  D  P  E  F  V  Q  Q  V  A  D  234

901  ACTTCTGTTCCTACATCTTTAGCAATTCCAAAACTAAAACTCTTTCAGGAGGCATCAAGG  960
235   F  C  S  Y  I  F  S  N  S  K  T  K  T  L  S  G  G  I  K  V  254
```

FIG. 4B

```
 961  TCAATGGGCCTTGTCTAGAGAGCCTAGTGCTGACCTATATCAATGCTATCAGCAGAGGGG  1020
 255    N  G  P  C  L  E  S  L  V  L  T  Y  I  N  A  I  S  R  G  D    274

1021  ATCTGCCCTGCATGGAGAACGCAGTCCTGGCCTTGGCCCAGATAGAGAACTCAGCCGCAG  1080
 275    L  P  C  M  E  N  A  V  L  A  L  A  Q  I  E  N  S  A  A  V    294

1081  TGCAAAAGGCTATTGCCCACTATGACCAGCAGATGGGCCAGAAGGTGCAGCTGCCCGCAG  1140
 295    Q  K  A  I  A  H  Y  D  Q  Q  M  G  Q  K  V  Q  L  P  A  E    314

1141  AAACCCTCCAGGAGCTGCTGGACCTGCACAGGGTTAGTGAGAGGGAGGCCACTGAAGTCT  1200
 315    T  L  Q  E  L  L  D  L  H  R  V  S  E  R  E  A  T  E  V  Y    334

1201  ATATGAAGAACTCTTTCAAGGATGTGGACCATCTGTTTCAAAAGAAATTAGCGGCCCAGC  1260
 335    M  K  N  S  F  K  D  V  D  H  L  F  Q  K  K  L  A  A  Q  L    354

1261  TAGACAAAAAGCGGGATGACTTTTGTAAACAGAATCAAGAAGCATCATCAGATCGTTGCT  1320
 355    D  K  K  R  D  D  F  C  K  Q  N  Q  E  A  S  S  D  R  C  S    374

1321  CAGCTTTACTTCAGGTCATTTTCAGTCCTCTAGAAGAAGAAGTGAAGGCGGGAATTTATT  1380
 375    A  L  L  Q  V  I  F  S  P  L  E  E  E  V  K  A  G  I  Y  S    394

1381  CGAAACCAGGGGGCTATTGTCTCTTTATTCAGAAGCTACAAGACCTGGAGAAAAAGTACT  1440
 395    K  P  G  G  Y  C  L  F  I  Q  K  L  Q  D  L  E  K  K  Y  Y    414

1441  ATGAGGAACCAAGGAAGGGGATACAGGCTGAAGAGATTCTGCAGACATACTTGAAATCCA  1500
 415    E  E  P  R  K  G  I  Q  A  E  E  I  L  Q  T  Y  L  K  S  K    434

1501  AGGAGTCTGTGACCGATGCAATTCTACAGACAGACCAGATTCTCACAGAAAAGGAAAAGG  1560
 435    E  S  V  T  D  A  I  L  Q  T  D  Q  I  L  T  E  K  E  K  E    454

1561  AGATTGAAGTGGAATGTGTAAAAGCTGAATCTGCACAGGCTTCAGCAAAAATGGTGGAGG  1620
 455    I  E  V  E  C  V  K  A  E  S  A  Q  A  S  A  K  M  V  E  E    474

1621  AAATGCAAATAAAGTATCAGCAGATGATGGAAGAGAAAGAGAAGAGTTATCAAGAACATG  1680
 475    M  Q  I  K  Y  Q  Q  M  M  E  E  K  E  K  S  Y  Q  E  H  V    494

1681  TGAAACAATTGACTGAGAAGATGGAGAGGGAGAGGGCCCAGTTGCTGGAAGAGCAAGAGA  1740
 495    K  Q  L  T  E  K  M  E  R  E  R  A  Q  L  L  E  E  Q  E  K    514

1741  AGACCCTCACTAGTAAACTTCAGGAACAGGCCCGAGTACTAAAGGAGAGATGCCAAGGTG  1800
 515    T  L  T  S  K  L  Q  E  Q  A  R  V  L  K  E  R  C  Q  G  E    534

1801  AAAGTACCCAACTTCAAAATGAGATACAAAAGCTACAGAAGACCCTGAAAAAAAAACCA   1860
 535    S  T  Q  L  Q  N  E  I  Q  K  L  Q  K  T  L  K  K  K  T  K    554
```

FIG. 4C

```
1861 AGAGATATATGTCGCATAAGCTAAAGATCTAAACAACAGAGCTTTTCTGTCATCCTAACC 1920
 555   R  Y  M  S  H  K  L  K  I                                   563

1921 CAAGGCATAACTGAAACAATTTTAGAATTTGGAACAAGTGTCACTATATTTGATAATAAT 1980

1981 TAGATCTTGCATCATAACACTAAAAGTTTACAAGAACATGCAGTTCAATGATCAAAATCA 2040

2041 TGTTTTTTCCTTAAAAAGATTGTAAATTGTGCAACAAAGATGCATTTACCTCTGTACCAA 2100

2101 CAGAGGAGGGATCATGAGTTGCCACCACTCAGAAGTTTATTCTTCCAGACGACCAGTGGA 2160

2161 TACTGAGGAAAGTCTTAGGTAAAAATCTTGGGACATATTTGGGCACTGGTTTGGCCAAGT 2220

2221 GTACAATAGGTCCCAATATCAGAAACAACCATCCTAGCTTCCTAGGGAAGACAGTGTACA 2280

2281 GTTCTCCATTATATCAAGGCTACAAGGTCTATGAGCAATAATGTGATTTCTGGACATTGC 2340

2341 CCATGGATAATTCTCACTGATGGATCTCAAGCTAAAGCAAACCATCTTATACAGAGATCT 2400

2401 AGAATCTTATATTTTCCATAGGAAGGTAAAGAAATCATTAGCAAGAGTAGGAATTGAATC 2460

2461 ATAAACAAATTGGCTAATGAAGAAATCTTTTCTTTCTTGTTCAATTCATCTAGATTATAA 2520

2521 CCTTAATGTGACACCTGAGACCTTTAGACAGTTGACCCTGAATTAAATAGTCACATGGTA 2580

2581 ACAATTATGCACTGTGTAATTTTAGTAATGTATAACATGCAATGATGCACTTTAACTGAA 2640

2641 GATAGAGACTATGTTAGAAAATTGAACTAATTTAATTATTTGATTGTTTTAATCCTAAAG 2700

2701 CATAAGTTAGTCTTTTCCTGATTCTTAAAGGTCATACTTGAAATCCTGCCAATTTTCCCC 2760

2761 AAAGGGAATATGGAATTTTTTTGACTTTCTTTTGAGCAATAAAATAATTGTCTTGCCAT 2820

2821 TACTTAGTATATGTAGACTTCATCCCAATTGTCAAACATCCTAGGTAAGTGGTTGACATT 2880

2881 TCTTACAGCAATTACAGATTATTTTTGAACTAGAAATAAACTAAACTAGAAACAAAAAAA 2940

2941 AAAAAAAAAAAA 2952
```

FIG. 5A

```
  1  GAATCGGGCGGGCGCAGCAGCAAGCCTAAAGGTGCTGAATCCAGGTAGCAGAGAATCCGG    60

61  TGCAGGCTGGTTACCATGGCATCTGGTCCCAACATGGAGGCTCCTGTGTGCCTAGTGGAA   120
  1                                    M  E  A  P  V  C  L  V  E    9

121  AATGAGAATGAAGAACTGAGGGTGAACTCCAAAGCAATAAACATTCTTGAGAGGATCACT   180
 10   N  E  N  E  E  L  R  V  N  S  K  A  I  N  I  L  E  R  I  T   29

181  CAGCCTGTAGTGGTGGTGGCCATTGTAGGACTATACCGTACGGGAAAATCCTACTTGATG   240
 30   Q  P  V  V  V  V  A  I  V  G  L  Y  R  T  G  K  S  Y  L  M   49

241  AACCGCTTGGCAGGACAGAACCATGGCTTCAATCTGGGCACCACAGTTAGGTCTGAAACT   300
 50   N  R  L  A  G  Q  N  H  G  F  N  L  G  T  T  V  R  S  E  T   69

301  AAGGGCATCTGGATGTGGTGTGTGCCTCACCCCAGCAAGCCCAAGTTCACACTCGTGCTT   360
 70   K  G  I  W  M  W  C  V  P  H  P  S  K  P  K  F  T  L  V  L   89

361  CTGGACACGGAGGGCTTAGGAGATGTGGAAAAGGGTGACCCTAAGAATGACTCGTGGATC   420
 90   L  D  T  E  G  L  G  D  V  E  K  G  D  P  K  N  D  S  W  I  109

421  TTCGCCCTGGCTGTGCTTCTGAGCAGCACCTTTGTCTACAACAGCATGAGCACCATCAAC   480
110   F  A  L  A  V  L  L  S  S  T  F  V  Y  N  S  M  S  T  I  N  129

481  CACCAGGCCCTGGAGCAGCTGCACTATGTCACAGAACTGACAGAGCGGATCAGGGCAAAG   540
130   H  Q  A  L  E  Q  L  H  Y  V  T  E  L  T  E  R  I  R  A  K  149

541  TCCACTTCACGGTCTGAAGAAGTGGATGACTCTGATGAGTTTGTAAGTTTCTTTCCAGAT   600
150   S  T  S  R  S  E  E  V  D  D  S  D  E  F  V  S  F  F  P  D  169

601  TTTATCTGGACTGTTCGAGATTTCGTTCTGGAGCTGAAGTTAGAGGGACGTGTCATCACA   660
170   F  I  W  T  V  R  D  F  V  L  E  L  K  L  E  G  R  V  I  T  189

661  GCAGACGAGTACCTAGAAAATGCCCTGAAGCTGATCCCAGGCATGAGTATCAAAGCCCAG   720
190   A  D  E  Y  L  E  N  A  L  K  L  I  P  G  M  S  I  K  A  Q  209

721  AAAGCTAACTTGCCTAGGGAATGCATCAGGCACTTCTTTCCAAGACGGAAGTGCTTTGTC   780
210   K  A  N  L  P  R  E  C  I  R  H  F  F  P  R  R  K  C  F  V  229

781  TTTGATCGACCTACAAAAGACAAAGAACTTTTAGTGCATGTTGAGGAAATGCCAGAGGAC   840
230   F  D  R  P  T  K  D  K  E  L  L  V  H  V  E  E  M  P  E  D  249

841  CAGTTGGATCACAGTTTCCAAGTGCAGTCAAAAGAATTCTGTTCCTACATCTTCTCCAAT   900
250   Q  L  D  H  S  F  Q  V  Q  S  K  E  F  C  S  Y  I  F  S  N  269

901  TCGAAGGCCAAGACCTTGAAAGAGGGAATCGTTGTCAATGGAAACCGACTGGCGACTCTG   960
270   S  K  A  K  T  L  K  E  G  I  V  V  N  G  N  R  L  A  T  L  289
```

FIG. 5B

```
 961  GTGACGACCTACGTGGATGCTATCAATAGTGGAGACGTGCCGTGTTTAGAGAACGCAGTA  1020
 290   V  T  T  Y  V  D  A  I  N  S  G  D  V  P  C  L  E  N  A  V   309

1021  ACAACCCTGGCCCAGCGTGAGAACTCCATAGCTGTGCAGAAGGCAGCTGACCACTACAGT  1080
 310   T  T  L  A  Q  R  E  N  S  I  A  V  Q  K  A  A  D  H  Y  S   329

1081  GAGCAGATGGCCCAGCGAATGAGGCTCCCCACAGACACGCTCCAGGAGCTGCTGACTGTG  1140
 330   E  Q  M  A  Q  R  M  R  L  P  T  D  T  L  Q  E  L  L  T  V   349

1141  CATACAGCCTGTGAGAAGGAAGCCATTGCTGTCTTCATGGAGCACTCCTTCAAGGATGAG  1200
 350   H  T  A  C  E  K  E  A  I  A  V  F  M  E  H  S  F  K  D  E   369

1201  AATCAGCAATTCCAGAAGAACTTGGTGGTCACCATAGAGGAAAAAAAGGAAGATTTCCTG  1260
 370   N  Q  Q  F  Q  K  N  L  V  V  T  I  E  E  K  K  E  D  F  L   389

1261  CGACAGAATGAAGCAGCGTCTCTCAGTCACTGCCAGGCTGAGCTGGACAAGCTCTCAGAG  1320
 390   R  Q  N  E  A  A  S  L  S  H  C  Q  A  E  L  D  K  L  S  E   409

1321  TCCCTGAGGGAGAGCATCTCACGTGGAGTTTTCTCTGTTCCTGGGGGTCACAGGCTCTAC  1380
 410   S  L  R  E  S  I  S  R  G  V  F  S  V  P  G  G  H  R  L  Y   429

1381  TTAGAGGCCAGGAAGAAGGTTGAACAGGACTATGAGCGAGTGCCCAGGAAGGGAGTGAAG  1440
 430   L  E  A  R  K  K  V  E  Q  D  Y  E  R  V  P  R  K  G  V  K   449

1441  GCAAATCATGTCCTTCAGAGCTTCCTACAGTCACAGATTTCCATTGAGGACTCCATTATG  1500
 450   A  N  H  V  L  Q  S  F  L  Q  S  Q  I  S  I  E  D  S  I  M   469

1501  CAGTCAGACAAAGCCCTCACTGATGGCCAGAAGGCCATGGAAGCTGAGCGAGCTCAGAAG  1560
 470   Q  S  D  K  A  L  T  D  G  Q  K  A  M  E  A  E  R  A  Q  K   489

1561  GAGGCAGCTGAGAAGGAGCAGGAGCTACTAAGACAGAAACAGAAGGAGCTGCAGCAGGTG  1620
 490   E  A  A  E  K  E  Q  E  L  L  R  Q  K  Q  K  E  L  Q  Q  V   509

1621  ATGGAAGCTCAAGAGAGAAGCTACAAGGAAAATGTGGCCCAGCTGCACGAGAAGATGGAG  1680
 510   M  E  A  Q  E  R  S  Y  K  E  N  V  A  Q  L  H  E  K  M  E   529

1681  ACAGAAAGGAAGAACATCCTGAGAGAGCAAGAGGTGAAGCTGGAACACAAGTTGAAGATT  1740
 530   T  E  R  K  N  I  L  R  E  Q  E  V  K  L  E  H  K  L  K  I   549

1741  CAAAAAGACATGCTTAATGAGGGATTTAAAAGGAAATGTGAAGCAATGGATTTGGAGATA  1800
 550   Q  K  D  M  L  N  E  G  F  K  R  K  C  E  A  M  D  L  E  I   569

1801  AGTCAACTACAAAAAGAGATTCAACTAAATAAGGAGAAGAATAGCTCATTGGGTGCAAAA  1860
 570   S  Q  L  Q  K  E  I  Q  L  N  K  E  K  N  S  S  L  G  A  K   589
```

FIG. 5C

```
1861 ATCCTTGATGGGTTTGGAGATGTATTAATTTCAGTAGTGCCTGGTTCTGGTAAGTACTTT 1920
 590  I  L  D  G  F  G  D  V  L  I  S  V  V  P  G  S  G  K  Y  F   609

1921 GGTCTAGGGTTGAAAATATTAAGCAGCCAAATGAATCAGACACAGAATTCAGACAAAGTT 1980
 610  G  L  G  L  K  I  L  S  S  Q  M  N  Q  T  Q  N  S  D  K  V   629

1981 AGAAAACTCTAAGTATAGCTTTCCCCCACCTCCCTGAGACTTACTTTTGAAGTCCATCTC 2040
 630  R  K  L                                                       632

2041 ACTTTAATTTCATTTATCAAATTTCAAAAACCAAGAATATAGGTCACTCTCTATAAATTA 2100

2101 ATGGCAAGACCCCATTGCTGAAAACAAATGTATACAACTCATTGATTGATGGAGAACTCA 2160

2161 AGCTGGTGCCCATAGATCCTTCTCCTTATATGCGGACATCTTTGGCACAGAATGACACTC 2220

2221 TGCATGCTACCAAAGGAAAAACACAAATGCCAGCCCAGCCACAAGCCCTTTGATCTACAA 2280

2281 TGGCATCCTGCCTGCAAAATATGCAAATGCAGTGGTGGCACAAACTGTGGGAGTAACTAA 2340

2341 CCAATATCTGATTTGATTTAAGGCCAACTTCACGGGATGAAACCCATGCCTACACTGCCT 2400

2401 GGGTGATCCAGAACCTAGATCAGATAGCCCAGCGAACCTTGAGTAAAACCAAATACTATT 2460

2461 GTTGTATTAAAAAAAAAAAAAAAA 2484
```

FIG. 6A

```
  1  ATGGAAGGAAAAGTATTACAGTGGAACTCGTACCTGTCTGAATTCCATTGTGACCAGGAT   60
  1   M  E  G  K  V  L  Q  W  N  S  Y  L  S  E  F  H  C  D  Q  D   20

61  GTGGTAACAAAGGTGTCTGTGCCTTCTGGCACCAAGGAAATAGCTCAATTGCCTCTAACC  120
 21   V  V  T  K  V  S  V  P  S  G  T  K  E  I  A  Q  L  P  L  T   40

121  CCCATCCCTAACCCACTCATCACTTCCCCAAAGAAGTACCCATTGAACTGTGGAGACCAA  180
 41   P  I  P  N  P  L  I  T  S  P  K  K  Y  P  L  N  C  G  D  Q   60

181  CGGAATGGTCACAAGAGTTGGTTAATGCATGGTTTACTGATGGTTCATCAACCACTGATG  240
 61   R  N  G  H  K  S  W  L  M  H  G  L  L  M  V  H  Q  P  L  M   80

241  GAGGCAAAACTAATGGAAAGCCAGAGCCTAGAGACATGGGGATGGAATGGCCAACACCAA  300
 81   E  A  K  L  M  E  S  Q  S  L  E  T  W  G  W  N  G  Q  H  Q  100

301  GGAAGGAACCACAAGATCAGCATAGCACTATTGGCTATAAAACAAACAACTAGGAAAACA  360
101   G  R  N  H  K  I  S  I  A  L  L  A  I  K  Q  T  T  R  K  T  120

361  AAAAGTTTTTCCATGGGCTCCACTGTGCAGTCTCAAACCAGGGGCATCTGGATGTGGTGT  420
121   K  S  F  S  M  G  S  T  V  Q  S  Q  T  R  G  I  W  M  W  C  140

421  GTGCCTCATCCCGAGAAACCTGACCACACCCTAGTTCTGGATGACACCGAGGGCCTAGGA  480
141   V  P  H  P  E  K  P  D  H  T  L  V  L  D  D  T  E  G  L  G  160

481  GATGTTGAGAAAGGTGACAACCAGAACGACTGCTGGATCTTTGCCCTGGCTATACTTCTA  540
161   D  V  E  K  G  D  N  Q  N  D  C  W  I  F  A  L  A  I  L  L  180

541  AGCAGCACCTTTGTCTACAACAGCATCGGGGCCATCAACCAGCAGGCCATGGACCAGCTG  600
181   S  S  T  F  V  Y  N  S  I  G  A  I  N  Q  Q  A  M  D  Q  L  200

601  CACTTTTTTCTTAATGCAACATGAAATGATGCTGATCAGCTATGTGACAGAGCTGACTGAC  660
201   H  F  F  L  M  Q  H  E  M  M  L  I  S  Y  V  T  E  L  T  D  220

661  AGAATCAGAACAAGACGCTCCCCTGACCATCAAGCTTTGGAGGACTCAGATGAATATGTG  720
221   R  I  R  T  R  R  S  P  D  H  Q  A  L  E  D  S  D  E  Y  V  240

721  AGCTTCTTCCCAGACTTTGTATGGACCCCGAGAGACTTCTGTCTTGAGCTGAAAACAAAT  780
241   S  F  F  P  D  F  V  W  T  P  R  D  F  C  L  E  L  K  T  N  260

781  GGACAACCCCTCTCAGCAGACGAATACCTAGGGAATTCCCTGAAGCTTCTTCAAGGTTGT  840
261   G  Q  P  L  S  A  D  E  Y  L  G  N  S  L  K  L  L  Q  G  C  280

841  AGTCAAAAAGAAAAAGAGTTAAATCTGTCTCAGCTCTGTATCCGTAAATTCTTCCCAACT  900
281   S  Q  K  E  K  E  L  N  L  S  Q  L  C  I  R  K  F  F  P  T  300
```

FIG. 6B

```
 901 AAGAAATGCTTTGTCTTTGAGCGCCCAGCACCCGGGAAGAAGATTGGCCAGCTGGAATCA  960
 301  K  K  C  F  V  F  E  R  P  A  P  G  K  K  I  G  Q  L  E  S   320

961 CTACAGGATAAAGACCTGGACTCTGACTTCGTGAAACAAGTGGCAGAGTTCTCTTCCTAT 1020
 321  L  Q  D  K  D  L  D  S  D  F  V  K  Q  V  A  E  F  S  S  Y   340

1021 GTTTTCAGGTCTTCCAAGATTAAAAAAATTCCAGGAGACCTCAAGGTCAATGGACCGCGA 1080
 341  V  F  R  S  S  K  I  K  K  I  P  G  D  L  K  V  N  G  P  R   360

1081 CTAAAGAATTTGGTGACAACCTATGTGAACACCATCAGCAATGGGTCTCTGCCCTGCATG 1140
 361  L  K  N  L  V  T  T  Y  V  N  T  I  S  N  G  S  L  P  C  M   380

1141 GAGAGTGCTGTCCTGGCTCTGTCAGAAACAGAGAACTCAGCAGCAGTGCGAAAGGCCATT 1200
 381  E  S  A  V  L  A  L  S  E  T  E  N  S  A  A  V  R  K  A  I   400

1201 GCCCACTATGACCAGCAGATGAGCCAGAGTCTGAAGCTGCCCACAGAGACCCTCCAGGAG 1260
 401  A  H  Y  D  Q  Q  M  S  Q  S  L  K  L  P  T  E  T  L  Q  E   420

1261 CTGCTGGACCTGCACAGGAGCAGTGAGAAAGAAGCCATCAAGATTTTCATGGAAAATTCC 1320
 421  L  L  D  L  H  R  S  S  E  K  E  A  I  K  I  F  M  E  N  S   440

1321 TTCAAAGATGTTGACCAAGTGTTCCTAACAAAATTAGAGAAAGAAGGCAAGCAAAGGGAA 1380
 441  F  K  D  V  D  Q  V  F  L  T  K  L  E  K  E  G  K  Q  R  E   460

1381 TTCTGTAAGAAGAATCAAGAGGCATCCTCAGATCGCTGTTCAGTTCTGCTTCGGGATATT 1440
 461  F  C  K  K  N  Q  E  A  S  S  D  R  C  S  V  L  L  R  D  I   480

1441 TTTGGTCCACTAGAAGAAGACTTGAAGCAGGGTGTTTTTTACAAACCAACGGGTTGCTGT 1500
 481  F  G  P  L  E  E  D  L  K  Q  G  V  F  Y  K  P  T  G  C  C   500

1501 CTTTTCAGCCAGAAGATACAGGGGTTGAAGAGAAAGTATGAGGAACCTGGGAAGGGCGCA 1560
 501  L  F  S  Q  K  I  Q  G  L  K  R  K  Y  E  E  P  G  K  G  A   520

1561 GGTAACCAAGGTAACCAAGGTTCCGCATGCCCTGGGAAGTTTCTTACCATCAGGCTGCAG 1620
 521  G  N  Q  G  N  Q  G  S  A  C  P  G  K  F  L  T  I  R  L  Q   540

1621 TGTCCCCAGGCATCACTGGGGAACGCCAGCTTATGCTGTTCGTGTATCACATACCTGAAG 1680
 541  C  P  Q  A  S  L  G  N  A  S  L  C  C  S  C  I  T  Y  L  K   560

1681 GTCTTCATACTGGATATTTCCTGCTCACCCATCAGAGACAGTCACTCACTTAACAGTCAG 1740
 561  V  F  I  L  D  I  S  C  S  P  I  R  D  S  H  S  L  N  S  Q   580

1741 ACAGTCACTCGCTTAACAACTGAGCTCAAACTGACCACCTTAGCCACCAGTGGGACTGTC 1800
 581  T  V  T  R  L  T  T  E  L  K  L  T  T  L  A  T  S  G  T  V   600

1801 ACCCTCTGTTTCAGCTAG 1818
 601  T  L  C  F  S         605
```

FIG. 7A

```
  1  GCCTGAGGAGGCAGCAGCAGCTGAGAACTGCACTTGGACCTGTGCTGTGGGACCAGATTC   60

61  ATCTACGTTGGCAGGTTGCTATGACCCAACCACAAATGGCTCCCATTTGTCTTGTGGAAA  120
  1                    M  T  Q  P  Q  M  A  P  I  C  L  V  E  N   14

121  ACCACAATGAACATCTGTCCATGAACCATGAAGCCATAGAGATTCTGGAGAAGATTTCTC  180
 15   H  N  E  H  L  S  M  N  H  E  A  I  E  I  L  E  K  I  S  Q   34

181  AGCCAGTGGTAGTCGTGGCTATTGTTGGATTGTACCGTACAGGGAAGTCCTATTTGATGA  240
 35   P  V  V  V  V  A  I  V  G  L  Y  R  T  G  K  S  Y  L  M  N   54

241  ACCGTCTGGCAGGACAGAATCACGGTTTCCCTCTGGGCTCCACTGTGCAATCTCAGACCA  300
 55   R  L  A  G  Q  N  H  G  F  P  L  G  S  T  V  Q  S  Q  T  K   74

301  AGGGCATCTGGATGTGGTGCATGCCACACCCCACTAAACCAGAGCACACCCTGGTCCTCC  360
 75   G  I  W  M  W  C  M  P  H  P  T  K  P  E  H  T  L  V  L  L   94

361  TGGACACCGAGGGCCTGGGGGATGTGGAAAAGGGTGATCCTAAGAACGACTTGTGGATCT  420
 95   D  T  E  G  L  G  D  V  E  K  G  D  P  K  N  D  L  W  I  F  114

421  TTGCCCTTGGCGTGCTTCTGAGCAGCACCTTCATCTACAACAGCATGAACACCATCAGCC  480
115   A  L  G  V  L  L  S  S  T  F  I  Y  N  S  M  N  T  I  S  H  134

481  ATGATTCCCTGGAGAAACTACATTATGTCACAGAACTCACTGAGCTGATCAGAGCAAAGT  540
135   D  S  L  E  K  L  H  Y  V  T  E  L  T  E  L  I  R  A  K  S  154

541  CTTCACCAAATCCTGATGGAATAAAGAATTCCACAGAGTTTGTGAGTTTCTTTCCAGACT  600
155   S  P  N  P  D  G  I  K  N  S  T  E  F  V  S  F  F  P  D  F  174

601  TTGTCTGGACTGTTCGGGATTTCATGCTAGAGCTGAAGTTAAATGGGGAAGATATCACAA  660
175   V  W  T  V  R  D  F  M  L  E  L  K  L  N  G  E  D  I  T  S  194

661  GTGATGAGTACCTGGAGAATGCCCTGAAGCTGATCCCAGGTTACAATCCCAGAGTGCAAG  720
195   D  E  Y  L  E  N  A  L  K  L  I  P  G  Y  N  P  R  V  Q  A  214

721  CATCCAATTCAGCCAGGGAATGCATCAGATGTTTCTTTCCTAACCGGAAGTGTTTTGTCT  780
215   S  N  S  A  R  E  C  I  R  C  F  F  P  N  R  K  C  F  V  F  234

781  TTGACCGGCCAACTCATGACAGAGAACTCTTACAAAAACTTGAGACTATTTCAGAAGACC  840
235   D  R  P  T  H  D  R  E  L  L  Q  K  L  E  T  I  S  E  D  Q  254

841  AACTGGATCTTAAGTTCCGGGAAGAAACAAACGCTTTTGTTTCTTACATCTTCAATTATG  900
255   L  D  L  K  F  R  E  E  T  N  A  F  V  S  Y  I  F  N  Y  A  274

901  CCAAGATTAAGACCCTCAAAGAGGGAATTAAGGTCACTGGGAATGGATTGGGGATTCTAG  960
275   K  I  K  T  L  K  E  G  I  K  V  T  G  N  G  L  G  I  L  V  294
```

FIG. 7B

```
 961  TGACAACCTATGTAGATGCCATCAACAGTGGAGCAGTGCCTTGTGTGGATGATGCTGTGA  1020
 295    T  T  Y  V  D  A  I  N  S  G  A  V  P  C  V  D  D  A  V  T   314

1021  CAACTCTGGCCCAGCATGAGAACTCAGTAGCTGTGCAGAGGGCAGCTGACCACTACAGTG  1080
 315    T  L  A  Q  H  E  N  S  V  A  V  Q  R  A  A  D  H  Y  S  E   334

1081  AGCAGATGGTCCAGCGACTGAGCCTTCCCACAGACACGCTCCAGGAGCTGCTGGATGTGC  1140
 335    Q  M  V  Q  R  L  S  L  P  T  D  T  L  Q  E  L  L  D  V  H   354

1141  ATGCAGCCTGCGAGAAGGAAGCCATGGCTGTCTTCATGGAGCATTCCTTCAAGGACGAAA  1200
 355    A  A  C  E  K  E  A  M  A  V  F  M  E  H  S  F  K  D  E  N   374

1201  ATCAGCAATTCCTGAAGAAGCTGGTGGTAATCTGTTGATGGCATTAACTATCATGGCTCT  1260
 375    Q  Q  F  L  K  K  L  V  V  I  C                              385

1261  ACCCCTTCAAGACTGTAGTATTGATGAGCCTTCATTGGCCATATGTGCATTTATTATTCA  1320

1321  AAGATATGTGTTTCAGAGTATCATGAATAATACAGTTATGAACGACTACATGTCCCCTTC  1380

1381  CAAAAATTTCAGGTGCTTTCAGTCTAGTAATGTCTAACAGATGGAATAATGAGTATATAG  1440

1441  TGTCCTAAATCCTTTACCCAGTTAATGTTTGTGGACTGTGATCCTGCCCAGGGCATCTAT  1500

1501  AGTGCATCCTTGAACTTGCTATATTCTTCTGTTCCTAAGAAACTGTTTCTCACTGGAGTC  1560

1561  TCACTACAGCCCAGTGTTCTTCTATTGCCCCTTGTTATATCATTGTGTCCTTGAAGATAG  1620

1621  AATTCCAGGATGTGACACCTACAAAGAACCAGAGATGGTTGGATGTACCCCATCTCTTTG  1680

1681  CAGAAGGTCTTGAAGACCAGGAACACCAAGAACATTTACTGTGGTCTTCCACAGCTTTTT  1740

1741  CAGCATCTGAGTTCAGGTTTTAGCACTTCACATTCCCATGAGTTCTTATTACATTGGAAT  1800

1801  GCTTTCTCATGAGGAATAGGTTGGCCCTTTTATAATGTTTCTTGGAATTTTATTCCTTCT  1860

1861  TTTCCTTCAATTATGTCAGATCTCTGTACACTTCCTTTGTAGGAATTAATAGGTGAGGCG  1920

1921  AAAGTGCTTTTCCTGTTGAAGAATGAAGAGGCATCTGATAAATACTGCCAGGAAGAACTG  1980

1981  GATCGACTTTCAAAGGATTTGATGGACAATATCTCAACATTTCTGTTCCTGGGGACAC    2040

2041  AGGCTCTACATGGACATGAGAGAGAAGATTGAGCATGATTACTGGCAAGTTCCCAGGAAA  2100
```

FIG. 7C

```
2101  GGGGTGAAGGCAAGAGAAGTCTTCCAGAGCTTTCTTCAGTCGCAGGCCATCATTGAGAGT  2160

2161  TCCATCCTGCAGGCAGACACAGCCCTCACTGCTGGGCAGAAGGCCATTGCAGAGGAGCGC  2220

2221  ACCAAGAAGGAGGCAGCTGAGAAGGAGCAGGATCTGCTAAGACAGAAGCAGAAGGAGCAG  2280

2281  CAGGAGTATATGGAGGCTCAAGAGAAAAGGAACAAGGAAAACATAGAGCAACTGAGAAGG  2340

2341  AAGCTGGAGCAGGAGAGAGAGCAGCTCATCAAAGACCATAACATGATGGTGGAGAAGAAG  2400

2401  CTGAAGGAACAAAAGGCTTTGCTTGAGGAAGGATTTAAGAAGAAAGCTGAAGAAATGGAC  2460

2461  GGAGAGATACAGCAACTGAAACATAACATCGAGGATATGAAAAAAAACAGTGGTTCCATT  2520

2521  TTCGATACTATTATAAGAGAAGTTGCTTCATTTATTTTTTCTCCCATTTCAATGATTGAA  2580

2581  AAGGGTATAAGGTCCCTTTTTTAGTAAAAATGATAGACTGTGATATACACTTTGTGTTAC  2640

2641  TTTGACGCTGCCTGTTTTCCATTTTCACTCCGCAGAGAAGTTTAAACATAAAAAGTGCTG  2700

2701  ATTAGAGGGCATCTGTGCCCCACACAGAAGACATAGAACAGCTCCTACATGTCTGCACAG  2760

2761  ACAATGCTTGCCTTTAGAGAACATATTTTGAAACCATTCCTATGAAAGCTATGCATTTAG  2820

2821  TCATCAGATGTGATCACTGCTGGCCAATTTAACTACATATAGAATCTGCATATAGAATCT  2880

2881  GTACTCCTATGAGGACCATGTAGCCCAGGATAGGTTGTACGGGATTCTCTCAGGTTAATA  2940

2941  TGGTAGGGAACCCATCCTAAGTGTGGGCAGCACCATTCCTGTGGACTGAAGACACAGTAG  3000

3001  AAAGATGAAAGCAATCTCCCTACCACTTGTGGCTTCGACTGTGGATGCCATACAACAAGC  3060

3061  CAGCCTTGACTTCTCTCAGAATGCATTATCCAGCCTTGACCGAATGTATCATCATGATAC  3120

3121  ATGGAGCTCAACAAACCATTCATTAAGTTGGTTTTGTGAGGGTATTTCATCACAGCAAGA  3180

3181  GGAAGTCACTGATATCATAATAGTGATAATCCTGGAAACTACTTAATCATCCCTGAGTTA  3240

3241  GATTGGCAATAAATTTTAATATGACTTGTTCTTGGAGTACTGTATAGTCAAGAAACAAAT  3300

3301  GTCAGTCAAACTATCTGTATAGTGATCTAAATTGAGCTAAAATATATCTTAAAAATAAAG  3360

3361  TCAAAACACTATAAAAAAAAAAAAAAA  3387
```

FIG. 8A

```
  1  GGAGCCTGAGGAGGCAGCAGCAGCTGAGAACTGCACTTGGACCTGTGCTGTGGGACCAGG    60

61  TTGCTATGACCCAACCACAAATGGCTCCCATTTGCCTTGTGGAAAACCACAATGAACAGC   120

121  TGTCAGTGAACCAGGAAGCCATAGAGATTCTGGACAAGATTTCTCAGCCAGTGGTAGTCG   180

181  TGGCTATTGTTGGATTGTACCGTACAGGGAAGTCCTATTTGATGAACTGTTTGGCGGGAC   240

241  AGAATCACGGGTGATCCTAAGAACGACTTGTGGATCTTTGCCCTCAGCGTGCTTCTGAGC   300

301  AGCACCTTCATCTACAACAGCATGATCACCATCAACCACCAGGCCCTGGAGCAGCTGCAT   360
  1                       M  I  T  I  N  H  Q  A  L  E  Q  L  H    13

361  TATGTCACAGAACTCACAGAGCTGATCAGAGCAAAGTCTTCCCCAAATCCTGCTGGAATA   420
 14   Y  V  T  E  L  T  E  L  I  R  A  K  S  S  P  N  P  A  G  I   33

421  AAGAATTCCACAGAGTTTGTGAGTTTCTTTCCAGACTTTGTCTGGACTGTTCGGGATTTC   480
 34   K  N  S  T  E  F  V  S  F  F  P  D  F  V  W  T  V  R  D  F   53

481  ATGCTGGAGCTGAAGTTAAATGGGGAAGACATCACAAGTGATGACTACCTGGAGAATGCC   540
 54   M  L  E  L  K  L  N  G  E  D  I  T  S  D  D  Y  L  E  N  A   73

541  TTGAAGCTGATCCCAGGTGACAAACCCAGAATGCAAGCATCCAATTCATGCAGGGAATGC   600
 74   L  K  L  I  P  G  D  K  P  R  M  Q  A  S  N  S  C  R  E  C   93

601  ATCAGACTTTTCTTTCCTAACCGGAAGTGTTTTGTCTTTGACCGGCCAACGCATGACAAA   660
 94   I  R  L  F  F  P  N  R  K  C  F  V  F  D  R  P  T  H  D  K  113

661  GAACTTTTACAAAAACTTGATTCTATCACAGAAGACCAACTGGATCCTAAGTTCCAGGAA   720
114   E  L  L  Q  K  L  D  S  I  T  E  D  Q  L  D  P  K  F  Q  E  133

721  GTAACAAAGGCTTTTGTTTCTTACATCTTCACTTATGCCAAGATCAAGACCCTAAAAGAG   780
134   V  T  K  A  F  V  S  Y  I  F  T  Y  A  K  I  K  T  L  K  E  153

781  GGAATTAAGGTCACTGGGAATAGACTAGGGATTCTGGTGACAACCTATGTGAATGCCATC   840
154   G  I  K  V  T  G  N  R  L  G  I  L  V  T  T  Y  V  N  A  I  173

841  AACAGTGGAGCAGTGCCTTGTCTGGATGATGCTGTGACAACTCTGGCCCAGCGTGAGAAC   900
174   N  S  G  A  V  P  C  L  D  D  A  V  T  T  L  A  Q  R  E  N  193

901  TCAGTAGCTGTGCAGAAAGCAGCCGACCACTATAGTGAGCAGATGGCCCAGCGACTGAGG   960
194   S  V  A  V  Q  K  A  A  D  H  Y  S  E  Q  M  A  Q  R  L  R  213

961  CTTCCTACAGAAACGCTCCAGGAGCTGCTGGATGTGCATGCAGCCTGCGAGAAGGAAGCC  1020
214   L  P  T  E  T  L  Q  E  L  L  D  V  H  A  A  C  E  K  E  A  233
```

FIG. 8B

```
1021 ATGGCTGTCTTCATGGAGCATTCCTTCAAGGACGAAAATCAGCAATTCCTGAAGAAGCTG 1080
 234  M  A  V  F  M  E  H  S  F  K  D  E  N  Q  Q  F  L  K  K  L  253

1081 GTGGAATTAATAGGAGAGAACAAAGAGCTTTTCCTGTCGAAGAATGAAGAGGCATCAAAT 1140
 254  V  E  L  I  G  E  N  K  E  L  F  L  S  K  N  E  E  A  S  N  273

1141 AAATACTGTCAAGAAGAACTGGATCGACTTTCAAAGGATTTTATGGAAAATATTTCAACA 1200
 274  K  Y  C  Q  E  E  L  D  R  L  S  K  D  F  M  E  N  I  S  T  293

1201 TTTTTTGTTCCTTGTGGACACAAGCTTTACATGGACAAGAGGGAGAAGATTGAACATGAC 1260
 294  F  F  V  P  C  G  H  K  L  Y  M  D  K  R  E  K  I  E  H  D  313

1261 TACTGGCAGGTTCCCAGGAAAGGGGTGAAGGCAAGTGAAGTCTTCCAGAGCTTTCTGCAG 1320
 314  Y  W  Q  V  P  R  K  G  V  K  A  S  E  V  F  Q  S  F  L  Q  333

1321 TCACAGGCCTTCATCGAGAGTTCCATCTTGCAGGCAGATACAGCGCTCACTGCTGGGGAG 1380
 334  S  Q  A  F  I  E  S  S  I  L  Q  A  D  T  A  L  T  A  G  E  353

1381 AAGGCCATTGCAGAGGAGCGTGCCCAGAAGGTGGCGGCAGAGAAGGAGCAAGAGCTGCTA 1440
 354  K  A  I  A  E  E  R  A  Q  K  V  A  A  E  K  E  Q  E  L  L  373

1441 AGACAGAAGCAGAAGGAGCAGCAGGAGTATATGGAGGCTCAAGAGAAAAGTCACAAGGAA 1500
 374  R  Q  K  Q  K  E  Q  Q  E  Y  M  E  A  Q  E  K  S  H  K  E  393

1501 AACCTAGAGCAACTGAGAAGGAAGCTGGAGCAGGAGAGAGAGCAGGACATCAAAGACCAT 1560
 394  N  L  E  Q  L  R  R  K  L  E  Q  E  R  E  Q  D  I  K  D  H  413

1561 GATATGATGCTGAAGAAGCTAATGAAGGATCAAAAGGCTTTCCTTGAGGAAGGATTTAAG 1620
 414  D  M  M  L  K  K  L  M  K  D  Q  K  A  F  L  E  E  G  F  K  433

1621 AAGAAAGCTGAAGAAATGAACAAAGAGATACAGCAACTGAGAGATGTCATCAAGGATAAG 1680
 434  K  K  A  E  E  M  N  K  E  I  Q  Q  L  R  D  V  I  K  D  K  453

1681 AAAAGAAACACTGATCGAATTAAGGAGGCTCTCTTAAATGGATTTTCTACAGTTCTTTTT 1740
 454  K  R  N  T  D  R  I  K  E  A  L  L  N  G  F  S  T  V  L  F  473

1741 CATTACCTTGTCCGTTATCTAAAGCATTTATGATTGAGTCCTTCACATTTGTGGAAATGA 1800
 474  H  Y  L  V  R  Y  L  K  H  L                                 483

1801 TAGACTGTGAAATACACTTTGTTTCATACATGCCTGCAAAGACAATGTTAGCCTTTAGAG 1860

1861 GACACATTTTTGAAATGAGTCCTATGGAAGCTATGCAAGTAGTAATTACATGTGATTACT 1920

1921 GTTGGCCAATTTGACTGCATAGAGAATCAGCAAGGAGACAAGGTTTTCTGTACTCCTATG 1980
```

FIG. 8C

```
1981  AGGACCATGTAGCCCAGGTTAGCTTGTGGGGGACTGTCTCAGGTTAATATTGTAGGAAAC  2040

2041  ACATCCTACGGGTGGGCAGCACTGTTCCTGTGGACTGAAGAAACAGAGAAAGATGAAAAC  2100

2101  AAATGGCCCTACCACTTGTGGCTTCCTGACTGTGGATGCTATACAACAAGCCAGGCTCAA  2160

2161  CTTCTCTCAGAATGCATTCTCCAGCCTTGACACAATGTATCATCATGATTCATAGACCCC  2220

2221  AACAAACCCTTTCTTAAGTTGGTTTTGTGAGGGTATTTCATCTCAGCAAGAGGAAAAGTC  2280

2281  ATTGATATCATAATCGTGATAATCCTGGAAACTACTTAAACATCACTTGTTAGATTGGCA  2340

2341  ATGAAATTTAATATGACTTGATCTTGGCGTACTATATAGTCAAGAAACAAATGTCAGTCA  2400

2401  AGCTATCTGTAAAATGATCTGAATTGTACTAAAATGTACCCAAAAGATAAAGTCAAAACA  2460

2461  CCATACAACTGTGTGATTATTATTAGAAATGCTACTATCCCATGCAAACATACAAGAACA  2520

2521  CAAATGAAATGCCCTCTGGAAGATTAGTAAAAAGCCTGGTCTACTGGCTTCATCTAGAGA  2580

2581  GATTAAGTTGGAGCCAAAAGTTGAAGGGATGTGTGCATTCCATGACGTTCTCAGTCTTAC  2640

2641  ACATTTCATGAAGAGTGCTGGGAAAGTGACAGTGATAGTGACAATAAGTTAAAACTCACC  2700

2701  ACTGCATGATGAAACATCTGCTTCTAGAAATGGTATAAGCCACTAGAAGTCACCCAAGAA  2760

2761  CAAGACTTGAGTACCAGGAAGCATAACATTTGCAGCTTAATGATGTTTTCCTTTAAGGCT  2820

2821  TTCCATTTTTAAAAGTAATTTAAATAGTGCATTTTTGTAAAACCACATATCAAAATGTT   2880

2881  ATTTCAACAGGCAATCAAAATAATTTATGCATGCTTTTACATCAAATTTATTTATTTGC   2940

2941  AAAGTAACAGGGAAACTGTATTAAGAGCCATATGATAATATAGAGTATAAGAGAATACAT  3000

3001  GGGGCACATGGGAGGTGGAGAGCTCAGAGATGGCTCTGGGTCAAGAATGCACAATGCTTA  3060

3061  TCCAGGGTAGCTCAGTTCCTGGGGCAGGTAACAACTACCTGTAAATCTAACTCCAAGGGA  3120

3121  CCTGACTTCCTTTTCTCAAACCCAAGGGTCACTGTTACTTCCATCACATATCCTCAGCTT  3180
```

FIG. 8D

```
3181  ACACATATACATACTTACAAGTAAGATTTAAAGGAATATACTGTTAACATTGATAATGGA  3240

3241  CCATATGAGTAAAGACACAAGGACACTTATTAGTGCATTAATGAATATGATTTATTTAAG  3300

3301  GTGTACCCACCCCAGCTCCTCTAAGACATCCTCAAATTACCCTCGCACCTTCATGTCTTC  3360

3361  TCTTCCCCCACCTCTTCCTCTTTCCTCATACCCTGAATAAATTAATGCTGCCCTCATGTC  3420

3421  CCTGGGCATTAGACACCATCTACCAGACCATGGACAATTGATCATGACCCAAACCCTCAT  3480

3481  AGAAAACACACTCCCTCTCCCAGTCACCAGATATCAACTGCTAGTAGTTCCTCAGCTAGG  3540

3541  GGTGGGGTCTCATGAGCTCACTGCCTCTCCACACTGGATGTTGACTGGCTTCATAGTATG  3600

3601  TATCTTGTTTCAACAAATATCACTATTGTCGTAGCCCCATCATATCCAGAAAATATTATT  3660

3661  TTAGAACAGTATGGTCTTATTTTTATGCTTAAATTAATTATTTCAAAATTAAAATGTAGA  3720

3721  CATTCTTAAGATTTCTGGAATCTTGGAGAAGCCTACTTCGTCTCTATTAATGCCTGTGAA  3780

3781  ATGTCAAGTTCAAAAGAATGAACTGTGTAAAGGAGAGAGAGAGATCTTGGTGCTGTTTTA  3840

3841  TTGGGAGCCATTTTGTTTGCTTCAGTGAAAGCTGACCTGCCAGGCACAATCAAGTCAGGT  3900

3901  TAGGGTCTGCTGGCAGATTTCCTGGCCTACTGACTCATGGAACTACAAGAGGAAATACAC  3960

3961  TTGAGGCTCAAGGCAAGGGGGTGAAAGTTCAATTCATCTTGGTGGTTGGAACAGGAAATC  4020

4021  CTCTGGATAAGAAAAGATGTCCTGTGTGTACATTAGCCATTATTTCTGCTACCTTGTGAC  4080

4081  ATTGTTTCTCATGATACTGAGAGATATAATAAAGCTAAGAAAAATAAACTTGAGGTTGAT  4140

4141  GTGGTATTCACCTGCAACCTTCCCAATTCTAAAAAAAAAAAAAAAAAAAAAAA  4193
```

FIG. 9

|  |  | Percent Similarity | Percent Identity |
|---|---|---|---|
| hGBP1 versus | FLJ10961 | 89.785 | 86.738 |
|  | AK096141 | 63.051 | 54.915 |
|  | 4843_1 | 62.881 | 52.712 |
|  | 4843_2 | 95.012 | 93.824 |
|  | LOC229900 | 64.041 | 54.795 |
|  | LOC229902 | 61.770 | 53.861 |
|  | BC031475 | 66.579 | 59.474 |
|  | BC007143 | 56.550 | 43.886 |
|  |  |  |  |
| mGbp1 versus | FLJ10961 | 76.302 | 66.607 |
|  | AK096141 | 62.479 | 53.650 |
|  | 4843_1 | 59.932 | 50.594 |
|  | 4843_2 | 77.435 | 69.596 |
|  | LOC229900 | 61.750 | 53.002 |
|  | LOC229902 | 58.077 | 47.885 |
|  | BC031475 | 65.885 | 60.417 |
|  | BC007143 | 55.361 | 43.326 |

FIG. 11A

```
                    1                                                    50
  4843_1r    (1)  ---------------MESGP MLA VCLVEN NEQLVNQ  AI IL K  S
  ak096141   (1)  ---------------MASEIHM GP VCLIEN  G  VVN  EAL  ILSAIT
  gbp-4      (1)  MGERTLHAAVPTPGYPE S IMMA ICLVENQ EQL VN   AL IL K  S
  gbp-5      (1)  ---------------MA LEIHMS PMCLIEN F EQLKVNQ AL ILSAIT T
  gbp-2      (1)  ---------------MA EI L GPM LIDNT  GQLVVNPEALKILSAIT
  flj10961   (1)  ---------------MA EIHMTGPMCLIENTNG LV  NPEALKILSAIT
  4843_2     (1)  ---------------M SEIHMTGPMCLIENTNG  LM  NPEALKILSAIT
  gbp-1      (1)  ---------------MASEIHMTGPMCLIENTNG  LM  NPEALKILSAIT
  Consensus  (1)                 MASEIHMTGPMCLIENTNGQLVVNPEALKILSAIT
                   51                                                  100
  4843_1r   (36)  QF-VVVVAIVGLYRTGKSYLMN  LAG N  GF  LGSTVQS  TKGIWMWCVPH
  ak096141  (36)  QPVVVVAIVGLYRTGKSYLMNKLAGKNKGF  LG  V  S  TKGIWMWCVPH
  gbp-4    (51)   QPVVVVAIVGLYRTGKSYLMNRLAGK   GF  LGSTVQS  TKGIWMWCVPH
  gbp-5    (36)   QPVVVVAIVGLYRTGKSYLMNKLAGKNKGFSVASTVQSHTKGIW IWCVPH
  gbp-2    (36)   QPVVVVAIVGL YRTGKSYLMNKLAGK   GFSLGSTV SHTKGIWMWCVPH
  flj10961 (36)   QPVVVVAIVGLYRTGKSYLMNKLAGKNKGFSLGSTV SHTKGIWMWCVPH
  4843_2   (36)   QPVVVVA TR----TGKSYL INKLA QK  KGFSLGSTVQSHTKGIWMWCMPH
  gbp-1    (36)   QPMVVAIVGLYRTGKSYLMNKLAGK  KGFSLGSTVQSHTKGIWMWCVPH
  Consensus(51)   QPVVVVAIVGLYRTGKSYLMNKLAGKNKGFSLGSTVQSHTKGIWMWCVPH
                  101                                                  150
  4843_1r   (85)  P KPNHTLVLLDTEGLGDVEKGD P KNDSWIFALAVLL  ST VYNSM  TIN
  ak096141  (86)  P KPNHTLILLDTEGLGDMEK  DPK  DSWIFALAVLLSS S VYNSMGTIN
  gbp-4    (101)  L KPNHTLVLLDTEGLGDVEK   PKNDSWIFALAVLLSS S VYNSV  TIN
  gbp-5    (86)   P W NHTLVLLDTEGLGDVEKADNKND IQ FALA LLLSSTFVYN TV    I
  gbp-2    (86)   PKKP HTLVLLDTEGLGD IEKGDN NDSWIFALA ILLSSTFVYNSMGTIN
  flj10961 (86)   PKKP HTLVLLDTEGLGDV KGDN NDSWIE LAVLLSS  VYNSMGTIN
  4843_2   (82)   PKKP HILVLLDTEGLGDVEKGDN NDSWIFALAVLL  S SMYNS IGTIN
  gbp-1    (86)   PKKP HILVLLDTEGLGDVEKGDN NDSWIFALAVLLSSTFVYNS IGTIN
  Consensus(101)  PKKPNHTLVLLDTEGLGDVEKGDNKNDSWIFALAVLLSSTFVYNSMGTIN
                  151                                                  200
  4843_1r  (135)  QALE QLHYVTELT EL IK AKSSP P G--VEDS  E FVSFPPDF LWT VRDF
  ak096141 (136)  QALE QLHYVTELT EL IRAKS  P  P E--VEDS SE FVSFPPDI WT VRDF
  gbp-4    (151)  QALE QLHYVTEL  EL IRAKS  P  P E--  EDSSE  SFFPDI WT VRDF
  gbp-5    (136)  QGAI DLLHNVTELT DLLK R  SPDL  --VED ADS  SFFPD  VW TLRDF
  gbp-2    (136)  QQAMDQLHYVTELTDR IK  SSP NN---V DSADFVSFFP A FW TLRDF
  flj10961 (136)  QQAMDQL YYVTELT  R PSKSSPDENEN--EDSADFVSFFPDF VW TLRDF
  4843_2   (132)  QQAMDQLHYVTELT RV PKSSPDENEN--EDSADF ESFFPD  G-----
  gbp-1    (136)  QQAMDQL YYVTELT R IKSKSSPDENENE VEDSADFVSFFPDF VW TLRDF
  Consensus(151)  QQAMDQLHYVTELTERIRAKSSPD NE   VEDSADFVSFFPDFVWTLRDF
                  201                                                  250
  4843_1r  (183)  TLEL  L G  PIT EDEYLEN ALKL IQ NNPRV GTS NF PPEC IRR  PKRKC
  ak096141 (184)  TLEL  LDG  PIT EDEYLEN ALKL ISGKNP  IQNS NKPREW IR FFPK  KC
  gbp-4    (199)  TLEL  LDGNPIT EDEYLEN ALKL IPGKNPKIQNS NMPREC IR  FRKRKC
  gbp-5    (184)  C GLE IDGQLV PDEYLEN SL RPKQ GSDQRV CNF NLPRLC   KFFPKKKC
  gbp-2    (184)  TLEL VDG  PIT ADDYLEL SLK RK TDKKS  SFNDPRLC IRKFFPKRKC
  flj10961 (184)  S DLE  DGQ LIPDEYLEY SL L TQ N-----------------------
  4843_2   (175)  --------------------------------------------------
  gbp-1    (186)  S DLE  DGQ LIPDEYL TYSLKL KK GTSQKD  TF NLPRLC IRKFFPK KKC
  Consensus(201)  TLELELDGQPIT DEYLENSLKL   G   KIQ N  PR CIRKFFPKRKC
```

Figure 11B

```
              251                                                    300
4843_1r  (233) FVFDRETNDKLLANIEKVSE  LDPFQEC NIFCSYIETHARLKTLRE
ak096141 (234) FVFDRPINDKKLLLVEEVRED LD VEQMESE FCSYIETHAKTKTLRE
gbp-4    (249) FVFDRPTNDRYLNLMDEVPEE LERLELMCSD FCSYIETHAKTKTLRE
gbp-5    (234) IE LPA-HCKKLAQLETLPDDEIEDEVQDVTE CSYIFSHSMIKLLPG
gbp-2    (234) VFLWEA-PEKYLAPELQLKEDEINPDGIEQVAEFCSYIFSHSVKTLSG
flj10961 (211) ---------R-KLAQLEKLQDEELDPEEVQQVADFCSYIFSSKTKTLSG
4843_2   (175) --------------------------------------------------
gbp-1    (236) FVFDREV-HRRKLEQLEKLQDEELDREEVQQVADFCSYIFSSKTKTLSG
Consensus(251) FVFDRP  KK LAQLE L EEELDPEFV QV DFCSYIFSHSKTKTL G
              301                                                    350
4843_1r  (283) ELTVIGNREGTLEVTYVEAT GCAVPGLENAVILEACRENSAAVQRASDY
ak096141 (284) ELTVIGNEIGMLVETLLENGEATPCLENEMAKEACCENSAAVQREANE
gbp-4    (299) EIVTGKPLGTLVVSYEAT SCAVPCLENAVTALACLENEAAVQREADE
gbp-5    (283) GIMVNGSRLELVLTYVNAISSGDLPCIENAVLALACRENSAAVQKAIAH
gbp-2    (283) ELAVIGPRLESLVLTYVNAISGDLPCMENAVLALAQIENSAAVQKAIAH
flj10961 (251) SLKVNCPCLESLVLTIIINATSRGDLPCMENAVLALAQIENSAAVQKAIAH
4843_2   (175) -------LESLVLTYVNAISSGDLPCMENAVLALAQIENSAAVQKAIAH
gbp-1    (285) GLQVNGPRLESLVLTYVNAISSGDLPMENAVLALAQIENSAAVQKAIAH
Consensus(301) GI VNG RLESLVLTYVNAISSGDLPCMENAVLALAQIENSAAVQKAIAH
              351                                                    400
4843_1r  (333) KCQMAGRVELPTDLQELLDVHAAEREDAIAIELHEPKDEEQEFQKKE
ak096141 (334) KCQMAGEVETPTDLLQELLDVEAVEREAIAVELYSEKDKEQEFQKKT
gbp-4    (349) KCQMAGELLLPTDLQELLDVHAAEREAIAVELHSEKDEIEDKKL
gbp-5    (333) IDQMGQKVQLMELLQELLDLHRTSEREAIEVELKNSFKDVEQSEQKE
gbp-2    (333) YEQQMGQKVQLPTETLQELLDLHRDSEREAIEVENKNSFKDVEQMFQRKT
flj10961 (301) IDQQMGQKVQLPAETLQELLDLHRVGEREATEVYKNSFKDVEILFQRKE
4843_2   (217) YEQQMGQKVQLPTTLTQELLDLIRDSESLATEVFIRSSFKDVEILFQKEI
gbp-1    (335) YEQQMGQKVQLPTESLQELLDLHRDSEREAIEVFIRSSFKDVDLFQKEL
Consensus(351) YEQQMGQKVQLPTETLQELLDLHR SEREAIEVFMK SFKDVDQLFQKKL
              401                                                    450
4843_1r  (383) METTMEKKEDELLQNEESSVEYQEAKENELSKGIMLEIGECSFEVPGGHK
ak096141 (384) EDTMEKKEDIVLQNEDASAEYQEAEDERLSELITESIRETFFVRGGHE
gbp-4    (399) EDTIEKKKEDLVLQNEDASAKYQEAELKRLSEHLTELILREIFSVRGGHE
gbp-5    (383) ELDAKENEGKRLLASSEVSALLKDIIGPLEDAVLQGIYSKRGGH
gbp-2    (383) GAQLEARRDDFCKQNSKASSLCMALLQDILGPLEEVKQLTFSKPGGYR
flj10961 (351) AAQIDKKRDDFCKQNQEASSDRCSALLQVTLSPLEEVKAGIYSKPGGYC
4843_2   (267) AFQIDKKRDDFCKQLQEASSDRCSALLQVTLSPLEEVKAGIYSKPGGYR
gbp-1    (385) AEQLEKKRDDFCKQNQEASSDRCSGLLQVISELEE VKAGIYSKPGGYR
Consensus(401) AAQLEKKRDDFCKQN EASSDYCSALLQ IF PLEESVKAGIFSKPGGHR
              451                                                    500
4843_1r  (433) EYM KEFIEQEEWQVPRK--------------------------------
ak096141 (434) IYLEAKEEILQEYTLVPRK-------------------------------
gbp-4    (449) EYLEKEVEWEYKLVPRK---------------------------------
gbp-5    (433) LEIQKTEEEAKYYREPRK--------------------------------
gbp-2    (433) LTIQKLQELENKYYQVPRK-------------------------------
flj10961 (401) LEIQKEDLEKKYYEEPRK--------------------------------
4843_2   (317) LTIQKLQDLEKKYYEEERKGIQGISPPRTTGQRKEFPEERMAGRQTGTPA
gbp-1    (435) LVQKLQDLEKKYYEEPRK--------------------------------
Consensus(451) LFIQKLQDLE KYY VPRK
              501                                                    550
```

Figure 11C

```
   4843_1r  (452) -------------GV AK V RF  S MVI ES IL SD  L DR  VA
  ak096141  (453) -------------GV D VL SF  S VVI ES IL SD  L AG  A A
     gbp-4  (468) -------------GV  EV   FL S VV  ES IL S   L AG K A A
     gbp-5  (452) -------------G QA  VL   L SK SVS  A L T Q ALT   KK E
     gbp-2  (452) -------------G A  M   L SK D   ALL T Q SLS KE AI
   flj10961 (420) -------------G QA  IL T L KS ESVT DAIL T    LTEKE E
    4843_2  (367) YSRLLLLTLCSL P  EILQTYLKSKESMTDAIL TDQ LTEKE E EV
     gbp-1  (454) -------------   E IL T L KS  SMTDAI  T Q LTEKE E EV
 Consensus  (501)              GIQAEEVLQTYLKSKESVTDAILQTDQALTEKEKAIEV
                  551                                                600
   4843_1r  (490) D  K  A  KEQ L K  KL  QQ Q M A VK R  E  IA  KE L MERE
  ak096141  (491) K   K A EKEQ L R  K K QQ MM A  ER  F E IA  K  KM E REN
     gbp-4  (506) E  MK A KEQ LLR KCK QQ MM A ERSF   IA  K KM  RE EN
     gbp-5  (490) A   A AE   A R AAI R   ER  LH E VR MEIAK      ----
     gbp-2  (490) E I A S   AKK L E I KN  MM QK  K S QE V  L TEKMER D AQ
   flj10961 (458) C  A S    AK VE M I YQ D  EK  KS YQE V  L TEK  KERAQ
    4843_2  (417) ERV A S   A AKML Q M RK   MME QKERSYQE L  QLTEKMESD --
     gbp-1  (492) ERV A SA A A KML Q M RK  QMME QKERSYQE HL  QLTEKME  D VQ
 Consensus  (551) ERVKAEAAEAEAKML EMQKKNQQMME KERSYQEHIKQLTEKMERER Q
                  601                                                650
   4843_1r  (540)  R   IMM EH  Q V  DW    G   KKYEEMNA     Q   RMIDTTKNDDT
  ak096141  (541) YMR L   M  SH M VL EL    G  EIFES NE  NR   EQIEAAENEEP
     gbp-4  (556)  R   RL KHH L  V  EM  K  E  KKSEQ NK  NQ  EKIESTKNEQ-
     gbp-5  (536) W A   KMQEQ  M   AAQ   TTE  AQ  RS LS LQHA  RTVNNDDPCVL
     gbp-2  (540)  MA   KT  AL    ERL  K G   NE KRL QKD WDI MRSKSLEPICN
   flj10961 (508)    Q  T  TS L Q  ARV  K RC GES TQL QN  QK  KTLKKKTKRYM
    4843_2  (465) ---------------------------------------------------
     gbp-1  (542)   KE  RT  AL KLQ Q  QL  KEG F KE RIM N  QD  TKMRRRKACTI
 Consensus  (601) LLREQEKML   KLQEQE LLKEGFQ  S  LN EIQ LQ  I
                  651                                                700
   4843_1r  (590) PWIARTLDNLADELTAILSAPAKLIGHGVKGVSSLFKKHKLPFKGGRADP
  ak096141  (591) SVFSQILDVAGSIFIAALPGAAKLVDLGMKILSSLCNRLRNPGKKIIS--
     gbp-4  (605) LRLLKILDMASNIMIVTLPGASKLLGVGTKYLGSRI--------------
     gbp-5  (586) L-------------------------------------------------
     gbp-2  (590) IL------------------------------------------------
   flj10961 (558) SHKLKI--------------------------------------------
    4843_2  (465) ---------------------------------------------------
     gbp-1  (592) S-------------------------------------------------
 Consensus  (651)
                  701                           735
   4843_1r  (640) AFLYKVVDLEGPRFEQKLISEEDLNMHTGHHHHHH
  ak096141  (639) -----------------------------------
     gbp-4  (641) -----------------------------------
     gbp-5  (587) -----------------------------------
     gbp-2  (592) -----------------------------------
   flj10961 (564) -----------------------------------
    4843_2  (465) -----------------------------------
     gbp-1  (593) -----------------------------------
 Consensus  (701)
```

FIG. 28
A.
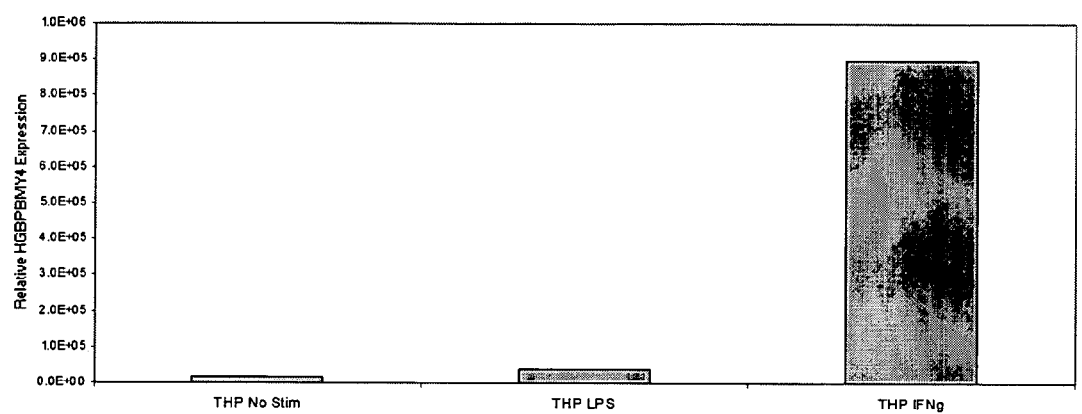
B.
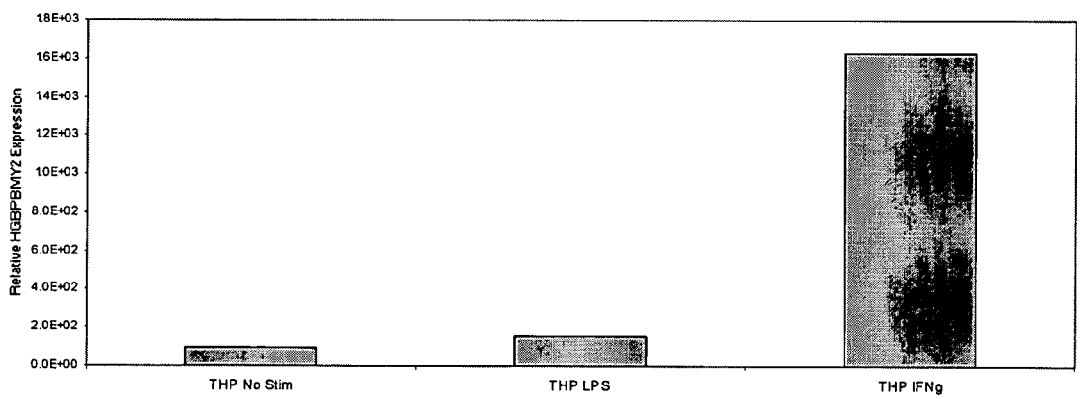
C.
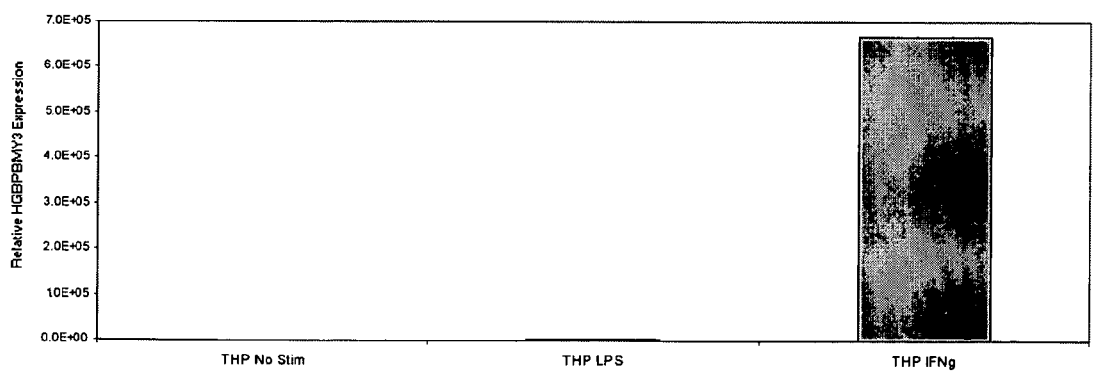

FIG. 29
A.
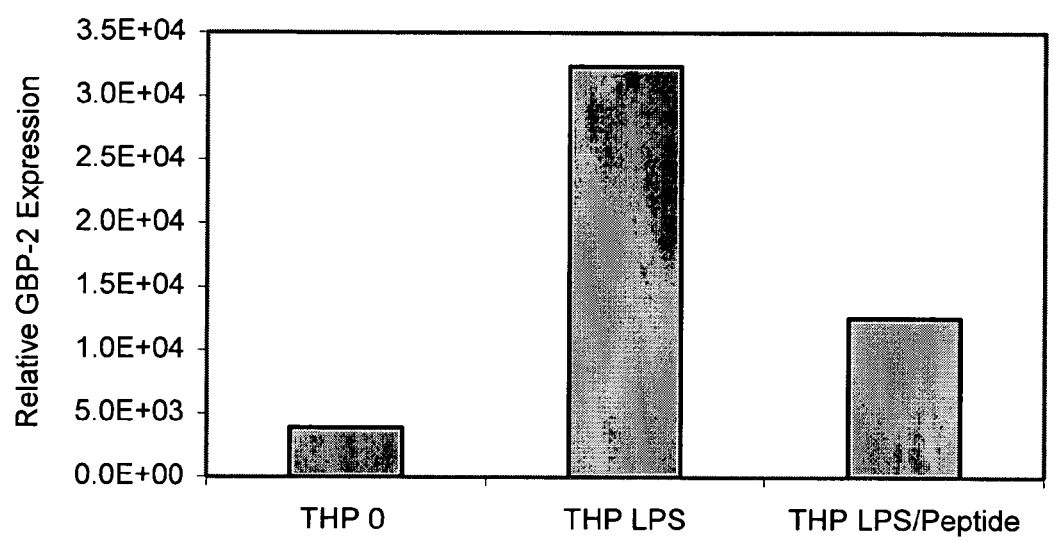
B.
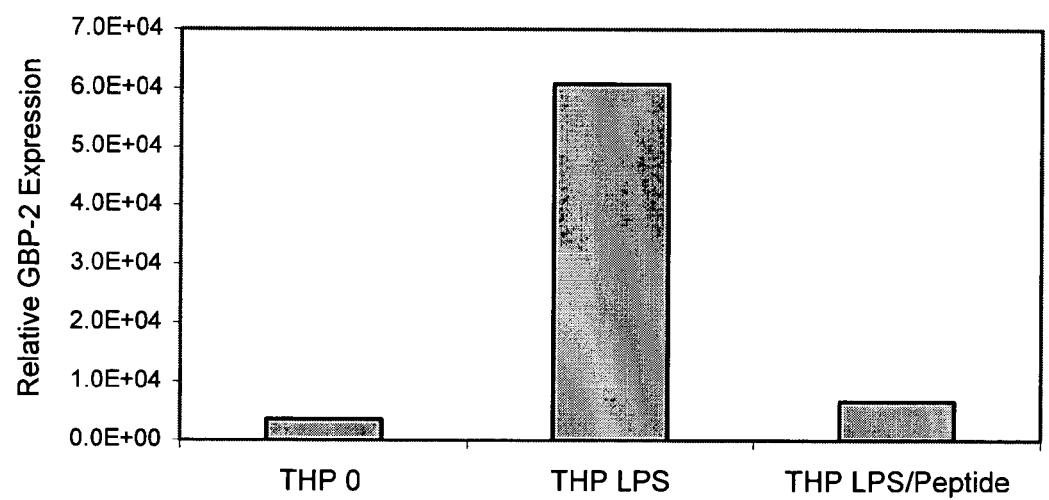

FIG. 30
A.
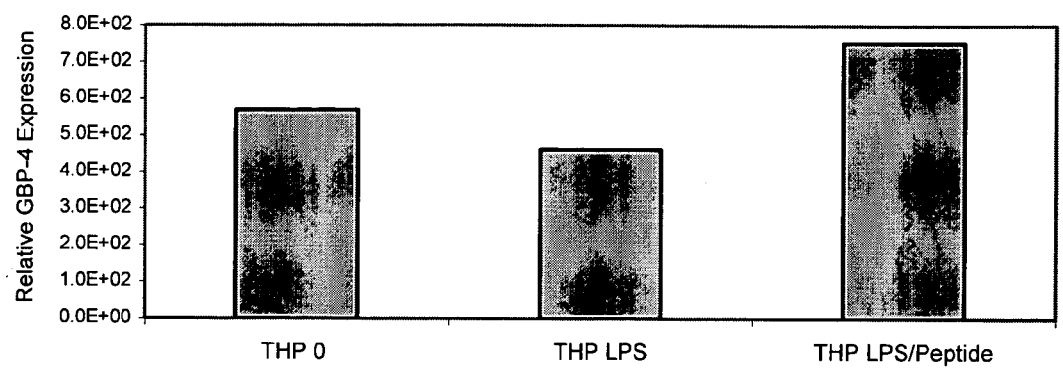
B.
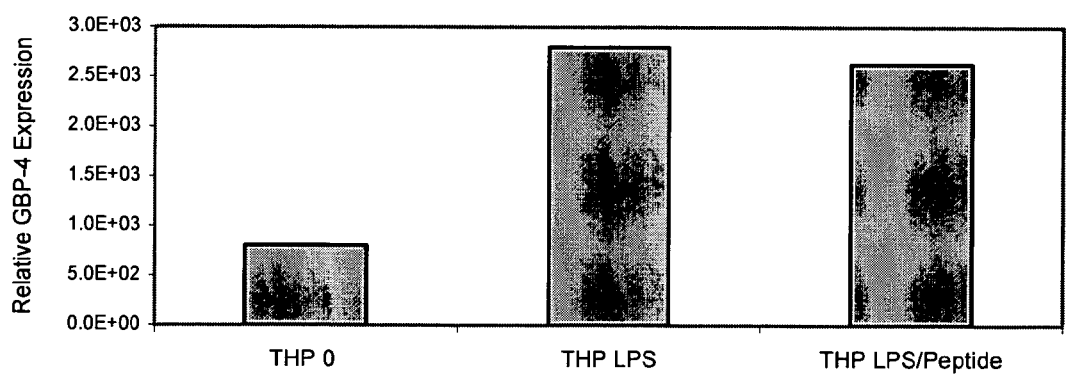

FIG. 31
A.
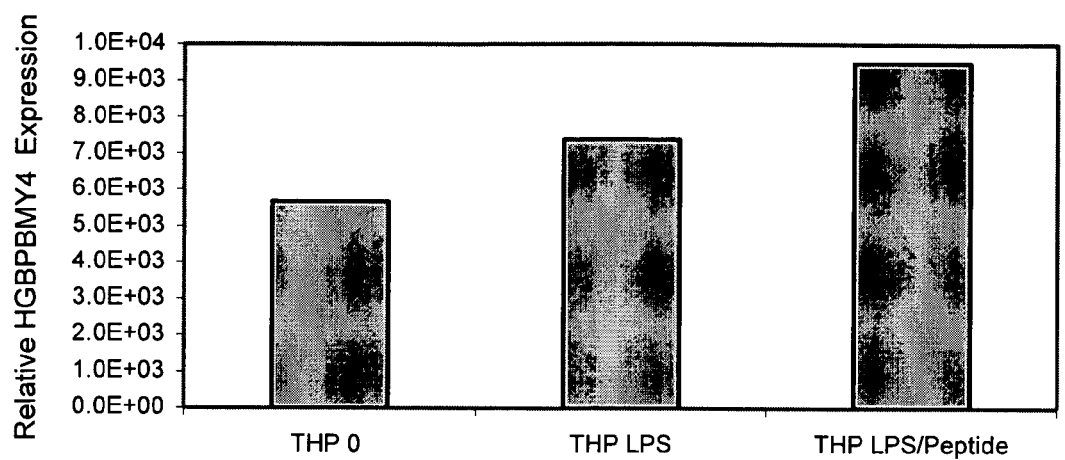
B.
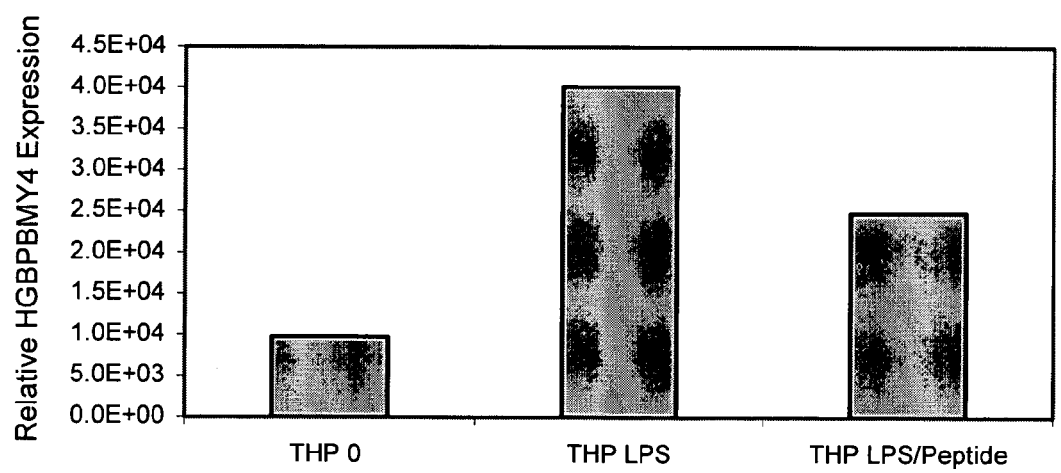

FIG. 32
A.
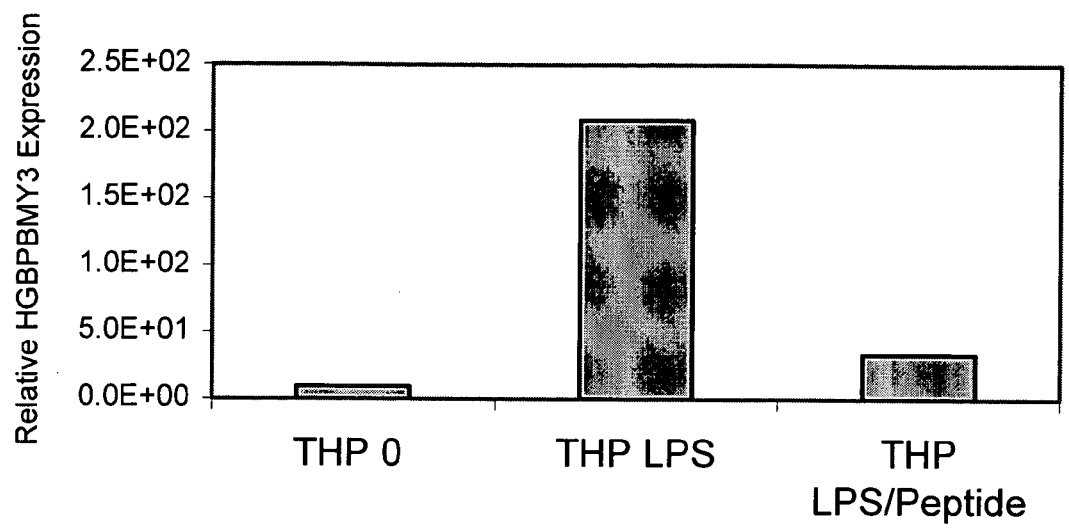
B.
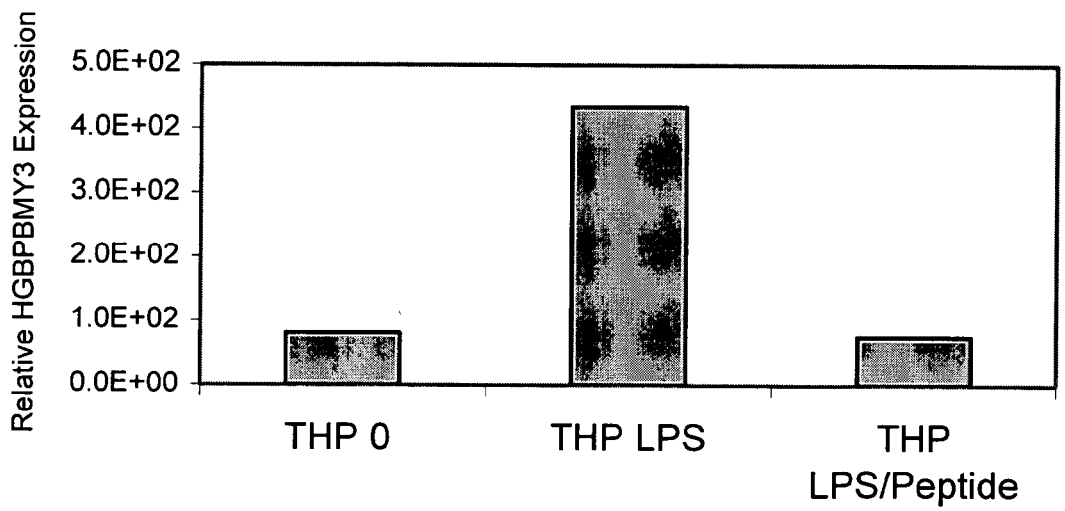

FIG. 50A
GPB-1
| CT | 1-3 | 582 |
GBP-2
| CT | 1-3 | 582 |

POLYNUCLEOTIDES ENCODING NOVEL GUANYLATE BINDING PROTEINS (GBP'S)

This application claims benefit to U.S. provisional patent application Ser. No. 60/475,234 filed on Jun. 2, 2003. The entire teachings of the referenced application are incorporated herein by reference.

FIELD OF THE INVENTION

The present invention provides novel polynucleotides encoding guanylate binding proteins, fragments and homologues thereof. Also provided are vectors, host cells, antibodies, and recombinant and synthetic methods for producing said polypeptides. The present invention further relates to diagnostic and therapeutic methods for applying these novel guanylate binding proteins to the diagnosis, treatment, and/or prevention of various diseases and/or disorders related to these polypeptides. The present invention further relates to screening methods for identifying agonists and antagonists of the polynucleotides and polypeptides of the present invention.

Amino Acid Abbreviations

| Single-Letter Code | Three-Letter Code | Name |
|---|---|---|
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

Functionally Equivalent Codons

| Amino Acid | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Methionine | Met | M | AUG |
| Asparagine | Asn | N | AAC AAU |
| Proline | Pro | P | CCA CCC CCG CCU |
| Glutamine | Gln | Q | CAA CAG |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |
| Leucine | Leu | L | UUA UUG CUA CUC CUG CUU |
| Arginine | Arg | R | AGA AGG CGA CGC CGG CGU |
| Serine | Ser | S | ACG AGU UCA UCC UCG UCU |

BACKGROUND OF THE INVENTION

Guanylate binding proteins (GBP) were first identified as interferon-inducible proteins in fibroblasts (Cheng et al., (1983) *J. Biol. Chem.* 258:7746–7750). They were identified by their ability to bind to guanylate-containing agaroses including GMP-agarose, GDP-agarose, and GTP-agarose. They failed to bind to ATP-agarose and all other nucleotide agaroses tested (Cheng et al., (1991) *Mol. Cell. Biol.* 11:4717–4725). Purified GBP-1 protein was shown to hydrolyze GTP, but not ATP, UTP, or CTP with a $K_m$ for substrate of 470 µM. The hydrolysis reaction occurred with a high turnover rate and yielded primarily GMP rather than GDP (Schwemmle et al., (1994) *J. Biol. Chem.* 269:11299–11305). The hydrolysis reaction was thought to occur in two successive steps since pyrophosphate was not detected as a reaction product. GBP-1 was also shown to possess a functional $CX_1X_2X_3$ (SEQ ID NO:1) isoprenylation signal at the C terminus of the molecule (the signal comprises a cysteine residue (C) followed by two typically, but not necessarily, aliphatic amino acids ($X_1$ and $X_2$) and another amino acid ($X_3$)).

The crystal structure of human GBP-1 in nucleotide free (Prakash et al., (2000) *Nature* 403:567–571) and bound states (Prakash et al., (2000) *EMBO J.* 17:4555–4564) was solved to 1.8 Å resolution. The structure resembled that of other large GTP-binding proteins including Mx and dynamin. The structure consists of a compact amino-terminal globular α,β domain and an elongated C-terminal α-helical domain separated by a short intermediate region. The globular domain contains the conserved regions characteristic of GTP-binding proteins with some additional insertions. Significant differences in the glycosidic bond angle and guanine base interaction domains were observed in GBP-1 relative to the canonical GTP binding protein Ras. Unlike Ras, the phosphate binding region of GBP1 is closed off from solvent, and therefore unavailable for interactions with external regulators such as GTPase activating proteins or guanine nucleotide exchange proteins. Similar to dynamins, nucleotide binding to GBP-1 induced oligomerization.

Expression of GBP-1 is regulated by interferon in fibroblasts and a number of other cell types. These include mouse 70Z/3 pre-B cells (Patrone et al., (2001) *Mol. Immunol.* 38:597–606); murine macrophage lines and peritoneal macrophages (Wynn et al., (1991) *J. Immunol.* 147:4384–4392); rat bone marrow-derived macrophages and microglia (Vestal et al., (1996) *Bioch. Biophys. Res. Commun.* 224:528–534); cultured mammary epithelial tumor cell lines (Sun et al., (1999) *Int. J. Cancer* 80:624–629); normal and transformed keratinocytes (Saunders et al., (1999) *J. Invest. Dermatol.* 112:977–983); and human endothelial cells (Lubeseder-Martellato et al., (2002) *Am. J. Pathol.* 161:1749–1759). Lipopolysaccharide (LPS) was also shown to induce GBP-1 in rat bone marrow derived macrophages and microglia (Vestal et al., (1996) *Bioch. Biophys. Res. Commun.* 224: 528–534), and in cultured mammary epithelial tumor lines (Sun et al., (1999) *Int. J. Cancer* 80:624–629). TNFα stimulation of human endothelial cells also induced GBP-1 expression (Lubeseder-Martellato et al., (2002) *Am. J. Pathol.* 161:1749–1759). In this study, GBP-1 expression was highly associated with vascular endothelial cells and was induced in vessels of skin diseases that have a high inflammatory component.

Since the original characterization of GBP-1, a number of related proteins have been identified in both mouse and human. In human, known GBPs include GBP-1, GBP-2 (Cheng et al., (1991) *Mol. Cell. Biol.* 11:4717–4725), GBP-4, and GBP-5. GBP-2 was shown to have similar nucleotide binding properties and GTPase activities as GBP-1 (Neun et al., (1996) *FEBS Lett.* 390:69–72). Some differences were noted in the product specificity of the GTPase reaction.

In mouse, the known GBPs include mGBP-1, mGBP-2 (Boehm et al., (1998) *J. Immunol.* 161:6715–6723), mGBP-3 (Han et al., (1998) *Bioch. Biophys. Acta* 1384: 373–386), mGBP-4/mag-2 (Wynn et al., (1991) *J. Immunol.* 12:4384–4392) and mGBP-5 (Nguyen et al., (2002) *J. Interferon Cytokine Res.* 22:899–909). Recombinant mGBP-3 protein was shown to possess similar nucleotide binding properties and GTPase activity as compared to other GBPs (Han et al., (1998) *Bioch. Biophys. Acta* 1384:373–386). The tissue expression and induction patterns of all the mouse GBPs were similar (Nguyen et al., (2002) *J. Interferon Cytokine Res.* 22:899–909). All five were induced in multiple organs in response to endotoxemia. In RAW264 and Swiss 3T3 cells, all five GBPs were induced in response to LPS, interleukin-1β (IL-1β), and TNFα.

Although GBP-1 represents one of the most abundant proteins induced in response to interferon treatment, its function, or the function of other family members is not clear. Stable transfection of human GBP-1 into HeLa cells increased the resistance of the cells to the cytopathic effects of both vesicular stomatitis virus (VSV) and encephalomyocarditis virus (EMCV, Anderson et al., (1999) *Virology* 256:8–14). Conversely, cells transfected with GBP-1-specific antisense were more sensitive to viral infection, suggesting that GBP-1 is required for an antiviral response to VSV and EMCV viruses.

Expression of GBP-1 was inversely correlated with the proliferation of human microvascular and macrovascular endothelial cells (Guenzi et al., (2001) *EMBO J.* 20:5568–5577). GBP-1 expression is induced by pro-inflammatory, anti-proliferative cytokines including IL-1β, TNFα, and TFN-γ. Overexpression of full length GBP-1 in HUVECs significantly slowed the proliferative rate of these cells without increasing cell death. Conversely, expression of antisense to GBP-1 in HUVECs resulted in increased proliferation of the cells. Overexpression of GBP-1 also inhibited the proliferative response of the cells to VEGF and bFGF. Activation of the MAP kinase pathway in response to VEGF or bFGF was not affected by GBP-1 overexpression. Overexpression did not inhibit IL-1β-induced adhesion of the cells to monocytes. The anti-proliferative effect of GBP-1 was mapped to the C-terminal α-helical domain. Mutants lacking GTPase activity or the prenylation motif were still able to inhibit proliferation. Expression of the α-helical domain alone inhibited proliferation whereas expression of the globular nucleotide binding domain alone was inactive.

In contrast to the anti-proliferative effect of GBP1 in HUVECs, overexpression of mGBP-2 in NIH3T3 stimulated proliferation (Gorbacheva et al., (2002) *J. Biol. Chem.* 277:6080–6087). Cells constitutively expressing mGBP-2 formed foci when grown to post-confluence. They failed to grow in soft agar suggesting that they retained anchorage-dependent growth. These cells also grew as tumors in nude mice. Mutation of the nucleotide binding domain of mGBP-2 eliminated the effect on cell proliferation. This study suggests that mGBP-2 is able to alter the growth characteristics of fibroblasts.

SUMMARY OF THE INVENTION

The present invention provides guanylate binding proteins (e.g. HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and MGBPBMY4 (BC007143)) encoded by polynucleotides that comprise, or alternatively consist of, the nucleotide sequences shown in FIGS. 1–8 (SEQ ID NO:2, 4, 6, 8, 10, 12, 14 and 16, respectively) and fragments thereof, that comprise, or alternatively consist of the amino acid sequences shown in FIGS. 1–8 (SEQ ID NO:3, 5, 7, 9, 11, 13, 15 and 17, respectively) and fragments thereof, and/or that are deposited as ATCC Deposit Number PTA-6007 on May 20, 2004.

The present invention also relates to recombinant vectors comprising one or more isolated nucleic acid molecules of the present invention, and to host cells containing the recombinant vectors, as well as to methods of making such vectors and host cells. In addition, the present invention relates to the use of such vectors in the production of guanylate binding proteins (e.g., HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and MGBPBMY4 (BC007143)) and/or peptides using recombinant techniques. Synthetic methods for producing the polypeptides and polynucleotides of the present invention are also provided.

The present invention also relates to diagnostic methods for detecting diseases, disorders, and/or conditions related to guanylate binding proteins (e.g., HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and MGBPBMY4 (BC007143)) and polynucleotides encoding guanylate binding proteins, and therapeutic methods for treating such diseases, disorders, and/or conditions. The present invention further relates to screening methods for identifying binding partners of the polypeptides.

In another aspect, the present invention provides an isolated guanlyate binding protein (e.g., HGBPBMY1

(AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and MGBPBMY4 (BC007143)) comprising an amino acid sequence described herein (e.g., SEQ ID NOs:3, 5, 7, 9, 11, 13, 15 and/or 17) encoded by a polynucleotide described herein (e.g., SEQ ID NOs:2, 4, 6, 8, 10, 12 14, and/or 16).

The present invention further relates to a nucleic acid molecule encoding a polypeptide fragment of SEQ ID NOs:3, 5, 7, 9, 11, 13, 15 and/or 17, or a polypeptide fragment encoded by a cDNA sequence included in a deposited clone that is hybridizable to SEQ ID NOs:2, 4, 6, 8, 10, 12, and/or 16 or a fragment thereof.

The present invention further relates to a nucleic acid molecule encoding a polypeptide domain of SEQ ID NOs:3, 5, 7, 9, 11, 13, 15 and/or 17 or a polypeptide domain encoded by a cDNA sequence included in a deposited clone that is hybridizable to SEQ ID NOs:2, 4, 6, 8, 10, 12, and/or 16.

The present invention further relates to a nucleic acid molecule encoding a polypeptide epitope of SEQ ID NOs:3, 5, 7, 9, 11, 13, 15 and/or 17 or a polypeptide epitope encoded by a cDNA sequence included in a deposited clone that is hybridizable to SEQ ID NOs:2, 4, 6, 8, 10, 12, and/or 16.

The present invention further relates to a nucleic acid molecule encoding a polypeptide comprising SEQ ID NOs: 3, 5, 7, 9, 11, 13, 15 and/or 17 or a cDNA sequence included in a deposited clone that is hybridizable SEQ ID NOs:2, 4, 6, 8, 10, 12, and/or 16.

The present invention further relates to a nucleic acid molecule that is a variant comprising SEQ ID NOs:2, 4, 6, 8, 10, 12, and/or 16.

The present invention further relates to a nucleic acid molecule that is an allelic variant comprising SEQ ID NOs:2, 4, 6, 8, 10, 12, and/or 16.

The present invention further relates to a nucleic acid molecule that encodes a species homologue comprising SEQ ID NOs:2, 4, 6, 8, 10, 12, and/or 16.

The present invention further relates to a nucleic acid molecule comprising a nucleic acid sequence that is complimentary (antisense) to a nucleic acid sequence comprising SEQ ID NOs:2, 4, 6, 8, 10, 12, and/or 16.

The present invention further relates to a nucleic acid molecule capable of hybridizing under stringent conditions to any one of the polynucleotides specified herein, wherein the polynucleotide does not hybridize under stringent conditions to a nucleic acid molecule having a nucleotide sequence of only A residues or of only T residues.

The present invention further relates to an isolated nucleic acid molecule comprising SEQ ID NOs:2, 4, 6, 8, 10, 12, and/or 16, wherein the polynucleotide comprises a nucleotide sequence encoding a guanylate binding protein.

The present invention further relates to an isolated nucleic acid molecule SEQ ID NOs:2, 4, 6, 8, 10, 12, and/or 16, wherein the nucleic acid molecule comprises one of a nucleotide sequence encoding a polypeptide SEQ ID NOs:3, 5, 7, 9, 11, 13, 15 and/or 17, and a polypeptide encoded by a cDNA sequence included in a deposited clone that is hybridizable to SEQ ID NOs:2, 4, 6, 8, 10, 12, and/or 16.

The present invention further relates to an isolated nucleic acid molecule comprising SEQ ID NOs:2, 4, 6, 8, 10, 12, and/or 16, wherein the nucleic acid molecule comprises one of the entire nucleotide SEQ ID NOs:2, 4, 6, 8, 10, 12, and/or 16, and a cDNA sequence included in a deposited clone that is hybridizable SEQ ID NOs:2, 4, 6, 8, 10, 12, and/or 16.

The present invention further relates to an isolated nucleic acid molecule comprising SEQ ID NOs:2, 4, 6, 8, 10, 12, and/or 16, wherein the nucleic acid molecule comprises one or more sequential nucleotide deletions from either the 5'-terminus or the 3'-terminus of the nucleic acid molecule.

The present invention further relates to an isolated polypeptide comprising a polypeptide fragment of SEQ ID NOs:3, 5, 7, 9, 11, 13, 15 and/or 17; the present invention also relates to a nucleotide sequence encoding a polypeptide fragment of SEQ ID NOs:3, 5, 7, 9, 11, 13, 15 and/or 17 included in a deposited clone.

The present invention further relates to a polypeptide domain of SEQ ID NOs:3, 5, 7, 9, 11, 13, 15 and/or 17, and to a nucleotide sequence encoding such a domain included in a deposited clone.

The present invention further relates to a polypeptide epitope of SEQ ID NOs:3, 5, 7, 9, 11, 13, 15 and/or 17, and to a nucleotide sequence encoding such an epitope included in a deposited clone.

The present invention further relates to a full length protein SEQ ID NOs:3, 5, 7, 9, 11, 13, 15 and/or 17, and to a nucleotide sequence encoding such a full length protein included in a deposited clone.

The present invention further relates to an isolated polypeptide comprising SEQ ID NOs:3, 5, 7, 9, 11, 13, 15 and/or 17, wherein the full length protein comprises sequential amino acid deletions from either the C-terminus or the N-terminus.

The present invention further relates to an isolated antibody that binds specifically to an isolated polypeptide of SEQ ID NOs:3, 5, 7, 9, 11, 13, 15 and/or 17.

The present invention further relates to a method for preventing, treating, or ameliorating a medical condition, comprising administering to a mammalian subject a therapeutically effective amount of a polypeptide SEQ ID NOs:3, 5, 7, 9, 11, 13, 15 and/or 17, or a fragment thereof, or a polynucleotide of SEQ ID NOs:2, 4, 6, 8, 10, 12, and/or 16, or a fragment thereof.

The present invention further relates to a method of diagnosing a pathological condition or a susceptibility to a pathological condition in a subject, the method comprising the steps of: (a) determining the presence or absence of a mutation in a polynucleotide comprising SEQ ID NOs:2, 4, 6, 8, 10, 12, and/or 16; and (b) diagnosing a pathological condition or a susceptibility to a pathological condition based on the presence or absence of the mutation.

The present invention further relates to a method of diagnosing a pathological condition or a susceptibility to a pathological condition in a subject, the method comprising the steps of: (a) determining the presence and/or amount of expression of a polypeptide comprising SEQ ID NOs:3, 5, 7, 9, 11, 13, 15 and/or 17 in a biological sample; and (b) diagnosing a pathological condition or a susceptibility to a pathological condition based on the presence and/or amount of expression of the polypeptide.

The present invention further relates to a method for identifying a binding partner to a polypeptide comprising SEQ ID NOs:3, 5, 7, 9, 11, 13, 15 and/or 17, the method comprising the steps of: (a) contacting a polypeptide SEQ ID NOs:3, 5, 7, 9, 11, 13, 15 and/or 17 with a binding partner; and (b) determining whether the binding partner effects an activity of the polypeptide.

The present invention further relates to a gene corresponding to a cDNA sequence comprising SEQ ID NOs:2, 4, 6, 8, 10, 12, and/or 16.

The present invention further relates to a method of identifying an activity in a biological assay, the method comprising the steps of (a) expressing a polypeptide of polypeptide SEQ ID NOs:3, 5, 7, 9, 11, 13, 15 and/or 17 in a cell, (b) isolating the supernatant; (c) detecting an activity in a biological assay; and (d) identifying the protein in the supernatant having the activity.

The present invention further relates to a process for making a polynucleotide sequence encoding a gene product having altered activity selected from the group consisting of polypeptide SEQ ID NOs:3, 5, 7, 9, 11, 13, 15 and/or 17, the method comprising the steps of: (a) shuffling a nucleotide sequence comprising SEQ ID NOs:2, 4, 6, 8, 10, 12, and/or 16; (b) expressing the resulting shuffled nucleotide sequences; and, (c) selecting for altered activity of a polypeptide selected from the group consisting of polypeptide SEQ ID NOs:3, 5, 7, 9, 11, 13, 15 and/or 17 as compared to the activity of of the gene product of an unmodified nucleotide sequence encoding a polypeptide selected from the group consisting SEQ ID NOs:3, 5, 7, 9, 11, 13, 15 and/or 17.

The present invention further relates to a shuffled polynucleotide sequence produced by a shuffling process, wherein the shuffled polynucleotide molecule encodes a gene product having enhanced tolerance to an inhibitor of any one of the activities of a polypeptide selected from the group consisting of SEQ ID NOs:3, 5, 7, 9, 11, 13, 15 and/or 17.

The present invention further relates to a method for preventing, treating, or ameliorating a medical condition by treating a subject with a polypeptide comprising SEQ ID NOs:3, 5, 7, 9, 11, 13, 15 and/or 17, in addition to, its encoding nucleic acid (SEQ ID NOs:2, 4, 6, 8, 10, 12, and/or 16), wherein the medical condition is selected from the group consisting of a disorder related to aberrant NF-κB activity and an autoimmune condition.

The present invention further relates to a method of identifying a compound that modulates a biological activity of a HGBPBMY3 (4843 30 2 1; 4843_2) and/or MGBPBMY4 (BC007143) polypeptide, the method comprising the steps of: (a) combining a candidate modulator compound with a HGBPBMY3 (4843 30 2 1; 4843_2) and/or MGBPBMY4 (BC007143) polypeptide having the sequence set forth in SEQ ID NO:7 and/or SEQ ID NO:17; and (b) measuring an effect of the candidate modulator compound on the biological activity of HGBPBMY3 (4843 30 2 1; 4843_2) and/or MGBPBMY4 (BC007143).

The present invention further relates to a method of identifying a compound that modulates a biological activity of a guanylate binding protein, the method comprising the steps of: (a) combining a candidate modulator compound with a host cell expressing a HGBPBMY3 (4843 30 2 1; 4843_2) and/or MGBPBMY4 (BC007143) polypeptide having the sequence as set forth in SEQ ID NO:7 and/or SEQ ID NO:17; and (b) measuring an effect of the candidate modulator compound on a biological activity of the expressed HGBPBMY3 (4843 30 2 1; 4843_2) and/or MGBPBMY4 (BC007143) polypeptide.

The present invention further relates to a method of identifying a compound that modulates a biological activity of a HGBPBMY3 (4843 30 2 1; 4843_2) and/or MGBPBMY4 (BC007143) polypeptide, the method comprising the steps of: (a) combining a candidate modulator compound with a host cell containing a vector described herein, whereby a HGBPBMY3 (4843 30 2 1; 4843_2) and/or MGBPBMY4 (BC007143) polypeptide is expressed by the cell; and (b) measuring an effect of the candidate modulator compound on a biological activity of the expressed HGBPBMY3 (4843 30 2 1; 4843_2) and/or MGBPBMY4 (BC007143) polypeptide.

The present invention further relates to a method of screening for a compound that is capable of modulating a biological activity of a HGBPBMY3 (4843 30 2 1; 4843_2) and/or MGBPBMY4 (BC007143) polypeptide, the method comprising the steps of: (a) providing a host cell as described herein; (b) determining a biological activity of HGBPBMY3 (4843 30 2 1; 4843_2) and/or MGBPBMY4 (BC007143) in the absence of a modulator compound; (c) contacting the cell with the modulator compound; and (d) determining the biological activity of HGBPBMY3 (4843 30 2 1; 4843_2) and/or MGBPBMY4 (BC007143) in the presence of the modulator compound, wherein a difference between the activity of HGBPBMY3 (4843 30 2 1; 4843_2) and/or MGBPBMY4 (BC007143) in the presence of the modulator compound and in the absence of the modulator compound indicates a modulating effect of the compound.

The present invention further relates to a compound that modulates a biological activity of human HGBPBMY3 (4843 30 2 1; 4843_2) and/or mouse MGBPBMY4 (BC007143) as identified by the methods described herein.

The invention further relates to a method for preventing, treating, or ameliorating a medical condition with the polypeptide provided as SEQ ID NO:3, in addition to, its encoding nucleic acid, or a modulator thereof, wherein the medical condition is a pulmonary condition, ovarian cancer, testicular cancer or a related proliferative condition of the ovary or testicle.

The invention further relates to a method of diagnosing a pathological condition or a susceptibility to a pathological condition in a subject comprising the steps of (a) determining the presence or amount of expression of the polypeptide of of SEQ ID NO:3 in a biological sample; (b) and diagnosing a pathological condition or a susceptibility to a pathological condition based on the presence or amount of expression of the polypeptide relative to a control, wherein said condition is a member of the group consisting of ovarian cancer, testicular cancer and a pulmonary condition.

The invention further relates to a method for preventing, treating, or ameliorating a medical condition with the polypeptide provided as SEQ ID NO:5, in addition to, its encoding nucleic acid, or a modulator thereof, wherein the medical condition is a pulmonary condition.

The invention further relates to a method of diagnosing a pathological condition or a susceptibility to a pathological condition in a subject comprising the steps of (a) determining the presence or amount of expression of the polypeptide of of SEQ ID NO:5 in a biological sample; (b) and diagnosing a pathological condition or a susceptibility to a pathological condition based on the presence or amount of expression of the polypeptide relative to a control, wherein said condition is a pulmonary condition.

The invention further relates to a method for preventing, treating, or ameliorating a medical condition with the polypeptide provided as SEQ ID NO:7, in addition to, its encoding nucleic acid, or a modulator thereof, wherein the medical condition is hyperthyroidism, prostatic hypertrophy and a pulmonary condition.

The invention further relates to a method of diagnosing a pathological condition or a susceptibility to a pathological condition in a subject comprising the steps of (a) determining the presence or amount of expression of the polypeptide of SEQ ID NO:7 in a biological sample; (b) and diagnosing a pathological condition or a susceptibility to a pathological condition based on the presence or amount of expression of the polypeptide relative to a control, wherein said condition is a member of the group consisting of hyperthyroidism, prostatic hypertrophy and a pulmonary condition.

The invention further relates to a method for preventing, treating, or ameliorating a medical condition with the polypeptide provided as SEQ ID NO:9, in addition to, its encoding nucleic acid, or a modulator thereof, wherein the medical condition is multiple sclerosis, Parkinson's disease, an immune system disease, breast cancer, testicular cancer, and a pulmonary condition.

The invention further relates to a method of diagnosing a pathological condition or a susceptibility to a pathological condition in a subject comprising the steps of (a) determining the presence or amount of expression of the polypeptide of of SEQ ID NO:9 in a biological sample; (b) and diagnosing a pathological condition or a susceptibility to a pathological condition based on the presence or amount of expression of the polypeptide relative to a control, wherein said condition is a member of the group consisting of multiple sclerosis, Parkinson's disease, an immune system disease, breast cancer, testicular cancer and a pulmonary condition.

The invention further relates to a method for preventing, treating, or ameliorating a medical condition with human GBP1, in addition to, its encoding nucleic acid, or a modulator thereof, wherein the medical condition is a neurological condition, including Parkinson's, Alzheimer's and multiple sclerosis.

The invention further relates to a method of diagnosing a pathological condition or a susceptibility to a pathological condition in a subject comprising the steps of (a) determining the presence or amount of expression of GBP1 in a biological sample; (b) and diagnosing a pathological condition or a susceptibility to a pathological condition based on the presence or amount of expression of the polypeptide relative to a control, wherein said condition is a member of the group consisting of Parkinson's disease, Alzheimer's disease and multiple sclerosis.

The invention further relates to a method for preventing, treating, or ameliorating a medical condition with human GBP5, in addition to, its encoding nucleic acid, or a modulator thereof, wherein the medical condition is a neurological condition, including Alzheimer's disease and multiple sclerosis, breast cancer, testicular cancer, Crohn's disease, or a pulmonary disease, including bronchitis.

The invention further relates to a method of diagnosing a pathological condition or a susceptibility to a pathological condition in a subject comprising the steps of (a) determining the presence or amount of expression of GBP5 in a biological sample; (b) and diagnosing a pathological condition or a susceptibility to a pathological condition based on the presence or amount of expression of the polypeptide relative to a control, wherein said condition is a member of the group consisting of Alzheimer's disease, multiple sclerosis, breast cancer, testicular cancer, Crohn's disease and bronchitis.

BRIEF DESCRIPTION OF THE FIGURES/DRAWINGS

FIGS. 1A–1C show the polynucleotide sequence (SEQ ID NO:2) and the deduced amino acid sequence (SEQ ID NO:3) of the human guanylate binding protein HGBPBMY1 (AK096141) of the present invention. The standard one-letter abbreviation for amino acids is used to illustrate the deduced amino acid sequence. The polynucleotide sequence contains a sequence of 2454 nucleotides (SEQ ID NO:2) encoding a polypeptide of 638 amino acids (SEQ ID NO:3).

FIGS. 2A–2C show the polynucleotide sequence (SEQ ID NO:4) and the deduced amino acid sequence (SEQ ID NO:5) of the human guanylate binding protein HGBPBMY2 (4843 30 1 1; 4843_1) of the present invention. The standard one-letter abbreviation for amino acids is used to illustrate the deduced amino acid sequence. The polynucleotide sequence contains a sequence of 2367 nucleotides (SEQ ID NO:4), encoding a polypeptide of 788 amino acids (SEQ ID NO:5).

FIGS. 3A–3B show the polynucleotide sequence (SEQ ID NO:6) and deduced amino acid sequence (SEQ ID NO:7) of the novel human guanylated binding protein HGBPBMY3 (4843 30 2 1; 4843_2) of the present invention. The standard one-letter abbreviation for amino acids is used to illustrate the deduced amino acid sequence. The polynucleotide sequence contains a sequence of 1392 nucleotides (SEQ ID NO:6), encoding a polypeptide of 464 amino acids (SEQ ID NO:7).

FIGS. 4A–4C show the polynucleotide sequence (SEQ ID NO:8) and deduced amino acid sequence (SEQ ID NO:9) of the human guanylate binding protein HGBPBMY4 (FLJ10961) of the present invention. The standard one-letter abbreviation for amino acids is used to illustrate the deduced amino acid sequence. The polynucleotide sequence contains a sequence of 2952 nucleotides (SEQ ID NO:8), encoding a polypeptide of 563 amino acids (SEQ ID NO:9).

FIGS. 5A–5C show the polynucleotide sequence (SEQ ID NO:10) and deduced amino acid sequence (SEQ ID NO:11) of the mouse guanylate binding protein MGBPBMY1 (LOC229900) of the present invention. The standard one-letter abbreviation for amino acids is used to illustrate the deduced amino acid sequence. The polynucleotide sequence contains a sequence of 2484 nucleotides (SEQ ID NO:10), encoding a polypeptide of 632 amino acids (SEQ ID NO:11).

FIGS. 6A–B show the polynucleotide sequence (SEQ ID NO:12) and deduced amino acid sequence (SEQ ID NO:13) of the mouse guanylate binding protein MGBPBMY2 (LOC229902) of the present invention. The standard one-letter abbreviation for amino acids is used to illustrate the deduced amino acid sequence. The polynucleotide sequence contains a sequence of 1818 nucleotides (SEQ ID NO:12), encoding a polypeptide of 605 amino acids (SEQ ID NO:13).

FIGS. 7A–7C show the polynucleotide sequence (SEQ ID NO:14) and deduced amino acid sequence (SEQ ID NO:15) of the mouse guanylate biding protein MGBPBMY3 (BC031475) of the present invention. The standard one-letter abbreviation for amino acids is used to illustrate the deduced amino acid sequence. The polynucleotide sequence contains a sequence of 3387 nucleotides (SEQ ID NO:13), encoding a polypeptide of 385 amino acids (SEQ ID NO:14).

FIGS. 8A–8D show the polynucleotide sequence (SEQ ID NO:15) and deduced amino acid sequence (SEQ ID NO:16) of the novel mouse guanlate binding protein MGBPBMY4 (BC007143) of the present invention. The standard one-letter abbreviation for amino acids is used to illustrate the deduced amino acid sequence. The polynucleotide sequence contains a sequence of 4193 nucleotides (SEQ ID NO:15), encoding a polypeptide of 483 amino acids (SEQ ID NO:16).

FIG. 9 is a table depicting the percent similarity and percent identity between human GBP1 and the polynucleotide sequences of the present invention.

FIG. 10 is a schematic depicting the chromosome organization of the GBP family. Panel A of FIG. 10 depicts human chromosome 1p22, Panel B of FIG. 10 depicts mouse chromosome 3H1 and Panel C of FIG. 10 depicts mouse chromosome 5E4. Arrows represent the direcion of transcription. The GBP genes of the present invention, with the exception of MGBPBMY3 (BC031475) and MGBPBMY4 (BC007143), are indicated.

FIG. 11A–11C is an alignment showing the regions of identity and similarity between the encoded GBP proteins of the present invention (SEQ ID NOs:3, 5, 7, 9, 11, 13, 15) to GBP family members. The alignment was performed using the CLUSTALW algorithm using default parameters as described herein (Vector NTI suite of programs). The darkly shaded amino acids represent regions of matching identity. The lightly shaded amino acids represent regions of matching similarity. Spaces between residues indicate gapped regions of non-identity for the aligned polypeptides.

FIG. 28 is a series of bar graphs depicting induction of GBP expression by LPS and IFN-γ. RNA was isolated from THP-1 monocytes stimulated for 6 hours with either medium, LPS, or IFN-γ. Levels of HGBPBMY4 (FLJ10961) (Panel A), HGBPBMY2 (4843 30 1 1; 4843_1) (Panel B), and HGBPBMY3 (4843 30 2 1; 4843_2) (Panel C) were measured by Real Time PCR.

FIG. 29 is a series of bar graphs depicting the effect of NF-kB inhibition on LPS-mediated induction of GBP-2. Panels A and B depict two independent groups of THP-1 monocytes that were stimulated with LPS in the presence and absence of the NF-κB inhibitor Compound 1 (denoted "peptide" in the figures). RNA was isolated and analyzed for GBP-2 expression by Real Time PCR.

FIG. 30 is a series of bar graphs depicting the effect of NF-κB inhibition on LPS-mediated induction of GBP-4. Panels A and B depict two independent groups of THP-1 monocytes that were stimulated with LPS in the presence and absence of the NF-kB inhibitor Compound 1 (denoted "peptide" in the figure). RNA was isolated and analyzed for GBP-4 expression by Real Time PCR.

FIG. 31 is a series of bar graphs depicting the effect of NF-kB inhibition on LPS-mediated induction of HGBPBMY4 (FLJ10961). Independent groups of THP-1 monocytes (Panels A and B) were stimulated with LPS in the presence and absence of the NF-kB inhibitor, Compound 1 (denoted peptide in the figure). RNA was isolated and analyzed for HGBPBMY4 (FLJ10961) expression by Real Time PCR.

FIG. 32 is a series of bar graphs depicting the effect of NF-κB inhibition on LPS-mediated induction of HGBPBMY3 (4843 30 2 1; 4843_2). Independent groups of THP-1 monocytes (Panels A and B) were stimulated with LPS in the presence and absence of the NF-kB inhibitor, Compound 1 (denoted peptide in the figure). RNA was isolated and analyzed for HGBPBMY3 (4843 30 2 1; 4843_2) expression by Real Time PCR.

Figure 33:
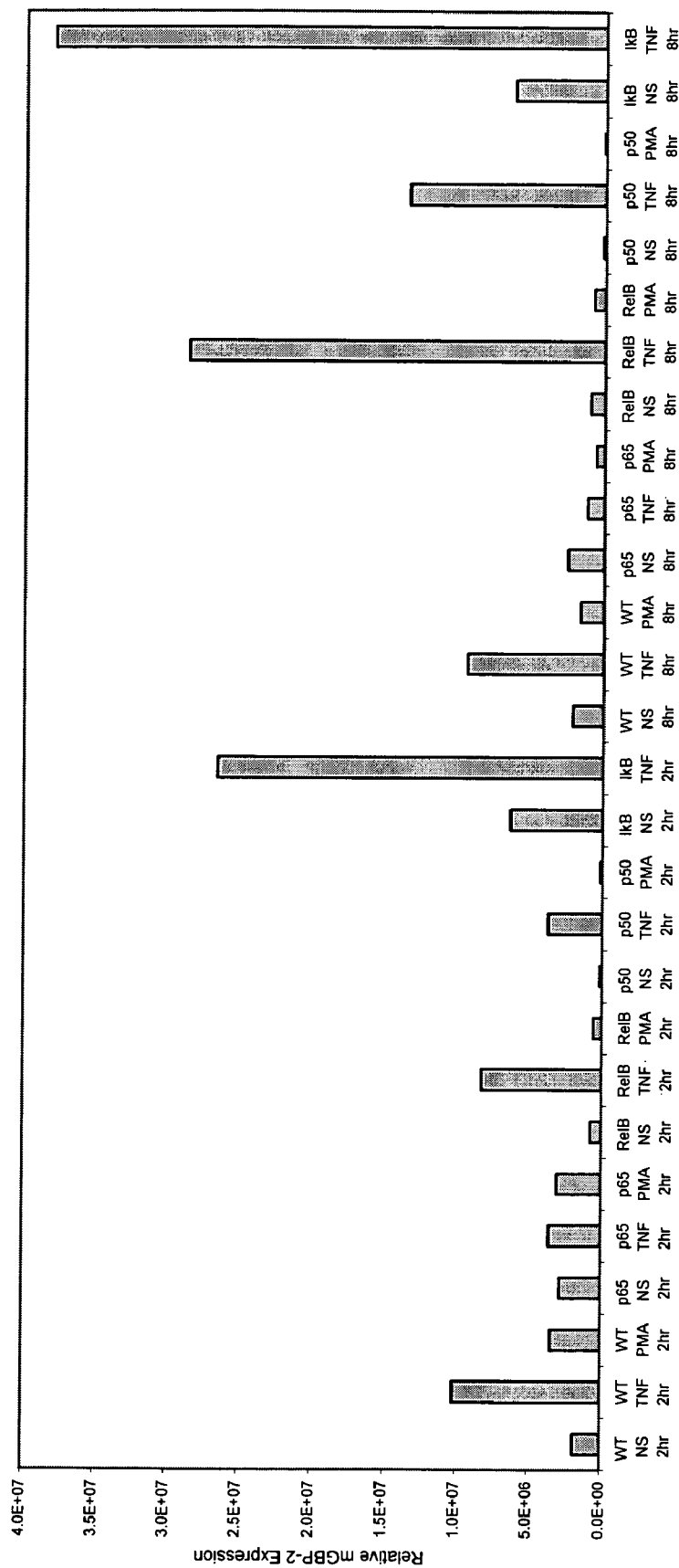

FIG. 33 is a bar graph depicting mGBP-2 expression in mouse embryonic fibroblast lines derived from NF-kB and IkBα germline knockouts. Embryonic fibroblast lines derived form different knockout animals were stimulated for 2 or 8 hours with eiher TNFα or PMA. At each time point, mRNA was isolated and analyzed by Real Time PCR for expression of mGBP-2.

Figure 34:
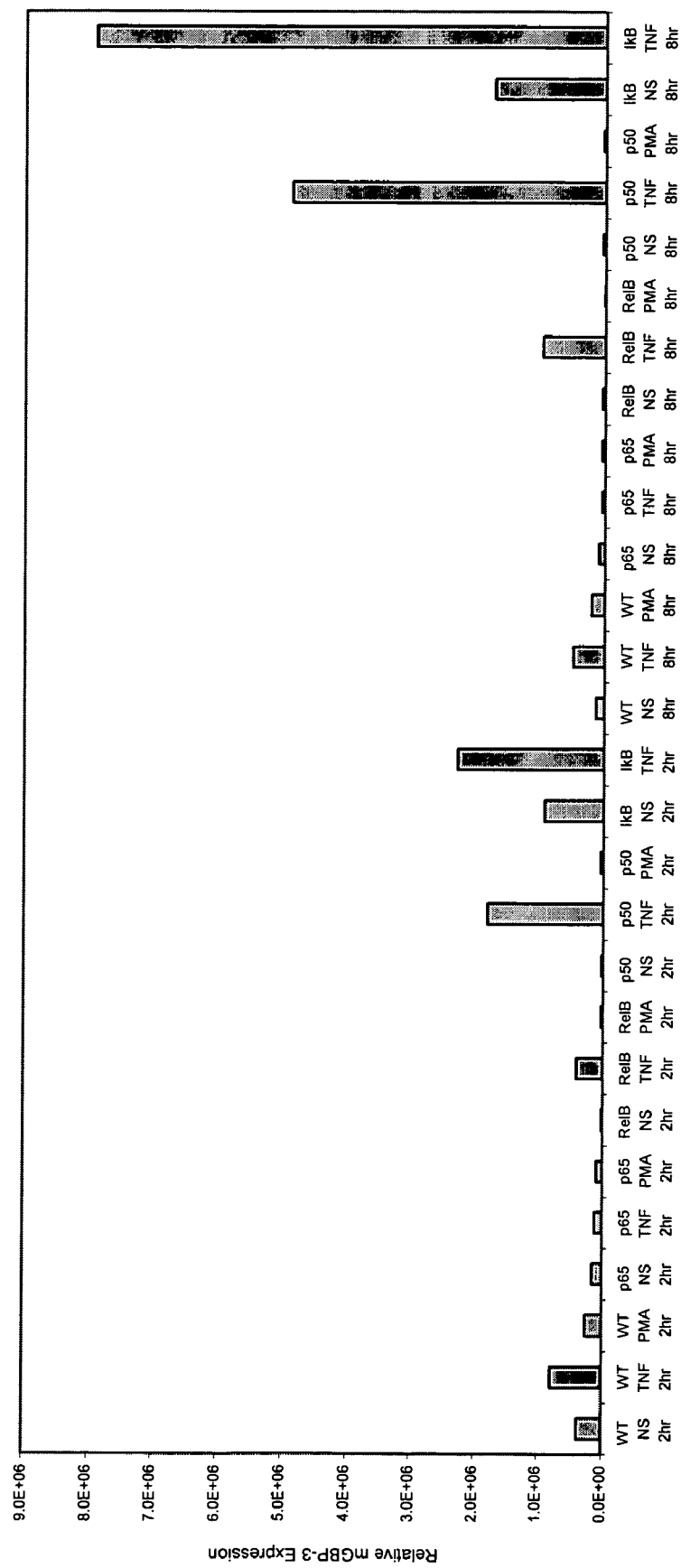

FIG. 34 is a bar graph depicting mGBP-3 expression in mouse embryonic fibroblast lines derived from NF-κB and IκBα germline knockouts. Embryonic fibroblast lines derived form different knockout animals were stimulated for 2 or 8 hours with either TNFα or PMA. At each time point, mRNA was isolated and analyzed by Real Time PCR for expression of mGBP-3.

Figure 35:
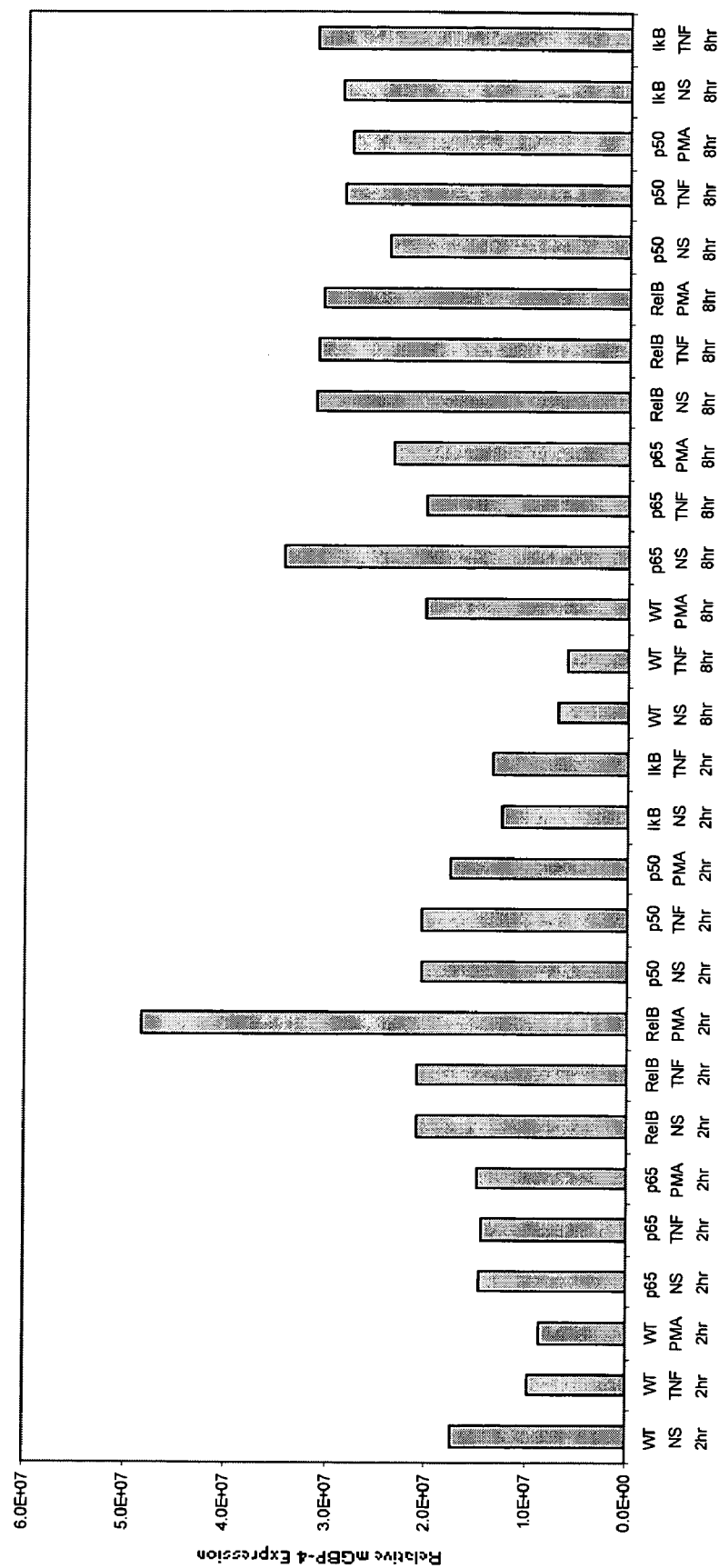

FIG. 35 is a bar graph depicting mGBP-4 expression in mouse embryonic fibroblast lines derived from NF-κB and IκBα germline knockouts. Embryonic fibroblast lines derived form different knockout animals were stimulated for 2 or 8 hours with either TNFα or PMA. At each time point, mRNA was isolated and analyzed by Real Time PCR for expression of mGBP-4.

Figure 36:
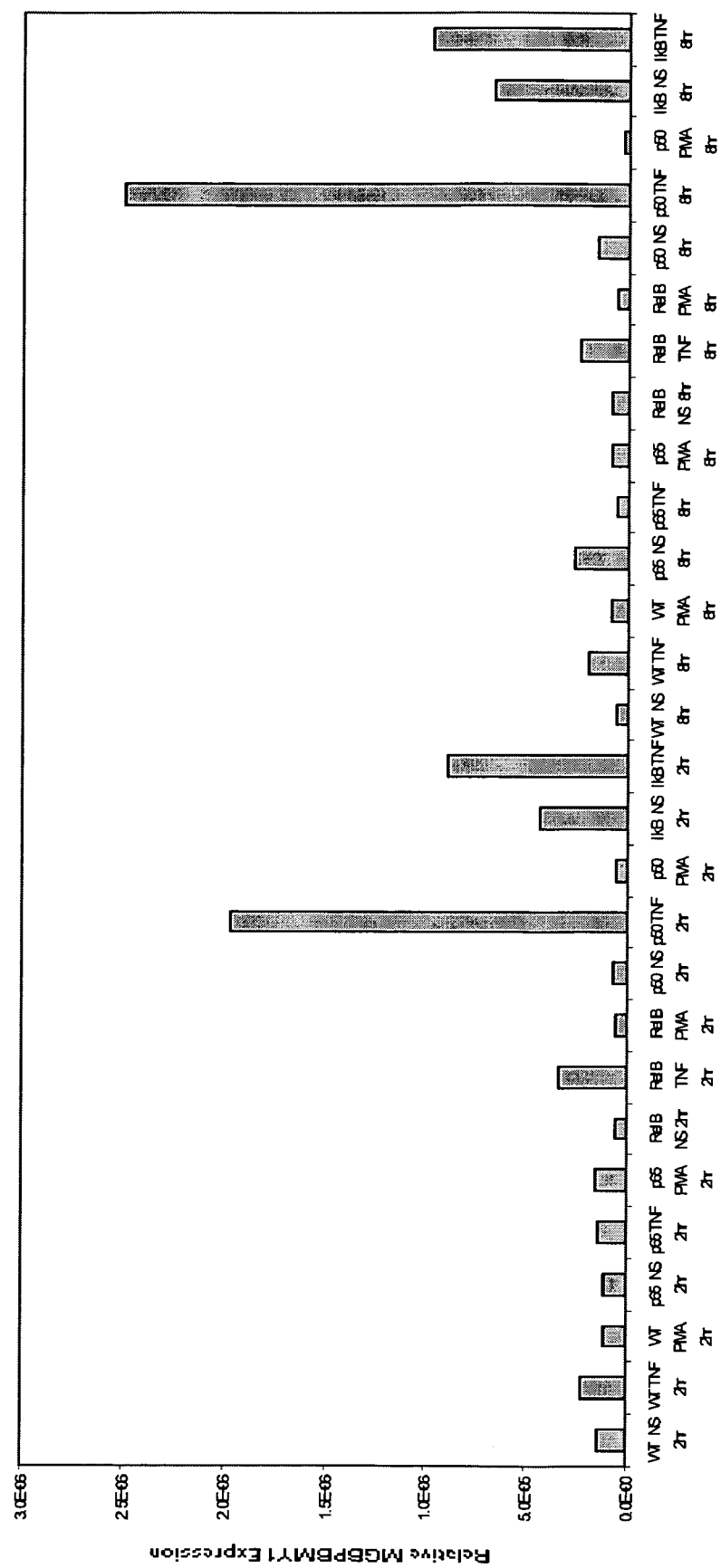

FIG. 36 is a bar graph depicting MGBPBMY1 (LOC229900) expression in mouse embryonic fibroblast lines derived from NF-κB and IκBα (germline knockouts. Embryonic fibroblast lines derived from different knockout animals were stimulated for 2 or 8 hours with either TNFα or PMA. At each time point, mRNA was isolated and analyzed by Real Time PCR for expression of MGBPBMY1 (LOC229900).

Figure 37:
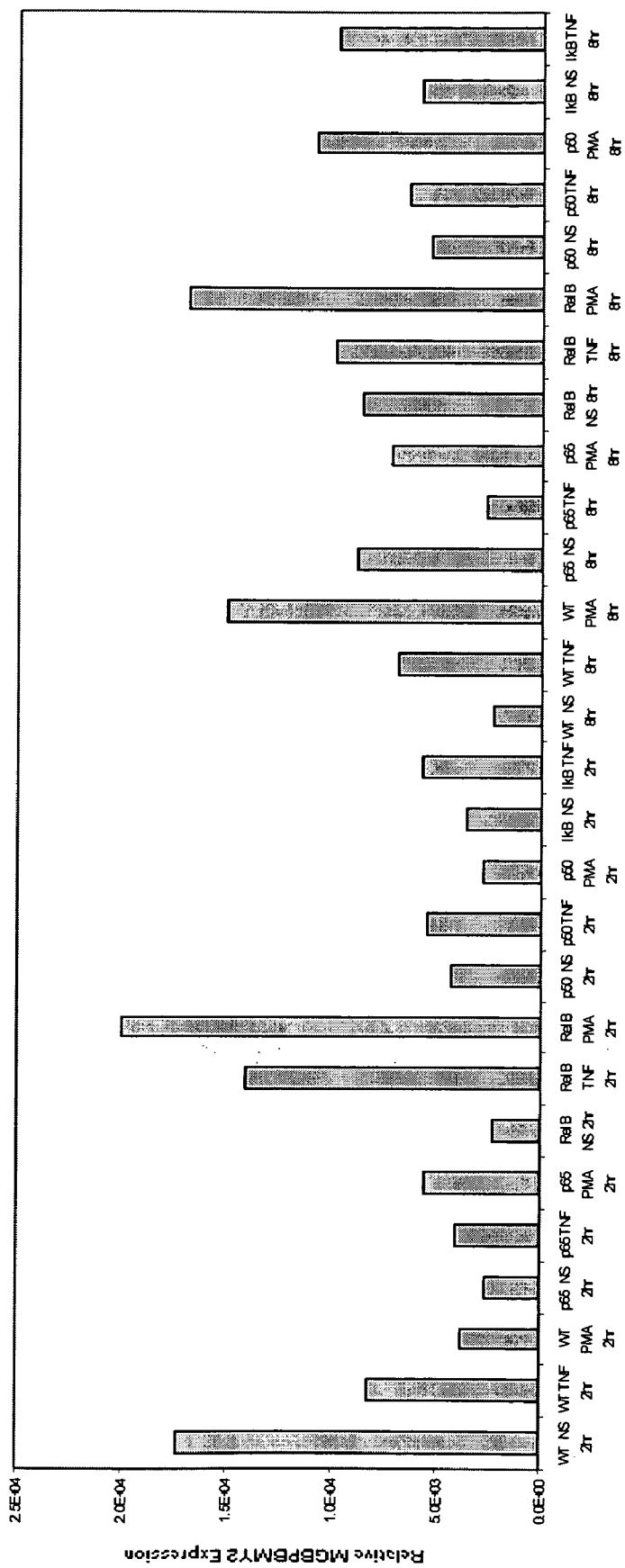

FIG. 37 is a bar graph depicting MGBPBMY2 (LOC229902) expression in mouse embryonic fibroblast lines derived from NF-κB and IκBα germline knockouts. Embryonic fibroblast lines derived form different knockout animals were stimulated for 2 or 8 hours with either TNFα or PMA. At each time point, mRNA was isolated and analyzed by Real Time PCR for expression of MGBPBMY2 (LOC229902).

Figure 38:
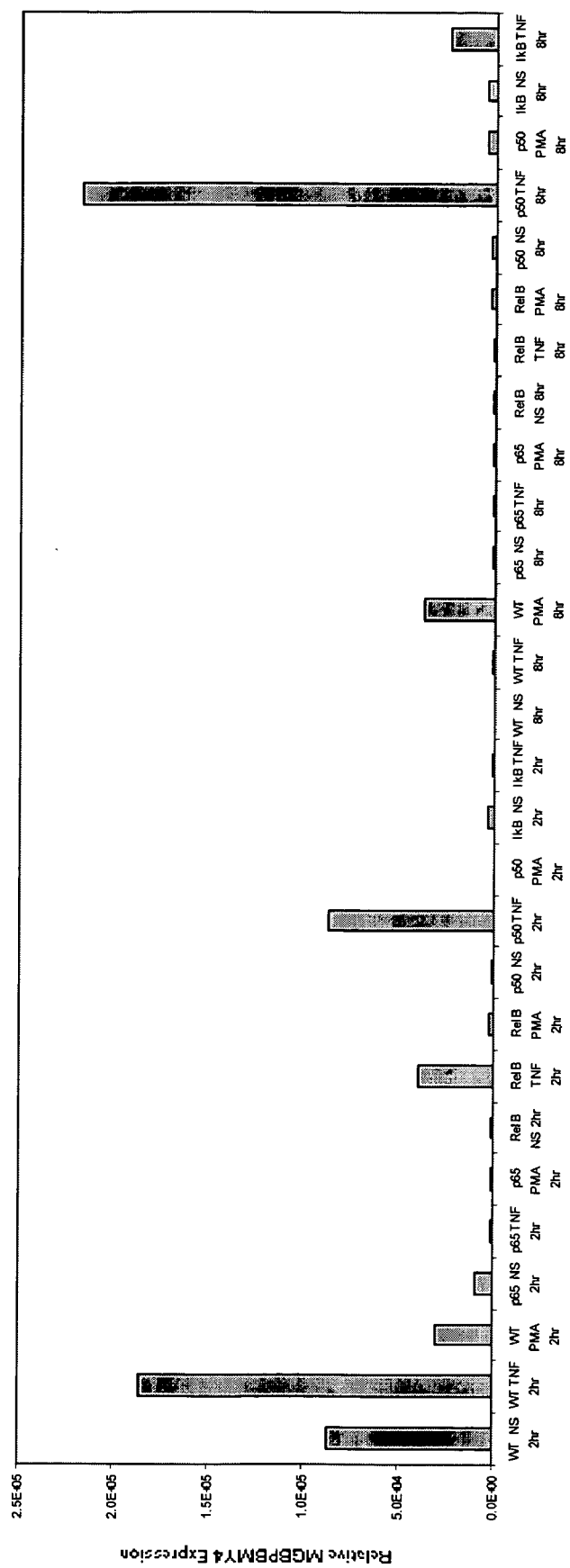

FIG. 38 is a bar graph depicting MGBPBMY4 (BC007143) expression in mouse embryonic fibroblast lines derived from NF-κB and IκBα germline knockouts. Embryonic fibroblast lines derived form different knockout animals were stimulated for 2 or 8 hours with either TNFα or PMA. At each time point, mRNA was isolated and analyzed by Real Time PCR for expression of MGBPBMY4 (BC007143).

Figure 39:
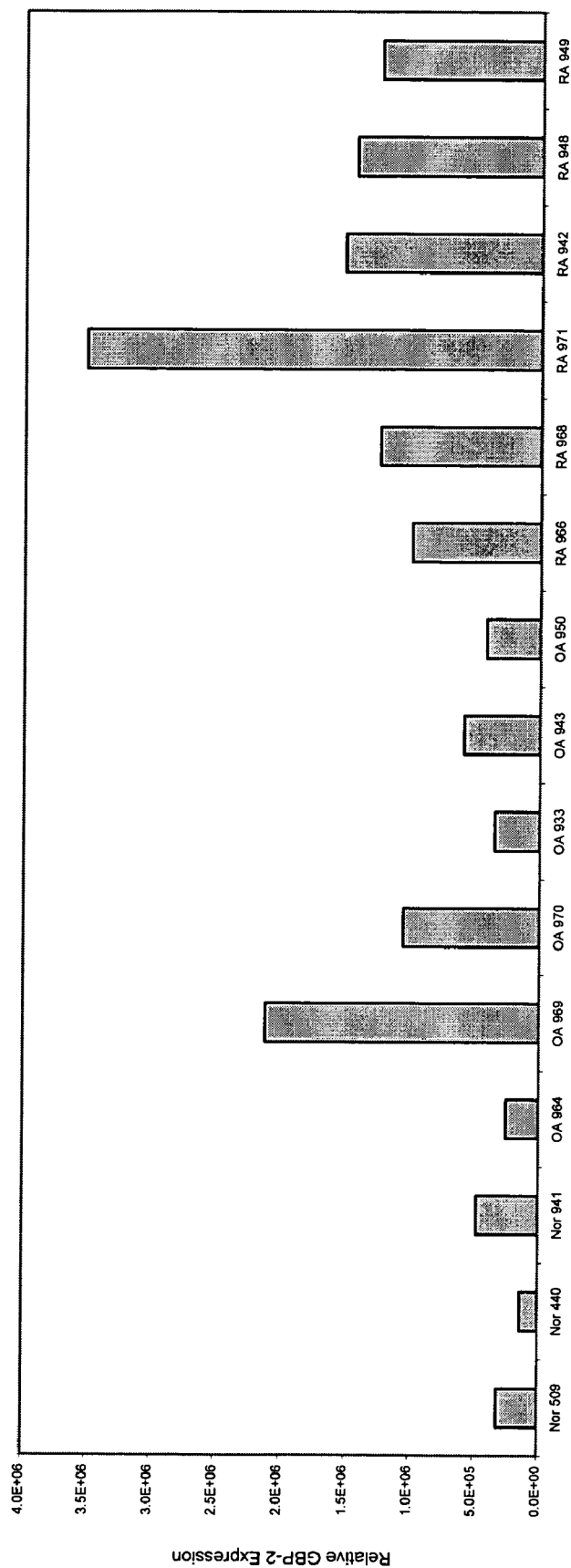

FIG. 39 is a bar graph depicting expression of GBP-2 in synovial tissue. RNA was isolated from synovial tissue derived from three normal controls (denoted "Nor" in the figure), six osteoarthritis subjects (denoted "OA" in the figure), and six rheumatoid arthritis subjects, and analyzed for GBP-2 mRNA by Real Time PCR.

Figure 40:
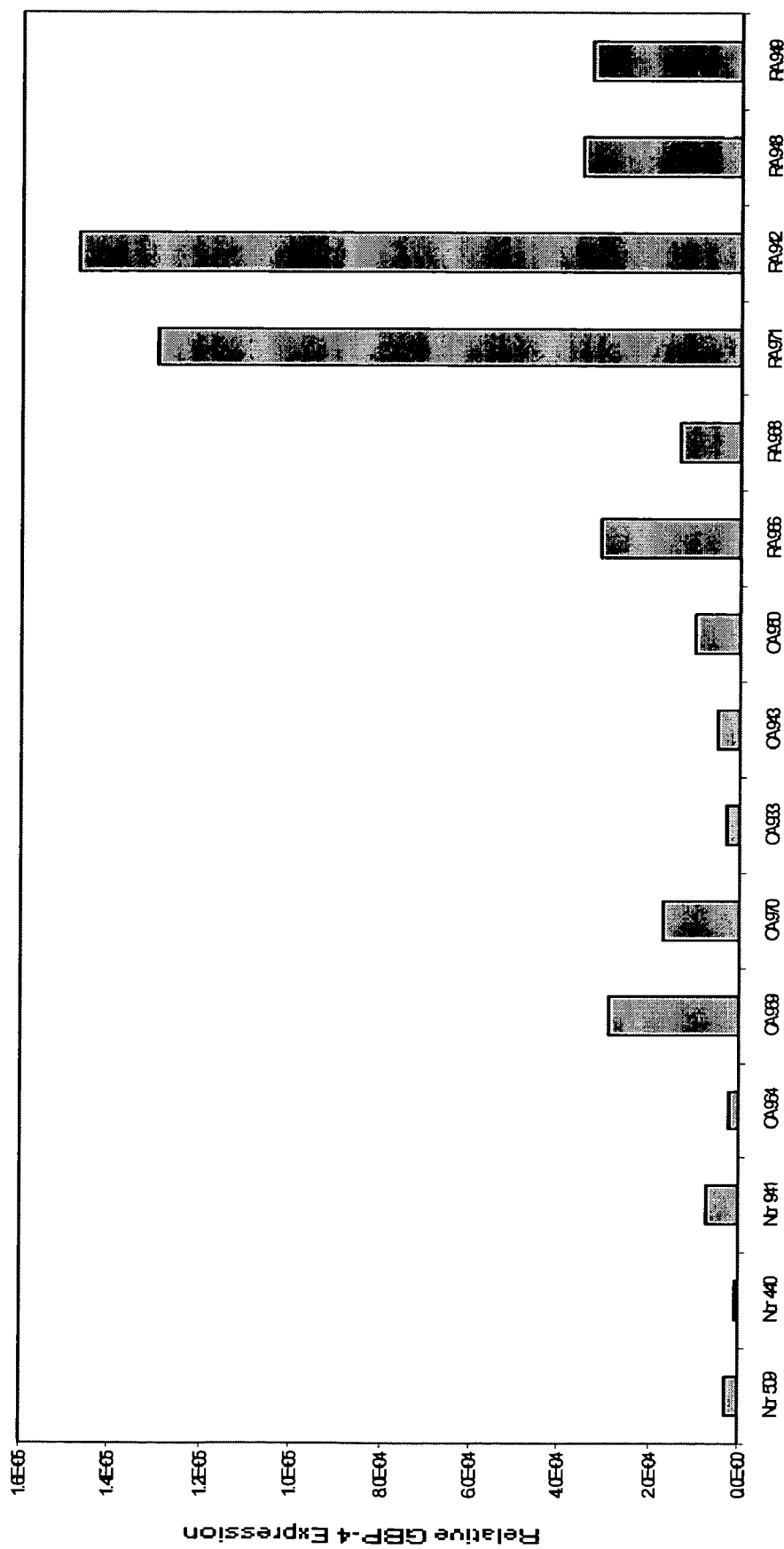

FIG. 40 is a bar graph depicting expression of GBP-4 in synovial tissue. RNA was isolated from synovial tissue derived from three normal controls (denoted "Nor" in the figure), six osteoarthritis subjects (denoted "OA" in the figure), and six rheumatoid arthritis subjects, and analyzed for GBP-4 mRNA by Real Time PCR.

Figure 41:
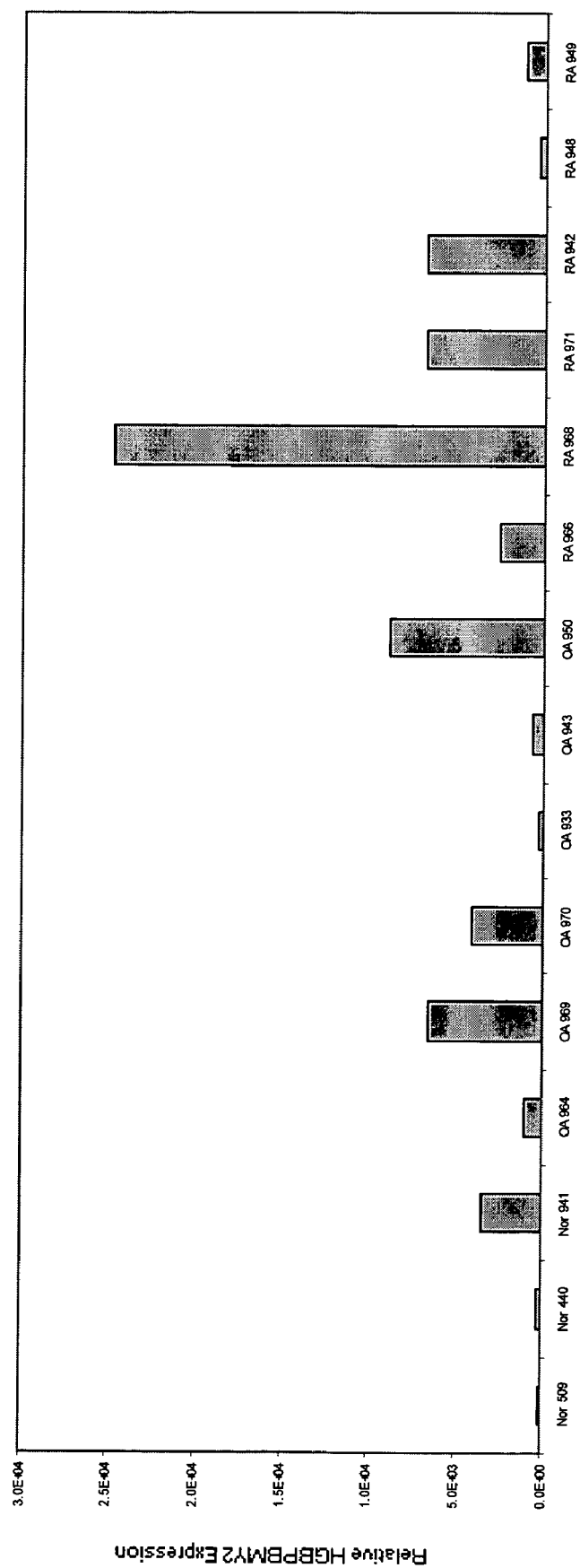

FIG. 41 is a bar graph depicting expression of HGBPBMY2 (4843 30 1 1; 4843_1) in synovial tissue. RNA was isolated from synovial tissue derived from three normal controls (denoted "Nor" in the figure), six osteoarthritis subjects (denoted "OA" in the figure), and six rheumatoid arthritis subjects, and analyzed for HGBPBMY2 (4843 30 1 1; 4843_1) mRNA by Real Time PCR.

Figure 42:
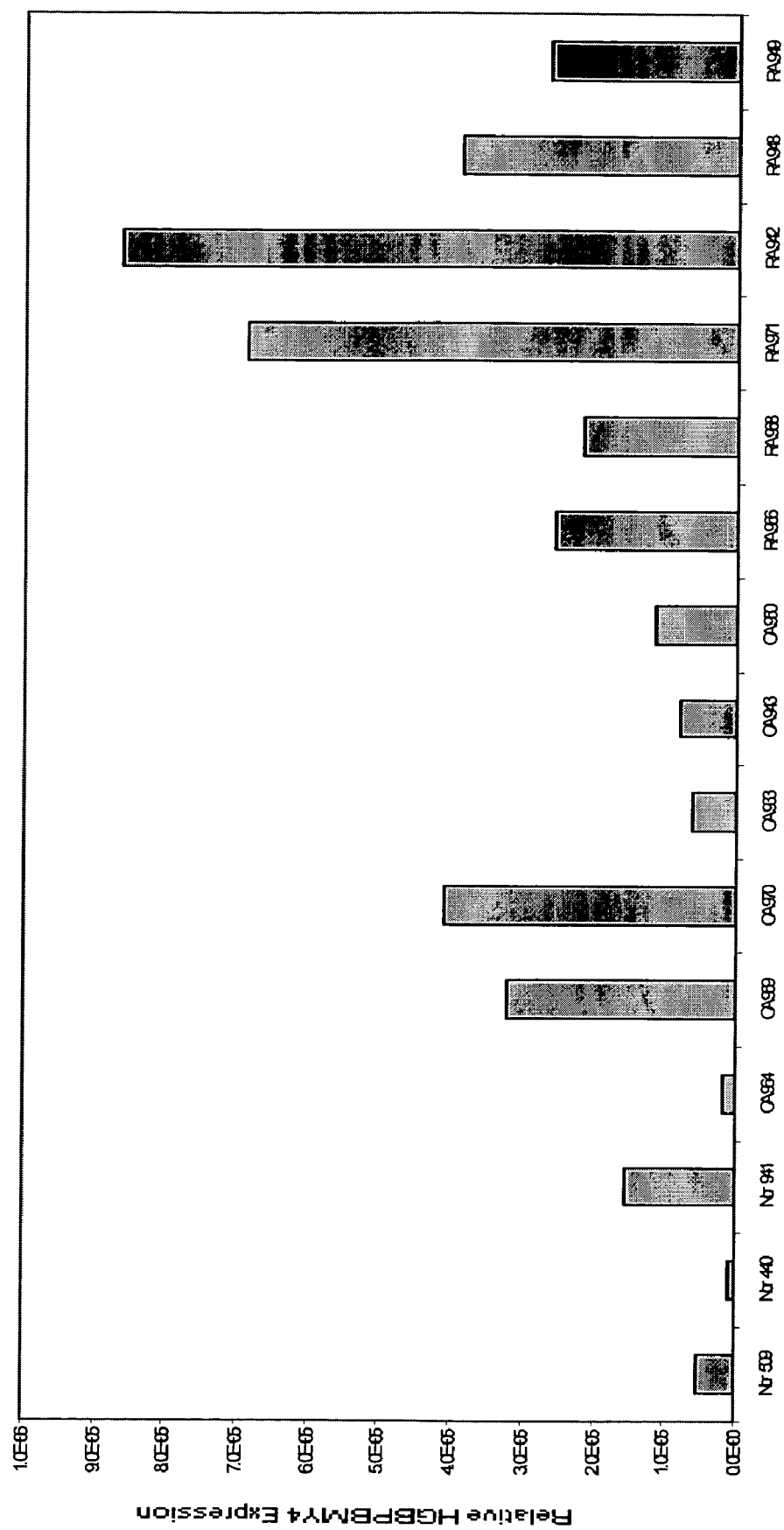

FIG. 42 is a bar graph depicting expression of HGBPBMY4 (FLJ10961) in synovial tissue. RNA was isolated from synovial tissue derived from three normal controls (denoted "Nor" in the figure), six osteoarthritis subjects (denoted "OA" in the figure), and six rheumatoid arthritis subjects, and analyzed for HGBPBMY4 (FLJ10961) mRNA by Real Time PCR.

Figure 43:
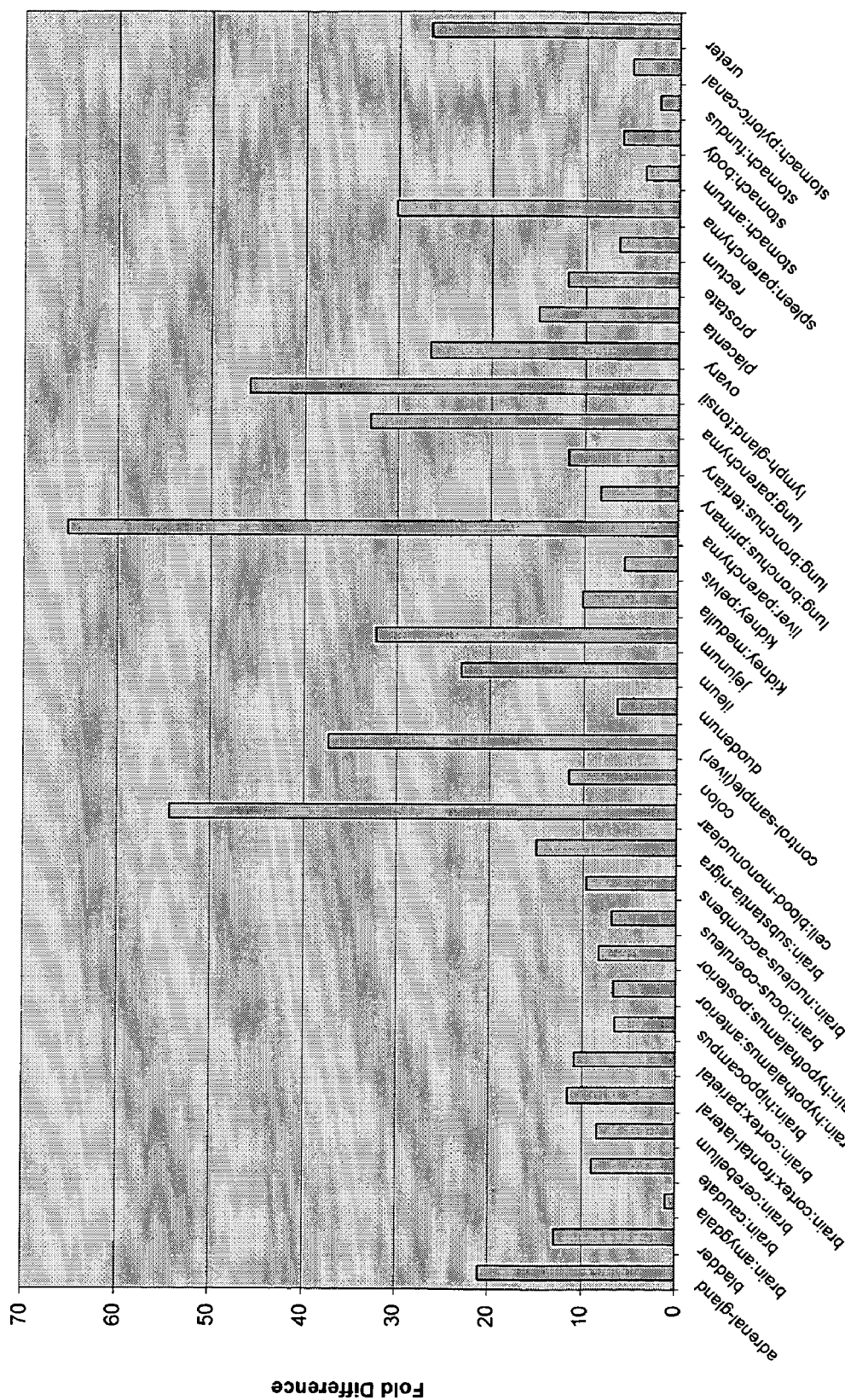

FIG. 43 shows an expanded expression profile of the GBP HGBPBMY1 (AK096141). The figure illustrates the relative expression level of HGBPBMY1 amongst various mRNA tissue sources. As shown, the HGBPBMY1 polypeptide exhibited high expression in normal spleen; tonsil; blood mononuclear cells; liver parenchyma; lung parenchyma; digestive system including stomach, duodenum, jejunum, ileum; placenta; ovary; and was detectable in regions of the brain, adrenal gland, ureter, bladder. FIG. 43 also illustrates the relative expression level of HGBPBMY1 amongst various mRNA tissue sources isolated from normal and diseased tissues. As shown, the HGBPBMY1 polypeptide showed increased expression in breast and testicle tumors relative to controls; and high expression in normal and diseased lung parenchyma. Expression data was obtained by measuring the steady state HGBPBMY1 mRNA levels by quantitative PCR using the PCR primer pair provided as SEQ ID NO:61 and 62, and a TAQMAN probe (SEQ ID NO:63) as described in Example 36 herein.

Figure 44:
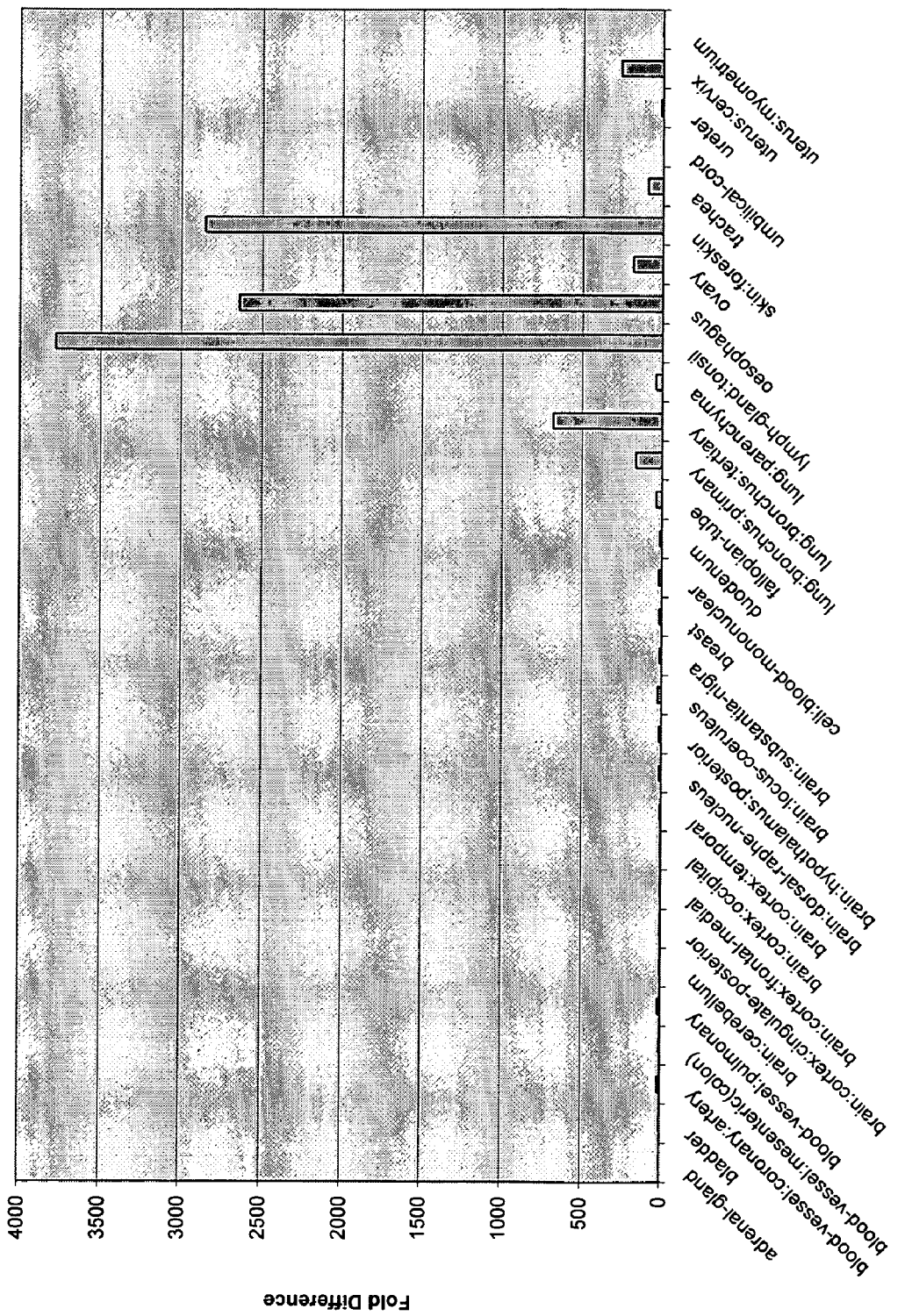

FIG. 44 shows an expanded expression profile of the GBP HGBPBMY2 (4843_1). The figure illustrates the relative expression level of HGBPBMY2 amongst various mRNA tissue sources. As shown, the HGBPBMY2 polypeptide showed the highest expression in tonsil, foreskin, esophagus; detectable in uterus cervix, tertiary lung bronchus, trachea. FIG. 44 also illustrates the relative expression level of HGBPBMY2 amongst various mRNA tissue sources isolated from normal and diseased tissues. Expression data was obtained by measuring the steady state HGBPBMY2 mRNA levels by quantitative PCR using the PCR primer pair provided as SEQ ID NO:64 and 65, and TAQMAN probe (SEQ ID NO:66) as described in Example 37 herein.

Figure 45:
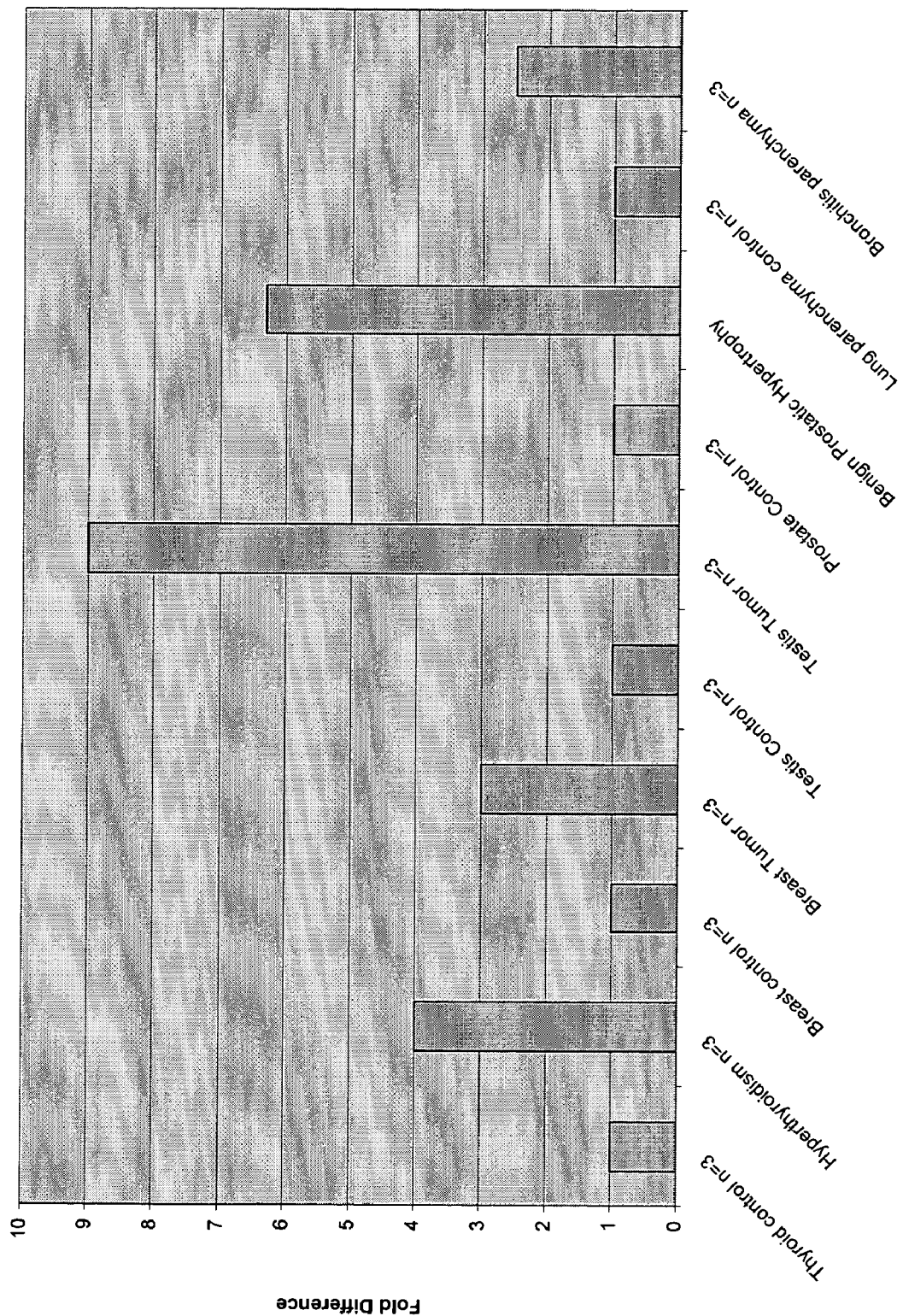

FIG. 45 shows an expanded expression profile of the GBP HGBPBMY3 (4843_2). The figure illustrates the relative expression level of HGBPBMY3 amongst various mRNA tissue sources. FIG. 45 illustrates the relative expression level of HGBPBMY3 amongst various mRNA tissue sources isolated from normal and diseased tissues. As shown, the HGBPBMY3 polypeptide showed increased expression in thyroids of hyperthyroidism patients compared to control thyroids. FIG. 45 also illustrates increased expression in breast and testicle tumors relative to controls; increased expression in prostatic hypertrophy relative to normal prostate; expressed in normal and diseased lung parenchyma; increased in bronchitis. Expression data was obtained by measuring the steady state HGBPBMY3 mRNA levels by quantitative PCR using the PCR primer pair provided as SEQ ID NO:38 and 39, and TAQMAN probe (SEQ ID NO:40) as described in Example 38 herein.

Figure 46:
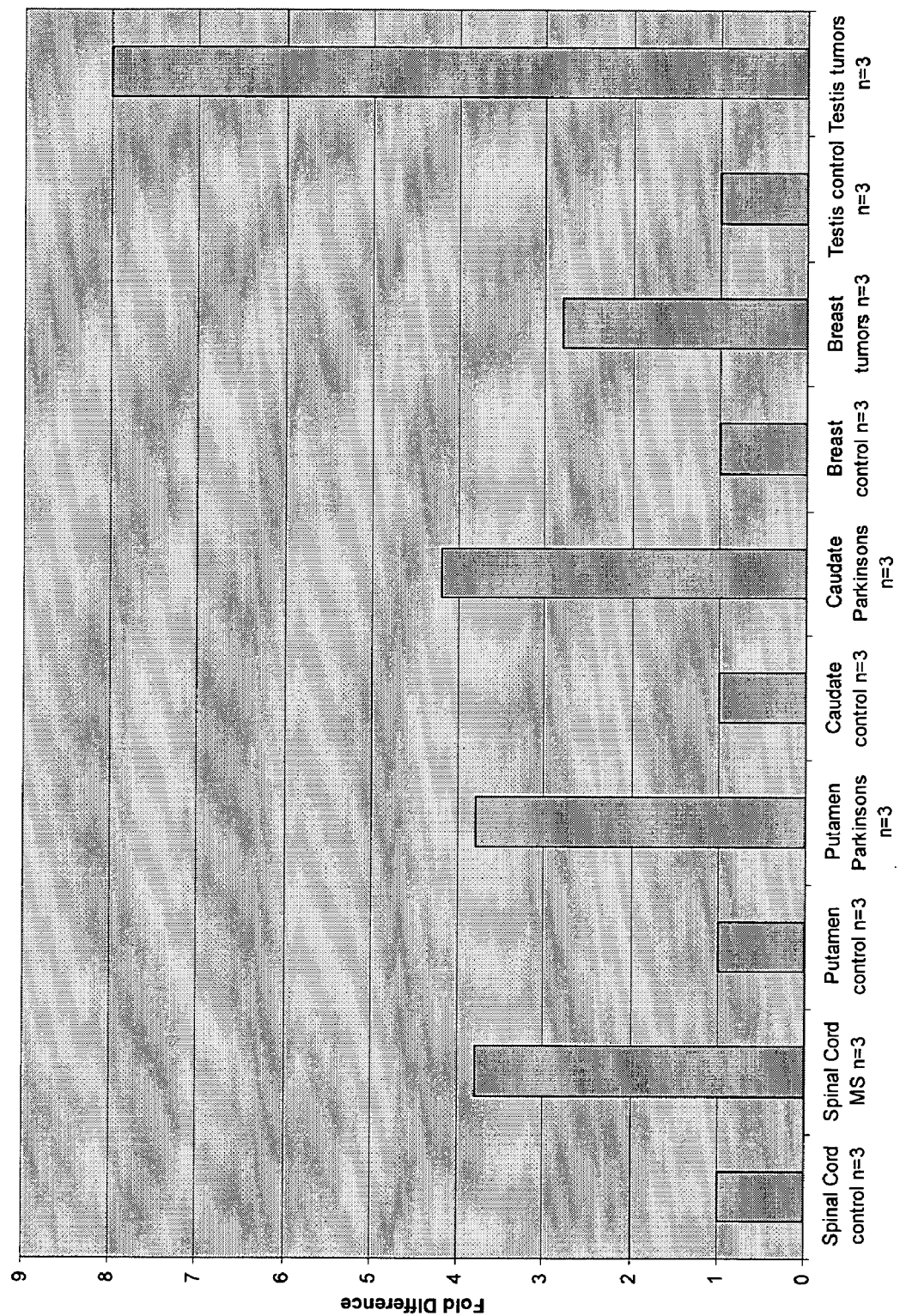

FIG. 46 shows an expanded expression profile of the GBP HGBPBMY4 (FLJ10961). The figure illustrates the relative expression level of HGBPBMY4 amongst various mRNA tissue sources. FIG. 46 also illustrates the relative expression level of HGBPBMY4 amongst various mRNA tissue sources isolated from normal and diseased tissues. As shown, the HGBPBMY4 polypeptide showed increased expression in spinal cord from multiple sclerosis patients compared to controls; increased expression in putamen and caudate from Parkinson's patients compared to controls; high expression in normal and diseased thryroid. Increased expression in breast and testicle tumors relative to controls. Expression data was obtained by measuring the steady state HGBPBMY4 mRNA levels by quantitative PCR using the PCR primer pair provided as SEQ ID NO:70 and 71, and TAQMAN probe (SEQ ID NO:72) as described in Example 39 herein.

Figure 47:
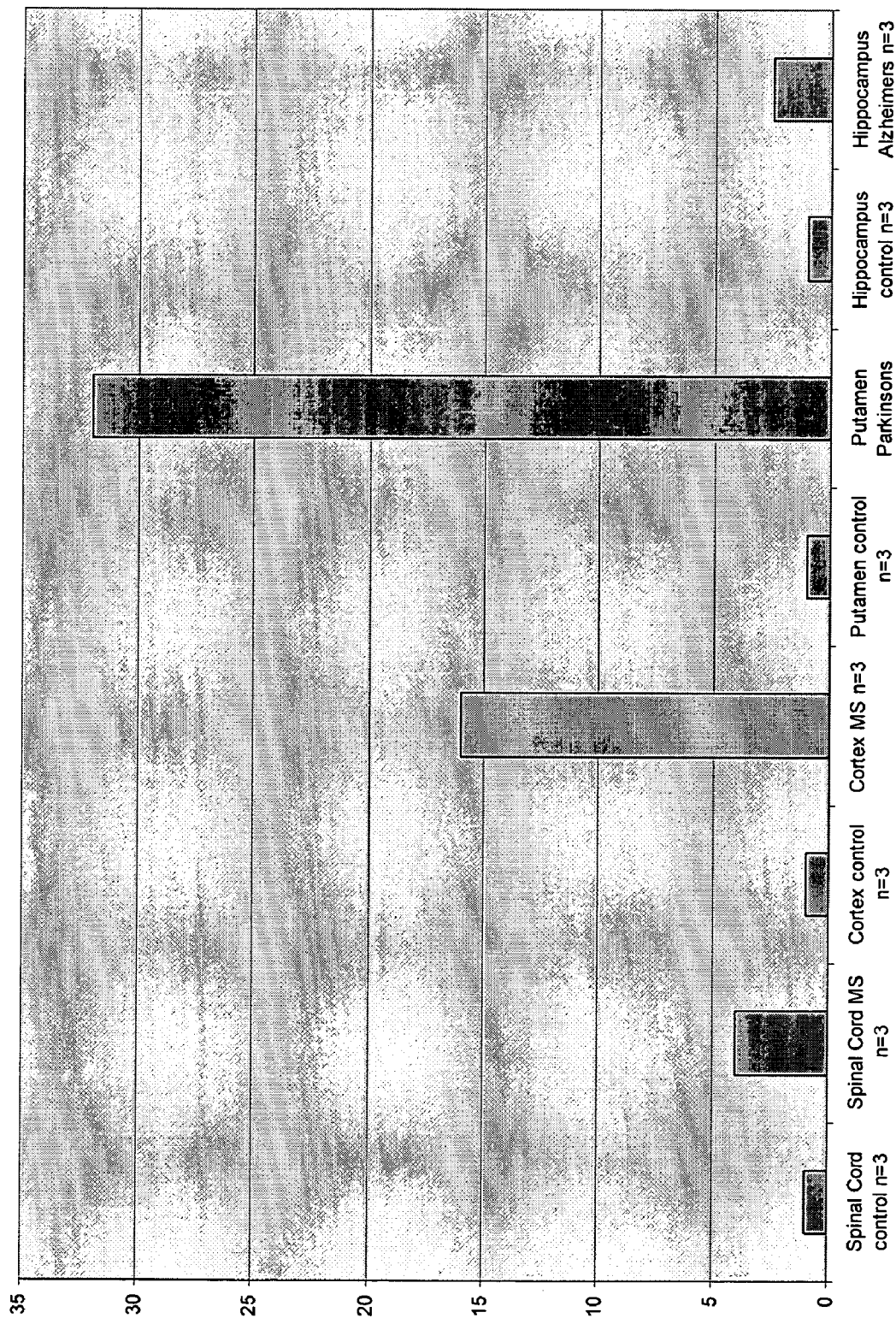

FIG. 47 shows an expanded expression profile of human GBP1 (GenBank Ref. No. NM_002053). The figure illustrates the relative expression level of GBP1 amongst various mRNA tissue sources. FIG. 47 also illustrates the relative expression level of GBP1 amongst various mRNA tissue sources isolated from normal and dieased tissues. As shown, the GBP1 polypeptide showed increased expression in spinal cord and brain cortex from multiple sclerosis patients relative to controls; increased expression in putamen from Parkinson's patients relative to controls; increased expression in hippocampus from Alzheimer's patients relative to controls. Expression data was obtained by measuring the steady state GBP1 mRNA levels by quantitative PCR using the PCR primer pair provided as SEQ ID NO:73 and 74, and TAQMAN probe (SEQ ID NO:75) as described in Example 40 herein.

Figure 48:
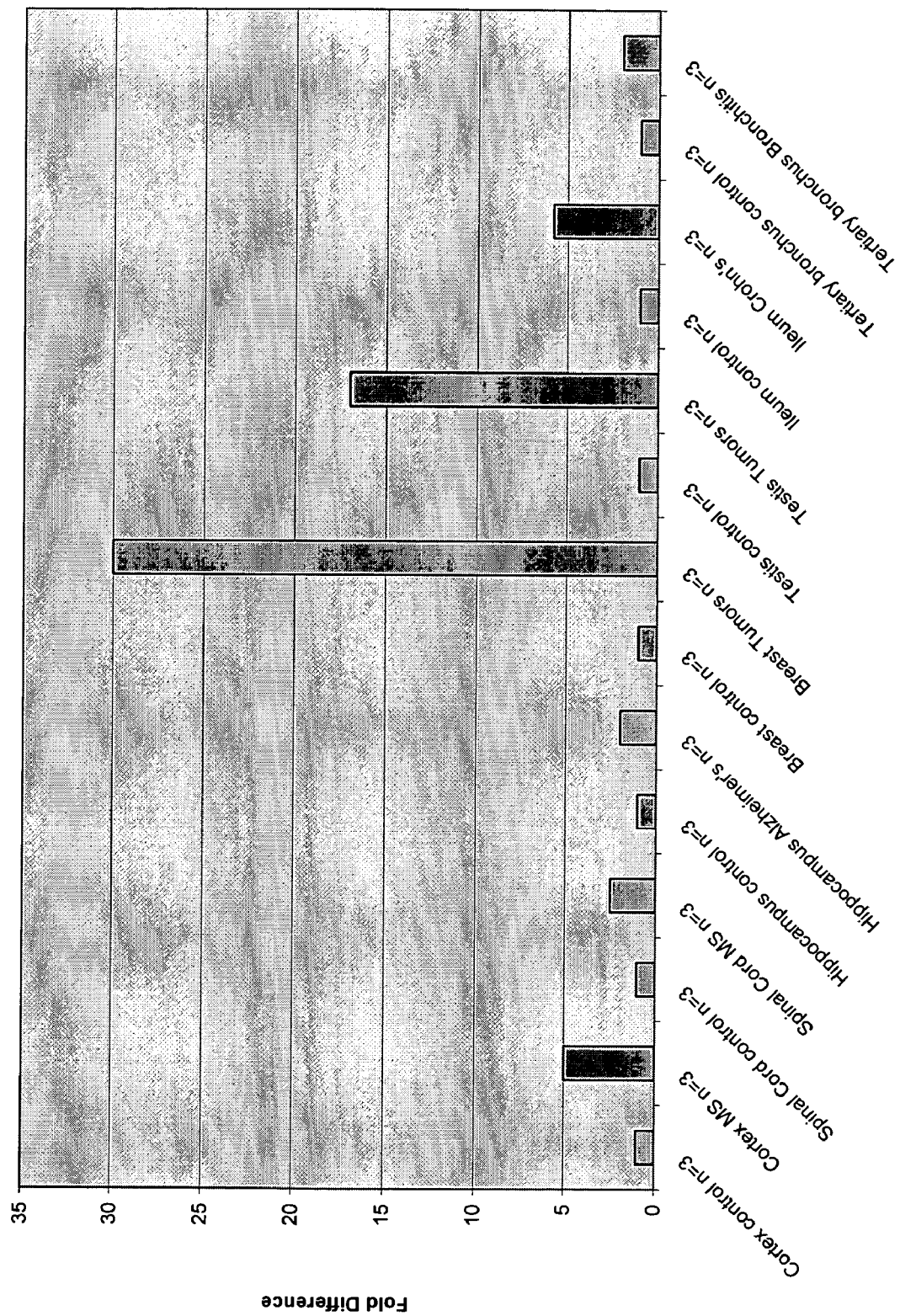

FIG. 48 shows an expanded expression profile of human GBP5 (GenBank Ref. No. NM_052942). The figure illustrates the relative expression level of GBP5 amongst various mRNA tissue sources. FIG. 48 also illustrates the relative expression level of GBP5 amongst various mRNA tissue sources isolated from normal and tumor tissues. As shown, the GBP5 polypeptide showed increased expression in cortex and spinal cord of multiple sclerosis patients relative to controls; increased expression in hippocampus form Alzheimer's patients relative to controls. Expression data was obtained by measuring the steady state GBP5 mRNA levels by quantitative PCR using the PCR primer pair provided as SEQ ID NO:76 and 77, and TAQMAN probe (SEQ ID NO:78) as described in Example 41 herein.

Figure 49:
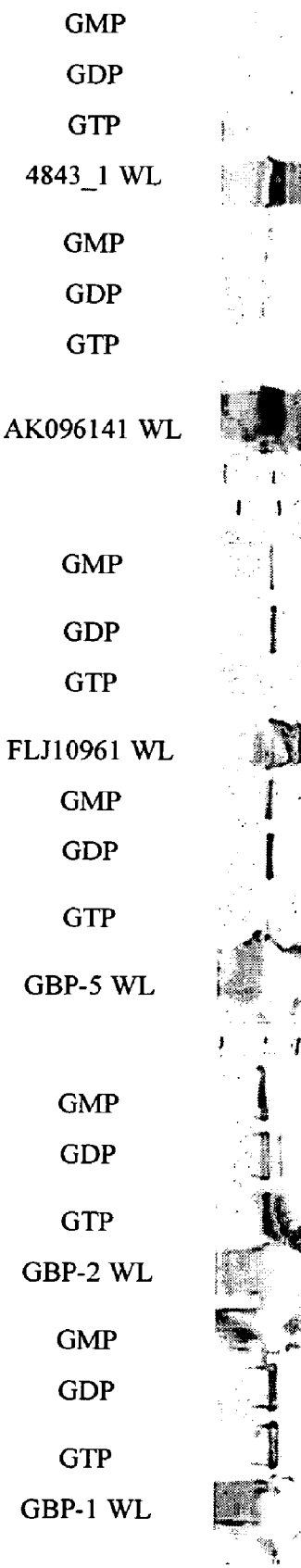

FIG. 49 is a a western blot depicting guanine nucleotide binding by the GBP family members described herein.

FIG. 50A is a western blot depicting the knockdown in GBP-1 and GBP-2 expression observed when GBP-1 and GBP-2 were coexpressed with siRNAs targeting these genes (siRNA 1-3 corresponds to GBP-1 and siRNA 582 corresponds to GBP-2).

Figure 50B:
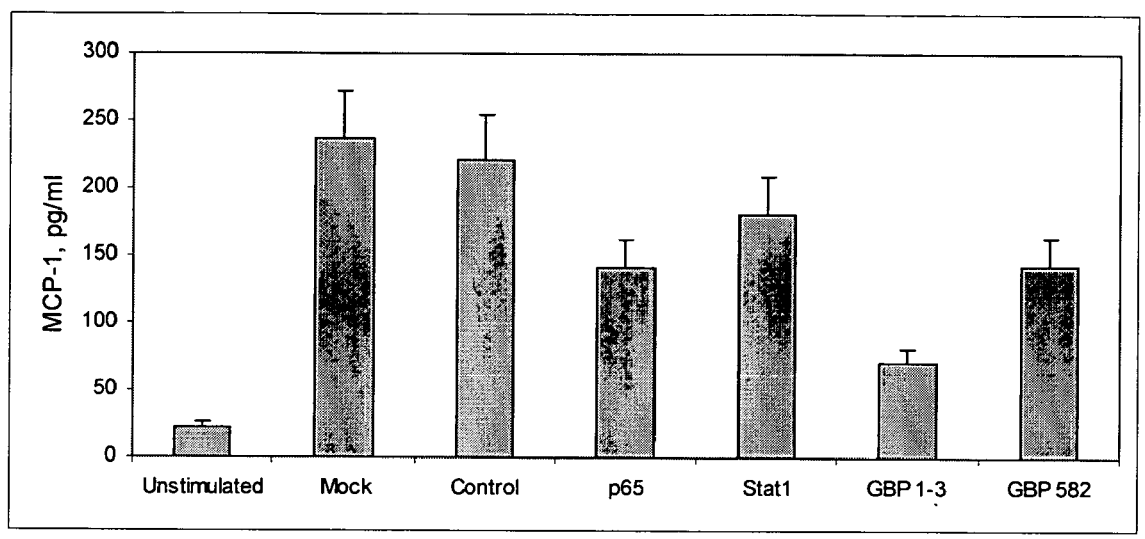

FIG. 50B is a bar graph depicting TNFα-induced MCP-1 expression in HUVECs transfected with siRNAs 1-3 (targeted to GBP-1) and 582 (targeted to GBP-2).

DETAILED DESCRIPTION OF THE INVENTION

The similar expression and induction patterns of the known GBP family members offered the possibility that the genes might share common regulatory elements. It was first determined whether the genes were localized to a similar region of the chromosome. In this process, four new members of the GBP family were identified in humans, and four new members were identified in the mouse. It was previously demonstrated that GBP-1 and GBP-5 expression is elevated in the synovium derived from rheumatoid arthritis subjects as compared to osteoarthritis subjects or normal control joints (U.S. patent application Ser. No. 10/308,279, incorporated herein by reference). It was also determined that expression of both GBP-1 and GBP-5 can be regulated by NF-κB. Aberrant activation of NF-κB has also been associated with rheumatoid arthritis (Marok et al., (1996) *Arthritis Rheum.* 39:583–591). These data suggest that members of the GBP family might be involved in the development of autoimmune diseases such as rheumatoid arthritis. They therefore represent candidate therapeutic targets and biomarkers for these diseases and other diseases associated with aberrant NF-kB activity. Thus, the present invention provides novel human sequences that encode guanylate binding proteins. Such proteins have been implicated in a number of diseases and/or disorders, which are known in the art or described herein.

Definitions

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or less (e.g., ±15%, ±10%, ±7%, ±5%, ±4%, ±3%, ±2%, ±1%, or ±0.1%) from the specified amount, as such variations are appropriate.

As used herein, the terms "amino acid" and "amino acid residue" are used interchangeably and mean any of the twenty naturally occurring amino acids. An amino acid is formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature abbreviations for amino acid residues are shown in tabular form presented hereinabove.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues, or a covalent bond to an amino-terminal group, such as $NH_2$, to an acetyl group or to a carboxy-terminal group, such as COOH.

As used herein, the term "antibody" refers to immunoglobulin molecules and immunologically active portions of immunoglobulin molecules, i.e., molecules that contain an antigen binding site that immunospecifically binds an antigen. Immunoglobulin molecules of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) includes intact molecules, as well as antibody fragments (such as, for example, Fab and F(ab')₂ fragments) that are capable of specifically binding to protein. Fab and F(ab')₂ fragments lack the Fc fragment of intact antibody, clear more rapidly from the circulation of the animal or plant, and can have less non-specific tissue binding than an intact antibody (Wahl et al., (1983) *J. Nucl. Med.* 24:316–325). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')₂, Fd, single-chain Fvs (scFv), single-chain antibodies, disulfide-linked Fvs (sdFv) and fragments comprising either a VL or VH domain. Antigen-binding antibody fragments, including single-chain antibodies, can comprise the variable region(s) alone or in combination with the entirety or a portion of the following: hinge region, CH1, CH2, and CH3 domains. Also included in the present invention are antigen-binding fragments also comprising any combination of variable region(s) with a hinge region, CH1, CH2, and CH3 domains. The antibodies of the present invention can be from any animal origin including birds and mammals. Antibodies of the present invention can be, for example, human, murine (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from transgenic animals for one or more human immunoglobulin and that do not express endogenous immunoglobulins, as described herein and, for example in, U.S. Pat. No. 5,939,598.

As used herein, the term "biological activity" means any observable effect flowing from a guanylate binding protein. Representative, but non-limiting, examples of biological activity in the context of the present invention includes guanylate binding ability and GTPase activity.

As used herein, the terms "cells," "host cells" or "recombinant host cells" are used interchangeably and mean not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the terms "chimeric protein" and "fusion protein" are used interchangeably and mean a fusion of a first amino acid sequence encoding a GBP polypeptide with a second amino acid sequence defining a polypeptide domain foreign to, and not homologous with, a GBP polypeptide. A chimeric protein can present a foreign domain that is found in an organism that also expresses the first protein, or it can be an "interspecies" or "intergenic" fusion of protein structures expressed by different kinds of organisms. In general, a fusion protein can be represented by the general formula X-GBP-Y, wherein GBP represents a portion of the protein which is derived from a GBP polypeptide, and X and Y are independently absent or represent amino acid sequences which are not related to a GBP sequence in an organism, which includes naturally occurring mutants. Analogously, the term "chimeric gene" refers to a nucleic acid construct that encodes a "chimeric protein" or "fusion protein" as defined herein.

As used herein the term "complementary" means a nucleic acid sequence that is capable of base-pairing according to the standard Watson-Crick complementarity rules. These rules generally hold that the larger purines will always base pair with the smaller pyrimidines to form only combinations of Guanine paired with Cytosine (G:C) and Adenine paired with either Thymine (A:T) in the case of DNA, or Adenine paired with Uracil (A:U) in the case of RNA.

As used herein, the term "DNA segment" means a DNA molecule that has been isolated free of total genomic DNA of a particular species. In one embodiment, a DNA segment encoding a guanylate binding protein refers to a DNA segment that comprises a sequence disclosed herein (e.g., a sequence selected from the group consisting of SEQ ID NOs: 2, 4, 6, 8, 10, 12, 14, and 16), but can optionally comprise fewer or additional nucleic acids, yet is isolated away from, or purified free from, total genomic DNA of a source species. Included within the scope of the term "DNA segment" are DNA segments and smaller fragments of such segments, as well as recombinant vectors, including, for example, plasmids, cosmids, phages, viruses, and the like, and primers and probes, such as those represented in SEQ ID NOs:1–59.

The term "epitope" as used herein, refers to a portion of a polypeptide having antigenic or immunogenic activity in an animal, preferably a mammal, and most preferably in a human. In a representative embodiment, the present invention encompasses a polypeptide comprising an epitope, as well as the polynucleotide encoding the polypeptide. An "immunogenic epitope" as used herein, is defined as a portion of a protein that elicits an antibody response in an animal, as determined by any method known in the art, for example, by the methods for generating antibodies described herein (see, for example, Geysen et al., (1983) *Proc. Natl. Acad. Sci. U.S.A.* 81:3998–4002). The term "antigenic epitope" as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

As used herein, the term "expression" generally refers to the cellular processes by which a polypeptide is produced from RNA.

As used herein, the term "GBP" means nucleic acids encoding a functional guanylate binding protein. The term "GBP" includes homologs. "GBP" further includes vertebrate homologs of GBP family members.

As used herein, the terms "GBP gene" and "recombinant GBP gene" mean a nucleic acid molecule comprising an open reading frame encoding a GBP polypeptide of the present invention, including both exon and (optionally) intron sequences.

As used herein, the terms "GBP gene product", "GBP protein", "GBP polypeptide", and "GBP peptide" are used interchangeably and mean peptides having amino acid sequences that are substantially identical to native amino acid sequences from an organism of interest and which are biologically active in that they comprise all or a part of the amino acid sequence of a GBP polypeptide, or cross-react with antibodies raised against a GBP polypeptide, or retain all or some of the biological activity (e.g., guanylate binding ability and GTPase activity) of the native amino acid sequence or protein. Such biological activity can include immunogenicity.

As used herein, the terms "GBP gene product", "GBP protein", "GBP polypeptide", and "GBP peptide" also include analogs of a GBP polypeptide. By "analog" is intended that a DNA or amino acid sequence can contain alterations relative to the sequences disclosed herein, yet retain all or some of the biological activity of those sequences. Analogs can be derived from genomic nucleotide sequences as are disclosed herein or from other organisms, or can be created synthetically. Those of ordinary skill in the art will appreciate that other analogs as yet undisclosed or undiscovered can be used to design and/or construct GBP analogs. There is no need for a "GBP gene product", "GBP protein", "GBP polypeptide", or "GBP peptide" to comprise all or substantially all of the amino acid sequence of a GBP polypeptide gene product. Shorter or longer sequences are anticipated to be of use in the present invention; shorter sequences are herein referred to as "segments". Thus, the terms "GBP gene product", "GBP protein", "GBP polypeptide", and "GBP peptide" also include fusion, chimeric or recombinant GBP polypeptides and proteins comprising sequences of the present invention. Methods of preparing such proteins are disclosed herein and/or are known in the art.

As used herein, the term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

As used herein, the term "hybridization" and grammatical derivations thereof means the binding of a molecule (e.g., a probe molecule, such as a molecule to which a detectable moiety has been bound), to a target sample (e.g., a target nucleic acid). The terms "hybridization" and "binding" are used interchangeably in the context of probes and denatured DNA. Probes that are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

As used herein, the term "hybridization techniques" refers to molecular biological techniques that involve the binding or hybridization of a probe to complementary sequences in a polynucleotide. Included among these techniques are northern blot analysis, Southern blot analysis, nuclease protection assay, etc.

As used herein, the terms "isolated" and "purified" are used interchangeably and refers to material (e.g., a nucleic acid or a protein) removed from its original environment (e.g., the natural environment, if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide and/or protein sequences of the present invention.

As used herein, the term "modified" means an alteration from an entity's normally occurring state. An entity can be modified by removing discrete chemical units or by adding discrete chemical units. The term "modified" encompasses detectable labels as well as those entities added as aids in purification.

As used herein the terms "modulate" and grammatical derivations thereof refer to an increase or decrease in the amount, quality or effect of a particular activity, DNA, RNA, or protein. The definition of "modulate" as used herein is meant to encompass agonists and/or antagonists of a particular activity, DNA, RNA, or protein.

Thus, as used herein, the term "modulate", and grammatical derivations thereof, means an increase, decrease, or other alteration of any and/or all chemical and biological activities or properties mediated by a nucleic acid sequence or a peptide. The term "modulation" as used herein refers to both upregulation (i.e., activation or stimulation) and downregulation (i.e. inhibition or suppression) of a response by any mode of action.

As used herein, the terms "nucleotide", "base" and "nucleic acid" are used interchangeably and are equivalent.

Additionally, the terms "nucleotide sequence", "nucleic acid sequence", "nucleic acid molecule" and "segment" are used interchangeably and are equivalent. The terms "nucleotide", "base", "nucleic acid", "nucleotide sequence", "nucleic acid sequence", "nucleic acid molecule" and "segment" mean any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., $\alpha$-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, allkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocylcic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

As used herein, the terms "oligonucleotide" and "polynucleotide" are used interchangeably and mean a single- or double-stranded DNA or RNA sequence. Typically, an oligonucleotide is a short segment of about 50 or less nucleotides. An oligonucleotide or a polynucleotide can be naturally occurring or synthetic, but oligonucleotides are typically prepared by synthetic means. In the context of the present invention, an "oligonucleotide" and/or a "polynucleotide" includes segments of DNA, and/or their complements. The segments can be, for example, between 1 and 250 bases, and, in some embodiments, between 5–10, 5–20, 10–20, 10–50, 20–50, 10–100 bases, or 100 or more bases in length.

The terms "oligonucleotide" and "polynucleotide" refer to a molecule comprising two or more nucleotides. For example, a polynucleotide can comprise a nucleotide sequence of a full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide", defined further herein, refers to a molecule having the translated amino acid sequence generated directly or indirectly from a polynucleotide. A "polynucleotide" of the present invention also includes those polynucleotides capable of hybridizing, under stringent hybridization conditions (examples of which are provided herein), to sequences described herein, or the complement thereof.

Thus, an oligonucleotide or a polynucleotide of the present invention can comprise any polyribonucleotide or polydeoxribonucleotide, and can comprise unmodified RNA or DNA or modified RNA or DNA. For example, a polynucleotide can comprise single- and double-stranded DNA, DNA that is a mixture of single- and double-stranded regions, single- and double-stranded RNA, RNA that is mixture of single- and double-stranded regions, hybrid molecules comprising DNA and RNA that can be single-stranded or, more typically, double-stranded or a mixture of single- and double-stranded regions. In addition, a polynucleotide can comprise triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

By employing the disclosure presented herein, a nucleic acid molecule of the present invention encoding a polypeptide of the present invention can be obtained using standard cloning and screening procedures, such as those for cloning cDNAs using mRNA as starting material.

Thus, the term "polynucleotide" encompasses a molecule having a nucleic acid sequence contained in SEQ ID NO:1, SEQ ID NO:2, SEQ ID NO:4, SEQ ID NO:6, SEQ ID NO:8, SEQ ID NO:10, SEQ ID NO:12, SEQ ID NO:14 and/or SEQ ID NO:16, or the cDNA contained within a clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" broadly refers to a molecule having a translated amino acid sequence generated from a polynucleotide.

As used herein, the terms "organism", "subject" and "subject" are used interchangeably and mean any organism referenced herein, including prokaryotes, though the terms preferably refer to eukaryotic organisms, more preferably to mammals, and most preferably to humans.

As used herein, the terms "protein", "polypeptide" and "peptide" are used interchangeably and mean any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. The terms "protein", "polypeptide" and "peptide" are used interchangeably herein.

Thus, a polypeptide of the present invention can comprise amino acids joined to each other by peptide bonds or modified peptide bonds, i.e., peptide isosteres, and can contain amino acids other than the 20 gene-encoded amino acids. A polypeptide can be modified by either natural processes, such as by posttranslational processing, or by chemical modification techniques which are well known in the art. Such modifications are described in basic texts and in more detailed monographs, as well as in research literature known to those of ordinary skill in the art. Modifications can occur anywhere in a polypeptide, including the peptide backbone, the amino acid side-chains and the amino or carboxyl termini. The same type of modification can be present in the same or varying degrees at several sites in a given polypeptide. Also, a given polypeptide can contain many types of modifications. A polypeptide can be branched, for example, as a result of ubiquitination, or a polypeptide can be cyclic, with or without branching.

Cyclic, branched, and branched cyclic polypeptides can result from posttranslation natural processes or can be made by synthetic methods. Representative modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., Creighton, *Proteins—Structure And Molecular Properties,* 2nd ed., W. H. Freeman and Company, New York, N.Y., USA (1993); *Posttranslational Covalent Modification Of Proteins,* (Johnson, ed.), Academic Press, New York, N.Y., USA, pp. 1–12 (1983); Seifter et al., (1990) *Method Enzymol.* 182:626–646; Rattan et al., (1992) *Ann. N.Y. Acad. Sci.* 663:48–62).

As used herein, "a polypeptide having biological activity" refers to a polypeptide exhibiting activity similar, but not necessarily identical to, an activity of a polypeptide of the present invention, including mature forms, as measured in a particular biological assay, with or without dose dependency. In a case where dose dependency does exist, it need not be identical to that of the polypeptide, but rather substantially similar to the dose-dependence in a given activity as compared to a polypeptide of the present invention (i.e., a candidate polypeptide will exhibit greater activity of not more than about 25-fold less and, preferably, not more than about ten-fold less activity, and most preferably, not more than about three-fold less activity relative to a polypeptide of the present invention.)

As used herein, the term "primer" means a single-stranded oligonucleotide sequence that acts as a point of initiation for template-directed DNA synthesis under appropriate conditions (e.g., in the presence of four different nucleoside triphosphates and an agent for polymerization, such as DNA or RNA polymerase or reverse transcriptase) in a suitable buffer and at a suitable temperature. The appropriate length of a primer can depend on the intended use of the primer, but typically ranges from to nucleotides. Short primer molecules generally require cooler temperatures to form sufficiently stable hybrid complexes with the template. A primer need not reflect the exact sequence of the template, but is preferably sufficiently complementary to hybridize with a template. The term primer site refers to the area of the target DNA to which a primer hybridizes. The term "primer pair" refers to a set of primers comprising a 5' (upstream) primer that hybridizes with the 5' end of the DNA sequence to be amplified and a 3' (downstream) primer that hybridizes with the complement of the 3' end of the sequence to be amplified. A primer can comprise, for example, two or more deoxyribonucleotides or ribonucleotides, more than three deoxyribonucleotides or ribonucleotides, more than eight deoxyribonucleotides or ribonucleotides or at least about 20 deoxyribonucleotides or ribonucleotides of an exonic or intronic region. Such oligonucleotides can be, for example, between ten and thirty bases in length.

As used herein, the term "probe" refers to an oligonucleotide or short fragment of DNA designed, known or suspected to be sufficiently complementary to a sequence in a denatured nucleic acid to be probed and to be bound under selected stringency conditions.

Continuing, in one embodiment a probe is a hybridization probe; such a probe can be an oligonucleotide that binds, in a base-specific manner, to a complementary strand of nucleic acid. Such probes include peptide nucleic acids, such as described for example in Nielsen et al., (1991) *Science* 254:1497–1500. A probe can be of any length suitable for specific hybridization to the target nucleic acid sequence. The most appropriate length of the probe can vary, depending upon the hybridization method in which it is being used; for example, particular lengths might be more appropriate for use in microfabricated arrays, while other lengths might be more suitable for use in classical hybridization methods. Such optimizations will be known to the skilled artisan upon consideration of the present disclosure. Representative probes and primers can range from about 5 nucleotides to about 40 nucleotides in length. For example, probes and primers can be 5, 6, 8, 10, 12, 14, 16, 18, 20, 22, 24, 25, 26, or 40 nucleotides in length. In some embodiments, the probe or primer overlaps at least one polymorphic site occupied by any of the possible variant nucleotides. The nucleotide sequence can correspond to the coding sequence of the allele or to the complement of the coding sequence of the allele.

As used herein, the term "recombination" and grammatical derivations thereof, means a re-assortment of genes or characters in combinations different from what they were in the parents, in the case of linked genes by crossing over.

As used herein, the term "related," when used in connection with a particular amino acid sequence means a sequence comprising the described sequence, as well as fragments thereof, functional equivalents. Thus, for example, the term "MGBPBMY4 (BC007143)-related polypeptide" encompasses a polypeptide sequence comprising MGBPBMY4 (BC007143), fragments of MGBPBMY4 (BC007143) (examples of which are provided herein) and polypeptides that are functionally equivalent to a MGBPBMY4 (BC007143) polypeptide.

As used herein, the term "sequencing" means determining the ordered linear sequence of nucleic acids or amino acids of a DNA, RNA or protein target sample, using manual or automated laboratory techniques. Unless otherwise indicated, the nucleotide sequence of all DNA sequences disclosed herein can be determined by employing an automated DNA sequencer (such as the Model 373 available from Applied Biosystems, Inc., Foster City, Calif., USA). All amino acid sequences of polypeptides encoded by DNA molecules disclosed herein can be predicted by translating a DNA sequence, or alternatively, by employing a known protein technique (e.g., Edman degradation).

As used herein, the term "stringent hybridization conditions", in the context of nucleic acid hybridization experiments such as Southern and northern blot analysis, means a set of conditions under which single stranded nucleic acid sequences are unlikely to hybridize to one another unless there is substantial complementarity between the sequences. Stringent hybridization conditions can be both sequence- and environment-dependent. Longer sequences hybridize specifically at higher temperatures. An extensive guide to the hybridization of nucleic acids is found in Tijssen, *Laboratory Techniques in Biochemistry and Molecular Biology-Hybridization with Nucleic Acid Probes*, Elsevier, New York, N.Y., USA, (1993), part I, chapter 2. Generally, highly stringent hybridization and wash conditions are selected to be about 5° C. lower than the thermal melting point ($T_m$) for the specific sequence at a defined ionic strength and pH.

Typically, under "stringent conditions" a probe will hybridize specifically to its target subsequence, but to no other sequences.

Continuing, the $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or northern blot analysis of complementary nucleic acids having more than about 100 complementary residues is overnight hybridization in 50% formamide with 1 mg of heparin at 42° C. An example of highly stringent wash conditions is 15 minutes in 0.15 M NaCl at 65° C. An example of stringent wash conditions is 15 minutes in 0.2×SSC buffer at 65° C. (see, e.g., Sambrook et al., *Molecular Cloning: A Laboratory Manual*, ($3^{rd}$ ed.) Cold Spring Harbor Laboratory Press, Cold Spring Harbor, N.Y., USA (2001) for a description of SSC buffer). Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4–6×SSC at 40° C. For short probes (e.g., about 10 to about 50 nucleotides), stringent conditions typically involve salt concentrations of less than about 1.0 M Na$^+$ ion, typically about 0.01 to 1.0 M Na$^+$ ion concentration (or other salts) at pH 7.0–8.3, and the temperature is typically at least about 30° C. Stringent conditions can also be achieved with the addition of destabilizing agents such as formamide. In general, a signal to noise ratio of 2-fold (or higher) than that observed for an unrelated probe in a particular hybridization assay indicates the presence of a specific hybridization.

The following are representative, but non-limiting, examples of stringent hybridization and wash conditions that can be employed in a hybridization-based operation (e.g., to clone homologous nucleotide sequences that are substantially identical to reference nucleotide sequences of the present invention): in one example, a probe nucleotide sequence hybridizes to a target nucleotide sequence in 7% sodium dodecyl sulfate (SDS), 0.5 M NaPO$_4$, 1 mM EDTA at 50° C. followed by washing in 2×SSC, 0.1% SDS at 50° C.; in another example, a probe and target sequence hybridize in 7% sodium dodecyl sulfate (SDS), 0.5 M NaPO$_4$, 1 mM EDTA at 50° C. followed by washing in 1×SSC, 0.1% SDS at 50° C.; in yet another example, a probe and target sequence hybridize in 7% sodium dodecyl sulfate (SDS), 0.5 M NaPO$_4$, 1 mM EDTA at 50° C. followed by washing in 0.5×SSC, 0.1% SDS at 50° C.; in a further example, a probe and target sequence hybridize in 7% sodium dodecyl sulfate (SDS), 0.5 M NaPO$_4$, 1 mM EDTA at 50° C. followed by washing in 0.1×SSC, 0.1% SDS at 50° C.; in yet a further example, a probe and target sequence hybridize in 7% sodium dodecyl sulfate (SDS), 0.5 M NaPO$_4$, 1 mM EDTA at 50° C. followed by washing in 0.1×SSC, 0.1% SDS at 65° C.

In yet another example of stringent conditions, hybridization is carried out with 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68° C. For the purposes of specifying additional conditions of high stringency, conditions can comprise, for example, a salt concentration of about 200 mM and temperature of about 45° C. One example of such stringent conditions is hybridization at 4×SSC, at 65° C., followed by washing in 0.1×SSC at 65° C. for one hour.

Another example stringent hybridization scheme uses 50% formamide, 4×SSC at 42° C. The above are only exemplary and additional high stringency conditions will be known to those of ordinary skill in the art upon consideration of the present disclosure.

As used herein, the term "substantially pure" means that a polynucleotide or polypeptide of interest is substantially free of the sequences and molecules with which it is associated in its natural state, as well as those molecules used in a given isolation or synthesis procedure. The term "substantially free" means that the sample is at least 50%, preferably at least 70%, more preferably 80% and most preferably 90% free of the materials and compounds with which is it associated in nature or in a medium in which the polynucleotide or polypeptide of interest is synthesized.

As used herein, the term "toxin" means a compound that binds and activates endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that can be used according to the methods of the present invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin.

As used herein, the term "transcription" means a cellular process involving the interaction of an RNA polymerase with a gene that directs the expression as RNA of the structural information present in the coding sequences of the gene. The process comprises, but is not limited to, the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

As used herein, the term "vector" means a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of an SREBP1 polypeptide, as described further herein. Some representative vectors include, but are not limited to, pCMV (Invitrogen, Carlsbad, Calif., USA) pBluescript (Stratagene, La Jolla, Calif., USA), pUC18, pBLCAT3 (Luckow & Schutz, (1987) *Nucleic Acids Res* 15: 5490), pLNTK (Gorman et al., (1996) *Immunity* 5: 241–252), and pBAD/gIII (Stratagene, La Jolla, Calif.).

Nucleic Acids of the Present Invention

In specific embodiments, the polynucleotides of the present invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the present invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the present invention do not contain the coding sequence of more than 1000, 500, 250, 100, 50, 25, 20, 15, 10, 5, 4, 3, 2, or 1 genomic flanking gene(s).

In the present invention, the full length sequences identified as SEQ ID NO:2, SEQ ID NO:4, SEQ ID NO:6, SEQ ID NO:8, SEQ ID NO:10, SEQ ID NO:12, SEQ ID NO:14 and/or SEQ ID NO:16 were generated by BLAST searches of genomic DNA.

Unless otherwise indicated, all nucleotide sequences determined by sequencing a DNA molecule herein were determined using an automated DNA sequencer (such as the Model 373, or a Model 3700, from Applied Biosystems, Inc., Foster City, Calif., USA), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein might contain an error. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–1C (SEQ ID NO:2), FIGS. 2A–2C (SEQ ID NO:4), FIGS. 3A–3B (SEQ ID NO:6), FIGS. 4A–4C (SEQ ID NO:8), FIGS. 5A–5C (SEQ ID NO:10), FIGS. 6A–6B (SEQ ID NO:12), FIGS. 7A–7C (SEQ ID NO:14), FIGS. 8A–8D (SEQ ID NO:16), a nucleic acid molecule of the present invention encoding the HGBPBMY1 (AK096141), HGBPBMY2 (4843 30 1 1; 4843__ 1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (SEQ ID Nos: 3, 5, 7, 9, 11, 13, 15, and 17, respectively) can be obtained using standard cloning and screening procedures, such as those for cloning cDNAs using mRNA as starting material. Illustrative of the present invention, the nucleic acid molecules described in FIGS. 1A–1C (SEQ ID NO:2), FIGS. 2A–2C (SEQ ID NO:4), FIGS. 3A–3B (SEQ ID NO:6), FIGS. 4A–4C (SEQ ID NO:8), FIGS. 5A–5C (SEQ ID NO:10), FIGS. 6A–6B (SEQ ID NO:12), FIGS. 7A–7C (SEQ ID NO:14), FIGS. 8A–8D (SEQ ID NO:16), were discovered in Human Multiple Tissue and Human Immune System MTC cDNA panels and a mouse–1 cDNA panel (Clontech, Palo Alto, Calif., USA).

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young, (1995) *Mol. Endocrinol.* 9(10): 1321–9; and Ozenberger and Young, (1995) *Ann. N.Y. Acad. Sci.* 766:279–81).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

Also, in preferred embodiments the present invention provides methods for further refining the biological function of the polynucleotides and/or polypeptides of the present invention.

Specifically, the present invention provides methods for using the polynucleotides and polypeptides of the present invention to identify orthologs, homologs, paralogs, variants, and/or allelic variants of the present invention. Also provided are methods of using the polynucleotides and polypeptides of the present invention to identify the entire coding region of the present invention, non-coding regions of the present invention, regulatory sequences of the present invention, and secreted, mature, pro-, prepro-, forms of the present invention (as applicable).

In some embodiments, the present invention provides methods for identifying glycosylation sites inherent in the polynucleotides and polypeptides of the present invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Present Invention

The following paragraphs provide additional details regarding the various polynucleotide and polypeptide sequences that form aspects of the present invention.

Features of the Polypeptide Encoded by Gene No. 1

The polypeptide encoded by this gene, HGBPBMY1 (AK096141), is provided as SEQ ID NO:3 (FIGS. 1A–1C) and is encoded by the polynucleotide sequence according to SEQ ID NO:3 (FIGS. 1A–1C) and/or by a polynucleotide contained within the deposited clone. HGBPBMY1 (AK096141) has significant homology at the nucleotide and amino acid level to a number of guanylate binding proteins, which include, for example, human GBP-1, human GBP-2, human GBP-3 and human GBP-4.

The determined nucleotide sequence of the HGBPBMY1 (AK096141), (i.e. the cDNA shown in FIGS. 1A–1C and in SEQ ID NO:2) comprises an open reading frame encoding a protein of about 638 amino acid residues. The predicted amino acid sequence of the HGBPBMY1 (AK096141) polypeptide is shown in FIGS. 1A–1C (SEQ ID NO:3). The percent identity and similarity values between the HGBPBMY1 (AK096141) polypeptide to the known GBP family member hGBP1 is provided in FIG. 9. The HGBPBMY1 (AK096141) protein shown in FIGS. 1A–1C was determined to share significant identity and similarity to several known GBP family members, as shown in FIG. 11A–11G.

Figure 18:
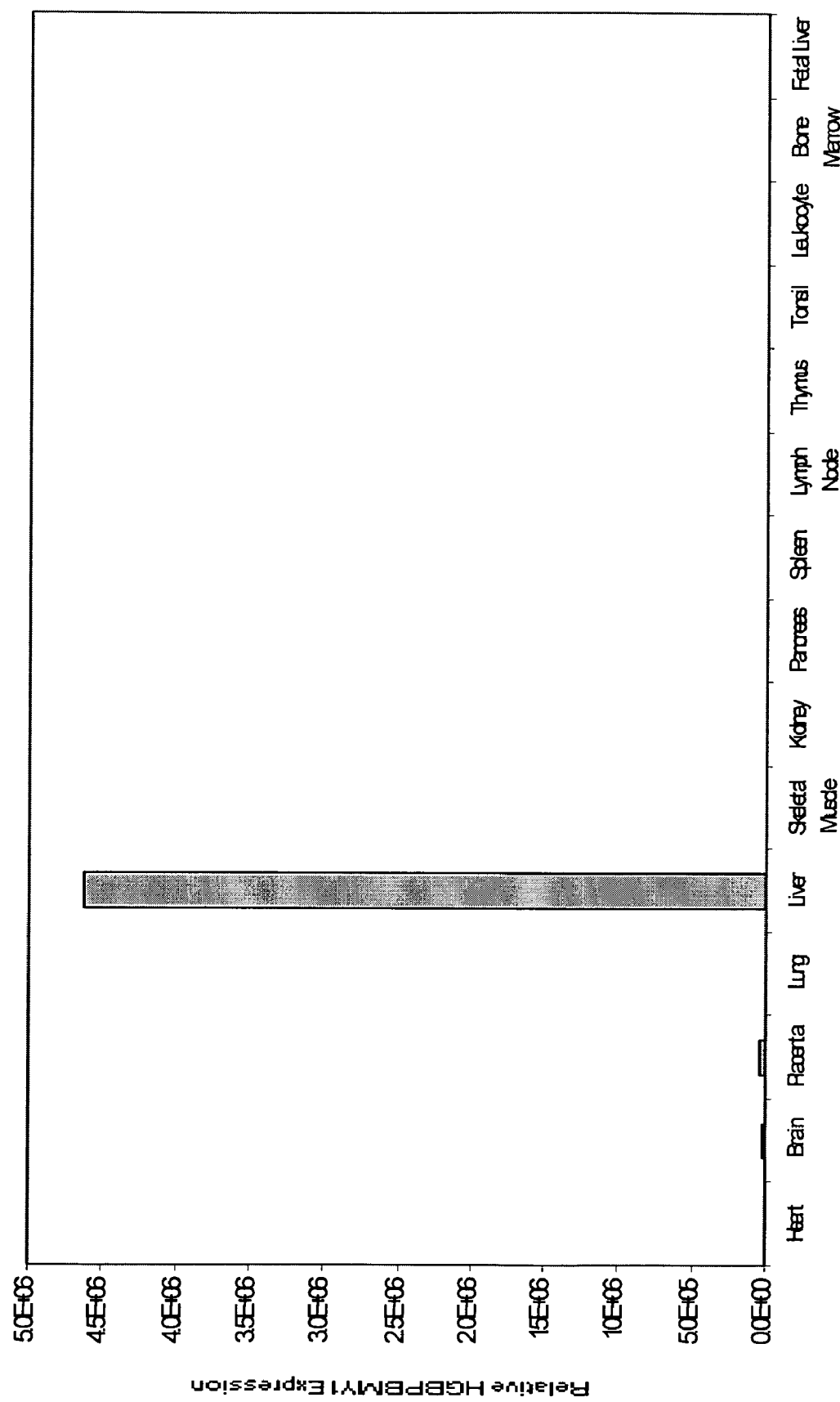
FIG. 18 is bar graph depicting the tissue expression pattern of human HGBPBMY1 (AK096141). Panels of cDNAs derived from normal and immune tissue were analyzed by Real Time PCR for expression of HGBPBMY1 (AK096141).

Expression profiling designed to measure the steady state mRNA levels encoding a HGBPBMY1 (AK096141) polypeptide showed expression predominantly in the liver (See FIG. 18).

Based upon the strong homology to members of the GBP family members, a HGBPBMY1 (AK096141) polypeptide is expected to share at least some biological activity with GBP family members, specifically hGBP-1, hGBP-2, hGBP-3 and hGBP-4.

The HGBPBMY1 (AK096141) polynucleotides and polypeptides of the present invention, including agonists and/or fragments thereof, may have uses that include detecting, prognosing, treating, preventing, and/or ameliorating at least diseases and conditions of the liver.

The HGBPBMY1 (AK096141) polynucleotides and polypeptides of the present invention, including agonists and/or fragments thereof, may have uses that include modulating signal transduction activity, in various cells, tissues, and organisms, and particularly in mammalian tissue, preferably human tissue.

The strong homology to human GBP family members, particularly hGBP-1, hGBP-2, hGBP-3 and hGBP-4, combined with the predominately localized HGBPBMY1 (AK096141) expression in liver tissue suggests a potential utility for HGBPBMY1 (AK096141) polynucleotides and polypeptides in treating, diagnosing, prognosing, and/or preventing liver diseases. In representative embodiments, HGBPBMY1 (AK096141) polynucleotides and polypeptides including agonists and fragments thereof, may have uses that include treating, diagnosing, prognosing, and/or preventing liver diseases. For example, the HGBPBMY1 (AK096141) protein can be used for the detection, treatment, amelioration, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, HGBPBMY1 (AK096141) polynucleotides and polypeptides, including fragments and/or antagonists thereof, may have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The protein can also be used to determine biological activity, raise antibodies, as tissuemarkers, to isolate cognate ligands or receptors, to identify agents that modulate their interactions. Further, proteins, as well as antibodies directed against a HGBPBMY1 (AK096141) protein, can show utility as a tumor marker and/or immunotherapy targets for liver tissue.

The HGBPBMY1 (AK096141) polynucleotides and polypeptides, including fragments and for antagonsists thereof, can have uses which include identification of modulators of HGBPBMY1 (AK096141) function including antibodies (for detection or neutralization), naturally-occurring modulators and small molecule modulators. Antibodies to a particular domain of the HGBPBMY1 (AK096141) protein could be used as diagnostic agents of conditions in subjects, are useful in monitoring the activation of signal transduction pathways, and can be used as a biomarker for the involvement of GBP's in disease states, as well as in the evaluation of inhibitors of GBP's in vivo.

HGBPBMY1 (AK096141) polypeptides and polynucleotides have additional uses which include diagnosing diseases related to the over and/or under expression of HGBPBMY1 (AK096141) by identifying mutations in a HGBPBMY1 (AK096141) gene by using HGBPBMY1 (AK096141) sequences as probes or by determining HGBPBMY1 (AK096141) protein or mRNA expression levels.

HGBPBMY1 (AK096141) polypeptides can be useful for screening compounds that affect the activity of the protein. HGBPBMY1 (AK096141) peptides can also be used for the generation of specific antibodies and as bait in yeast two hybrid screens to find proteins the specifically interact with HGBPBMY1 (AK096141), as described herein.

Although it is believed the encoded polypeptide could share at least some biological activities with human guanylate binding proteins (particularly hGBP-1, hGBP-2, hGBP-3, hGBP-4 and/or hGBP-5), a number of methods of determining the exact biological function of this clone are either known in the art or are described elsewhere herein. For example, the function of this clone can be determined by applying microarray methodology. Nucleic acids corresponding to a HGBPBMY1 (AK096141) polynucleotide, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased liver tissue, as compared to normal tissue might indicate a function in modulating liver function, for example. In the case of HGBPBMY1 (AK096141), liver tissue can be used, for example, to extract RNA to prepare the probe.

In addition, the function of the protein can be assessed, for example, by applying quantitative PCR methodology. Real time quantitative PCR would provide the capability of following the expression of a HGBPBMY1 (AK096141) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of HGBPBMY1 (AK096141), a disease correlation related to HGBPBMY1 (AK096141) can be made by comparing the mRNA expression level of HGBPBMY1 (AK096141) in normal tissue, as compared to diseased tissue (particularly diseased liver tissue). Significantly higher or lower levels of HGBPBMY1 (AK096141) expression in the diseased tissue can suggest HGBPBMY1 (AK096141) plays a role in disease progression, and antagonists against HGBPBMY1 (AK096141) polypeptides would be useful therapeutically in treating, preventing, and/or ameliorating the disease. Alternatively, significantly higher or lower levels of HGBPBMY1 (AK096141) expression in the diseased tissue can suggest HGBPBMY1 (AK096141) plays a defensive role against disease progression, and agonists of HGBPBMY1 (AK096141) polypeptides can be useful therapeutically in treating, preventing, and/or ameliorating the disease. Also encompassed by the present invention are quantitative PCR probes corresponding to the polynucleotide sequence provided as SEQ ID NO:2 (FIGS. 1A–1C).

The function of the protein can also be assessed through complementation assays in yeast. For example, in the case of a HGBPBMY1 (AK096141), transforming yeast deficient in GBP activity, for example, and assessing their ability to grow would provide convincing evidence a HGBPBMY1 (AK096141) polypeptide has GBP activity. Additional assay conditions and methods that can be used in assessing the function of the polynucleotides and polypeptides of the present invention are known in the art, some of which are disclosed herein.

Alternatively, the biological function of the encoded polypeptide can be determined by disrupting a homologue of this polypeptide in mice and/or rats and observing the resulting phenotype. Such knock-out experiments are known in the art, some of which are disclosed elsewhere herein.

Moreover, the biological function of a polypeptide can be determined by the application of antisense and/or sense methodology and the resulting generation of transgenic mice and/or rats or other animal. Expressing a particular gene in either sense or antisense orientation in a transgenic mouse or rat, for example, could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a liver tissue-specific promoter), or it can be expressed at a specified time of development using an inducible and/or a developmentally regulated promoter.

In the case of HGBPBMY1 (AK096141) transgenic mice or rats, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic mice or rats to refine the biological function of the polypeptide is encompassed by the present invention.

In some embodiments, the following N-terminal HGBPBMY1 (AK096141) deletion polypeptides are encompassed by the present invention: M1-S638, A2-S638, S3-S638, E4-S638, I5-S638, H6-S638, M7-S638, P8-S638, G9-S638, P10-S638, V11-S638, C12-S638, L13-S638, I14-S638, E15-S638, N16-S638, T17-S638, K18-S638, G19-S638, H20-S638, L21-S638, V22-S638, V23-S638, N24-S638, S25-S638, E26-S638, A27-S638, L28-S638, E29-S638, I30-S638, L31-S638, S32-S638, A33-S638, I34-S638, T35-S638, Q36-S638, P37-S638, V38-S638, V39-S638, V40-S638, V41-S638, A42-S638, I43-S638, V44-S638, G45-S638, L46-S638, Y47-S638, R48-S638, T49-S638, G50-S638, K51-S638, S52-S638, Y53-S638, L54-S638, M55-S638, N56-S638, K57-S638, L58-S638, A59-S638, G60-S638, K61-S638, N62-S22638, K63-S638, G64-S638, F65-S638, P66-S638, L67-S638, G68-S638, C69-S638, T70-S638, V71-S638, K72-S638, S73-S638, E74-S638, T75-S638, K76-S638, G77-S638, I78-S638, W79-S638, M80-S638, W81-S638, C82-S638, V83-S638, P84-S638, H85-S638, P86-S638, S87-S638, K88-S638, P89-S638, N90-S638, H91-S638, T92-S638, L93-S638, I94-S638, L95-S638, L96-S638, D97-S638, T98-S638, E99-S638, G100-S638, L101-S638, G102-S638, D103-S638, M104-S638, E105-S638, K106-S638, S107-S638, D108-S638, P109-S638, K110-S638, S111-S638, D112-S638, S113-S638, W114-S638, I115-S638, F116-S638, A117-S638, L118-S638, A119-S638, V120-S638, L121-S638, L122-S638, S123-S638, S124-S638, S125-S638, F126-S638, V127-S638, Y128-S638, N129-S638, S130-S638, M131-S638, G132-S638, T133-S638, I134-S638, N135-S638, H136-S638, Q137-S638, A138-S638, L139-S638, E140-S638, Q141-S638, L142-S638, H143-S638, Y144-S638, V145-S638, T146-S638, E147-S638, L148-S638, T149-S638, E150-S638, L151-S638, I152-S638, R153-S638, A154-S638, K155-S638, S156-S638, C157-S638, P158-S638, R159-S638, P160-S638, D161-S638, E162-S638, V163-S638, E164-S638, D165-S638, S166-S638, S167-S638, E168-S638, F169-S638, V170-S638, S171-S638, F172-S638, F173-S638, P174-S638, D175-S638, F176-S638, I177-S638, W178-S638, T179-S638, V180-S638, R181-S638, D182-S638, F183-S638, T184-S638, L185-S638, E186-S638, L187-S638, K188-S638, L189-S638, D190-S638, G191-S638, H192-S638, P193-S638, I194-S638, T195-S638, E196-S638, D197-S638, E198-S638, Y199-S638, L200-S638, E201-S638, N202-S638, A203-S638, L204-S638, K205-S638, L206-S638, I207-S638, S208-S638, G209-S638, K210-S638, N211-S638, P212-S638, Q213-S638, I214-S638, Q215-S638, N216-S638, S217-S638, N218-S638, K219-S638, P220-S638, R221-S638, E222-S638, W223-S638, I224-S638, R225-S638, H226-S638, F227-S638, F228-S638, P229-S638, K230-S638, Q231-S638, K232-S638, C233-S638, F234-S638, V235-S638, F236-S638, D237-S638, R238-S638, P239-S638, I240-S638, N241-S638, D242-S638, K243-S638, K244-S638, L245-S638, L246-S638, L247-S638, H248-S638, V249-S638, E250-S638, E251-S638, V252-S638, R253-S638, E254-S638, D255-S638, Q256-S638, L257-S638, D258-S638, S259-S638, N260-S638, F261-S638, Q262-S638, M263-S638, Q264-S638, S265-S638, E266-S638, N267-S638, F268-S638, C269-S638, S270-S638, Y271-S638, I272-S638, F273-S638, T274-S638, H275-S638, A276-S638, K277-S638, T278-S638, K279-S638, T280-S638, L281-S638, R282-S638, E283-S638, G284-S638, I285-S638, L286-S638, V287-S638, T288-S638, G289-S638, N290-S638, R291-S638, L292-S638, G293-S638, M294-S638, L295-S638, V296-S638, E297-S638, T298-S638, Y299-S638, L300-S638, D301-S638, A302-S638, I303-S638, N304-S638, S305-S638, G306-S638, A307-S638, T308-S638, P309-S638, C310-S638, L311-S638, E312-S638, N313-S638, A314-S638, M315-S638, A316-S638, V317-S638, L318-S638, A319-S638, Q320-S638, C321-S638, E322-S638, N323-S638, S324-S638, A325-S638, A326-S638, V327-S638, Q328-S638, R329-S638, A330-S638, A331-S638, N332-S638, H333-S638, Y334-S638, S335-S638, Q336-S638, Q337-S638, M338-S638, A339-S638, Q340-S638, Q341-S638, V342-S638, R343-S638, F344-S638, P345-S638, T346-S638, D347-S638, T348-S638, L349-S638, Q350-S638, E351-S638, L352-S638, L353-S638, D354-S638, V355-S638, H356-S638, A357-S638, V358-S638, C359-S638, E360-S638, R361-S638, E362-S638, A363-S638, I364-S638, A365-S638, V366-S638, F367-S638, M368-S638, E369-S638, Y370-S638, S371-S638, F372-S638, K373-S638, D374-S638, K375-S638, S376-S638, Q377-S638, E378-S638, F379-S638, Q380-S638, K381-S638, K382-S638, L383-S638, V384-S638, D385-S638, T386-S638, M387-S638, E388-S638, K389-S638, K390-S638, K391-S638, E392-S638, D393-S638, F394-S638, V395-S638, L396-S638, Q397-S638, N398-S638, E399-S638, E400-S638, A401-S638, S402-S638, A403-S638, K404-S638, Y405-S638, C406-S638, Q407-S638, A408-S638, E409-S638, L410-S638, K411-S638, R412-S638, M413-S638, S414-S638, E415-S638, M416-S638, M417-S638, T418-S638, E419-S638, S420-S638, I421-S638, S422-S638, R423-S638, G424-S638, T425-S638, F426-S638, F427-S638, V428-S638, P429-S638, G430-S638, G431-S638, H432-S638, N433-S638, I434-S638, Y435-S638, L436-S638, E437-S638, S438-S638, A438-S638, K439-S638, K440-S638, K441-S638, I442-S638, E443-S638, Q444-S638, D445-S638, Y446-S638, T447-S638, L448-S638, V449-S638, P450-S638, R451-S638, K452-S638, G453-S638, V454-S638, K455-S638, A456-S638, D457-S638, E458-S638, V459-S638, L460-S638, Q461-S638, S462-S638, F463-S638, L-464-S638, Q465-S638, S466-S638, Q467-S638, V468-S638, V469-S638, I470-S638, E471-S638, E472-S638, S473-S638, L474-S638, L475-S638, Q476-S638, S477-S638, D478-S638, K479-S638, A480-S638, L481-S638, T482-S638, A483-S638, G484-S638, E485-S638, K486-S638, A487-S638, I488-S638, A489-S638, A490-S638, K491-S638, Q492-S638, A493-S638, K494-S638, K495-S638, E496-S638, A497-S638, A498-S638, E499-S638, K500-S638, E501-S638, Q502-S638, E503-S638, L504-S638, L505-S638, R506-S638, Q507-S638, K508-S638, Q509-S638, K510-S638, E511-S638, Q512-S638, Q513-S638, Q514-S638, M515-S638, M516-S638, E517-S638, A518-S638, Q519-S638, E520-S638, R521-S638, S522-S638, F523-S638, Q524-S638, E525-S638, N526-S638, I527-S638, A528-S638, Q529-S638, L530-S638, K531-S638, K532-S638, K533-S638, M534-S638, E535-S638, R536-S638, E537-S638, R538-S638, E539-S638, N540-S638, Y541-S638, M542-S638, R543-S638, E544-S638, L545-S638, R546-S638, K547-S638, M548-S638, L549-S638, S550-S638, H551-S638, K552-S638, M553-S638, K554-S638, V555-S638, L556-S638, E557-S638, E558-S638, L559-S638, L560-S638, T561-S638, E562-S638, G563-S638, F564-S638, K565-S638, E566-S638, I567-S638, F568-S638, E569-S638, S570-S638, L571-S638, N572-S638, E573-S638, E574-S638, I575-S638, N576-S638, R577-S638, L578-S638, K579-S638, E580-S638, Q581-S638, I582-S638, E583-S638, A584-S638, A585-S638, E586-S638, N587-S638, E588-S638, E589-S638, P590-S638, S591-S638, V592-S638, F593-S638, S594-S638, Q595-S638, I596-S638, L597-S638, D598-S638, V599-S638, A600-S638, G601-S638, S602-S638, I603-S638, F604-S638, I605-S638, A606-S638, A607-S638, L608-S638, P609-S638, G610-S638, A611-S638, A612-S638, K613-S638, L614-S638, V615-S638, D616-S638, L617-S638, G618-S638, M619-S638, K620-S638, I621-S638, L622-S638, S623-S638, S624-S638, L625-S638, C626-S638, N627-S638, R628-S638, L629-S638, R630-S638, N631-S638, P632-S638, G633-S638, K634-S638, K635-S638, I636-S638, I637-S638 of SEQ ID NO:3. Polynucleotide sequences encoding these polypeptides are also provided. The present invention also encompasses the use of these N-terminal HGBPBMY1 (AK096141) deletion polypeptides as immunogenic and/or antigenic epitopes as described elsewhere herein.

In other embodiments, the following C-terminal HGBPBMY1 (AK096141) deletion polypeptides are encompassed by the present invention: M1-A2, M1-S3, M1-E4, M1-I5, M1-H6, M1-M7, M1-P8, M1-G9, M1-P10, M1-V11, M1-C12, M1-L13, M1-I14, M1-E15, M1-N16, M1-T17, M1-K18, M1-G19, M1-H20, M1-L21, M1-V22, M1-V23, M1-N24, M1-S25, M1-E26, M1-A27, M1-L28, M1-E29, M1-I30, M1-L31, M1-S32, M1-A33, M1-I34, M1-T35, M1-Q36, M1-37P, M1-V38, M1-V39, M1-V40, M1-V41, M1-A42, M1-I43, M1-V44, M1-G45, M1-L46, M1-Y47, M1-R48, M1-T49, M1-G50, M1-K51, M1-S52, M1-Y53, M1-L54, M1-M55, M1-N56, M1-K57, M1-L58, M1-A59, M1-G60, M1-K61, M1-N62, M1-K63, M1-G64, M1-F65, M1-P66, M1-L67, M1-G68, M1-C69, M1-T70, M1-V71, M1-K72, M1-S73, M1-E74, M1-T75, M1-K76, M1-G77, M1-I78, M1-W79, M1-M80, M1-W81, M1-C82, M1-V83, M1-P84, M1-H85, M1-P86, M1-S87, M1-K88, M1-P89, M1-N90, M1-H91, M1-T92, M1-L93, M1-I94, M1-L95, M1-L96, M1-D97, M1-T98, M1-E99, M1-G100, M1-L101, M1-G102, M1-D103, M1-M104, M1-E105, M1-K106, M1-S107, M1-D108, M1-P109, M1-K110, M1-S111, M1-D112, M1-S113, M1-W114, M-I115, M1-F 116, M1-A117, M1-L118, M1-A119, M1-V120, M1-L121, M1-L122, M1-S123, M1-S124, M1-S125, M1-F126, M1-V127, M1-Y128, M1-N129, M1-S130, M1-M131, M1-G132, M1-T133, M1-I134, M1-N135, M1-H136, M1-Q137, M1-A138, M1-L139, M1-E140, M1-Q141, M1-L142, M1-H143, M1-Y144, M1-V145, M1-T146, M1-E147, M1-L148, M1-T149, M1-E150, M1-L151, M1-I152, M1-R153, M1-A154, M1-K155, M1-S156, M1-C157, M1-P158, M1-R159, M1-P160, M1-D161, M1-E162, M1-V163, M1-E164, M1-D165, M1-S166, M1-S167, M1-E168, M1-F169, M1-V170, M1-S171, M1-F172, M1-F173, M1-P174, M1-D175, M1-F176, M1-I177, M1-W178, M1-T179, M1-V180, M1-R181, M1-D182, M1-F183, M1-T184, M1-L185, M1-E186, M1-L187, M1-K188, M1-L189, M1-D190, M1-G191, M1-H192, M1-P193, M1-I194, M1-T195, M1-E196, M1-D197, M1-E198, M1-Y199, M1-L200, M1-E201, M1-N202, M1-A203, M1-L204, M1-K205, M1-L206, M1-I207, M1-S208, M1-G209, M1-K210, M1-N211, M1-P212, M1-Q213, M1-I214, M1-Q215, M1-N216, M1-S217, M1-N218, M1-K219, M1-P220, M1-R221, M1-E222, M1-W223, M1-I224, M1-R225, M1-H226, M1-F227, M1-F228, M1-P229, M1-K230, M1-Q231, M1-K232, M1-C233, M1-F234, M1-V235, M1-F236, M1-D237, M1-R238, M1-P239, M1-I240, M1-N241, M1-D242, M1-K243, M1-K244, M1-L245, M1-L246, M1-L247, M1-H248, M1-V249, M1-E250, M1-E251, M1-V252, M1-R253, M1-E254, M1-D255, M1-Q256, M1-L257, M1-D258, M1-S259, M1-N260, M1-F261, M1-Q262, M1-M263, M1-Q264, M1-S265, M1-E266, M1-N267, M1-F268, M1-C269, M1-S270, M1-Y271, M1-I272, M1-F273, M1-T274, M1-H275, M1-A276, M1-K277, M1-T278, M1-K279, M1-T280, M1-L281, M1-R282, M1-E283, M1-G284, M1-I285, M1-L286, M1-V287, M1-T288, M1-G289, M1-290, M1-R291, M1-L292, M1-G293, M1-M294, M1-L295, M1-V296, M1-E297, M1-T298, M1-Y299, M1-L300, M1-D301, M1-A302, M1-I303, M1-N304, M1-S305, M1-G306, M1-A307, M1-T308, M1-P309, M1-C310, M1-L311, M1-E312, M1-N313, M1-A314, M1-M315, M1-A316, M1-V317, M1-L318, M1-A319, M1-Q320, M1-C321, M1-E322, M1-N323, M1-S324, M1-A325, M1-A326, M1-V327, M1-Q328, M1-R329, M1-A330, M1-A331, M1-N332, M1-H333, M1-Y334, M1-S335, M1-Q336, M1-Q337, M1-M338, M1-A339, M1-Q340, M1-Q341, M1-V342, M1-R343, M1-F344, M1-P345, M1-T346, M1-D347, M1-T348, M1-L349, M1-Q350, M1-E351, M1-L352, M1-L353, M1-D354, M1-V355, M1-H356, M1-A357, M1-V358, M1-C359, M1-E360, M1-R361, M1-E362, M1-A363, M1-I364, M1-A365, M1-V366, M1-F367, M1-M368, M1-E369, M1-Y370, M1-S371, M1-F372, M1-K373, M1-D374, M1-K375, M1-S376, M1-Q377, M1-E378, M1-F379, M1-Q380, M1-K381, M1-K382, M1-L383, M1-V384, M1-D385, M1-T386, M1-M387, M1-E388, M1-K389, M1-K390, M1-K391, M1-E392, M1-D393, M1-F394, M1-V395, M1-L396, M1-Q397, M1-N398, M1-E399, M1-E400, M1-A401, M1-S402, M1-A403, M1-K404, M1-Y405, M1-C406, M1-Q407, M1-A408, M1-E409, M1-L410, M1-K411, M1-R412, M1-L413, M1-S414, M1-E415, M1-L416, M1-L417, M1-T418, M1-E419, M1-S420, M1-I421, M1-S422, M1-R423, M1-G424, M1-T425, M1-F426, M1-F427, M1-V428, M1-P429, M1-G430, M1-G431, M1-H432, M1-N433, M1-I434, M1-Y435, M1-L436, M1-E437, M1-A438, M1-K439, M1-K440, M1-K441, M1-I442, M1-E443, M1-Q444, M1-D445, M1-Y446, M1-T447, M1-L448, M1-V449, M1-P450, M1-R451, M1-K452, M1-G453, M1-V454, M1-K455, M1-A456, M1-D457, M1-E458, M1-V459, M1-L460, M1-Q461, M1-S462, M1-F463, M1-L464, M1-Q465, M1-S466, M1-Q467, M1-V468, M1-V469, M1-I470, M1-E471, M1-E472, M1-S473, M1-I474, M1-L475, M1-Q476, M1-S477, M1-D478, M1-K479, M1-A480, M1-L481, M1-T482, M1-A483, M1-G484, M1-E485, M1-K486, M1-A487, M1-I488, M1-A489, M1-A490, M1-K491, M1-Q492, M1-A493, M1-K494, M1-K495, M1-E496, M1-A497, M1-A498, M1-E499, M1-K500, M1-E501, M1-Q502, M1-E503, M1-L504, M1-L505, M1-R506, M1-Q507, M1-K508, M1-Q509, M1-K510, M1-E511, M1-Q512, M1-Q513, M1-Q514, M1-M515, M1-M516, M1-E517, M1-A518, M1-Q519, M1-E520, M1-R521, M1-S522, M1-F523, M1-Q524, M1-E525, M1-N526, M1-I527, M1-A528, M1-Q529, M1-L530, M1-K531, M1-K532, M1-K533, M1-M534, M1-E535, M1-R536, M1-E537, M1-R538, M1-E539, M1-N540, M1-Y541, M1-M542, M1-R543, M1-E544, M1-L545, M1-R546, M1-K547, M1-M548, M1-L549, M1-S550, M1-H551, M1-K552, M1-M553, M1-K554, M1-V555, M1-L556, M1-E557, M1-E558, M1-L559, M1-L560, M1-T561, M1-E562, M1-G563, M1-F564, M1-K565, M1-E566, M1-I567, M1-F568, M1-E569, M1-S570, M1-L571, M1-N572, M1-E573, M1-E574, M1-I575, M1-N576, M1-R577, M1-L578, M1-K579, M1-E580, M1-Q581, M1-I582, M1-E583, M1-A584, M1-A585, M1-E586, M1-N587, M1-E588, M1-E589, M1-P590, M1-S591, M1-V592, M1-F593, M1-S594, M1-Q595, M1-I596, M1-L597, M1-D598, M1-V599, M1-A600, M1-G601, M1-S602, M1-I603, M1-F604, M1-I605, M1-A606, M1-A607, M1-L608, M1-P609, M1-G610, M1-A611, M1-A612, M1-K613, M1-L614, M1-V615, M1-D616, M1-L617, M1-G618, M1-M619, M1-K620, M1-I621, M1-L622, M1-S623, M1-S624, M1-L625, M1-C626, M1-N627, M1-R628, M1-L629, M1-R630, M1-N631, M1-P632, M1-G633, M1-K634, M1-K635, M1-I636 and/or M1-I637 of SEQ ID NO:3. Polynucleotide sequences encoding these polypeptides are also provided. The present invention also encompasses the use of these C-terminal HGBPBMY1 (AK096141) deletion polypeptides as immunogenic and/or antigenic epitopes as described elsewhere herein.

Alternatively, polypeptides of the present invention may comprise polypeptide sequences corresponding to, for example, internal regions of a HGBPBMY1 (AK096141) polypeptide (e.g., any combination of both N- and C-terminal HGBPBMY1 (AK096141) polypeptide deletions) of SEQ ID NO:3. For example, internal regions could be defined by the equation: amino acid NX to amino acid CX, wherein NX refers to any N-terminal deletion polypeptide amino acid of HGBPBMY1 (AK096141) (SEQ ID NO:3), and where CX refers to any C-terminal deletion polypeptide amino acid of HGBPBMY1 (AK096141) (SEQ ID NO:3). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the HGBPBMY1 (AK096141) polypeptide.

The present invention encompasses the identification of compounds and drugs which stimulate HGBPBMY1 (AK096141) on the one hand (i.e., agonists) and which inhibit the function of HGBPBMY1 (AK096141) on the other hand (i.e., antagonists). In general, such screening procedures involve providing appropriate cells which express a polypeptide of the present invention on the surface thereof. Such cells can include, for example, cells from mammals, yeast, *Drosophila* or *E. coli*. In a representative embodiment, a polynucleotide encoding a polypeptide of the present invention can be employed to transfect cells to thereby express a HGBPBMY1 (AK096141) polypeptide. The expressed polypeptide can then be contacted with a test compound to observe binding, stimulation or inhibition of a functional response.

FIG. 43 shows an expanded expression profile of the GBP HGBPBMY1 (AK096141). The figure illustrates the relative expression level of HGBPBMY1 amongst various mRNA tissue sources. As shown, the HGBPBMY1 polypeptide exhibited high expression in normal spleen; tonsil; blood mononuclear cells; liver parenchyma; lung parenchyma; digestive system including stomach, duodenum, jejunum, ileum; placenta; ovary; and was detectable in regions of the brain, adrenal gland, ureter, and bladder. FIG. 43 also illustrates the relative expression level of HGBPBMY1 amongst various mRNA tissue sources isolated from normal and diseased tissues. As shown, the HGBPBMY1 polypeptide showed increased expression in breast and testicle tumors relative to controls; and high expression in normal and diseased lung parenchyma. Expression data was obtained by measuring the steady state HGBPBMY1 mRNA levels by quantitative PCR using the PCR primer pair provided as SEQ ID NO:61 and 62, and TAQMAN probe (SEQ ID NO:63) as described in Example 36 herein. These data support a role of HGBPBMY1 in regulating various functions. HGBPBMY1 may also be participating in the formation of testicle and breast tumors and thus small molecule modulators of HGBPBMY1 function may represent a novel therapeutic option in the treatment of breast and testicle cancers, as well as pulmonary, gastrointestinal and/or immune system diseases.

Features of the Polypeptide Encoded by Gene No. 2

The polypeptide encoded by this gene, HGBPBMY2 (4843 30 1 1; 4843_1), is provided as SEQ ID NO:5 (FIGS. 2A–2C) and is encoded by the polynucleotide sequence according to SEQ ID NO:4 (FIGS. 2A–2C) and/or by a polynucleotide contained within the deposited clone. HGBPBMY2 (4843 30 1 1; 4843_1) has significant homology at the nucleotide and amino acid level to a number of guanylate binding proteins, which include, for example, human GBP-1, human GBP-2, human GBP-3, human GBP-4 and human GBP-5.

The determined nucleotide sequence of a HGBPBMY2 (4843 30 1 1; 4843_1), (i.e., the cDNA shown in FIGS. 2A–2C and in SEQ ID NO:4) comprises an open reading frame encoding a protein of about 788 amino acid residues. The predicted amino acid sequence of a HGBPBMY2 (4843 30 1 1; 4843_1) polypeptide is shown in FIGS. 2A–2C (SEQ ID NO:5). The percent identity and similarity values between the HGBPBMY2 (4843 30 1 1; 4843_1) polypeptide to the known GBP family member hGBP1 is provided in FIG. 9. The HGBPBMY2 (4843 30 1 1; 4843_1) protein shown in FIGS. 2A–2C was determined to share significant identity and similarity to several known GBP family members, as shown in FIG. 11A–11G.

Figure 16:
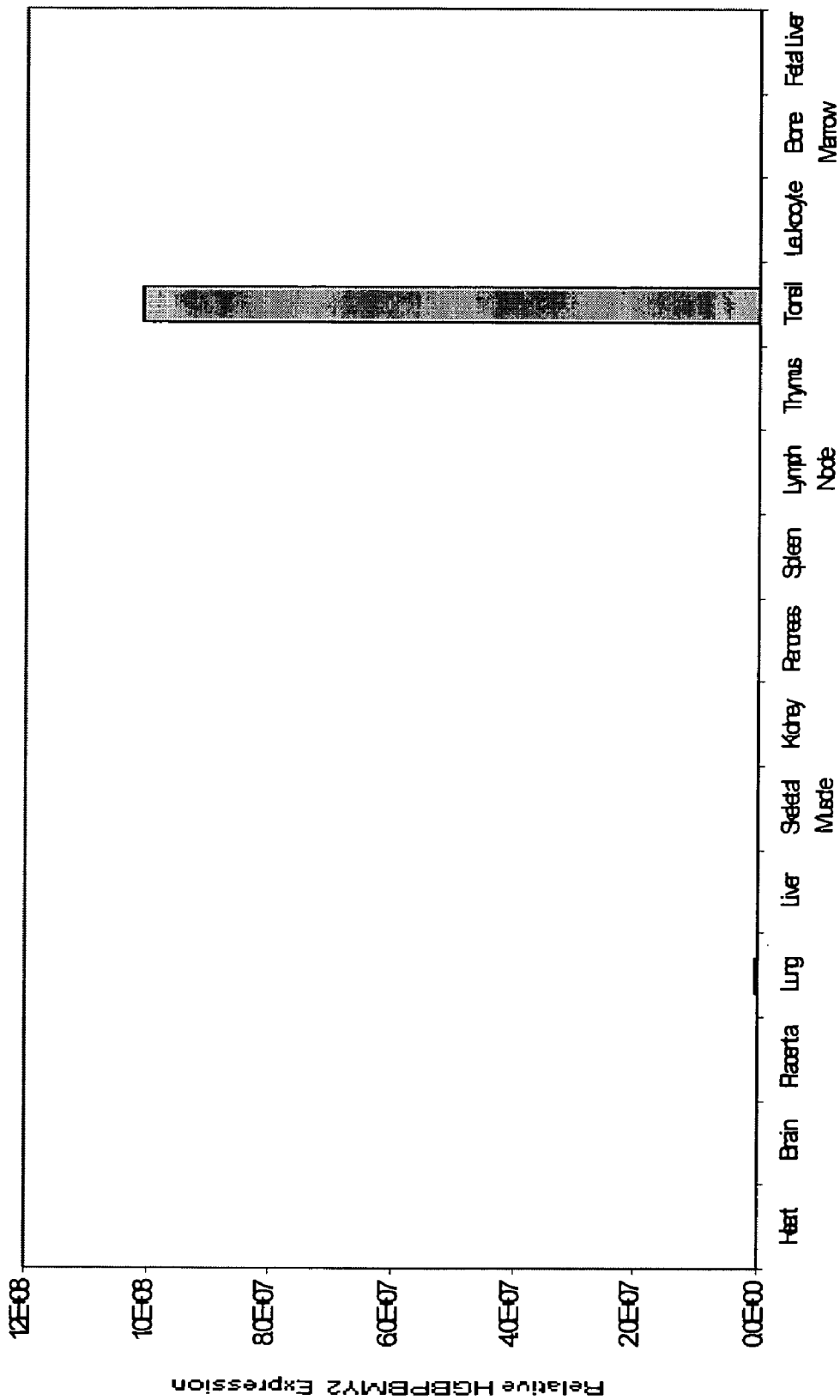
FIG. 16 is bar graph depicting the tissue expression pattern of human HGBPBMY2 (4843 30 1 1; 4843_1). Panels of cDNAs derived from normal and immune tissue were analyzed by real Time PCR for expression of HGBPBMY2 (4843 30 1 1; 4843_1).

Expression profiling designed to measure the steady state mRNA levels encoding the HGBPBMY2 (4843 30 1 1; 4843_1) polypeptide showed expression predominantly in tonsil (see FIG. 16).

Based upon the strong homology to members of the GBP family members, a HGBPBMY2 (4843 30 1 1; 4843_1) polypeptide is expected to share at least some biological activity with GBP family members, specifically hGBP-1, hGBP-2, hGBP-3, and/or hGBP-4.

The HGBPBMY2 (4843 30 1 1; 4843_1) polynucleotides and polypeptides of the present invention, including agonists and/or fragments thereof, may have uses that include detecting, prognosing, diagnosing, treating, preventing, and/or ameliorating at least diseases and conditions of the immune system related directly or indirectly to tonsil function.

The HGBPBMY2 (4843 30 1 1; 4843_1) polynucleotides and polypeptides of the present invention, including agonists and/or fragments thereof, may have uses that include modulating signal transduction activity, in various cells, tissues, and organisms, and particularly in mammalian tissue, preferably human tissue.

The strong homology to human GBP family members, particularly hGBP-1, hGBP-2, hGBP3 and hGBP-4, combined with HGBPBMY2 (4843 30 1 1; 4843_1) expression in tonsil tissue suggests a potential utility for HGBPBMY2 (4843 30 1 1; 4843_1) polynucleotides and polypeptides in treating, diagnosing, prognosing, and/or preventing diseases and conditions of the immune system. In representative embodiments, HGBPBMY2 (4843 30 1 1; 4843_1) polynucleotides and polypeptides including agonists and fragments thereof, may have uses that include treating, diagnosing, prognosing, and/or preventing diseases and conditions of the immune system. The HGBPBMY2 (4843 30 1 1; 4843_1) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. The HGBPBMY2 (4843 30 1 1; 4843_1) polypeptide may be useful for modulating cytokine production, antigen presentation, or other processes, such as for boosting immune responses, etc.

Additional immunolgical disorders that a HGBPBMY2 (4843 30 1 1; 4843_1) polypeptide of the present invention can be useful in the treatment of include various autoimmune diseases such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A HGBPBMY2 (4843 30 1 1; 4843_1) polypeptide of the present invention can also be useful in treating or ameliorating primary immune diseases, as well as immune diseases associated with or secondary to other diseases. Such diseases and conditions include, for example, Eecombinase activating gene (RAG 1/2) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimike immuno-osseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The protein can also be used to determine biological activity, raise antibodies, as tissue markers, to isolate cognate ligands or receptors, to identify agents that modulate their interactions. Further, proteins, as well as antibodies directed against the HGBPBMY2 (4843 30 1 1; 4843_1) protein, may show utility as a tumor marker and/or immunotherapy targets.

The HGBPBMY2 (4843 30 1 1; 4843_1) polynucleotides and polypeptides, including fragments and for antagonsists thereof, may have uses which include identification of modulators of HGBPBMY2 (4843 30 1 1; 4843_1) function including antibodies (for detection or neutralization), naturally-occurring modulators and small molecule modulators. Antibodies to a particular domain of the HGBPBMY2 (4843 30 1 1; 4843_1) protein could be used as diagnostic agents of conditions in subjects, are useful in monitoring the activation of signal transduction pathways, and can be used as a biomarker for the involvement of GBP's in disease states, as well as in the evaluation of inhibitors of GBP's in vivo.

HGBPBMY2 (4843 30 1 1; 4843_1) polypeptides and polynucleotides have additional uses which include diagnosing diseases related to the over and/or under expression of HGBPBMY2 (4843 30 1 1; 4843_1) by identifying mutations in the HGBPBMY2 (4843 30 1 1; 4843_1) gene by using HGBPBMY2 (4843 30 1 1; 4843_1) sequences as probes or by determining HGBPBMY2 (4843 30 1 1; 4843_1) protein or mRNA expression levels. HGBPBMY2 (4843 30 1 1; 4843_1) polypeptides can be useful for screening compounds that affect the activity of the protein. HGBPBMY2 (4843 30 1 1; 4843_1) peptides can also be used for the generation of specific antibodies and as bait in yeast two hybrid screens to find proteins the specifically interact with HGBPBMY2 (4843 30 1 1; 4843_1), as described herein.

Although it is believed the encoded polypeptide could share at least some biological activities with human guanylate binding proteins (particularly hGBP-1, hGBP-2, hGBP-3 and hGBP-4), a number of methods of determining the exact biological function of this clone are either known in the art or are described elsewhere herein. For example, the function of this clone can be determined by applying microarray methodology. Nucleic acids corresponding to the HGBPBMY2 (4843 30 1 1; 4843_1) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased immune system tissue, as compared to normal tissue might indicate a function in modulating immune system function, for example. In the case of HGBPBMY2 (4843 30 1 1; 4843_1), tonsil can be used, for example, to extract RNA to prepare the probe.

In addition, the function of the protein can be assessed, for example, by applying quantitative PCR methodology. Real time quantitative PCR would provide the capability of following the expression of the HGBPBMY2 (4843 30 1 1; 4843_1) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of HGBPBMY2 (4843 30 1 1; 4843_1), a disease correlation related to HGBPBMY2 (4843 30 1 1; 4843_1) can be made by comparing the mRNA expression level of HGBPBMY2 (4843 30 1 1; 4843_1) in normal tissue, as compared to diseased tissue (particularly diseased immune system tissue, such as diseased tonsil tissue). Significantly higher or lower levels of HGBPBMY2 (4843 30 1 1; 4843_1) expression in the diseased tissue can suggest HGBPBMY2 (4843 30 1 1; 4843_1) plays a role in disease progression, and antagonists against HGBPBMY2 (4843 30 1 1; 4843_1) polypeptides would be useful therapeutically in treating, preventing, and/or ameliorating the disease. Alternatively, significantly higher or lower levels of HGBPBMY2 (4843 30 1 1; 4843_1) expression in the diseased tissue can suggest HGBPBMY2 (4843 30 1 1; 4843_1) plays a defensive role against disease progression, and agonists of HGBPBMY2 (4843 30 1 1; 4843_1) polypeptides can be useful therapeutically in treating, preventing, and/or ameliorating the disease. Also encompassed by the present invention are quantitative PCR probes corresponding to the polynucleotide sequence provided as SEQ ID NO:4 (FIGS. 2A–2C).

The function of the protein can also be assessed through complementation assays in yeast. For example, in the case of the HGBPBMY2 (4843 30 1 1; 4843_1), transforming yeast deficient in GBP activity, for example, and assessing their ability to grow would provide convincing evidence the HGBPBMY2 (4843 30 1 1; 4843_1) polypeptide has GBP activity. Additional assay conditions and methods that can be used in assessing the function of the polynucleotides and polypeptides of the present invention are known in the art, some of which are disclosed herein. GTPase activity assays can also be employed.

Alternatively, the biological function of the encoded polypeptide can be determined by disrupting a homologue of this polypeptide in mice and/or rats (e.g. by RNAi or homologous recombination) and observing the resulting phenotype. Such knock-out experiments are known in the art, some of which are disclosed elsewhere herein.

Moreover, the biological function of this polypeptide can be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a tonsil tissue-specific promoter), or it can be expressed at a specified time of development using an inducible and/or a developmentally regulated promoter.

In the case of HGBPBMY2 (4843 30 1 1; 4843_1) transgenic mice or rats, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic mice or rats to refine the biological function of the polypeptide is encompassed by the present invention.

In preferred embodiments, the following N-terminal HGBPBMY2 (4843 30 1 1; 4843_1) deletion polypeptides are encompassed by the present invention: M1-K788, E2-K788, S3-K788, G4-K788, P5-K788, K6-K788, M7-K788, L8-K788, A9-K788, P10-K788, V11-K788, C12-K788, L13-K788, V14-K788, E15-K788, N16-K788, N17-K788, N18-K788, E19-K788, Q20-K788, L21-K788, L22-K788, V23-K788, N24-K788, Q25-K788, Q26-K788, A27-K788, I28-K788, Q29-K788, I30-K788, L31-K788, E32-K788, K33-K788, I34-K788, S35-K788, Q36-K788, P37-K788, V38-K788, V39-K788, V40-K788, V41-K788, A42-K788, I43-K788, V44-K788, G45-K788, L46-K788, Y47-K788, R48-K788, T49-K788, G50-K788, K51-K788, S52-K788, Y53-K788, L54-K788, M55-K788, N56-K788, H57-K788, L58-K788, A59-K788, G60-K788, Q61-K788, N62-K788, H63-K788, G64-K788, F65-K788, P66-K788, L67-K788, G68-K788, S69-K788, T70-K788, V71-K788, Q72-K788, S73-K788, E74-K788, T75-K788, K76-K788, G77-K788, I78-K788, W79-K788, M80-K788, W81-K788, C82-K788, V83-K788, P84-K788, H85-K788, P86-K788, S87-K788, K88-K788, P89-K788, N90-K788, H91-K788, T92-K788, L93-K788, V94-K788, L95-K788, L96-K788, D97-K788, T98-K788, E99-K788, G100-K788, L101-K788, G102-K788, D103-K788, V104-K788, E105-K788, K106-K788, G107-K788, D108-K788, P109-K788, K110 N111-K788, D112-K788, S113-K788, W114-K788, I115-K788, F116-K788, A117-K788, L118-K788, A119-K788, V120-

K788, L121-K788, L122-K788, C123-K788, S124-K788, T125-K788, F126-K788, V127-K788, Y128-K788, N129-K788, S130-K788, M131-K788, S132-K788, T133-K788, I134-K788, N135-K788, H136-K788, Q137-K788, A138-K788, L139-K788, E140-K788, Q141-K788, L142-K788, Q143-K788, Y144-K788, P145-K788, S146-K788, R147-K788, N148-K788, R149-K788, T150-K788, E151-K788, P152-K788P153-K788, G154-K788, F155-K788, I156-K788, D157-K788, F158-K788, I159-K788, G160-K788, M161-K788, E162-K788, I163-K788, N164-K788, P165-K788, S166-K788, Y167-K788, V168-K788, T169-K788, E170-K788, L171-K788, T172-K788, E173-K788, L174-K788, I175-K788, K176-K788, A177-K788, K178-K788, S179-K788, S180-K788, P181-K788, R182-K788, P183-K788, D184-K788, G185-K788, V186-K788, E187-K788, D188-K788, S189-K788, T190-K788, E191-K788, F192-K788, V193-K788, S194-K788, F195-K788, F196-K788, P197-K788, D198-K788, F199-K788, L200-K788, W201-K788, T202-K788, V203-K788, R204-K788, D205-K788, F206-K788, T207-K788, L208-K788, E209-K788, L210-K788, K211-K788, L212-K788, N213-K788, G214-K788, H215-K788, P216-K788, I217-K788, T218-K788, E219-K788, D220-K788, E221-K788, Y222-K788, L223-K788, E224-K788, N225-K788, A226-K788, L227-K788, K228-K788, L229-K788, I230-K788, Q231-K788, G232-K788, N233-K788, N234-K788, P235-K788, R236-K788, V237-K788, Q238-K788, T239-K788, S240-K788, N241-K788, F242-K788, P243-K788, R244-K788, E245-K788, C246-K788, I247-K788, R248-K788, R249-K788, F250-K788, F251-K788, P252-K788, K253-K788, R254-K788, K255-K788, C256-K788, F257-K788, V258-K788, F259-K788, D260-K788, R261-K788, P262-K788, T263-K788, N264-K788, D265-K788, K266-K788, D267-K788, L268-K788, L269-K788, A270-K788, N271-K788, I272-K788, E273-K788, K274-K788, V275-K788, S276-K788, E277-K788, K278-K788, Q279-K788, L280-K788, D281-K788, P282-K788, K283-K788, F284-K788, Q285-K788, E286-K788, Q287-K788, T288-K788, N289-K788, I290-K788, F291-K788, C292-K788, S293-K788, Y294-K788, I295-K788, F296-K788, T296-K788, H298-K788, A299-K788, R300-K788, T301-K788, K302-K788, T303-K788, L304-K788, R305-K788, E306-K788, G307-K788, I308-K788, T309-K788, V310-K788, T311-K788, G312-K788, N313-K788, R314-K788, L315-K788, G316-K788, T317-K788, L318-K788, A319-K788, V320-K788, T321-K788, Y322-K788, V323-K788, E324-K788, A325-K788, I326-K788, N327-K788, S328-K788, G329-K788, A330-K788, V331-K788, P332-K788, C333-K788, L334-K788, E335-K788, N336-K788, A337-K788, V338-K788, I339-K788, T340-K788, L341-K788, A342-K788, Q343-K788, R344-K788, E345-K788, N346-K788, S347-K788, A348-K788, A349-K788, V350-K788, Q351-K788, R352-K788, A353-K788, A354-K788, D355-K788, Y356-K788, Y357-K788, S358-K788, Q359-K788, Q360-K788, M361-K788, A362-K788, Q363-K788, R364-K788, V365-K788, K366-K788, L367-K788, P368-K788, T369-K788, D370-K788, T371-K788, L372-K788, Q373-K788, E374-K788, L375-K788, L376-K788, D377-K788, M378-K788, H379-K788, A380-K788, A381-K788, C382-K788, E383-K788, R384-K788, E385-K788, A386-K788, I387-K788, A388-K788, I389-K788, F390-K788, M391-K788, E392-K788, H393-K788, S394-K788, F395-K788, K396-K788, D397-K788, E398-K788, N399-K788, Q400-K788, E401-K788, F402-K788, Q403-K788, K404-K788, K405-K788, F406-K788, M407-K788, E408-K788, T409-K788, T410-K788, M411-K788, N412-K788, K413-K788, K414-K788, G415-K788, D416-K788, F417-K788, L418-K788, L419-K788, Q420-K788, N421-K788, E422-K788, E423-K788, S424-K788, S425-K788, V426-K788, Q427-K788, Y428-K788, C429-K788, Q430-K788, A431-K788, K432-K788, L433-K788, N434-K788, E435-K788, L436-K788, S437-K788, K438-K788, G439-K788, L440-K788, M441-K788, E442-K788, S443-K788, I444-K788, S445-K788, A446-K788, G447-K788, S448-K788, F449-K788, S450-K788, V451-K788, P452-K788, G453-K788, G454-K788, H455-K788, K456-K788, L457-K788, Y458-K788, M459-K788, E460-K788, T461-K788, K462-K788, E463-K788, R464-K788, I465-K788, E466-K788, Q467-K788, D468-K788, Y469-K788, W470-K788, Q471-K788, V472-K788, P473-K788, R474-K788, K475-K788, G476-K788, V477-K788, K478-K788, A479-K788, K480-K788, E481-K788, V482-K788, F483-K788, Q484-K788, R485-K788, F486-K788, L487-K788, E488-K788, S489-K788, Q490-K788, M491-K788, V492-K788, I493-K788, E494-K788, E495-K788, S496-K788, I497-K788, L498-K788, Q499-K788, S500-K788, D501-K788, K502-K788, A503-K788, L504-K788, T505-K788, D506-K788, R507-K788, E508-K788, K509-K788, A510-K788, V511-K788, A512-K788, V513-K788, D514-K788, R515-K788, A516-K788, K517-K788, K518-K788, E519-K788, A520-K788, A521-K788, E522-K788, K523-K788, E524-K788, Q525-K788, E526-K788, L527-K788, L528-K788, K529-K788, Q530-K788, K531-K788, L532-K788, Q533-K788, E534-K788, Q535-K788, Q536-K788, Q537-K788, Q538-K788, M539-K788, E540-K788, A541-K788, Q542-K788, D543-K788, K544-K788, S545-K788, R546-K788, K547-K788, E548-K788, N549-K788, I550-K788, A551-K788, Q552-K788, L553-K788, K554-K788, E555-K788, K556-K788, L557-K788, Q558-K788, M559-K788, E560-K788, R561-K788, E562-K788, H563-K788, L564-K788, L565-K788, R566-K788, E567-K788, Q568-K788, I569-K788, M570-K788, M571-K788, L572-K788, E573-K788, H574-K788, T575-K788, Q576-K788, K577-K788, V578-K788, Q579-K788, N580-K788, D581-K788, W582-K788, L583-K788, H584-K788, E585-K788, G586-K788, F587-K788, K588-K788, K589-K788, K590-K788, Y591-K788, E592-K788, E593-K788, M594-K788, N595-K788, A596-K788, E597-K788, I598-K788, S599-K788, Q600-K788, F601-K788, K602-K788, R603-K788, M604-K788, I605-K788, D606-K788, T607-K788, T608-K788, K609-K788, N610-K788, D611-K788, D612-K788, T613-K788, P614-K788, W615-K788, I616-K788, A617-K788, R618-K788, T619-K788, L620-K788, D621-K788, N622-K788, L623-K788, A624-K788, D625-K788, E626-K788, L627-K788, T628-K788, A629-K788, I630-K788, L631-K788, S632-K788, A633-K788, P634-K788, A635-K788, K636-K788, L637-K788, I638-K788, G639-K788, H640-K788, G641-K788, V642-K788, K643-K788, G644-K788, N645-K788, E646-K788, L647-K788, T648-K788, R649-K788, N650-K788, M651-K788, S652-K788, P653-K788, H654-K788, I655-K788, Q656-K788, R657-K788, S658-K788, G659-K788, S660-K788, Q661-K788, F662-K788, F663-K788, S664-K788, R665-K788, G666-K788, R667-K788, R668-K788, G669-K788, G670-K788, R671-K788, V672-K788, A673-K788, V674-K788, C675-K788, F676-K788, L677-K788, G678-K788, G679-K788, I680-K788, I681-K788, S682-K788, S683-K788, I684-K788, M685-K788, E686-K788, V687-K788, A688-K788, T689-K788, Q690-K788, H691-K788, N692-K788, L693-K788, E694-K788, P695-K788, L696-K788, P697-K788, Q698-K788, H699-K788, T700-K788, H701-K788, C702-K788, S703-K788, N704-K788, T705-K788, E706-K788, A707-K788, N708-K788, K709-K788, S710-K788, E711-K788, E712-K788, V713-K788, H714-K788, H715-K788, F716-K788, W717-K788, R718-K788, L719-K788, F720-K788, A721-K788, R722-K788, L723-

K788, A724-K788, G725-K788, D726-K788, D727-K788, I728-K788, E729-K788, V730-K788, S731-K788, G732-K788, T733-K788, E734-K788, L735-K788, M736-K788, N737-K788, V738-K788, V739-K788, N740-K788, K741-K788, V742-K788, V743-K788, I744-K788, S745-K788, R746-K788, T747-K788, E748-K788, L749-K788, K750-K788, T751-K788, H752-K788, G753-K788, F754-K788, G755-K788, I756-K788, D757-K788, T758-K788, C759-K788, Q760-K788, S761-K788, M762-K788, V763-K788, A764-K788, M765-K788, M766-K788, D767-K788, S768-K788, D769-K788, T770-K788, I771-K788, G772-K788, K773-K788, L774-K788, D775-K788, F776-K788, E777-K788, E778-K788, F779-K788, N780-K788, Y781-K788, L782-K788, W783-K788, N784-K788, N785-K788, I786-K788, and or K787-K788 of SEQ ID NO:5. Polynucleotide sequences encoding these polypeptides are also provided. The present invention also encompasses the use of these N-terminal HGBPBMY2 (4843 30 1 1; 4843_1) deletion polypeptides as immunogenic and/or antigenic epitopes as described elsewhere herein.

In other embodiments, the following C-terminal HGBPBMY2 (4843 30 1 1; 4843_1) deletion polypeptides are encompassed by the present invention: M1-E2, M1-S3, M1-G4, M1-P5, M1-K6, M1-M7, M1-L8, M1-A9, M1-P10, M1-V11, M1-C12, M1-L13 M1-V14, M1-E15, M1-N16, M1-N17, M1-N18, M1-E19, M1-Q20, M1-L21, M1-L22, M1-V23, M1-N24, M1-Q25, M1-Q26, M1-A27, M1-I28, M1-Q29, M1-I30, M1-L31, M1-E32, M1-K33, M1-I34, M1-S35, M1-Q36, M1-P37, M1-V38, M1-V39, M1-V40, M1-V41, M1-A42, M1-I43, M1-V44, M1-G45, M1-L46, M1-Y47, M1-R48, M1-T49, M1-G50, M1-K51, M1-S52, M1-Y53, M1-L54, M1-M55, M1-N56, M1-H57, M1-L58, M1-A59, M1-G60, M1-Q61, M1-N62, M1-H63, M1-G64, M1-F65, M1-P66, M1-L67, M1-G68, M1-S69, M1-T70, M1-V71, M1-Q72, M1-S73, M1-E74, M1-T75, M1-K76, M1-G77, M1-I78, M1-W79, M1-M80, M1-W81, M1-C82, M1-V83, M1-P84, M1-H85, M1-P86, M1-S87, M1-K88, M1-P89, M1-N90, M1-H91, M1-T92, M1-L93, M1-V94, M1-L95, M1-L96, M1-D97, M1-T98, M1-E99, M1-G100, M1-L101, M1-G102, M1-D103, M1-V104, M1-E105, M1-K106, M1-G107, M1-D108, M1-P109, M1-K110, M1-N111, M1-D112, M1-S113, M1-W114, M1-I115, M1-F116, M1-A117, M1-L118, M1-A119, M1-V120, M1-L121, M1-L122, M1-C123, M1-S124, M1-T125, M1-F126, M1-V127, M1-Y128, M1-N129, M1-S130, M1-M131, M1-S132, M1-T133, M1-I134, M1-N135, M1-H136, M1-Q137, M1-A138, M1-L139, M1-E140, M1-Q141, M1-L142, M1-Q143, M1-Y144, M1-P145, M1-S146, M1-R147, M1-N148, M1-R149, M1-T150, M1-E151, M1-P152, M1-P153, M1-G154, M1-F155, M1-I156, M1-D157, M1-F158, M1-I159, M1-G160, M1-M161, M1-E162, M1-I163, M1-N164, M1-P165, M1-S166, M1-Y167, M1-V168, M1-T169, M1-E170, M1-L171, M1-T172, M1-E173, M1-L174, M1-I175, M1-K176, M1-A177, M1-K178, M1-S179, M1-S180, M1-P181, M1-R182, M1-P183, M1-D184, M1-G185, M1-V186, M1-E187, M1-D188, M1-S189, M1-T190, M1-E191, M1-F192, M1-V193, M1-S194, M1-F195, M1-F196, M1-P197, M1-D198, M1-F199, M1-L200, M1-W201, M1-T202, M1-V203, M1-R204, M1-D205, M1-F206, M1-T207, M1-L208, M1-E209, M1-L210, M1-K211, M1-L212, M1-N213, M1-G214, M1-H215, M1-P216, M1-I217, M1-T218, M1-E219, M1-D220, M1-E221, M1-Y222, M1-L223, M1-E224, M1-N225, M1-A226, M1-L227, M1-K228, M1-L229, M1-I230, M1-Q231, M1-G232, M1-N233, M1-N234, M1-P235, M1-R236, M1-V237, M1-Q238, M1-T239, M1-S40, M1-N241, M1-F242, M1-P243, M1-R244, M1-E245, M1-C246, M1-I247, M1-R248, M1-R249, M1-F250, M1-F251, M1-P252, M1-K253, M1-R254, M1-K255, M1-C256, M1-F257, M1-V258, M1-F259, M1-D260, M1-R261, M1-P262, M1-T263, M1-N264, M1-D265, M1-K266, M1-D267, M1-L268, M1-L269, M1-A270, M1-N271, M1-I272, M1-E273, M1-K274, M1-V275, M1-S276, M1-E277, M1-K278, M1-Q279, M1-L280, M1-D281, M1-P282, M1-K283, M1-F284, M1-Q285, M1-E286, M1-Q287, M1-T288, M1-N289, M1-I290, M1-F291, M1-C292, M1-S293, M1-Y294, M1-I295, M1-F296, M1-T297, M1-H298, M1-A299, M1-R300, M1-T301, M1-K302, M1-T303, M1-L304, M1-R305, M1-E306, M1-G307, M1-I308, M1-T309, M1-V310, M1-T311, M1-G312, M1-N313, M1-R314, M1-L315, M1-G316, M1-T317, M1-L318, M1-A319, M1-V320, M1-T321, M1-Y322, M1-V323, M1-E324, M1-A325, M1-I326, M1-N327, M1-S328, M1-G329, M1-A330, M1-V331, M1-P332, M1-C333, M1-L334, M1-E335, M1-N336, M1-A337, M1-V338, M1-I339, M1-T340, M1-L341, M1-A342, M1-Q343, M1-R344, M1-E345, M1-N346, M1-S347, M1-A348, M1-A349, M1-V350, M1-Q351, M1-R352, M1-A353, M1-A354, M1-D355, M1-Y356, M1-Y357, M1-S358, M1-Q359, M1-Q360, M1-M361, M1-A362, M1-Q363, M1-R364, M1-V365, M1-K366, M1-L367, M1-P368, M1-T369, M1-D370, M1-T371, M1-L372, M1-Q373, M1-E374, M1-L375, M1-L376, M1-D377, M1-M378, M1-H379, M1-A380, M1-A381, M1-C382, M1-E383, M1-R384, M1-E385, M1-A386, M1-I387, M1-A388, M1-I389, M1-F390, M1-M391, M1-E392, M1-H393, M1-S394, M1-F395, M1-K396, M1-D397, M1-E398, M1-N399, M1-Q400, M1-E401, M1-F402, M1-Q403, M1-K404, M1-K405, M1-F406, M1-M407, M1-E408, M1-T409, M1-T410, M1-M411, M1-N412, M1-K413, M1-K414, M1-G415, M1-D416, M1-F417, M1-L418, M1-L419, M1-Q420, M1-N421, M1-E422, M1-E423, M1-S424, M1-S425, M1-V426, M1-Q427, M1-Y428, M1-C429, M1-Q430, M1-A431, M1-K432, M1-L433, M1-N434, M1-E435, M1-L436, M1-S437, M1-K438, M1-G439, M1-L440, M1-M441, M1-E442, M1-S443, M1-I444, M1-S445, M1-A446, M1-G447, M1-S448, M1-F449, M1-S450, M1-V451, M1-P452, M1-G453, M1-G454, M1-H455, M1-K456, M1-L457, M1-Y458, M1-M459, M1-E460, M1-T461, M1-K462, M1-E463, M1-R464, M1-I465, M1-E466, M1-Q467, M1-D468, M1-Y469, M1-W470, M1-Q471, M1-V472, M1-P473, M1-R474, M1-K475, M1-G476, M1-V477, M1-K478, M1-A479, M1-K480, M1-E481, M1-V482, M1-F483, M1-Q484, M1-R485, M1-F486, M1-L487, M1-E488, M1-S489, M1-Q490, M1-M491, M1-V492, M1-I493, M1-E494, M1-E495, M1-S496, M1-I497, M1-L498, M1-Q499, M1-S500, M1-D501, M1-K502, M1-A503, M1-L504, M1-T508, M1-D506, M1-R507, M1-E508, M1-K509, M1-A510, M1-V511, M1-A512, M1-V513, M1-D514, M1-R515, M1-A516, M1-K517, M1-K518, M1-E519, M1-A520, M1-A521, M1-E522, M1-K523, M1-E524, M1-Q525, M1-E526, M1-L527, M1-L528, M1-K529, M1-Q530, M1-K531, M1-L532, M1-Q533, M1-E534, M1-Q535, M1-Q536, M1-Q537, M1-Q538, M1-M539, M1-E540, M1-A541, M1-Q542, M1-D543, M1-K544, M1-S545, M1-R546, M1-K547, M1-E548, M1-N549, M1-I550, M1-A551, M1-Q552, M1-L553, M1-K554, M1-E555, M1-K556, M1-L557, M1-M558, M1-E559, M1-E560, M1-R561, M1-E562, M1-H563, M1-L564, M1-L565, M1-R566, M1-E567, M1-Q568, M1-I569, M1-M570, M1-M571, M1-L572, M1-E573, M1-H574, M1-T575, M1-Q576, M1-K577, M1-V578, M1-Q579, M1-N580, M1-D581, M1-W582, M1-L583, M1-H584, M1-E585, M1-G586, M1-F587, M1-K588, M1-K589, M1-K590, M1-Y591, M1-E592, M1-E593, M1-M594, M1-N595, M1-A596, M1-E597, M1-I598, M1-S599, M1-Q600, M1-F601, M1-K602, M1-R603, M1-M604, M1-I605, M1-D606, M1-T607, M1-T608, M1-K609, M1-N610, M1-D611, M1-D612, M1-T613, M1-P614, M1-W615, M1-I616, M1-A617, M1-R618, M1-T619, M1-L620, M1-D621, M1-N622, M1-L623, M1-A624, M1-D625, M1-E626, M1-L627, M1-T628, M1-A629, M1-I630, M1-L631, M1-S632, M1-A633, M1-P634, M1-A635, M1-K636, M1-L637, M1-I638, M1-G639, M1-H640, M1-G641, M1-V642, M1-K643, M1-G644, M1-N645, M1-E646, M1-L647, M1-T648, M1-R649, M1-N650, M1-M651, M1-S652, M1-P653, M1-H654, M1-I655, M1-Q656, M1-R657, M1-S658, M1-G659, M1-S660, M1-Q661, M1-F662, M1-F663, M1-S664, M1-R665, M1-G666, M1-R667, M1-R668, M1-G669, M1-G670, M1-R671, M1-V672, M1-A672, M1-V674, M1-C675, M1-F676, M1-L677, M1-G678, M1-G679, M1-I680, M1-I681, M1-S682, M1-S683, M1-I684, M1-M685, M1-E686, M1-V687, M1-A688, M1-T689, M1-Q690, M1-H691, M1-N692, M1-L693, M1-E694, M1-P695, M1-L696, M1-P697, M1-Q698, M1-H699, M1-T700, M1-H701, M1-C702, M1-S703, M1-N704, M1-T705, M1-E706, M1-A707, M1-N708, M1-K709, M1-S710, M1-E711, M1-E712, M1-V713, M1-H714, M1-H715, M1-F716, M1-W717, M1-R718, M1-L719, M1-F720, M1-A721, M1-R722, M1-L723, M1-A724, M1-G725, M1-D726, M1-D727, M1-I728, M1-E729, M1-V730, M1-S731, M1-G732, M1-T733, M1-E734, M1-L735, M1-M736, M1-N737, M1-V738, M1-V739, M1-N740, M1-K741, M1-V742, M1-V743, M1-I744, M1-S745, M1-R746, M1-T747, M1-E748, M1-L749, M1-K750, M1-T751, M1-H752, M1-G753, M1-F754, M1-G755, M1-I756, M1-D757, M1-T758, M1-C759, M1-Q760, M1-S761, M1-M762, M1-V763, M1-A764, M1-M765, M1-M766, M1-D767, M1-S768, M1-D769, M1-T770, M1-I771, M1-G772, M1-K773, M1-L774, M1-D775, M1-F776, M1-E777, M1-E778, M1-F779, M1-N780, M1-Y781, M1-L782, M1-W783, M1-N784, M1-N785, M1-I786 and/or M1-K787 of SEQ ID NO:5. Polynucleotide sequences encoding these polypeptides are also provided. The present invention also encompasses the use of these C-terminal HGBPBMY2 (4843 30 1 1; 4843_1) deletion polypeptides as immunogenic and/or antigenic epitopes as described elsewhere herein.

Alternatively, preferred polypeptides of the present invention can comprise polypeptide sequences corresponding to, for example, internal regions of the HGBPBMY2 (4843 30 1 1; 4843_1) polypeptide (e.g., any combination of both N- and C-terminal HGBPBMY2 (4843 30 1 1; 4843_1) polypeptide deletions) of SEQ ID NO:5. For example, internal regions could be defined by the equation: amino acid NX to amino acid CX, wherein NX refers to any N-terminal deletion polypeptide amino acid of HGBPBMY2 (4843 30 1 1; 4843_1) (SEQ ID NO:5), and where CX refers to any C-terminal deletion polypeptide amino acid of HGBPBMY2 (4843 30 1 1; 4843_1) (SEQ ID NO:5). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the HGBPBMY2 (4843 30 1 1; 4843_1) polypeptide.

The present invention encompasses the identification of compounds and drugs which stimulate HGBPBMY2 (4843 30 1 1; 4843_1) on the one hand (i.e., agonists) and which inhibit the function of HGBPBMY2 (4843 30 1 1; 4843_1) on the other hand (i.e., antagonists). In general, such screening procedures involve providing appropriate cells which express a polypeptide of the present invention on the surface thereof. Such cells can include, for example, cells from mammals, yeast, *Drosophila* or *E. coli*. In a representative embodiment, a polynucleotide encoding a polypeptide of the present invention can be employed to transfect cells to thereby express a HGBPBMY2 (4843 30 1 1; 4843_1) polypeptide. The expressed polypeptide can then be contacted with a test compound to observe binding, stimulation or inhibition of a functional response.

FIG. 44 shows an expanded expression profile of the GBP HGBPBMY2 (4843_1). The figure illustrates the relative expression level of HGBPBMY2 amongst various mRNA tissue sources. As shown, the HGBPBMY2 polypeptide showed the highest expression in tonsil, foreskin, esophagus, and was detectable in uterus cervix, tertiary lung bronchus and trachea. FIG. 44 also illustrates the relative expression level of HGBPBMY2 amongst various mRNA tissue sources isolated from normal and diseased tissues. Expression data was obtained by measuring the steady state HGBPBMY2 mRNA levels by quantitative PCR using the PCR primer pair provided as SEQ ID NO:64 and 65, and TAQMAN probe (SEQ ID NO:66) as described in Example 37 herein. These data support a role of HGBPBMY2 in regulating various functions, including immune system and pulmonary functions, and thus small molecule modulators of HGBPBMY2 function may represent a novel therapeutic option in the treatment of lung cancers, as well as other pulmonary diseases, and in the treatment of immune system diseases.

Features of the Polypeptide Encoded by Gene No. 3

A polypeptide encoded by this gene, HGBPBMY3 (4843 30 2 1; 4843_2), is provided as SEQ ID NO:7 (FIGS. 3A–3B) and is encoded by the polynucleotide sequence according to SEQ ID NO:6 (FIGS. 3A–3B) and/or by a polynucleotide contained within the deposited clone. HGBPBMY3 (4843 30 2 1; 4843_2) has significant homology at the nucleotide and amino acid level to a number of guanylate binding proteins, which include, for example, human GBP-1, human GBP-2, human GBP-3 and human GBP-4.

The determined nucleotide sequence of the HGBPBMY3 (4843 30 2 1; 4843_2), (i.e., the cDNA shown in FIGS. 3A–3B and in SEQ ID NO:6) comprises an open reading frame encoding a protein of about 464 amino acid residues. The predicted amino acid sequence of the HGBPBMY3 (4843 30 2 1; 4843_2) polypeptide is shown in FIGS. 3A–3B (SEQ ID NO:7). The percent identity and similarity values between the HGBPBMY3 (4843 30 2 1; 4843_2) polypeptide to the known GBP family member hGBP1 is provided in FIG. 9. The HGBPBMY3 (4843 30 2 1; 4843_2) protein shown in FIGS. 3A–3B was determined to share significant identity and similarity to several known GBP family members, as shown in FIG. 11A–11G.

Figure 17:
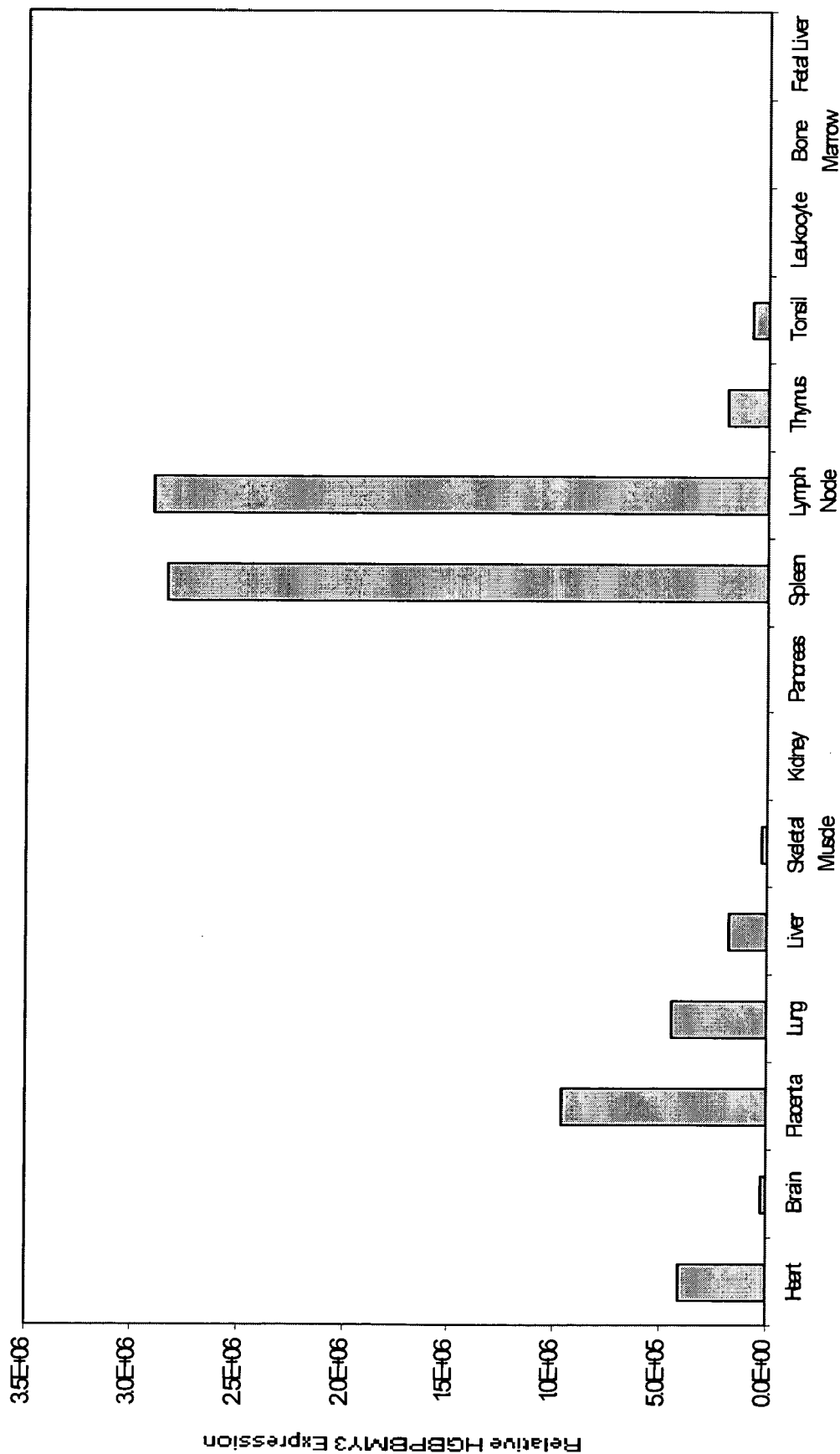
FIG. 17 is bar graph depicting the bar graph depicting the tissue expression pattern of human HGBPBMY3 (4843 30 2 1; 4843_2). Panels of cDNAs derived from normal and immune tissue were analyzed by Real Time PCR for expression of HGBPBMY3 (4843 30 2 1; 4843_2).

Expression profiling designed to measure the steady state mRNA levels encoding the HGBPBMY3 (4843 30 2 1; 4843_2) polypeptide showed expression predominately in spleen and lymph node; expression was also observed in heart, placenta, lung, liver, thymus and tonsil (see FIG. 17).

Based upon the strong homology to members of the GBP family members, the HGBPBMY3 (4843 30 2 1; 4843_2) polypeptide is expected to share at least some biological activity with GBP family members, specifically hGBP-1, hGBP-2, hGBP3 and hGBP-4.

The HGBPBMY3 (4843 30 2 1; 4843_2) polynucleotides and polypeptides of the present invention, including agonists and/or fragments thereof, may have uses that include detecting, prognosing, treating, preventing, and/or ameliorating at least diseases and conditions of the immune system, the reproductive system, heart, lung, and liver.

The HGBPBMY3 (4843 30 2 1; 4843_2) polynucleotides and polypeptides of the present invention, including agonists and/or fragments thereof, may have uses that include modulating signal transduction activity, in various cells, tissues, and organisms, and particularly in mammalian tissue, preferably human tissue.

The strong homology to human GBP family members, particularly hGBP-1, hGBP-2, hGBP-3 and hGBP-4, combined with significant HGBPBMY3 (4843 30 2 1; 4843_2) expression in liver tissue suggests a potential utility for HGBPBMY3 (4843 30 2 1; 4843_2) polynucleotides and polypeptides in treating, diagnosing, prognosing, and/or preventing liver diseases. In representative embodiments, HGBPBMY3 (4843 30 2 1; 4843_2) polynucleotides and polypeptides including agonists and fragments thereof, may have uses that include treating, diagnosing, prognosing, and/or preventing liver diseases. For example, the HGBPBMY3 (4843 30 2 1; 4843_2) protein may be useful for the detection, treatment, amelioration, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, HGBPBMY3 (4843 30 2 1; 4843_2) polynucleotides and polypeptides, including fragments and/or antagonists thereof, may have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The strong homology to human GBP family members, particularly hGBP-1, hGBP-2, hGBP-3 and hGBP-4, combined with the high level of HGBPBMY3 (4843 30 2 1; 4843_2) expression in some immune system tissues (i.e., spleen, lymph node, thymus and/or tonsil) suggests that HGBPBMY3 (4843 30 2 1; 4843_2) polynucleotides and polypeptides may be useful in treating, diagnosing, prognosing, and/or preventing diseases and conditions of the immune system. In representative embodiments, HGBPBMY3 (4843 30 2 1; 4843_2) polynucleotides and polypeptides including agonists and fragments thereof, may have uses that include treating, diagnosing, prognosing, and/or preventing diseases and conditions of the immune system. The HGBPBMY3 (4843 30 2 1; 4843_2) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. The HGBPBMY3 (4843 30 2 1; 4843_2) polypeptide may also be useful for modulating cytokine production, antigen presentation, or other processes, such as for boosting immune responses, etc.

Additional immunolgical disorders that a HGBPBMY3 (4843 30 2 1; 4843_2) polypeptide of the present invention can be useful in the treatment of include various autoimmune diseases such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A HGBPBMY3 (4843 30 2 1; 4843_2) polypeptide of the present invention can also be useful in treating or ameliorating primary immune diseases, as well as immune diseases associated with or secondary to other diseases. Such diseases and conditions include Recombinase activating gene (RAG 1/2) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimke immuno-osseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The strong homology to human GBP family members, particularly GBP-1, GBP-2, GBP-3 and GBP-4, combined with HGBPMY3 (4843 30 2 1; 4843_2) expression in heart tissue suggests the HGBPMY3 polynucleotides and polypeptides may be useful in treating, diagnosing, prognosing, and/or preventing cardiovascular diseases and/or disorders, which include, but are not limited to: myocardio infarction, congestive heart failure, arrthymias, cardiomyopathy, atherosclerosis, arterialsclerosis, microvascular disease, embolism, thrombosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, HGBPBMY3 (4843 30 2 1; 4843_2) polynucleotides and polypeptides may be useful for treating and/or ameliorating cardiovascular diseases and symptoms which result indirectly from various non-cardiavascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, may have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a *streptococci* infection, group b *streptococci* infection, *Enterococcus* infection, nonenterococcal group D *streptococci* infection, nonenterococcal group C *streptococci* infection, nonenterococcal group G *streptococci* infection, *Streptoccus viridans* infection, *Staphylococcus aureus* infection, coagulase-negative staphylococci infection, gram-negative *Bacilli* infection, Enterobacteriaceae infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous Mycobacteria infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Likewise, the expression in lung tissue also emphasizes a potential utility for HGBPMY3 (4843 30 2 1; 4843_2) polynucleotides and polypeptides in treating, diagnosing, prognosing, and/or preventing pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, HGBPBMY3 (4843 30 2 1; 4843__2) polynucleotides and polypeptides, including fragments and/or antagonists thereof, may have uses which include, directly or indirectly, treating, preventing, diagnosing, and/or prognosing the following, non-limiting, pulmonary infections: pnemonia, bacterial pnemonia, viral pnemonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pnemonia (for example, as caused by *Mycobacterium tuberculosis*, etc.) mycoplasma pnemonia, fungal pnemonia (for example, as caused by *Pneumocystis carinii, Histoplasma capsulatum, Coccidioides immitis, Blastomyces dermatitidis, Candida* sp., *Cryptococcus neoformans, Aspergillus* sp., Zygomycetes, etc.), Legionnaires' Disease, *Chlamydia* pnemonia, aspiration pnemonia, *Nocordia* sp. Infections, parasitic pnemonia (for example, as caused by *Strongyloides, Toxoplasma gondii*, etc.) necrotizing pnemonia, in addition to any other pulmonary disease and/or disorder (e.g., non-pneumonia) implicated by the causative agents listed above or elsewhere herein.

Additionally, the expression in placenta tissue also emphasizes a potential utility for HGBPBMY3 (4843 30 2 1; 4843__2) polynucleotides and polypeptides in treating, diagnosing, prognosing, and/or preventing placenta disorders, in addition to reproductive disorders. Such diseases and conditions include, but are not limited to, dysfunctional uterine bleeding, amenorrhea, primary dysmenorrhea, sexual dysfunction, infertility, pelvic inflammatory disease, endometriosis, placental aromatase deficiency, premature menopause, and placental dysfunction.

The HGBPBMY3 (4843 30 2 1; 4843__2) protein can also be used to determine biological activity, raise antibodies, as tissue markers, to isolate cognate ligands or receptors, to identify agents that modulate their interactions. Further, proteins, as well as antibodies directed against the HGBPBMY3 (4843 30 2 1; 4843__2) protein, can show utility as a tumor marker and/or immunotherapy targets for heart, placenta, lung, imune system and liver tissue.

The HGBPBMY3 (4843 30 2 1; 4843__2) polynucleotides and polypeptides, including fragments and for antagonsists thereof, can have uses which include identification of modulators of HGBPBMY3 (4843 30 2 1; 4843__2) function including antibodies (for detection or neutralization), naturally-occurring modulators and small molecule modulators. Antibodies to a particular domain of the HGBPBMY3 (4843 30 2 1; 4843__2) protein could be used as diagnostic agents of conditions in subjects, are useful in monitoring the activation of signal transduction pathways, and can be used as a biomarker for the involvement of GBP's in disease states, as well as in the evaluation of inhibitors of GBP's in vivo.

HGBPBMY3 (4843 30 2 1; 4843__2) polypeptides and polynucleotides have additional uses which include diagnosing diseases related to the over and/or under expression of HGBPBMY3 (4843 30 2 1; 4843__2) by identifying mutations in the HGBPBMY3 (4843 30 2 1; 4843__2) gene by using HGBPBMY3 (4843 30 2 1; 4843__2) sequences as probes or by determining HGBPBMY3 (4843 30 2 1; 4843__2) protein or mRNA expression levels. HGBPBMY3 (4843 30 2 1; 4843__2) polypeptides can be useful for screening compounds that affect the activity of the protein. HGBPBMY3 (4843 30 2 1; 4843__2) peptides can also be used for the generation of specific antibodies and as bait in yeast two hybrid screens to find proteins the specifically interact with HGBPBMY3 (4843 30 2 1; 4843__2), as described herein.

Although it is believed the encoded polypeptide could share at least some biological activities with human guanylate binding proteins (particularly hGBP-1, hGBP-2, hGBP-3 and hGBP-4), a number of methods of determining the exact biological function of this clone are either known in the art or are described elsewhere herein. For example, the function of this clone can be determined by applying microarray methodology. Nucleic acids corresponding to the HGBPBMY3 (4843 30 2 1; 4843__2) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased liver tissue, as compared to normal tissue might indicate a function in modulating liver function, for example. In the case of HGBPBMY3 (4843 30 2 1; 4843__2), spleen, lymph node, heart, placenta, lung, liver thymus and tonsil tissue can be used, for example, to extract RNA to prepare the probe.

In addition, the function of the protein can be assessed, for example, by applying quantitative PCR methodology. Real time quantitative PCR would provide the capability of following the expression of the HGBPBMY3 (4843 30 2 1; 4843__2) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of HGBPBMY3 (4843 30 2 1; 4843__2), a disease correlation related to HGBPBMY3 (4843 30 2 1; 4843__2) can be made by comparing the mRNA expression level of HGBPBMY3 (4843 30 2 1; 4843__2) in normal tissue, as compared to diseased tissue (for example, diseased immune system tissue). Significantly higher or lower levels of HGBPBMY3 (4843 30 2 1; 4843__2) expression in the diseased tissue can suggest HGBPBMY3 (4843 30 2 1; 4843__2) plays a role in disease progression, and antagonists against HGBPBMY3 (4843 30 2 1; 4843__2) polypeptides would be useful therapeutically in treating, preventing, and/or ameliorating the disease. Alternatively, significantly higher or lower levels of HGBPBMY3 (4843 30 2 1; 4843__2) expression in the diseased tissue can suggest HGBPBMY3 (4843 30 2 1; 4843__2) plays a defensive role against disease progression, and agonists of HGBPBMY3 (4843 30 2 1; 4843__2) polypeptides can be useful therapeutically in treating, preventing, and/or ameliorating the disease. Also encompassed by the present invention are quantitative PCR probes corresponding to the polynucleotide sequence provided as SEQ ID NO:6 (FIGS. 3A–3B).

The function of the protein can also be assessed through complementation assays in yeast. For example, in the case of the HGBPBMY3 (4843 30 2 1; 4843__2), transforming yeast deficient in GBP activity, for example, and assessing their ability to grow would provide convincing evidence the HGBPBMY3 (4843 30 2 1; 4843__2) polypeptide has GBP activity. Additional assay conditions and methods that can be used in assessing the function of the polynucleotides and polypeptides of the present invention are known in the art, some of which are disclosed herein. For example, a GTPase activity assay could be employed.

Alternatively, the biological function of the encoded polypeptide can be determined by disrupting a homologue of this polypeptide in mice and/or rats and observing the resulting phenotype. Such knock-out experiments are known in the art, some of which are disclosed elsewhere herein.

Moreover, the biological function of this polypeptide can be determined by the application of antisense and/or sense methodology (including RNAi and/or homolgous recombination) and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a spleen tissue-specific promoter), or it can be expressed at a specified time of development using an inducible and/or a developmentally regulated promoter.

In the case of HGBPBMY3 (4843 30 2 1; 4843_2) transgenic mice or rats, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic mice or rats to refine the biological function of the polypeptide is encompassed by the present invention.

In preferred embodiments, the following N-terminal HGBPBMY3 (4843 30 2 1; 4843_2) deletion polypeptides are encompassed by the present invention: M1-R464, V2-R464, S3-R464, E4-R464, I5-R464, H6-R464, M7-R464, T8-R464, G9-R464, P10-R464, M11-R464, C12-R464, L13-R464, I14-R464, E15-R464, N16-R464, T17-R464, N18-R464, G19-R464, R20-R464, L21-R464, M22-R464, A23-R464, N24-R464, P25-R464, E26-R464, A27-R464, L28-R464, K29-R464, I30-R464, L31-R464, S32-R464, A33-R464, I34-R464, T35-R464, Q36-R464, P37-R464, V38-R464, V39-R464, V40-R464, V41-R464, A42-R464, T43-R464, R44-R464, T45-R464, G46-R464, K47-R464, S48-R464, Y49-R464, L50-R464, I51-R464, N52-R464, K53-R464, L54-R464, A55-R464, Q56-R464, K57-R464, K58-R464, K59-R464, G60-R464, F61-R464, S62-R464, L63-R464, G64-R464, S65-R464, T66-R464, V67-R464, Q68-R464, S69-R464, H70-R464, T71-R464, K72-R464, G73-R464, I74-R464, W75-R464, M76-R464, W77-R464, C78-R464, M79-R464, P80-R464, H81-R464, P82-R464, K83-R464, K84-R464, P85-R464, G86-R464, H87-R464, I88-R464, L89-R464, V90-R464, L91-R464, L92-R464, D93-R464, T94-R464, E95-R464, G96-R464, L97-R464, G98-R464, D99-R464, V100-R464, E101-R464, K102-R464, G103-R464, D104-R464, N105-R464, Q106-R464, N107-R464, D108-R464, S109-R464, W110-R464, I111-R464, F112-R464, A113-R464, L114-R464, A115-R464, V116-R464, L117-R464, L118-R464, N119-R464, S120-R464, T121-R464, S122-R464, M123-R464, Y124-R464, N125-R464, S126-R464, I127-R464, G128-R464, T129-R464, I130-R464, N131-R464, Q132-R464, Q133-R464, A134-R464, M135-R464, D136-R464, Q137-R464, L138-R464, H139-R464, Y140-R464, V141-R464, T142-R464, E143-R464, L144-R464, T145-R464, H146-R464, R147-R464, V148-R464, Q149-R464, P150-R464, K151-R464, S152-R464, S153-R464, P154-R464, D155-R464, E156-R464, N157-R464, E158-R464, N159-R464, E160-R464, D161-R464, S162-R464, A163-R464, D164-R464, F165-R464, E166-R464, S167-R464, F168-R464, F169-R464, P170-R464, D171-R464, F172-R464, A173-R464, G174-R464, L175-R464, E176-R464, S177-R464, L178-R464, V179-R464, L180-R464, T181-R464, Y182-R464, V183-R464, N184-R464, A185-R464, I186-R464, S187-R464, S188-R464, G189-R464, D190-R464, L191-R464, P192-R464, C193-R464, M194-R464, E195-R464, N196-R464, A197-R464, V198-R464, L199-R464, A200-R464, L201-R464, A202-R464, Q203-R464, I204-R464, E205-R464, N206-R464, S207-R464, A208-R464, A209-R464, V210-R464, Q211-R464, K212-R464, A213-R464, I214-R464, A215-R464, H216-R464, Y217-R464, E218-R464, K219-R464, Q220-R464, M221-R464, G222-R464, Q223-R464, K224-R464, V225-R464, Q226-R464, L227-R464, P228-R464, T229-R464, E230-R464, T231-R464, L232-R464, Q233-R464, E234-R464, L235-R464, L236-R464, D237-R464, 238-R464, H239-R464, R240-R464, D214-R464, S242-R464, E243-R464, S244-R464, K245-R464, A246-R464, T247-R464, E248-R464, V249-R464, F250-R464, I251-R464, R252-R464, S253-R464, S254-R464, F255-R464, K256-R464, D257-R464, V258-R464, D259-R464, H260-R464, L261-R464, F262-R464, Q263-R464, K264-R464, E265-R464, L266-R464, A267-R464, A268-R464, Q269-R464, L270-R464, D271-R464, K272-R464, K273-R464, R274-R464, D275-R464, D276-R464, F277-R464, C278-R464, K279-R464, Q280-R464, N281-R464, Q282-R464, E283-R464, A284-R464, S285-R464, S286-R464, D287-R464, R288-R464, C289-R464, S290-R464, A291-R464, L292-R464, L293-R464, Q294-R464, V295-R464, I296-R464, F297-R464, S298-R464, P299-R464, L300-R464, E301-R464, E302-R464, E303-R464, V304-R464, K305-R464, A306-R464, G307-R464, I308-R464, Y309-R464, S310-R464, K311-R464, P312-R464, G313-R464, G314-R464, Y315-R464, R316-R464, L317-R464, F318-R464, I319-R464, Q320-R464, K321-R464, L322-R464, Q323-R464, D324-R464, L325-R464, E326-R464, K327-R464, K328-R464, Y329-R464, Y330-R464, E 331-R464, E332-R464, P333-R464, R334-R464, K335-R464, G336-R464, I337-R464, Q338-R464, G339-R464, I340-R464, S341-R464, P342-R464, P343-R464, R344-R464, T345-R464, T346-R464, G347-R464, Q348-R464, R349-R464, K350-R464, E351-R464, F352-R464, P353-R464, E354-R464, E355-R464, R356-R464, M357-R464, A358-R464, G359-R464, R360-R464, Q361-R464, T362-R464, G363-R464, T364-R464, P365-R464, A366-R464, Y367-R464, S368-R464, R369-R464, L370-R464, L371-R464, L372-R464, L373-R464, T374-R464, L375-R464, C376-R464, S377-R464, L378-R464, G379-R464, P380-R464, K381-R464, A382-R464, E383-R464, E384-R464, I385-R464, L386-R464, Q387-R464, T388-R464, Y389-R464, L390-R464, K391-R464, S392-R464, K393-R464, E394-R464, S395-R464, M396-R464, T397-R464, D398-R464, A399-R464, I400-R464, L401-R464, Q402-R464, T403-R464, D404-R464, Q405-R464, T406-R464, L407-R464, T408-R464, E409-R464, K410-R464, E411-R464, K412-R464, E413-R464, I414-R464, E415-R464, V416-R464, E417-R464, R418-R464, V419-R464, K420-R464, A421-R464, E422-R464, S423-R464, A424-R464, Q425-R464, A426-R464, S427-R464, A428-R464, K429-R464, M430-

R464, L431-R464, Q432-R464, Q433-R464, M434-R464, Q435-R464, R436-R464, K437-R464, N438-R464, E439-R464, Q440-R464, M441-R464, M442-R464, E443-R464, Q444-R464, K445-R464, E446-R464, R447-R464, S448-R464, Y449-R464, Q450-R464, E451-R464, H452-R464, L453-R464, K454-R464, Q455-R464, L456-R464, T457-R464, E458-R464, K459-R464, M460-R464, E461-R464, S462-R464 and/or D463-R464 of SEQ ID NO:7. Polynucleotide sequences encoding these polypeptides are also provided. The present invention also encompasses the use of these N-terminal HGBPBMY3 (4843 30 2 1; 4843_2) deletion polypeptides as immunogenic and/or antigenic epitopes as described elsewhere herein.

In other embodiments, the following C-terminal HGB-PBMY3 (4843 30 2 1; 4843_2) deletion polypeptides are encompassed by the present invention: M1-V2, M1-S3, M1-E4, M1-I5, M1-H6, M1-M7, M1-T8, M1-G9, M1-P10, M1-M11, M1-C12, M1-L13, M1-I14, M1-E15, M1-N16, M1-T17, M1-N18, M1-G19, M1-R20, M1-L21, M1-M22, M1-A23, M1-N24, M1-P25, M1-E26, M1-A27, M1-L28, M1-K29, M1-I30, M1-L31, M1-S32, M1-A33, M1-I34, M1-T35, M1-Q36, M1-P37, M1-V38, M1-V39, M1-V40, M1-V41, M1-A42, M1-T43, M1-R44, M1-T45, M1-G46, M1-K47, M1-S48, M1-Y49, M1-L50, M1-151, M1-N52, M1-K53, M1-L54, M1-A55, M1-Q56, M1-K57, M1-K58, M1-K59, M1-G60, M1-F61, M1-S62, M1-L63, M1-G64, M1-S65, M1-T66, M1-V67, M1-Q68, M1-S69, M1-H70, M1-T71, M1-K72, M1-G73, M1-I74, M1-W75, M1-M76, M1-W77, M1-C78, M1-M79, M1-P80, M1-H81, M1-P82, M1-K83, M1-K84, M1-P85, M1-G86, M1-H87, M1-I88, M1-L89, M1-V90, M1-L91, M1-L92, M1-D93, M1-T94, M1-E95, M1-G96, M1-L97, M1-G98, M1-D99, M1-V100, M1-E101, M1-K102, M1-G103, M1-D104, M1-N105, M1-Q106, M1-N107, M1-D108, M1-S109, M1-W110, M1-I111, M1-F112, M1-A113, M1-L114, M1-A115, M1-V116, M1-L117, M1-L118, M1-N119, M1-S120, M1-T121, M1-S122, M1-M123, M1-Y124, M1-N125, M1-S126, M1-1127, M1-G128, M1-T129, M1-I130, M1-N131, M1-Q132, M1-Q133, M1-A134, M1-M135, M1-D136, M1-Q137, M1-L138, M1-H139, M1-Y140, M1-V141, M1-T142, M1-E143, M1-L144, M1-T145, M1-H146, M1-R147, M1-V148, M1-Q149, M1-P150, M1-K151, M1-S152, M1-S153, M1-P154, M1-D155, M1-E156, M1-S157, M1-E158, M1-N159, M1-E160, M1-D161, M1-S162, M1-A163, M1-D164, M1-F165, M1-E166, M1-S167, M1-F168, M1-F169, M1-P170, M1-D171, M1-F172, M1-A173, M1-G174, M1-L175, M1-E176, M1-S177, M1-L178, M1-V179, M1-L180, M1-T181, M1-Y182, M1-V183, M1-N184, M1-A185, M1-I186, M1-S187, M1-S188, M1-G189, M1-D190, M1-L191, M1-P192, M1-C193, M1-M194, M1-E195, M1-N196, M1-A197, M1-V198, M1-L199, M1-A200, M1-L201, M1-A202, M1-Q203, M1-1204, M1-E205, M1-N206, M1-S207, M1-A208, M1-A209, M1-V210, M1-Q211, M1-K212, M1-A213, M1-I214, M1-A215, M1-H216, M1-Y217, M1-E218, M1-K219, M1-Q220, M1-M221, M1-G222, M1-Q223, M1-224, M1-V225, M1-Q226, M1-L227, M1-P228, M1-T229, M1-E230, M1-T231, M1-L232, M1-Q233, M1-E234, M1-L235, M1-L236, M1-D237, M1-L238, M1-H239, M1-R240, M1-D241, M1-S242, M1-E243, M1-S244, M1-K245, M1-A246, M1-T247, M1-E248, M1-V249, M1-F250, M1-I251, M1-R252, M1-S253, M1-S254, M1-F255, M1-K256, M1-D257, M1-V258, M1-D259, M1-H260, M1-L261, M1-F262, M1-Q263, M1-K264, M1-E265, M1-L266, M1-A267, M1-A268, M1-Q269, M1-L270, M1-D271, M1-K272, M1-K273, M1-R274, M1-D275, M1-D276, M1-F277, M1-C278, M1-K279, M1-Q280, M1-N281, M1-Q282, M1-E283, M1-A284, M1-S285, M1-S286, M1-D287, M1-R288, M1-C289, M1-S290, M1-A291, M1-L292, M1-L293, M1-Q294, M1-V295, M1-I296, M1-F297, M1-S298, M1-P299, M1-L300, M1-E301, M1-E302, M1-E303, M1-V304, M1-K305, M1-A306, M1-G307, M1-I308, M1-Y309, M1-S310, M1-K311, M1-P312, M1-G313, M1-G314, M1-Y315, M1-R316, M1-L317, M1-F318, M1-I319, M1-Q320, M1-K321, M1-L322, M1-Q323, M1-D324, M1-L325, M1-E326, M1-K327, M1-K328, M1-Y329, M1-Y330, M1-E331, M1-E332, M1-P333, M1-R334, M1-K335, M1-G336, M1-I337, M1-Q338, M1-G339, M1-I340, M1-S341, M1-P342, M1-P343, M1-R344, M1-T345, M1-T346, M1-G347, M1-Q348, M1-R349, M1-K350, M1-E351, M1-F352, M1-P353, M1-E354, M1-E355, M1-R356, M1-M357, M1-A358, M1-G359, M1-R360, M1-Q361, M1-T362, M1-G363, M1-T364, M1-P365, M1-A366, M1-Y367, M1-S368, M1-R369, M1-L370, M1-L371, M1-L372, M1-L373, M1-T374, M1-L375, M1-C376, M1-S377, M1-L378, M1-G379, M1-P380, M1-K381, M1-A382, M1-E383, M1-E384, M1-I385, M1-L386, M1-Q387, M1-T388, M1-Y389, M1-L390, M1-K391, M1-S392, M1-K393, M1-E394, M1-S395, M1-M396, M1-T397, M1-D398, M1-A399, M1-I400, M1-L401, M1-Q402, M1-T403, M1-D404, M1-Q405, M1-T406, M1-L407, M1-T408, M1-409, M1-K410, M1-E411, M1-K412, M1-E413, M1-I414, M1-E415, M1-V416, M1-E417, M1-R418, M1-V419, M1-K420, M1-A421, M1-E422, M1-S423, M1-A424, M1-Q425, M1-A426, M1-S427, M1-A428, M1-K429, M1-M430, M1-L431, M1-Q432, M1-Q433, M1-M434, M1-Q435, M1-R436, M1-K437, M1-N438, M1-E439, M1-Q440, M1-M441, M1-M442, M1-E443, M1-Q444, M1-K445, M1-E446, M1-R447, M1-S448, M1-Y449, M1-Q450, M1-E451, M1-H452, M1-L453, M1-K454, M1-Q455, M1-L456, M1-T457, M1-E458, M1-K459, M1-M460, M1-E461, M1-S462, M1-D463 and/or M1-R464 of SEQ ID NO:7. Polynucleotide sequences encoding these polypeptides are also provided. The present invention also encompasses the use of these C-terminal HGBPBMY3 (4843 30 2 1; 4843_2) deletion polypeptides as immunogenic and/or antigenic epitopes as described elsewhere herein.

Alternatively, preferred polypeptides of the present invention can comprise polypeptide sequences corresponding to, for example, internal regions of the HGBPBMY3 (4843 30 2 1; 4843_2) polypeptide (e.g., any combination of both N- and C-terminal HGBPBMY3 (4843 30 2 1; 4843_2) polypeptide deletions) of SEQ ID NO:7. For example, internal regions could be defined by the equation: amino acid NX to amino acid CX, wherein NX refers to any N-terminal deletion polypeptide amino acid of HGBPBMY3 (4843 30 2 1; 4843_2) (SEQ ID NO:7), and where CX refers to any C-terminal deletion polypeptide amino acid of HGBPBMY3 (4843 30 2 1; 4843_2) (SEQ ID NO:7). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the HGBPBMY3 (4843 30 2 1; 4843_2) polypeptide.

The present invention encompasses the identification of compounds and drugs which stimulate HGBPBMY3 (4843 30 2 1; 4843_2) on the one hand (i.e., agonists) and which inhibit the function of HGBPBMY3 (4843 30 2 1; 4843_2) on the other hand (i.e., antagonists). In general, such screening procedures involve providing appropriate cells which express a polypeptide of the present invention on the surface thereof. Such cells can include, for example, cells from mammals, yeast, Drosophila or E. coli. In a representative embodiment, a polynucleotide encoding a polypeptide of the present invention can be employed to transfect cells to thereby express the HGBPBMY3 (4843 30 2 1; 4843_2) polypeptide. The expressed polypeptide can then be contacted with a test compound to observe binding, stimulation or inhibition of a functional response.

FIG. 45 shows an expanded expression profile of the GBP HGBPBMY3 (4843_2). The figure illustrates the relative expression level of HGBPBMY3 amongst various mRNA tissue sources. FIG. 45 illustrates the relative expression level of HGBPBMY3 amongst various mRNA tissue sources isolated from normal and diseased tissues. As shown, the HGBPBMY3 polypeptide showed increased expression in thyroids of hyperthyroidism patients compared to control thyroids. FIG. 45 also illustrates increased expression in breast and testicle tumors relative to controls; increased expression in prostatic hypertrophy relative to normal prostate; expressed in normal and diseased lung parenchyma; increased in bronchitis. Expression data was obtained by measuring the steady state HGBPBMY3 mRNA levels by quantitative PCR using the PCR primer pair provided as SEQ ID NO:67 and 68, and TAQMAN probe (SEQ ID NO:69) as described in Example 38 herein. These data support a role of HGBPBMY3 in regulating various functions. HGBPBMY3 may also be participating in the formation of testicle and breast tumors and thus small molecule modulators of HGBPBMY3 function may represent a novel therapeutic option in the treatment of breast and testicle cancers, as well as diseases of the prostate.

Features of the Polypeptide Encoded by Gene No. 4

A polypeptide encoded by this gene, HGBPBMY4 (FLJ10961), is provided as SEQ ID NO:9 (FIGS. 4A–4C) and is encoded by the polynucleotide sequence according to SEQ ID NO:8 (FIGS. 4A–4C) and/or by a polynucleotide contained within the deposited clone. HGBPBMY4 (FLJ10961) has significant homology at the nucleotide and amino acid level to a number of guanylate binding proteins, which include, for example, human GBP-1, human GBP-2, human GBP-3 and human GBP-4.

The determined nucleotide sequence of the HGBPBMY4 (FLJ10961), (i.e. the cDNA shown in FIGS. 4A–4C and in SEQ ID NO:8) comprises an open reading frame encoding a protein of about 563 amino acid residues. The predicted amino acid sequence of the HGBPBMY4 (FLJ10961) polypeptide is shown in FIGS. 4A–4C (SEQ ID NO:9). The percent identity and similarity values between the HGBPBMY4 (FLJ10961) polypeptide to the known GBP family member hGBP1 is provided in FIG. 9. The HGBPBMY4 (FLJ10961) protein shown in FIGS. 4A–4C was determined to share significant identity and similarity to several known GBP family members, as shown in FIG. 11A–11G.

Figure 15:
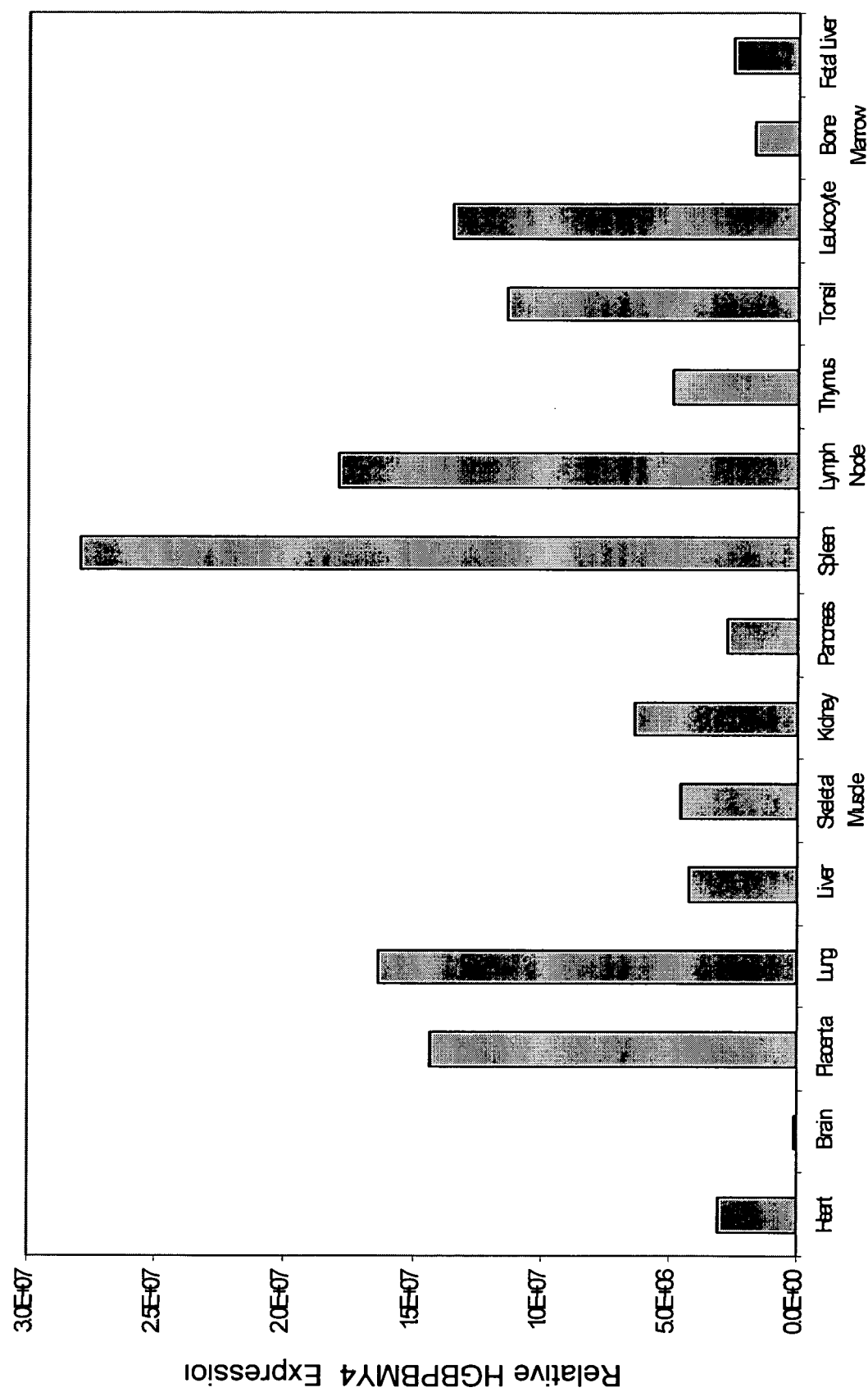
FIG. 15 is bar graph depicting the tissue expression pattern of human HGBPBMY4 (FLJ10961). Panels of cDNAs derived from normal and immune tissue were analyzed by real Time PCR for expression of HGBPBMY4 (FLJ10961).

Expression profiling designed to measure the steady state mRNA levels encoding the HGBPBMY4 (FLJ10961) polypeptide showed expression in spleen, lymph node, tonsil, leukocyte, placenta and lung, as well as expression in heart, liver, skeletal muscle, kidney and thymus; expression in bone marrow and pancreas was also observed (see FIG. 15).

Based upon the strong homology to members of the GBP family members, the HGBPBMY4 (FLJ10961) polypeptide is expected to share at least some biological activity with GBP family members, specifically hGBP-1, hGBP-2, hGBP3 and hGBP-4.

The HGBPBMY4 (FLJ10961) polynucleotides and polypeptides of the present invention, including agonists and/or fragments thereof, may have uses that include detecting, diagnosing, prognosing, treating, preventing, and/or ameliorating at least diseases and conditions of the immune system (e.g., spleen, lymph node, tonsil, thymus), the pulmonary system (e.g., lung), the reproductive system (e.g., placenta), renal system (e.g., kidney), skeletal muscle, liver, cardiovascular system (e.g., heart), pancreas and hematopoesis (e.g., bone marrow).

The HGBPBMY4 (FLJ10961) polynucleotides and polypeptides of the present invention, including agonists and/or fragments thereof, may have uses that include modulating signal transduction activity, in various cells, tissues, and organisms, and particularly in mammalian tissue, preferably human tissue.

The strong homology to human GBP family members, particularly hGBP-1, hGBP-2, hGBP-3 and hGBP-4, combined with HGBPBMY4 (FLJ10961) expression in liver tissue suggests HGBPBMY4 (FLJ10961) polynucleotides and polypeptides may be useful in treating, diagnosing, prognosing, and/or preventing liver diseases. In representative embodiments, HGBPBMY4 (FLJ10961) polynucleotides and polypeptides including agonists and fragments thereof, may have uses that include treating, diagnosing, prognosing, and/or preventing liver diseases. For example, the HGBPBMY4 (FLJ10961) protein can be used for the detection, treatment, amelioration, and/or prevention of hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, HGBPBMY4 (FLJ10961) polynucleotides and polypeptides, including fragments and/or antagonists thereof, may have uses which include, directly or indirectly, treating, preventing, diagnosing, and/or prognosing the following, non-limiting, hepatic infections: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The strong homology to human GBP family members, particularly hGBP-1, hGBP-2, hGBP-3 and hGBP-4, combined with HGBPBMY4 (FLJ10961) expression in some immune system tissues (i.e., spleen, lymph node, thymus and tonsil) suggests a potential utility for HGBPBMY4 (FLJ10961) polynucleotides and polypeptides in treating, diagnosing, prognosing, and/or preventing diseases and conditions of the immune system. In representative embodiments, HGBPBMY4 (FLJ10961) polynucleotides and polypeptides including agonists and fragments thereof, may have uses that include treating, diagnosing, prognosing, and/or preventing diseases and conditions of the immune system. The HGBPBMY4 (FLJ10961) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. The HGBPBMY4 (FLJ10961) polypeptide may also be useful for modulating cytokine production, antigen presentation, or other processes, such as for boosting immune responses, etc.

Additional immunological disorders that a HGBPBMY4 (FLJ10961) polypeptide of the present invention may be useful in the treatment of include various autoimmune diseases such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A HGBPBMY4 (FLJ10961) polypeptide of the present invention may also be useful in treating or ameliorating primary immune diseases, as well as immune diseases associated with or secondary to other diseases. Such diseases and conditions include Recombinase activating gene (RAG 1/2) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimke immuno-osseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The strong homology to human GBP family members, particularly hGBP-1, hGBP-2, hGBP-3 and hGBP-4, combined with HGBPBMY4 (FLJ10961) expression levels in heart tissue suggests the HGBPMY4 polynucleotides and polypeptides may be useful in treating, diagnosing, prognosing, and/or preventing cardiovascular diseases and/or disorders, which include, but are not limited to: myocardio infarction, congestive heart failure, arrthymias, cardiomyopathy, atherosclerosis, arterialsclerosis, microvascular disease, embolism, thromobosis, pulmonary edema, palpitation, dyspnea, angina, hypotension, syncope, heart murmer, aberrant ECG, hypertrophic cardiomyopathy, the Marfan syndrome, sudden death, prolonged QT syndrome, congenital defects, cardiac viral infections, valvular heart disease, and hypertension.

Similarly, HGBPBMY4 (FLJ10961) polynucleotides and polypeptides may be useful for treating and/or ameliorating cardiovascular diseases and symptoms which result indirectly from various non-cardiavascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, may have uses which include, directly or indirectly, treating, preventing, diagnosing, and/or prognosing the following, non-limiting, cardiovascular infections: blood stream invasion, bacteremia, sepsis, *Streptococcus pneumoniae* infection, group a *streptococci* infection, group b *streptococci* infection, *Enterococcus* infection, nonenterococcal group D *streptococci* infection, nonenterococcal group C *streptococci* infection, nonenterococcal group G *streptococci* infection, *Streptoccus viridans* infection, *Staphylococcus aureus* infection, coagulase-negative *staphylococci* infection, gram-negative *Bacilli* infection, Enterobacteriaceae infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous Mycobacteria infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Likewise, the expression in lung tissue also emphasizes a potential utility for HGBPBMY4 (FLJ10961) polynucleotides and polypeptides in treating, diagnosing, prognosing, and/or preventing pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, polynucleotides and polypeptides, including fragments and/or antagonists thereof, may have uses which may include, directly or indirectly, treating, preventing, diagnosing, and/or prognosing the following, non-limiting, pulmonary infections: pneumonia, bacterial pneumonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pneumonia (for example, as caused by *Mycobacterium tuberculosis*, etc.) *mycoplasma* pnemonia, fungal pneumonia (for example, as caused by *Pneumocystis carinii*, *Histoplasma capsulatum*, *Coccidioides immitis*, *Blastomyces dermatitidis*, *Candida* sp., *Cryptococcus neoformans*, *Aspergillus* sp., Zygomycetes, etc.), Legionnaires' Disease, *Chlamydia* pnemonia, aspiration pnemonia, *Nocordia* sp. Infections, parasitic pnemonia (for example, as caused by *Strongyloides, Toxoplasma gondii*, etc.) necrotizing pnemonia, in addition to any other pulmonary disease and/or disorder (e.g., non-pneumonia) implicated by the causative agents listed above or elsewhere herein.

Additionally, the expression in placenta tissue also emphasizes a potential utility for HGBPBMY4 (FLJ10961) polynucleotides and polypeptides in treating, diagnosing, prognosing, and/or preventing placenta disorders, in addition to reproductive disorders. Such diseases and conditions include, but are not limited to, dysfunctional uterine bleeding, amenorrhea, primary dysmenorrhea, sexual dysfunction, infertility, pelvic inflammatory disease, endometriosis, placental aromatase deficiency, premature menopause, and placental dysfunction.

Further, the expression in skeletal muscle tissue emphasizes a potential utility for HGBPBMY4 (FLJ10961) polynucleotides and polypeptides in treating, diagnosing, prognosing, and/or preventing skeletal muscle disorders. In representative embodiments, HGBPBMY4 (FLJ10961) polynucleotides and polypeptides including agonists and fragements thereof, may have uses which include treating, diagnosing, prognosing, and/or preventing the following, non-limiting, diseases or disorders of skeletal muscled: dystrophies, pseudohypertrophic muscular dystrophy, Duchenne dystrophy, Becker muscular dystrophy, limb-girdle muscular dystrophy, muscle weakness, Emery-Dreifuss muscular dystrophy, Congenital muscular dystrophy, endometriosis, placental aromatase deficiency, premature menopause, Fukuyama congenital muscular dystrophy, laminin alpha 2 chain deficiency, alpha 7 integrin deficiency, Walker-Warburg syndrome, myotonic dystrophy, congenital myotonic dystrophy, facioscapulohumeral muscular dystrophy, distal myopathies, central core disease, nemaline (rod) myopathy, centronuclear (myotubular) myopathy, central core disease, delay in motor milestones, delayed walking, nemaline myopathy, congenital nemaline myopathy, muscle hypotonia, centronuclear myopathies, skeletal muscle energy metabolism disorders, disorders associated with aberrant skeletal muscle-fatty acid metabolism, disorders associated with aberrant skeletal glucose metabolism, acid maltase deficiency, debranching enzyme deficiency, branching enzyme deficiency, exercise intolerance, myophosphorylase deficiency (type V glycogenosis), phosphofructokinase deficiency (type VII glycogenosis), phosphoglycerate kinase deficiency (type IX glycogenosis), phosphoglycerate mutase deficiency (type X glycogenosis), lactate dehydrogenase deficiency (glycogensosis type XI), glycogen storage disorders, skeletal muscle lipid metabolism, carnitine deficiency, myoglobinuria, muscle cramping, myoadenylate deaminase deficiency, mitochondrial myopathies, Kearns-Sayre syndrome, myoclonic epilepsy, disorders of muscle membrane excitability, calcium channel disorders of muscle, sodium channel disorders of muscle, hyperkalemic periodic paralysis, paramyotonia congenita, potassium-aggravated myotonia, myotonia congenita, chloride channel disorders of muscle, thyrotoxic periodic paralysis, and/or Andersen's syndrome.

Continuing, the expression of HGBPBMY4 (FLJ10961) in pancreas tissue suggests a potential utility for HGBPBMY4 (FLJ10961) polynucleotides and polypeptides in treating, diagnosing, prognosing, and/or preventing pancreatic, in addition to metabolic and gastrointestinal disorders.

In representative embodiments, HGBPBMY4 (FLJ10961) polynucleotides and polypeptides including agonists, antagonists, and fragments thereof, may have uses which may include treating, diagnosing, prognosing, and/or preventing the following, non-limiting, diseases or disorders of the pancreas: diabetes mellitus, diabetes, type 1 diabetes, type 2 diabetes, adult onset diabetes, indications related to islet cell transplantation, indications related to pancreatic transplantation, pancreatitis, pancreatic cancer, pancreatic exocrine insufficiency, alcohol induced pancreatitis, maldigestion of fat, maldigestion of protein, hypertriglyceridemia, vitamin b12 malabsorption, hypercalcemia, hypocalcemia, hyperglycemia, ascites, pleural effusions, abdominal pain, pancreatic necrosis, pancreatic abscess, pancreatic pseudocyst, gastrinomas, pancreatic islet cell hyperplasia, multiple endocrine neoplasia type 1 (men 1) syndrome, insulitis, amputations, diabetic neuropathy, pancreatic autoimmune disease, genetic defects of -cell function, HNF-1 aberrations (formerly MODY3), glucokinase aberrations (formerly MODY2), HNF-4 aberrations (formerly MODY1), mitochondrial DNA aberrations, genetic defects in insulin action, type a insulin resistance, leprechaunism, Rabson-Mendenhall syndrome, lipoatrophic diabetes, pancreatectomy, cystic fibrosis, hemochromatosis, fibrocalculous pancreatopathy, endocrinopathies, acromegaly, Cushing's syndrome, glucagonoma, pheochromocytoma, hyperthyroidism, somatostatinoma, aldosteronoma, drug- or chemical-induced diabetes such as from the following drugs: Vacor, Pentamdine, Nicotinic acid, Glucocorticoids, Thyroid hormone, Diazoxide, Adrenergic agonists, Thiazides, Dilantin, and Interferon, pancreatic infections, congenital rubella, cytomegalovirus, uncommon forms of immune-mediated diabetes, "stiff-man" syndrome, anti-insulin receptor antibodies, in addition to other genetic syndromes sometimes associated with diabetes which include, for example, Down's syndrome, Klinefelter's syndrome, Turner's syndrome, Wolfram's syndrome, Friedrich's ataxia, Huntington's chorea, Lawrence Moon Beidel syndrome, Myotonic dystrophy, Porphyria, and Prader Willi syndrome, and/or Gestational diabetes mellitus (GDM).

Further, the expression of HGBPBMY4 (FLJ-10961) in kidney tissue suggests a potential utility for HGBPBMY4 (FLJ10961) polynucleotides and polypeptides in treating, diagnosing, prognosing, and/or preventing diseases and disorders of the kidney.

In representative embodiments, HGBPBMY4 (FLJ10961) polynucleotides and polypeptides including agonists, antagonists, and fragments thereof, may have uses which include treating, diagnosing, prognosing, and/or preventing the following, non-limiting, diseases or disorders of the kidney: Plasma cell infiltration, Hypercalcemia, Myeloma kidney, Amyloidosis, Light chain deposition disease, Type I/II cryoglobulinemia, Immunotactoid glomerulopathy, Reduced glomerular filtration rate, Fanconi syndrome, Hyperchloremic acidosisa, Tubular or small-molecular-weight proteinuria, Polyuria, isothenuria, Hyperkalemia, Salt wasting, Nephrocalcinosis, hyperoxaluria, Cystinosis, Fabry's disease, Sjögren's Syndrome Further, the expression of HGBPBMY4 (FLJ10961) in bone marrow and leukocyte suggests a potential utility for HGBPBMY4 (FLJ10961) polynucleotides and polypeptides in treating, diagnosing, prognosing, and/or preventing bone marrow and leukocyte diseases and disorders.

In representative embodiments, HGBPBMY4 (FLJ10961) polynucleotides and polypeptides including agonists, antagonists, and fragments thereof, may have uses which include treating, diagnosing, prognosing, and/or preventing the following, non-limiting, bone marrow and leukocyte diseases or disorders: Acute lymphocytic leukemia, acute myeloid leukemia, acute promyelocytic leukemia, chronic lymphocytic leukemia, chronic myeloid leukemia, myelodysplastic syndrome, myeloproliferative disorders, multiple myeloma, prolymphocytic, leukemia, amyloidosis, aplastic anemia, myelodysplasia, Polycythemia Vera, Fanconi's anemia, myelodysplasia syndromes, Rare aleukemic leukemia (AML), Myelodysplasia syndromes, Paroxysmal nocturnal hemoglobinuria, Myelofibrosis, Myelophthisis, Bone marrow lymphoma, Hairy cell leukemia, Systemic lupus erythematosus, Hypersplenism, Brucellosis, Sarcoidosis, Tuberculosis, Leishmaniasis, Hypocellular bone marrow±cytopenia, Q fever, Legionnaire's disease A HGBPBMY4 (FLJ10961) protein can also be used to determine biological activity, raise antibodies, as tissue markers, to isolate cognate ligands or receptors, to identify agents that modulate their interactions. Further, proteins, as well as antibodies directed against a HGBPBMY4 (FLJ10961) protein, can show utility as a tumor marker and/or immunotherapy targets for heart, placenta, lung, imune system and liver tissue.

The HGBPBMY4 (FLJ10961) polynucleotides and polypeptides, including fragments and for antagonsists thereof, can have uses which include identification of modulators of HGBPBMY4 (FLJ10961) function including antibodies (for detection or neutralization), naturally-occurring modulators and small molecule modulators. Antibodies to a particular domain of the HGBPBMY4 (FLJ10961) protein could be used as diagnostic agents of conditions in subjects, are useful in monitoring the activation of signal transduction pathways, and can be used as a biomarker for the involvement of GBP's in disease states, as well as in the evaluation of inhibitors of GBP's in vivo.

HGBPBMY4 (FLJ10961) polypeptides and polynucleotides may have additional uses which include diagnosing diseases related to the over and/or under expression of HGBPBMY4 (FLJ10961) by identifying mutations in the HGBPBMY4 (FLJ10961) gene by using HGBPBMY4 (FLJ10961) sequences as probes or by determining HGBPBMY4 (FLJ10961) protein or mRNA expression levels. HGBPBMY4 (FLJ10961) polypeptides can be useful for screening compounds that affect the activity of the protein. HGBPBMY4 (FLJ10961) peptides can also be used for the generation of specific antibodies and as bait in yeast two hybrid screens to find proteins the specifically interact with HGBPBMY4 (FLJ10961), as described herein.

Although it is believed the encoded polypeptide could share at least some biological activities with human guanylate binding proteins (particularly hGBP-1, hGBP-2, hGBP-3 and hGBP-4), a number of methods of determining the exact biological function of this clone are either known in the art or are described elsewhere herein. For example, the function of this clone can be determined by applying microarray methodology. Nucleic acids corresponding to HGBPBMY4 (FLJ10961) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased liver tissue, as compared to normal tissue might indicate a function in modulating liver function, for example. In the case of HGBPBMY4 (FLJ10961), spleen, lymph node, tonsil, thymus, lung, placenta, kidney, skeletal muscle, liver, heart, pancreas and bone marrow can be used, for example, to extract RNA to prepare the probe.

In addition, the function of the protein can be assessed, for example, by applying quantitative PCR methodology. Real time quantitative PCR would provide the capability of following the expression of the HGBPBMY4 (FLJ10961) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of HGBPBMY4 (FLJ10961), a disease correlation related to HGBPBMY4 (FLJ10961) can be made by comparing the mRNA expression level of HGBPBMY4 (FLJ10961) in normal tissue, as compared to diseased tissue (for example diseased immune system tissue, such as spleen and lymph nodes). Significantly higher or lower levels of HGBPBMY4 (FLJ10961) expression in the diseased tissue can suggest HGBPBMY4 (FLJ10961) plays a role in disease progression, and antagonists against HGBPBMY4 (FLJ10961) polypeptides would be useful therapeutically in treating, preventing, and/or ameliorating the disease. Alternatively, significantly higher or lower levels of HGBPBMY4 (FLJ10961) expression in the diseased tissue can suggest HGBPBMY4 (FLJ10961) plays a defensive role against disease progression, and agonists of HGBPBMY4 (FLJ10961) polypeptides can be useful therapeutically in treating, preventing, and/or ameliorating the disease. Also encompassed by the present invention are quantitative PCR probes corresponding to the polynucleotide sequence provided as SEQ ID NO:8 (FIGS. 4A–4C).

The function of the protein can also be assessed through complementation assays in yeast. For example, in the case of HGBPBMY4 (FLJ10961), transforming yeast deficient in GBP activity, for example, and assessing their ability to grow would provide convincing evidence a HGBPBMY4 (FLJ10961) polypeptide has GBP activity. Additional assay conditions and methods that can be used in assessing the function of the polynucleotides and polypeptides of the present invention are known in the art, some of which are disclosed herein. For example, a GTPase activity assay could be employed.

Alternatively, the biological function of the encoded polypeptide can be determined by disrupting a homologue of this polypeptide in mice and/or rats and observing the resulting phenotype. Such knock-out experiments are known in the art, some of which are disclosed elsewhere herein.

Moreover, the biological function of this polypeptide can be determined by the application of antisense and/or sense methodology (including RNAi and homologous recombination) and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a spleen tissue-specific promoter), or it can be expressed at a specified time of development using an inducible and/or a developmentally regulated promoter.

In the case of HGBPBMY4 (FLJ10961), transgenic mice or rats, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic mice or rats to refine the biological function of the polypeptide is encompassed by the present invention.

In preferred embodiments, the following N-terminal HGBPBMY4 (FLJ10961) deletion polypeptides are encompassed by the present invention: M1-I563, A2-I563, P3-I563, E4-I563, I5-I563, H6-I563, M7-I563, T8-I563, G9-I563, P10-I563, M11-I563, C12-I563, L13-I563, I14-I563, E15-I563, N16-I563, T17-I563, N18-I563, G19-I563, E20-I563, L21-I563, V22-I563, A23-I563, N24-I563, P25-I563, E26-I563, A27-I563, L28-I563, K29-I563, I30-I563, L31-I563, S32-I563, A33-I563, I34-I563, T35-I563, Q36-I563, P37-I563, V38-I563, V39-I563, V40-I563, V41-I563, A42-I563, I43-I563, V44-I563, G45-I563, L46-I563, Y47-I563, R48-I563, T49-I563, G50-I563, K51-I563, S52-I563, Y53-I563, L54-I563, M55-I563, N56-I563, K57-I563, L58-I563, A59-I563, G60-I563, K61-I563, N62-I563, K63-I563, G64-I563, F65-I563, S66-I563, L67-I563, G68-I563, S69-I563, T70-I563, V71-I563, K72-I563, S73-I563, H74-I563, T75-I563, K76-I563, G77-I563, I78-I563, W79-I563, M80-I563, W81-I563, C82-I563, V83-I563, P84-I563, H85-I563, P86-I563, K87-I563, K88-I563, P89-I563, E90-I563, H91-I563, T92-I563, L93-I563, V94-I563, L95-I563, L96-I563, D97-I563, T98-I563, E99-I563, G100-I563, L101-I563, G102-I563, D103-I563, V104-I563, K105-I563, K106-I563, G107-I563, D108-I563, N109-I563, Q110-I563, N111-I563, D112-I563, S113-I563, W114-I563, I115-I563, F116-I563, T117-I563, L118-I563, A119-I563, V120-I563, L121-I563, L122-I563, S123-I563, S124-I563, T125-I563, L126-I563, V127-I563, Y128-I563, N129-I563, S130-I563, M131-I563, G132-I563, T133-I563, I134-I563, N135-I563, Q136-I563, Q137-I563, A138-I563, M139-I563, D140-I563, Q141-I563, L142-I563, Y143-I563, Y144-I563, V145-I563, T146-I563, E147-I563, L148-I563, T149-I563, H150-I563, R151-I563, I152-I563, R153-I563, S154-I563, K155-I563, S156-I563, S157-I563, P158-I563, D159-I563, E160-I563, N161-I563, E162-I563, N163-I563, E164-I563, D165-I563, S665-I563, A167-I563, D168-I563, F169-I563, V170-I563, S171-I563, F172-I563, F173-I563, P174-I563, D175-I563, F176-I563, V177-I563, W178-I563, T179-I563, L180-I563, R181-I563, D182-I563, F183-I563, S184-I563, L185-I563, D186-I563, L187-I563, E188-I563, A189-I563, D190-I563, G191-I563, Q192-I563, P193-I563, L194-I563, T195-I563, P196-I563, D197-I563, E198-I563, Y199-I563, L200-I563, E201-I563, Y202-I563, S203-I563, L204-I563, K205-I563, L206-I563, T207-I563, Q208-I563, G209-I563, N210-I563, R211-I563, K212-I563, L213-I563, A214-I563, Q215-I563, L216-I563, E217-I563, K218-I563, L219-I563, Q220-I563, D221-I563, E222-I563, E223-I563, L224-I563, D225-I563, P226-I563, E227-I563, F228-I563, V229-I563, Q230-I563, Q231-I563, V232-I563, A233-I563, D234-I563, F235-I563, C236-I563, S237-I563, Y238-I563, I239-I563, F240-I563, S241-I563, N242-I563, S243-I563, K244-I563, T245-I563, K246-I563, T247-I563, L248-I563, S249-I563, G250-I563, G251-I563, I252-I563, K253-I563, V254-I563, N255-I563, G256-I563, P257-I563, C258-I563, L259-I563, E260-I563, S261-I563, L262-I563, V263-I563, L264-I563, T265-I563, Y266-I563, I267-I563, N268-I563, A269-I563, I270-I563, S271-I563, R272-I563, G273-I563, D274-I563, L275-I563, P276-I563, C277-I563, M278-I563, E279-I563, N280-I563, A281-I563, V282-I563, L283-I563, A284-I563, L285-I563, A286-I563, Q287-I563, I288-I563, E289-I563, N290-I563, S291-I563, A292-I563, A293-I563, V294-I563, Q295-I563, K296-I563, A297-I563, I298-I563, A299-I563, H300-I563, Y301-I563, D302-I563, Q303-I563, Q304-I563, M305-I563, G306-I563, Q307-I563, K308-I563, V309-I563, Q310-I563, L311-I563, P312-I563, A313-I563, E314-I563, T315-I563, L316-I563, Q317-I563, E318-I563, L319-I563, L320-I563, D321-I563, L322-I563, H323-I563, R324-I563, V325-I563, S325-I563, E326-I563, R327-I563, E328-I563, A329-I563, T330-I563, E331-I563, V332-I563, Y334-I563, M335-I563, K336-I563, N337-I563, S338-I563, F339-I563, K340-I563, D341-I563, V342-I563, D343-I563, H344-I563, L345-I563, F346-I563, Q347-I563, K348-I563, K349-I563, L350-I563, A351-I563, A352-I563, Q353-I563, L354-I563, D355-I563, K356-I563, K357-I563, R358-I563, D359-I563, D360-I563, F361-I563, C362-I563, K363-I563, Q364-I563, N365-I563, Q366-I563, E367-I563, A368-I563, S369-I563, S370-I563, D371-I563, R372-I563, C373-I563, S374-I563, A375-I563, L376-I563, L377-I563, Q378-I563, V379-I563, I380-I563, F381-I563, S382-I563, P383-I563, L384-I563, E385-I563, E386-I563, E387-I563, V388-I563, K389-I563, A390-I563, G391-I563, I392-I563, Y393-I563, S394-I563, K395-I563, P396-I563, G397-I563, G398-I563, Y399-I563, C400-I563, L401-I563, F402-I563, I403-I563, Q404-I563, K405-I563, L406-I563, Q407-I563, D408-I563, L409-I563, E410-I563, K411-I563, K412-I563, Y413-I563, Y414-I563, E415-I563, E416-I563, P417-I563, R418-I563, K419-I563, G420-I563, I421-I563, Q422-I563, A423-I563, E424-I563, E425-I563, I426-I563, L427-I563, Q428-I563, T429-I563, Y430-I563, L431-I563, K432-I563, S433-I563, K434-I563, E435-I563, S436-I563, V437-I563, T438-I563, D439-I563, A440-I563, I441-I563, L442-I563, Q443-I563, T444-I563, D445-I563, Q446-I563, I447-I563, L448-I563, T449-I563, E450-I563, K451-I563, E452-I563, K453-I563, E454-I563, I455-I563, E456-I563, V457-I563, E458-I563, C459-I563, V460-I563, K461-I563, A462-I563, E463-I563, S464-I563, A465-I563, Q466-I563, A467-I563, S468-I563, A469-I563, K470-I563, M471-I563, V472-I563, E473-I563, E474-I563, M475-I563, Q476-I563, I477-I563, K478-I563, Y479-I563, Q480-I563, Q481-I563, M482-I563, M483-I563, E484-I563, E485-I563, K486-I563, E487-I563, K488-I563, S489-I563, Y490-I563, Q491-I563, E492-I563, H493-I563, V494-I563, K495-I563, Q496-I563, L497-I563, T498-I563, E499-I563, K500-I563, M501-I563, E502-I563, R503-I563, E504-I563, R505-I563, A506-I563, Q507-I563, L508-I563, L509-I563, E510-I563, E511-I563, Q512-I563, E513-I563, K514-I563, T515-I563, L516-I563, T517-I563, S518-I563, K519-I563, L520-I563, Q521-I563, E522-I563, Q523-I563, A524-I563, R525-I563, V526-I563, L527-I563, K528-I563, E529-I563, R530-I563, C531-I563, Q532-I563, G533-I563, E534-I563, S535-I563, T536-I563, Q537-I563, L538-I563, Q539-I563, N540-I563, E541-I563, I542-I563, Q543-I563, K544-I563, L545-I563, Q546-I563, K547-I563, T548-I563, L549-I563, K550-I563, K551-I563, K552-I563, T553-I563, K554-I563, R555-I563, Y556-I563, M557-I563, S558-I563, H559-I563, K560-I563, L561-I563 and/or K562-I563 of SEQ ID NO:9. Polynucleotide sequences encoding these polypeptides are also provided. The present invention also encompasses the use of these N-terminal HGBPBMY4 (FLJ10961) deletion polypeptides as immunogenic and/or antigenic epitopes as described elsewhere herein.

In other embodiments, the following C-terminal HGBPBMY4 (FLJ10961) deletion polypeptides are encompassed by the present invention: M1-A2, M1-P3, M1-E4, M1-I5, M1-H6, M1-M7, M1-T8, M1-G9, M1-P10, M1-M 1, M1-C12, M1-L13, M1-I14, M1-E15, M1-N16, M1-T17, M1-N18, M1-G19, M1-E20, M1-L21, M1-V22, M1-A23, M1-N24, M1-P25, M1-E26, M1-A27, M1-L28, M1-K29, M1-I30, M1-L31, M1-S32, M1-A33, M1-I34, M1-T35, M1-Q36, M1-P37, M1-V38, M1-V39 M1-V40, M1-V41, M1-A42, M1-I43, M1-V44, M1-G45, M1-L46, M1-Y47, M1-R48, M1-T49, M1-G50, M1-K51, M1-S52, M1-Y53, M1-L54, M1-M55, M1-N56, M1-K57, M1-L58, M1-A59, M1-G60, M1-K61, M1-N62, M1-K63, M1-G64, M1-F65, M1-S66, M1-L67, M1-G68, M1-S69, M1-T70, M1-V71, M1-K72, M1-S73, M1-H74, M1-T75, M1-K76, M1-G77, M1-I78, M1-W79, M1-M80, M1-W81, M1-C82, M1-V83, M1-P84, M1-H85, M1-P86, M1-K87, M1-K88, M1-P89, M1-E90, M1-H91, M1-T92, M1-L93, M1-V94, M1-L95, M1-L96, M1-D97, M1-T98, M1-E99, M1-G100, M1-L101, M1-G102, M1-D103, M1-V104, M1-K105, M1-K106, M1-G107, M1-D108, M1-N109, M1-Q110, M1-N111, M1-D112, M1-S113, M1-W114, M1-I115, M1-F116, M1-T117, M1-L118, M1-A119, M1-V120, M1-L121, M1-L122, M1-S123, M1-S124, M1-T125, M1-L126, M1-V127, M1-Y128, M1-N129, M1-S130, M1-M131, M1-G132, M1-T133, M1-I134, M1-N135, M1-Q136, M1-Q137, M1-A138, M1-M139, M1-D140, M1-Q141, M1-L142, M1-Y143, M1-Y144, M1-V145, M1-T146, M1-E147, M1-L148, M1-T149, M1-H150, M1-R151, M1-I152, M1-R153, M1-S154, M1-K155, M1-S156, M1-S157, M1-P158, M1-D159, M1-E160, M1-N161, M1-E162, M1-N163, M1-E164, M1-D165, M1-S166, M1-A167, M1-D168, M1-F169, M1-V170, M1-S171, M1-F172, M1-F173, M1-P174 M1-D175, M1-F176, M1-V177, M1-W178, M1-T179, M1-L180, M1-R181, M1-D182, M1-F183, M1-S184, M1-L185, M1-D186, M1-L187, M1-E188, M1-A189, M1-D190, M1-G191, M1-Q192, M1-P193, M1-L194, M1-T195, M1-P196, M1-D197, M1-E198, M1-Y199, M1-L200, M1-E201, M1-Y202, M1-S203, M1-L204, M1-K205, M1-L206, M1-T207, M1-Q208, M1-G209, M1-N210, M1-R211, M1-K212, M1-L213, M1-A214, M1-Q215, M1-L216, M1-E217, M1-K218, M1-L219, M1-Q220, M1-D221, M1-E222, M1-E223, M1-L224, M1-D225, M1-P226, M1-E227, M1-F228, M1-V229, M1-Q230, M1-Q231, M1-V232, M1-A233, M1-D234, M1-F235, M1-C236, M1-S237, M1-Y238, M1-I239, M1-F240, M1-S241, M1-N242, M1-S243, M1-K244, M1-T245, M1-K246, M1-T247, M1-L248, M1-S249, M1-G250, M1-G251, M1-I252, M1-K253, M1-V254, M1-N255, M1-G256, M1-P257, M1-C258, M1-L259, M1-E260, M1-S261, M1-L262, M1-V263, M1-L264, M1-T265, M1-Y266, M1-I267, M1-N268, M1-A269, M1-I270, M1-S271, M1-R272, M1-G273, M1-D274, M1-L275, M1-P276, M1-C277, M1-M278, M1-E279, M1-N280, M1-A281, M1-V282, M1-L283, M1-A284, M1-L285, M1-A286, M1-Q287, M1-I288, M1-E289, M1-N290, M1-S291, M1-A292, M1-A293, M1-V294, M1-Q295, M1-K296, M1-A297, M1-I298, M1-A299, M1-H300, M1-Y301, M1-D302, M1-Q303, M1-Q304, M1-M305, M1-G306, M1-Q307, M1-K308, M1-V309, M1-Q310, M1-L311, M1-P312, M1-A313, M1-E314, M1-T315, M1-L316, M1-Q317, M1-E318, M1-L319, M1-L320, M1-D321, M1-L322, M1-H323, M1-R324, M1-V325, M1-S326, M1-E327, M1-R328, M1-E329, M1-A330, M1-T331, M1-E332, M1-V333, M1-Y334, M1-M335, M1-K336, M1-N337, M1-S338, M1-F339, M1-K340, M1-D341, M1-V342, M1-D343, M1-H344, M1-L345, M1-F346, M1-Q347, M1-K348, M1-K349, M1-L350, M1-A351, M1-A352, M1-Q353, M1-L354, M1-D355, M1-K356, M1-K357, M1-R358, M1-D359, M1-D360, M1-F361, M1-C362, M1-K363, M1-Q364, M1-N365, M1-Q366, M1-E367, M1-A368, M1-S369, M1-S370, M1-D371, M1-R372, M1-C373, M1-S374, M1-A375, M1-L376, M1-L377, M1-Q378, M1-V379, M1-I380, M1-F381, M1-S382, M1-P383, M1-L384, M1-E385, M1-E386, M1-E387, M1-V388, M1-K389, M1-A390, M1-G391, M1-I392, M1-Y393, M1-S394, M1-K395, M1-P396, M1-G397, M1-G398, M1-Y399, M1-C400, M1-L401, M1-F402, M1-I403, M1-Q404, M1-K405, M1-L406, M1-Q407, M1-D408, M1-L409, M1-E410, M1-K411, M1-K412, M1-Y413, M1-Y414, M1-E415, M1-E416, M1-P417, M1-R418, M1-K419, M1-G420, M1-I421, M1-Q422, M1-A423, M1-E424, M1-E425, M1-I426, M1-L427, M1-Q428, M1-T429, M1-Y430, M1-L431, M1-K432, M1-S433, M1-K434, M1-E435, M1-S436, M1-V437, M1-T438, M1-D439, M1-A440, M1-I441, M1-L442, M1-Q443, M1-T444, M1-D445, M1-Q446, M1-I447, M1-L448, M1-T449, M1-E450, M1-K451, M1-E452, M1-K453, M1-E454, M1-I455, M1-E456, M1-V457, M1-E458, M1-C459, M1-V460, M1-K461, M1-A462, M1-E463, M1-S464, M1-A465, M1-Q466, M1-A467, M1-S468, M1-A469, M1-K470, M1-M471, M1-V472, M1-E473, M1-E474, M1-M475, M1-Q476, M1-I477, M1-K478, M1-Y479, M1-Q480, M1-Q481, M1-M482, M1-M483, M1-E484, M1-E485, M1-K486, M1-E487, M1-K488, M1-S489, M1-Y490, M1-Q491, M1-E492, M1-H493, M1-V494, M1-K495, M1-Q496, M1-L497, M1-T498, M1-E499, M1-K500, M1-M501, M1-E502, M1-R503, M1-E504, M1-R505, M1-A506, M1-Q507, M1-L508, M1-L509, M1-E510, M1-E511, M1-Q512, M1-E513, M1-K514, M1-T515, M1-L516, M1-T517, M1-S518, M1-K519, M1-L520, M1-Q521, M1-E522, M1-Q523, M1-A542, M1-R525, M1-V526, M1-L527, M1-K528, M1-E529, M1-R530, M1-C531, M1-Q532, M1-G533, M1-E534, M1-S535, M1-T536, M1-Q537, M1-L538, M1-Q539, M1-N540, M1-E541, M1-I542, M1-Q543, M1-K544, M1-L545, M1-Q546, M1-K547, M1-T548, M1-L549, M1-K550, M1-K551, M1-K552, M1-T553, M1-K554, M1-R555, M1-Y556, M1-M557, M1-S558, M1-H559, M1-K560, M1-L561 and/or M1-K562 of SEQ ID NO:9. Polynucleotide sequences encoding these polypeptides are also provided. The present invention also encompasses the use of these C-terminal HGBPBMY4 (FLJ10961) deletion polypeptides as immunogenic and/or antigenic epitopes as described elsewhere herein.

Alternatively, preferred polypeptides of the present invention can comprise polypeptide sequences corresponding to, for example, internal regions of the HGBPBMY4 (FLJ10961) polypeptide (e.g., any combination of both N- and C-terminal HGBPBMY4 (FLJ10961) polypeptide deletions) of SEQ ID NO:9. For example, internal regions could be defined by the equation: amino acid NX to amino acid CX, wherein NX refers to any N-terminal deletion polypeptide amino acid of HGBPBMY4 (FLJ10961) (SEQ ID NO:9), and where CX refers to any C-terminal deletion polypeptide amino acid of HGBPBMY4 (FLJ10961) (SEQ ID NO:9). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the HGBPBMY4 (FLJ10961) polypeptide.

The present invention encompasses the identification of compounds and drugs which stimulate HGBPBMY4 (FLJ10961) on the one hand (i.e., agonists) and which inhibit the function of HGBPBMY4 (FLJ10961) on the other hand (i.e., antagonists). In general, such screening procedures involve providing appropriate cells which express a polypeptide of the present invention on the surface thereof. Such cells can include, for example, cells from mammals, yeast, Drosophila or E. coli. In a representative embodiment, a polynucleotide encoding a polypeptide of the present invention can be employed to transfect cells to thereby express the HGBPBMY4 (FLJ10961) polypeptide. The expressed polypeptide can then be contacted with a test compound to observe binding, stimulation or inhibition of a functional response.

FIG. 46 shows an expanded expression profile of the GBP HGBPBMY4 (FLJ10961). The figure illustrates the relative expression level of HGBPBMY4 amongst various mRNA tissue sources. FIG. 46 also illustrates the relative expression level of HGBPBMY4 amongst various mRNA tissue sources isolated from normal and diseased tissues. As shown, the HGBPBMY4 polypeptide showed increased expression in spinal cord from multiple sclerosis patients compared to controls; increased expression in putamen and caudate from Parkinson's patients compared to controls; high expression in normal and diseased thryroid. Increased expression in breast and testicle tumors relative to controls. Expression data was obtained by measuring the steady state HGBPBMY4 mRNA levels by quantitative PCR using the PCR primer pair provided as SEQ ID NO:70 and 71, and TAQMAN probe (SEQ ID NO:72) as described in Example 39 herein. These data support a role of HGBPBMY4 in regulating various functions, including immune functions and neurological functions. HGBPBMY4 may also be participating in the formation of testicle and breast tumors and thus small molecule modulators of HGBPBMY4 function may represent a novel therapeutic option in the treatment of breast and testicle cancers, as well as multiple sclerosis, Parkinson's disease and various immune system diseases.

Features of the Polypeptide Encoded by Gene No. 5

A polypeptide encoded by this gene, MGBPBMY1 (LOC229900), is provided as SEQ ID NO:11 (FIGS. 5A–5C) and is encoded by the polynucleotide sequence according to SEQ ID NO:10 (FIGS. 5A–5C) and/or by a polynucleotide contained within a deposited clone. MGB-PBMY1 (LOC229900) has significant homology at the nucleotide and amino acid level to a number of guanylate binding proteins, which include, for example, mouse GBP-1, mouse GBP-2, mouse GBP-3 and mouse GBP-4.

The determined nucleotide sequence of the MGBPBMY1 (LOC229900), (i.e. the cDNA shown in FIGS. 5A–5C and in SEQ ID NO:10) comprises an open reading frame encoding a protein of about 632 amino acid residues. The predicted amino acid sequence of the MGBPBMY1 (LOC229900) polypeptide is shown in FIGS. 5A–5C (SEQ ID NO:11). The percent identity and similarity values between the MGBPBMY1 (LOC229900) polypeptide to the known GBP family member mGBP1 is provided in FIG. 9. The MGBPBMY1 (LOC229900) protein shown in FIGS. 5A–5C was determined to share significant identity and similarity to several known GBP family members, as shown in FIG. 11A–11G.

Figure 25:
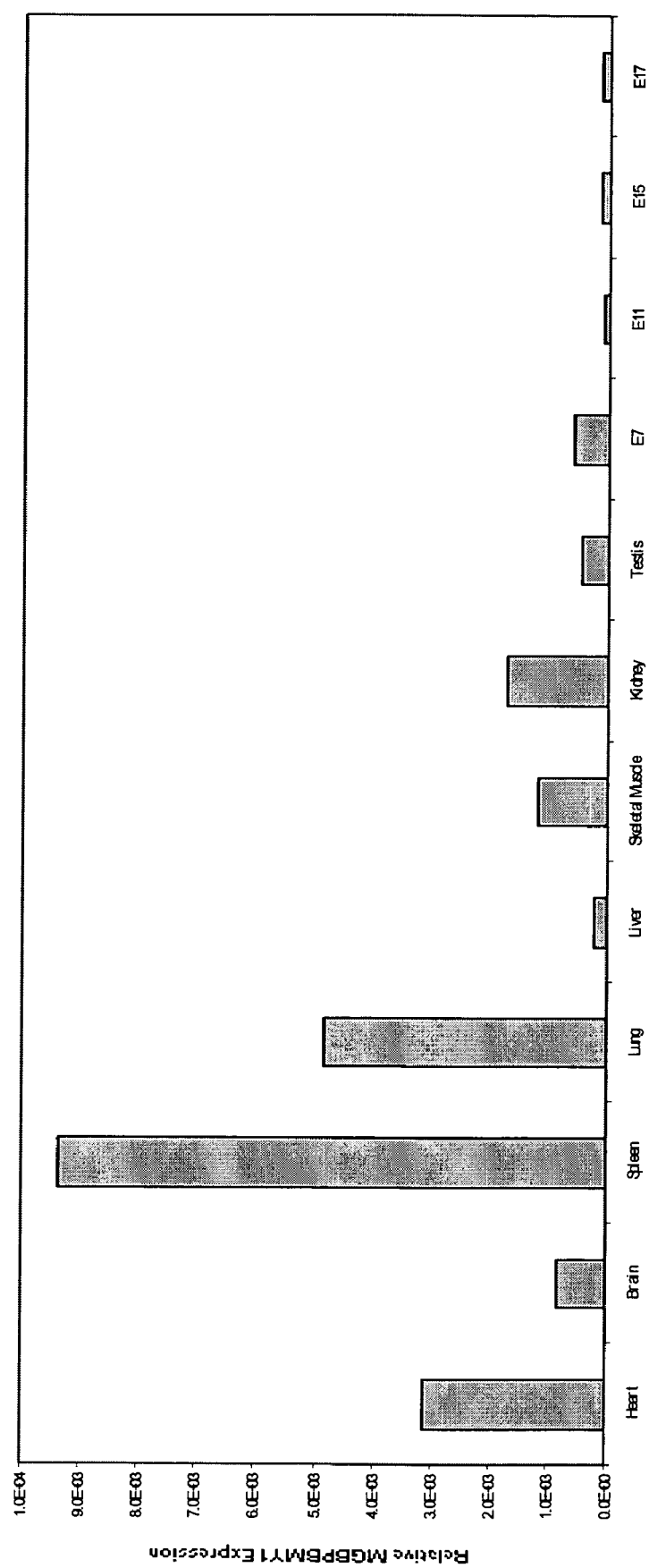
FIG. 25 is bar graph depicting the tissue expression pattern of mouse MGBPBMY1 (LOC229900). Panels of cDNAs derived from normal and immune tissue were analyzed by Real Time PCR for expression of MGBPBMY1 (LOC229900).

Expression profiling designed to measure the steady state mRNA levels encoding the MGBPBMY1 (LOC229900) polypeptide showed expression in spleen, lung, heart, kidney, skeletal muscle and brain (see FIG. 25).

Based upon the strong homology to members of the GBP family members, the MGBPBMY1 (LOC229900) polypeptide is expected to share at least some biological activity with GBP family members, specifically mGBP-1, mGBP-2, mGBP3 and mGBP-4.

The MGBPBMY1 (LOC229900) polynucleotides and polypeptides of the present invention, including agonists and/or fragments thereof, may have uses that include detecting, prognosing, treating, preventing, and/or ameliorating at least diseases and conditions of the immune system, lung, heart kidney, skeletal muscle and brain/nervous system in a mouse model of a human condition.

The MGBPBMY1 (LOC229900) polynucleotides and polypeptides of the present invention, including agonists and/or fragments thereof, may have uses that include modulating signal transduction activity, in various cells, tissues, and organisms, particularly in mammalian tissue and more preferably in a mouse model of a human condition.

The strong homology to mouse GBP family members, particularly mGBP-1, mGBP-2, mGBP3 and mGBP-4, combined with the observed MGBPBMY1 (LOC229900) expression in some immune system tissues (i.e., spleen) suggests a potential utility for MGBPBMY1 (LOC229900) polynucleotides and polypeptides in treating, diagnosing, prognosing, and/or preventing diseases and conditions of the immune system in a mouse model of a human condition. In representative embodiments, MGBPBMY1 (LOC229900) polynucleotides and polypeptides including agonists and fragments thereof, may have uses that include treating, diagnosing, prognosing, and/or preventing diseases and conditions of the immune system in a mouse model of a human condition. The MGBPBMY1 (LOC229900) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. The MGBPBMY1 (LOC229900) polypeptide may also be useful for modulating cytokine production, antigen presentation, or other processes, such as for boosting immune responses, etc.

Additional immunolgical disorders that a MGBPBMY1 (LOC229900) polypeptide of the present invention may be useful in the treatment of include various autoimmune diseases in a mouse model of a human condition, such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A MGBPBMY1 (LOC229900) polypeptide of the present invention may also be useful in treating or ameliorating primary immune diseases, as well as immune diseases associated with or secondary to other diseases in a mouse model of a human condition. Such diseases and conditions include Recombinase activating gene (RAG 1/2) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimke immunoosseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The strong homology to mouse GBP family members, particularly mGBP-1, mGBP-2, mGBP-3 and mGBP-4, combined with MGBPBMY1 (LOC229900) expression levels in heart tissue suggests the MGBPBMY1 (LOC229900) polynucleotides and polypeptides may be useful in treating, diagnosing, prognosing, and/or preventing cardiovascular diseases and/or disorders in a mouse model of a human condition, which include, but are not limited to: myocardio infarction, congestive heart failure, arrthymias, cardiomyopathy, atherosclerosis, arterialsclerosis, microvascular disease, embolism, thromobosis, pulmonary edema, palpitation, dyspnea, angina, hypotension, syncope, heart murmer, aberrant ECG, hypertrophic cardiomyopathy, the Marfan syndrome, sudden death, prolonged QT syndrome, congenital defects, cardiac viral infections, valvular heart disease, and hypertension.

Similarly, MGBPBMY1 (LOC229900) polynucleotides and polypeptides may be useful for treating and/or ameliorating cardiovascular diseases and symptoms in a mouse model of a human condition which result indirectly from various non-cardiavascular effects, which include, but are not limited to, the following, obesity, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, may have uses which include, directly or indirectly, treating, preventing, diagnosing, and/or prognosing the following, non-limiting, cardiovascular infections in a mouse model of a human condition: blood stream invasion, bacteremia, sepsis, *Streptococcus pneumoniae* infection, group a *streptococci* infection, group b *streptococci* infection, *Enterococcus* infection, nonenterococcal group D *streptococci* infection, nonenterococcal group C *streptococci* infection, nonenterococcal group G *streptococci* infection, *Streptoccus viridans* infection, *Staphylococcus aureus* infection, coagulase-negative *staphylococci* infection, gram-negative *Bacilli* infection, Enterobacteriaceae infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative *coccobacilli* infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous Mycobacteria infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

The strong homology to mouse GBP family members, particularly mGBP-1, mGBP-2, mGBP3 and mGBP-4, combined with the observed MGBPBMY1 (LOC229900) expression in lung tissue suggests a potential utility for MGBPBMY1 (LOC229900) polynucleotides and polypeptides in treating, diagnosing, prognosing, and/or preventing pulmonary diseases and disorders in a mouse model of a human condition which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, polynucleotides and polypeptides, including fragments and/or antagonists thereof, may have uses which include, directly or indirectly, treating, preventing, diagnosing, and/or prognosing the following, non-limiting, pulmonary infections in a mouse model of a human condition: pneumonia, bacterial pneumonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pneumonia (for example, as caused by Mycobacterium tuberculosis, etc.) mycoplasma pneumonia, fungal pneumonia (for example, as caused by *Pneumocystis carinii, Histoplasma capsulatum, Coccidioides immitis, Blastomyces dermatitidis, Candida* sp., *Cryptococcus neoformans, Aspergillus* sp., Zygomycetes, etc.), Legionnaires' Disease, *Chlamydia pnemonia*, aspiration pneumonia, *Nocordia* sp. Infections, parasitic pneumonia (for example, as caused by Strongyloides, *Toxoplasma gondii*, etc.) necrotizing pnemonia, in addition to any other pulmonary disease and/or disorder (e.g., non-pneumonia) implicated by the causative agents listed above or elsewhere herein.

Further, the strong homology to mouse GBP family members, particularly mGBP-1, mGBP-2, mGBP3 and mGBP-4, combined with the observed MGBPBMY 1 (LOC229900) expression in skeletal muscle suggests a potential utility for MGBPBMY1 (LOC229900) polynucleotides and polypeptides in treating, diagnosing, prognosing, and/or preventing skeletal muscle disorders in a mouse model of a human condition. In representative embodiments, MGBPBMY1 (LOC229900) polynucleotides and polypeptides including agonists and fragements thereof, may have uses which include treating, diagnosing, prognosing, and/or preventing the following, non-limiting, diseases or disorders of skeletal muscled: dystrophies, pseudohypertrophic muscular dystrophy, Duchenne dystrophy, Becker muscular dystrophy, limb-girdle muscular dystrophy, muscle weakness, Emery-Dreifuss muscular dystrophy, Congenital muscular dystrophy, endometriosis, placental aromatase deficiency, premature menopause, Fukuyama congenital muscular dystrophy, laminin alpha 2 chain deficiency, alpha 7 integrin deficiency, Walker-Warburg syndrome, myotonic dystrophy, congenital myotonic dystrophy, facioscapulohumeral muscular dystrophy, distal myopathies, central core disease, nemaline (rod) myopathy, centronuclear (myotubular)

myopathy, central core disease, delay in motor milestones, delayed walking, nemaline myopathy, congenital nemaline myopathy, muscle hypotonia, centronuclear myopathies, skeletal muscle energy metabolism disorders, disorders associated with aberrant skeletal muscle-fatty acid metabolism, disorders associated with aberrant skeletal glucose metabolism, acid maltase deficiency, debranching enzyme deficiency, branching enzyme deficiency, exercise intolerance, myophosphorylase deficiency, (type V glycogenosis), phosphofructokinase deficiency (type VII glycogenosis), phosphoglycerate kinase deficiency (type IX glycogenosis), phosphoglycerate mutase deficiency (type X glycogenosis), lactate dehydrogenase deficiency (glycogensosis type XI), glycogen storage disorders, skeletal muscle lipid metabolism, carnitine deficiency, myoglobinuria, muscle cramping, myoadenylate deaminase deficiency, mitochondrial myopathies, Kearns-Sayre syndrome, myoclonic epilepsy, disorders of muscle membrane excitability, calcium channel disorders of muscle, sodium channel disorders of muscle, hyperkalemic periodic paralysis, paramyotonia congenita, potassium-aggravated myotonia, myotonia congenita, chloride channel disorders of muscle, thyrotoxic periodic paralysis, and/or Andersen's syndrome.

Additionally, the strong homology to mouse GBP family members, particularly mGBP-1, mGBP-2, mGBP3 and mGBP-4, combined with the high level of MGBPBMY1 (LOC229900) expression in kidney suggests a potential utility for MGBPBMY1 (LOC229900) polynucleotides and polypeptides in treating, diagnosing, prognosing, and/or preventing diseases and disorders of the kidney in a mouse model of a human condition.

In representative embodiments, MGBPBMY1 (LOC229900) polynucleotides and polypeptides including agonists, antagonists, and fragments thereof, may have uses which include treating, diagnosing, prognosing, and/or preventing the following, non-limiting, diseases or disorders of the kidney in a mouse model of a human condition: Plasma cell infiltration, Hypercalcemia, Myeloma kidney, Amyloidosis, Light chain deposition disease, Type I/II cryoglobulinemia, Immunotactoid glomerulopathy, Reduced glomerular filtration rate, Fanconi syndrome, Hyperchloremic acidosisa, Tubular or small-molecular-weight proteinuria, Polyuria, isothenuria, Hyperkalemia, Salt wasting, Nephrocalcinosis, hyperoxaluria, Cystinosis, Fabry's disease, Sjogren's Syndrome The strong homology to mouse GBP family members, particularly mGBP-1, mGBP-2, mGBP3 and mGBP-4, combined with the high level of MGBPBMY1 (LOC229900) expression in brain suggests a potential utility for MGBPBMY1 (LOC229900) polynucleotides and polypeptides in treating, diagnosing, prognosing, and/or preventing diseases and disorders of the brain and neurological tissue in a mouse model of a human condition.

In representative embodiments, MGBPBMY1 (LOC229900) polynucleotides and polypeptides including agonists, antagonists, and fragments thereof, may have uses which include treating, diagnosing, prognosing, and/or preventing the following, non-limiting, brain and neurological diseases or disorders in a mouse model of a human condition: the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a representative embodiment, the MGBPBMY1 (LOC229900) polypeptides, polynucleotides, or agonists or antagonists of the present invention may be used to protect neural cells from the damaging effects of cerebral hypoxia. According to this embodiment, the compositions of the invention are used to treat, prevent, and/or diagnose neural cell injury associated with cerebral hypoxia in a mouse model of a human condition. In one aspect of this embodiment, the MGBPBMY1 (LOC229900) polypeptides, polynucleotides, or agonists or antagonists of the invention are used to treat, prevent, and/or diagnose neural cell injury associated with cerebral ischemia. In another aspect of this embodiment, the MGBPBMY1 (LOC229900) polypeptides, polynucleotides, or agonists or antagonists of the invention may be used to treat, prevent, and/or diagnose neural cell injury associated with cerebral infarction in a mouse model of a human condition. In another aspect of this embodiment, the polypeptides, polynucleotides, or agonists or antagonists of the invention may be used to treat, prevent, and/or diagnose or prevent neural cell injury associated with a stroke. In a further aspect of this embodiment, the MGBPBMY1 (LOC229900) polypeptides, polynucleotides, or agonists or antagonists of the invention may be used to treat, prevent, and/or diagnose neural cell injury associated with a heart attack.

The MGBPBMY1 (LOC229900) polypeptides and/or polynucleotides of the present invention which may be useful for treating or preventing a nervous system disorder may be selected by testing for biological activity in promoting the survival or differentiation of neurons in a mouse model of a human condition. For example, and not by way of limitation, compositions of the invention which elicit any of the following effects may be useful according to the invention: (1) increased survival time of neurons in culture;

(2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In representative, non-limiting embodiments, increased survival of neurons may routinely be measured using a method set forth herein or otherwise known in the art, such as, for example, the method set forth in Arakawa et al. (Arakawa et al., (1990) *J. Neurosci.* 10:3507–3515); increased sprouting of neurons may be detected by methods known in the art, such as, for example, the methods set forth in Pestronk et al. (Pestronk et al., (1980) *Exp. Neurol.* 70:65–82) or Brown et al. (Brown et al., (1981) *Ann. Rev. Neurosci.* 4:17–42); increased production of neuron-associated molecules may be measured by bioassay, enzymatic assay, antibody binding, northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed in a mouse model of a human condition according to the present invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

It is noted that the use of mouse models to understand, diagnose, predict, treat and/or ameliorate human conditions is well documented. Thus, the uses for the MGBPBMY1 (LOC229900) may often be extrapolated to human conditions, as well as to further research such conditions and their treatments.

A MGBPBMY1 (LOC229900) protein may also be used to determine biological activity, raise antibodies, as tissue markers, to isolate cognate ligands or receptors, to identify agents that modulate their interactions. Further, proteins, as well as antibodies directed against a MGBPBMY1 (LOC229900) protein, can show utility as a tumor marker and/or immunotherapy targets for spleen, lung, heart, kidney, skeletal muscle and/or brain tissue.

The MGBPBMY1 (LOC229900) polynucleotides and polypeptides, including fragments and for antagonists thereof, may have uses which include identification of modulators of MGBPBMY1 (LOC229900) function including antibodies (for detection or neutralization), naturally-occurring modulators and small molecule modulators. Antibodies to a particular domain of the MGBPBMY1 (LOC229900) protein could be used as diagnostic agents of conditions in subjects, are useful in monitoring the activation of signal transduction pathways, and can be used as a biomarker for the involvement of GBP's in disease states, as well as in the evaluation of inhibitors of GBP's in vivo.

MGBPBMY1 (LOC229900) polypeptides and polynucleotides may have additional uses which include diagnosing diseases related to the over and/or under expression of MGBPBMY1 (LOC229900) by identifying mutations in the MGBPBMY1 (LOC229900) gene by using MGBPBMY1 (LOC229900) sequences as probes or by determining MGBPBMY1 (LOC229900) protein or mRNA expression levels. MGBPBMY1 (LOC229900) polypeptides can be useful for screening compounds that affect the activity of the protein. MGBPBMY1 (LOC229900) peptides can also be used for the generation of specific antibodies and as bait in yeast two hybrid screens to find proteins the specifically interact with MGBPBMY1 (LOC229900), as described herein.

Although it is believed the encoded polypeptide could share at least some biological activities with human guanylate binding proteins (particularly mGBP-1, mGBP-2, mGBP-3 and mGBP-4), a number of methods of determining the exact biological function of this clone are either known in the art or are described elsewhere herein. For example, the function of this clone can be determined by applying microarray methodology. Nucleic acids corresponding to the MGBPBMY1 (LOC229900) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased liver tissue, as compared to normal tissue might indicate a function in modulating liver function, for example. In the case of MGBPBMY1 (LOC229900), heart, brain, spleen, lung, liver, skeletal muscle, kidney and/or testis, as well as various embryonic tissues, can be used, for example, to extract RNA to prepare the probe.

In addition, the function of the protein may be assessed, for example, by applying quantitative PCR methodology. Real time quantitative PCR would provide the capability of following the expression of the MGBPBMY1 (LOC229900) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of MGBPBMY1 (LOC229900), a disease correlation related to MGBPBMY1 (LOC229900) can be made by comparing the mRNA expression level of MGBPBMY1 (LOC229900) in normal tissue, as compared to diseased tissue. Significantly higher or lower levels of MGBPBMY1 (LOC229900) expression in the diseased tissue can suggest MGBPBMY1 (LOC229900) plays a role in disease progression, and antagonists against MGBPBMY1 (LOC229900) polypeptides would be useful therapeutically in treating, preventing, and/or ameliorating the disease. Alternatively, significantly higher or lower levels of MGBPBMY1 (LOC229900) expression in the diseased tissue can suggest MGBPBMY1 (LOC229900) plays a defensive role against disease progression, and agonists of MGBPBMY1 (LOC229900) polypeptides can be useful therapeutically in treating, preventing, and/or ameliorating the disease. Also encompassed by the present invention are quantitative PCR probes corresponding to the polynucleotide sequence provided as SEQ ID NO:10 (FIGS. 5A–5C).

The function of the protein can also be assessed through complementation assays in yeast. For example, in the case of the MGBPBMY1 (LOC229900), transforming yeast deficient in GBP activity, for example, and assessing their ability to grow would provide convincing evidence the MGB-PBMY1 (LOC229900) polypeptide has GBP activity. Additional assay conditions and methods that can be used in assessing the function of the polynucleotides and polypeptides of the present invention are known in the art, some of which are disclosed herein. For example, a GTPase activity assay could be employed.

Alternatively, the biological function of the encoded polypeptide can be determined by disrupting a homologue of this polypeptide in another species (e.g., a mammalian species) and observing the resulting phenotype. Such knockout experiments are known in the art, some of which are disclosed elsewhere herein.

Moreover, the biological function of this polypeptide can be determined by the application of antisense and/or sense methodology (including RNAi and homologous recombination) and the resulting generation of transgenic animals. Expressing a particular gene in either sense or antisense orientation in a transgenic animal could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a spleen tissue-specific promoter), or it can be expressed at a specified time of development using an inducible and/or a developmentally regulated promoter.

In the case of MGBPBMY1 (LOC229900) transgenic animals, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic animals to refine the biological function of the polypeptide is encompassed by the present invention.

In preferred embodiments, the following N-terminal MGBPBMY1 (LOC229900) deletion polypeptides are encompassed by the present invention: M1-L632, E2-L632, A3-L632, P4-L632, V5-L632, C6-L632, L7-L632, V8-L632, E9-L632, N10-L632, E11-L632, N12-L632, E13-L632, E14-L632, L15-L632, R16-L632, V17-L632, N18-L632, S19-L632, K20-L632, A21-L632, I22-L632, N23-L632, I24-L632, L25-L632, E26-L632, R27-L632, I28-L632, T29-L632, Q30-L632, P31-L632, V32-L632, V33-L632, V34-L632, V35-L632, A36-L632, I37-L632, V38-L632, G39-L632, L40-L632, Y41-L632, R42-L632, T43-L632, G44-L632, K45-L632, S46-L632, Y47-L632, L48-L632, M49-L632, N50-L632, R51-L632, L52-L632, A53-L632, G54-L632, Q55-L632, N56-L632, H57-L632, G58-L632, F59-L632, N60-L632, L61-L632, G62-L632, T63-L632, T64-L632, V65-L632, R66-L632, S67-L632, E68-L632, T69-L632, K70-L632, G71-L632, I72-L632, W73-L632, M74-L632, W75-L632, C76-L632, V77-L632, P78-L632, H79-L632, P80-L632, S81-L632, K82-L632, P83-L632, K84-L632, F85-L632, T86-L632, L87-L632, V88-L632, L89-L632, L90-L632, D81-L632, T92-L632, E93-L632, G94-L632, L95-L632, G96-L632, D97-L632, V98-L632, E99-L632, K100-L632, G101-L632, D102-L632, P103-L632, K104-L632, N105-L632, D106-L632, S107-L632, W108-L632, I109-L632, F110-L632, A111-L632, L112-L632, A113-L632, V114-L632, L115-L632, L116-L632, S117-L632, S118-L632, T119-L632, F120-L632, V121-L632, Y122-L632, N123-L632, S124-L632, M125-L632, S126-L632, T127-L632, I128-L632, N129-L632, H130-L632, Q131-L632, A132-L632, L133-L632, E134-L632, Q135-L632, L136-L632, H137-L632, Y138-L632, V139-L632, T140-L632, E141-L632, L142-L632, T143-L632, E144-L632, R145-L632, I146-L632, R147-L632, A148-L632, K149-L632, S150-L632, T151-L632, S152-L632, R153-L632, S154-L632, E155-L632, E156-L632, V157-L632, D158-L632, D159-L632, S160-L632, D161-L632, E162-L632, F163-L632, V164-L632, S165-L632, F166-L632, F167-L632, P168-L632, D169-L632, F170-L632, I171-L632, W172-L632, T173-L632, V174-L632, R175-L632, D176-L632, F177-L632, V178-L632, L179-L632, E180-L632, L181-L632, K182-L632, L183-L632, E184-L632, G185-L632, R186-L632, V187-L632, I188-L632, T189-L632, A190-L632, D191-L632, E192-L632, Y193-L632, L194-L632, E195-L632, N196-L632, A197-L632, L198-L632, K199-L632, L200-L632, I201-L632, P202-L632, G203-L632, M204-L632, S205-L632, I206-L632, K207-L632, A208-L632, Q209-L632, K210-L632, A211-L632, N212-L632, L213-L632, P214-L632, R215-L632, E216-L632, C217-L632, I218-L632, R219-L632, H220-L632, F221-L632, F222-L632, P223-L632, R224-L632, R225-L632, K226-L632, C227-L632, F228-L632, V229-L632, F230-L632, D231-L632, R232-L632, P233-L632, T234-L632, K235-L632, D236-L632, K237-L632, E238-L632, L239-L632, L240-L632, V241-L632, H242-L632, V243-L632, E244-L632, E245-L632, M246-L632, P247-L632, E248-L632, D249-L632, Q250-L632, L251-L632, D252-L632, H253-L632, S254-L632, F255-L632, Q256-L632, V257-L632, Q258-L632, S259-L632, K260-L632, E261-L632, F262-L632, C263-L632, S264-L632, Y265-L632, I266-L632, F267-L632, S268-L632, N269-L632, S270-L632, K271-L632, A272-L632, K273-L632, T274-L632, L275-L632, K276-L632, E277-L632, G278-L632, I279-L632, V280-L632, V281-L632, N282-L632, G283-L632, N284-L632, R285-L632, L286-L632, A287-L632, T288-L632, L289-L632, V290-L632, T291-L632, T292-L632, Y293-L632, V294-L632, D295-L632, A296-L632, I297-L632, N298-L632, S299-L632, G300-L632, D301-L632, V302-L632, P303-L632, C304-L632, L305-L632, E306-L632, N307-L632, A308-L632, V309-L632, T310-L632, T311-L632, L312-L632, A313-L632, Q314-L632, R315-L632, E316-L632, N317-L632, S318-L632, I319-L632, A320-L632, V321-L632, Q322-L632, K323-L632, A324-L632, A325-L632, D326-L632, H327-L632, Y328-L632, S329-L632, E330-L632, Q331-L632, M332-L632, A333-L632, Q334-L632, R335-L632, M336-L632, R337-L632, L338-L632, P339-L632, T340-L632, D341-L632, T342-L632, L343-L632, Q344-L632, E345-L632, L346-L632, L347-L632, T348-L632, V349-L632, H350-L632, T351-L632, A352-L632, C353-L632, E354-L632, K355-L632, E356-L632, A357-L632, I358-L632, A359-L632, V360-L632, F361-L632, M362-L632, E363-L632, H364-L632, S365-L632, F366-L632, K367-L632, D368-L632, E369-L632, N370-L632, Q371-L632, Q372-L632, F373-L632, Q374-L632, K375-L632, N376-L632, L377-L632, V378-L632, V379-L632, T380-L632, I381-L632, E382-L632, E383-L632, K384-L632, K385-L632, E386-L632, D387-L632, F388-L632, L389-L632, R390-L632, Q391-L632, N392-L632, E393-L632, A394-L632, A395-L632, S396-L632, L397-L632, S398-L632, H399-L632, C400-L632, Q401-L632, A402-L632, E403-L632, L404-L632, D405-L632, K406-L632, L407-L632, S408-L632, E409-L632, S410-L632, L411-L632, R412-L632, E413-L632, S414-L632, I415-L632, S416-L632, R417-L632, G418-L632, V419-L632, F420-L632, S421-L632, V422-L632, P423-L632, G424-L632, G425-L632, H426-L632, R427-L632, L428-L632, Y429-L632, L430-L632, E431-L632, A432-L632, R433-L632, K434-L632, K435-L632, V436-L632, E437-L632, Q438-L632, D439-L632, Y440-L632, E441-L632, R442-L632, V443-L632, P444-L632, R445-L632, K446-L632, G447-L632, V448-L632, K449, A450-L632, N451-L632, H452-L632, V453-L632, L454-L632, Q455-L632, S456-L632, F457-L632, L458-L632, Q459-L632, S460-L632, Q461-L632, I462-L632, S463-L632, I464-L632, E465-L632, D466-L632, S467-L632, I468-L632, M469-L632, Q470-L632, S471-L632, D472-L632, K473-L632, A474-L632, L475-L632, T476-L632, D477-L632, G478-L632, Q479-L632, K480-L632, A481-L632, M482-L632, E483-L632, A484-L632, E485-L632, R486-L632, A487-L632, Q488-L632, K489-L632, E490-L632, A491-L632, A492-L632, E493-L632, K494-L632, E495-L632, Q496-L632, E497-L632, L498-L632, L499-L632, R500-L632, Q501-L632, K502-L632, Q503-L632, K504-L632, E505-L632, L506-L632, Q507-L632, Q508-L632, V509-L632, M510-L632, E511-L632, A512-L632, Q513-L632, E514-L632, R515-L632, S516-L632, Y517-L632, K518-L632, E519-L632, N520-L632, V521-L632, A522-L632, Q523-L632, L524-L632, H525-L632, E526-L632, K527-L632, M528-L632, E529-L632, T530-L632, E531-L632, R532-L632, K533-L632, N534-L632, I535-L632, L536-L632, R537-L632, E538-L632, Q539-L632, E540-L632, V541-L632, K542-L632, L543-L632, E544-L632, H545-L632, K546-L632, L547-L632, K548-L632, I549-L632, Q550-L632, K551-L632, D552-L632, M553-L632, L554-L632, N555-L632, E556-L632, G557-L632, F558-L632, K559-L632, R560-L632, K561-L632, C562-L632, E563-L632, A564-L632, M565-L632, D566-L632, L567-L632, E568-L632, I569-L632, S570-L632, Q571-L632, L572-L632, Q573-L632, K574-L632, E575-L632, I576-L632, Q577-L632, L578-L632, N579-L632, K580-L632, E581-L632, K582-L632, N583-L632, S584-L632, S585-L632, L586-L632, G587-L632, A588-L632, K589-L632, I590-L632, L591-L632, D592-L632, G593-L632, F594-L632, G595-L632, D596-L632, V597-L632, L598-L632, I599-L632, S600-L632, V601-L632, V602-L632, P603-L632, G604-L632, S605-L632, G606-L632, K607-L632, Y608-L632, F609-L632, G610-L632, L611-L632, G612-L632, L613-L632, K614-L632, I615-L632, L616-L632, S617-L632, S618-L632, Q619-L632, M620-L632, N621-L632, Q622-L632, T623-L632, Q624-L632, N625-L632, S262-L632, D627-L632, K628-L632, V629-L632, R630-L632 and/or K631-L632, of SEQ ID NO:11. Polynucleotide sequences encoding these polypeptides are also provided. The present invention also encompasses the use of these N-terminal MGBPBMY1 (LOC229900) deletion polypeptides as immunogenic and/or antigenic epitopes as described elsewhere herein.

In other embodiments, the following C-terminal MGBPBMY1 (LOC229900) deletion polypeptides are encompassed by the present invention: M1-E2, M1-A3, M1-P4, M1-V5, M1-C6, M1-L7, M1-V8, M1-E9, M1-N10, M1-E11, M1-N12, M1-E13, M1-E14, M1-L15, M1-R16, M1-V17, M1-N18, M1-S19, M1-K20, M1-A21, M1-I22, M1-N23, M1-I24, M1-L25, M1-E26, M1-R27, M1-I28, M1-T29, M1-Q30, M1-P31, M1-V32, M1-V33, M1-V34, M1-V35, M1-A36, M1-I37, M1-V38, M1-G39, M1-L40, M1-Y41, M1-R42, M1-T43, M1-G44, M1-K45, M1-S46, M1-Y47, M1-L48, M1-M49, M1-N50, M1-R51, M1-L52, M1-A53, M1-G54, M1-Q55, M1-N56, M1-H57, M1-G58, M1-F59, M1-N60, M1-L61, M1-G62, M1-T63, M1-T64, M1-V65, M1-R66, M1-S67, M1-E68, M1-T69, M1-K70, M1-G71, M1-I72, M1-W73, M1-M74, M1-W75, M1-C76, M1-V77, M1-P78, M1-H79, M1-P80, M1-S81, M1-K82, M1-P83, M1-K84, M1-F85, M1-T86, M1-L87, M1-V88, M1-L89, M1-L90, M1-D91, M1-T92, M1-E93, M1-G94, M1-L95, M1-G96, M1-D97, M1-V98, M1-E99, M1-K100, M1-G10, M1-D102, M1-P103, M1-K104, M1-N105, M1-D106, M1-S107, M1-W108, M1-I109, M1-F110, M1-A111, M1-L112, M1-A113, M1-V114, M1-L115, M1-L116, M1-S117, M1-S118, M1-T119, M1-F120, M1-V121, M1-Y122, M1-N123, M1-S124, M1-M125, M1-S126, M1-T127, M1-I128, M1-N129, M1-H130, M1-Q131, M1-A132, M1-L133, M1-E134, M1-Q135, M1-L136, M1-H137, M1-Y138, M1-V139, M1-T140, M1-E141, M1-L142, M1-T143, M1-E144, M1-R145, M1-I146, M1-R147, M1-A148, M1-K149, M1-S150, M1-T151, M1-S152, M1-R153, M1-S154, M1-E155, M1-E156, M1-V157, M1-D158, M1-D159, M1-S160, M1-D161, M1-E162, M1-F163, M1-V164, M1-S165, M1-F166, M1-F167, M1-P168, M1-D169, M1-F170, M1-I171, M1-W172, M1-T173, M1-V174, M1-R175, M1-D176, M1-F177, M1-V178, M1-L179, M1-E180, M1-L181, M1-K182, M1-L183, M1-E184, M1-G185, M1-R186, M1-V187, M1-L188, M1-T189, M1-A190, M1-D191, M1-E192, M1-Y193, M1-L194, M1-E195, M1-N196, M1-A197, M1-L198, M1-K199, M1-L200, M1-I201, M1-P202, M1-G203, M1-M204, M1-S205, M1-I206, M1-K207, M1-A208, M1-Q209, M1-K210, M1-A211, M1-N212, M1-L213, M1-P214, M1-R215, M1-E216, M1-C217, M1-I218, M1-R219, M1-H220, M1-F221, M1-F222, M1-P223, M1-R224, M1-R225, M1-K226, M1-C227, M1-F228, M1-V229, M1-F230, M1-D231, M1-R232, M1-P233, M1-T234, M1-K235, M1-D236, M1-K237, M1-E238, M1-L239, M1-L240, M1-V241, M1-H242, M1-V243, M1-E244, M1-E245, M1-M246, M1-P247, M1-E248, M1-D249, M1-Q250, M1-L251, M1-D252, M1-H253, M1-S254, M1-F255, M1-Q256, M1-V257, M1-Q258, M1-S259, M1-K260, M1-E261, M1-F262, M1-C263, M1-S264, M1-Y265, M1-I266, M1-F267, M1-S268, M1-N269, M1-S270, M1-K271, M1-A272, M1-K273, M1-T374, M1-L275, M1-K276, M1-E277, M1-G278, M1-I279, M1-V280, M1-V281, M1-N282, M1-G283, M1-N284, M1-R285, M1-L286, M1-A287, M1-T288, M1-L289, M1-V290, M1-T291, M1-T292, M1-Y293, M1-V294, M1-D295, M1-A296, M1-I297, M1-N298, M1-S299, M1-G300, M1-D301, M1-V302, M1-P303, M1-C304, M1-L305, M1-E306, M1-N307, M1-A308, M1-V309, M1-T310, M1-T311, M1-L312, M1-A313, M1-Q314, M1-R315, M1-E316, M1-N317, M1-S318, M1-I319, M1-A320, M1-V321, M1-Q322, M1-K323, M1-A324, M1-A325, M1-D326, M1-H327, M1-Y328, M1-S329, M1-E330, M1-Q331, M1-M332, M1-A333, M1-Q334, M1-R335, M1-M336, M1-R337, M1-L338, M1-P339, M1-T340, M1-D341, M1-T342, M1-L343, M1-Q344, M1-E345, M1-L346, M1-L347, M1-T348, M1-V349, M1-H350, M1-T351, M1-A352, M1-C353, M1-E354, M1-K355, M1-E356, M1-A357, M1-I358, M1-A359, M1-V360, M1-F361, M1-M362, M1-E363, M1-H364, M1-S365, M1-F366, M1-K367, M1-D368, M1-E369, M1-N370, M1-Q371, M1-Q372, M1-F373, M1-Q374, M1-K375, M1-N376, M1-L377, M1-V378, M1-V379, M1-T380, M1-I381, M1-E382, M1-E383, M1-K384, M1-K385, M1-E386, M1-D387, M1-F388, M1-L389, M1-R390, M1-Q391, M1-N392, M1-E393, M1-A394, M1-A395, M1-S396, M1-L397, M1-S398, M1-H399, M1-C400, M1-Q401, M1-A402, M1-E403, M1-L404, M1-D405, M1-K406, M1-L407, M1-S408, M1-E409, M1-S410, M1-L411, M1-R412, M1-E413, M1-S414, M1-I415, M1-S416, M1-R417, M1-G418, M1-V419, M1-F420, M1-S421, M1-V422, M1-P423, M1-G424, M1-G425, M1-H426, M1-R427, M1-L428, M1-Y429, M1-L430, M1-E431, M1-A432, M1-R433, M1-K434, M1-K435, M1-V436, M1-E437, M1-Q438, M1-D439, M1-Y440, M1-E441, M1-R442, M1-V443, M1-P444, M1-R445, M1-K446, M1-G447, M1-V448, M1-K449, M1-A450, M1-N451, M1-H452, M1-V453, M1-L454, M1-Q455, M1-S456, M1-F457, M1-L458, M1-Q459, M1-S460, M1-Q461, M1-I462, M1-S463, M1-I464, M1-E465, M1-D466, M1-S467, M1-I468, M1-M469, M1-Q470, M1-S471, M1-D472, M1-K473, M1-A474, M1-L475, M1-T476, M1-D477, M1-G478, M1-Q479, M1-K480, M1-A481, M1-M482, M1-E483, M1-A484, M1-E485, M1-R486, M1-A487, M1-Q488, M1-K489, M1-E490, M1-A491, M1-A492, M1-E493, M1-K494, M1-E495, M1-Q496, M1-E497, M1-L498, M1-L499, M1-R500, M1-Q501, M1-K502, M1-Q503, M1-K504, M1-E505, M1-L506, M1-Q507, M1-Q508, M1-V509, M1-M510, M1-E511, M1-A512, M1-Q513, M1-E514, M1-R515, M1-S516, M1-Y517, M1-K518, M1-E519, M1-N520, M1-V521, M1-A522, M1-Q523, M1-L524, M1-H525, M1-E526, M1-K527, M1-M528, M1-E529, M1-T530, M1-E531, M1-R532, M1-K533, M1-N534, M1-I535, M1-L536, M1-R537, M1-E538, M1-Q539, M1-E540, M1-V541, M1-K542, M1-L543, M1-E544, M1-H545, M1-K546, M1-L547, M1-K548, M1-I549, M1-Q550, M1-K551, M1-D552, M1-M553, M1-L554, M1-N555, M1-E556, M1-G557, M1-F558, M1-K559, M1-R560, M1-K561, M1-C562, M1-E563, M1-A564, M1-M565, M1-D566, M1-L567, M1-E568, M1-I569, M1-S570, M1-Q571, M1-L572, M1-Q573, M1-K574, M1-E575, M1-I576, M1-Q577, M1-L578, M1-N579, M1-K580, M1-E581, M1-K582, M1-N583, M1-S584, M1-S585, M1-L586, M1-G587, M1-A588, M1-K589, M1-I590, M1-L591, M1-D592, M1-G593, M1-F594, M1-G595, M1-D596, M1-V597, M1-L598, M1-I599, M1-S600, M1-V601, M1-V602, M1-P603, M1-G604, M1-S605, M1-G606, M1-K607, M1-Y608, M1-F609, M1-G610, M1-L611, M1-G612, M1-L613, M1-K614, M1-I615, M1-L616, M1-S617, M1-S618, M1-Q619, M1-M620, M1-N621, M1-Q622, M1-T623, M1-Q624, M1-N625, M1-S626, M1-D627, M1-K628, M1-V629, M1-R630 and/or M1-K631 of SEQ ID NO:11. Polynucleotide sequences encoding these polypeptides are also provided. The present invention also encompasses the use of these C-terminal MGBPBMY1 (LOC229900) deletion polypeptides as immunogenic and/or antigenic epitopes as described elsewhere herein.

Alternatively, preferred polypeptides of the present invention can comprise polypeptide sequences corresponding to, for example, internal regions of the MGBPBMY1 (LOC229900) polypeptide (e.g., any combination of both N- and C-terminal MGBPBMY1 (LOC229900) polypeptide deletions) of SEQ ID NO:11. For example, internal regions could be defined by the equation: amino acid NX to amino acid CX, wherein NX refers to any N-terminal deletion polypeptide amino acid of MGBPBMY1 (LOC229900) (SEQ ID NO:11), and where CX refers to any C-terminal deletion polypeptide amino acid of MGBPBMY1 (LOC229900) (SEQ ID NO:11). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the MGBPBMY1 (LOC229900) polypeptide.

The present invention encompasses the identification of compounds and drugs which stimulate MGBPBMY1 (LOC229900) on the one hand (i.e., agonists) and which inhibit the function of MGBPBMY1 (LOC229900) on the other hand (i.e., antagonists). In general, such screening procedures involve providing appropriate cells which express a polypeptide of the present invention on the surface thereof. Such cells can include, for example, cells from mammals, yeast, Drosophila or E. coli. In a representative embodiment, a polynucleotide encoding a polypeptide of the present invention can be employed to transfect cells to thereby express the MGBPBMY1 (LOC229900) polypeptide. The expressed polypeptide can then be contacted with a test compound to observe binding, stimulation or inhibition of a functional response.

Features of the Polypeptide Encoded by Gene No. 6

A polypeptide encoded by this gene, MGBPBMY2 (LOC229902), is provided as SEQ ID NO:13 (FIGS. 6A–6B) and is encoded by the polynucleotide sequence according to SEQ ID NO:12 (FIGS. 6A–6B) and/or by a polynucleotide contained within a deposited clone. MGBPBMY2 (LOC229902) has significant homology at the nucleotide and amino acid level to a number of guanylate binding proteins, which include, for example, mouse GBP-1, mouse GBP-2, mouse GBP-3 and mouse GBP-4.

The determined nucleotide sequence of the MGBPBMY2 (LOC229902), (i.e. the cDNA shown in FIGS. 6A–6B and in SEQ ID NO:12) comprises an open reading frame encoding a protein of about 605 amino acid residues. The predicted amino acid sequence of the MGBPBMY2 (LOC229902) polypeptide is shown in FIGS. 6A–6B (SEQ ID NO:13). The percent identity and similarity values between the MGBPBMY2 (LOC229902) polypeptide to the known GBP family member mGBP1 is provided in FIG. 9. The MGBPBMY2 (LOC229902) protein shown in FIGS. 6A–6B was determined to share significant identity and similarity to several known GBP family members, as shown in FIG. 11A–11G.

Figure 24:
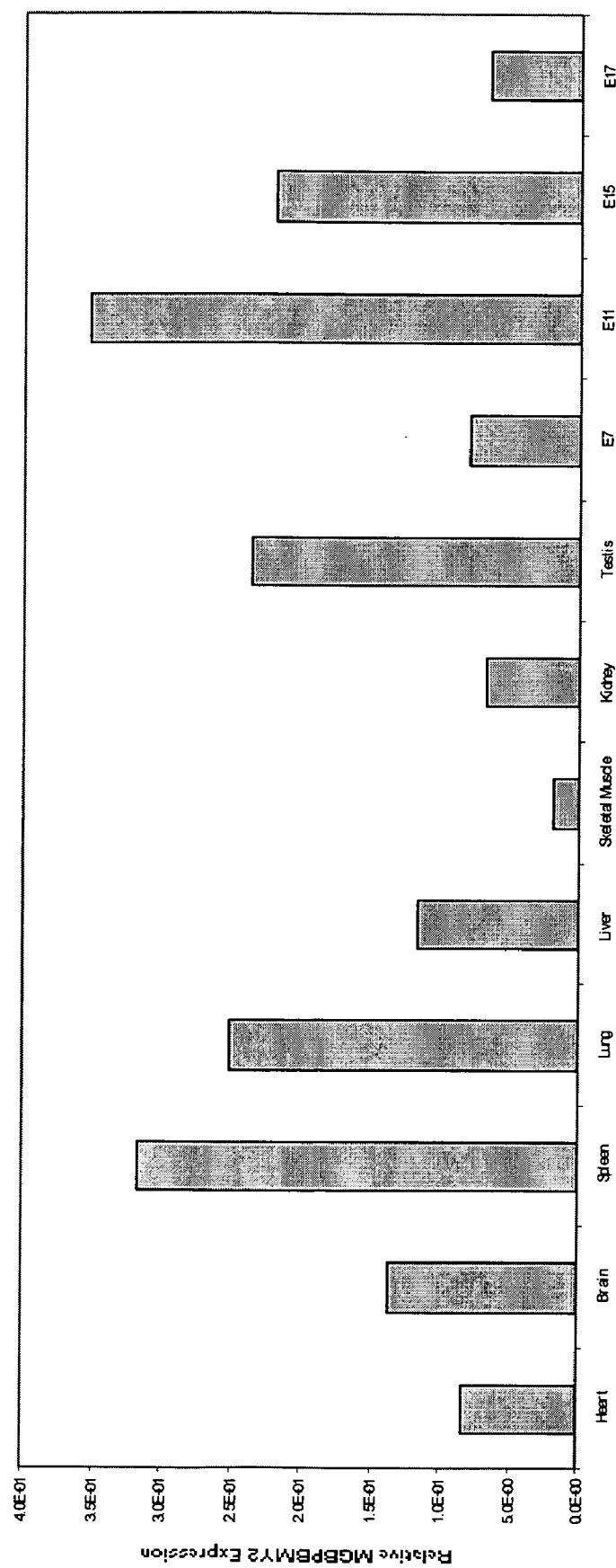
FIG. 24 is bar graph depicting the tissue expression pattern of mouse MGBPBMY2 (LOC229902). Panels of cDNAs derived from normal and immune tissue were analyzed by Real Time PCR for expression of MGBPBMY2 (LOC229902).

Expression profiling designed to measure the steady state mRNA levels encoding the MGBPBMY2 (LOC2299002) polypeptide showed expression in embryonic tissue and in adult, in spleen, as well as in lung, testis, brain, liver, heart, kidney and skeletal muscle (see FIG. 24).

Based upon the strong homology to members of the GBP family members, the MGBPBMY2 (LOC229902) polypeptide is expected to share at least some biological activity with GBP family members, specifically mGBP-1, mGBP-2, mGBP3 and mGBP-4.

The MGBPBMY2 (LOC229902) polynucleotides and polypeptides of the present invention, including agonists and/or fragments thereof, may have uses that include detecting, prognosing, treating, preventing, and/or ameliorating at least diseases and conditions of the immune system, lung, the reproductive system, brain and nervous system, liver, heart, kidney and skeletal muscle in a mouse model of a human condition.

The MGBPBMY2 (LOC229902) polynucleotides and polypeptides of the present invention, including agonists and/or fragments thereof, may have uses that include modulating signal transduction activity, in various cells, tissues, and organisms, and particularly in mammalian tissue and more preferably in a mouse model of a human condition.

The strong homology to mouse GBP family members, particularly mGBP-1, mGBP-2, mGBP3 and mGBP-4, combined with observed MGBPBMY2 (LOC229902) expression in some immune system tissues (i.e., spleen) suggests a potential utility for MGBPBMY2 (LOC229902) polynucleotides and polypeptides in treating, diagnosing, prognosing, and/or preventing diseases and conditions of the immune system in a mouse model of a human condition. In representative embodiments, MGBPBMY2 (LOC229902) polynucleotides and polypeptides including agonists and fragments thereof, may have uses that include treating, diagnosing, prognosing, and/or preventing diseases and conditions of the immune system in a mouse model of a human condition. The MGBPBMY2 (LOC229902) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. The MGBPBMY2 (LOC229902) polypeptide may also be useful for modulating cytokine production, antigen presentation, or other processes, such as for boosting immune responses, etc.

Additional immunolgical disorders that a MGBPBMY2 (LOC229902) polypeptide of the present invention may be useful in the treatment of include various autoimmune diseases in a mouse model of a human condition, such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A MGBPBMY2 (LOC229902) polypeptide of the present invention may also be useful in treating or ameliorating primary immune diseases, as well as immune diseases associated with or secondary to other diseases in a mouse model of a human condition. Such diseases and conditions include Recombinase activating gene (RAG ½) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimke immunoosseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The strong homology to mouse GBP family members, particularly mGBP-1, mGBP-2, mGBP-3 and mGBP-4, combined with observed MGBPBMY2 (LOC229902) expression in heart tissue, suggests the MGBPBMY2 (LOC229902) polynucleotides and polypeptides may be useful in treating, diagnosing, prognosing, and/or preventing cardiovascular diseases and/or disorders in a mouse model of a human condition, which include, but are not limited to: myocardio infarction, congestive heart failure, arrthymias, cardiomyopathy, atherosclerosis, arterialsclerosis, microvascular disease, embolism, thromobosis, pulmonary edema, palpitation, dyspnea, angina, hypotension, syncope, heart murmer, aberrant ECG, hypertrophic cardiomyopathy, the Marfan syndrome, sudden death, prolonged QT syndrome, congenital defects, cardiac viral infections, valvular heart disease, and hypertension.

Similarly, MGBPBMY2 (LOC229902) polynucleotides and polypeptides may be useful for treating and/or ameliorating cardiovascular diseases and symptoms in a mouse model of a human condition which result indirectly from various non-cardiavascular effects, which include, but are not limited to, the following, obesity, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, may have uses which include, directly or indirectly, treating, preventing, diagnosing, and/or prognosing the following, non-limiting, cardiovascular infections in a mouse model of a human condition: blood stream invasion, bacteremia, sepsis, *Streptococcus pneumoniae* infection, group a *streptococci* infection, group b *streptococci* infection, *Enterococcus* infection, nonenterococcal group D *streptococci* infection, nonenterococcal group C *streptococci* infection, nonenterococcal group G *streptococci* infection, *Streptoccus* viridans infection, *Staphylococcus aureus* infection, coagulase-negative *staphylococci* infection, gram-negative *Bacilli* infection, Enterobacteriaceae infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative *coccobacilli* infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous Mycobacteria infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

The strong homology to mouse GBP family members, particularly mGBP-1, mGBP-2, mGBP3 and mGBP-4, combined with the observed MGBPBMY2 (LOC229902) expression in lung tissue suggests a potential utility for MGBPBMY2 (LOC229902) polynucleotides and polypeptides in in treating, diagnosing, prognosing, and/or preventing pulmonary diseases and disorders in a mouse model of a human condition which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, MGBPBMY2 (LOC229902) polynucleotides and polypeptides, including fragments and/or antagonists thereof, may have uses which include, directly or indirectly, treating, preventing, diagnosing, and/or prognosing the following, non-limiting, pulmonary infections in a mouse model of a human condition: pnemonia, bacterial pnemonia, viral pnemonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pnemonia (for example, as caused by *Mycobacterium tuberculosis*, etc.) mycoplasma pnemonia, fungal pnemonia (for example, as caused by *Pneumocystis carinii, Histoplasma capsulatum, Coccidioides immitis, Blastomyces dermatitidis, Candida* sp., *Cryptococcus neoformans, Aspergillus* sp., Zygomycetes, etc.), Legionnaires' Disease, *Chlamydia pnemonia*, aspiration pnemonia, *Nocordia* sp. Infections, parasitic pnemonia (for example, as caused by *Strongyloides, Toxoplasma gondii*, etc.) necrotizing pnemonia, in addition to any other pulmonary disease and/or disorder (e.g., non-pneumonia) implicated by the causative agents listed above or elsewhere herein.

Further, the strong homology to mouse GBP family members, particularly mGBP-1, mGBP-2, mGBP3 and mGBP-4, combined with the observed MGBPBMY2 (LOC229902) expression in skeletal muscle suggests a potential utility for MGBPBMY2 (LOC229902) polynucleotides and polypeptides in treating, diagnosing, prognosing, and/or preventing skeletal muscle disorders in a mouse model of a human condition. In representative embodiments, MGBPBMY2 (LOC229902) polynucleotides and polypeptides including agonists and fragments thereof, may have uses which include treating, diagnosing, prognosing, and/or preventing the following, non-limiting, diseases or disorders of skeletal muscled: dystrophies, pseudohypertrophic muscular dystrophy, Duchenne dystrophy, Becker muscular dystrophy, limb-girdle muscular dystrophy, muscle weakness, Emery-Dreifuss muscular dystrophy, Congenital muscular dystrophy, endometriosis, placental aromatase deficiency, premature menopause, Fukuyama congenital muscular dystrophy, laminin alpha 2 chain deficiency, alpha 7 integrin deficiency, Walker-Warburg syndrome, myotonic dystrophy, congenital myotonic dystrophy, facioscapulohumeral muscular dystrophy, distal myopathies, central core disease, nemaline (rod) myopathy, centronuclear (myotubular) myopathy, central core disease, delay in motor milestones, delayed walking, nemaline myopathy, congenital nemaline myopathy, muscle hypotonia, centronuclear myopathies, skeletal muscle energy metabolism disorders, disorders associated with aberrant skeletal muscle-fatty acid metabolism, disorders associated with aberrant skeletal glucose metabolism, acid maltase deficiency, debranching enzyme deficiency, branching enzyme deficiency, exercise intolerance, myophosphorylase deficiency (type V glycogenosis), phosphofructokinase deficiency (type VII glycogenosis), phosphoglycerate kinase deficiency (type IX glycogenosis), phosphoglycerate mutase deficiency (type X glycogenosis), lactate dehydrogenase deficiency (glycogensosis type XI), glycogen storage disorders, skeletal muscle lipid metabolism, carnitine deficiency, myoglobinuria, muscle cramping, myoadenylate deaminase deficiency, mitochondrial myopathies, Kearns-Sayre syndrome, myoclonic epilepsy, disorders of muscle membrane excitability, calcium channel disorders of muscle, sodium channel disorders of muscle, hyperkalemic periodic paralysis, paramyotonia congenita, potassium-aggravated myotonia, myotonia congenita, chloride channel disorders of muscle, thyrotoxic periodic paralysis, and/or Andersen's syndrome.

Further, the strong homology to mouse GBP family members, particularly mGBP-1, mGBP-2, mGBP3 and mGBP-4, combined with the observed MGBPBMY2 (LOC229902) expression in kidney suggests a potential utility for MGBPBMY2 (LOC229902) polynucleotides and polypeptides in treating, diagnosing, prognosing, and/or preventing diseases and disorders of the kidney in a mouse model of a human condition.

In representative embodiments, MGBPBMY2 (LOC229902) polynucleotides and polypeptides including agonists, antagonists, and fragments thereof, may have uses which include treating, diagnosing, prognosing, and/or preventing the following, non-limiting, diseases or disorders of the kidney in a mouse model of a human condition: Plasma cell infiltration, Hypercalcemia, Myeloma kidney, Amyloidosis, Light chain deposition disease, Type I/II cryoglobulinemia, Immunotactoid glomerulopathy, Reduced glomerular filtration rate, Fanconi syndrome, Hyperchloremic acidosisa, Tubular or small-molecular-weight proteinuria, Polyuria, isothenuria, Hyperkalemia, Salt wasting, Nephrocalcinosis, hyperoxaluria, Cystinosis, Fabry's disease, Sjogren's Syndrome The strong homology to mouse GBP family members, particularly mGBP-1, mGBP-2, mGBP3 and mGBP-4, combined with the observed MGBPBMY2 (LOC229902) expression in brain suggests a potential utility for MGBPBMY2 (LOC229902) polynucleotides and polypeptides in treating, diagnosing, prognosing, and/or preventing diseases and disorders of the brain and neurological tissue in a mouse model of a human condition.

In representative embodiments, MGBPBMY2 (LOC229902) polynucleotides and polypeptides including agonists, antagonists, and fragments thereof, may have uses which include treating, diagnosing, prognosing, and/or preventing the following, non-limiting, brain and neurological diseases or disorders in a mouse model of a human condition: the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a representative embodiment, the MGBPBMY2 (LOC229902) polypeptides, polynucleotides, or agonists or antagonists of the present invention may used to protect neural cells from the damaging effects of cerebral hypoxia. According to this embodiment, the compositions of the invention are used to treat, prevent, and/or diagnose neural cell injury associated with cerebral hypoxia in a mouse model of a human condition. In one aspect of this embodiment, the MGBPBMY2 (LOC229902) polypeptides, polynucleotides, or agonists or antagonists of the invention are used to treat, prevent, and/or diagnose neural cell injury associated with cerebral ischemia. In another aspect of this embodiment, the MGBPBMY2 (LOC229902) polypeptides, polynucleotides, or agonists or antagonists of the invention are used to treat, prevent, and/or diagnose neural cell injury associated with cerebral infarction in a mouse model of a human condition. In another aspect of this embodiment, the polypeptides, polynucleotides, or agonists or antagonists of the invention are used to treat, prevent, and/or diagnose or prevent neural cell injury associated with a stroke. In a further aspect of this embodiment, the MGBPBMY2 (LOC229902) polypeptides, polynucleotides, or agonists or antagonists of the invention are used to treat, prevent, and/or diagnose neural cell injury associated with a heart attack.

MGBPBMY2 (LOC229902) polypeptides and/or polynucleotides of the present invention that are useful for treating or preventing a nervous system disorder may be selected by testing for biological activity in promoting the survival or differentiation of neurons in a mouse model of a human condition. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In representative, non-limiting embodiments, increased survival of neurons may routinely be measured using a method set forth herein or otherwise known in the art, such as, for example, the method set forth in Arakawa et al. (Arakawa et al., (1990) *J. Neurosci.* 10:3507–3515); increased sprouting of neurons may be detected by methods known in the art, such as, for example, the methods set forth in Pestronk et al. (Pestronk et al., (1980) *Exp. Neurol.* 70:65–82) or Brown et al. (Brown et al., (1981) *Ann. Rev. Neurosci.* 4:17–42); increased production of neuron-associated molecules may be measured by bioassay, enzymatic assay, antibody binding, northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed in a mouse model of a human condition according to the present invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

The strong homology to mouse GBP family members, particularly mGBP-1, mGBP-2, mGBP-3 and mGBP-4, combined with MGBPBMY2 (LOC229902) expression in liver tissue suggests a potential utility for MGBPBMY2 (LOC229902) polynucleotides and polypeptides in treating, diagnosing, prognosing, and/or preventing liver diseases in a mouse model of a human condition. In representative embodiments, MGBPBMY2 (LOC229902) polynucleotides and polypeptides including agonists and fragments thereof, may have uses that include treating, diagnosing, prognosing, and/or preventing liver diseases in a mouse model of a human condition. For example, an MGBPBMY2 (LOC229902) protein can be used for the detection, treatment, amelioration, and/or prevention of diseases and conditions in a mouse model of a human condition including, but not limited to: hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, MGBPBMY2 (LOC229902) polynucleotides and polypeptides, including fragments and/or antagonists thereof, may have uses which include, directly or indirectly, treating, preventing, diagnosing, and/or prognosing the following, non-limiting, hepatic infections in a mouse model of a human condition: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

The strong homology to mouse GBP family members, particularly mGBP-1, mGBP-2, mGBP-3 and mGBP-4, combined with the observed MGBPBMY2 (LOC229902) expression in testis tissue suggests a potential utility for MGBPBMY2 (LOC229902) polynucleotides and polypeptides in treating, diagnosing, prognosing, and/or preventing testis diseases in a mouse model of a human condition. In representative embodiments, MGBPBMY2 (LOC229902) polynucleotides and polypeptides including agonists and fragments thereof, may have uses that include treating, diagnosing, prognosing, and/or preventing testis diseases in a mouse model of a human condition. For example, an MGBPBMY2 (LOC229902) protein may be used for the detection, treatment, amelioration, diagnosis and/or prevention of diseases and conditions in a mouse model of a human condition including, but not limited to the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The MGBPBMY2 (LOC229902) polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the observed MGBPBMY2 (LOC229902) expression in testis tissue also emphasizes a potential utility for MGBPBMY2 (LOC229902) polynucleotides and polypeptides in treating, diagnosing, prognosing, and/or preventing metabolic diseases and disorders in a mouse model of a human condition which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

MGBPBMY2 (LOC229902) polynucleotides and/or poplypeptides may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

It is noted that the use of mouse models to understand, diagnose, predict, treat and/or ameliorate human conditions is well documented. Thus, the uses for the MGBPBMY2

(LOC229902) can often be extrapolated to human conditions, as well as to further research such conditions and their treatments.

A MGBPBMY2 (LOC229902) protein can also be used to determine biological activity, raise antibodies, as tissue markers, to isolate cognate ligands or receptors, to identify agents that modulate their interactions. Further, proteins, as well as antibodies directed against a MGBPBMY2 (LOC229902) protein, can show utility as a tumor marker and/or immunotherapy targets for spleen, lung, heart, kidney, skeletal muscle and/or brain tissue.

The MGBPBMY2 (LOC229902) polynucleotides and polypeptides, including fragments and for antagonists thereof, can have uses which include identification of modulators of MGBPBMY2 (LOC229902) function including antibodies (for detection or neutralization), naturally-occurring modulators and small molecule modulators. Antibodies to a particular domain of the MGBPBMY2 (LOC229902) protein could be used as diagnostic agents of certain conditions in subjects, are useful in monitoring the activation of signal transduction pathways, and can be used as a biomarker for the involvement of GBP's in disease states, as well as in the evaluation of inhibitors of GBP's in vivo.

MGBPBMY2 (LOC229902) polypeptides and polynucleotides may have additional uses which include diagnosing diseases related to the over and/or under expression of MGBPBMY2 (LOC229902) by identifying mutations in the MGBPBMY2 (LOC229902) gene by using MGBPBMY2 (LOC229902) sequences as probes or by determining MGBPBMY2 (LOC229902) protein or mRNA expression levels. MGBPBMY2 (LOC229902) polypeptides may be useful for screening compounds that affect the activity of the protein. MGBPBMY2 (LOC229902) peptides can also be used for the generation of specific antibodies and as bait in yeast two hybrid screens to find proteins the specifically interact with MGBPBMY2 (LOC229902), as described herein.

Although it is believed the encoded polypeptide could share at least some biological activities with human guanylate binding proteins (particularly mGBP-1, mGBP-2, mGBP-3 and mGBP-4), a number of methods of determining the exact biological function of this clone are either known in the art or are described elsewhere herein. For example, the function of this clone can be determined by applying microarray methodology. Nucleic acids corresponding to the MGBPBMY2 (LOC229902) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased liver tissue, as compared to normal tissue might indicate a function in modulating liver function, for example. In the case of MGBPBMY2 (LOC229902), heart, brain, spleen, lung, liver, skeletal muscle, kidney and/or testis, as well as various embryonic tissues, can be used, for example, to extract RNA to prepare the probe.

In addition, the function of the protein can be assessed, for example, by applying quantitative PCR methodology. Real time quantitative PCR would provide the capability of following the expression of the MGBPBMY2 (LOC229902) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of MGBPBMY2 (LOC229902), a disease correlation related to MGBPBMY2 (LOC229902) can be made by comparing the mRNA expression level of MGBPBMY2 (LOC229902) in normal tissue, as compared to diseased tissue. Significantly higher or lower levels of MGBPBMY2 (LOC229902) expression in the diseased tissue can suggest MGBPBMY2 (LOC229902) plays a role in disease progression, and antagonists against MGBPBMY2 (LOC229902) polypeptides would be useful therapeutically in treating, preventing, and/or ameliorating the disease. Alternatively, significantly higher or lower levels of MGBPBMY2 (LOC229902) expression in the diseased tissue can suggest MGBPBMY2 (LOC229902) plays a defensive role against disease progression, and agonists of MGBPBMY2 (LOC229902) polypeptides can be useful therapeutically in treating, preventing, and/or ameliorating the disease. Also encompassed by the present invention are quantitative PCR probes corresponding to the polynucleotide sequence provided as SEQ ID NO:12 (FIGS. 6A–6B).

The function of the protein can also be assessed through complementation assays in yeast. For example, in the case of the MGBPBMY2 (LOC229902), transforming yeast deficient in GBP activity, for example, and assessing their ability to grow would provide convincing evidence the MGBPBMY2 (LOC229902) polypeptide has GBP activity. Additional assay conditions and methods that can be used in assessing the function of the polynucleotides and polypeptides of the present invention are known in the art, some of which are disclosed herein. For example, a GTPase activity assay can be employed.

Alternatively, the biological function of the encoded polypeptide can be determined by disrupting a homologue of this polypeptide in another species (e.g., a mammalian species) and observing the resulting phenotype. Such knock-out experiments are known in the art, some of which are disclosed elsewhere herein.

Moreover, the biological function of this polypeptide can be determined by the application of antisense and/or sense methodology (including RNAi and homlogous recombination) and the resulting generation of transgenic animals. Expressing a particular gene in either sense or antisense orientation in a transgenic animal could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a spleen tissue-specific promoter), or it can be expressed at a specified time of development using an inducible and/or a developmentally regulated promoter.

In the case of MGBPBMY2 (LOC229902), transgenic animals, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic animals to refine the biological function of the polypeptide is encompassed by the present invention.

In preferred embodiments, the following N-terminal MGBPBMY2 (LOC229902) deletion polypeptides are encompassed by the present invention: M1-S605, E2-S605, G3-S605, K4-S605, V5-S605, L6-S605, Q7-S605, W8-S605, N9-S605, S10-S605, Y11-S605, L12-S605, S13-S605, E14-S605, F15-S605, H16-S605, C17-S605, D18-S605, Q19-S605, D20-S605, V21-S605, V22-S605, T23-S605, K24-S605, V25-S605, S26-S605, V27-S605, P28-S605, S29-S605, G30-S605, T31-S605, K32-S605, E33-S605, I34-S605, A35-S605, Q36-S605, L37-S605, P38-S605, L39-S605, T40-S605, P41-S605, I42-S605, P43-S605, N44-S605, P45-S605, L46-S605, I47-S605, T48-S605, S49-S605, P50-S605, K51-S605, K52-S605, Y53-S605, P54-S605, L55-S605, N56-S605, C57-S605, G58-S605, D59-S605, Q60-S605, R61-S605, N62-S605, G63-S605, H64-S605, K65-S605, S66-S605, W67-S605, L68-S605, M69-S605, H70-S605, G71-S605, L72-S605, L73-S605, M74-S605, V75-S605, H76-S605, Q77-S605, P78-S605, L79-S605, M80-S605, E81-S605, A82-S605, K83-S605, L84-S605, M85-S605, E86-S605, S87-S605, Q88-S605, S89-S605, L90-S605, E91-S605, T92-S605, W93-S605, G94-S605, W95-S605, N96-S605, G97-S605, Q98-S605, H99-S605, Q100-S605, G101-S605, R102-S605, N103-S605, H104-S605, K105-S605, I106-S605, S107-S605, I108-S605, A109-S605, L110-S605, L111-S605, A112-S605, I113-S605, K114-S605, Q115-S605, T116-S605, T117-S605, R118-S605, K119-S605, T120-S605, K121-S605, S122-S605, F123-S605, S124-S605, M125-S605, G126-S605, S127-S605, T128-S605, V129-S605, Q130-S605, S131-S605, Q132-S605, T133-S605, R134-S605, G135-S605, I136-S605, W137-S605, M138-S605, W139-S605, C140-S605, V141-S605, P142-S605, H143-S605, P144-S605, E145-S605, K146-S605, P147-S605, D148-S605, H149-S605, T150-S605, L151-S605, V152-S605, L153-S605, D154-S605, D155-S605, T156-S605, E157-S605, G158-S605, L159-S605, G160-S605, D161-S605, V162-S605, E163-S605, K164-S605, G165-S605, D166-S605, N167-S605, Q168-S605, N169-S605, D170-S605, C171-S605, W172-S605, I173-S605, F174-S605, A175-S605, L176-S605, A177-S605, I178-S605, L179-S605, L180, S181-S605, S182-S605, T183-S605, F184-S605, V185-S605, Y186-S605, N187-S605, S188-S605, I189-S605, G190-S605, A191-S605, I192-S605, N193-S605, Q194-S605, Q195-S605, A196-S605, M197-S605, D198-S605, Q199-S605, L200-S605, H201-S605, F202-S605, F203-S605, L204-S605, M205-S605, Q206-S605, H207-S605, E208-S605, M209-S605, M210-S605, L211-S605, I212-S605, S213-S605, Y214-S605, V215-S605, T216-S605, E217-S605, L218-S605, T219-S605, D220-S605, R221-S605, I222-S605, R223-S605, T224-S605, R225-S605, R226-S605, S227-S605, P228-S605, D229-S605, H230-S605, Q231-S605, A232-S605, L233-S605, E234-S605, D235-S605, S236-S605, D237-S605, E238-S605, Y239-S605, V240-S605, S241-S605, F242-S605, F243-S605, P244-S605, D245-S605, F246-S605, V247-S605, W248-S605, T249-S605, P250-S605, R251-S605, D252-S605, F253-S605, C254-S605, L255-S605, E256-S605, L257-S605, K258-S605, T259-S605, N260-S605, G261-S605, Q262-S605, P263-S605, L264-S605, S265-S605, A266-S605, D267-S605, E268-S605, Y269-S605, L270-S605, G271-S605, N272-S605, S273-S605, L274-S605, K275-S605, L276-S605, L277-S605, Q278-S605, G279-S605, C280-S605, S281-S605, Q282-S605, K283-S605, E284-S605, L285-S605, E286-S605, L287-S605, N288-S605, L289-S605, S290-S605, Q291-S605, L292-S605, C293-S605, I294-S605, R295-S605, K296-S605, F297-S605, F298-S605, P299-S605, T300-S605, K301-S605, S605, K302-S605, C303-S605, F304-S605, V305-S605, F306-S605, E307-S605, R308-S605, P309-S605, A310-S605, P311-S605, G312-S605, K313-S605, K314-S605, I315-S605, G316-S605, Q317-S605, L318-S605, E319-S605, S320-S605, L321-S605, Q322-S605, D323-S605, K324-S605, D325-S605, L326-S605, D327-S605, S328-S605, D329-S605, F330-S605, V331-S605, K332-S605, Q333-S605, V334-S605, A335-S605, E336-S605, F337-S605, S338-S605, S339-S605, Y340-S605, V341-S605, F342-S605, R343-S605, S344-S605, S345-S605, K346-S605, I347-S605, K348-S605, K349-S605, I350-S605, P351-S605, G352-S605, D353-S605, L354-S605, K355-S605, V356-S605, N357-S605, G358-S605, P359-S605, R360-S605, L361-S605, K362-S605, N363-S605, L364-S605, V365-S605, T366-S605, T367-S605, Y368-S605, V369-S605, N370-S605, T371-S605, I372-S605, S373-S605, N374-S605, G375-S605, S376-S605, L377-S605, P378-S605, C379-S605, M380-S605, E381-S605, S382-S605, A383-S605, V384-S605, L385-S605, A386-S605, L387-S605, S388-S605, E389-S605, T390-S605, E391-S605, N392-S605, S393-S605, A394-S605, A395-S605, V396-S605, R397-S605, K398-S605, A399-S605, I400-S605, A401-S605, H402-S605, Y403-S605, D404-S605, Q405-S605, Q406-S605, M407-S605, S408-S605, Q409-S605, S410-S605, L411-S605, K412-S605, L413-S605, P414-S605, T415-S605, E416-S605, T417-S605, L418-S605, Q419-S605, E420-S605, L421-S605, L422-S605, D423-S605, L424-S605, H425-S605, R426-S605, S427-S605, S428-S605, E429-S605, K430-S605, E431-S605, A432-S605, I433-S605, K434-S605, I435-S605, F436-S605, M437-S605, E438-S605, N439-S605, S440-S605, F441-S605, K442-S605, D443-S605, V444-S605, D445-S605, Q446-S605, V447-S605, F448-S605, L449-S605, T450-S605, K451-S605, L452-S605, E453-S605, K454-S605, E455-S605, G456-S605, K457-S605, Q458-S605, R459-S605, E460-S605, F461-S605, C462-S605, K463-S605, K464-S605, N465-S605, Q466-S605, E467-S605, A468-S605, S469-S605, S470-S605, D471-S605, R472-S605, C473-S605, S474-S605, V475-S605, L476-S605, L477-S605, R478-S605, D479-S605, I480-S605, F481-S605, G482-S605, P483-S605, L484-S605, E485-S605, E486-S605, D487-S605, L488-S605, K489-S605, Q490-S605, Q491-S605, V492-S605, F493-S605, Y494-S605, K495-S605, P496-S605, T497-S605, Q498-S605, C499-S605, C500-S605, L501-S605, F502-S605, S503-S605, Q504-S605, K505-S605, I506-S605, Q507-S605, G508-S605, L509-S605, K510-S605, R511-S605, K512-S605, Y513-S605, E514-S605, E515-S605, P516-S605, G517-S605, K518-S605, G519-S605, A520-S605, G521-S605, N522-S605, Q523-S605, G524-S605, N525-S605, Q526-S605, G527-S605, S528-S605, A529-S605, C530-S605, P531-S605, G532-S605, K533-S605, F534-S605, L535-S605, T536-S605, I537-S605, R538-S605, L539-S605, Q540-S605, C541-S605, P542-S605, Q543-S605, A544-S605, S545-S605, L546-S605, G547-S605, N548-S605, A549-S605, S550-S605, L551-S605, C552-S605, C553-S605, S554-S605, C555-S605, I556-S605, T557-S605, Y558-S605, L559-S605, K560-S605, V561-S605, F562-S605, I563-S605, L564-S605, D565-S605, I566-S605, S567-S605, C568-S605, S569-S605, P570-S605, I571-S605, R572-S605, D573-S605, S574-S605, H575-S605, S576-S605, L577-S605, N578-S605, S579-S605, Q580-S605, T581-S605, V582-S605, T583-S605, R584-S605, L585-S605, T586-S605, T587-S605, E588-S605, L589-S605, K590-S605, L591-S605, T592-S605, T593-S605, L594-S605, A595-S605, T596-S605, S597-S605, G598-S605, T599-S605, V600-S605, T601-S605, L602-S605, C603-S605 and/or F604-S605 of SEQ ID NO:13. Polynucleotide sequences encoding these polypeptides are also provided. The present invention also encompasses the use of these N-terminal MGBPBMY2 (LOC229902) deletion polypeptides as immunogenic and/or antigenic epitopes as described elsewhere herein.

In other embodiments, the following C-terminal MGBPBMY2 (LOC229902) deletion polypeptides are encompassed by the present invention: M1-E2, M1-G3, M1-K4, M1-V5, M1-L6, M1-Q7, M1-W8, M1-N9, M1-S10, M1-Y11, M1-L12, M1-S13, M1-E14, M1-F15, M1-H16, M1-C17, M1-D18, M1-Q19, M1-D20, M1-V21, M1-V22, M1-T23, M1-K24, M1-V25, M1-S26, M1-V27, M1-P28, M1-S29, M1-G30, M1-T31, M1-K32, M1-E33, M1-I34, M1-A35, M1-Q36, M1-L37, M1-P38, M1-L39, M1-T40, M1-P41, M1-I42, M1-P43, M1-N44, M1-P45, M1-L46, M1-I47, M1-T48, M1-S49, M1-P50, M1-K51, M1-K52, M1-Y53, M1-P54, M1-L55, M1-N56, M1-C57, M1-G58, M1-D59, M1-Q60, M1-R61, M1-N62, M1-G63, M1-H64, M1-K65, M1-S66, M1-W67, M1-L68, M1-M69, M1-H70, M1-G71, M1-L72, M1-L73, M1-M74, M1-V75, M1-H76, M1-Q77, M1-P78, M1-L79, M1-M80, M1-E81, M1-A82, M1-K83, M1-L84, M1-M85, M1-E86, M1-S87, M1-Q88, M1-S89, M1-L90, M1-E91, M1-T92, M1-W93, M1-G94, M1-W95, M1-N96, M1-G97, M1-Q98, M1-H99, M1-Q100, M1-G101, M1-R102, M1-N103, M1-H104, M1-K105, M1-I106, M1-S107, M1-I108, M1-A109, M1-L110, M1-L111, M1-A112, M1-I113, M1-K114, M1-Q115, M1-T116, M1-T117, M1-R118, M1-K119, M1-T120, M1-K121, M1-S122, M1-F123, M1-S124, M1-M125, M1-G126, M1-S127, M1-T128, M1-V129, M1-Q130, M1-S131, M1-Q132, M1-T133, M1-R134, M1-G135, M1-I136, M1-W137, M1-M138, M1-W139, M1-C140, M1-V141, M1-P142, M1-H143, M1-P144, M1-E145, M1-K146, M1-P147, M1-D148, M1-H149, M1-T150, M1-L151, M1-V152, M1-L153, M1-D154, M1-D155, M1-T156, M1-E157, M1-G158, M1-L159, M1-G160, M1-D161, M1-V162, M1-E163, M1-K164, M1-G165, M1-D166, M1-N167, M1-Q168, M1-N169, M1-D170, M1-C171, M1-W172, M1-I173, M1-F174, M1-A175, M1-L176, M1-A177, M1-I178, M1-L179, M1-L180, M1-S181, M1-S182, M1-T183, M1-F184, M1-V185, M1-Y186, M1-N187, M1-S188, M1-I189, M1-G190, M1-A191, M1-I192, M1-N193, M1-Q194, M1-Q195, M1-A196, M1-M197, M1-D198, M1-Q199, M1-L200, M1-H201, M1-F202, M1-F203, M1-L204, M1-M205, M1-Q206, M1-H207, M1-E208, M1-M209, M1-M210, M1-L211, M1-I212, M1-S213, M1-Y214, M1-V215, M1-T216, M1-E217, M1-L218, M1-T219, M1-D220, M1-R221, M1-I222, M1-R223, M1-T224, M1-R225, M1-R226, M1-S227, M1-P228, M1-D229, M1-H230, M1-Q231, M1-A232, M1-L233, M1-E234, M1-D235, M1-S236, M1-D237, M1-E238, M1-Y239, M1-V240, M1-S241, M1-F242, M1-F243, M1-P244, M1-D245, M1-F246, M1-V247, M1-W248, M1-T249, M1-P250, M1-R251, M1-D252, M1-F253, M1-C254, M1-L255, M1-E256, M1-L257, M1-K258, M1-T259, M1-N260, M1-G261, M1-Q262, M1-P263, M1-L264, M1-S265, M1-A266, M1-D267, M1-E268, M1-Y269, M1-L270, M1-G271, M1-N272, M1-S273, M1-L274, M1-K275, M1-L276, M1-L277, M1-Q278, M1-G279, M1-C280, M1-S281, M1-Q282, M1-K283, M1-E284, M1-K285, M1-E286, M1-L287, M1-N288, M1-L289, M1-S290, M1-Q291, M1-L292, M1-C293, M1-I294, M1-R295, M1-K296, M1-F297, M1-F298, M1-P299, M1-T300, M1-K301, M1-K302, M1-C303, M1-F304, M1-V305, M1-F306, M1-E307, M1-R308, M1-P309, M1-A310, M1-P311, M1-G312, M1-K313, M1-K314, M1-I315, M1-G316, M1-Q317, M1-L318, M1-E319, M1-S320, M1-L321, M1-Q322, M1-D323, M1-K324, M1-D325, M1-L326, M1-D327, M1-S328, M1-D329, M1-F330, M1-V331, M1-K332, M1-Q333, M1-V334, M1-A335, M1-E336, M1-F337, M1-S338, M1-S339, M1-Y340, M1-V341, M1-F342, M1-R343, M1-S344, M1-S345, M1-K346, M1-I347, M1-K348, M1-K349, M1-I350, M1-P351, M1-G352, M1-D353, M1-L354, M1-K355, M1-V356, M1-N357, M1-G358, M1-P359, M1-R360, M1-L361, M1-K362, M1-N363, M1-L364, M1-V365, M1-T366, M1-T367, M1-Y368, M1-V369, M1-N370, M1-T371, M1-I372, M1-S373, M1-N374, M1-G375, M1-S376, M1-L377, M1-P378, M1-C379, M1-M380, M1-E381, M1-S382, M1-A383, M1-V384, M1-L385, M1-A386, M1-L387, M1-S388, M1-E389, M1-T390, M1-E391, M1-N392, M1-S393, M1-A394, M1-A395, M1-V396, M1-R397, M1-K398, M1-A399, M1-I400, M1-A401, M1-H402, M1-Y403, M1-D404, M1-Q405, M1-Q406, M1-M407, M1-S408, M1-Q409, M1-S410, M1-L411, M1-K412, M1-L413, M1-P414, M1-T415, M1-E416, M1-T417, M1-L418, M1-Q419, M1-E420, M1-L421, M1-L422, M1-D423, M1-L424, M1-H425, M1-R426, M1-S427, M1-S428, M1-E429, M1-K430, M1-E431, M1-A432, M1-I433, M1-K434, M1-I435, M1-F436, M1-M437, M1-E438, M1-N439, M1-S440, M1-F441, M1-K442, M1-D443, M1-V444, M1-D445, M1-Q446, M1-V447, M1-F448, M1-L449, M1-T450, M1-K451, M1-L452, M1-E453, M1-K454, M1-E455, M1-G456, M1-K457, M1-Q458, M1-R459, M1-E460, M1-F461, M1-C462, M1-K463, M1-K464, M1-N465, M1-Q466, M1-E467, M1-A468, M1-S469, M1-S470, M1-D471, M1-R472, M1-C473, M1-S474, M1-V475, M1-L476, M1-L477, M1-R478, M1-D479, M1-I480, M1-F481, M1-G482, M1-P483, M1-L484, M1-E485, M1-E486, M1-D487, M1-L488, M1-K489, M1-Q490, M1-G491, M1-V492, M1-F493, M1-Y494, M1-K495, M1-P496, M1-T497, M1-G498, M1-C499, M1-C500, M1-L501, M1-F502, M1-S503, M1-Q504, M1-K505, M1-I506, M1-Q507, M1-G508, M1-L509, M1-K510, M1-R511, M1-K512, M1-Y513, M1-E514, M1-E515, M1-P516, M1-G517, M1-K518, M1-G519, M1-A520, M1-Q521, M1-N522, M1-Q523, M1-G524, M1-N525, M1-Q526, M1-G527, M1-S528, M1-A529, M1-C530, M1-P531, M1-G532, M1-K533, M1-F534, M1-L535, M1-T536, M1-I537, M1-R538, M1-L539, M1-Q540, M1-C541, M1-P542, M1-Q543, M1-A544, M1-S545, M1-L546, M1-G547, M1-N548, M1-A549, M1-S550, M1-L551, M1-C552, M1-C553, M1-S554, M1-C555, M1-I556, M1-T557, M1-Y557, M1-L559, M1-K560, M1-V561, M1-F562, M1-I563, M1-L564, M1-D565, M1-I566, M1-S567, M1-C568, M1-S569, M1-P570, M1-I571, M1-R572, M1-D573, M1-S574, M1-H575, M1-S576, M1-L577, M1-N578, M1-S579, M1-Q580, M1-T581, M1-V582, M1-T583, M1-R584, M1-L585, M1-T586, M1-T587, M1-E588, M1-L589, M1-K590, M1-L591, M1-T592, M1-T593, M1-L594, M1-A595, M1-T596, M1-S597, M1-G598, M1-T599, M1-V600, M1-T601, M1-L602, M1-C603 and/or M1-F604 of SEQ ID NO:13. Polynucleotide sequences encoding these polypeptides are also provided. The present invention also encompasses the use of these C-terminal MGBPBMY2 (LOC229902) deletion polypeptides as immunogenic and/or antigenic epitopes as described elsewhere herein.

Alternatively, preferred polypeptides of the present invention can comprise polypeptide sequences corresponding to, for example, internal regions of the MGBPBMY2

(LOC229902) polypeptide (e.g., any combination of both N- and C-terminal MGBPBMY2 (LOC229902) polypeptide deletions) of SEQ ID NO:13. For example, internal regions could be defined by the equation: amino acid NX to amino acid CX, wherein NX refers to any N-terminal deletion polypeptide amino acid of MGBPBMY2 (LOC229902) (SEQ ID NO:13), and where CX refers to any C-terminal deletion polypeptide amino acid of MGBPBMY2 (LOC229902) (SEQ ID NO:13). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the MGBPBMY2 (LOC229902) polypeptide.

The present invention encompasses the identification of compounds and drugs which stimulate MGBPBMY2 (LOC229902) on the one hand (i.e., agonists) and which inhibit the function of MGBPBMY2 (LOC229902) on the other hand (i.e., antagonists). In general, such screening procedures involve providing appropriate cells which express a polypeptide of the present invention on the surface thereof. Such cells can include, for example, cells from mammals, yeast, Drosophila or E. coli. In a representative embodiment, a polynucleotide encoding a polypeptide of the present invention can be employed to transfect cells to thereby express the MGBPBMY2 (LOC229902) polypeptide. The expressed polypeptide can then be contacted with a test compound to observe binding, stimulation or inhibition of a functional response.

Features of the Polypeptide Encoded by Gene No. 7

A polypeptide encoded by this gene, MGBPBMY3 (BC031475), is provided as SEQ ID NO:15 (FIGS. 7A–7C) and is encoded by the polynucleotide sequence according to SEQ ID NO:14 (FIGS. 7A–7C) and/or by a polynucleotide contained within a deposited clone. MGBPBMY3 (BC031475) has significant homology at the nucleotide and amino acid level to a number of guanylate binding proteins, which include, for example, mouse GBP-1, mouse GBP-2, mouse GBP-3 and mouse GBP-4.

The determined nucleotide sequence of the MGBPBMY3 (BC031475), (i.e. the cDNA shown in FIGS. 7A–7C and in SEQ ID NO:14) comprises an open reading frame encoding a protein of about 385 amino acid residues. The predicted amino acid sequence of the MGBPBMY3 (BC031475) polypeptide is shown in FIGS. 7A–7C (SEQ ID NO:15). The percent identity and similarity values between the MGBPBMY3 (BC031475) polypeptide to the known GBP family member mGBP1 is provided in FIG. 9. The MGBPBMY3 (BC031475) protein shown in FIGS. 7A–7C was determined to share significant identity and similarity to several known GBP family members, as shown in FIG. 11A–11G.

Figure 26:
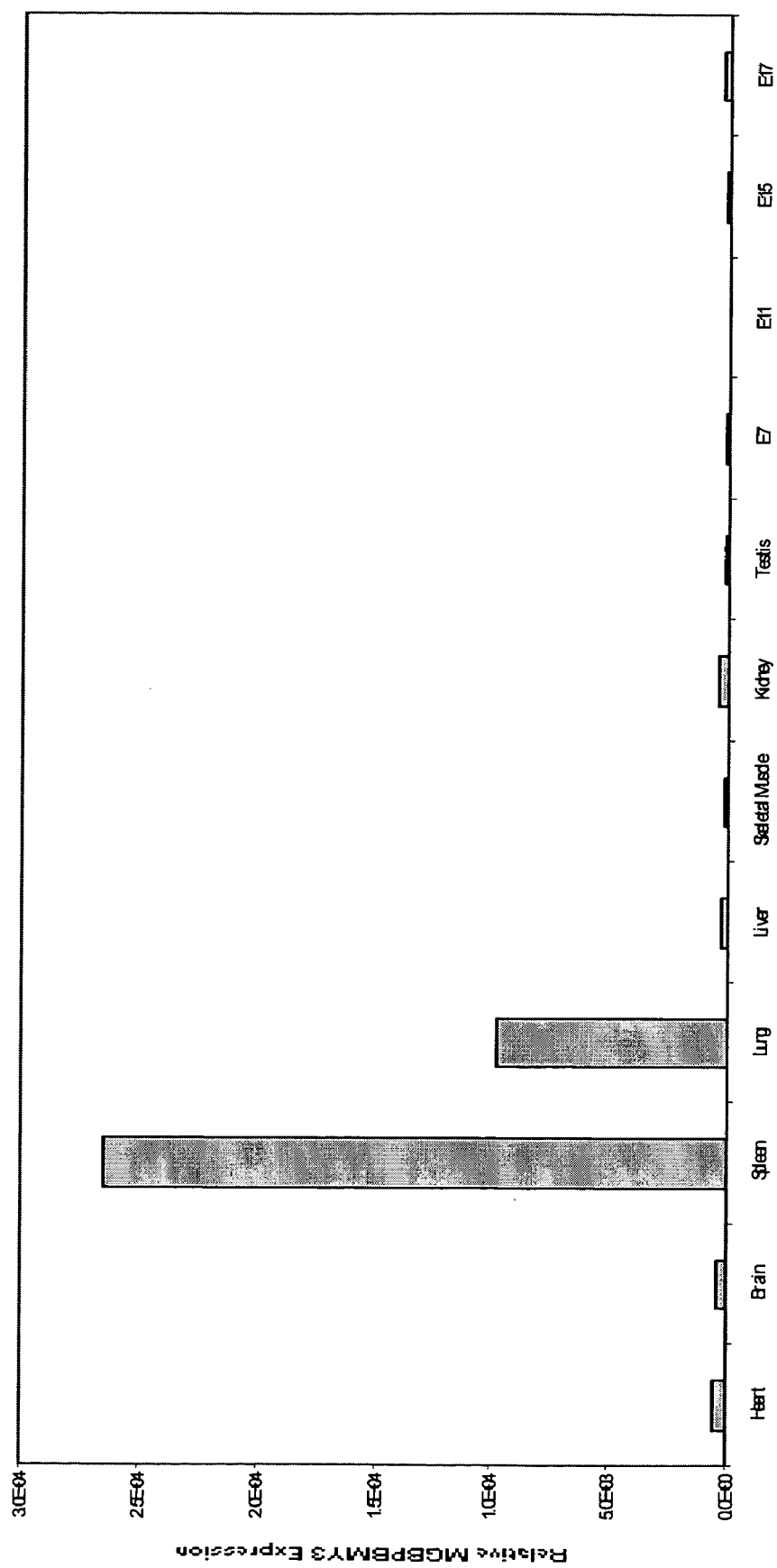
FIG. 26 is bar graph depicting the tissue expression pattern of mouse MGBPBMY3 (BC031475). Panels of cDNAs derived from normal and immune tissue were analyzed by Real Time PCR for expression of MGBPBMY3 (BC031475).

Expression profiling designed to measure the steady state mRNA levels encoding the MGBPBMY3 (BC031475) polypeptide showed experession in spleen and lung (see FIG. 26).

Based upon the strong homology to members of the GBP family members, the MGBPBMY3 (BC031475) polypeptide is expected to share at least some biological activity with GBP family members, specifically mGBP-1, mGBP-2, mGBP3 and mGBP-4.

The MGBPBMY3 (BC031475) polynucleotides and polypeptides of the present invention, including agonists and/or fragments thereof, may have uses that include detecting, prognosing, diagnosing treating, preventing, and/or ameliorating at least diseases and conditions of the immune system and lung in a mouse model of a human condition.

The MGBPBMY3 (BC031475) polynucleotides and polypeptides of the present invention, including agonists and/or fragments thereof, may have uses that include modulating signal transduction activity, in various cells, tissues, and organisms, and particularly in mammalian tissue and more preferably in a mouse model of a human condition.

The strong homology to mouse GBP family members, particularly mGBP-1, mGBP-2, mGBP3 and mGBP-4, combined with MGBPBMY3 (BC031475) expression in some immune system tissues (i.e., spleen) suggests a potential utility for MGBPBMY3 (BC031475) polynucleotides and polypeptides in treating, diagnosing, prognosing, and/or preventing diseases and conditions of the immune system in a mouse model of a human condition. In representative embodiments, MGBPBMY3 (BC031475) polynucleotides and polypeptides including agonists and fragments thereof, may have uses that include treating, diagnosing, prognosing, and/or preventing diseases and conditions of the immune system in a mouse model of a human condition. The MGBPBMY3 (BC031475) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. A MGBPBMY3 (BC031475) polypeptide may also be useful for modulating cytokine production, antigen presentation, or other processes, such as for boosting immune responses, etc.

Additional immunolgical disorders that a MGBPBMY3 (BC031475) polypeptide of the present invention may be useful in the treatment of include various autoimmune diseases in a mouse model of a human condition, such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A MGBPBMY3 (BC031475) polypeptide of the present invention amy also be useful in treating or ameliorating primary immune diseases, as well as immune diseases associated with or secondary to other diseases in a mouse model of a human condition. Such diseases and conditions include Recombinase activating gene (RAG 1/2) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimke immunoosseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The strong homology to mouse GBP family members, particularly mGBP-1, mGBP-2, mGBP-3 and mGBP-4, combined with observed MGBPBMY3 (BC031475) expression levels in heart tissue suggests the MGBPBMY3 (BC031475) polynucleotides and polypeptides may be useful in treating, diagnosing, prognosing, and/or preventing cardiovascular diseases and/or disorders in a mouse model of a human condition, which include, but are not limited to: myocardio infarction, congestive heart failure, arrthymias, cardiomyopathy, atherosclerosis, arterialsclerosis, microvascular disease, embolism, thromobosis, pulmonary edema, palpitation, dyspnea, angina, hypotension, syncope, heart murmur, aberrant ECG, hypertrophic cardiomyopathy, the Marfan syndrome, sudden death, prolonged QT syndrome, congenital defects, cardiac viral infections, valvular heart disease, and hypertension.

Similarly, MGBPBMY3 (BC031475) polynucleotides and polypeptides may be useful for treating and/or ameliorating cardiovascular diseases and symptoms in a mouse model of a human condition which result indirectly from various non-cardiavascular effects, which include, but are not limited to, the following, obesity, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, may have uses which include, directly or indirectly, treating, preventing, diagnosing, and/or prognosing the following, non-limiting, cardiovascular infections in a mouse model of a human condition: blood stream invasion, bacteremia, sepsis, *Streptococcus pneumoniae* infection, group a *streptococci* infection, group b *streptococci* infection, *Enterococcus* infection, nonenterococcal group D *streptococci* infection, nonenterococcal group C *streptococci* infection, nonenterococcal group G *streptococci* infection, *Streptoccus* viridans infection, *Staphylococcus aureus* infection, coagulase-negative *staphylococci* infection, gram-negative *Bacilli* infection, *Enterobacteriaceae* infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative *coccobacilli* infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous Mycobacteria infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

The strong homology to mouse GBP family members, particularly mGBP-1, mGBP-2, mGBP3 and mGBP-4, combined with the observed MGBPBMY3 (BC031475) expression in lung tissue suggests a potential utility for MGBPBMY3 (BC031475) polynucleotides and polypeptides in in treating, diagnosing, prognosing, and/or preventing pulmonary diseases and disorders in a mouse model of a human condition which include the following, non-limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, MGBPBMY3 (BC031475) polynucleotides and polypeptides, including fragments and/or antagonists thereof, may have uses which include, directly or indirectly, treating, preventing, diagnosing, and/or prognosing the following, non-limiting, pulmonary infections in a mouse model of a human condition: pnemonia, bacterial pnemonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pneumonia (for example, as caused by *Mycobacterium tuberculosis*, etc.) mycoplasma pneumonia, fungal pneumonia (for example, as caused by *Pneumocystis carinii, Histoplasma capsulatum, Coccidioides immitis, Blastomyces dermatitidis, Candida* sp., *Cryptococcus neoformans, Aspergillus* sp., Zygomycetes, etc.), Legionnaires' Disease, *Chlamydia pneumonia*, aspiration pneumonia, *Nocordia* sp. Infections, parasitic pneumonia (for example, as caused by Strongyloides, *Toxoplasma gondii*, etc.) necrotizing pneumonia, in addition to any other pulmonary disease and/or disorder (e.g., non-pneumonia) implicated by the causative agents listed above or elsewhere herein.

It is noted that the use of mouse models to understand, diagnose, predict, treat and/or ameliorate human conditions is well documented. Thus, the uses for the MGBPBMY3 (BC031475) can often be extrapolated to human conditions, as well as to further research such conditions and their treatments.

A MGBPBMY3 (BC031475) protein can also be used to determine biological activity, raise antibodies, as tissue markers, to isolate cognate ligands or receptors, to identify agents that modulate their interactions. Further, proteins, as well as antibodies directed against a MGBPBMY3 (BC031475) protein, can show utility as a tumor marker and/or immunotherapy targets for spleen and lung brain tissue.

The MGBPBMY3 (BC031475) polynucleotides and polypeptides, including fragments and for antagonists thereof, can have uses which include identification of modulators of MGBPBMY3 (BC031475) function including antibodies (for detection or neutralization), naturally-occurring modulators and small molecule modulators. Antibodies to a particular domain of the MGBPBMY3 (BC031475) protein could be used as diagnostic agents of certain conditions in subjects, are useful in monitoring the activation of signal transduction pathways, and can be used as a biomarker for the involvement of GBP's in disease states, as well as in the evaluation of inhibitors of GBP's in vivo.

MGBPBMY3 (BC031475) polypeptides and polynucleotides have additional uses which include diagnosing diseases related to the over and/or under expression of MGBPBMY3 (BC031475) by identifying mutations in the MGBPBMY3 (BC031475) gene by using MGBPBMY3 (BC031475) sequences as probes or by determining MGBPBMY3 (BC031475) protein or mRNA expression levels. MGBPBMY3 (BC031475) polypeptides can be useful for screening compounds that affect the activity of the protein. MGBPBMY3 (BC031475) peptides can also be used for the generation of specific antibodies and as bait in yeast two hybrid screens to find proteins the specifically interact with MGBPBMY3 (BC031475), as described herein.

Although it is believed the encoded polypeptide could share at least some biological activities with human guanylate binding proteins (particularly mGBP-1, mGBP-2, mGBP-3 and mGBP-4), a number of methods of determining the exact biological function of this clone are either known in the art or are described elsewhere herein. For example, the function of this clone can be determined by applying microarray methodology. Nucleic acids corresponding to the MGBPBMY3 (BC031475) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased spleen tissue, as compared to normal tissue might indicate a function in modulating spleen function, for example. In the case of MGBPBMY3 (BC031475), spleen and/or lung tissues, can be used, for example, to extract RNA to prepare the probe.

In addition, the function of the protein can be assessed, for example, by applying quantitative PCR methodology. Real time quantitative PCR would provide the capability of following the expression of the MGBPBMY3 (BC031475) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of MGBPBMY3 (BC031475), a disease correlation related to MGBPBMY3 (BC031475) can be made by comparing the mRNA expression level of MGBPBMY3 (BC031475) in normal tissue, as compared to diseased tissue. Significantly higher or lower levels of MGBPBMY3 (BC031475) expression in the diseased tissue can suggest MGBPBMY3 (BC031475) plays a role in disease progression, and antagonists against MGBPBMY3 (BC031475) polypeptides would be useful therapeutically in treating, preventing, and/or ameliorating the disease. Alternatively, significantly higher or lower levels of MGBPBMY3 (BC031475) expression in the diseased tissue can suggest MGBPBMY3 (BC031475) plays a defensive role against disease progression, and agonists of MGBPBMY3 (BC031475) polypeptides can be useful therapeutically in treating, preventing, and/or ameliorating the disease. Also encompassed by the present invention are quantitative PCR probes corresponding to the polynucleotide sequence provided as SEQ ID NO:14 (FIGS. 7A–7C).

The function of the protein can also be assessed through complementation assays in yeast. For example, in the case of the MGBPBMY3 (BC031475), transforming yeast deficient in GBP activity, for example, and assessing their ability to grow would provide convincing evidence the MGBPBMY3 (BC031475) polypeptide has GBP activity. Additional assay conditions and methods that can be used in assessing the function of the polynucleotides and polypeptides of the present invention are known in the art, some of which are disclosed herein. For example, a GTPase activity assay can be employed.

Alternatively, the biological function of the encoded polypeptide can be determined by disrupting a homologue of this polypeptide in another species (e.g., a mammalian species) and observing the resulting phenotype. Such knock-out experiments are known in the art, some of which are disclosed elsewhere herein.

Moreover, the biological function of this polypeptide can be determined by the application of antisense and/or sense methodology (including RNAi and homologous recombination) and the resulting generation of transgenic animals. Expressing a particular gene in either sense or antisense orientation in a transgenic animal could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a spleen tissue-specific promoter), or it can be expressed at a specified time of development using an inducible and/or a developmentally regulated promoter.

In the case of MGBPBMY3 (BC031475), transgenic animals, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic animals to refine the biological function of the polypeptide is encompassed by the present invention.

In preferred embodiments, the following N-terminal MGBPBMY3 (BC031475) deletion polypeptides are encompassed by the present invention: M1-C385, T2-C385, Q3-C385, P4-C385, Q5-C385, M6-C385, A7-C385, P8-C385, I9-C385, C10-C385, L11-C385, V12-C385, E13-C385, N14-C385, H15-C385, N16-C385, E17-C385, H18-C385, L19-C385, S20-C385, M21-C385, N22-C385, H23-C385, E24-C385, A25-C385, I26-C385, E27-C385, I28-C385, L29-C385, E30-C385, K31-C385, I32-C385, S33-C385, Q34-C385, P35-C385, V36-C385, V37-C385, V38-C385, V39-C385, A40-C385, I41-C385, V42-C385, G43-C385, L44-C385, Y45-C385, R46-C385, T47-C385, G48-C385, K49-C385, S50-C385, Y51-C385, L52-C385, M53-C385, N54-C385, R55-C385, L56-C385, A57-C385, G58-C385, Q59-C385, N60-C385, H61-C385, G62-C385, F63-C385, P64-C385, L65-C385, G66-C385, S67-C385, T68-C385, V69-C385, Q70-C385, S71-C385, Q72-C385, T73-C385, K74-C385, G75-C385, I76-C385, W77-C385, M78-C385, W79-C385, C80-C385, M81-C385, P82-C385, H83-C385, P84-C385, T85-C385, K86-C385, P87-C385, E88-C385, H89-C385, T90-C385, L91-C385, V92-C385, L93-C385, L94-C385, D95-C385, T96-C385, E97-C385, G98-C385, L99-C385, G100-C385, D101-C385, V102-C385, E103-C385, K104-C385, G105-C385, D106-C385, P107-C385, K108-C385, N109-C385, D110-C385, L111-C385, W112-C385, I113-C385, F114-C385, A115-C385, L116-C385, G117-C385, V118-C385, L119-C385, L120-C385, S121-C385, S122-C385, T123-C385, F124-C385, I125-C385, Y126-C385, N127-C385, S128-C385, M129-C385, N130-C385, T131-C385, I132-C385, S133-C385, H134-C385, D135-C385, S136-C385, L137-C385, E138-C385, K139-C385, L140-C385, H141-C385, Y142-C385, V143-C385, T144-C385, E145-C385, L146-C385, T147-C385, E148-C385, L149-C385, I150-C385, R151-C385, A152-C385, K153-C385, S154-C385, S155-C385, P156-C385, N157-C385, P158-C385, D159-C385, G160-C385, I161-C385, K162-C385, N163-C385, S164-C385, T165-C385, E166-C385, F167-C385, V168-C385, S169-C385, F170-C385, F171-C385, P172-C385, D173-C385, F174-C385, V175-C385, W176-C385, T177-C385, V178-C385, R179-C385, D180-C385, F181-C385, M182-C385, L183-C385, E184-C385, L185-C385, K186-C385, L187-C385, N188-C385, G189-C385, E190-C385, D191-C385, I192-C385, T193-C385, S194-C385, D195-C385, E196-C385, Y197-C385, L198-C385, E199-C385, N200-C385, A201-C385, L202-C385, K203-C385, L204-C385, I205-C385, P206-C385, G207-C385, Y208-C385, N209-C385, P210-C385, R211-C385, V212-C385, Q213-C385, A214-C385, S215-C385, N216-C385, S217-C385, A218-C385, R219-C385, E220-C385, C221-C385, I222-C385, R223-C385, C224-C385, F225-C385, F226-C385, P227-C385, N228-C385, R229-C385, K230-C385, C231-C385, F232-C385, V233-C385, F234-C385, D235-C385, R236-C385, P237-C385, T238-C385, H239-C385, D240-C385, R241-C385, E242-C385, C385, L243-C385, L244-C385, Q245-C385, K246-C385, L247-C385, E248-C385, T249-C385, I250-C385, S251-C385, E252-C385, D253-C385, Q254-C385, L255-C385, D256-C385, L257-C385, K258-C385, F259-C385, R260-C385, E261-C385, E262-C385, T263-C385, N264-C385, A265-C385, F266-C385, V267-C385, S268-C385, Y269-C385, I270-C385, F271-C385, N272-C385, Y273-C385, A274-C385, K275-C385, I276-C385, K277-C385, T278-C385, L279-C385, K280-C385, E281-C385, G282-C385, I283-C385, K284-C385, V285-C385, T286-C385, G287-C385, N288-C385, G289-C385, L290-C385, G291-C385, I292-C385, L293-C385, V294-C385, T295-C385, T296-C385, Y297-C385, V298-C385, D299-C385, A300-C385, I301-C385, N302-C385, S303-C385, G304-C385, A305-C385, V306-C385, P307-C385, C308-C385, V309-C385, D310-C385, D311-C385, A312-C385, V313-C385, T314-C385, T315-C385, L316-C385, A317-C385, Q318-C385, H319-C385, E320-C385, N321-C385, S322-C385, V323-C385, A324-C385, V325-C385, Q326-C385, P327-C385, A328-C385, A329-C385, D330, H331-C385, Y332-C385, S333-C385, E334-C385, Q335-C385, M336-C385, V337-C385, Q338-C385, R339-C385, L340-C385, S341-C385, L342-C385, P343-C385, T344-C385, D345-C385, T346-C385, L347-C385, Q348-C385, E349-C385, L350-C385, L351-C385, D352-C385, V353-C385, H354-C385, A355-C385, A356-C385, C357-C385, E358-C385, K359-C385, E360-C385, A361-C385, M362-C385, A363-C385, V364-C385, F365-C385, M366-C385, E367-C385, H368-C385, S369-C385, F370-C385, K371-C385, D372-C385, E373-C385, N374-C385, Q375-C385, Q376-C385, F377-C385, L378-C385, K379-C385, K380-C385, L381-C385, V382-C385, V383-C385 and/or I384-C385, of SEQ ID NO:15. Polynucleotide sequences encoding these polypeptides are also provided. The present invention also encompasses the use of these N-terminal MGBPBMY3 (BC031475) deletion polypeptides as immunogenic and/or antigenic epitopes as described elsewhere herein.

In other embodiments, the following C-terminal MGBPBMY3 (BC031475) deletion polypeptides are encompassed by the present invention: M1-T2, M1-Q3, M1-P4, M1-Q5, M1-M6, M1-A7, M1-P8, M1-I9, M1-C10, M1-L11, M1-V12, M1-E13, M1-N14, M1-H15, M1-N16, M1-E17, M1-H18, M1-L19, M1-S20, M1-M21 M1-N22, M1-H23 M1-E24, M1-A25, M1-I26, M1-E27, M1-I28, M1-L29, M1-E30, M1-K31, M1-I32, M1-S33, M1-Q34, M1-P35, M1-V36, M1-V37, M1-V38, M1-V39, M1-A40, M1-I41, M1-V42, M1-G43, M1-L44, M1-Y45, M1-R46, M1-T47, M1-G48, M1-K49, M1-S50, M1-Y51, M1-L52, M1-M53, M1-N54, M1-R55, M1-L56, M1-A57, M1-G58, M1-Q59, M1-N60, M1-H61, M1-G62, M1-F63, M1-P64, M1-L65, M1-G66, M1-S67, M1-T68, M1-V69, M1-Q70, M1-S71, M1-Q72, M1-T73, M1-K74, M1-G75, M1-I76, M1-W77, M1-M78, M1-W79, M1-C80, M1-M81, M1-P82, M1-H83, M1-P84, M1-T85, M1-K86, M1-P87, M1-E88, M1-H89, M1-T90, M1-L91, M1-V92, M1-L93, M1-L94, M1-D95, M1-T96, M1-E97, M1-G98, M100, M1-D10, M1-V102, M1-E103, M1-K104, M1-G105, M1-D106, M1-P107, M1-K108, M1-N109, M1-D110, M1-L111, M1-W112, M1-I113, M1-F114, M1-A115, M1-L116, M1-G117, M1-V118, M1-L119, M1-L120, M1-S121, M1-S122, M1-T123, M1-F124, M1-I125, M1-Y126, M1-N127, M1-S128, M1-M129, M1-N130, M1-T131, M1-I132, M1-S133, M1-H134, M1-D135, M1-S136, M1-L137, M1-E138, M1-K139, M1-L140, M1-H141, M1-Y142, M1-V143, M1-T144, M1-E145, M1-L146, M1-T147, M1-E148, M1-L149, M1-I150, M1-R151, M1-A152, M1-K153, M1-S154, M1-S155, M1-P156, M1-N157, M1-P158, M1-D159, M1-G160, M1-I161, M1-K162, M1-N163, M1-S164, M1-T165, M1-E166, M1-F167, M1-V168, M1-S169, M1-F170, M1-F171, M1-P172, M1-D173, M1-F174, M1-V175, M1-W176, M1-T177, M1-V178, M1-R179, M1-D180, M1-F181, M1-M182, M1-L183, M1-E184, M1-L185, M1-K186, M1-L187, M1-N188, M1-G189, M1-E190, M1-D191, M1-I192, M1-T193, M1-S194, M1-D195, M1-E196, M1-Y197, M1-L198, M1-E199, M1-N200, M1-A201, M1-L202, M1-K203, M1-L204, M1-I205, M1-P206, M1-G207, M1-Y208, M1-N209, M1-P210, M1-R211, M1-V212, M1-Q213, M1-A214, M1-S215, M1-N216, M1-S217, M1-A218, M1-R219, M1-E220, M1-C221, M1-I222, M1-R223, M1-C224, M1-F225, M1-F226, M1-P227, M1-N228, M1-R229, M1-K230, M1-C231, M1-F232, M1-V233, M1-F234, M1-D235, M1-R236, M1-P237, M1-T238, M1-H239, M1-D240, M1-R241, M1-E242, M1-L243, M1-L244, M1-Q245, M1-K246, M1-L247, M1-E248, M1-T249, M1-I250, M1-S251, M1-E252, M1-D253, M1-Q254, M1-L255, M1-D256, M1-L257, M1-K258, M1-F259, M1-R260, M1-E261, M1-E262, M1-T263, M1-N264, M1-A265, M1-F266, M1-V267, M1-S268, M1-Y269, M1-I270, M1-F271, M1-N272, M1-Y273, M1-A274, M1-K275, M1-I276, M1-K277, M1-T278, M1-L279, M1-K280, M1-E281, M1-G282, M1-I283, M1-K284, M1-V285, M1-T286, M1-G287, M1-N288, M1-G289, M1-L290, M1-G291, M1-I292, M1-L293, M1-V294, M1-T295, M1-T296, M1-Y297, M1-V298, M1-D299, M1-A300, M1-I301, M1-N302, M1-S303, M1-G304, M1-A305, M1-V306, M1-P307, M1-C308, M1-V309, M1-D310, M1-D311, M1-A312, M1-V313, M1-T314, M1-T315, M1-L316, M1-A317, M1-Q318, M1-H319, M1-E320, M1-N321, M1-S322, M1-V323, M1-A324, M1-V325, M1-Q326, M1-R327, M1-A328, M1-A329, M1-D330, M1-H331, M1-Y332, M1-S333, M1-E334, M1-Q335, M1-M336, M1-V337, M1-Q338, M1-R339, M1-L340, M1-S341, M1-L342, M1-P343, M1-T344, M1-D345, M1-T346, M1-L347, M1-Q348, M1-E349, M1-L350, M1-L351, M1-D352, M1-V353, M1-H354, M1-A355, M1-A356, M1-C357, M1-E358, M1-K359, M1-E360, M1-A361, M1-M362, M1-A363, M1-V364, M1-F365, M1-M366, M1-E367, M1-H368, M1-S369, M1-F370, M1-K371, M1-D372, M1-E373, M1-N374, M1-Q375, M1-Q376, M1-F377, M1-L378, M1-K379, M1-K380, M1-L381, M1-V382, M1-V383 and/or M1-I384 of SEQ ID NO:15. Polynucleotide sequences encoding these polypeptides are also provided. The present invention also encompasses the use of these C-terminal MGBPBMY3 (BC031475) deletion polypeptides as immunogenic and/or antigenic epitopes as described elsewhere herein.

Alternatively, preferred polypeptides of the present invention can comprise polypeptide sequences corresponding to, for example, internal regions of the MGBPBMY3 (BC031475) polypeptide (e.g., any combination of both N- and C-terminal MGBPBMY3 (BC031475) polypeptide deletions) of SEQ ID NO:15. For example, internal regions could be defined by the equation: amino acid NX to amino acid CX, wherein NX refers to any N-terminal deletion polypeptide amino acid of MGBPBMY3 (BC031475) (SEQ ID NO:15), and where CX refers to any C-terminal deletion polypeptide amino acid of MGBPBMY3 (BC031475) (SEQ ID NO:15). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the MGBPBMY3 (BC031475) polypeptide.

The present invention encompasses the identification of compounds and drugs which stimulate MGBPBMY3 (BC031475) on the one hand (i.e., agonists) and which inhibit the function of MGBPBMY3 (BC031475) on the other hand (i.e., antagonists). In general, such screening procedures involve providing appropriate cells which express a polypeptide of the present invention on the surface thereof. Such cells can include, for example, cells from mammals, yeast, Drosophila or E. coli. In a representative embodiment, a polynucleotide encoding a polypeptide of the present invention can be employed to transfect cells to thereby express the MGBPBMY3 (BC031475) polypeptide. The expressed polypeptide can then be contacted with a test compound to observe binding, stimulation or inhibition of a functional response.

Features of the Polypeptide Encoded by Gene No. 8

A polypeptide encoded by this gene, MGBPBMY4 (BC007143), is provided as SEQ ID NO:17 (FIGS. 8A–8D) and is encoded by the polynucleotide sequence according to SEQ ID NO:16 (FIGS. 8A–8D) and/or by a polynucleotide contained within a deposited clone. MGBPBMY4 (BC007143) has significant homology at the nucleotide and amino acid level to a number of guanylate binding proteins, which include, for example, mouse GBP-1, mouse GBP-2, mouse GBP-3 and mouse GBP-4.

The determined nucleotide sequence of the MGBPBMY4 (BC007143), (i.e. the cDNA shown in FIGS. 8A–8D and in SEQ ID NO:16) comprises an open reading frame encoding a protein of about 483 amino acid residues. The predicted amino acid sequence of the MGBPBMY4 (BC007143) polypeptide is shown in FIGS. 8A–8D (SEQ ID NO:17). The percent identity and similarity values between the MGBPBMY4 (BC007143) polypeptide to the known GBP family member mGBP1 is provided in FIG. 9. The MGBPBMY4 (BC007143) protein shown in FIGS. 8A–8D was determined to share significant identity and similarity to several known GBP family members, as shown in FIG. 11A–11G.

Figure 27:
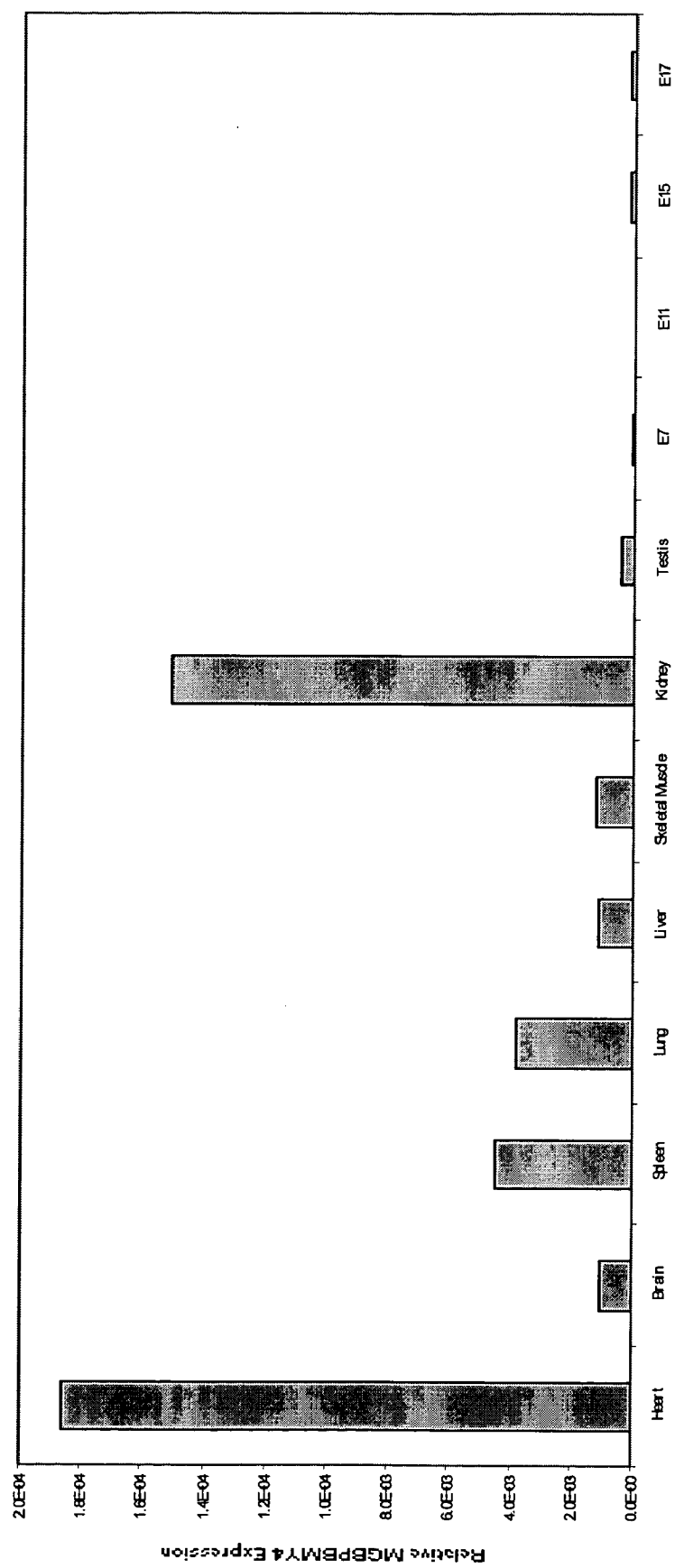
FIG. 27 is bar graph depicting the tissue expression pattern of mouse MGBPBMY4 (BC007143). Panels of cDNAs derived from normal and immune tissue were analyzed by Real Time PCR for expression of MGBPBMY4 (BC007143).

Expression profiling designed to measure the steady state mRNA levels encoding the MGBPBMY4 (BC007143) polypeptide showed experession in heart, kidney, spleen, liver, brain and skeletal muscle (see FIG. 27).

Based upon the strong homology to members of the GBP family members, the MGBPBMY4 (BC007143) polypeptide is expected to share at least some biological activity with GBP family members, specifically mGBP-1, mGBP-2, mGBP3 and mGBP-4.

The MGBPBMY4 (BC007143) polynucleotides and polypeptides of the present invention, including agonists and/or fragments thereof, may have uses that include detecting, prognosing, treating, preventing, and/or ameliorating at least diseases and conditions of the immune system (e.g. spleen), heart, kidney, liver, brain and/or skeletal muscle in a mouse model of a human condition.

The MGBPBMY4 (BC007143) polynucleotides and polypeptides of the present invention, including agonists and/or fragments thereof, may have uses that include modulating signal transduction activity, in various cells, tissues, and organisms, and particularly in mammalian tissue and more preferably in a mouse model of a human condition.

The strong homology to mouse GBP family members, particularly mGBP-1, mGBP-2, mGBP3 and mGBP-4, combined with MGBPBMY4 (BC007143) expression in some immune system tissues (i.e., spleen) suggests a potential utility for MGBPBMY4 (BC007143) polynucleotides and polypeptides in treating, diagnosing, prognosing, and/or preventing diseases and conditions of the immune system in a mouse model of a human condition. In representative embodiments, MGBPBMY4 (BC007143) polynucleotides and polypeptides including agonists and fragments thereof, may have uses that include treating, diagnosing, prognosing, and/or preventing diseases and conditions of the immune system in a mouse model of a human condition. A MGBPBMY4 (BC007143) polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, drug induced hemolytic anemia, and scleroderma. A MGBPBMY4 (BC007143) polypeptide may also be useful for modulating cytokine production, antigen presentation, or other processes, such as for boosting immune responses, etc.

Additional immunolgical disorders that a MGBPBMY4 (BC007143) polypeptide of the present invention may be useful in the treatment of include various autoimmune diseases in a mouse model of a human condition, such as Myasthenia gravis, Antiphospholipid syndrome, Insulin-resistant diabetes mellitus, Pernicious anemia, Graves' disease, Wegener's granulomatosis, Pemphigus vulgaris, Goodpastures' syndrome, Systemic lupus erythematosus (SLE), Rheumatoid arthritis, Autoimmune thrombocytopenic purpura, Autoimmune hemolytic anemia, Hashimoto's thyroiditis, Multiple sclerosis, Insulin-dependent diabetes mellitus, Autoimmune polyglandular syndrome, Immune-mediated infertility, Autoimmune Addison's disease, Pemphigus foliaceus, Dermatitis herpetiformis, Autoimmune alopecia, Vitiligo, Guillain-Barré syndrome, Stiff-man syndrome, Acute rheumatic fever, Sympathetic ophthalmia, Systemic necrotizing vasculitis, Sjögren's syndrome.

A MGBPBMY4 (BC007143) polypeptide of the present invention may also be useful in treating or ameliorating primary immune diseases, as well as immune diseases associated with or secondary to other diseases in a mouse model of a human condition. Such diseases and conditions include Recombinase activating gene (RAG 1/2) deficiency, Adenosine deaminase (ADA) deficiency, Interleukin receptor chain (c) deficiency, Janus-associated kinase 3 (JAK3) deficiency, Reticular dysgenesis, DiGeorge syndrome, Nude syndrome, T cell receptor deficiency, MHC class II deficiency, TAP-2 deficiency (MHC class I deficiency), ZAP70 tyrosine kinase deficiency, Purine nucleotide phosphorylase (PNP) deficiency, X-linked agammaglobulinemia (Bruton's tyrosine kinase deficiency), Autosomal recessive agammaglobulinemia: Mu heavy chain deficiency, Surrogate light chain (5/14.1) deficiency), Hyper-IgM syndrome: X-linked (CD40 ligand deficiency), Ig heavy chain gene deletions, IgA deficiency, Selective deficiency of IgG subclasses (with or without IgA deficiency), Common variable immunodeficiency (CVID), Antibody deficiency with normal immunoglobulins, Transient hypogammaglobulinemia of infancy, Interferon receptor (IFNGR1, IFNGR2) deficiency, Interleukin 12 and interleukin 12 receptor deficiency, Immunodeficiency with thymoma, Wiskott-Aldrich syndrome (WAS protein deficiency), Ataxia telangiectasia (ATM deficiency), X-linked lymphoproliferative syndrome (SH2D1A/SAP deficiency), Hyper IgE syndrome, Bloom syndrome, Xeroderma pigmentosum, Fanconi anemia, ICF syndrome, Nijmegen breakage syndrome, Seckel syndrome, Down syndrome (Trisomy 21), Turner syndrome, Deletions or rings of chromosome 18 (18p- and 18q-), Short-limbed skeletal dysplasia (short-limbed dwarfism), Cartilage-hair hypoplasia (metaphyseal chondroplasia), Schimke immuno-osseous dysplasia, Dubowitz syndrome, Kyphomelic dysplasia with SCID, Mulibrey's nannism, Growth retardation, facial anomalies and immunodeficiency, Progeria (Hutchinson-Gilford syndrome), Ectrodactyly-ectodermal dysplasia-clefting syndrome, Immunodeficiency with absent thumbs, anosmia and ichthyosis, Partial albinism, Dyskeratosis congenita, Netherton syndrome, Anhidrotic ectodermal dysplasia, Papillon-Lefevre syndrome, Congenital ichthyosis, Acrodermatitis enteropathica, Transcobalamin 2 deficiency, Type 1 hereditary orotic aciduria, Intractable diarrhea, abnormal facies, trichorrhexis and immunodeficiency, Methylmalonic acidemia, Biotin dependent carboxylase deficiency, Mannosidosis, Glycogen storage disease, type 1b, Chediak-Higashi syndrome, Familial hypercatabolism, Intestinal lymphangiectasia, Chronic muco-cutaneous candidiasis, Hereditary or congenital hyposplenia or asplenia, Ivermark syndrome.

The strong homology to mouse GBP family members, particularly mGBP-1, mGBP-2, mGBP-3 and mGBP-4, combined with observed MGBPBMY4 (BC007143) expression levels in heart tissue suggests the MGBPBMY4 (BC007143) polynucleotides and polypeptides may be useful in treating, diagnosing, prognosing, and/or preventing cardiovascular diseases and/or disorders in a mouse model of a human condition, which include, but are not limited to: myocardio infarction, congestive heart failure, arrthymias, cardiomyopathy, atherosclerosis, arterialsclerosis, microvascular disease, embolism, thromobosis, pulmonary edema, palpitation, dyspnea, angina, hypotension, syncope, heart murmer, aberrant ECG, hypertrophic cardiomyopathy, the Marfan syndrome, sudden death, prolonged QT syndrome, congenital defects, cardiac viral infections, valvular heart disease, and hypertension.

Similarly, MGBPBMY4 (BC007143) polynucleotides and polypeptides may be useful for treating and/or ameliorating cardiovascular diseases and symptoms in a mouse model of a human condition which result indirectly from various non-cardiavascular effects, which include, but are not limited to, the following, obesity, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Moreover, polynucleotides and polypeptides, including fragments and/or antagonists thereof, may have uses which include, directly or indirectly, treating, preventing, diagnosing, and/or prognosing the following, non-limiting, cardiovascular infections in a mouse model of a human condition: blood stream invasion, bacteremia, sepsis, *Streptococcus pneumoniae* infection, group a *streptococci* infection, group b *streptococci* infection, *Enterococcus* infection, nonenterococcal group D *streptococci* infection, nonenterococcal group C *streptococci* infection, nonenterococcal group G *streptococci* infection, *Streptoccus viridans* infection, *Staphylococcus aureus* infection, coagulase-negative *staphylococci* infection, gram-negative *Bacilli* infection, *Enterobacteriaceae* infection, *Psudomonas* spp. Infection, *Acinobacter* spp. Infection, *Flavobacterium meningosepticum* infection, *Aeromonas* spp. Infection, *Stenotrophomonas maltophilia* infection, gram-negative coccobacilli infection, *Haemophilus influenza* infection, *Branhamella catarrhalis* infection, anaerobe infection, *Bacteriodes fragilis* infection, *Clostridium* infection, fungal infection, *Candida* spp. Infection, non-albicans *Candida* spp. Infection, *Hansenula anomala* infection, *Malassezia furfur* infection, nontuberculous *Mycobacteria* infection, *Mycobacterium avium* infection, *Mycobacterium chelonae* infection, *Mycobacterium fortuitum* infection, spirochetal infection, *Borrelia burgdorferi* infection, in addition to any other cardiovascular disease and/or disorder (e.g., non-sepsis) implicated by the causative agents listed above or elsewhere herein.

Further, the strong homology to mouse GBP family members, particularly mGBP-1, mGBP-2, mGBP3 and mGBP-4, combined with the observed MGBPBMY4 (BC007143) expression in skeletal muscle suggests a potential utility for MGBPBMY4 (BC007143) polynucleotides and polypeptides in treating, diagnosing, prognosing, and/or preventing skeletal muscle disorders in a mouse model of a human condition. In representative embodiments, MGBPBMY4 (BC007143) polynucleotides and polypeptides including agonists and fragements thereof, may have uses which include treating, diagnosing, prognosing, and/or preventing the following, non-limiting, diseases or disorders of skeletal muscled: dystrophies, pseudohypertrophic muscular dystrophy, Duchenne dystrophy, Becker muscular dystrophy, limb-girdle muscular dystrophy, muscle weakness, Emery-Dreifuss muscular dystrophy, Congenital muscular dystrophy, endometriosis, placental aromatase deficiency, premature menopause, Fukuyama congenital muscular dystrophy, laminin alpha 2 chain deficiency, alpha 7 integrin deficiency, Walker-Warburg syndrome, myotonic dystrophy, congenital myotonic dystrophy, facioscapulohumeral muscular dystrophy, distal myopathies, central core disease, nemaline (rod) myopathy, centronuclear (myotubular) myopathy, central core disease, delay in motor milestones, delayed walking, nemaline myopathy, congenital nemaline myopathy, muscle hypotonia, centronuclear myopathies, skeletal muscle energy metabolism disorders, disorders associated with aberrant skeletal muscle-fatty acid metabolism, disorders associated with aberrant skeletal glucose metabolism, acid maltase deficiency, debranching enzyme deficiency, branching enzyme deficiency, exercise intolerance, myophosphorylase deficiency (type V glycogenosis), phosphofructokinase deficiency (type VII glycogenosis), phosphoglycerate kinase deficiency (type IX glycogenosis), phosphoglycerate mutase deficiency (type X glycogenosis), lactate dehydrogenase deficiency (glycogensosis type XI), glycogen storage disorders, skeletal muscle lipid metabolism, carnitine deficiency, myoglobinuria, muscle cramping, myoadenylate deaminase deficiency, mitochondrial myopathies, Kearns-Sayre syndrome, myoclonic epilepsy, disorders of muscle membrane excitability, calcium channel disorders of muscle, sodium channel disorders of muscle, hyperkalemic periodic paralysis, paramyotonia congenita, potassium-aggravated myotonia, myotonia congenita, chloride channel disorders of muscle, thyrotoxic periodic paralysis, and/or Andersen's syndrome.

Further, the strong homology to mouse GBP family members, particularly mGBP-1, mGBP-2, mGBP3 and mGBP-4, combined with the observed MGBPBMY4 (BC007143) expression in kidney suggests a potential utility for MGBPBMY4 (BC007143) polynucleotides and polypeptides in treating, diagnosing, prognosing, and/or preventing diseases and disorders of the kidney in a mouse model of a human condition.

In representative embodiments, MGBPBMY4 (BC007143) polynucleotides and polypeptides including agonists, antagonists, and fragments thereof, may have uses which include treating, diagnosing, prognosing, and/or preventing the following, non-limiting, diseases or disorders of the kidney in a mouse model of a human condition: Plasma cell infiltration, Hypercalcemia, Myeloma kidney, Amyloidosis, Light chain deposition disease, Type I/II cryoglobulinemia, Immunotactoid glomerulopathy, Reduced glomerular filtration rate, Fanconi syndrome, Hyperchloremic acidosisa, Tubular or small-molecular-weight proteinuria, Polyuria, isothenuria, Hyperkalemia, Salt wasting, Nephrocalcinosis, hyperoxaluria, Cystinosis, Fabry's disease, Sjogren's Syndrome The strong homology to mouse GBP family members, particularly mGBP-1, mGBP-2, mGBP3 and mGBP-4, combined with the observed MGBPBMY4 (BC007143) expression in brain suggests a potential utility for MGBPBMY4 (BC007143) polynucleotides and polypeptides in treating, diagnosing, prognosing, and/or preventing diseases and disorders of the brain and neurological tissue in a mouse model of a human condition.

In representative embodiments, MGBPBMY4 (BC007143) polynucleotides and polypeptides including agonists, antagonists, and fragments thereof, may have uses which include treating, diagnosing, prognosing, and/or preventing the following, non-limiting, brain and neurological diseases or disorders in a mouse model of a human condition: the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wemicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a representative embodiment, the MGBPBMY4 (BC007143) polypeptides, polynucleotides, or agonists or antagonists of the present invention may be used to protect neural cells from the damaging effects of cerebral hypoxia. According to this embodiment, the compositions of the invention are used to treat, prevent, and/or diagnose neural cell injury associated with cerebral hypoxia in a mouse model of a human condition. In one aspect of this embodiment, the MGBPBMY4 (BC007143) polypeptides, polynucleotides, or agonists or antagonists of the invention are used to treat, prevent, and/or diagnose neural cell injury associated with cerebral ischemia. In another aspect of this embodiment, the MGBPBMY4 (BC007143) polypeptides, polynucleotides, or agonists or antagonists of the invention are used to treat, prevent, and/or diagnose neural cell injury associated with cerebral infarction in a mouse model of a human condition. In another aspect of this embodiment, the polypeptides, polynucleotides, or agonists or antagonists of the invention are used to treat, prevent, and/or diagnose or prevent neural cell injury associated with a stroke. In a further aspect of this embodiment, the MGBPBMY4 (BC007143) polypeptides, polynucleotides, or agonists or antagonists of the invention are used to treat, prevent, and/or diagnose neural cell injury associated with a heart attack.

The MGBPBMY4 (BC007143) polypeptides and/or polynucleotides of the present invention which are useful for treating or preventing a nervous system disorder may be selected by testing for biological activity in promoting the survival or differentiation of neurons in a mouse model of a human condition. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In representative, non-limiting embodiments, increased survival of neurons may routinely be measured using a method set forth herein or otherwise known in the art, such as, for example, the method set forth in Arakawa et al. (Arakawa et al., (1990) *J. Neurosci.* 10:3507–3515); increased sprouting of neurons may be detected by methods known in the art, such as, for example, the methods set forth in Pestronk et al. (Pestronk et al., (1980) *Exp. Neurol.* 70:65–82) or Brown et al. (Brown et al., (1981) *Ann. Rev. Neurosci.* 4:17–42); increased production of neuron-associated molecules may be measured by bioassay, enzymatic assay, antibody binding, northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed in a mouse model of a human condition according to the present invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

The strong homology to mouse GBP family members, particularly mGBP-1, mGBP-2, mGBP-3 and mGBP-4, combined with MGBPBMY4 (BC007143) expression in liver tissue suggests a potential utility for MGBPBMY4 (BC007143) polynucleotides and polypeptides in treating, diagnosing, prognosing, and/or preventing liver diseases in a mouse model of a human condition. In representative embodiments, MGBPBMY4 (BC007143) polynucleotides and polypeptides including agonists and fragments thereof, may have uses that include treating, diagnosing, prognosing, and/or preventing liver diseases in a mouse model of a human condition. For example, an MGBPBMY4 (BC007143) protein can be used for the detection, treatment, amelioration, and/or prevention of diseases and conditions in a mouse model of a human condition including, but not limited to: hepatoblastoma, jaundice, hepatitis, liver metabolic diseases and conditions that are attributable to the differentiation of hepatocyte progenitor cells, cirrhosis, hepatic cysts, pyrogenic abscess, amebic abcess, hydatid cyst, cystadenocarcinoma, adenoma, focal nodular hyperplasia, hemangioma, hepatocellulae carcinoma, cholangiocarcinoma, and angiosarcoma, granulomatous liver disease, liver transplantation, hyperbilirubinemia, jaundice, parenchymal liver disease, portal hypertension, hepatobiliary disease, hepatic parenchyma, hepatic fibrosis, anemia, gallstones, cholestasis, carbon tetrachloride toxicity, beryllium toxicity, vinyl chloride toxicity, choledocholithiasis, hepatocellular necrosis, aberrant metabolism of amino acids, aberrant metabolism of carbohydrates, aberrant synthesis proteins, aberrant synthesis of glycoproteins, aberrant degradation of proteins, aberrant degradation of glycoproteins, aberrant metabolism of drugs, aberrant metabolism of hormones, aberrant degradation of drugs, aberrant degradation of drugs, aberrant regulation of lipid metabolism, aberrant regulation of cholesterol metabolism, aberrant glycogenesis, aberrant glycogenolysis, aberrant glycolysis, aberrant gluconeogenesis, hyperglycemia, glucose intolerance, hyperglycemia, decreased hepatic glucose uptake, decreased hepatic glycogen synthesis, hepatic resistance to insulin, portal-systemic glucose shunting, peripheral insulin resistance, hormonal abnormalities, increased levels of systemic glucagon, decreased levels of systemic cortisol, increased levels of systemic insulin, hypoglycemia, decreased gluconeogenesis, decreased hepatic glycogen content, hepatic resistance to glucagon, elevated levels of systemic aromatic amino acids, decreased levels of systemic branched-chain amino acids, hepatic encephalopathy, aberrant hepatic amino acid transamination, aberrant hepatic amino acid oxidative deamination, aberrant ammonia synthesis, aberrant albumin secretion, hypoalbuminemia, aberrant cytochromes b5 function, aberrant P450 function, aberrant glutathione S-acyltransferase function, aberrant cholesterol synthesis, and aberrant bile acid synthesis.

Moreover, MGBPBMY4 (BC007143) polynucleotides and polypeptides, including fragments and/or antagonists thereof, may have uses which include, directly or indirectly, treating, preventing, diagnosing, and/or prognosing the following, non-limiting, hepatic infections in a mouse model of a human condition: liver disease caused by sepsis infection, liver disease caused by bacteremia, liver disease caused by Pneomococcal pneumonia infection, liver disease caused by Toxic shock syndrome, liver disease caused by Listeriosis, liver disease caused by Legionnaries' disease, liver disease caused by Brucellosis infection, liver disease caused by *Neisseria gonorrhoeae* infection, liver disease caused by *Yersinia* infection, liver disease caused by Salmonellosis, liver disease caused by Nocardiosis, liver disease caused by Spirochete infection, liver disease caused by *Treponema pallidum* infection, liver disease caused by *Brrelia burgdorferi* infection, liver disease caused by Leptospirosis, liver disease caused by *Coxiella burnetii* infection, liver disease caused by *Rickettsia richettsii* infection, liver disease caused by *Chlamydia trachomatis* infection, liver disease caused by *Chlamydia psittaci* infection, liver disease caused by hepatitis virus infection, liver disease caused by Epstein-Barr virus infection in addition to any other hepatic disease and/or disorder implicated by the causative agents listed above or elsewhere herein.

It is noted that the use of mouse models to understand, diagnose, predict, treat and/or ameliorate human conditions is well documented. Thus, the uses for the MGBPBMY4 (BC007143) can often be extrapolated to human conditions, as well as to further research such conditions and their treatments.

A MGBPBMY4 (BC007143) protein can also be used to determine biological activity, raise antibodies, as tissue markers, to isolate cognate ligands or receptors, to identify agents that modulate their interactions. Further, proteins, as well as antibodies directed against a MGBPBMY4 (BC007143) protein, can show utility as a tumor marker and/or immunotherapy targets for heart, kidney, spleen liver, skeletal muscle and/or brain tissue.

The MGBPBMY4 (BC007143) polynucleotides and polypeptides, including fragments and for antagonsists thereof, can have uses which include identification of modulators of MGBPBMY4 (BC007143) function including antibodies (for detection or neutralization), naturally-occurring modulators and small molecule modulators. Antibodies to a particular domain of the MGBPBMY4 (BC007143) protein could be used as diagnostic agents of certain conditions in subjects, are useful in monitoring the activation of signal transduction pathways, and can be used as a biomarker for the involvement of GBP's in disease states, as well as in the evaluation of inhibitors of GBP's in vivo.

MGBPBMY4 (BC007143) polypeptides and polynucleotides have additional uses which include diagnosing diseases related to the over and/or under expression of MGBPBMY4 (BC007143) by identifying mutations in the MGBPBMY4 (BC007143) gene by using MGBPBMY4 (BC007143) sequences as probes or by determining MGBPBMY4 (BC007143) protein or mRNA expression levels. MGBPBMY4 (BC007143) polypeptides can be useful for screening compounds that affect the activity of the protein. MGBPBMY4 (BC007143) peptides can also be used for the generation of specific antibodies and as bait in yeast two hybrid screens to find proteins the specifically interact with MGBPBMY4 (BC007143), as described herein.

Although it is believed the encoded polypeptide could share at least some biological activities with human guanylate binding proteins (particularly mGBP-1, mGBP-2, mGBP-3 and mGBP-4), a number of methods of determining the exact biological function of this clone are either known in the art or are described elsewhere herein. For example, the function of this clone can be determined by applying microarray methodology. Nucleic acids corresponding to the MGBPBMY4 (BC007143) polynucleotides, in addition to, other clones of the present invention, can be arrayed on microchips for expression profiling. Depending on which polynucleotide probe is used to hybridize to the slides, a change in expression of a specific gene can provide additional insight into the function of this gene based upon the conditions being studied. For example, an observed increase or decrease in expression levels when the polynucleotide probe used comes from diseased liver tissue, as compared to normal tissue might indicate a function in modulating liver function, for example. In the case of MGBPBMY4 (BC007143), heart, kidney, spleen, liver, brain and/or skeletal muscle, can be used, for example, to extract RNA to prepare the probe.

In addition, the function of the protein can be assessed, for example, by applying quantitative PCR methodology. Real time quantitative PCR would provide the capability of following the expression of the MGBPBMY4 (BC007143) gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of MGBPBMY4 (BC007143), a disease correlation related to MGBPBMY4 (BC007143) can be made by comparing the mRNA expression level of MGBPBMY4 (BC007143) in normal tissue, as compared to diseased tissue. Significantly higher or lower levels of MGBPBMY4 (BC007143) expression in the diseased tissue can suggest MGBPBMY4 (BC007143) plays a role in disease progression, and antagonists against MGBPBMY4 (BC007143) polypeptides would be useful therapeutically in treating, preventing, and/or ameliorating the disease. Alternatively, significantly higher or lower levels of MGBPBMY4 (BC007143) expression in the diseased tissue can suggest MGBPBMY4 (BC007143) plays a defensive role against disease progression, and agonists of MGBPBMY4 (BC007143) polypeptides can be useful therapeutically in treating, preventing, and/or ameliorating the disease. Also encompassed by the present invention are quantitative PCR probes corresponding to the polynucleotide sequence provided as SEQ ID NO:16 (FIGS. 8A–8D).

The function of the protein can also be assessed through complementation assays in yeast. For example, in the case of the MGBPBMY4 (BC007143), transforming yeast deficient in GBP activity, for example, and assessing their ability to grow would provide convincing evidence the MGBPBMY4 (BC007143) polypeptide has GBP activity. Additional assay conditions and methods that can be used in assessing the function of the polynucleotides and polypeptides of the present invention are known in the art, some of which are disclosed herein. For example, a GTPase activity assay can be employed.

Alternatively, the biological function of the encoded polypeptide can be determined by disrupting a homologue of this polypeptide in another species (e.g., a mammalian species) and observing the resulting phenotype. Such knockout experiments are known in the art, some of which are disclosed elsewhere herein.

Moreover, the biological function of this polypeptide can be determined by the application of antisense and/or sense methodology (including RNAi and homlogous recombination) and the resulting generation of transgenic animals. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a spleen tissue-specific promoter), or it can be expressed at a specified time of development using an inducible and/or a developmentally regulated promoter.

In the case of MGBPBMY4 (BC007143), transgenic animals, if no phenotype is apparent in normal growth conditions, observing the organism under diseased conditions (e.g., reproductive, cardiovascular, endocrine, immune, renal, gastrointestinal, pulmonary, and/or neural disorders, in addition to cancers, etc.) can lead to understanding the function of the gene. Therefore, the application of antisense and/or sense methodology to the creation of transgenic animals to refine the biological function of the polypeptide is encompassed by the present invention.

In preferred embodiments, the following N-terminal MGBPBMY4 (BC007143) deletion polypeptides are encompassed by the present invention: M1-A209, I2-A209, T3-A209, I4-A209, N5-A209, H6-A209, Q7-A209, A8-A209, L9-A209, E10-A209, Q11-A209, L12-A209, H13-A209, Y14-A209, V15-A209, T16-A209, E17-A209, L18-A209, T19-A209, E20-A209, L21-A209, I22-A209, R23-A209, A24-A209, K25-A209, S26-A209, S27-A209, P28-A209, N29-A209, P30-A209, A31-A209, G32-A209, I33-A209, K34-A209, N35-A209, S36-A209, T37-A209, E38-A209, F39-A209, V40-A209, S41-A209, F42-A209, F43-A209, P44-A209, D45-A209, F46-A209, V47-A209, W48-A209, T49-A209, V50-A209, R51-A209, D52-A209, F53-A209, M54-A209, L55-A209, E56-A209, L57-A209, K58-A209, L59-A209, N60-A209, G61-A209, E62-A209, D63-A209, I64-A209, T65-A209, S66-A209, D67-A209, D68-A209, Y69-A209, L70-A209, E71-A209, N72-A209, A73-A209, L74-A209, K75-A209, L76-A209, I77-A209, P78-A209, G79-A209, D80-A209, K81-A209, P82-A209, R83-A209, M84-A209, Q85-A209, A86-A209, S87-A209, N88-A209, S89-A209, C90-A209, R91-A209, E92-A209, C93-A209, I94-A209, R95-A209, L96-A209, F97-A209, F98-A209, P99-A209, N100-A209, R101-A209, K102-A209, C103-A209, F104-A209, V105-A209, F106-A209, D107-A209, R108-A209, P109-A209, T110-A209, H111-A209, D112-A209, K113-A209, E114-A209, L115-A209, L116-A209, Q117-A209, K118-A209, L119-A209, D120-A209, S121-A209, I122-A209, T123-A209, E124-A209, D125-A209, Q126-A209, L127-A209, D128-A209, P129-A209, K130-A209, F131-A209, Q132-A209, E133-A209, V134-A209, T135-A209, K136-A209, A137-A209, F138-A209, V139-A209, S140-A209, Y141-A209, I142-A209, F143-A209, T144-A209, Y145-A209, A146-A209, K147-A209, I148-A209, K149-A209, T150-A209, L151-A209, K152-A209, E153-A209, G154-A209, I155-A209, K156-A209, V157-A209, T158-A209, G159-A209, N160-A209, R161-A209, L162-A209, G163-A209, I164-A209, L165-A209, V166-A209, T167-A209, T168-A209, Y169-A209, V170-A209, N171-A209, A172-A209, I173-A209, N174-A209, S175-A209, G176-A209, A177-A209, V178-A209, P179-A209, C180-A209, L181-A209, D182-A209, D183-A209, A184-A209, V185-A209, T186-A209, T187-A209, L188-A209, A189-A209, Q190-A209, R191-A209, E192-A209, N193-A209, S194-A209, V195-A209, A196-A209, V197-A209, Q198-A209, K199-A209, A200-A209, A201-A209, D202-A209, H203-A209, Y204-A209, S205-A209, E206-A209, Q207-A209 and/or M208-A209, of SEQ ID NO:17. Polynucleotide sequences encoding these polypeptides are also provided. The present invention also encompasses the use of these N-terminal MGBPBMY4 (BC007143) deletion polypeptides as immunogenic and/or antigenic epitopes as described elsewhere herein.

In other embodiments, the following C-terminal MGBPBMY4 (BC007143) deletion polypeptides are encompassed by the present invention: M1-I2, M1-T3, M1-I4, M1-N5, M1-H6, M1-Q7, M1-A8, M1-L9, M1-E10, M1-Q11, M1-L12, M1-H13, M1-Y14, M1-V15, M1-T16, M1-E17, M1-L18, M1-T19, M1-E20, M1-L21, M1-I22, M1-R23, M1-A24, M1-K25, M1-S26, M1-S27, M1-P28, M1-N29, M1-P30, M1-A31, M1-G32, M1-I33, M1-K34, M1-N35, M1-S36, M1-T37, M1-E38, M1-F39, M1-V40, M1-S41, M1-F42, M1-F43, M1-P44, M1-D45, M1-F46, M1-V47, M1-W48, M1-T49, M1-V50, M1-R51, M1-D52, M1-F53, M1-M54, M1-L55, M1-E56, M1-L57, M1-K58, M1-L59, M1-N60, M1-G61, M1-E62, M1-D63, M1-I64, M1-T65, M1-S66, M1-D67, M1-D68, M1-Y69, M1-L70, M1-E71, M1-N72, M1-A73, M1-L74, M1-K75, M1-L76, M1-I77, M1-P78, M1-G79, M1-D80, M1-K81, M1-P82, M1-R83, M1-M84, M1-Q85, M1-A86, M1-S87, M1-N88, M1-S89, M1-C90, M1-R91, M1-E92, M1-C93, M1-I94, M1-R95, M1-L96, M1-F97, M1-F98, M1-P99, M1-N100, M1-R101, M1-K102, M1-C103, M1-F104, M1-VIO5, M1-F106, M1-D107, M1-R108, M1-P109, M1-T110, M1-H111, M1-D112, M1-K113, M1-E114, M1-L115, M1-L116, M1-Q117, M1-K118, M1-L119, M1-D120, M1-S121, M1-I22, M1-T123, M1-E124, M1-D125, M1-Q126, M1-L127, M1-D128, M1-P129, M1-K130, M1-F131, M1-Q132, M1-E133, M1-V134, M1-T135, M1-K136, M1-A137, M1-F138, M1-V139, M1-S140, M1-Y141, M1-I42, M1-F143, M1-T144, M1-Y145, M1-A146, M1-K147, M1-I148, M1-K149, M1-T150, M1-L151, M1-K152, M1-E153, M1-G154, M1-I155, M1-K156, M1-V157, M1-T158, M1-G159, M1-N160, M1-R161, M1-L162, M1-G163, M1-I164, M1-L165, M1-V166, M1-T167, M1-T168, M1-Y169, M1-V170, M1-N171, M1-A172, M1-I173, M1-N174, M1-S175, M1-G176, M1-A177, M1-V178, M1-P179, M1-C180, M1-L181, M1-D182, M1-D183, M1-A184, M1-V185, M1-T186, M1-T187, M1-L188, M1-A189, M1-Q190, M1-R191, M1-E192, M1-N193, M1-S194, M1-V195, M1-A196, M1-V197, M1-A198, M1-Q198, M1-K199, M1-A200, M1-A201, M1-D202, M1-H203, M1-Y204, M1-S205, M1-E206, M1-Q207 and/or M1-M208 of SEQ ID NO:17. Polynucleotide sequences encoding these polypeptides are also provided. The present invention also encompasses the use of these C-terminal MGBPBMY4 (BC007143) deletion polypeptides as immunogenic and/or antigenic epitopes as described elsewhere herein.

Alternatively, preferred polypeptides of the present invention can comprise polypeptide sequences corresponding to, for example, internal regions of the MGBPBMY4 (BC007143) polypeptide (e.g., any combination of both N- and C-terminal MGBPBMY4 (BC007143) polypeptide deletions) of SEQ ID NO:17. For example, internal regions could be defined by the equation: amino acid NX to amino acid CX, wherein NX refers to any N-terminal deletion polypeptide amino acid of MGBPBMY4 (BC007143) (SEQ ID NO:17), and where CX refers to any C-terminal deletion polypeptide amino acid of MGBPBMY4 (BC007143) (SEQ ID NO:17). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the MGBPBMY4 (BC007143) polypeptide.

The present invention encompasses the identification of compounds and drugs which stimulate MGBPBMY4 (BC007143) on the one hand (i.e., agonists) and which inhibit the function of MGBPBMY4 (BC007143) on the other hand (i.e., antagonists). In general, such screening procedures involve providing appropriate cells which express a polypeptide of the present invention on the surface thereof. Such cells can include, for example, cells from mammals, yeast, Drosophila or E. coli. In a representative embodiment, a polynucleotide encoding a polypeptide of the present invention can be employed to transfect cells to thereby express the MGBPBMY4 (BC007143) polypeptide. The expressed polypeptide can then be contacted with a test compound to observe binding, stimulation or inhibition of a functional response.

Features of GBP1

The tissue expression profile of GBP1 was investigated. FIG. 47 shows an expanded expression profile of human GBP1. FIG. 47 illustrates the relative expression level of GBP1 amongst various mRNA tissue sources. FIG. 47 also illustrates the relative expression level of GBP1 amongst various mRNA tissue sources isolated from normal and diseased tissues. As shown, the GBP1 polypeptide showed increased expression in spinal cord and brain cortex from multiple sclerosis patients relative to controls; increased expression in putamen from Parkinson's patients relative to controls; increased expression in hippocampus from Alzheimer's patients relative to controls. Expression data was obtained by measuring the steady state GBP1 mRNA levels by quantitative PCR using the PCR primer pair provided as SEQ ID NO:73 and 74, and TAQMAN probe (SEQ ID NO:75) as described in Example 40 herein. These data support a role of GBP1 in regulating various functions, including neurological functions. Thus small molecule modulators of GBP1 function may represent a novel therapeutic option in the treatment of multiple sclerosis, Parkinson's disease and Alzheimer's disease.

Features of GBP5

The tissue expression profile of GBP5 was investigated. FIG. 48 shows an expanded expression profile of human GBP5. FIG. 48 illustrates the relative expression level of GBP5 amongst various mRNA tissue sources. FIG. 48 also illustrates the relative expression level of GBP5 amongst various mRNA tissue sources isolated from normal and tumor tissues. As shown, the GBP5 polypeptide showed increased expression in cortex and spinal cord of multiple sclerosis patients relative to controls; increased expression in hippocampus form Alzheimer's patients relative to controls. Expression data was obtained by measuring the steady state GBP5 mRNA levels by quantitative PCR using the PCR primer pair provided as SEQ ID NO:76 and 77, and TAQMAN probe (SEQ ID NO:78) as described in Example 41 herein. These data support a role of GBP5 in regulating various functions, including digestive functions, neurological functions reproductive functions and pulmonary functions. Thus small molecule modulators of GBP5 function may represent a novel therapeutic option in the treatment of breast and testicle cancers, as well as multiple sclerosis, Alzheimer's disease, Crohn's disease, and bronchitis.

Table I, presented herein below, summarizes the information corresponding to each "Gene No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date."

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y" although other reading frames can also be easily translated using molecular biology techniques known to those of ordinary skill in the art. The polypeptides produced by these alternative open reading frames are specifically contemplated by the present invention.

The total number of amino acids within the open reading frame of SEQ ID NO:Y is identified as "Total AA of ORF".

SEQ ID NO:X (where X s any of the polynucleotide sequences disclosed in the Sequence Listing) and the translated SEQ ID NO:Y (where Y is any of the polypeptide sequences disclosed in the Sequence Listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the present invention. Similarly, polypeptides identified from SEQ ID NO:Y can be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides might cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a cDNA of the present invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:X, SEQ ID NO:Y, or the corresponding deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:X, SEQ ID NO:Y, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides can be in the form of a complete protein, can be fragments of the protein or can be a part of a larger protein, such as a fusion protein, as described herein. It can be desirable to include an additional amino acid sequence that contains secretory or leader sequences, pro-sequences, sequences that can aid in purification, such as multiple histidine residues, or an additional sequence for stability during recombinant production.

The polypeptides of the present invention are preferably, but not necessarily, provided in an isolated form, and preferably, but not necessarily, are substantially purified. A recombinantly produced version of a polypeptide, can be substantially purified using techniques described herein or otherwise known in the art, such as, for example, by the one-step method described in Smith & Johnson, (1988) *Gene* 67:31–40. Polypeptides of the present invention also can be purified from natural, synthetic or recombinant sources using protocols described herein or otherwise known in the art, such as, for example, antibodies of the present invention raised against the full-length form of the protein.

The present invention also provides a polynucleotide comprising, or alternatively consisting of, the sequence identified as SEQ ID NO:X, and/or a cDNA provided in corresponding ATCC Deposit No. Z. The present invention also provides a polypeptide comprising, or alternatively consisting of, the sequence identified as SEQ ID NO:Y, and/or a polypeptide encoded by the cDNA provided in corresponding ATCC Deposit No:Z. The present invention also provides polynucleotides encoding a polypeptide comprising, or alternatively consisting of the polypeptide sequence of SEQ ID NO:Y, and/or a polypeptide sequence encoded by the cDNA contained in ATCC Deposit No:Z.

In one embodiment, the present invention is directed to a polynucleotide comprising, or alternatively consisting of, the sequence identified as SEQ ID NO:X, and/or a cDNA provided in corresponding ATCC Deposit No.:Z that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences can be complementary to the sequence disclosed as SEQ ID NO:X, the sequence contained in an ATCC deposit, and/or the nucleic acid sequence encoding the polypeptide sequence disclosed as SEQ ID NO:Y.

The present invention also encompasses polynucleotides capable of hybridizing, for example under reduced stringency conditions, stringent conditions or highly stringent conditions, to polynucleotides described herein. Examples of stringency conditions are described herein above and in Table II). Refering to Table II, highly stringent conditions are those that are at least as stringent as, for example, conditions A–F; stringent conditions are at least as stringent as, for example, conditions G–L; and reduced stringency conditions are at least as stringent as, for example, conditions M–R.

TABLE II

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C.; 1xSSC - or - 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC - or - 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC - or - 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC - or - 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC - or - 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC - or - 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC - or - 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC - or - 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC - or - 45° C.; 6xSSC, 50% formamide | 60° C.; 2xSSC |
| R | RNA:RNA | <50 | Tr*; 4xSSC | Tr*; 4xSSC |

The following annotations pertain to Table II.

‡—The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., the MEGALIGN program of the suite of programs available from DNA*Star of Madison, Wis., USA, etc).

†—SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hydridizations and washes can optionally include 5x Denhardt's reagent, 0.5–1.0% SDS, 100 µg/ml denatured, fragmented salmon sperm DNA, 0.5% sodium pyrophosphate, and up to 50% formamide.

*Tb–Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6($\log_{10}$ [Na$^+$])+ 0.41(% G+C)— (600/N), where N is the number of bases in the hybrid, and [Na$^+$] is the concentration of sodium ions in the hybridization buffer ([NA$^+$] for 1xSSC=0.165 M).

±—The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook et al., *Molecular Cloning: A Laboratory Manual*, (3$^{rd}$ ed.) Cold Spring Harbor Laboratory Press, Cold Spring Harbor, N.Y., USA (2001), chapters 9 and 11, and *Current Protocols in Molecular Biology*, (Ausubel et al., eds.), Greene Publishing Associates and Wiley-Interscience, New York (2002) sections 2.10 and 6.3–6.4, which are hereby incorporated by reference herein.

In some cases it can be desirable that such hybridizing polynucleotides have at least 70% sequence identity (e.g., at least 80% identity; at least 90% or at least 95% identity) with a polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The present invention encompasses the application of PCR methodology to the polynucleotide sequences of the present invention, the clone deposited with the ATCC, and/or the cDNA encoding the polypeptides of the present invention. PCR techniques for the amplification of nucleic acids are known (see, e.g., U.S. Pat. Nos. 4,683,195 and 4,800,159 and Saiki et al., (1988) *Science* 239:487–491). PCR, for example, can include the following steps, of denaturation of template nucleic acid (if double-stranded), annealing of primer to target, and polymerization. The nucleic acid probed or used as a template in the amplification reaction can be genomic DNA, cDNA, RNA, or a PNA. PCR can be used to amplify specific sequences from genomic DNA, specific RNA sequence, and/or cDNA transcribed from mRNA. References for the general use of PCR techniques, including specific method parameters, include Mullis et al., (1987) *Cold Spring Harbor Symp. Quant. Biol.* 51:263; *PCR Technology*, (Ehrlich, ed.), Stockton Press, New York, N.Y., USA (1989); Ehrlich et al., (1991) *Science* 252:1643–1650; and *PCR Protocols, A Guide to Methods and Applications*, (Innis et al., eds.), Academic Press, New York, N.Y., USA (1990). See also U.S. Pat. No. 4,800,159.

Polynucleotide and Polypeptide Variants

Polynucleotide Variants

The present invention also encompasses variants (e.g., allelic variants, orthologs, etc.) of the polynucleotide sequence disclosed herein in SEQ ID NO:X, the complementary strand thereto, and/or the cDNA sequence contained in the deposited clone.

The present invention also encompasses variants of the polypeptide sequence, and/or fragments therein, disclosed in SEQ ID NO:Y, a polypeptide encoded by the polynucleotide sequence in SEQ ID NO:X, and/or a polypeptide encoded by a cDNA in the deposited clone.

As used herein, the term "variant" means a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the present invention provides an isolated nucleic acid molecule comprising, or alternatively consisting of, a polynucleotide having a nucleotide sequence selected from the group consisting of: (a) a nucleotide sequence encoding a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence as shown in the sequence listing and described in SEQ ID NO:X or the cDNA contained in ATCC Deposit No:Z; (b) a nucleotide sequence encoding a mature HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having the amino acid sequence as shown in the sequence listing and described in SEQ ID NO:X or the cDNA contained in ATCC Deposit No:Z; (c) a nucleotide sequence encoding a biologically active fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence shown in the sequence listing and described in SEQ ID NO:X or the cDNA contained in ATCC Deposit No:Z; (d) a nucleotide sequence encoding an antigenic fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence shown in the sequence listing and described in SEQ ID NO:X or the cDNA contained in ATCC Deposit No:Z; (e) a nucleotide sequence encoding a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide comprising the complete amino acid sequence encoded by a human cDNA plasmid contained in SEQ ID NO:X or the cDNA contained in ATCC Deposit No:Z; (f) a nucleotide sequence encoding a mature HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence encoded by a human cDNA plasmid contained in SEQ ID NO:X or the cDNA contained in ATCC Deposit No:Z; (g) a nucleotide sequence encoding a biologically active fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence encoded by a human cDNA plasmid contained in SEQ ID NO:X or the cDNA contained in ATCC Deposit No:Z; (h) a nucleotide sequence encoding an antigenic fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence encoded by a human cDNA plasmid contained in SEQ ID NO:X or the cDNA contained in ATCC Deposit No:Z; and (i) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the present invention. In another embodiment, the present invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides that hybridize to the complement of these nucleic acid molecules under stringent hybridization conditions or alternatively, under lower stringency conditions, are also encompassed by the present invention, as are polypeptides encoded by these polypeptides.

Another aspect of the present invention provides an isolated nucleic acid molecule comprising, or alternatively, consisting of, a polynucleotide having a nucleotide sequence selected from the group consisting of: (a) a nucleotide sequence encoding a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence as shown in the sequence listing and described in Table I; (b) a nucleotide sequence encoding a mature HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having the amino acid sequence as shown in the sequence listing and descried in Table I; (c) a nucleotide sequence encoding a biologically active fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence as shown in the sequence listing and described in Table I; (d) a nucleotide sequence encoding an antigenic fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence as shown in the sequence listing and described in Table I; (e) a nucleotide sequence encoding a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide comprising the complete amino acid sequence encoded by a human cDNA in a cDNA plasmid contained in the coresponding ATCC Deposit and described in Table I; (f) a nucleotide sequence encoding a mature HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence encoded by a human cDNA in a cDNA plasmid contained in the ATCC Deposit and described in Table I; (g) a nucleotide sequence encoding a biologically active fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence encoded by a human cDNA in a cDNA plasmid contained in the correspoding ATCC Deposit and described in Table I; (h) a nucleotide sequence encoding an antigenic fragment of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)-related polypeptide having an amino acid sequence encoded by a human cDNA in a cDNA plasmid contained in the corresponding ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the following non-limited examples: the polypeptide sequence identified as SEQ ID NO:Y, the polypeptide sequence encoded by a cDNA provided in the deposited clone, and/or polypeptide fragments of any of the polypeptides provided herein. Polynucleotides encoded by these nucleic acid molecules are also encompassed by the present invention. In another embodiment, the present invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the present invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:Y, a polypeptide sequence encoded by the nucleotide sequence in SEQ ID NO:X, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence can include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence can be an entire sequence referenced in Table I, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs.

A representative method for determining the best overall match between a query sequence (e.g., a sequence of the present invention) and a subject sequence, also referred to as a global sequence alignment, can be determined using the CLUSTALW computer program (Thompson et al., (1994) Nucl. Acids Res. 2(22):4673–4680), which is based on the algorithm of Higgins et al., (1992) Computer Applications in the Biosciences (CABIOS) 8(2):189–191. In a sequence alignment, the query and subject sequences are both DNA sequences. An RNA sequence can be compared by converting U's to T's. However, the CLUSTALW algorithm automatically converts U's to T's when comparing RNA sequences to DNA sequences. The result of a global sequence alignment is expressed in percent identity.

Representative parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the ALIGNX® software program (Vector NTI suite of programs, version 6.0, Informax, Frederick, Md., USA).

The present invention encompasses the application of an optional manual correction to the percent identity results, in the instance where the subject sequence is shorter than the query sequence because of 5' or 3' deletions, not because of internal deletions. If only the local pairwise percent identity is required, no manual correction is needed. However, a manual correction can be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score can be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence that are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it can be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm can provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations that produce silent substitutions, additions, or deletions, but do not alter the properties or activities of the encoded polypeptide. Nucleotide variants produced by silent substitutions due to the degeneracy of the genetic code are often desirable. Moreover, variants in which 5–10, 1–5, or 1–2 amino acids are substituted, deleted, or added in any combination are also often desirable. Polynucleotide variants can be produced for a variety of reasons, e.g., to optimize codon expression for a particular host (change codons in the mRNA to those preferred by a bacterial host such as E. coli).

Naturally occurring variants are called "allelic variants" and refer to one of several alternate forms of a gene occupying a given locus on a chromosome of an organism. (see, e.g., Lewin, Genes VII, Oxford University Press, New York, USA (2000), incorporated herein in its entirety). These allelic variants can vary at either the polynucleotide and/or polypeptide level and are included in the present invention. Alternatively, non-naturally occurring variants may be produced by mutagenesis techniques or by direct synthesis.

Polypeptide Variants

Using methods of protein engineering and recombinant DNA technology known to those of ordinary skill in the art, variants can be generated to improve or alter the characteristics of the polypeptides of the present invention. For instance, one or more amino acids can be deleted from the N-terminus or C-terminus of the protein without substantial loss of biological function. For example, it has been reported that variant KGF proteins having heparin binding activity even after deleting 3, 8, or 27 amino-terminal amino acid residues (Ron et al., (1993) *J. Biol. Chem.* 268:2984–2988). Similarly, interferon gamma exhibited up to ten times higher activity after deleting 8–10 amino acid residues from the carboxy terminus of this protein (Dobeli et al., (1988) *J. Biotechnol.* 7:199–216).

Moreover, ample evidence demonstrates that variants often retain a biological activity similar to that of the naturally occurring protein. For example, an extensive mutational analysis of human cytokine IL-1a was conducted (Gayle et al., (1993) *J. Biol. Chem.* 268:22105–22111). In this study, random mutagenesis as employed to generate over 3,500 individual IL-1a mutants that averaged 2.5 amino acid changes per variant over the entire length of the molecule. Multiple mutations were examined at every possible amino acid position. It was found that "[m]ost of the molecule could be altered with little effect on either [binding or biological activity]." Gayle et al. at 22109. In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities might still be retained. For example, the ability of a deletion variant to induce and/or to bind antibodies that recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known to those of ordinary skill in the art.

Alternatively, such N-terminus or C-terminus deletions of a polypeptide of the present invention might, in fact, result in a significant increase in one or more of the biological activities of the polypeptide(s). For example, a given biological activity of many polypeptides is governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide can effectively be rendered biologically active in the absence of an activation event.

Thus, the present invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in several references (e.g., Bowie et al., (1990) *Science* 247:1306–1310), wherein it is indicated that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy employs genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be employed (Cunningham & Wells, (1989) *Science* 244:1081–1085). The resulting mutant molecules can then be tested for biological activity.

These two strategies have revealed that proteins are surprisingly tolerant of amino acid substitutions. The referenced studies further indicate which amino acid changes are likely to be permissive at certain amino acid positions in the protein. For example, most amino acid residues buried within the tertiary structure of the protein require nonpolar side chains, whereas few features of surface side chains are generally conserved.

In one aspect, the present invention encompasses polypeptides having a lower degree of identity but having sufficient similarity so as to perform one or more of the same functions performed by a polypeptide of the present invention. Similarity is determined by conserved amino acid substitution. Conservative substitutions are substitutions that replace a given amino acid in a polypeptide by another amino acid having like characteristics (e.g., chemical properties). Such conservative substitutions are likely to be phenotypically silent (Cunningham & Wells, (1989) *Science* 244:1081–1085). Other references supply additional guidance concerning which amino acid changes are likely to be phenotypically silent (see, e.g., Bowie et al., (1990) *Science* 247:1306–1310).

In one embodiment, tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III:

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |

TABLE III-continued

| For Amino Acid | Code | Replace with any of: |
|---|---|---|
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions can also increase protein or peptide stability. The present invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids. Both identity and similarity can be readily calculated by those of ordinary skill in the art (see, e.g., *Computational Molecular Biology*, (Lesk, ed.), Oxford University Press, New York, N.Y., USA (1988); *Biocomputing: Informatics and Genome Projects*, (Smith, ed.), Academic Press, New York, N.Y., USA (1993); *Informatics Computer Analysis of Sequence Data, Part 1*, (Griffin & Griffin, eds.), Humana Press, Totowa, N.J., USA (1994); von Heinje, *Sequence Analysis in Molecular Biology*, Academic Press, New York, N.Y., USA (1987); and Sequence Analysis Primer, (Gribskov & Devereux, eds.), Stockton Press, New York, N.Y., USA (1991)).

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the present invention also encompasses substitutions which are typically not classified as conservative, but that can be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of lysozyme, the Ile-16 residue of chymotrypsin, the His-159 residue of papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Variants of the present invention are not limited to conservative substitutions. Besides conservative amino acid substitution, variants of the present invention include, but are not limited to, the following: (i) substitutions with one or more of the non-conserved amino acid residues, where the substituted amino acid residues may or may not be one encoded by the genetic code; (ii) substitution with one or more of amino acid residues having a substituent group; (iii) fusion of the mature polypeptide with another compound, such as a compound to increase the stability and/or solubility of the polypeptide (for example, polyethylene glycol); and (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art upon consideration of the present disclosure.

For example, polypeptide variants containing amino acid substitutions of charged amino acids with other charged or neutral amino acids might produce proteins with improved characteristics, such as less aggregation. Aggregation of pharmaceutical formulations both reduces activity and increases clearance due to the aggregate's immunogenic activity (see Pinckard et al., (1967) *Clin. Exp. Immunol.* 2:331–340; Robbins et al., (1987) *Diabetes* 36: 838–845; Cleland et al., (1993) *Crit. Rev. Therapeutic Drug Carrier Systems* 10:307–377).

The present invention further includes polypeptide variants created through the application of molecular evolution ("DNA Shuffling") methodology to the polynucleotide disclosed as SEQ ID NO:X, the sequence of the clone submitted in a deposit, and/or the cDNA encoding the polypeptide disclosed as SEQ ID NO:Y. Such DNA Shuffling technology is known in the art and more particularly described elsewhere herein (e.g., Stemmer, (1994) *Proc. Natl. Acad. Sci. U.S.A.* 91:10747), and in the Examples provided herein).

Thus, an embodiment of the present invention relates to a polypeptide comprising an amino acid sequence of the present invention containing at least one amino acid substitution, but not more than 50 amino acid substitutions (e.g., 40 amino acid substitutions, 30 amino acid substitutions, 20 amino acid substitutions, 10 amino acid substitutions or 5 amino acid substitutions). In one embodiment, an amino acid sequence of the present invention can comprise at least one, but not more than 10, 9, 8, 7, 6, 5, 4, 3, 2 or 1 amino acid substitutions. In specific embodiments, the number of additions, substitutions, and/or deletions in an amino acid sequence of the present invention or fragments thereof (e.g., the mature form and/or other fragments described herein), is 1–5,5–10, 5–25, 5–50, 10–50 or 50–150 and conservative amino acid substitutions can be desirable under some circumstances.

Polynucleotide and Polypeptide Fragments

In addition to the full-length polypeptides encoded by full-length polynucleotides, the present invention is directed to polynucleotide fragments of the polynucleotides of the present invention, as well as to polypeptides encoded by such polynucleotides and/or fragments.

In the present invention, a "polynucleotide fragment" refers to a short polynucleotide having a nucleic acid sequence which: (i) is a portion of that contained in a deposited clone, or encodes a portion of a polypeptide encoded by the cDNA in a deposited clone; (ii) is a portion of that shown in SEQ ID NO:X or the complementary strand thereto; or (iii) is a portion of a polynucleotide sequence encoding a polypeptide of SEQ ID NO:Y. The nucleotide fragments of the present invention are, for example, at least about 15 nt, at least about 20 nt, at least about 30 nt, at least about 40 nt, at least about 50 nt, at least about 75 nt, or at least about 150 nt in length. A fragment "at least 20 nt in length" for example, includes 20 or more contiguous bases from the cDNA sequence contained in a deposited clone or a nucleotide sequence shown in SEQ ID NO:X. In this context "about" includes the particularly recited value, a value larger or smaller by several (e.g., 5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are contemplated and can be desirable in certain circumstances.

Moreover, representative examples of polynucleotide fragments of the present invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 (as applicabale based on the length of SEQ ID NO:X) to the end of SEQ ID NO:X, or the complementary strand thereto, or the cDNA contained in a deposited clone. In this context "about" includes the particularly recited ranges, and ranges larger or smaller by several (e.g., 5, 4, 3, 2, or 1) nucleotides, at either terminus or at both termini. In one embodiment, these fragments encode a polypeptide that has biological activity. These polynucleotides can be used as probes or primers as discussed herein. Also encompassed by the present invention are polynucleotides that hybridize to these nucleic acid molecules under stringent hybridization conditions or lower stringency conditions, as are the polypeptides encoded by these polynucleotides.

In the present invention, a "polypeptide fragment" refers to an amino acid sequence that is a portion of a sequence of SEQ ID NO:Y or encoded by the cDNA contained in a deposited clone. Protein (polypeptide) fragments can be "free-standing" or comprised within a larger polypeptide of which the fragment forms a part or region, most preferably as a single continuous region. Representative examples of polypeptide fragments of the present invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (e.g., 5, 4, 3, 2, or 1) amino acids, at either extreme or at both extremes. Polynucleotides encoding these polypeptides are also encompassed by the present invention.

In one embodiment, a polypeptide fragment includes the full-length protein. Further preferred polypeptide fragments include the full-length protein having a continuous series of deleted residues from either the amino or the carboxy terminus of the polypeptide, or both. For example, any number of amino acids, e.g. ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions can be employed. Similarly, polynucleotides encoding these polypeptide fragments are also an aspect of the present invention. Examples of N- and C-terminal deletions are provided hereinabove.

In yet other embodiments, polypeptide and polynucleotide fragments can be characterized by structural or functional domains, such as fragments that comprise alpha-helix and alpha-helix-forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated and are within the scope of the present invention.

In another embodiment, a polypeptide fragment is a biologically active fragment. Biologically active fragments are those exhibiting activity similar, but not necessarily identical, to an activity of a polypeptide of the present invention. The biological activity of the fragments can include an improved desired activity, or a decreased undesirable activity. Polynucleotides encoding these polypeptide fragments are also encompassed by the present invention.

In a representative embodiment, the functional activity displayed by a polypeptide encoded by a polynucleotide fragment of the present invention can comprise one or more biological activities typically associated with a full-length polypeptide of the present invention. Illustrative examples of these biological activities include a fragment's ability to bind to at least one of the same antibodies which bind to the full-length protein; a fragment's ability to interact with at least one of the same proteins that bind to the full-length protein; a fragment's ability to elicit at least one of the same immune responses as the full-length protein (i.e., to cause the immune system to create antibodies specific to the same epitope, etc.); a fragment's ability to bind to at least one of the same polynucleotides as the full-length protein; the fragment's ability to bind to a receptor of the full-length protein; a fragment's ability to bind to a ligand of the full-length protein; and a fragment's ability to multimerize with the full-length protein. However, the skilled artisan will appreciate that some fragments may have biological activities that are desirable and directly inapposite to the biological activity of the full-length protein. The functional activity of polypeptides of the present invention, including fragments, variants, derivatives, and analogs thereof can be determined by numerous methods available to the skilled artisan and will be apparent upon consideration of the present disclosure, some of which are described herein.

Polypeptide and Polypeptide Fragment Epitopes

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC Deposit No.:Z or encoded by a polynucleotide that hybridizes to the complement of the sequence of SEQ ID NO:X or contained in ATCC Deposit No.:Z under stringent hybridization conditions or lower stringency hybridization conditions as defined herein or known to those of ordinary skill in the art. Such epitopes can comprise a polypeptide fragment. The present invention further encompasses polynucleotide sequences encoding an epitope of a polypeptide sequence of the present invention (such as, for example, an epitope of a sequence disclosed in SEQ ID NO:Y), polynucleotide sequences of the complementary strand of a polynucleotide sequence encoding an epitope of the present invention, and polynucleotide sequences that hybridize to a complementary strand under stringent hybridization conditions or lower stringency hybridization conditions, as defined herein or known to those or ordinary skill in the art.

Fragments that function as epitopes can be produced by any conventional means (see, e.g., Houghten, (1985) *Proc. Natl. Acad. Sci. USA* 82:5131–5135 and U.S. Pat. No. 4,631,211).

In embodiments of the present invention, antigenic epitopes, as defined herein, contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Representative polypeptides comprising immunogenic or antigenic epitopes are at least 5, 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Examples of antigenic epitopes include the antigenic epitopes disclosed herein, as well as any combination of two, three, four, five or more of these antigenic epitopes. Antigenic epitopes can be used as the target molecules in immunoassays (see, e.g., Wilson et al., (1984) *Cell* 37:767–778; Sutcliffe et al., (1983) *Science* 219:660–666).

Similarly, immunogenic epitopes can be used, for example, to induce antibodies according to methods well known in the art (see, e.g., Sutcliffe et al., (1983) *Science* 219:660–666; Wilson et al., (1984) *Cell* 37:767–778; Chow et al., *Proc. Natl. Acad. Sci. USA* 82:910–914; and Bittle et al., (1985) *J. Gen. Virol.* 66:2347–2354). Examples of immunogenic epitopes include the immunogenic epitopes disclosed herein, as well as any combination of two, three, four, five or more of these immunogenic epitopes.

A polypeptide comprising one or more immunogenic epitopes can be presented for eliciting an antibody response together with a carrier protein, such as an albumin, to an animal system (such as rabbit or mouse), or, if the polypeptide is of sufficient length (e.g., at least about 25 amino acids), the polypeptide can be presented without a carrier. Immunogenic epitopes comprising as few as 8 to 10 amino acids have, however, been shown to be sufficient to raise antibodies capable of binding to, at the very least, linear epitopes in a denatured polypeptide (e.g., in western blotting).

Epitope-bearing polypeptides of the present invention can be used to induce antibodies according to methods well known in the art including, but not limited to, in vivo immunization, in vitro immunization, and phage display methods (see, e.g., Sutcliffe et al., (1983) *Science* 219:660–666; Wilson et al., (1984) *Cell* 37:767–778; Chow et al., *Proc. Natl. Acad. Sci. USA* 82:910–914; and Bittle et al., (1985) *J. Gen. Virol.* 66:2347–2354). If in vivo immunization is employed, animals can be immunized with free peptide; however, anti-peptide antibody titer can be boosted by coupling the peptide to a macromolecular carrier, such as keyhole limpet hemacyanin (KLH) or tetanus toxoid. For instance, peptides containing cysteine residues can be coupled to a carrier using a linker such as maleimidobenzoyl-N-hydroxysuccinimide ester (MBS), while other peptides can be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections might be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal can be increased by selection of anti-peptide antibodies, for instance, by adsorption to the peptide on a solid support and elution of the selected antibodies according to methods well known in the art.

As those of ordinary skill in the art will appreciate, and as discussed herein, a polypeptide of the present invention comprising an immunogenic or antigenic epitope can be fused to other polypeptide sequences. For example, a polypeptide of the present invention can be fused with a constant domain of an immunoglobulin (IgA, IgE, IgG, IgM), or a portion thereof (e.g., CH1, CH2, CH3, or any combination thereof and portions thereof), resulting in a chimeric polypeptide. As described further herein, in the context of the present invention a chimeric polypeptide comprises a full-length or fragment of SEQ ID NO:X fused with a sequence not derived from the same SEQ ID NO:X. Such fusion proteins can facilitate purification and can increase half-life in vivo. This has been shown for chimeric proteins consisting of the first two domains of the human CD4-polypeptide and various domains of the constant regions of the heavy or light chains of mammalian immunoglobulins (see, e.g., EP 394,827; Traunecker et al., (1988) *Nature* 331:84–86). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG fusion proteins that have a disulfide-linked dimeric structure due to the IgG portion disulfide bonds have also been found to be more efficient in binding and neutralizing other molecules than monomeric polypeptides or fragments thereof alone (see, e.g., Fountoulakis et al., (1995) *J. Biochem.* 270: 3958–3964).

Nucleic acids encoding the above epitopes can also be recombined with a gene of interest as an epitope tag (e.g., the hemagglutinin ("HA") tag or FLAG® tag (Sigma, St. Louis, Mo., USA; SEQ ID NO:18) to aid in detection and purification of the expressed polypeptide. For example, one system allows for the ready purification of non-denatured fusion proteins expressed in human cell lines (Janknecht et al., (1991) *Proc. Natl. Acad. Sci. USA* 88:8972–897). In this system, the gene of interest is subcloned into a vaccinia recombination plasmid such that the open reading frame of the gene is translationally fused to an amino-terminal tag conssting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the present invention may be generated through the techniques of gene-shuffling, motif-shuffling, exon-shuffling, and/or codon-shuffling (collectively referred to as "DNA shuffling"). DNA shuffling can be employed to modulate the activities of a polypeptide of the present invention, and such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458; and Patten et al., (1997) *Curr. Opinion Biotechnol.* 8:724–33; Harayama, (1998) *Trends Biotechnol.* 16(2): 76–82; Hansson et al., (1999) *J. Mol. Biol.* 287:265–76; and Lorenzo & Blasco, (1998) *Biotechniques* 24(2):308–13. In one embodiment, alteration of a polynucleotide corresponding to SEQ ID NO:X and a polypeptide encoded by such polynucleotides can be achieved by DNA shuffling. DNA shuffling involves the assembly of two or more DNA segments by homologous or site-specific recombination to generate variation in the polynucleotide sequence. In another embodiment, a polynucleotide of the present invention, or an encoded polypeptide, can be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the present invention can be recombined with one or more components, motifs, sections, parts, domains, fragments, etc. of one or more heterologous molecules.

Antibodies

Further polypeptides of the present invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the present invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the present invention), and epitope-binding fragments of any of the polypeptides and peptides disclosed herein.

The antibodies of the present invention can be monospecific, bispecific, trispecific or of greater multispecificity. Multispecific antibodies can be specific for different epitopes of a polypeptide of the present invention or can be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; U.S. Pat. Nos. 4,474,893; 4,714,681; 4,925,648; 5,573,920; 5,601,819; Kostelny et al., (1992) *J. Immunol.* 148:1547–1553; Tutt et al., (1991) *J. Immunol.* 147:60–69.

Antibodies of the present invention can be described or specified in terms of an epitope(s) or portion(s) of a polypeptide of the present invention that a given antibody recognizes or specifically binds. The epitope(s) or polypeptide portion(s) may be specified as described herein, e.g., by N-terminal and C-terminal positions, by size in contiguous amino acid residues, or listed in the Tables, Figures and/or Sequence Listing. Antibodies that specifically bind any epitope or polypeptide of the present invention can also be excluded. Therefore, the present invention includes antibodies that specifically bind polypeptides of the present invention, and allows for the exclusion of the same.

Antibodies of the present invention can also be described or specified in terms of their cross-reactivity. Antibodies that do not bind any other analog, ortholog, or homologue of a polypeptide of the present invention are included in the scope of the present invention. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also encompassed by the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also encompassed by the present invention.

In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies that bind polypeptides encoded by polynucleotides which hybridize to a polynucleotide of the present invention under stringent hybridization conditions (such as those described herein). Antibodies of the present invention can also be described or specified in terms of their binding affinity to a polypeptide of the present invention. Representative binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $1\times10^{-5}$ M, $5\times10^{-6}$ M, $1\times10^{-6}$ M, $5\times10^{-7}$ M, $1\times10^{-7}$ M, $5\times10^{-8}$ M, $1\times10^{-8}$ M, $5\times10^{-9}$ M, $1\times10^{-9}$ M, $5\times10^{-10}$ M, $1\times10^{-10}$ M, $5\times10^{-11}$ M, $1\times10^{-11}$ M, $5\times10^{-12}$ M, $10^{-12}$ M, $5\times10^{-13}$ M, $1\times10^{-13}$ M, $5\times10^{-14}$ M, $1\times10^{-14}$ M, $5\times10^{-15}$ M, or $1\times10^{-15}$ M.

The present invention also provides antibodies that competitively inhibit binding of an antibody to an epitope of the present invention as determined by any method known in the art for determining competitive binding, for example, the immunoassays described herein. In representative embodiments, the antibody competitively inhibits binding to the epitope by at least 95%, at least 90%, at least 85%, at least 80%, at least 75%, at least 70%, at least 60%, or at least 50%.

Antibodies as Agonists and Antagonists

Antibodies of the present invention may act as agonists or antagonists of the polypeptides of the present invention. For example, the present invention includes antibodies that disrupt the receptor/ligand interactions with the polypeptides of the present invention either partially or fully. In some cases, antibodies of the present invention bind an antigenic epitope disclosed herein, or a portion thereof. The present invention features both receptor-specific antibodies and ligand-specific antibodies. The present invention also features receptor-specific antibodies that do not prevent ligand binding but prevent receptor activation. Receptor activation (i.e., signaling) can be determined by techniques described herein or otherwise known in the art. For example, receptor activation can be determined by detecting the phosphorylation state of the receptor or its substrate (e.g., whether a given site, such as a tyrosine or serine/threonine residue is phosphorylated) by immunoprecipitation followed by western blot analysis (for example, as described herein). In specific embodiments, antibodies are provided that inhibit ligand activity and/or receptor activity by at least 95%, at least 90%, at least 85%, at least 80%, at least 75%, at least 70%, at least 60%, or at least 50% of the activity in absence of the antibody.

The present invention also features receptor-specific antibodies that both prevent ligand binding and receptor activation as well as antibodies that recognize the receptor-ligand complex, and, in some cases, do not specifically recognize the unbound receptor or the unbound ligand. Likewise, included in the present invention are neutralizing antibodies that bind the ligand and prevent binding of the ligand to the receptor, as well as antibodies that bind the ligand, thereby preventing receptor activation, but do not prevent the ligand from binding the receptor. Also included in the present invention are antibodies that activate the receptor. These antibodies can act as receptor agonists, i.e., potentiate or activate either all or a subset of the biological activities of the ligand-mediated receptor activation, for example, by inducing dimerization of the receptor. The antibodies can be specified as agonists, antagonists or inverse agonists for biological activities comprising the specific biological activities of the peptides of the present invention disclosed herein. The above antibody agonists can be made using methods known in the art (see, e.g., PCT publication WO 96/40281; U.S. Pat. No. 5,811,097; Deng et al., (1998) *Blood* 92(6):1981–1988; Chen et al., (1998) *Cancer Res.* 58(16):3668–3678; Harrop et al., (1998) *J. Immunol.* 161(4):1786–1794; Zhu et al., (1998) *Cancer. Res.* 58(15):3209–3214; Yoon et al., (1998) *J. Immunol.* 160(7): 3170–3179; Prat et al., (1998) *J. Cell. Sci.* 111(Pt2): 237–247; Pitard et al., (1997) *J. Immunol. Methods* 205(2): 177–190; Liautard et al., (1997) *Cytokine* 9(4):233–241; Carlson et al., (1997) *J. Biol. Chem.* 272(17):11295–11301; Taryman et al., (1995) *Neuron* 14(4):755–762; Muller et al., (1998) *Structure* 6(9): 1153–1167; Bartunek et al., (1996) *Cytokine* 8(1): 14–20).

Uses of Antibodies

Antibodies of the present invention can be used in a variety of applications. A representative, but non-limiting, list of applications for antibodies of the present invention includes to purify, detect, and target the polypeptides of the present invention, including both in vitro and in vivo diagnostic and therapeutic methods. For example, the antibodies have use in immunoassays for qualitatively and quantitatively measuring expression levels and amounts of the polypeptides of the present invention in biological samples (see, e.g., Harlow et al., *Antibodies: A Laboratory Manual*, $2^{nd}$ ed., Cold Spring Harbor Laboratory Press, Cold Spring Harbor, N.Y., USA (1988)).

As discussed in more detail below, the antibodies of the present invention can be used either alone or in combination with other compositions. The antibodies can further be recombinantly fused to a heterologous polypeptide at the N- or C-terminus or chemically conjugated (including covalently and non-covalently conjugations) to polypeptides or other compositions. For example, antibodies of the present invention can be recombinantly fused or conjugated to molecules useful as labels in detection assays and effector molecules such as heterologous polypeptides, drugs, radionucleotides, or toxins (see, e.g., PCT publications WO 92/08495; WO 91/14438; WO 89/12624; U.S. Pat. No. 5,314,995; and EP 396,387).

The antibodies of the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids. The antibodies of the present invention can be generated by any suitable method known in the art.

Polyclonal Antibodies

The antibodies of the present invention can comprise polyclonal antibodies. Methods of preparing polyclonal antibodies are known to the skilled artisan (Harlow et al., *Antibodies: A Laboratory Manual*, $2^{nd}$ ed., Cold Spring Harbor Laboratory Press, Cold Spring Harbor, N.Y., USA (1988)). In a preferred method, a preparation of the HGB-PBMY1 (AK096141), HGBPBMY2 (4843 30 1 1; 4843_ 1), HGBPBMY3 (4843 30 2 1; 4843_2), HGBPBMY4

(FLJ10961), MGBPBMY1 (LOC229900), MGBPBMY2 (LOC229902), MGBPBMY3 (BC031475) and/or MGBPBMY4 (BC007143) protein is prepared and purified to render it substantially free of natural contaminants. Such a preparation is then introduced into an animal in order to produce polyclonal antisera of greater specific activity. For example, a polypeptide of the present invention can be administered to various host animals including, but not limited to, rabbits, mice, rats, etc. to induce the production of sera containing polyclonal antibodies specific for the antigen. The administration of the polypeptides, of the present invention can entail one or more injections of an immunizing agent and, if desired, an adjuvant. Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known to those or ordinary skill in the art. For the purposes of the present invention, "immunizing agent" is defined as a polypeptide of the present invention, including fragments, variants, and/or derivatives thereof, in addition to fusions with heterologous polypeptides and other forms of the polypeptides described herein.

In some embodiments, the immunizing agent and/or adjuvant is injected in the mammal by multiple subcutaneous or intraperitoneal injections, though they may also be given intramuscularly, and/or through IV injection. The immunizing agent can include polypeptides of the present invention or a fusion protein or variants thereof. Depending upon the nature of the polypeptides (i.e., percent hydrophobicity, percent hydrophilicity, stability, net charge, isoelectric point, etc.), it can be useful to conjugate the immunizing agent to a protein known to be immunogenic in the mammal being immunized. Such conjugation includes either chemical conjugation by derivitizing active chemical functional groups to both a polypeptide of the present invention and the immunogenic protein such that a covalent bond is formed, or through fusion-protein based methodology, or other methods known to those of ordinary skill in the art. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants that can be employed include the MPL-TDM adjuvant (monophosphoryl lipid A, synthetic trehalose dicorynomycolate). A suitable immunization protocol can be selected by one of ordinary skill in the art upon consideration of the present disclosure.

Monoclonal Antibodies

The antibodies of the present invention can comprise monoclonal antibodies. Monoclonal antibodies can be prepared using known hybridoma methods, (see, e.g., Köhler & Milstein, (1975) *Nature* 256:495; U.S. Pat. No. 4,376,110, Harlow et al., *Antibodies: A Laboratory Manual*, $2^{nd}$ ed., Cold Spring Harbor Laboratory Press, Cold Spring Harbor, N.Y., USA (1988); Hammerling et al., *Monoclonal Antibodies and T-Cell Hybridomas*, Elsevier, New York, N.Y., USA, (1981) pp. 563–681; Köhler et al., (1976) *Eur. J. Immunol.* 6:511; Köhler et al., (1976) *Eur. J. Immunol.* 6:292). Other examples of methods that can be employed for producing monoclonal antibodies include, but are not limited to, the human B-cell hybridoma technique (Kosbor et al., (1983) *Immunology Today* 4:72; Cole et al., (1983) *Proc. Natl. Acad. Sci. USA* 80:2026–2030), and the EBV-hybridoma technique (Cole et al., *Monoclonal Antibodies And Cancer Therapy*, Alan R. Liss, Inc., New York, N.Y., USA (1985) pp. 77–96). Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this presently a preferred method of production in some situations.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent typically, but not necessarily, includes polypeptides of the present invention or a fusion protein thereof. In some examples, the immunizing agent consists of an HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475), and/or MGBPBMY4 (BC007143) polypeptide-expressing cell. Such cells can be cultured in any suitable tissue culture medium; however, it is sometimes desirable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line-using a suitable fusing agent, such as polyethylene glycol, to form a hybridoma cell (Goding, *Monoclonal Antibodies: Principles and Practice*, Academic Press, New York, N.Y., USA (1986), pp. 59–103). Immortalized cell lines are often transformed mammalian cells, particularly myeloma cells of rodent, bovine and human origin. Often, rat or mouse myeloma cell lines are employed. The hybridoma cells can be cultured in a suitable culture medium that can optionally comprise one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some embodiments, preferred immortalized cell lines are those that fuse efficiently, support stable high level expression of antibody by the selected antibody-producing cells, and are sensitive to a medium such as HAT medium. Other useful immortalized cell lines are murine myeloma lines, which can be obtained, for instance, from the Salk Institute Cell Distribution Center, San Diego, Calif., USA and the American Type Culture Collection, Manassas, Va., USA. Yet other useful immortalized cell lines are the parent myeloma cell line (SP2O) as provided by the ATCC. As noted and implied throughout the specification, human myeloma and mouse-human heteromyeloma cell lines also have been described for the production of human monoclonal antibodies (see, e.g., Kozbor, (1984) *J. Immunol.* 133:3001; Brodeur et al., *Monoclonal Antibody Production Techniques and Applications*, Marcel Dekker, Inc., New York, N.Y., USA (1987) pp. 51–63).

The culture medium in which the hybridoma cells are cultured can then be assayed for the presence of monoclonal antibodies directed against the polypeptides of the present invention. The binding specificity of monoclonal antibodies produced by the hybridoma cells can be determined, for example by immunoprecipitation or by an in vitro binding assay, such as radioimmunoassay (RIA) or enzyme-linked immunoabsorbant assay (ELISA). Such techniques are known in the art. The binding affinity of the monoclonal antibody can, for example, be determined by a Scatchard analysis (see Munson & Pollart, (1980) *Anal. Biochem.* 107:220.

After the desired hybridoma cells are identified, the clones can be subcloned by limiting dilution procedures and grown by standard methods (see, e.g., Goding, *Monoclonal Antibodies: Principles and Practice*, Academic Press, New York, N.Y., USA (1986) and/or Wands et al., (1981) *Gastroenterology* 80:225–232). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones can be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography, all of which techniques will be known to those of ordinary skill in the art.

A variety of methods exist in the art for the production of monoclonal antibodies and thus, the present invention is not limited to their sole production in hydridomas. For example, the monoclonal antibodies can be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the present invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the present invention serve as a preferred source of such DNA. Once isolated, the DNA can be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, (1985) *Science* 229:1202) or by covalently joining to the immunoglobulin coding sequence all or part of the coding sequence for a non-immunoglobulin polypeptide. Such a non-immunoglobulin polypeptide can be substituted for the constant domains of an antibody of the present invention, or can be substituted for the variable domains of one antigen-combining site of an antibody of the present invention to create a chimeric bivalent antibody.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, $2^{nd}$ ed., Cold Spring Harbor Laboratory Press, Cold Spring Harbor, N.Y., USA (1988); Hammerling et al., in: *Monoclonal Antibodies and T-Cell Hybridomas*, Elsevier, New York, N.Y., USA, (1981) pp. 563–681. The term "monoclonal antibody" as used herein is not limited to antibodies produced through hybridoma technology. Rather, the term "monoclonal antibody" broadly refers to an antibody that is derived from a single clone, including any eukaryotic, prokaryotic, or phage clone, and not the method by which it is produced.

Methods for producing and screening for specific antibodies using hybridoma technology are routine and well known in the art and are discussed herein. In a non-limiting example, mice can be immunized with a polypeptide of the present invention or a cell expressing such peptide. Once an immune response is detected, e.g., antibodies specific for the antigen are detected in the mouse serum, the mouse spleen is harvested and splenocytes isolated. The splenocytes are then fused by known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the present invention. Ascites fluid, which generally contains high levels of antibodies, can be generated by immunizing mice with positive hybridoma clones.

Accordingly, in one aspect the present invention provides methods of generating monoclonal antibodies, as well as antibodies produced by the method, comprising: (i) culturing a hybridoma cell secreting an antibody of the present invention, optionally wherein the hybridoma is generated by fusing splenocytes isolated from a mouse immunized with an antigen of the present invention with myeloma cells and (ii) screening the hybridomas resulting from the fusion for hybridoma clones that secrete an antibody able to bind a polypeptide of the present invention.

Antibody fragments that recognize specific epitopes can be generated by known techniques. For example, Fab and F(ab')$_2$ fragments of the present invention can be produced by proteolytic cleavage of immunoglobulin molecules, using enzymes such as papain (to produce Fab fragments) or pepsin (to produce F(ab')$_2$ fragments). F(ab')$_2$ fragments contain a variable region, a light chain constant region and a CH1 domain of the heavy chain.

The antibodies of the present invention can also be generated using various phage display methods known in the art. In phage display methods, functional antibody domains are displayed on the surface of phage particles that carry the polynucleotide sequences encoding them. In a particular embodiment, such phage particles can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., (1995) *J. Immunol. Methods* 182:41–50; Ames et al., (1995) *J. Immunol. Methods* 184:177–186; Kettleborough et al., (1994) *Eur. J. Immunol.* 24:952–958; Persic et al., (1997) *Gene* 187 9–18; Burton et al., (1994) *Adv. Immunology* 57:191–280; PCT Publications PCT/ GB91/01134; WO 90/02809; WO 91/10737; WO 92/01047; WO 92/18619; WO 93/11236; WO 95/15982; WO 95/20401; and in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described herein. For example, techniques to recombinantly produce Fab, Fab' and F(ab')$_2$ fragments can also be employed using methods known in the art such as those disclosed in PCT Publication WO 92/22324; Mullinax et al., (1992) *BioTechniques* 12(6):864–869; and Sawai et al., (1995) *AJRI* 34:26–34; and Better et al., (1988) *Science* 240:1041–1043. Examples of techniques that can be used to produce single-chain Fvs and antibodies include those described in U.S. Pat. Nos. 4,946,778 and 5,258,498; Huston et al., (1991) *Method Enzymol.* 203:46–88; Shu et al., (1993) *Proc. Natl. Acad. Sci. USA* 90:7995–7999; and Skerra et al., (1988) *Science* 240:1038–1040.

For some uses, including in vivo use of antibodies in humans and in vitro detection assays, it can be desirable to use chimeric, humanized, or human antibodies.

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art (see, e.g., Morrison, (1985) *Science* 229:1202; Oi et al., (1986) *BioTechniques* 4:214; Gillies et al., (1989) *J. Immunol. Methods* 125:191–202; EP 171496; EP 173494; PCT Publications WO 8601533; WO 8702671; Boulianne et al., (1984) *Nature* 312:643; Neuberger et al., (1985) *Nature* 314:268; U.S. Pat. Nos. 5,807, 715; 4,816,567; and 4,816,397).

Humanized Antibodies

Humanized antibodies are antibody molecules from non-human species antibody that binds the desired antigen having one or more complementarity determining regions (CDRs) from the non-human species and a framework region from a human immunoglobulin molecule. Often, framework residues in the human framework regions can be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions (see, e.g., U.S. Pat. No. 5,585,089; Riechmann et al., (1988) *Nature* 332:323). Antibodies can be humanized using a variety of techniques known in the art including, for example, CDR-grafting (EP 239,400; PCT Publication WO 91/09967; U.S. Pat. Nos. 5,225,539; 5,530,101; and 5,585, 089), veneering or resurfacing (EP 592,106; EP 519,596; Padlan, (1991) *Molecular Immunology* 28(4/5):489–498; Studnicka et al., (1994) *Protein Engineering* 7(6):805–814; Roguska et al., (1994) *Proc. Natl. Acad. Sci. U.S.A.* 91:969–973), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following known methods (Jones et al., (1986) *Nature* 321:522–525 (1986); Reichmann et al., (1988) *Nature* 332:323–327; Verhoeyen et al., (1988) *Science* 239:1534–1536) by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, a humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody can also comprise at least a portion of an immunoglobulin constant region (Fc), typically that of a human immunoglobulin (see Jones et al., (1986) *Nature* 321:522–525; Riechmann et al., (1988) *Nature* 332:323–329 and Presta, (1992) *Curr. Opin. Struct. Biol.* 2:593–596).

Completely human antibodies are particularly desirable for therapeutic treatment of human subjects. Human antibodies can be made by a variety of methods known in the art including phage display methods described herein using antibody libraries derived from human immunoglobulin sequences. See also, U.S. Pat. Nos. 4,444,887 and 4,716, 111; and PCT Publications WO 98/46645, WO 98/50433, WO 98/24893, WO 98/16654, WO 96/34096, WO 96/33735, and WO 91/10741. Other techniques are also available for the preparation of human monoclonal antibodies (Cole et al., *Monoclonal Antibodies and Cancer Therapy*, Alan R. Liss, New York, N.Y., USA (1985); and Boemer et al., (1991) *J. Immunol.* 147(1):86–95).

Human antibodies can also be produced using transgenic mice that are incapable of expressing functional endogenous immunoglobulins, but can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring, which express human antibodies. The transgenic mice are immunized in the normal fashion with a selected antigen, e.g., all or a portion of a polypeptide of the present invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg & Huszar, (1995) *Int. Rev. Immunol.* 13:65–93. See also PCT Publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (Fremont, Calif., USA), Genpharm (San Jose, Calif., USA), and Medarex, Inc. (Princeton, N.J., USA) can be engaged to provide human antibodies directed against a selected antigen using technology similar to that described herein.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., (1992) *Biotechnol.* 10:779–783; Lonberg et al., (1994) *Nature* 368:856–859; Fishwild et al., (1996) *Nature Biotechnol.* 14:845–51; Neuberger, (1996) *Nature Biotechnol.* 14:826; Lonberg & Huszer, (1995) *Intern. Rev. Immunol.* 13:65–93.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., (1988) *Bio/technology* 12:899–903).

Anti-Idiotype Antibodies

Further, antibodies to the polypeptides of the present invention can, in turn, be utilized to generate anti-idiotype antibodies that "mimic" polypeptides of the present invention using techniques known to those skilled in the art. (See, e.g., Greenspan & Bona, (1989) *FASEB J.* 7(5):437–444; and Nissinoff, (1991) *J. Immunol.* 147(8):2429–2438). For example, antibodies that bind to and competitively inhibit polypeptide multimerization, and/or binding of a polypeptide of the present invention to a ligand, can be used to generate anti-idiotypes that "mimic" the polypeptide multimerization and/or binding domain and, as a consequence, bind to and neutralize the polypeptide and/or its ligand. Neutralizing anti-idiotypes or Fab fragments of such anti-idiotypes can be used in therapeutic regimens to neutralize polypeptide ligand. For example, such anti-idiotypic antibodies can be used to bind a polypeptide of the present invention and/or to bind its ligands/receptors, and thereby block the polypeptide/ligand/receptor's biological activity.

Such anti-idiotypic antibodies capable of binding to a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475), and/or MGBPBMY4 (BC007143) polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, for example a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

Monospecific/Monovalent Antibodies

The antibodies of the present invention can be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Bispecific/Bivalent Antibodies

The antibodies of the present invention can be bispecific antibodies. Bispecific antibodies are monoclonal antibodies (e.g., human or humanized monoclonal antibodies) that have binding specificities for at least two different antigens. In a bispecific antibody of the present invention, one of the binding specificities can be directed towards a polypeptide of the present invention, the other can be for any other antigen (e.g., a cell-surface protein, receptor, receptor subunit, tissue-specific antigen, virally derived protein, virally encoded envelope protein, bacterially derived protein, or bacterial surface protein, etc.).

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein & Cuello, (1983) *Nature* 305:537–539). Because of the random assortment of immunoglobulin heavy and light chains, these hybridomas (quadromas) produce a potential mixture of ten different antibody molecules, of which only one has the correct bispecific structure. The purification of the correct molecule can be, and typically is, accomplished by affinity chromatography steps. Similar procedures are disclosed in PCT Publication WO 93/08829 and in Traunecker et al., (1991) *EMBO J.* 10:3655–3659.

Antibody variable domains with the desired binding specificities (antibody-antigen combining sites) can be fused to immunoglobulin constant domain sequences. The fusion can be with an immunoglobulin heavy-chain constant domain, comprising at least part of the hinge, CH2, and CH3 regions. It is is often desirable to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, e.g., Suresh et al., (1986) *Meth. Enzymol.* 121:210.

Heteroconjugate Antibodies

Heteroconjugate antibodies are also contemplated by the present invention. Heteroconjugate antibodies are composed of two covalently joined antibodies. Such antibodies have, for example, been proposed for targeting immune system cells to unwanted cells (U.S. Pat. No. 4,676,980), and for the treatment of HIV infection (PCT Publications WO 91/00360; WO 92/20373; and EP03089). It is contemplated that the antibodies can be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The present invention further provides polynucleotides comprising a nucleotide sequence encoding an antibody of the present invention and fragments thereof. The present invention also encompasses polynucleotides that hybridize under stringent or lower stringency hybridization conditions, e.g., as defined herein, to polynucleotides that encode an antibody, preferably, that specifically binds to a polypeptide of the present invention, preferably, an antibody that binds to a polypeptide having the amino acid sequence of SEQ ID NO:Y or a fragment thereof.

The polynucleotides can be obtained, and the nucleotide sequence of the polynucleotides determined, by any method known in the art. For example, if the nucleotide sequence of the antibody is known, a polynucleotide encoding the antibody can be assembled from chemically synthesized oligonucleotides (e.g., as described in Kutmeier et al., (1994) *BioTechniques* 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody can be generated from a nucleic acid derived from a suitable source. If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library, or a cDNA library generated from a nucleic acid, preferably poly A+ RNA, isolated from, any tissue or cells expressing the antibody, such as hybridoma cells selected to express an antibody of the present invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

Once the nucleotide sequence and corresponding amino acid sequence of the antibody is determined, the nucleotide sequence of the antibody can be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning: A Laboratory Manual*, (3$^{rd}$ ed.) Cold Spring Harbor Laboratory Press, Cold Spring Harbor, N.Y., USA (2001), and *Current Protocols in Molecular Biology*, (Ausubel et al., eds.), Greene Publishing Associates and Wiley-Interscience, New York (2002)), to generate antibodies having a different amino acid sequence, for example to create amino acid substitutions, deletions, and/or insertions.

In a specific embodiment, an amino acid sequence of the heavy and/or light chain variable domains can be inspected to identify the sequences of the complementarity determining regions (CDRs) by methods that are known in the art, e.g., by comparison to known amino acid sequences of other heavy and light chain variable regions to determine a region(s) of sequence hypervariability. Using routine recombinant DNA techniques, one or more of the CDRs can be inserted within framework regions, e.g., into human framework regions to humanize a non-human antibody, as described herein. The framework regions can be naturally occurring or consensus framework regions, (e.g., human framework regions (see, e.g., Chothia et al., (1998) *J. Mol. Biol.* 278:457–479 for a listing of representative human framework regions). Preferably, the polynucleotide generated by the combination of the framework regions and CDRs encodes an antibody that specifically binds a polypeptide of the present invention. As discussed herein, one or more amino acid substitutions can be made within the framework regions, and the amino acid substitutions improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and will be known to those of ordinary skill of the art upon consideration of the present disclosure.

In addition, techniques developed for the production of "chimeric antibodies" (Morrison et al., (1984) *Proc. Natl. Acad. Sci. USA* 81:851–855; Neuberger et al., (1984) Nature 312:604–608; Takeda et al., (1985) *Nature* 314:452–454) by splicing genes from a mouse antibody molecule of appropriate antigen specificity together with genes from a human antibody molecule of appropriate biological activity can be used. As described herein, a chimeric antibody is a molecule in which different portions are derived from different animal species, such as those having a variable region derived from a murine mAb and a human immunoglobulin constant region, e.g., humanized antibodies.

Alternatively, techniques for the production of single chain antibodies are known (see, e.g., U.S. Pat. No. 4,946, 778; Bird, (1988) *Science* 242:423–42; Huston et al., (1988) *Proc. Natl. Acad. Sci. USA* 85:5879–5883; and Ward et al., (1989) *Nature* 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (Skerra et al., (1988) *Science* 242:1038–1041).

A clone encoding an antibody of the present invention can be obtained according to the methods described herein.

Methods of Producing Antibodies

The antibodies of the present invention can be produced by any method known in the art for the synthesis of antibodies, in particular, by chemical synthesis or preferably, by recombinant expression techniques. The following is presented in addition to the discussion above regarding antibody production.

Recombinant expression of an antibody of the present invention, or a fragment, derivative or analog thereof, (e.g., a heavy or light chain of an antibody of the present invention or a single chain antibody of the present invention), requires the construction of an expression vector containing a polynucleotide that encodes the antibody. Once a polynucleotide encoding an antibody molecule or a heavy or light chain of an antibody, or portion thereof (preferably containing the heavy or light chain variable domain) of the present invention has been obtained, a vector for the production of the antibody molecule can be produced by recombinant DNA technology using techniques known in the art. Methods for preparing a protein by expressing a polynucleotide containing an antibody-encoding nucleotide sequence are described herein.

Methods known to those of ordinary skill in the art can be used to construct expression vectors containing antibody coding sequences and appropriate transcriptional and translational control signals. These methods include, for example, in vitro recombinant DNA techniques, synthetic techniques, and in vivo genetic recombination. The present invention, thus, provides replicable vectors comprising a nucleotide sequence encoding an antibody molecule of the present invention, or a heavy or light chain thereof, or a heavy or light chain variable domain, operably linked to a promoter. Such vectors can include the nucleotide sequence encoding the constant region of an antibody molecule (see, e.g., PCT Publication WO 86/05807; PCT Publication WO 89/01036; and U.S. Pat. No. 5,122,464), and a variable domain of the antibody can be cloned into such a vector for expression of the entire heavy or light chain.

The expression vector is transferred to a host cell by conventional techniques and the transfected cells are then cultured by conventional techniques to produce an antibody of the present invention. Thus, the present invention includes host cells containing a polynucleotide encoding an antibody of the present invention, or a heavy or light chain thereof, or a single chain antibody of the present invention, operably linked to a heterologous promoter. In representative embodiments for the expression of double-chained antibodies, vectors encoding both the heavy and light chains may be co-expressed in the host cell for expression of the entire immunoglobulin molecule, as detailed herein.

A variety of host-expression vector systems can be employed to express the antibody molecules of the present invention. Such host-expression systems represent vehicles by which a coding sequence of interest can be produced and subsequently purified, but also represent cells that may, when transformed or transfected with the appropriate nucleotide coding sequences, express an antibody molecule of the present invention in situ. These include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, (CaMV); tobacco mosaic virus, (TMV)) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Under some conditions it can be desirable that bacterial cells such as *Escherichia coli*, or eukaryotic cells are used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., (1986) *Gene* 45:101; Cockett et al., (1990) *Bio/Technology* 8:2).

In bacterial systems, a number of expression vectors can be advantageously employed, depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited, to the *E. coli* expression vector pUR278 (Ruther et al., (1983) *EMBO J.* 2:1791), in which the antibody coding sequence can be ligated individually into the vector in frame with the lac Z coding region so that a fusion protein is produced; pIN vectors (Inouye & Inouye, (1985) *Nucleic Acids Res.* 13:3101–3109; Van Heeke & Schuster, (1989) *J. Biol. Chem.* 24:5503–5509); and the like pGEX vectors can also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (see, e.g., Logan & Shenk, (1984) *Proc. Natl. Acad. Sci. U.S.A.* 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., (1987) *Method Enzymol.* 153:51–544).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines that stably express the antibody molecule can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the antibody molecule. Such engineered cell lines may be particularly useful in screening and evaluation of compounds that interact directly or indirectly with the antibody molecule.

A number of selection systems can be used. For example, the herpes simplex virus thymidine kinase (Wigler et al., (1977) *Cell* 11:223), hypoxanthine-guanine phosphoribosyltransferase (Szybalska & Szybalski, (1992) *Proc. Natl. Acad. Sci. USA* 48:202), and adenine phosphoribosyltransferase (Lowy et al., (1980) *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., (1980) *Proc. Natl. Acad. Sci. USA* 77:357; O'Hare et al., (1981) *Proc. Natl. Acad. Sci. USA* 78:1527); gpt, which confers resistance to mycophenolic acid (Mulligan & Berg, (1981) *Proc. Natl. Acad. Sci. USA* 78:2072); neo, which confers resistance to the aminoglycoside G-418 (*Clinical Pharmacy* 12:488–505; Wu & Wu, (1991) *Biotherapy* 3:87–95; Tolstoshev, (1993) *Ann. Rev. Pharmacol. Toxicol.* 32:573–596; Mulligan, (1993) *Science* 260:926–932; and Morgan & Anderson, (1993) *Ann. Rev. Biochem.* 62:191–217; *TIB TECH* 11(5): 155–215, May, 1993); and hygro, which confers resistance to hygromycin (Santerre et al., (1984) *Gene* 30:147). Methods commonly known in the art of recombinant DNA technology can be routinely applied to select the desired recombinant clone, and such methods are described, for example, in *Current Protocols in Molecular Biology*, (Ausubel et al., eds.), Greene Publishing Associates and Wiley-Interscience, New York (2002); Kriegler, *Gene Transfer and Expression, A Laboratory Manual*, Stockton Press, New York, N.Y., USA (1990); *Current Protocols in Human Genetics*, (Dracopoli et al., eds.), John Wiley & Sons, New York, N.Y., USA (1994), Chapters 12 and 13; Colberre-Garapin et al., (1981) *J. Mol. Biol.* 150:1).

The expression levels of an antibody molecule can be increased by vector amplification (for a review, see Bebbington & Hentschel, in *DNA Cloning*, vol.3. Academic Press, New York, N.Y., USA (1987)). When a marker in the vector system expressing antibody is amplifiable, an increase in the level of inhibitor present in culture of host cell will increase the number of copies of the marker gene. Since the amplified region is associated with the antibody gene, production of the antibody will also increase (Crouse et al., (1983) *Mol. Cell. Biol.* 3:257).

The host cell can be co-transfected with two expression vectors of the present invention, the first vector encoding a heavy chain derived polypeptide and the second vector encoding a light chain derived polypeptide. The two vectors can contain identical selectable markers that enable equal expression of heavy and light chain polypeptides. Alternatively, a single vector can be used which encodes, and is capable of expressing, both heavy and light chain polypeptides. In such situations, the light chain should be placed before the heavy chain to avoid an excess of toxic free heavy chain (Proudfoot, (1986) *Nature* 322:52; Kohler, (1980) *Proc. Natl. Acad. Sci. USA* 77:2197). The coding sequences for the heavy and light chains can comprise cDNA or genomic DNA.

Once an antibody molecule of the present invention has been produced by an animal, chemically synthesized, or recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Fusion Proteins Comprising an Antibody

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but can occur through linker sequences. The antibodies can be specific for antigens other than polypeptides (or portion thereof, preferably at least 10, 20, 30, 40, 50, 60, 70, 80, 90 or 100 amino acids of the polypeptide) of the present invention. For example, antibodies can be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention can also be used in in vitro immunoassays and purification methods using methods known in the art. See e.g., PCT Publication WO 93/21232; EP 439,095; Naramura et al., (1994) Immunol. Lett. 39:91–99; U.S. Pat. No. 5,474,981; Gillies et al., (1992) Proc. Natl. Acad. Sci. USA 89:1428–1432; Fell et al., (1991) J. Immunol. 146:2446–2452.

The present invention further includes compositions comprising the polypeptides of the present invention fused or conjugated to antibody domains other than the variable regions. For example, the polypeptides of the present invention can be fused or conjugated to an antibody Fc region, or portion thereof. The antibody portion fused to a polypeptide of the present invention can comprise the constant region, hinge region, CH1 domain, CH2 domain, and CH3 domain or any combination of whole domains or portions thereof. The polypeptides can also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., (1991) Proc. Natl. Acad. Sci. USA 88:10535–10539 (1991); Zheng et al., (1995) J. Immunol. 154:5590–5600; and Vil et al., (1992) Proc. Natl. Acad. Sci. USA 89:11337–11341.

As discussed herein, a polypeptide comprising a full length polypeptide, polypeptide fragment, or a variant of SEQ ID NO:Y may be fused or conjugated to the above antibody portions to increase the in vivo half life of the polypeptides or for use in immunoassays using methods known in the art. Further, a polypeptide corresponding to SEQ ID NO:Y can be fused or conjugated to the above antibody portions to facilitate purification. One reported example describes chimeric proteins consisting of the first two domains of the human CD4-polypeptide and various domains of the constant regions of the heavy or light chains of mammalian immunoglobulins (see, e.g., EP 394,827; Traunecker et al., (1988) Nature 331:84–86). The polypeptides of the present invention fused or conjugated to an antibody having disulfide-linked dimeric structures (due to the IgG) can also be more efficient in binding and neutralizing other molecules, than the monomeric secreted protein or protein fragment alone (see, e.g., Fountoulakis et al., (1995) J. Biochem. 270:3958–3964). In some cases, the Fc part in a fusion protein is beneficial in therapy and diagnosis, and thus can result in, for example, improved pharmacokinetic properties (see, e.g., EP A 232,262). Alternatively, deleting the Fc part after the fusion protein has been expressed, detected, and purified, would be desired. For example, the Fc portion might hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5 (see, e.g., Bennett et al., (1995) J. Molecular Recognition 8:52–58; Johanson et al., (1995) J. Biol. Chem. 270:9459–9471).

Moreover, the antibodies or fragments thereof of the present invention can be fused to marker sequences, such as a peptide to facilitate purification. In some embodiments, the marker amino acid sequence is a hexa-histidine peptide, such as the tag provided in a pQE vector (Qiagen, Inc., La Jolla, Calif.), among others, many of which are commercially available. As described in Gentz et al., (1989) Proc. Natl. Acad. Sci. USA 86:821–824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., (1984) Cell 37:767) and the FLAG® tag (Sigma, St. Louis, Mo., USA; SEQ ID NO:18).

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. See, for example, U.S. Pat. No. 4,741,900, disclosing metal ions that can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof can be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Representative therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the present invention can be used to modify a given biological response, and the therapeutic agent or drug moiety is not to be construed as limited to classical chemical therapeutic agents. For example, a drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, $\alpha$-interferon, $\beta$-interferon, nerve growth factor, platelet derived growth factor, tissue plasminogen activator, an apoptotic agent, e.g., TNF-alpha, TNF-beta, AIM I (see, PCT Publication WO 97/33899), AIM II (see, PCT Publication WO 97/34911), Fas Ligand (Takahashi et al., (1994) *Int. Immunol.* 6:1567–1574), VEGI (see, PCT Publication WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are known, (see, e.g., Arnon et al., in *Monoclonal Antibodies And Cancer Therapy*, (Reisfeld et al., eds.), Alan R. Liss, Inc., New York, N.Y., USA (1985) pp. 243–56; Hellstrom et al., in *Controlled Drug Delivery*, ($2^{nd}$ ed.), (Robinson et al., eds.), Marcel Dekker, Inc., New York, N.Y., USA (1987) pp. 623–53; Thorpe, in *Monoclonal Antibodies '84: Biological And Clinical Applications*, (Pinchera et al., eds.), (1985) pp. 475–506; *Monoclonal Antibodies For Cancer Detection And Therapy*, (Baldwin et al., eds), Academic Press, New York, N.Y., USA (1985) pp. 303–16, and Thorpe et al., (1982) *Immunol. Rev.* 62:119–58).

Alternatively, an antibody can be conjugated to a second antibody to form an antibody heteroconjugate (see U.S. Pat. No. 4,676,980).

An antibody, with or without a therapeutic moiety conjugated to it, administered alone or in combination with cytotoxic factor(s) and/or cytokine(s) can be used as a therapeutic.

Synthetic Antibodies

The present invention also encompasses the creation of synthetic antibodies directed against the polypeptides of the present invention (see, e.g., Radrizzani et al., (1999) *Medicina*, (Aires) 59(6):753–8). Recently, a new class of synthetic antibodies has been described and are referred to as molecularly imprinted polymers (MIPs) (commercially available from Semorex, Inc., Jerusalem, Israel). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent "super" MIPs can be coated onto beads or wells for use in highly sensitive separations or assays, or for use in high throughput screening of proteins.

Moreover, MIPs based upon the structure of a polypeptide of the present invention can be useful in screening for compounds that bind to the polypeptide(s) of the present invention. Such a MIP could serve the role of a synthetic "receptor" by minimicking the native architecture of the polypeptide. In fact, the ability of a MIP to serve the role of a synthetic receptor has already been demonstrated for the estrogen receptor (Ye et al., (2001) *Analyst* 126(6):760–5; Dickert et al., (2001) *Analyst* 126(6):766–71). A synthetic receptor can either be mimicked in its entirety (e.g., as the entire protein), or mimicked as a series of short peptides corresponding to the protein (Rachkov & Minoura, (2001) *Biochim. Biophys. Acta.* 1544(1–2):255–66). Such synthetic receptor MIPs can be employed in any one or more of the screening methods described elsewhere herein.

MIPs have also been shown to be useful in "sensing" the presence of its mimicked molecule (Cheng et al., (2001) *Biosens. Bioelectron.* 16(3):179–85; Jenkins et al., (2001) *Analyst* 126(6):798–802; Jenkins et al., (2001) *Analyst* 126 (6):798–802). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several representative methods are described by Esteban et al. in Esteban et al., (2001) *J. Anal. Chem.* 370(7):795–802, which is hereby incorporated herein by reference in its entirety in addition to any references cited therein. Additional methods are known in the art and are encompassed by the present invention, (see, e.g., Hart & Shea, (2001) *J. Am. Chem. Soc.* 123(9):2072–3; and Quaglia et al., (2001) *J. Am. Chem. Soc.* 123(10):2146–54).

Uses for Antibodies Directed Against Polypeptides of the Present Invention

The antibodies of the present invention have various utilities. For example, such antibodies can be used in diagnostic assays to detect the presence or quantification of the polypeptides of the present invention in a sample. Such a diagnostic assay can comprise at least two steps. The first step can comprise contacting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (see, e.g., Arenkov et al., (2000) *Anal. Biochem.* 278(2):123–131), or a chromatography column, etc. A second step can comprise quantifying an amount of antibody bound to the substrate. Alternatively, the method can optionally involve a step of attaching the antibody, either covalently, electrostatically, or reversibly, to a solid support, and a second step of subjecting the bound antibody to the sample, as defined above and elsewhere herein.

Diagnostic Assays Employing an Antibody of the Present Invention

Various diagnostic assay techniques are known in the art, such as competitive binding assays, direct or indirect sandwich assays and immunoprecipitation assays conducted in either heterogeneous or homogenous phases (Zola, *Monoclonal Antibodies: A Manual of Techniques*, CRC Press, Inc., Boca Raton, Fla., USA (1987), pp. 147–158). The antibodies used in the diagnostic assays can be labeled with a detectable moiety. The detectable moiety can be capable of producing, either directly or indirectly, a detectable signal. For example, the detectable moiety can be an isotope, such as $^2$H, $^{14}$C, $^{32}$P, or $^{125}$I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety can be employed, including those methods described in Hunter et al., (1962) *Nature* 144:945; Dafvid et al., (1974) *Biochem.* 13:1014; Pain et al., (1981) *J. Immunol. Method.* 40:219; and Nygren, (1982) *J. Histochem. Cytochem.* 30:407.

Antibodies directed against the polypeptides of the present invention are useful for the affinity purification of such polypeptides from recombinant cell culture or natural sources. In this process, the antibodies against a particular polypeptide are immobilized on a suitable support, such as a SEPHADEX™ (Amersham, Piscatraway, N.J., USA) resin or filter paper, using methods known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping Using an Antibody of the Present Invention

The antibodies of the present invention can be utilized for immunophenotyping of cell lines and biological samples. The translation product of the gene of the present invention can be useful as a cell specific marker, or more specifically as a cellular marker that is differentially expressed at various stages of differentiation and/or maturation of particular cell types. Monoclonal antibodies directed against a specific epitope, or combination of epitopes, allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (see, e.g., U.S. Pat. No. 5,985,660; and Morrison et al., (1999) *Cell* 96:737–49).

These techniques allow for the screening of particular populations of cells, such as might be found with hematological malignancies (i.e. minimal residual disease (MRD) in acute leukemic subjects) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the present invention can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, *Current Protocols in Molecular Biology*, (Ausubel et al., eds.), Greene Publishing Associates and Wiley-Interscience, New York (2002)). Exemplary immunoassays are described briefly below (but are not intended to be in any way limiting).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. Those of ordinary skill in the art will be knowledgeable as to the parameters that can be modified to increase the binding of the antibody to an antigen and decrease the background (e.g., pre-clearing the cell lysate with sepharose beads), upon consideration of the present disclosure. Additional immunoprecipitation protocols are presented *Current Protocols in Molecular Biology*, (Ausubel et al., eds.), Greene Publishing Associates and Wiley-Interscience, New York (2002).

Western blot analysis generally comprises preparing protein samples, electrophoresis of the protein samples in a polyacrylamide gel (e.g., about 8–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with about 3% BSA or non-fat milk), washing the membrane in washing buffer (e.g., PBS-TWEEN 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. Those of ordinary skill in the art will be knowledgeable as to the parameters that can be modified to increase the signal detected and to reduce the background noise, upon consideration of the present disclosure. Additional western blot protocols are presented in *Current Protocols in Molecular*

Biology, (Ausubel et al., eds.), Greene Publishing Associates and Wiley-Interscience, New York (2002).

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. When performing an ELISA, the antibody of interest does not need to be conjugated to a detectable compound; instead, a second antibody (which recognizes the antibody of interest) conjugated to a detectable compound can be added to the well. Further, instead of coating the well with the antigen, the antibody may be coated to the well. In this case, a second antibody conjugated to a detectable compound can be added following the addition of the antigen of interest to the coated well. One of ordinary skill in the art will be knowledgeable as to the parameters that can be modified to increase the signal detected as well as other variations of ELISA protocols known in the art. For further discussion regarding ELISA protocols see, e.g., Current Protocols in Molecular Biology, (Ausubel et al., eds.), Greene Publishing Associates and Wiley-Interscience, New York (2002).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Therapeutic Applications of Antibodies

The present invention is further directed to antibody-based therapies which involve administering antibodies of the present invention to an animal subject, preferably a mammal (and more preferably a human), for treating one or more of the disclosed diseases, disorders, or conditions. Therapeutic compounds of the present invention include, but are not limited to, antibodies of the present invention (including fragments, analogs and derivatives thereof as described herein) and nucleic acids encoding antibodies of the present invention (including fragments, analogs and derivatives thereof and anti-idiotypic antibodies as described herein). The antibodies of the present invention can be used to treat, inhibit or prevent diseases, disorders or conditions associated with aberrant expression and/or activity of a polypeptide of the present invention, including, but not limited to, any one or more of the diseases, disorders, or conditions described herein. The treatment and/or prevention of diseases, disorders, or conditions associated with aberrant expression and/or activity of a polypeptide of the present invention includes, but is not limited to, alleviating symptoms associated with those diseases, disorders or conditions. Antibodies of the present invention can be provided in pharmaceutically acceptable compositions as known in the art or as described herein.

A summary of the ways in which the antibodies of the present invention can be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Upon consideration of the present disclosure, one of ordinary skill in the art will know how to use the antibodies of the present invention for diagnostic, monitoring or therapeutic purposes.

The antibodies of this invention can be advantageously utilized in combination with other monoclonal or chimeric antibodies, or with lymphokines or hematopoietic growth factors (such as, e.g., IL-2, IL-3 and IL-7), for example, which serve to increase the number or activity of effector cells that interact with the antibodies.

The antibodies of the present invention can be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the subject is preferred. Thus, in one embodiment, human antibodies, fragments derivatives, analogs, or nucleic acids, are administered to a human subject for therapy or prophylaxis.

High affinity and/or potent in vivo inhibiting and/or neutralizing antibodies against polypeptides or polynucleotides of the present invention, fragments or regions thereof, can be used for both immunoassays directed to and therapy of disorders related to polynucleotides or polypeptides, including fragments thereof, of the present invention. Such antibodies, fragments, or regions, can have an affinity for polynucleotides or polypeptides of the present invention, including fragments thereof. Representative binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $1 \times 10^{-5}$ M, $5 \times 10^{-6}$ M, $1 \times 10^{-6}$ M, $5 \times 10^{-7}$ M, $1 \times 10^{-7}$ M, $5 \times 10^{-8}$ M, $1 \times 10^{-8}$ M, $5 \times 10^{-9}$ M, $1 \times 10^{-9}$ M, $5 \times 10^{-10}$ M, $1 \times 10^{-10}$ M, $5 \times 10^{-11}$ M, $1 \times 10^{-11}$ M, $5 \times 10^{-12}$ M, $10^{-12}$ M, $5 \times 10^{-13}$ M, $1 \times 10^{-13}$ M, $5 \times 10^{-14}$ M, $1 \times 10^{-14}$ M, $5 \times 10^{-15}$ M, or $1 \times 10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one of ordinary skill in the art could clone the gene encoding an antibody directed against a polypeptide of the present invention, the polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide.

Moreover, such a use of the antibodies of the present invention may have particular utility in preventing and/or ameliorating autoimmune diseases and/or disorders, as such conditions are typically a result of antibodies being directed against endogenous proteins. For example, in the case in which a polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against a polypeptide of the present invention could effective inhibit the organisms immune system from eliciting an immune response to the auto-antigen(s). Additional descriptions of therapeutic and/or gene therapy applications of the present invention are provided herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (see, for example, U.S. Pat. Nos. 5,914,123 and 6,034,298).

In another embodiment, antibodies of the present invention, in one example polyclonal antibodies, an in another example monoclonal antibodies, and in yet another example single-chain antibodies, can be used as a means of inhibiting gene expression of a particular gene, or genes, in a human, mammal, and/or other organism. See, for example, PCT Publication WO 00/05391. The application of such methods for the antibodies of the present invention are known in the art, and are additionally described herein.

In yet another embodiment, antibodies of the present invention can be useful for multimerizing a polypeptide (or a combination of different polypeptides) of the present invention. For example, certain proteins can confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the present invention, by way of gene therapy. Gene therapy refers to therapy performed by the administration to a subject of an expressed or expressible nucleic acid. In this embodiment of the present invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., (1993) *Clin. Pharm.* 12:488–505; Wu & Wu, (1991) *Biotherapy* 3:87–95; U, (1993) *Ann. Rev. Pharmacol. Toxicol.* 32:573–596; Mulligan, (1993) *Science* 260: 926–932; Morgan & Anderson, (1993) *Ann. Rev. Biochem.* 62:191–217; May, (1993) *TIBTECH* 11(5): 155–215. Methods commonly known in the art of recombinant DNA technology which can be used are described in *Current Protocols in Molecular Biology*, (Ausubel et al., eds.), Greene Publishing Associates and Wiley-Interscience, New York (2002); and Kriegler, *Gene Transfer and Expression, A Laboratory Manual*, Stockton Press, New York, N.Y., USA (1990).

In one aspect, the compound comprises nucleic acid sequences encoding an antibody, the nucleic acid sequences being part of expression vectors that express the antibody or fragments or chimeric proteins or heavy or light chains thereof in a suitable host. In particular, such nucleic acid sequences have promoters operably linked to the antibody coding region, the promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller & Smithies, (1989) *Proc. Natl. Acad. Sci. USA* 86:8932–8935; Zijlstra et al., (1989) *Nature* 342: 435–438. In specific embodiments, the expressed antibody molecule is a single chain antibody; alternatively, the nucleic acid sequences include sequences encoding both the heavy and light chains, or fragments thereof, of the antibody.

Delivery of the nucleic acids into a subject can be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; BIOLISTIC®, Dupont, Wilmington, Del., USA), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu & Wu, (1987) *J. Biol. Chem.* 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller & Smithies, (1989) *Proc. Natl. Acad. Sci. USA* 86:8932–8935; Zijlstra et al., (1989) *Nature* 342:435–438).

In a specific embodiment, a viral vector that contains nucleic acid sequences encoding an antibody of the present invention is used. For example, a retroviral vector can be used (see, e.g., Miller et al., (1993) *Meth. Enzymol.* 217: 581–599). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a subject. More detail about retroviral vectors can be found in Boesen et al., (1994) *Biotherapy* 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., (1994) *J.*

*Clin. Invest.* 93:644–651; Kiem et al., (1994) *Blood* 83:1467–1473; Salmons & Gunzberg, (1993) *Human Gene Therapy* 4:129–141; and Grossman & Wilson, (1993) *Curr. Opin. Genet. Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky & Wilson (Kozarsky & Wilson, (1993) *Current Opinion Genet. Devel.* 3:499–503) present a review of adenovirus-based gene therapy. Bout et al. (Bout et al., (1994) *Human Gene Therapy* 5:3–10) demonstrated the use of adenovirus vectors to transfer genes to the respiratory epithelia of rhesus monkeys. Other instances of the use of adenoviruses in gene therapy are known (see, e.g., Rosenfeld et al., (1991) *Science* 252:431–434; Rosenfeld et al., (1992) *Cell* 68:143–155; Mastrangeli et al., (1993) *J. Clin. Invest.* 91:225–234; PCT Publication WO94/12649; and Wang et al., (1995) *Gene Therapy* 2:775–783. In one embodiment, adenovirus vectors are used.

Adeno-associated virus (AAV) has also been proposed for use in gene therapy (Walsh et al., (1993) *Proc. Soc. Exp. Biol. Med.* 204:289–300; U.S. Pat. No. 5,436,146).

Another approach to gene therapy involves transferring a gene to cells in tissue culture by such methods as electroporation, lipofection, calcium phosphate mediated transfection, or viral infection. Often, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler & Behr, (1993) *Meth. Enzymol.* 217:599–618; Cohen et al., (1993) *Meth. Enzymol.* 217:618–644; Cline, (1985) *Pharmac. Ther.* 29:69–92) and can be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. For example, recombinant blood cells (e.g., hematopoietic stem or progenitor cells) can be administered intravenously. The amount of cells envisioned for use depends on the desired effect, subject state, etc., and such a determination can be made by one of ordinary skill in the art, upon consideration of the present disclosure.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In one embodiment, the cell used for gene therapy is autologous to the subject.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple & Anderson, (1992) *Cell* 71:973–985; Rheinwald, (1980) *Meth. Cell Bio.* 21A:229; and Pittelkow & Scott, (1986) *Mayo Clinic Proc.* 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds and/or pharmaceutical compositions of the present invention are preferably tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a subject tissue sample. The effect of the compound or composition on the cell line and/or tissue sample can be determined utilizing techniques known to those of skill in the art including, but not limited to, rosette formation assays and cell lysis assays. In accordance with the present invention, in vitro assays that can be used to determine whether administration of a specific compound is indicated, include in vitro cell culture assays in which a subject tissue sample is grown in culture, and exposed to or otherwise administered a compound, and the effect of such compound upon the tissue sample is observed.

Therapeutic/Prophylactic Administration and Compositions

The present invention provides methods of treatment, inhibition and prophylaxis by administration to a subject of an effective amount of a compound or pharmaceutical composition of the present invention, for example an antibody of the present invention. In one aspect, the compound is substantially purified (e.g., substantially free from substances that limit its effect or produce undesired side-effects). The subject can be an animal, including, but not limited to, animals such as cows, pigs, horses, chickens, cats, dogs, rats mice, rabbits, monkeys, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Delivery Systems

Various delivery systems are known and can be used to administer a compound of the present invention, e.g., encapsulation in liposomes, microparticles, microcapsules, recombinant cells capable of expressing the compound, receptor-mediated endocytosis (see, e.g., Wu & Wu, (1987) *J. Biol. Chem.* 262:4429–4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds and/or compositions of the present invention can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it might be desirable to introduce the pharmaceutical compounds or compositions of the present invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it can be desirable to administer the pharmaceutical compounds and/or compositions of the present invention locally to the area in need of treatment. This can be achieved by, for example, and not by way of limitation, local infusion during surgery, topical application (e.g., in conjunction with a wound dressing after surgery), by injection, by means of a catheter, by means of a suppository, or by means of an implant, the implant being formed of a porous, non-porous, or gelatinous material, including membranes, such as sialastic membranes, or fibers. When administering a protein, including an antibody, of the present invention, care should be taken to use materials to which the protein does not absorb.

In another embodiment, a compound and/or composition can be delivered in a vesicle, in particular a liposome (see, e.g., Langer, (1990) *Science* 249:1527–1533; Treat et al., in *Liposomes in the Therapy of Infectious Disease and Cancer*, (Lopez-Berestein and Fidler, eds.), Alfred R. Liss, New York, N.Y., USA (1989) pp. 353–365; Lopez-Berestein, in *Liposomes in the Therapy of Infectious Disease and Cancer*, (Lopez-Berestein and Fidler, eds.), Alfred R. Liss, New York, N.Y., USA (1989) pp. 317–327; see generally *Liposomes in the Therapy of Infectious Disease and Cancer*, (Lopez-Berestein and Fidler, eds.), Alfred R. Liss, New York, N.Y., USA (1989)).

In yet another embodiment, the compound or composition can be delivered in a controlled release system. In one embodiment, a pump may be used (see, e.g., Langer, (1990) *Science* 249:1527–1533; Sefton, (1987) *CRC Crit. Ref. Biomed. Eng.* 14:201; Buchwald et al., (1980) *Surgery* 88:507; Saudek et al., (1989) *N. Engl. J. Med.* 321:574). In another embodiment, polymeric materials can be used (see, e.g., *Medical Applications of Controlled Release*, (Langer & Wise, eds.), CRC Press, Boca Raton, Fla., USA (1974); *Controlled Drug Bioavailability, Drug Product Design and Performance*, (Smolen and Ball, eds.), Wiley, New York, N.Y., USA (1984); Ranger & Peppas, (1983) *J. Macromol. Sci. Rev. Macromol. Chem.* 23:61; see also Levy et al., (1985) *Science* 228:190; During et al., (1989) *Ann. Neurol.* 25:351; Howard et al., (1989) *J. Neurosurg.* 71:105). In yet another embodiment, a controlled release system can be placed in proximity of the therapeutic target, i.e., the brain, thus requiring only a fraction of the systemic dose (see, e.g., Goodson, in *Medical Applications of Controlled Release*, (Langer & Wise, eds.), CRC Press, Boca Raton, Fla., USA (1974), vol. 2, pp. 115–138 (1984)). Other controlled release systems are discussed in the review by Langer (Langer, (1990) *Science* 249:1527–1533).

In a specific embodiment where a compound of the present invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; BIOLISTIC®, Dupont, Wilmington, Del., USA), or coating with lipids or cell-surface receptors or transfecting agents, or by administering it in linkage to a homeobox-like peptide which is known to enter the nucleus (see e.g., Joliot et al., (1991) *Proc. Natl. Acad. Sci. USA* 88:1864–1868), etc. Alternatively, a nucleic acid can be introduced intracellularly and incorporated within host cell DNA for expression, by homologous recombination.

Pharmaceutical Compositions

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water and water-based formulations are desirable carriers when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences*, (Gennaro, ed.) 20th ed., Mack Publishing, Easton, Pa., USA (2000). Such compositions will contain a therapeutically effective amount of the compound, for example in purified form, together with a suitable amount of carrier so as to provide the form for proper administration to the subject. The formulation should suit the mode of administration.

In one embodiment, a composition is formulated in accordance with routine procedures as a pharmaceutical composition adapted for intravenous administration to human beings. Typically, compositions for intravenous administration are solutions in sterile isotonic aqueous buffer. Where necessary, a composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a composition is to be administered by infusion, it can be dispensed with an infusion bottle containing sterile pharmaceutical grade water or saline. Where a composition is administered by injection, an ampoule of sterile water for injection or saline can be provided so that the ingredients may be mixed prior to administration.

The compounds of the present invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the present invention which will be effective in the treatment, inhibition and prevention of a disease or disorder associated with aberrant expression and/or activity of a polypeptide of the present invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

For antibodies, the dosage administered to a subject is typically 0.1 mg/kg to 100 mg/kg of the subject's body weight. Preferably, the dosage administered to a subject is between 0.1 mg/kg and 20 mg/kg of the subject's body weight, more preferably 1 mg/kg to 10 mg/kg of the subject's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the present invention might be reduced by enhancing uptake and tissue penetration (e.g., into the brain) of the antibodies by modifications such as, for example, lipidation.

The present invention also provides a pharmaceutical pack or kit comprising one or more containers filled with one or more of the ingredients of the pharmaceutical compositions of the present invention. Optionally a notice can be associated with such container(s) in the form prescribed by a governmental agency regulating the manufacture, use or sale of pharmaceuticals or biological products, which notice reflects approval by the agency of manufacture, use or sale for human administration. Such a notice can also provide guidance on how to use the pack or kit.

Diagnosis and Imaging with Antibodies

Labeled antibodies, and derivatives and analogs thereof, that specifically bind to a polypeptide of interest can be used for diagnostic purposes to detect, diagnose, or monitor diseases, disorders, and/or conditions associated with the aberrant expression and/or activity of a polypeptide of the present invention. The present invention provides for the detection of aberrant expression of a polypeptide of interest (e.g., SEQ ID NO:Y, and fragments thereof), comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The present invention provides a diagnostic assay for diagnosing a disorder, comprising: (a) assaying the expression of the polypeptide of interest in cells or body fluid of an individual using one or more antibodies specific to the polypeptide interest; and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type can allow health professionals to employ preventative measures or aggressive treatment earlier thereby preventing the development or further progression of the cancer.

Antibodies of the present invention can be used to assay protein levels in a biological sample using classical immunohistological methods known to those of ordinary skill in the art (see, e.g., Jalkanen et al., (1985) J. Cell. Biol. 101:976–985; Jalkanen et al., (1987) J. Cell. Biol. 105: 3087–3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

Another aspect of the present invention is the detection and diagnosis of a disease or disorder associated with aberrant expression of a polypeptide of interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to a polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest.

Background level can be determined by various methods including, comparing the amount of labeled molecule detected to a standard value previously determined for a particular system.

It will be understood in the art that the size of the subject and the imaging system used can determine, in part, the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described by Burchiel et al., in *Tumor Imaging: The Radiochemical Detection of Cancer*, (Burchiel & Rhodes, eds.), Masson Publishing Inc., New York, N.Y., USA (1982), Chapter 13.

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of a disease or disorder is carried out by repeating the method for diagnosing the disease or disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Upon consideration of the presnt disclosure, those of ordinary skill in the art will be able to determine the appropriate method for detecting a particular label. Methods and devices that can be used in the diagnostic methods of the present invention include, but are not limited to, computed tomography (CT), whole body scan such as position emission tomography (PET), magnetic resonance imaging (MRI), and sonography.

In a specific embodiment, the molecule is labeled with a radioisotope and is detected in the subject using a radiation responsive surgical instrument (U.S. Pat. No. 5,441,050). In another embodiment, the molecule is labeled with a fluorescent compound and is detected in the subject using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a subject using magnetic resonance imaging (MRI).

Kits of the Present Invention

The present invention provides kits that can be used in the methods disclosed herein. In one embodiment, a kit comprises an antibody of the present invention, for example a purified antibody, in one or more containers. In a specific embodiment, a kit of the present invention contains a substantially isolated polypeptide comprising an epitope that is specifically immunoreactive with an antibody included in the kit. A kit of the present invention can further comprise a control antibody that does not react with the polypeptide of interest. In another specific embodiment, a kit of the present invention comprises a means for detecting the binding of an antibody to a polypeptide of interest. For example, an antibody can be conjugated to a detectable substrate such as a fluorescent compound, an enzymatic substrate, a radioactive compound or a luminescent compound, or a second antibody that recognizes the first antibody may be conjugated to a detectable substrate.

In another specific embodiment of the present invention, a kit is a diagnostic kit for use in screening serum containing antibodies specific against proliferative and/or cancerous polynucleotides and polypeptides. Such a kit can comprise a control antibody that does not react with the polypeptide of interest. Such a kit can include a substantially isolated polypeptide antigen comprising an epitope that is specifically immunoreactive with at least one anti-polypeptide antigen antibody. Further, such a kit can include means for detecting the binding of said antibody to the antigen (e.g., the antibody can be conjugated to a fluorescent compound, such as fluorescein or rhodamine, which can be detected by flow cytometry). In specific embodiments, a kit can comprse a recombinantly produced or chemically synthesized polypeptide antigen. A polypeptide antigen of the kit can also be attached to a solid support.

In a more specific embodiment the detecting means of the above-described kit includes a solid support to which said polypeptide antigen is attached. Such a kit can also include a non-attached reporter-labeled anti-human antibody. In this embodiment, binding of the antibody to the polypeptide antigen can be detected via the binding of the reporter-labeled antibody.

In an additional embodiment, the present invention includes a diagnostic kit for use in screening serum containing antigens of a polypeptide of the present invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody can be a monoclonal antibody. The detecting means of the kit can also include a second, labeled monoclonal antibody. Alternatively, or in addition, the detecting means can include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Often, the reporter is an enzyme that is detected by incubating the solid phase in the presence of a suitable fluorometric, luminescent or colorimetric substrate (Sigma, St. Louis, Mo., USA).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can also be used in conjunction with biotinylated antigen(s).

Thus, the present invention provides an assay system or kit for carrying out this diagnostic method. Such a kit generally comprises a support with surface-bound recombinant antigens, and a reporter-labeled anti-human antibody for detecting surface-bound anti-antigen antibody.

Fusion Proteins

Any polypeptide of the present invention can be used to generate fusion (e.g., chimeric) proteins. For example, a polypeptide of the present invention, when fused to a second protein, can be used as an antigenic tag. Antibodies raised against a polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but can occur through linker sequences.

Moreover, fusion proteins can also be engineered to improve characteristics of a polypeptide of the present invention. For instance, a region of additional amino acids, particularly charged amino acids, can be added to the N-terminus of the polypeptide to improve stability and persistence during purification from the host cell or subsequent handling and storage. Peptide moieties can be added to the polypeptide to facilitate purification. Such regions can be removed prior to final preparation of the polypeptide. Similarly, peptide cleavage sites can be introduced between such peptide moieties, which could additionally be subjected to protease activity to remove said peptide(s) from a protein of the present invention. The addition of peptide moieties, including peptide cleavage sites, to facilitate handling of polypeptides are familiar and routine techniques will be known to those of ordinary skill in the art, upon consideration of the present disclosure.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. In some cases, these fusion proteins can facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., (1988) *Nature* 331:84–86). Fusion proteins having disulfide-linked dimeric structures (due to the IgG) can also be more efficient in binding and neutralizing other molecules, than the monomeric secreted protein or protein fragment alone (Fountoulakis et al., (1995) *J. Biochem.* 270:3958–3964).

Similarly, EP-A-O 464 533 (Canadian counterpart 2045869) discloses fusion proteins comprising various portions of the constant region of immunoglobulin molecules and another human protein or part thereof. In many cases, the Fc part of a fusion protein is beneficial in therapy and diagnosis, and thus can result in, for example, improved pharmacokinetic properties (see, e.g, EP-A 0232 262). Alternatively, deleting the Fc part after the fusion protein has been expressed, detected, and purified, would be desired. For example, the Fc portion can hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5 (see, e.g., Bennett et al., (1995) *J. Molecular Recognition* 8:52–58; Johanson et al., (1995) *J. Biol. Chem.* 270:9459–9471).

Moreover, the polypeptides of the present invention can be fused to marker sequences (also referred to as "tags"). Due to the availability of antibodies specific to such "tags", purification of the fused polypeptide of the present invention, and/or its identification is significantly facilitated since antibodies specific to the polypeptides of the present invention are not required. Such purification can be in the form of an affinity purification whereby an anti-tag antibody or another type of affinity matrix (e.g., anti-tag antibody attached to the matrix of a flow-thru column) that binds to the epitope tag is present. In one embodiment, the marker amino acid sequence is a hexa-histidine peptide, such as the tag provided in a pQE vector (Qiagen, Inc.), among others, many of which are commercially available. In one example, a hexa-histidine tag provides for convenient purification of the fusion protein (Gentz et al., (1989) *Proc. Natl. Acad. Sci. U.S.A.* 86:821–824). Another peptide tag useful for purification, the "HA" tag, corresponds to an epitope derived from the influenza hemagglutinin protein. (Wilson et al., (1984) *Cell* 37:767).

Those of ordinary skill in the art will be aware of other "tags" which could be readily substituted for the tags referred to herein for purification and/or identification of polypeptides of the present invention (see, e.g., Jones et al., (1995) *J Chromatogr A* 707(1):3–22). For example, the c-myc tag and the 8F9, 3C7, 6E10, G4m B7 and 9E10 antibodies thereto (Evan et al., (1985) *Mol. Cell. Biol.* 5:3610–3616); the Herpes Simplex virus glycoprotein D (gD) tag and its antibody (Paborsky et al., (1990) *Prot. Eng.* 3(6):547–553), the FLAG® tag (Sigma, St. Louis, Mo., USA)—i.e., the octapeptide sequence DYKDDDDK (SEQ ID NO:18), (Hopp et al., (1988) *Biotech.* 6:1204–1210); the KT3 epitope peptide (Martin et al., (1992) *Science* 255: 192–194); a-tubulin epitope peptide (Skinner et al., (1991) *J. Biol. Chem.* 266:15136–15166); the T7 gene 10 protein peptide tag (Lutz-Freyermuth et al., (1990) *Proc. Natl. Sci. USA* 87:6363–6397), the FITC epitope (Zymed, Inc., South San Francisco, Calif., USA), the GFP epitope (Zymed, Inc., South San Francisco, Calif., USA), and the rhodamine epitope (Zymed, Inc., South San Francisco, Calif., USA).

The present invention also encompasses the attachment of up to nine codons encoding a repeating series of up to nine arginine amino acids to the coding region of a polynucleotide of the present invention. The present invention also encompasses chemically derivitizing a polypeptide of the present invention with a repeating series of up to nine arginine amino acids. Such a tag, when attached to a polypeptide, can serve as a "universal pass", allowing compounds access to the interior of cells without additional derivitization or manipulation.

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc., South San Francisco, Calif., USA)). Due to the availability of monoclonal antibodies specific to such haptens, the protein could be readily purified using immunoprecipitation, for example.

Polypeptides of the present invention, including fragments and/or variants thereof, in addition to antibodies directed against such polypeptides, fragments, and/or variants, can be fused to any of a number of known, and yet to be determined, toxins, such as ricin, saporin (Mashiba et al., (1999) *Ann. N.Y. Acad. Sci.* 886:233–35), or HC toxin (Tonukari et al., (2000) *Plant Cell* 12(2):237–248), for example. Such fusions could be used to deliver the toxins to desired tissues for which a ligand or a protein capable of binding to the polypeptides of the present invention exists.

The present invention encompasses the fusion of antibodies directed against polypeptides of the present invention, including variants and fragments thereof, to a toxin for the purpose of delivering the toxin to specific locations in a cell, to specific tissues, and/or to specific species. Such bifunctional antibodies are known in the art, though a review describing additional advantageous fusions, including citations for methods of production, can be found in Hudson, (1999) *Curr. Opin. Immunol.* 11:548–557. In this context, the term "toxin" can be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. Upon consideration of the present disclosure, one of ordinary skill in the art could determine whether any particular "toxin" could be used in the compounds of the present invention. Examples of suitable "toxins" listed above are exemplary only and are not intended to limit the "toxins" that can be used in the present invention.

Thus, any of these above fusions can be engineered using the polynucleotides or the polypeptides of the present invention.

Vectors, Host Cells, and Protein Production

The present invention also relates to vectors comprising a polynucleotide of the present invention, host cells, and the production of polypeptides by recombinant techniques. A vector can be, for example, a phage, plasmid, viral, or retroviral vector. Retroviral vectors can be replication competent or replication defective. In the latter case, viral propagation generally will occur only in complementing host cells.

A polynucleotide can be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The polynucleotide insert can be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to those of ordinary skill in the art upon consideration of the present disclosure. The expression constructs can further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, an expression vector can comprise at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells will be known to those of ordinary skill in the art upon consideration of the present disclosure.

Representative vectors that can be employed in bacterial systems include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc. of La Jolla, Calif., USA; and ptrc99a, pKK223-3, pKK233-3, pDR540, pRIT5 available from Pharmacia Biotech, Inc of Peakpack, N.J., USA. Representative eukaryotic vectors are pWLNEO, pSV2CAT, pOG44, pXT1 and pSG available from Stratagene (La Jolla, Calif., USA); and pSVK3, pBPV, pMSG and pSVL available from Pharmacia (Peakpack, N.J., USA). Representative vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif., USA). Other suitable vectors will be readily apparent to those of ordinary skill in the art, upon consideration of the present disclosure.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology*, Appleton & Lange, (1995). It is specifically contemplated that the polypeptides of the present invention can in fact be expressed by a host cell lacking a recombinant vector.

A polypeptide of the present invention can be recovered and purified from recombinant cell cultures by known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Often, high performance liquid chromatography ("HPLC") techniques can be employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention can be glycosylated or can be non-glycosylated. In addition, polypeptides of the present invention can also include an initial modified methionine residue, in some cases as a result of host-mediated processes. Thus, it is known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

In one embodiment, the yeast Pichia pastoris is used to express a polypeptide of the present invention in a eukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris (see, e.g., Ellis et al., (1985) Mol. Cell. Biol. 5:1111–21; Koutz et al., Yeast 5:167–77 (1989); Tschopp et al., (1987) Nucl. Acids Res. 15:3859–76). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the present invention, as set forth herein, in a Pichia yeast system essentially as described in Pichia Protocols: Methods in Molecular Biology (Higgins & Cregg, eds.) The Humana Press, Totowa, N.J., USA (1998). This expression vector allows expression and secretion of a protein of the present invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one of ordinary skill in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the present invention into an expression vector such as, for example, pGAPZ or pGAPZalpha, and growing the yeast culture in the absence of methanol.

In addition to encompassing host cells containing the vector constructs discussed herein, the present invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with a polynucleotide of the present invention, and that activates, alters, and/or amplifies endogenous polynucleotides. For example, techniques known in the art can be used to operably associate heterologous control regions (e.g., promoter and/or enhancer) and endogenous polynucleotide sequences via homologous recombination, resulting in the formation of a new transcription unit (see, e.g., U.S. Pat. Nos. 5,641,670 and 5,733,761; PCT Publications WO 96/29411 and WO 94/12650; Koller et al., (1989) Proc. Natl. Acad. Sci. USA 86:8932–8935; and Zijlstra et al., (1989) Nature 342:435–438).

In addition, a polypeptide of the present invention can be chemically synthesized using techniques known in the art (see, e.g., Creighton, Proteins: Structures and Molecular Principles, W.H. Freeman & Co., New York, N.Y., USA (1983), and Hunkapiller et al., (1984) Nature 310:105–111). For example, a polypeptide corresponding to a fragment of a polypeptide sequence of the present invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The present invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the present invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides can also be modified with a detectable label, such as an enzymatic, fluorescent, isotopic or affinity label to allow for detection and isolation of the protein, the addition of epitope tagged peptide fragments (e.g., FLAG® tag (Sigma, St. Louis, Mo., USA; SEQ ID NO:18), HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Chemically Modified Derivatives

Also provided by the present invention are chemically modified derivatives of a polypeptide of the present invention that might provide additional advantages such as increased solubility, stability and circulating time of the polypeptide, or decreased immunogenicity (see U.S. Pat. No. 4,179,337). The chemical moieties for derivitization can be selected from water soluble polymers such as polyethylene glycol, ethylene glycol/propylene glycol copolymers, carboxymethylcellulose, dextran, polyvinyl alcohol and the like. A polypeptide can be modified at random positions within the molecule, or at predetermined positions within the molecule and can include one, two, three or more attached chemical moieties.

The present invention further encompasses chemical derivitization of a polypeptide of the present invention, preferably where the chemical is a hydrophilic polymer residue. Exemplary hydrophilic polymers, including derivatives, can be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers can vary, and is generally about 50 to about 5,000,000, with polymers having a molecular weight of about 100 to about 50,000 being preferred in some situations. The polymers can be branched or unbranched. Polymers having a molecular weight of about 150 to about 10,000 are preferred in some situations, with molecular weights of 200 to about 8,000 being preferred in other situations.

For polyethylene glycol, the preferred molecular weight is often, but not always, between about 1 kDa and about 100 kDa (the term "about" indicating that in preparations of polyethylene glycol, some molecules will weigh more, some less, than the stated molecular weight) for ease in handling and manufacturing. Other sizes can be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional polymers that can be used to derivatize polypeptides of the present invention, include, for example, poly(ethylene glycol) (PEG), poly(vinylpyrrolidine), polyoxomers, polysorbate and poly(vinyl alcohol), with PEG polymers being particularly preferred in many situations. Among the PEG polymers, PEG polymers having a molecular weight of from about 100 to about 10,000, from about 200 to about 8,000 can be employed, with PEG 2,000, PEG 5,000 and PEG 8,000, which have molecular weights of 2,000, 5,000 and 8,000, respectively, being preferred under many circumstances. Other suitable hydrophilic polymers, in addition to those exemplified above, will be readily apparent to one of ordinary skill in the art upon consideratoin of the present disclosure. Generally, the polymers used may include polymers that can be attached to the polypeptides of the present invention via alkylation or acylation reactions.

The polyethylene glycol molecules (or other chemical moieties) can be attached to the protein with consideration of effects on functional or antigenic domains of the protein. There are a number of attachment methods available to those skilled in the art, (see, e.g., EP 0 401 384 (coupling PEG to G-CSF), and Malik et al., (1992) *Exp. Hematol.* 20:1028–1035 (reporting pegylation of GM-CSF using tresyl chloride)). For example, polyethylene glycol can be covalently bound through amino acid residues via a reactive group, such as, a free amino or carboxyl group. Reactive groups are those to which an activated polyethylene glycol molecule can be bound. The amino acid residues having a free amino group can include lysine residues and the N-terminal amino acid residues; those having a free carboxyl group can include aspartic acid residues glutamic acid residues and the C-terminal amino acid residue. Sulfhydryl groups can also be used as a reactive group for attaching the polyethylene glycol molecules. For therapeutic purposes, attachment at an amino group, such as attachment at the N-terminus or lysine group, can be desirable.

One may specifically desire proteins chemically modified at the N-terminus. Using polyethylene glycol as an illustration of the present composition, one can select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) can be by purification of the N-terminally pegylated material from a population of pegylated protein molecules. Selective proteins chemically modified at the N-terminus modification can be formed by reductive alkylation, which exploits differential reactivity of different types of primary amino groups (lysine versus the N-terminus) available for derivatization in a particular protein. Under appropriate reaction conditions, substantially selective derivatization of the protein at the N-terminus with a carbonyl group containing polymer is achieved.

As with the various polymers exemplified above, the polymeric residues can comprise functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Non-limiting examples of materials that can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Representative saccharides that can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art upon consideration of the present disclosure. Generally, saccharides that can be used for derivitization include saccharides that can be attached to a polypeptide of the present invention via alkylation or acylation reactions.

Moreover, the present invention also encompasses derivitization of a polypeptide of the present invention, for example, with lipids (including cationic, anionic, polymerized, charged, synthetic, saturated, unsaturated, and any combination of the above, etc.) and stabilizing agents.

The present invention encompasses derivitization of the polypeptides of the present invention, for example, with compounds that can serve a stabilizing function (e.g., to increase the polypeptides half-life in solution, to make the polypeptides more water soluble, to increase the polypeptides hydrophilic or hydrophobic character, etc.). Representative polymers useful as stabilizing materials can be of natural, semi-synthetic (modified natural) or synthetic origin. Representative natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers.

Representative semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as PLURONICS®, commercially available from BASF, Parsippany, N.J., USA), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of a derivatized polypeptide of the present invention that employ polymers as stabilizing compounds will be readily apparent to those of ordinary skill in the art, in view of the present disclosure, when coupled with information known in the art, such as that described and referred to in U.S. Pat. No. 5,205,290.

Moreover, the present invention encompasses additional modifications of a polypeptide of the present invention. Such additional modifications are known in the art, and are specifically provided, in addition to methods of derivitization, etc., in U.S. Pat. No. 6,028,066.

Multimers

A polypeptide of the present invention can take the form of monomers or multimers (i.e., dimers, trimers, tetramers and higher multimers). Accordingly, the present invention relates to monomers and multimers of the polypeptides of the present invention, their preparation, and compositions (e.g., therapeutics) containing them. In specific embodiments, the polypeptides of the present invention are monomers, dimers, trimers or tetramers. In additional embodiments, the multimers of the present invention are at least dimers, at least trimers, or at least tetramers.

Multimers encompassed by the present invention may be homomers or heteromers. As used herein, the term "homomer", refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers can contain polypeptides having identical or different amino acid sequences. In a specific embodiment, a homomer of the present invention is a multimer containing only polypeptides having an identical amino acid sequence. In another specific embodiment, a homomer of the present invention is a multimer containing polypeptides having different amino acid sequences. In specific embodiments, a multimer of the present invention is a homodimer (e.g., containing polypeptides having identical or different amino acid sequences) or a homotrimer (e.g., containing polypeptides having identical and/or different amino acid sequences). In additional embodiments, the homomeric multimer of the present invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the present invention. In a specific embodiment, the multimer of the present invention is a heterodimer, a heterotrimer, or a heterotetramer. In additional embodiments, the heteromeric multimer of the present invention is at least a heterodimer, at least a heterotrimer, or at least a heterotetramer.

Multimers of the present invention can be the result of hydrophobic, hydrophilic, ionic and/or covalent associations and/or may be indirectly linked, by for example, liposome formation. Thus, in one embodiment, multimers of the present invention, such as, for example, homodimers or homotrimers, are formed when polypeptides of the present invention contact one another in solution. In another embodiment, heteromultimers of the present invention, such as, for example, heterotrimers or heterotetramers, are formed when polypeptides of the present invention contact antibodies to the polypeptides of the present invention (including antibodies to the heterologous polypeptide sequence in a fusion protein of the present invention) in solution. In other embodiments, multimers of the present invention are formed by covalent associations with and/or between polypeptides of the present invention. Such covalent associations can involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in a heterologous polypeptide sequence in a fusion protein of the present invention.

In one example, covalent associations are between the heterologous sequence contained in a fusion protein of the present invention (see, e.g., U.S. Pat. No. 5,478,925). In a specific example, the covalent associations are between the heterologous sequence contained in a Fc fusion protein of the present invention (as described herein). In another specific example, covalent associations of fusion proteins of the present invention are between heterologous polypeptide sequence from another protein that is capable of forming covalently associated multimers, such as for example, osteoprotegerin (see, e.g., PCT Publication WO 98/49305). In another embodiment, two or more polypeptides of the present invention are joined through peptide linkers. Examples include those peptide linkers described in U.S. Pat. No. 5,073,627. Proteins comprising multiple polypeptides of the present invention separated by peptide linkers can be produced using conventional recombinant DNA technology.

Another method for preparing multimer polypeptides of the present invention involves the use of polypeptides of the present invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., (1988) *Science* 240:1759), and have since been found in a variety of different proteins. Among the known leucine zippers are naturally occurring peptides and derivatives thereof that dimerize or trimerize. Examples of leucine zipper domains suitable for producing soluble multimeric proteins of the present invention are those described in PCT Publication WO 94/10308. Recombinant fusion proteins comprising a polypeptide of the present invention fused to a polypeptide sequence that dimerizes or trimerizes in solution are expressed in suitable host cells, and the resulting soluble multimeric fusion protein is recovered from the culture supernatant using techniques known to those of ordinary skill in the art.

Trimeric polypeptides of the present invention can offer the advantage of enhanced biological activity. Representative leucine zipper moieties and isoleucine moieties are those that preferentially form trimers. One example is a leucine zipper derived from lung surfactant protein D (SPD) (Hoppe et al., (1994) *FEBS Lett.* 344:191). Other peptides derived from naturally occurring trimeric proteins can be employed in preparing trimeric polypeptides of the present invention.

In another example, proteins of the present invention are associated by interactions between a FLAG® tag (Sigma, St. Louis, Mo., USA) contained in fusion proteins of the present invention containing a FLAG® tag sequence. In a further embodiment, associations proteins of the present invention are associated by interactions between heterologous polypeptide sequence contained in a FLAG® tag fusion proteins of the present invention and anti-FLAG® antibody.

Multimers of the present invention can be generated using chemical techniques known in the art. For example, for polypeptides desired to be contained in the multimers of the present invention can be chemically cross-linked using linker molecules and linker molecule length optimization techniques known in the art (see, e.g., U.S. Pat. No. 5,478, 925). Additionally, multimers of the present invention can be generated using techniques known in the art to form one or more inter-molecule cross-links between the cysteine residues located within the sequence of the polypeptides desired to be contained in the multimer (see, e.g., U.S. Pat. No. 5,478,925). Further, polypeptides of the present invention can be routinely modified by the addition of cysteine or biotin to the C terminus or N-terminus of the polypeptide, and techniques known in the art can be employed to generate multimers comprising one or more of these modified polypeptides (see, e.g., U.S. Pat. No. 5,478,925). Additionally, techniques known in the art can be applied to generate liposomes containing the polypeptide components desired to be contained in the multimer of the present invention (see, e.g., U.S. Pat. No. 5,478,925).

Alternatively, multimers of the present invention can be generated using genetic engineering techniques known in the art. In one embodiment, polypeptides contained in multimers of the present invention are produced recombinantly using fusion protein technology described herein or otherwise known in the art (see, e.g., U.S. Pat. No. 5,478, 925). In a specific embodiment, polynucleotides coding for a homodimer of the present invention are generated by ligating a polynucleotide sequence encoding a polypeptide of the present invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925). In another embodiment, recombinant techniques described herein or otherwise known in the art are applied to generate recombinant polypeptides of the present invention that contain a transmembrane domain (or hydrophobic or signal peptide) and that can be incorporated by membrane reconstitution techniques into liposomes (see, e.g., U.S. Pat. No. 5,478,925).

In addition, a polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. For example, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Representative Applications for the Polynucleotides of the Present Invention

Each of the polynucleotides identified herein can be used in numerous ways as reagents. The following description highlights only a few of the possible applications for the polynucleotides of the present invention. The described applications all employ techniques known to those of ordinary skill in the art, in conjunction with the polynucleotides of the present invention.

The polynucleotides of the present invention are useful for chromosome identification. There exists an ongoing need to identify new chromosome markers, since few chromosome-marking reagents, based on actual sequence data (repeat polymorphisms), are presently available. Each polynucleotide of the present invention can be used as a chromosome marker.

Briefly, sequences can be mapped to chromosomes by preparing PCR primers (e.g., about 15 to about 25 bp) from the sequences shown in SEQ ID NO:X. Primers can be selected using computer analysis so that primers do not span more than one predicted exon in the genomic DNA. These primers can then be used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique can use polynucleotides as short as about 500 or about 600 bases; however, polynucleotides 2,000–4,000 bp are typically employed. For a review of this technique, see Verma et al. (Verma et al., *Human Chromosomes: a Manual of Basic Techniques* Pergamon Press, New York, N.Y., USA (1988).

For chromosome mapping, the polynucleotides can be used individually (to mark a single chromosome or a single site on that chromosome) or in panels (for marking multiple sites and/or multiple chromosomes). Representative polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. For example, assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using a polynucleotide of the present invention. Any of these alterations (altered expression, chromosomal rearrangement, or mutation) can be used as a diagnostic or prognostic marker.

The present invention, therefore, also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

The term "measuring the expression level of a polynucleotide of the present invention" means qualitatively or quantitatively measuring or estimating the level of a polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). In one embodiment, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

The term "biological sample" means any biological sample obtained from an organism, body fluids, cell line, tissue culture, or other source which contains a polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) that contain a polypeptide of the present invention, and other tissue sources found to express a polypeptide of the present invention. Methods for obtaining tissue biopsies and body fluids from organisms are known in the art. Where the biological sample is to include mRNA, a tissue biopsy is a preferred source.

The method(s) provided herein can be applied in a diagnostic method and/or kits in which polynucleotides and/or polypeptides are attached to a solid support. In one representative method, the support is a "gene chip" or a "biological chip" as described in U.S. Pat. Nos. 5,837,832, 5,874,219, and 5,856,174. Further, such a gene chip, comprising polynucleotides of the present invention attached thereto, can be used to identify polymorphisms between the polynucleotide sequences, with polynucleotides isolated from a test subject. The knowledge of such polymorphisms (i.e. their location, as well as, their existence) can be beneficial in identifying disease loci for many disorders, including proliferative diseases and conditions. Such a method is described in U.S. Pat. Nos. 5,858,659 and 5,856,104.

The present invention encompasses polynucleotides of the present invention that are chemically synthesized, or reproduced as peptide nucleic acids (PNA), or according to other methods known in the art. The use of PNAs can be desirable if the polynucleotides are incorporated onto a solid support, or gene chip. For the purposes of the present invention, a peptide nucleic acid (PNA) comprises a polyamide type of DNA analog and the monomeric units for adenine, guanine, thymine and cytosine are available commercially (Perseptive Biosystems, Foster City, Calif., USA).

Certain components of DNA, such as phosphorus, phosphorus oxides, or deoxyribose derivatives, are not present in PNAs. PNAs bind specifically and tightly to complementary DNA strands and are not degraded by nucleases (Nielsen et al., (1991) *Science* 254:1497; and Egholm et al., (1993) *Nature* 365:666). In fact, PNA binds more strongly to DNA than DNA itself does. PNA/DNA duplexes also bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (Tm) by 8°–20° C., vs. 4°–16° C. for the DNA/DNA 15-mer duplex. Also, the absence of charged groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are known (Okano, (1991) *J. Neurochem.* 56: 560; *Oligodeoxynucleotides as Antisense Inhibitors of Gene Expression*, CRC Press, Boca Raton, Fla., USA (1988)). Triple helix formation is discussed, for instance, in Lee et al., (1979) *Nucl. Acid Res.* 6:3073; Cooney et al., (1988) *Science* 241:456; and Dervan et al., (1991) *Science* 251:1360. Both methods rely on binding of the polynucleotide to a complementary DNA or RNA. For these techniques, representative polynucleotides are usually oligonucleotides 20 to 40 bases in length and complementary to either the region of the gene involved in transcription (triple helix—Lee et al., (1979) *Nucl. Acid Res.* 6:3073; Cooney et al., (1988) *Science* 241: 456; and Dervan et al., (1991) *Science* 251: 1360) or to the mRNA itself (antisense—Okano, (1991) *J. Neurochem.* 56: 560; *Oligodeoxynucleotides as Antisense Inhibitors of Gene Expression*, CRC Press, Boca Raton, Fla., USA (1988)). Triple helix formation optimally results in a shut-off of RNA transcription from DNA, while antisense RNA hybridization blocks translation of a mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention (see, for example, Cutrona et al., (2000) *Nat. Biotechnol.* 18:300–303).

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention can be used to construct chimeric RNA/DNA oligonucleotides corresponding to said sequences, specifically designed to induce host cell mismatch repair mechanisms in an organism upon systemic injection, for example (Bartlett et al., (2000) *Nat. Biotechnol.* 18:615–622). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention can be used to construct duplex oligonucleotides corresponding to the sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see, e.g., EP 1007712).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organism's genome. These sequences can be used to prepare PCR primers for amplifying and isolating such selected DNA, which can then be sequenced. Using this technique, organisms can be identified because each organism will have a unique set of DNA sequences. Once a unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

Further, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Representative Applications for the Polypeptides of
the Present Invention

Each of the polypeptides identified herein can be used in numerous ways. The following description highlights only a few of the possible applications for the polynucleotides of the present invention. The described applicaitons all employ known techniques in conjunction with the polynucleotides of the present invention.

A polypeptide of the present invention can be used to assay protein levels in a biological sample using antibody-based techniques. For example, protein expression in tissues can be studied with classical immunohistological methods (Jalkanen et al., (1985) *J. Cell. Biol.* 101:976–985; Jalkanen et al., (1987) *J. Cell. Biol.* 105:3087–3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radio-isotopes, such as iodine ($^{125}$I, 121I), carbon ($^{14}$C), sulfur ($^{35}$S), tritium ($^{3}$H), indium ($^{112}$In), and technetium ($^{99}$Tc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the antibody by labeling of nutrients for the relevant hybridoma.

A protein-specific antibody or antibody fragment which has been labeled with an appropriate detectable imaging moiety, such as a radioisotope (for example, $^{131}$I, $^{112}$In, $^{99}$Tc), a radio-opaque substance, or a material detectable by nuclear magnetic resonance, is introduced (for example, parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described in *Tumor Imaging: The Radiochemical Detection of Cancer*, (Burchiel and Rhodes, eds.), Masson Publishing Inc., New York, N.Y., USA (1982), Chapter 13)

Thus, the present invention provides a diagnostic method of a disorder, comprising: (a) assaying the expression of a polypeptide of the present invention in cells or body fluid of an individual; and (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual can indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, subjects can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

Additionally, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the present invention that operatively linked to a promoter and any other genetic elements necessary for the expression of the polypeptide by the target tissue. Such gene therapy and delivery techniques are known in the art (see, for example, PCT Publication WO 90/11092).

Thus, for example, cells from a subject may be engineered with a polynucleotide (DNA or RNA) comprising a promoter operably linked to a polynucleotide of the present invention ex vivo, with the engineered cells then being provided to a subject to be treated with the polypeptide. Such methods are known in the art (see, e.g., Belldegrun et al., (1993) *J. Natl. Cancer Inst.* 85:207–216; Ferrantini et al., (1993) *Cancer Res.* 53:107–1112; Ferrantini et al., (1994) *J. Immunol.* 153: 4604–4615; Kaido et al., (1995) *Int. J. Cancer* 60: 221–229; Ogura et al., (1990) *Cancer Res.* 50:5102–5106; Santodonato et al., (1996) *Human Gene Therapy* 7:1–10; Santodonato et al., (1997) *Gene Therapy* 4:1246–1255; and Zhang et al., (1996) *Cancer Gene Therapy* 3:31–38). In one embodiment, the cells that are engineered are arterial cells. The arterial cells can be reintroduced into the subject through direct injection to the artery, the tissues surrounding the artery, or through catheter injection.

As discussed in more detail herein, a polynucleotide construct can be delivered by any method that delivers injectable materials to the cells of an animal, such as, injection into the interstitial space of tissues (heart, muscle, skin, lung, liver, and the like). The polynucleotide constructs can be delivered in a pharmaceutically acceptable liquid or aqueous carrier.

In one embodiment, a polynucleotide of the present invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the present invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859.

The polynucleotide vector constructs of the present invention used in the gene therapy method can comprise constructs that will not integrate into the host genome nor will they contain sequences that allow for replication. Representative vectors include pWLNEO, pSV2CAT, pOG44, pXT1 and pSG available from Stratagene (La Jolla, Calif., USA); pSVK3, pBPV, pMSG and pSVL available from Pharmacia (Peapack, N.J., USA); and pEF1/V5, pcDNA3.1, and pRc/CMV2 available from Invitrogen (Carlsbad, Calif., USA). Other suitable vectors will be readily apparent to those of ordinary skill in the art upon consideration of the present disclosure.

Any strong promoter known to those skilled in the art can be used for driving the expression of polynucleotide sequence of the present invention. Representative promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also can be the native promoter for the polynucleotides of the present invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the present invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is often, but not always, preferred for the reasons discussed below. Polynucleotides can be conveniently delivered by injection into the tissues comprising these cells. They can be delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. In some situations, the dosage will be from about 0.005 mg/kg to about 20 mg/kg and in other situatoins from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and can depend on the condition being treated and the route of administration.

Often, a preferred route of administration is by the parenteral route of injection into the interstitial space of tissues. However, other parenteral routes can also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides can be delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, a polynucleotide construct of the present invention is complexed in a liposome preparation. Representative liposomal preparations for use in the instant invention include cationic (positively charged), anionic (negatively charged) and neutral preparations. However, cationic liposomes are often preferred because a tight charge complex can be formed between the cationic liposome and the polyanionic nucleic acid. Cationic liposomes have been shown to mediate intracellular delivery of plasmid DNA (Felgner et al., (1987) Proc. Natl. Acad. Sci. U.S.A. 84:7413–7416); mRNA (Malone et al., (1989) Proc. Natl. Acad. Sci. U.S.A. 86:6077–6081); and purified transcription factors (Debs et al., (1990) J. Biol. Chem. 265:10189–10192) in functional form.

Cationic liposomes are readily available. For example, N[1-2,3-dioleyloxy)propyl]-N,N,N-triethylammonium (DOTMA) liposomes are particularly useful and are available under the trademark LIPOFECTIN®, from GIBCO BRL, Grand Island, N.Y., USA (see, also, Felgner et al., (1987) Proc. Natl. Acad. Sci. USA 84:7413–7416). Other commercially available liposomes include transfectace (DDAB/DOPE) and DOTAP/DOPE (Boehringer).

Other cationic liposomes can be prepared from readily available materials using techniques known in the art (see, e.g. PCT Publication WO 90/11092 for a description of the synthesis of DOTAP (1,2-bis(oleoyloxy)-3-(trimethylammonio)propane) liposomes). Preparation of DOTMA liposomes is also explained in the literature (see, e.g., Felgner et al., (1987) Proc. Natl. Acad. Sci. USA 84:7413–7416). Similar methods can be used to prepare liposomes from other cationic lipid materials.

Similarly, anionic and neutral liposomes are readily available, such as from Avanti Polar Lipids (Birmingham, Ala., USA), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, (e.g., using a Heat Systems (Plainsview, N.Y., USA) Model 350 sonicator equipped with an inverted cup (bath type) probe at the maximum setting) while the bath is circulated at 15° C. Alternatively, negatively charged vesicles can be prepared without sonication to produce multilamellar vesicles or by extrusion through nucleopore membranes to produce unilamellar vesicles of discrete size. Other methods are known and available to those of ordinary skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods known in the art (see, e.g., Straubinger et al., (1983) *Method. Immunol.* 101:512–527). For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., (1975) *Biochim. Biophys. Acta* 394:483; Wilson et al., (1979) *Cell* 17:77); ether injection (Deamer et al., (1976) *Biochim. Biophys. Acta* 443:629; Ostro et al., (1977) *Biochem. Biophys. Res. Commun.* 76:836; Fraley et al., (1979) *Proc. Natl. Acad. Sci. USA* 76:3348); detergent dialysis (Enoch et al., (1979) *Proc. Natl. Acad. Sci. USA* 76:145); and reverse-phase evaporation (REV) (Fraley et al., (1980) *J. Biol. Chem.* 255:10431; Szoka et al., (1978) *Proc. Natl. Acad. Sci. USA* 75:145; Schaefer-Ridder et al., (1982) *Science* 215:166).

In one embodiment, the ratio of DNA to liposomes can be from about 10:1 to about 1:10. In other embodiments, the ratio can be from about 5:1 to about 1:5. In yet other embodiments, the ratio can be from about 3:1 to about 1:3. In still further embodiments, the ratio can be about 1:1.

U.S. Pat. No. 5,676,954 reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and PCT Publication WO 94/9469 provide cationic lipids for use in transfecting DNA into cells and mammals. U.S. Pat. Nos. 5,589,466, 5,693,622, 5,580,859, 5,703,055, and PCT Publication WO 94/9469 provide methods for delivering DNA-cationic lipid complexes to mammals.

In certain embodiments, cells are engineered, ex vivo or in vivo, using a retroviral particle containing RNA that comprises a sequence encoding polypeptides of the present invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

A retroviral plasmid vector can be employed to transduce packaging cell lines to form producer cell lines. Examples of packaging cells that can be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, (1990) *Human Gene Therapy*, 1:5–14. A vector can transduce the packaging cells through any means known in the art. Such means include, but are not limited to, electroporation, the use of liposomes, and $CaPO_4$ precipitation. In one alternative, the retroviral plasmid vector can be encapsulated into a liposome, or coupled to a lipid, and then administered to a host.

The producer cell line generates infectious retroviral vector particles, including polynucleotides encoding polypeptides of the present invention. Such retroviral vector particles can then be employed, to transduce eukaryotic cells, either in vitro or in vivo. The transduced eukaryotic cells will then express the polypeptides of the present invention.

In certain other embodiments, cells are engineered, ex vivo or in vivo, with polynucleotides of the present invention contained in an adenovirus vector. Adenovirus can be manipulated such that it encodes and expresses polypeptides of the present invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., (1974) *Am. Rev. Respir. Dis.* 109:233–238). Additionally, adenovirus mediated gene transfer has been demonstrated in a number of instances including transfer of alpha-1-antitrypsin and CFTR to the lungs of cotton rats (Rosenfeld et al., (1991) *Science* 252:431–434; Rosenfeld et al., (1992) *Cell* 68:143–155). Furthermore, extensive studies to attempt to establish adenovirus as a causative agent in human cancer were uniformly negative (Green et al., (1979) *Proc. Natl. Acad. Sci. U.S.A.* 76:6606).

Suitable adenoviral vectors useful in the present invention are known (see, e.g., Kozarsky & Wilson, (1993) *Curr. Opin. Genet. Devel.* 3:499–503; Rosenfeld et al., (1992) *Cell* 68:143–155; Engelhardt et al., (1993) *Human Genet. Ther.* 4:759–769; Yang et al., (1994) *Nature Genet.* 7:362–369; Wilson et al., (1993) *Nature* 365:691–692; and U.S. Pat. No. 5,652,224). For example, the adenovirus vector Ad2 is useful and can be grown in human embryonic kidney 293 (HEK293) cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Adenoviruses used in the present invention can be replication deficient. Replication deficient adenoviruses require the aid of a helper virus and/or packaging cell line to form infectious particles. The resulting virus is capable of infecting cells and can express a polynucleotide of interest that is operably linked to a promoter, but cannot replicate in most cells. Replication deficient adenoviruses can be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, (1992) *Curr. Topics in Microbiol. Immunol.* 158:97). It is also one of the few viruses that may integrate its DNA into non-dividing cells. Vectors containing as little as about 300 base pairs of AAV can be packaged and can integrate, but space for exogenous DNA is limited to about 4.5 kb. Methods for producing and using such AAVs are known in the art (see, for example, U.S. Pat. Nos. 5,139,941, 5,173,414, 5,354,678, 5,436,146, 5,474,935, 5,478,745, and 5,589,377).

In one example, an appropriate AAV vector for use in the present invention can include all the sequences necessary for DNA replication, encapsidation, and host-cell integration. A polynucleotide construct containing polynucleotides of the present invention is inserted into the AAV vector using standard cloning methods (see, e.g., Sambrook et al., *Molecular Cloning: A Laboratory Manual*, (3$^{rd}$ ed.) Cold Spring Harbor Laboratory Press, Cold Spring Harbor, N.Y., USA (2001)). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain a polynucleotide construct of the present invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670; PCT Publication WO 96/29411; PCT Publication WO 94/12650; Koller et al., (1989) *Proc. Natl. Acad. Sci. U.S.A.* 86:8932–8935; and Zijlstra et al., (1989) *Nature* 342:435–438). This method involves the activation of a gene that is present in the target cells, but is not normally expressed in the cells, or is expressed at a lower level than desired.

Polynucleotide constructs are made, using standard techniques known in the art, that contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. In one embodiment, the amplified promoter comprises distinct restriction enzyme sites on the 5' and 3' ends. For example, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. These methods are described herein.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

Polynucleotides encoding polypeptides of the present invention can be administered along with other polynucleotides encoding angiogenic proteins. Representative angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

A polynucleotide encoding a polypeptide of the present invention can contain a secretory signal sequence that facilitates secretion of the protein. Often, the signal sequence is positioned in the coding region of the polynucleotide to be expressed towards or at the 5' end of the coding region. The signal sequence can be homologous or heterologous to the polynucleotide of interest and may be homologous or heterologous to the cells to be transfected. Additionally, the signal sequence can be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., (1989) *Science* 243:375).

A representative method of local administration is by direct injection. For example, a recombinant molecule of the present invention complexed with a delivery vehicle can be administered by direct injection into or locally within the area of arteries. Administration of a composition "locally within the area of arteries" refers to injecting the composition centimeters and preferably, millimeters within arteries.

Another method of local administration is to contact a polynucleotide construct of the present invention in or around a surgical wound. For example, a subject can undergo surgery and the polynucleotide construct can be coated on the surface of tissue inside the wound or the construct can be injected into areas of tissue inside the wound.

Therapeutic compositions useful in systemic administration, can comprise recombinant molecules of the present invention complexed to a targeted delivery vehicle of the present invention. Suitable delivery vehicles for use with systemic administration comprise liposomes comprising ligands for targeting the vehicle to a particular site.

Representative methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., (1992) *Proc. Natl. Acad. Sci. U.S.A.* 189:11277–11281). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Representative mammals include humans, dogs, cats, rats, mice, rats, rabbits sheep, cattle, horses and pigs, with humans being particularly preferred.

Testing for a Biological Activity

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention can be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions can be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions associated with NF-kB. NF-kB is a central regulator of inflammation, cell growth, differentiation, and survival. Therefore, a polynucleotide, polypeptide, agonist or antagonist of the present invention could be used to treat a condition characterized by aberrant cell growth, differentiation or survival, and inflammation, such as rheumatoid arthritis, osteoarthritis, inflammatory bowel disease, lupus, atherosclerosis, stroke, cancer.

A polynucleotide, polypeptide, agonist or antagonist of the present invention could also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotide, polypeptide, agonist or antagonist of the present invention that inhibits an immune response, and could be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated, prevented, and/or diagnosed by a polynucleotide, polypeptide, agonist or antagonist of the present invention. Moreover, these molecules may be used to treat anaphylaxis, hypersensitivity to an antigenic molecule, or blood group incompatibility.

A polynucleotide, polypeptide, agonist or antagonist of the present invention might also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotide, polypeptide, agonist or antagonist of the present invention that inhibits an immune response, particularly the proliferation, differentiation, or chemotaxis of T-cells, can be an effective therapy in preventing organ rejection or GVHD.

Similarly, a polynucleotide, polypeptide, agonist or antagonist of the present invention might also be used to modulate inflammation. For example, the polynucleotide, polypeptide, agonist or antagonist might inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotide, polypeptide, agonist or antagonist of the present invention can be used to treat, prevent, and/or diagnose hyperproliferative diseases, disorders, and/or conditions, including neoplasms. A polynucleotide, polypeptide, agonist or antagonist of the present invention can inhibit the proliferation of the disorder through direct or indirect interactions. Alternatively, a polynucleotides or polypeptides, or agonists or antagonists of the present invention can proliferate other cells that can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response can be increased by either enhancing an existing immune response, or by initiating a new immune response. Alternatively, decreasing an immune response can also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by a polynucleotide, polypeptide, agonist or antagonist of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotide, polypeptide, agonist or antagonist of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One embodiment of the present invention utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a representative embodiment, a polynucleotide of the present invention is a DNA construct comprising a recombinant expression vector effective in expressing a DNA sequence encoding the polynucleotide. In another embodiment of the present invention, a DNA construct encoding the polynucleotides of the present invention is inserted into cells to be treated utilizing a retrovirus, or an adenoviral vector (see Nabel et. al., (1999) Proc. Natl. Acad. Sci. U.S.A. 96: 324–326). In yet another embodiment, the viral vector is defective and will not transform non-proliferating cells, only proliferating cells. Moreover, a polynucleotide of the present invention inserted into proliferating cells either alone, or in combination with or fused to other polynucleotides, can then be modulated via an external stimulus (i.e. magnetic, specific small molecule, chemical, or drug administration, etc.), that acts upon the promoter upstream of said polynucleotides to induce expression of the encoded protein product. As such, a beneficial therapeutic affect of the present invention can be expressly modulated (i.e. to increase, decrease, or inhibit expression of the present invention) based upon an external stimulus.

Polynucleotides of the present invention may be useful in repressing expression of oncogenic genes or antigens. The term "repressing expression of the oncogenic genes" encompasses the suppression of the transcription of the gene, the degradation of the gene transcript (pre-message RNA), the inhibition of splicing, the destruction of the messenger RNA, the prevention of the post-translational modifications of the protein, the destruction of the protein or the inhibition of the normal function of the protein.

For local administration to abnormally proliferating cells, a polynucleotide of the present invention can be administered by any method known to those of skill in the art including, but not limited to transfection, electroporation, microinjection of cells, or in vehicles such as liposomes, lipofectin, or as naked polynucleotides, or any other method described herein. A polynucleotide of the present invention can be delivered by known gene delivery systems such as, but not limited to, retroviral vectors (Gilboa, (1982) J. Virology 44:845; Hocke, (1986) Nature 320:275; Wilson et al., Proc. Natl. Acad. Sci. U.S.A. 85:3014), vaccinia virus system (Chakrabarty et al., (1985) Mol. Cell Biol. 5:3403) or other efficient DNA delivery systems (see, e.g., Yates et al., (1985) Nature 313:812) known to those of ordinary skill in the art. In order to specifically deliver or transfect cells which are abnormally proliferating and spare non-dividing cells, it is often preferable to utilize a retrovirus, or adenoviral (as described in the art and herein) delivery system known to those of ordinary skill in the art. Since host DNA replication is required for retroviral DNA to integrate and the retrovirus will be unable to self-replicate due to the lack of the retrovirus genes needed for its life cycle. Utilizing such a retroviral delivery system for polynucleotides of the present invention will target the gene and constructs to abnormally proliferating cells, and will spare the non-dividing normal cells.

A polynucleotide of the present invention can be delivered directly to cell proliferative disorder/disease sites in internal organs, body cavities and the like by use of imaging devices used to guide an injecting needle directly to the disease site. A polynucleotide of the present invention can also be administered to disease sites at the time of surgical intervention.

By "cell proliferative disease" is meant any human or animal disease or disorder, affecting any one or any combination of organs, cavities, or body parts, that is characterized by single or multiple local abnormal proliferations of cells, groups of cells, or tissues, whether benign or malignant.

Any amount of a polynucleotide of the present invention can be administered as long as it has a biologically inhibiting effect on the proliferation of the treated cells. Moreover, it is possible to administer more than one polynucleotide of the present invention simultaneously to the same site. By "biologically inhibiting" is meant partial or total growth inhibition as well as decreases in the rate of proliferation or growth of the cells. A biologically inhibitory dose can be determined by assessing the effects of a polynucleotide of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, subject for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies can be provided in pharmaceutically acceptable compositions as known in the art or as described herein.

A summary of some of the ways in which the antibodies of the present invention can be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail herein. Upon consideration of the present disclosure, one of ordinary skill in the art will know how to use the antibodies of the present invention for diagnostic, monitoring or therapeutic purposes.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of the present invention can be advantageously employed in combination with other monoclonal or chimeric antibodies, or with lymphokines or hematopoietic growth factors, for example, which serve to increase the number or activity of effector cells that interact with the antibodies.

It can be desirable to use high affinity and/or potent in vivo inhibiting and/or neutralizing antibodies against polypeptides or polynucleotides of the present invention, or fragments or regions thereof, for both immunoassays directed to, and therapy of, diseases, disorders, and/or conditions related to polynucleotides or polypeptides, including fragments thereof, of the present invention. Such antibodies, fragments, or regions, can have an affinity for polynucleotides or polypeptides, including fragments thereof. As noted hereinabove, representative binding affinities include those with a dissociation constant or Kd less than about $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $1 \times 10^{-5}$ M, $5 \times 10^{-6}$ M, $1 \times 10^{-6}$ M, $5 \times 10^{-7}$ M, $1 \times 10^{-7}$ M, $5 \times 10^{-8}$ M, $1 \times 10^{-8}$ M, $5 \times 10^{-9}$ M, $1 \times 10^{-9}$ M, $5 \times 10^{-10}$ M, $1 \times 10^{-10}$ M, $5 \times 10^{-11}$ M, $1 \times 10^{-11}$ M, $5 \times 10^{-12}$ M, $10^{-12}$ M, $5 \times 10^{-13}$ M, $1 \times 10^{-14}$ M, $5 \times 10^{-14}$ M, $1 \times 10^{-14}$ M, $5 \times 10^{-15}$ M, or $1 \times 10^{-15}$ M.

In another embodiment, the present invention provides a method of delivering compositions containing a polypeptide of the present invention (e.g., compositions containing polypeptides or polypeptide antibodies associated with heterologous polypeptides, heterologous nucleic acids, toxins, or prodrugs) to targeted cells expressing a polypeptide of the present invention. A polypeptide or polypeptide antibody of the present invention can be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention "vaccinated" the immune response to respond to proliferative antigens and immunogens, or indirectly, such as in activating the expression of proteins known to enhance the immune response (e.g. chemokines), to said antigens and immunogens.

Chemotaxis

A polypeptide, polynucleotide, agonist and/or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polypeptide, polynucleotide, agonist and/or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polypeptide, polynucleotide, agonist and/or antagonist of the present invention may inhibit chemotactic activity. These molecules could also be used to treat, prevent, and/or diagnose diseases, disorders, and/or conditions. Thus, a polypeptide, polynucleotide, agonist and/or antagonist of the present invention could be used as an inhibitor of chemotaxis.

Binding Activity

A polypeptide of the present invention may be used to screen for molecules that bind to the polypeptide, or for molecules to which the polypeptide binds. The binding of the polypeptide and the molecule could activate (agonist), increase, inhibit (antagonist), or decrease activity of the polypeptide or the molecule bound. Examples of such molecules include antibodies, oligonucleotides, proteins (e.g., receptors), or small molecules.

In one example, the molecule is closely related to the natural ligand of the polypeptide, e.g., a fragment of the ligand, or a natural substrate, a ligand, a structural or functional mimetic (see, e.g., Coligan et al., *Current Protocols in Immunology* Greene Publishing Associates and Wiley Interscope, New York, New or, USA 1(2):Chapter 5 (2001)). Similarly, the molecule can be closely related to the natural receptor to which the polypeptide binds, or at least, a fragment of the receptor capable of being bound by the polypeptide (e.g., active site). In either case, the molecule can be rationally designed using techniques known to those of ordinary skill in the art.

In one example, the screening for these molecules involves producing appropriate cells that express the polypeptide, either as a secreted protein or on the cell membrane. Representative cells include cells from mammals, yeast, *Drosophila*, or *E. coli*. Cells expressing the polypeptide (or cell membrane containing the expressed polypeptide) are then contacted with a test compound potentially containing the molecule to observe binding, stimulation, or inhibition of activity of either the polypeptide or the molecule.

The assay can simply test binding of a candidate compound to the polypeptide, wherein binding is detected by a label, or in an assay involving competition with a labeled competitor. Further, the assay can test whether the candidate compound results in a signal generated by binding to the polypeptide.

Alternatively, the assay can be carried out using cell-free preparations, polypeptide/molecule affixed to a solid support, chemical libraries, or natural product mixtures. The assay can also simply comprise the steps of mixing a candidate compound with a solution containing a polypeptide, measuring polypeptide/molecule activity or binding, and comparing the polypeptide/molecule activity or binding to a standard.

For example, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, a receptor to which a polypeptide of the present invention binds can be identified by numerous methods known to those of skill in the art, for example, ligand panning and FACS sorting (Coligan et al., *Current Protocols in Immunology* Greene Publishing Associates and Wiley Interscope, New York, New or, USA 1(2), Chapter 5, (1991)). For example, expression cloning is employed wherein polyadenylated RNA is prepared from a cell responsive to the polypeptides and a cDNA library created from this RNA is divided into pools and used to transfect COS cells or other cells that are not responsive to the polypeptides. Transfected cells which are grown on glass slides are exposed to a polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor.

As an alternative approach for receptor identification, a labeled polypeptide can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the present invention thereby effectively generating agonists and antagonists of polypeptides of the present invention (see generally, U.S. Pat. Nos. 5,605,793, 5,811,238, 5,830,721, 5,834,252, and 5,837,458, and Patten et al., (1997) *Curr. Opinion Biotechnol.* 8:724–33; Harayama, (1998) *Trends Biotechnol.* 16(2): 76–82; Hansson et al., (1999) *J. Mol. Biol.* 287:265–76 (1999); and Lorenzo & Blasco, (1998) *Biotechniques* 24(2): 308–13). In one embodiment, alteration of polynucleotides and corresponding polypeptides of the present invention can be achieved by DNA shuffling. DNA shuffling involves the assembly of two or more DNA segments into a desired polynucleotide sequence of the present invention molecule by homologous, or site-specific, recombination. In another embodiment, polynucleotides and corresponding polypeptides of the present invention can be altered by being subjected to random mutagenesis by error-prone PCR, random nucleotide insertion or other methods prior to recombination. In another embodiment, one or more components, motifs, sections, parts, domains, fragments, etc., of the polypeptides of the present invention can be recombined with one or more components, motifs, sections, parts, domains, fragments, etc. of one or more heterologous molecules. In representative embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other representative fragments are biologically active fragments of a polypeptide of the present invention. Biologically active fragments are those exhibiting activity similar, but not necessarily identical, to an activity of the polypeptide. The biological activity of the fragments can include an improved desired activity, or a decreased undesirable activity.

Additionally, this invention provides a method of screening compounds to identify those that modulate the action of a polypeptide of the present invention. An example of such an assay comprises combining a mammalian fibroblast cell, a polypeptide of the present invention, the compound to be screened and $^3$H thymidine under cell culture conditions where the fibroblast cell would normally proliferate. A control assay can be performed in the absence of the compound to be screened and compared to the amount of fibroblast proliferation in the presence of the compound to determine if the compound stimulates proliferation by determining the uptake of $^3$H thymidine in each case. The amount of fibroblast cell proliferation is measured by liquid scintillation chromatography, which measures the incorporation of $^3$H thymidine. Both agonist and antagonist compounds can be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a subject (e.g., blood vessel growth) by activating or inhibiting the polypeptide/molecule. Moreover, the assays can discover agents that can inhibit or enhance the production of the polypeptides of the present invention from suitably manipulated cells or tissues. Therefore, the present invention includes a method of identifying compounds that bind to the polypeptides of the present invention comprising the steps of: (a) incubating a candidate binding compound with the polypeptide; and (b) determining if binding has occurred. Moreover, the present invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules that bind a polypeptide of the present invention experimentally by using the beta-pleated sheet regions contained in the polypeptide sequence of the protein. Accordingly, specific embodiments of the present invention are directed to polynucleotides encoding polypeptides which comprise, or alternatively consist of, the amino acid sequence of each beta pleated sheet region in a disclosed polypeptide sequence. Additional embodiments of the present invention are directed to polynucleotides encoding polypeptides that comprise, or alternatively consist of, any combination or all of contained in the polypeptide sequences of the present invention. Additional preferred embodiments of the present invention are directed to polypeptides that comprise, or alternatively consist of, the amino acid sequence of each of the beta pleated sheet regions in one of the polypeptide sequences of the present invention. Additional embodiments of the present invention are directed to polypeptides that comprise, or alternatively consist of, any combination, or all, of the beta pleated sheet regions in one of the polypeptide sequences of the present invention.

Targeted Delivery

In another embodiment, the present invention provides a method of delivering compositions to targeted cells expressing a receptor for a polypeptide of the present invention, or cells expressing a cell bound form of a polypeptide of the present invention.

As discussed herein, polypeptides or antibodies of the present invention can be associated with heterologous polypeptides, heterologous nucleic acids, toxins, or prodrugs via hydrophobic, hydrophilic, ionic and/or covalent interactions. In one embodiment, the present invention provides a method for the specific delivery of compositions of the present invention to cells by administering polypeptides of the present invention (including antibodies) that are associated with heterologous polypeptides or nucleic acids. In one example, the present invention provides a method for delivering a therapeutic protein into the targeted cell. In another example, the present invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the present invention provides a method for the specific destruction of cells (e.g., the destruction of tumor cells) by administering a polypeptide of the present invention (e.g., a polypeptide of the present invention or antibodies to a polypeptide of the present invention) in association with toxins or cytotoxic prodrugs.

Drug Screening

Another aspect of the present invention is the use of the polypeptides of the present invention, or the polynucleotides encoding these polypeptides, to screen for molecules that modify the activities of the polypeptides of the present invention. Such a method would include contacting a polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test can be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One can measure, for example, the formulation of complexes between the agent being tested and a polypeptide of the present invention.

Thus, the present invention provides methods of screening for drugs or any other agents that affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to a polypeptide of the present invention.

Another technique for drug screening provides high throughput screening for compounds having suitable binding affinity to the polypeptides of the present invention, and is described in great detail in European Patent Application 84/03564. Briefly stated, large numbers of different small peptide test compounds are synthesized on a solid substrate, such as plastic pins or some other surface. The peptide test compounds are reacted with one or more polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide that shares one or more antigenic epitopes with a polypeptide of the present invention.

The HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptides and/or peptides of the present invention, or immunogenic fragments or oligopeptides thereof, can be used for screening therapeutic drugs or compounds in a variety of drug screening techniques. The fragment employed in such a screening assay can be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y), or a bindable peptide fragment, of this invention, comprising (a) providing a plurality of compounds, (b) combining the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, or a bindable peptide fragment, with each of a plurality of compounds for a time sufficient to allow binding under suitable conditions and (c) detecting binding of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or peptide to each of the plurality of test compounds, thereby identifying the compounds that specifically bind to the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or peptide.

Methods of identifying compounds that modulate the activity of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptides and/or peptides are provided by the present invention and comprise (a) combining a potential or candidate compound or drug modulator of GBP biological activity with an HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or peptide, for example, the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) amino acid sequence as set forth in SEQ ID NO:Y, and (b) measuring an effect of the candidate compound or drug modulator on the biological activity of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) or fragment thereof. Such measurable effects include, for example, physical binding interaction; the ability to cleave a suitable GBP substrate; effects on native and cloned HGBPBMY1 (AK096141), HGBPBMY2 (4843 30 1 1; 4843_1), HGBPBMY3 (4843 30 2 1; 4843_2), HGBPBMY4 (FLJ 10961), MGBPBMY1 (LOC229900), MGBPBMY2 (LOC229902), MGBPBMY3 (BC031475) and/or MGBPBMY4 (BC007143)-expressing cell line; and effects of modulators or other GBP-mediated physiological measures.

The host cell can also be capable of being induced to express a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y), e.g., via inducible expression. Physiological effects of a given modulator candidate on the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) can also be measured. Thus, cellular assays for particular GBP modulators can be either direct measurement or quantification of the physical biological activity of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y), or they can be measurement or quantification of a physiological effect. Such methods preferably employ a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) as described herein, or an overexpressed recombinant HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) in suitable host cells containing an expression vector as described herein, wherein the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) is expressed, overexpressed, or undergoes upregulated expression.

Another aspect of the present invention embraces a method of screening for a compound that is capable of modulating the biological activity of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y), comprising (a) providing a host cell containing an expression vector harboring a nucleic acid sequence encoding a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y), or a functional peptide or portion thereof; (b) determining the biological activity of the expressed HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide in the absence of a modulator compound; and (c) contacting the cell with the modulator compound and determining the biological activity of the expressed HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide in the presence of the modulator compound. In such a method, a difference between the activity of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide in the presence of the modulator compound and in the absence of the modulator compound indicates a modulating effect of the compound.

Essentially any chemical compound can be employed as a potential modulator or ligand in the assays according to the present invention. Compounds tested as GBP modulators can be any small chemical compound, or biological entity (e.g., protein, carbohydrate, nucleic acid, lipid, etc.). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo., USA), Aldrich (St. Louis, Mo., USA), Sigma-Aldrich (St. Louis, Mo., USA), and Fluka Chemika-Biochemica Analytika (Buchs, Switzerland), for example. Also, compounds can be synthesized by methods known in the art.

High throughput screening methodologies are particularly envisioned for the detection of modulators of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polynucleotides (e.g., SEQ ID NO:X) and polypeptides (e.g., SEQ ID NO:Y) described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

Methods of preparating and screening combinatorial chemical libraries are known to those of ordinary skill in the art. Combinatorial libraries include, but are not limited to, peptide libraries (see, e.g. U.S. Pat. No. 5,010,175; Furka, (1991) *Int. J. Pept. Prot. Res.* 37:487–493; and Houghton et al., (1991) *Nature* 354:84–88). Other chemistries for generating chemical diversity libraries can also be used. Nonlimiting examples of chemical diversity library chemistries include, peptides (PCT Publication WO 91/019735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., (1993) *Proc. Natl. Acad. Sci. USA* 90:6909–6913), vinylogous polypeptides (Hagihara et al., (1992) *J. Amer. Chem. Soc.* 114:6568), nonpeptidal peptidomimetics with glucose scaffolding (Hirschmann et al., (1992) *J. Amer. Chem. Soc.* 114:9217–9218), analogous organic synthesis of small compound libraries (Chen et al., (1994) *J. Am. Chem. Soc.* 116:2661), oligocarbamates (Cho et al., (1993) *Science,* 261:1303), and/or peptidyl phosphonates (Campbell et al., (1994) *J. Org. Chem.,* 59:658), nucleic acid libraries (see Ausubel, Berger and Sambrook, all referenced herein), peptide nucleic acid libraries (U.S. Pat. No. 5,539,083), antibody libraries (e.g., Vaughn et al., (1996) *Nature Biotechnol.* 14(3):309–314) and PCT Publication US96/10287), carbohydrate libraries (e.g., Liang et al., (1996) *Science* 274–1520–1522) and U.S. Pat. No. 5,593,853), small organic molecule libraries (e.g., benzodiazepines, Baum, C&EN, Jan. 18, 1993, page 33; and U.S. Pat. No. 5,288, 514); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); and morpholino compounds (U.S. Pat. No. 5,506,337; and the like).

Devices for the preparation of combinatorial libraries are commercially available (e.g., 357 MPS, 390 MPS, Advanced Chem Tech, Louisville Ky., USA; SYMPHONY®, Rainin, Woburn, Mass., USA; 433A Applied Biosystems, Foster City, Calif., USA; and the 9050 Plus, Millipore, Bedford, Mass., USA). In addition, a large number of combinatorial libraries are commercially available (e.g., ComGenex, Princeton, N.J., USA; Asinex, Moscow, Russia; Tripos, Inc., St. Louis, Mo., USA; ChemStar, Ltd., Moscow, Russia; 3D Pharmaceuticals, Exton, Pa.; Martek Biosciences, Columbia, Md., USA, and the like).

In one embodiment, the present invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another aspect, the present invention encompasses screening and small molecule (e.g., drug) detection assays which involve the detection or identification of small molecules that can bind to a given protein, i.e., a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or peptide (e.g., SEQ ID NO:Y). Assays suitable for high throughput screening methodologies, can be desirable in certain situations.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. It can be desirable that most small molecules that bind to the target protein will modulate activity in some manner, due to preferential, higher affinity binding to functional areas or sites on the protein.

An example of such an assay is the fluorescence based thermal shift assay (3D Pharmaceuticals, Inc., (3DP), Exton, Pa., USA) as described in U.S. Pat. Nos. 6,020,141 and 6,036,920; see also, Zimmerman, (2000) *Gen. Eng. News*, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) or peptide to measure a biological binding or ligand binding activity, the source may be a whole cell lysate that can be prepared by successive freeze-thaw cycles (e.g., one to three) in the presence of standard protease inhibitors.

A HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (e.g., SEQ ID NO:Y) can be partially or completely purified by standard protein purification methods, e.g., affinity chromatography using specific antibody described herein, or by ligands specific for an epitope tag engineered into the recombinant HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide molecule, also as described herein. Binding activity can then be measured using assays known to those of ordinary skill in the art and as described herein.

Compounds which are identified according to the methods provided herein, and that modulate or regulate the biological activity or physiology of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide of to the present invention (e.g., SEQ ID NO:Y) are a representative embodiment of the present invention. Such modulatory compounds can be employed in treatment and therapeutic methods for treating a condition that is mediated by a MGBPBMY1 (LOC229900), MGBPBMY2 (LOC229902), MGBPBMY3 (BC031475), MGBPBMY4 (BC007143), HGBPBMY1 (AK096141), HGBPBMY2 (4843 30 1 1; 4843_1), HGBPBMY3 (4843 30 2 1; 4843_2) and/or HGBPBMY4 (FLJ10961) polypeptide of the present invention by administering to an individual in need of such treatment a therapeutically effective amount of the compound identified by the methods described herein.

In addition, the present invention provides methods for treating a subject in need of such treatment for a disease, disorder, or condition that is mediated by a MGBPBMY1 (LOC229900), MGBPBMY2 (LOC229902), MGBPBMY3 (BC031475), MGBPBMY4 (BC007143), HGBPBMY1 (AK096141), HGBPBMY2 (4843 30 1 1; 4843_1), HGBPBMY3 (4843 30 2 1; 4843_2) and/or HGBPBMY4 (FLJ10961) polypeptide of the present invention, comprising administering to the individual a therapeutically effective amount of a MGBPBMY1 (LOC229900), MGBPBMY2 (LOC229902), MGBPBMY3 (BC031475), MGBPBMY4 (BC007143), HGBPBMY1 (AK096141), HGBPBMY2 (4843 30 1 1; 4843_1), HGBPBMY3 (4843 30 2 1; 4843_2) and/or HGBPBMY4 (FLJ10961)-modulating compound identified by a method provided herein.

Antisense and Ribozyme (Antagonists)

In specific embodiments, antagonists of to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, (1991) *Neurochem.* 56:560; *Oligodeoxynucleotides as Antisense Inhibitors of Gene Expression*, CRC Press, Boca Raton, Fla., USA (1988)). Antisense technology can be used to control gene expression through antisense DNA or RNA, or through triple-helix formation.

Antisense techniques are discussed for example, in Okano, (1991) *Neurochem.* 56:560 and *Oligodeoxynucleotides as Antisense Inhibitors of Gene Expression*, CRC Press, Boca Raton, Fla. (1988). Triple helix formation is discussed in, for instance, Lee et al., (1979) *Nucl. Acid Res.* 6:3073; Cooney et al., (1988) *Science* 241:456; and Dervan et al., (1991) *Science* 251:1300. The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines has been described (Wickstrom et al., (1988) *Proc. Natl. Acad. Sci. U.S.A.* 85(4):1028–32; Anfossi et al., (1989) *Proc. Natl. Acad. Sci. U.S.A.* 86(9):3379–83). These experiments were performed in vitro by incubating cells with the oligoribonucleotide. A similar procedure for in vivo use is described in PCT Publication WO 91/15580. Briefly, a pair of oligonucleotides for a given antisense RNA is produced as follows: A sequence complimentary to the first 15 bases of the open reading frame is flanked by an EcoR1 site on the 5' end and a HindIII site on the 3' end. Next, the pair of oligonucleotides is heated at 90° C. for one minute and then annealed in 2× ligation buffer (20 mM TRIS HCl pH 7.5, 101M $MgCl_2$, 10 MM dithiothreitol (DTT) and 0.2 mM ATP) and then ligated to the EcoR1/Hind III site of the retroviral vector PMV7 (see PCT Publication WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the present invention is produced intracellularly by transcription from an exogenous sequence. For example, a vector or a portion thereof, is transcribed, producing an antisense nucleic acid (RNA) of the present invention. Such a vector would contain a sequence encoding the antisense nucleic acid of the present invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the present invention, or fragments thereof, can be by any promoter known in the art to act in vertebrate, for example human, cells. Such promoters can be inducible or constitutive. Such promoters include, but are not limited to, the SV40 early promoter region (Bemoist & Chambon, (1981) *Nature* 29:304–310), the promoter contained in the 3' long terminal repeat of Rous sarcoma virus (Yamamoto et al., (1980) *Cell* 22:787–797), the herpes thymidine promoter (Wagner et al., (1981) *Proc. Natl. Acad. Sci. USA* 78:1441–1445), the regulatory sequences of the metallothionein gene (Brinster et al., (1982) *Nature* 296:39–42), etc.

The antisense nucleic acids of the present invention comprise a sequence complementary to at least a portion of an RNA transcript of a gene of interest. However, absolute complementarity, although preferred, is not required. A sequence "complementary to at least a portion of an RNA" referred to herein, means a sequence having sufficient complementarity to be able to hybridize with the RNA, forming a stable duplex; in the case of double stranded antisense nucleic acids of the present invention, a single strand of the duplex DNA can thus be tested, or triplex formation may be assayed. The ability to hybridize will depend on both the degree of complementarity and the length of the antisense nucleic acid. Generally, the larger the hybridizing nucleic acid, the more base mismatches with a RNA sequence of the present invention it can contain and still form a stable duplex (or triplex as the case may be). One of ordinary skill in the art can ascertain a tolerable degree of mismatch by use of standard procedures to determine the melting point of the hybridized complex, upon consideration of the present disclosure.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well (see, e.g., Wagner, (1994) *Nature* 372: 333–335). Thus, oligonucleotides complementary to either the 5'- or 3'-non-translated, non-coding regions of a polynucleotide sequence of the present invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the present invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the present invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., (1989) *Proc. Natl. Acad. Sci. U.S.A.* 86:6553–6556; Lemaitre et al., (1987) *Proc. Natl. Acad. Sci. U.S.A.* 84:648–652; PCT Publication WO 88/09810) or the blood-brain barrier (see, e.g., PCT Publication WO 89/10134), hybridization-triggered cleavage agents. (see, e.g., Krol et al., (1988) *BioTechniques* 6:958–976) or intercalating agents (see, e.g., Zon, (1988) *Pharm. Res.* 5:539–549). To this end, the oligonucleotide can be conjugated to another molecule, e.g., a peptide, hybridization triggered cross-linking agent, transport agent, hybridization-triggered cleavage agent, etc.

An antisense oligonucleotide can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide is an α-anomeric oligonucleotide. An a-anomeric oligonucleotide forms specific double-stranded hybrids with complementary RNA in which, contrary to the usual b-units, the strands run parallel to each other (Gautier et al., (1987) *Nucl. Acids Res.* 15:6625–6641). The oligonucleotide is a 2-0-methylribonucleotide (Inoue et al., (1987) *Nucl. Acids Res.* 15:6131–6148), or a chimeric RNA-DNA analogue (Inoue et al., (1987) *FEBS Lett.* 215:327–330).

Polynucleotides of the present invention can be synthesized by standard methods known in the art, e.g. by use of an automated DNA synthesizer (such as are commercially available, for example from Biosearch, Applied Biosystems, Foster City, Calif., USA). As examples, phosphorothioate oligonucleotides may be synthesized by the method of Stein et al. (Stein et al., (1988) *Nucl. Acids Res.* 16:3209), methylphosphonate oligonucleotides can be prepared by use of controlled pore glass polymer supports (Sarin et al., (1988) *Proc. Natl. Acad. Sci. U.S.A.* 85:7448–7451), etc.

While antisense nucleotides complementary to the coding region sequence of the present invention could be used, those complementary to the transcribed untranslated region are often most desirable.

Potential antagonists according to the present invention also include catalytic RNA, or a ribozyme (see, e.g., PCT Publication WO 90/11364; Sarver et al., (1990) *Science* 247:1222–1225). While ribozymes that cleave mRNA at site specific recognition sequences can be used to destroy mRNAs corresponding to a polynucleotide of the present invention, the use of hammerhead ribozymes is desirable in certain situations. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is known in the art (see, e.g., Haseloff & Gerlach, (1988) *Nature* 334:585–591). There are numerous potential hammerhead ribozyme cleavage sites within each nucleotide sequence disclosed in the sequence listing. In one embodiment, the ribozyme is engineered so that the cleavage recognition site is located near the 5' end of the mRNA corresponding to a polynucleotide of the present invention; i.e., to increase efficiency and minimize the intracellular accumulation of non-functional mRNA transcripts.

As in the antisense approach, the ribozymes of the present invention can comprise modified oligonucleotides (e.g. for improved stability, targeting, etc.) and can be delivered to cells that express a polynucleotide of the present invention in vivo. DNA constructs encoding the ribozyme may be introduced into the cell in the same manner as described above for the introduction of antisense encoding DNA. A representative method of delivery involves using a DNA construct "encoding" the ribozyme under the control of a strong constitutive promoter, such as, for example, pol III or pol 11 promoter, so that transfected cells will produce sufficient quantities of the ribozyme to destroy endogenous messages and inhibit translation. Since ribozymes unlike antisense molecules, are catalytic, a lower intracellular concentration is required for efficiency.

In another embodiment, small interfering RNAs (siRNAs; reviewed in Scherr et al., (2003) *Curr. Med. Chem.* 10:245–256) can be employed in a gene silencing approach. SiRNAs are short double stranded pieces of RNA, generally about 21 nt in size, often with dTdT or UU overhangs on the ends of the siRNA. These pieces of RNA can induce RNA interference, dsRNA-mediated destruction of target mRNA and ultimately the silencing of a gene siRNAs can be employed to post-transcriptionally silence a given gene, such as a gene of the present invention. Thus, siRNA approaches can be employed in the present invention.

Homologous recombination techniques can also be employed to silence a gene. Generally, a transgene (often the neo gene) can be inserted into the gene to be silenced, disrupting the coding sequence of the gene. Upon recombination, the allele carrying the transgene becomes a null allele for the silenced gene.

Antagonist/agonist compounds may be employed to modulate an immune response, including autoimmune conditions. Such compounds can also be employed to modulate aberrant NF-κB-related activity.

An antagonist/agonist may also be employed to treat, prevent, and/or diagnose the diseases described herein, notably rheumatoid arthritis and conditions related to aberrant NF-κB activity.

An antagonist/agonist may also be employed in combination with additional therapies to treat or prevent the diseases described herein. For example, an antagonist or agonist of the present invention (including single, double and antisense nucleic acids) may be employed in combination with an anti-TNF therapy. Alternatively, an an antagonist or agonist of the present invention may be employed in combination with KINERET for the treatment of a condition such as rheumatoid arthritis.

Thus, the present invention provides a method of treating or preventing diseases, disorders, and/or conditions, including but not limited to the diseases, disorders, and/or conditions listed throughout this application, associated with overexpression of a polynucleotide of the present invention by administering to a subject (a) an antisense molecule directed to a polynucleotide of the present invention, and/or (b) a ribozyme directed to a polynucleotide of the present invention.

Other Activities

A polypeptide and/or polynucleotide of the present invention may be employed in methods in which antiviral activity is desired. For example, such polypeptides and/or polynucleotides can be employed in the treatment prevention or diagnosis of viral infections.

A polypeptide of the present invention may be employed for treating immune system conditions, including rheumatoid arthritis.

A polypeptide and/or polynucleotide of the present invention may also be used for treating some NF-κB-related conditions.

A polynucleotide, polypeptide, agonist and/or antagonist of the present invention can also increase or decrease the differentiation or proliferation of embryonic stem cells, besides, as discussed herein, hematopoietic lineage.

A polynucleotide, polypeptide, agonist and/or antagonist of the present invention can also be used to increase the efficacy of a pharmaceutical composition, either directly or indirectly. Such a procedure can be administered in simultaneous conjunction with said pharmaceutical, or separately through either the same or different route of administration (e.g., intravenous for the polynucleotide or polypeptide of the present invention, and orally for the pharmaceutical, among others described herein.).

In another aspect, the present invention comprises a method of treatment of an individual in need of an increased level of a protein activity. In one embodiment the method comprises administering to such an individual a pharmaceutical composition comprising an amount of an isolated polypeptide, polynucleotide, or antibody of the claimed invention effective to increase the level of said protein activity in the individual.

Having generally described the present invention, the same will be more readily understood by reference to the following examples, which are provided by way of illustration.

EXAMPLES

The following Examples have been included to illustrate various exemplary modes of the present invention. Certain aspects of the following Examples are described in terms of techniques and procedures found or contemplated by the inventors to work well in the practice of the present invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the present invention.

Example 1

Identification of Novel Human GBPs

Figure 10:
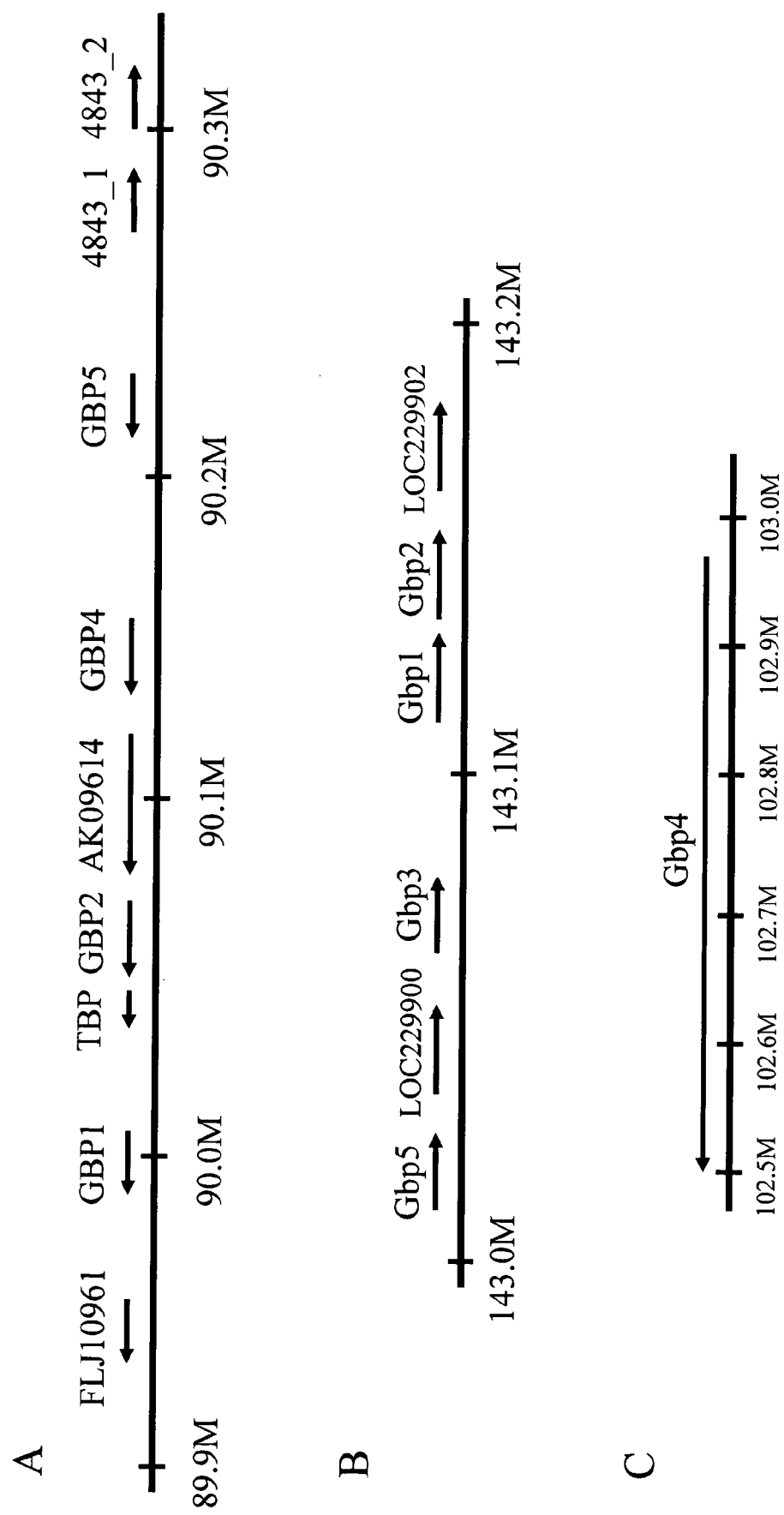

The loci of human GBP-1, GBP-2, GBP-4, and GBP-5 were analyzed on NCBI's Genome View map of human chromosome 1p22 from position 89,500K through position 90,750K. A number of annotated hypothetical genes flanking the GBP locus were BLAST searched against the non-redundant protein database. Hypothetical protein HGBPBMY4 (FLJ10961) had high homology to the other GBP family members and was immediately distal to GBP-1 (FIG. 10A). Modeled gene sequences predicted by Genome Scan in and around the GBP locus were BLAST searched against the non-redundant protein database. Sequence HGBPBMY1 (AK096141) located between GBP-2 and GBP-4 and sequence HGBPBMY2 (4843 30 1 1; 4843_1) and novel sequence HGBPBMY3 (4843 30 2 1; 4843_2) immediately proximal to GBP-5 (FIG. 10A) had high homology to the GBP family members (FIGS. 11A–11G).

Example 2

Identification of Novel Mouse GBPs

The loci of mouse GBP-1, GBP-2, GBP-3, and GBP-5 were analyzed on NCBI's Genome View map of mouse chromosome 3H1 from position 142,900K through position 143,300K. A number of annotated hypothetical genes flanking the GBP locus were BLAST searched against the non-redundant protein database. Hypothetical protein MGBPBMY1 (LOC229900) located between GBP-5 and GBP-3 and hypothetical protein MGBPBMY2 (LOC229902) immediately distal to GBP-2 (FIG. 10B) had high homology to the GBP family (FIGS. 11A–11G).

The locus of GBP-4 was analyzed on NCBI's Genome View map of mouse chromosome 5E4 from position 102,100K through position 103,300K (FIG. 10C). A number of annotated hypothetical genes flanking the GBP locus were BLAST searched against the non-redundant protein database. Hypothetical proteins MGBPBMY3 (BC031475) and MGBPBMY4 (BC007143) distal to GBP-4 (FIG. 10B) had high homology to the GBP family (FIGS. 11A–11G).

Example 3

TAQMAN Analyses

Reactions were performed in a total volume of 40 µl. The master mix contained SYBR Green I Dye, 50 mM Tris-HCl pH=8.3, 75 mM KCl, DMSO, Rox reference dye, SmNM $MgCl_2$, 2 mM dNTP, Platinum Taq High Fidelity (IU/reaction), and 0.5 µM of each primer. The cDNA was diluted 1:36 from the synthesis reaction and eight microliters was used in each PCR reaction. For tissue distribution analyses, two microliters of cDNA from the Human Multiple Tissue and Human Immune System MTC cDNA panels (Clontech, Palo Alto, Calif., USA) were used as templates. For the mouse GBPs, the Clontech mouse-1 cDNA panel was used as the template. The amplification program consisted of a 10 minute incubation at 95° C. followed by forty cycles of incubations at 95° C. for 15 seconds and 60° C. for 1 minute. Amplification was followed by melting curve analysis at 60° C. to demonstrate that the amplification was specific to a single amplicon. A negative control without cDNA template was run to assess the overall specificity.

For THP-1 experiments, THP-1 cells (5×10 6) were cultured in triplicate at $10^6$/ml in RPMI containing 10% heat inactivated fetal calf serum, 2 mM L-glutamine with either medium, LPS (100 ng/ml, Sigma Chemical Company, St. Louis, Mo., USA), or 100 U/ml interferon-γ (IFN-γ, Peprotech, Rocky Hill, N.J.) for 6 hours at 37° C. in 5% $CO_2$. In some experiments, cells were pretreated with either Compound 1 (2 µM) or dexamethasone (100 nM) for 30 minutes before addition of 100 ng/ml LPS. Compound 1 has the formula: PKKKRKVAAVALLPAVLLALLAPKKKRKV (SEQ ID NO:60) Compound 1 preferably comprises D amino acids, but can also comprise L amino acids or a combination of D and L amino acids.

The cells were stimulated for 0.5–8 hr as described. At each time point, cells were pelleted and washed with PBS.

RNA was isolated using Qiagen RNease® mini columns (Qiagen, Inc.) according to manufacturer's instructions. The RNA was eluted with 50 μl of RNase-free water.

For synovial tissue experiments, human knee biopsy samples were homogenized in 3 ml TRIZOL® Reagent (Life Technologies, Rockville, Md., USA) and frozen in liquid nitrogen. The samples were thawed, one-third (1 ml) of the sample removed, mixed with 1 ml TRIZOL®, homogenized, and snap frozen in liquid nitrogen. Following a thaw, the samples were spun at 14,000 rpm for 10 minutes at 4° C. The supernatants were transferred to new microfuge tubes, extracted with chloroform, and precipitated with isopropanol overnight at −20° C. The RNA was pelleted by centrifugation at 14,000 rpm for 30 minutes. The supernatant was aspirated, and the samples washed two times with 75% ethanol. Following the last spin, the pellets were air-dried, and resuspended in 20 μl of ultra-pure RNase-free water. The RNA samples were further purified using Qiagen RNease mini columns (Qiagen, Inc.) according to manufacturer's instructions. The RNA was eluted with 50 ul of RNase-free water.

Example 4

Data Analysis

A relative value for the initial target concentration in each reaction was determined using the TAQMAN® 5700 software (Applied Biosystems, Foster City, Calf., USA). The threshold value was set to 0.5 to obtain cycle threshold values that were used to assign relative message levels for each target. The message levels of GAPDH were determined for each cDNA sample and were used to normalize all other genes tested from the same cDNA sample.

Primers

Gene specific primers for were designed using the Primer Express software and synthesized by Sigma Genosys (The Woodlands, Tex., USA). Primer names and sequences are below:

```
GBP1
F4      CATTGGTCTGGCCAAGTCTACA          2181  (SEQ ID NO: 19)

R4      TTCACTAAGAAGCTAGGGTGGTTGT       2244  (SEQ ID NO: 20)

GBP2
F4      GGAGGAAGAGCTGAACCCTGAT           912  (SEQ ID NO: 21)

R4      GACTGCAATGCCACCTGAAAG           1014  (SEQ ID NO: 22)

GBP4
F       GGCATTAGAGATTCTTGACAAGATTTC      123  (SEQ ID NO: 23)

R       CCTGCAAGACGATTCATGAGATAG         224  (SEQ ID NO: 24)

GBP5
F2      CAGCACAACATTCCAAGCTCAA          1665  (SEQ ID NO: 25)

R2      GGATCATCGTTATTAACAGTCCTCTG      1745  (SEQ ID NO: 26)

HGBPBMY1 (AK096141)
F2      GGGAGTGGATCAGGCATTTCT            801  (SEQ ID NO: 27)

R2      ACTATCCAGTTGGTCTTCTCGTACTTC      916  (SEQ ID NO: 28)

HGBPBMY2 (4843 30 1 1; 4843_1)
F2      GGAGTGCATCAGGCGTTTCT             732  (SEQ ID NO: 29)

R2      CCAGTTGCTTTTCTGACACCTTCT         841  (SEQ ID NO: 30)

HGBPBMY3 (4843 30 2 1; 4843_2)
F       AGGATGGCAGGAAGACAAACA           1066  (SEQ ID NO: 31)

R       CTGGTCTGTCTGGAGAATTGCA          1215  (SEQ ID NO: 32)

HGBPBMY4 (FLJ10961)
F       GATCATGAGTTGCCACCACTCA          2110  (SEQ ID NO: 33)

R       GTGCCCAAATATGTCCCAAGA           2206  (SEQ ID NO: 34)

mGBP1
F       GAGATGCTGATGGAACAGAAGGA         1691  (SEQ ID NO: 35)

R       TCCTGCTCCATCTTCTCAGTCA          1764  (SEQ ID NO: 36)

mGBP2
F       CAGGCTTTGAAACAACTGCTATGA        2006  (SEQ ID NO: 37)

R       CAGTGCCCAGTGGTCAGACA            2104  (SEQ ID NO: 38)

mGBP3
F       GGAAACCCTCACTGTTTGGTCA          1850  (SEQ ID NO: 39)
```

```
                              -continued
R       CTTAGTGAGCCGAGGAATTTCAG         1964  (SEQ ID NO: 40)

mGBP4
F       GTCCATGTGAGGCGAGGAA             3015  (SEQ ID NO: 41)

R       AACGACTCGGGCACTGTTGT            3088  (SEQ ID NO: 42)

mGBP5
F       GCTGAAGCAAGGTAGCGATGA            666  (SEQ ID NO: 43)

R       CCTCGTTGCTGAGTGTTGGA             814  (SEQ ID NO: 44)

MGBPBMY1 (LOC229900)
F3      CTGAGGGTGAACTCCAAAGC             136  (SEQ ID NO: 45)

R3      CCCAGATTGAAGCCATGGTT             278  (SEQ ID NO: 46)

MGBPBMY2 (LOC229902)
F2      CACCATCAGCAATGGGTCTCT           1110  (SEQ ID NO: 47)

R2      CTGGCTCATCTGCTGGTCATAGT         1227  (SEQ ID NO: 48)

MGBPBMY3 (BC031475)
F2      CACAGCAAGAGGAAGTCACTGATATC      3171  (SEQ ID NO: 49)

R2      TGCCAATCTAACTCAGGGATGA          3248  (SEQ ID NO: 50)

MGBPBMY4 (BC007143)
F       CACAATGCTTATCCAGGGTAGCT         3050  (SEQ ID NO: 51)

R       GTCCCTTGGAGTTAGATTTACAGGTAGT    3121  (SEQ ID NO: 52)

mGAPDH
F       CATGGCCTTCCGTGTTCCTA             730  (SEQ ID NO: 53)

R       CCTGCTTCACCACCTTCTTGA            833  (SEQ ID NO: 54)

hGAPDH
F3      AGCCGAGCCACATCGCT                     (SEQ ID NO: 55)

R1      GTGACCAGGCGCCCAATAC                   (SEQ ID NO: 56)
```

RESULTS

Figure 12:
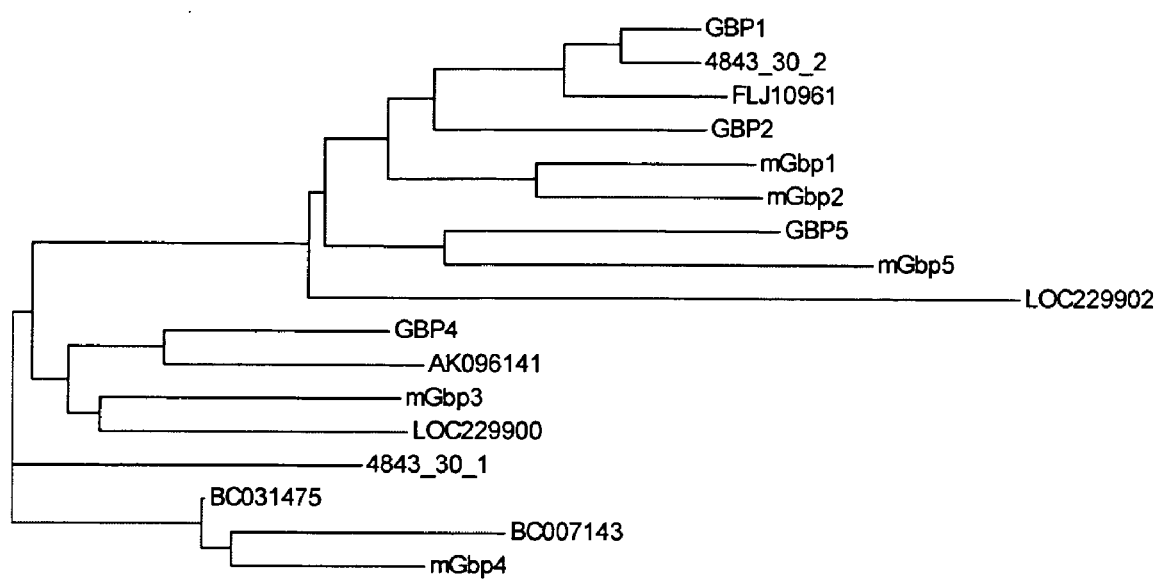
FIG. 12 is a phylogenic tree of the mouse and human GBP families.
Figure 13:
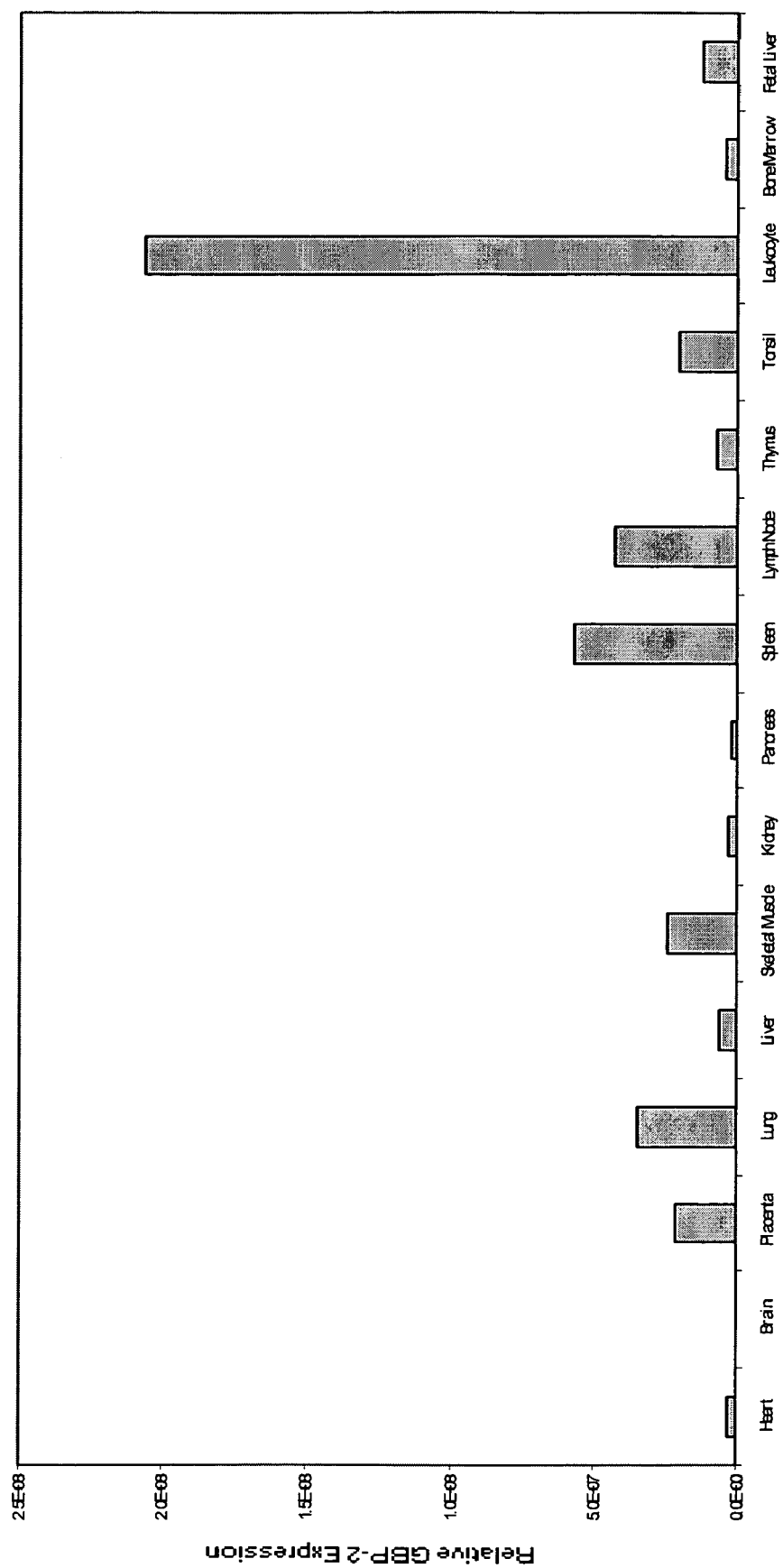
FIG. 13 is tissue expression pattern of human GBP-2. Panels of cDNAs derived from normal and immune tissue were analyzed by Real Time PCR for expression of GBP-2.

In the course of analyzing the chromosomal localization of guanylate binding proteins (GBPs) four GBPs in the human (HGBPBMY1 (AK096141), HGBPBMY2 (4843 30 1 1; 4843_1), HGBPBMY3 (4843 30 2 1; 4843_2) and HGBPBMY4 (FLJ10961)) and four mouse GBPs (MGBPBMY1 (LOC229900), MGBPBMY2 (LOC229902), MGBPBMY3 (BC031475) and MGBPBMY4 (BC007143)) were identified. A combined alignment of the human and mouse GBPs is shown in FIGS. 11A–11G; and the phylogenetic tree is shown in FIG. 12.

Figure 14:
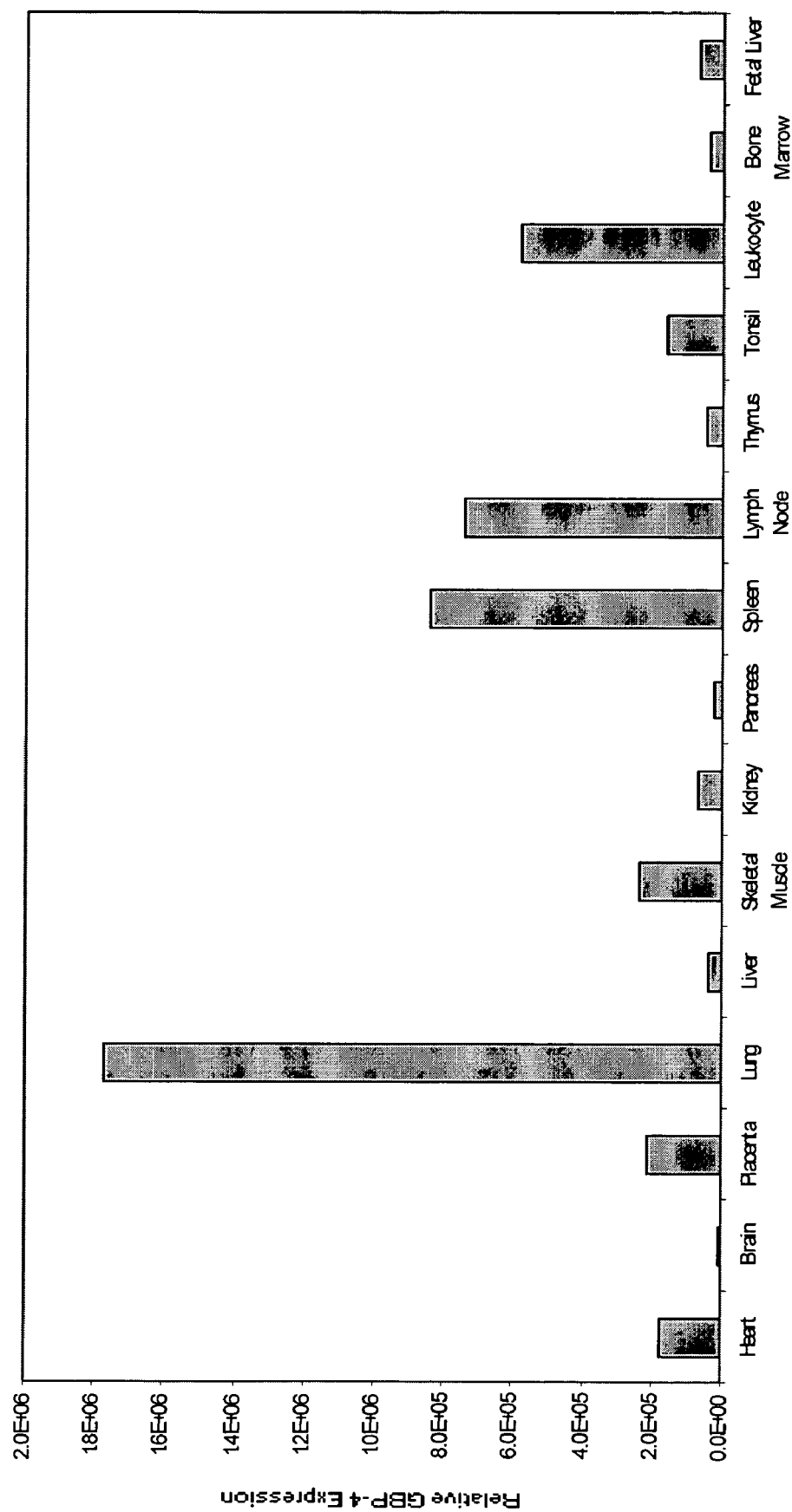
FIG. 14 is bar graph depicting the tissue expression pattern of human GBP-4. Panels of cDNAs derived from normal and immune tissue were analyzed by real Time PCR for expression of human GBP-4.

It was previously determined that members of the GBP family are highly expressed in hematopoietic tissue (U.S. patent application Ser. No. 10/308,279, incorporated herein by reference). The highest levels of human GBP-1 were detected in spleen and lymph node, followed by leukocytes, lung, placenta, tonsil, liver, thymus and fetal liver. The highest levels of human GBP-5 were detected in spleen, leukocytes, followed by lymph node and lung. High levels of human GBP-2 were detected in leukocytes, followed by spleen, lymph node, lung, placenta, skeletal muscle, tonsil, fetal liver and thymus. The highest levels of human GBP-4 were detected in lung, followed by spleen, lymph node, leukocytes, skeletal muscle, placenta, and heart (FIG. 14).

Of the identified GBPs, HGBPBMY4 (FLJ10961) had the broadest expression pattern. High levels were detected in spleen, followed by lymph node, lung, placenta, leukocytes, tonsil, thymus, kidney, skeletal muscle, liver, heart, pancreas, fetal liver, and bone marrow (FIG. 15). Expression of HGBPBMY2 (4843 30 1 1; 4843_1) was restricted to tonsil (FIG. 16). Expression of the novel HGBPBMY3 (4843 30 2 1; 4843_2) was highest in spleen and lymph node, followed by placenta, heart, lung, liver, thymus, and tonsil (FIG. 17). Expression of HGBPBMY1 (AK096141) was restricted to liver (FIG. 18).

Figure 19:
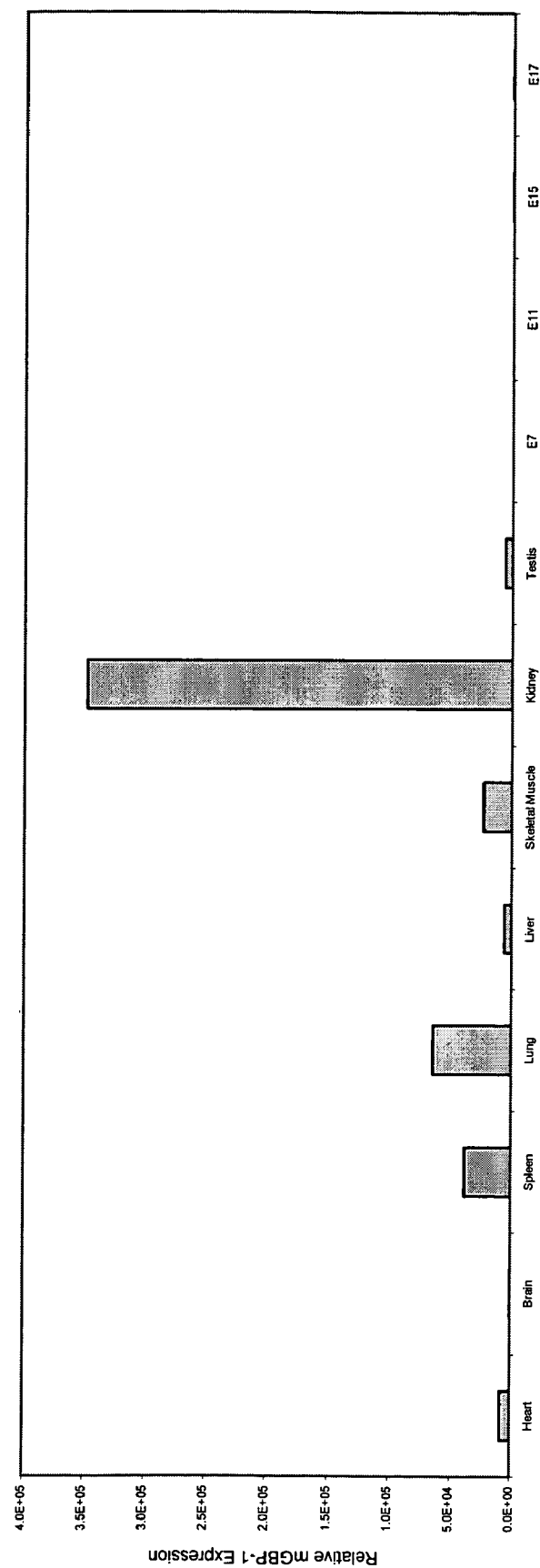
FIG. 19 is bar graph depicting the tissue expression pattern of mouse mGBP-1. Panels of cDNAs derived from normal and immune tissue were analyzed by Real Time PCR for expression of mGBP-1.
Figure 20:
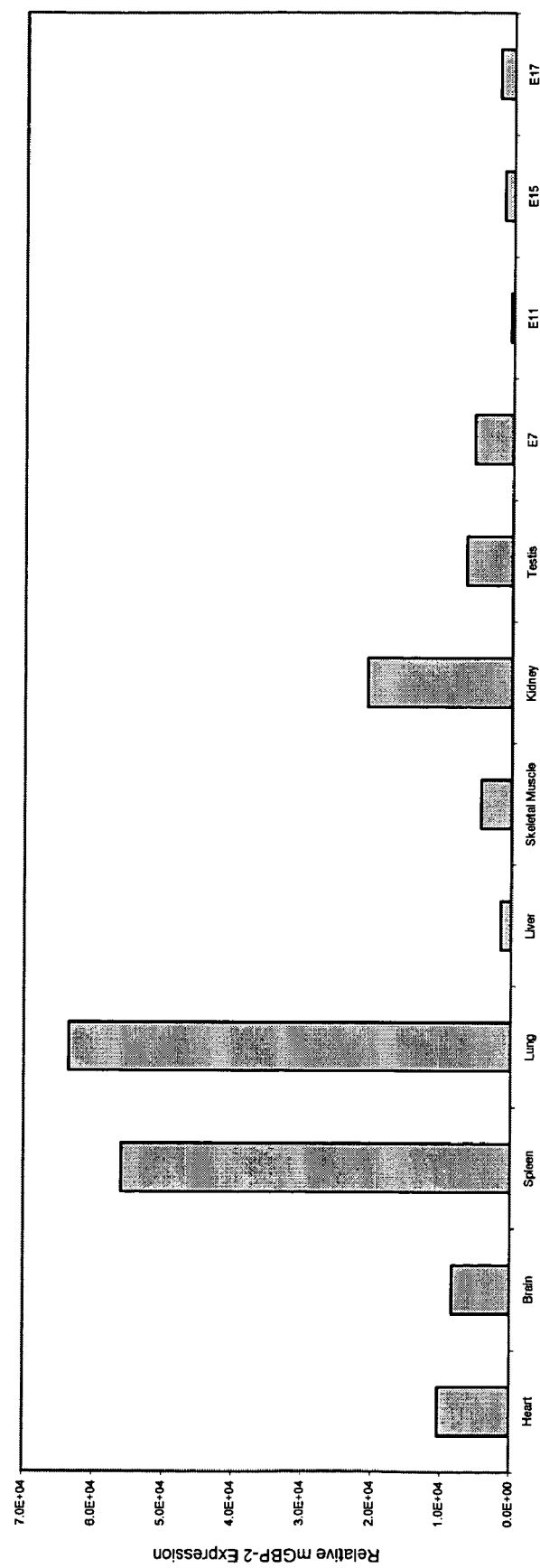
FIG. 20 is bar graph depicting the tissue expression pattern of mouse mGBP-2. Panels of cDNAs derived from normal and immune tissue were analyzed by Real Time PCR for expression of mGBP-2.
Figure 21:
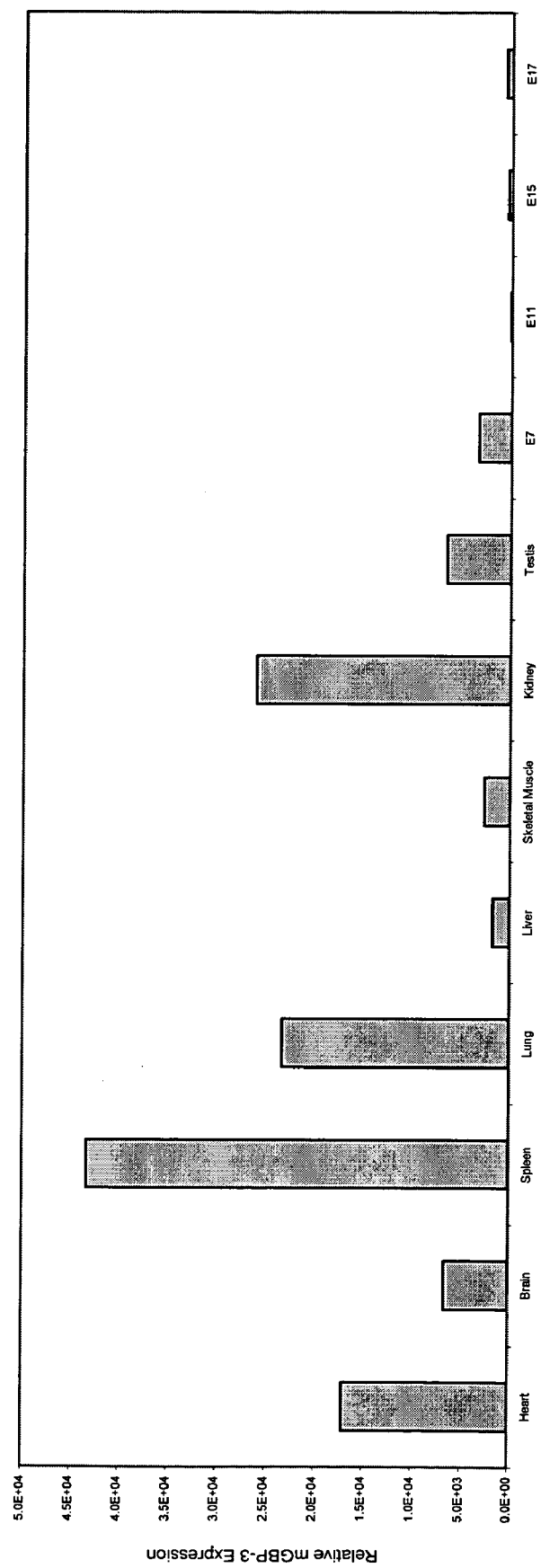
FIG. 21 is bar graph depicting the tissue expression pattern of mouse mGBP-3. Panels of cDNAs derived from normal and immune tissue were analyzed by Real Time PCR for expression of mGBP-3.
Figure 22:
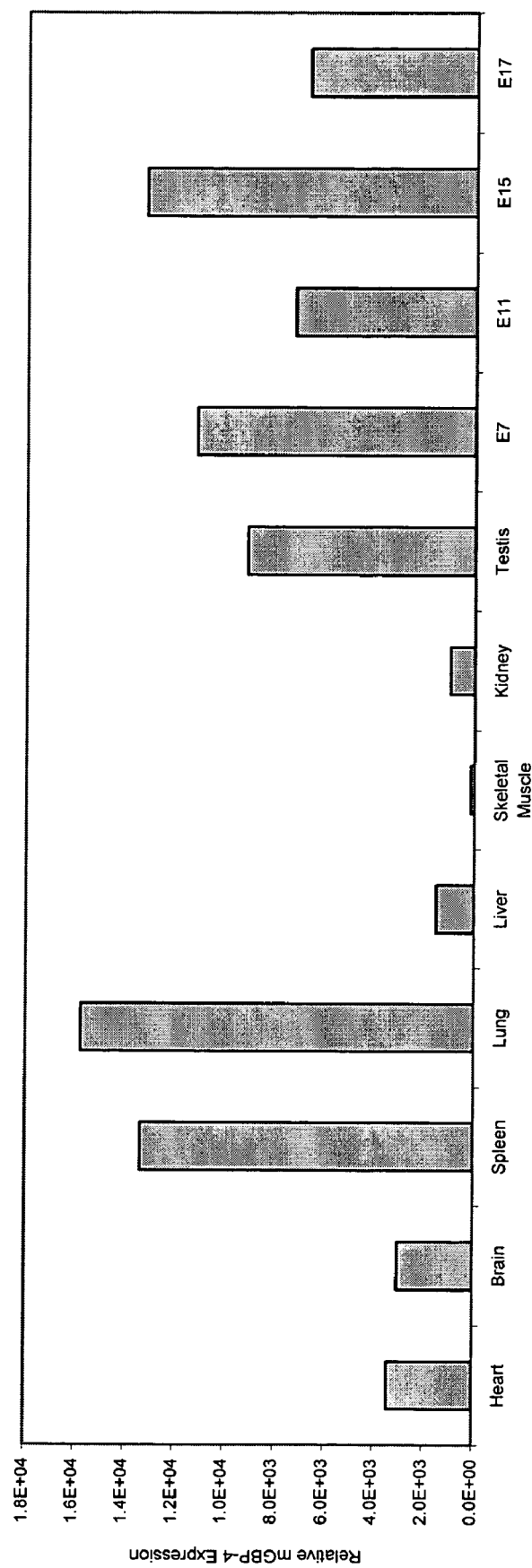
FIG. 22 is bar graph depicting the tissue expression pattern of mouse mGBP-4. Panels of cDNAs derived from normal and immune tissue were analyzed by Real Time PCR for expression of mGBP-4.
Figure 23:
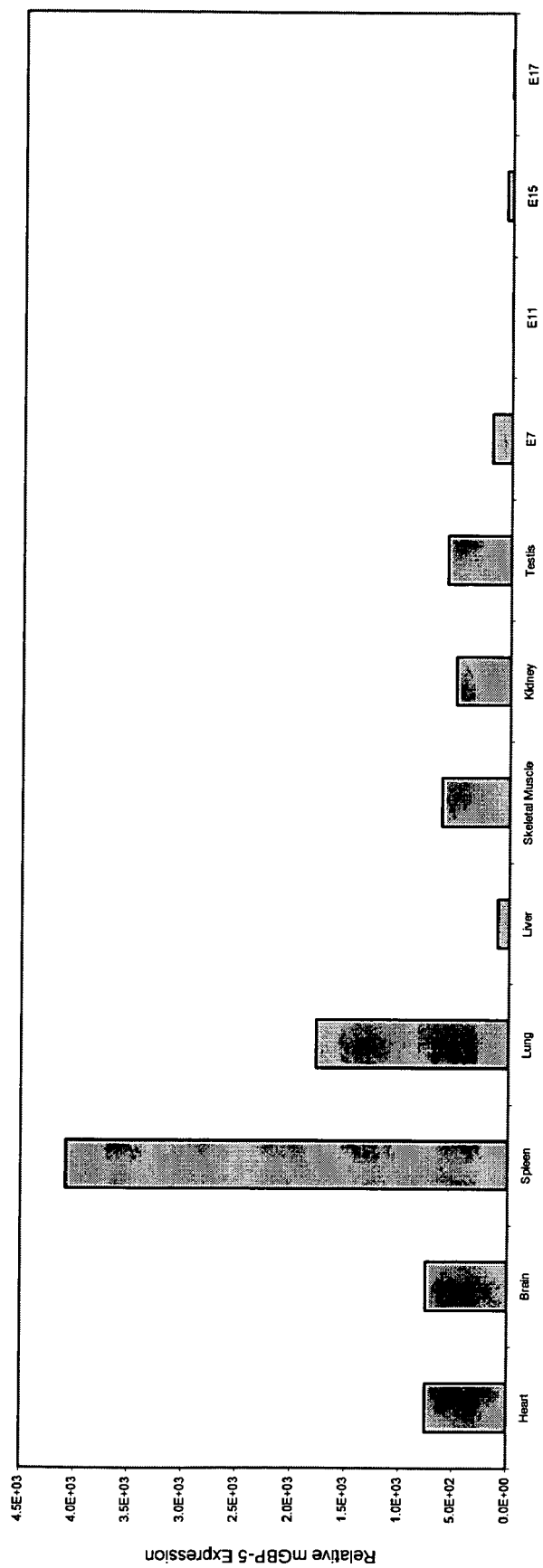
FIG. 23 is bar graph depicting the tissue expression pattern of mouse mGBP-5. Panels of cDNAs derived from normal and immune tissue were analyzed by Real Time PCR for expression of mGBP-5.

For the mouse family members, the highest levels of mouse GBP-1 were detected in kidney, with much lower levels in spleen and lung (FIG. 19). Mouse GBP-2 was most abundant in lung and spleen, followed by kidney, heart, and brain (FIG. 20). Mouse GBP-3 was most abundant in spleen, followed by kidney, lung, heart, brain, and testis (FIG. 21). Mouse GBP-4 was abundantly expressed in embryonic tissue. In adult tissue, the highest levels were detected in lung and spleen, followed by testis, heart, brain, liver and kidney (FIG. 22). The highest levels of mouse GBP-5 were detected in spleen, followed by lung, heart, brain, skeletal muscle, kidney, and testis (FIG. 23).

Of the identified mouse GBP family members, MGBPBMY2 (LOC229902) had the broadest expression pattern. High expression was detected in embryonic tissue. In adult tissue, the highest expression was detected in spleen, followed by lung, testis, brain, liver, heart, kidney, and skeletal muscle (FIG. 24). Expression of MGBPBMY1 (LOC229900) was highest in adult spleen, followed by lung, heart, kidney, skeletal muscle, and brain (FIG. 25). Expression of MGBPBMY3 (BC031475) was restricted to spleen and lung (FIG. 26). Expression of the novel MGBPBMY4 (BC007143) was highest in adult heart and kidney, followed by spleen, lung, liver, brain, and skeletal muscle (FIG. 27).

Message levels of all the known GBPs are upregulated in response to IFN-γ. Therefore an experiment was performed to determine whether the identified GBPs are similarly induced by treatment with IFN-γ. Levels of HGBPBMY4 (FLJ10961) (FIG. 28A), HGBPBMY2-(4843_1) (FIG. 28B), and the novel HGBPBMY3 (4843_2) (FIG. 28C) were all strongly upregulated by treatment with IFN-γ. Much lower levels of expression were induced in response to LPS. Expression of HGBPBMY1 (AK096141) was not detected in resting or stimulated THP-1 cells.

It was previously determined that LPS-mediated induction of GBP-1 and GBP-5 is dependent on NF-κB activity (U.S. patent Ser. No. 10/308,279, incorporated by reference). An experiment was then performed to determine whether inductions of other known GBPs as well as the identified GBPs were similarly dependent on NF-κB activity. Two independent sets of THP-1 monocytes were stimulated with LPS in the presence and absence of a specific inhibitor of NF-κB nuclear localization, Compound 1 (Fujihara et al., (2000) *J. Immunol.* 165:1004–1012). Expression of GBP-2 was induced in response to LPS stimulation. This induction was significantly inhibited by Compound 1 (FIG. 29). In contrast to GBP-2, induction of GBP-4 in response to LPS was variable (FIG. 30). The expression of GBP-4 was not affected by the NF-κB inhibitor. A similar pattern of expression was observed for HGBPBMY4 (FLJ10961). The response to LPS was variable, and unaffected by Compound 1 (FIG. 31). Expression of the novel HGBPBMY3 (4843 30 2 1; 4843_2) was significantly induced by LPS. The induction was significantly inhibited by Compound 1 (FIG. 32). Expression of HGBPBMY2 (4843 30 1 1; 4843_1) and HGBPBMY1 (AK096141) was not detected in resting and LPS-stimulated THP-1 cells.

To determine whether expression of the mouse GBPs was dependent on NF-κB activity, their expression in mouse embryonic fibroblasts derived from germline knockouts of different NF-κB family members as profiled. Wild type 3T3 cells, embryonic fibroblasts derived from germline knockouts of p65, RelB, p50, and IκBα were stimulated for 2 or 8 hours with either TNFα or PMA. At each time point, mRNA was isolated and real time PCR was performed mGBP-2 expression was induced in wild type fibroblasts in response to TNFα (FIG. 33). Significantly less induction was seen in fibroblasts derived from the p65 knockouts, suggesting that p65 is required for mGBP-2 expression. Induction was maintained in fibroblasts from the RelB and p50 knockouts mGBP-2 expression was superinduced in the IκBα-deficient fibroblasts, suggesting that IκBα negatively regulates mGBP-2 expression. IκBα is a known inhibitor of NF-κB activity (Baeuerle et al., (1988) *Science* 242:540–545).

Lower levels of mGBP-3 were detected in wild type fibroblasts. The message was induced with TNFα treatment (FIG. 34). This induction was absent in fibroblasts derived from p65-deficient mice, suggesting that p65 regulates mGBP-3 expression. The induction was normal in fibroblasts derived from the RelB knockouts. Expression was superinduced in fibroblasts derived from the p50 and IκBα germline knockouts, suggesting that both proteins negatively regulate mGBP-3 expression. Homodimers of p50 have also been shown to repress certain genes (Plaksin et al., (1993) *J. Exp. Med.* 177:1651–1662).

In contrast to mGBP-2 and mGBP-3, mGBP-4 was constitutively expressed in wild type fibroblasts (FIG. 35). Expression was maintained in fibroblast lines derived from the different NF-κB knockout lines. These data suggest that mGBP-4 is not regulated by NF-κB. This is also consistent with the NF-κB independent expression of human GBP-4 described above.

Of the identified mouse GBPs, very low levels of MGBPBMY1 (LOC229900) were detected in wild type fibroblasts (FIG. 36). The message was superinduced in fibroblasts derived from the p50 and IκBα knockouts, suggesting that some NF-κB family members are able to regulate MGBPBMY1 (LOC229900) expression. Expression of MGBPBMY2 (LOC229902) was low and variable in the different fibroblast lines (FIG. 37). No consistent differences were observed between the fibroblast lines, suggesting that MGBPBMY2 (LOC229902) is not regulated by NF-κB. Expression of the novel MGBPBMY4 (BC007143) was inducible by TNFα at two hours, and by PMA at 8 hours (FIG. 38). No induction was observed in fibroblasts derived from the p65 knockouts. Reduced induction was observed in the RelB knockout line. Superinduction was observed at 8 hours in the TNFα-stimulated p50 and IκBα knockout lines. These data are consistent with NF-κB-dependent regulation of the novel MGBPBMY4 (BC007143). Expression of MGBPBMY3 (BC031475) was not detected in any of the fibroblast lines.

High expression of GBP-1 and GBP-5 in synovial tissue derived from rheumatoid arthritis subjects as compared to osteoarthritis subjects or normal controls (U.S. patent application Ser. No. 10/308,279) was previously detected. Therefore an experiment was performed to determine whether other members of the GBP family were overexpressed in synovia derived from rheumatoid arthritis subjects. High expression of GBP-2 was detected in six out of six rheumatoid arthritis synovial samples, and in two out of six osteoarthritis synovial samples (FIG. 39). High levels of GBP-4 expression were detected in five out of six rheumatoid arthritis synovial samples, and in two out of six osteoarthritis samples (FIG. 40). High levels of HGBPBMY2 (4843 30 1 1; 4843_1) expression were detected in three out of six rheumatoid arthritis synovial samples, and in two out of six osteoarthritis samples (FIG. 41). High levels of HGBPBMY4 (FLJ10961) expression were detected in six out of six rheumatoid arthritis samples, and in two out of six osteoarthritis samples (FIG. 42). Expression of HGBPBMY1 (AK096141) was not detected in the synovial samples.

Overexpression of several members of the GBP family in rheumatoid arthritis-derived and osteoarthritis-derived synovial tissue suggests that this family might play an important role in inflammatory disease pathology. Members of this family therefore have utility as biomarkers of inflammatory disease and as therapeutic targets for the treatment of inflammatory diseases.

Example 5

Method of Assessing the Physiological Function of a HGBPBMY1 (AK096141), HGBPBMY2 (4843 30 1 1; 4843 1), HGBPBMY3 (4843 30 2 1; 4843 2), HGBPBMY4 (FLJ10961), MGBPBMY1 (LOC229900), MGBPBMY2 (LOC229902), MGBPBMY3 (BC031475) and/or MGBPBMY4 (BC007143) Polypeptide at the Cellular Level The physiological function of the a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4

(BC007143) polypeptide (e.g., SEQ ID NO:Y) can be assessed by expressing a sequence encoding a HGBPBMY1 (AK096141), HGBPBMY2 (4843 30 1 1; 4843__1), HGB-PBMY3 (4843 30 2 1; 4843__2), HGBPBMY4 (FLJI10961), MGBPBMY1 (LOC229900), MGBPBMY2 (LOC229902), MGBPBMY3 (BC031475) and/or MGBPBMY4 (BC007143) polypeptide at physiologically elevated levels in mammalian cell culture systems. cDNA is subcloned into a mammalian expression vector containing a strong promoter that drives high levels of cDNA expression (examples are provided elsewhere herein). Vectors of choice include pCMV SPORT (Life Technologies, Rockville, Md., USA) and pCR3.1 (Invitrogen, Carlsbad Calif., USA), both of which contain the cytomegalovirus promoter. 5–10, μg of recombinant vector are transiently transfected into a human cell line, for example of endothelial or hematopoietic origin, using either liposome formulations or electroporation. 1–2 μg of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech, Palo Alto, Calif., USA), CD64, or a CD64-GFP fusion protein.

Flow cytometry (FCM), an automated, laser optics-based technique, can be used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events can include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, *Flow Cyometry*, Oxford, New York, N.Y., USA (1994).

The influence of a HGBPBMY1 (AK096141), HGB-PBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide on gene expression can be assessed using highly purified populations of cells transfected with sequences encoding a HGBPBMY1 (AK096141), HGBPBMY2 (4843 30 1 1; 4843__1), HGBPBMY3 (4843 30 2 1; 4843__2), HGB-PBMY4 (FLJ-10961), MGBPBMY1 (LOC229900), MGB-PBMY2 (LOC229902), MGBPBMY3 (BC031475) and/or MGBPBMY4 (BC007143) and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y., USA). mRNA can be purified from the cells using methods well known by those of ordinary skill in the art. Expression of mRNA encoding HGBPBMY1 (AK096141), HGBPBMY2 (4843 30 1 1; 4843__1), HGBPBMY3 (4843 30 2 1; 4843__2), HGB-PBMY4 (FLJ10961), MGBPBMY1 (LOC229900), MGB-PBMY2 (LOC229902), MGBPBMY3 (BC031475) and/or MGBPBMY4 (BC007143) polypeptides and other genes of interest can be analyzed by northern analysis or microarray techniques.

Example 6

Method of Assessing the Physiological Function of a HGBPBMY1 (AK096141). HGBPBMY2 (4843 30 1 1; 4843 1), HGBPBMY3 (4843 30 2 1, 4843 2), HGBPBMY4 (FLJ10961), MGBPBMY1 (LOC229900), MGBPBMY2 (LOC229902), MGB-PBMY3 (BC031475) and/or MGBPBMY4 (BC007143) Polypeptides Using Microphysiometric Assays Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR® microphysiometer (Molecular Devices Ltd., Menlo Park, Calif., USA). The CYTOSENSOR® is thus capable of detecting the activation of a protein, such as a receptor, that is coupled to an energy utilizing intracellular signaling pathway.

Example 7

Method of Screening for Compounds that Interact with a HGBPBMY1 (AK096141), HGBPBMY2 (4843 30 1 1; 4843 1), HGBPBMY3 (4843 30 2 1: 4843 2), HGBPBMY4 (FLJ10961), MGBPBMY1 (LOC229900), MGBPBMY2 (LOC229902), MGB-PBMY3 (BC031475) and/or MGBPBMY4 (BC007143) Polypeptide The following assays are designed to identify compounds that bind to a HGBPBMY1 (AK096141), HGBPBMY2 (4843 30 1 1; 4843__1), HGBPBMY3 (4843 30 2 1; 4843__ 2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, bind to other cellular proteins that interact with a HGBPBMY1 (AK096141), HGBPBMY2 (4843 30 1 1; 4843__1), HGB-PBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, and to compounds that interfere with the interaction of a HGBPBMY1 (AK096141), HGB-PBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising a portion of a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, and members of random peptide libraries (see, e.g., Lam et al., (1991) *Nature* 354:82–84; Houghton et al., (1991) *Nature* 354:84–86), made of D- and/or L-configuration amino acids, phosphopeptides (including, but not limited to, members of random or partially degenerate phosphopeptide libraries (see, e.g., Songyang et al., (1993) *Cell* 72:767–778); antibodies (including, but not limited to, polyclonal, monoclonal, humanized, anti-idiotypic, chimeric or single chain antibodies, and FAb, F(ab')$_2$ and FAb expression libary fragments, and epitope-binding fragments thereof), and small organic or inorganic molecules.

Compounds identified via assays such as those described herein can be useful, for example, in elaborating the biological function of a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, and for ameliorating symptoms of tumor progression, for example. In instances, for example, whereby a tumor progression state or disorder results from a lower overall level of a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) expression, a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, and/or a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide activity in a cell involved in the tumor progression state or disorder, compounds that interact with a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide can include ones which accentuate or amplify the activity of the bound a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143). Such compounds would bring about an effective increase in the level of HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide activity, thus ameliorating symptoms of the tumor progression disorder or state.

In instances whereby mutations within a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide cause aberrant HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptides to be made which have a deleterious effect that leads to tumor progression, compounds that bind a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide can be identified that inhibit the activity of the bound HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide. Assays for testing the effectiveness of such compounds are known in the art and discussed, elsewhere herein.

Example 8

Method of Screening, In Vitro, Compounds that Bind to a HGBPBMY1 (AK096141), HGBPBMY2 (4843 30 1 1, 4843 1), HGBPBMY3 (4843 30 2 1, 4843 2), HGBPBMY4 (FLJ10961), MGBPBMY1 (LOC229900), MGBPBMY2 (LOC229902), MGBPBMY3 (BC031475) and/or MGBPBMY4 (BC007143) Polypeptide In vitro systems can be designed to identify compounds capable of binding a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide of the present invention. Compounds identified can be useful, for example, in modulating the activity of wild type and/or mutant HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, preferably mutant HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, can be useful in elaborating the biological function of a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, can be utilized in screens for identifying compounds that disrupt normal HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide interactions, or can in themselves disrupt such interactions.

One assay that can be used to identify compounds that bind to a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide involves preparing a reaction mixture of a HGBPBMY1 (AK096141), HGBPBMY2 (4843 30 1 1; 4843__1), HGBPBMY3 (4843 30 2 1; 4843__2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring a HGB-PBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or the test substance onto a solid phase and detecting a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide/test compound complex anchored on the solid phase at the end of the reaction. In one embodiment of such a method, a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide can be anchored onto a solid surface, and the test compound, which is not anchored, can be labeled, either directly or indirectly.

In practice, a microtiter plate can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or the test compound to anchor any complexes formed in solution, and a labeled antibody specific for the other component of the possible complex to detect anchored complexes.

Another example of a screening assay to identify compounds that bind to a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, relates to the application of a cell membrane-based scintillation proximity assay ("SPA"). Such an assay would require the idenification of a ligand for a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide. Once identified, unlabeled ligand is added to assay-ready plates that would serve as a positive control. The SPA beads and membranes are added next, and then $^{125}$I-labeled ligand is added. After an equilibration period of 2–4 hours at room temperature, the plates can be counted in a scintillation counting machine, and the percent inhibition or stimulation calculated.

Such an SPA assay can be based upon a manual, automated, or semi-automated platform, and encompass 96, 384, 1536-well plates or more. Any number of SPA beads can be used as applicable to each assay. The utilized membranes can also be derived from a number of cell line and tissue sources depending upon the expression profile of the respective polypeptide and the adaptability of such a cell line or tissue source to the development of a SPA-based assay. Examples of membrane preparations include, for example, cell lines transformed to express the receptor to be assayed in CHO cells or HEK cells, for example. SPA-based assays are well known in the art and are encompassed by the present invention. One such assay is described in U.S. Pat. No. 4,568,649, which is incorporated herein by reference The skilled artisan would acknowledge that certain modifications of known SPA assays may be required to adapt such assays to each respective polypeptide.

One such screening procedure involves the use of melanophores which are transfected to express a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide of the present invention. Such a screening technique is described in PCT WO 92/01810. Such an assay can be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i.e., inhibits activation of the receptor.

The technique can also be employed for screening of compounds thta activate the receptor by contacting such cells with compounds to be screened and determining whether such compound generates a signal, i.e., activates the receptor. Other screening techniques include the use of cells which express a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide (for example, transfected CHO cells) in a system which measures extracellular pH changes caused by receptor activation. In this technique, compounds can be contacted with cells expressing the receptor polypeptide of the present invention. A second messenger response, e.g., signal transduction or pH changes, is then measured to determine whether the potential compound activates or inhibits the receptor.

Another method involves screening for HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide inhibitors by determining inhibition or stimulation of HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide-mediated cAMP and/or adenylate cyclase accumulation or diminution. Such a method involves transiently or stably transfecting a eukaryotic cell with a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide to express the polypeptide on the cell surface.

The cell is then exposed to potential antagonists or agonists in the presence of HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide ligand. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits HGPRBMY30_1, HGPRBMY30_2, HGPRBMY30_3, HGPRBMY41_1, HGPRBMY41_2, HGPRBMY41_3, HGPRBMY42, HGPRBMY42_1, HGPRBMY43, and/or HGPRBMY44 polypeptide-ligand binding, the levels of HGPRBMY30_1, HGPRBMY30_2, HGPRBMY30_3, HGPRBMY41_1, HGPRBMY41_2, HGPRBMY41_3, HGPRBMY42, HGPRBMY42_1, HGPRBMY43, and/or HGPRBMY44 polypeptide-mediated cAMP, or adenylate cyclase activity, will be reduced or increased.

Alternatively, a GTPase assay can be employed to identify a binding event. For example, the GBP's of the present invention possess GTPase activity. Thus, a screening method can employ this property to identify compounds that bind to a GBP of the present invention. In one embodiment, a test compound is a GTP analog and liberates one or more phosphate groups when acted upon by a GBP of the present invention. Various GTPase assays are known in the art and can be employed in the present invention. For example, a test compound can comprise a detectable label. When a GBP acts on the test compound, the label is liberated and can be detected and/or quantitated.

Further, a labeled test compound can be employed and the formation of a GBP-test compound complex can be detected after removing unbound test compound.

Examples of labels that can be employed in a screening process include $^{32}P$ and other radiolabels, as well as various fluorescent moieties.

Example 9

Method for Identifying a Putative Ligand for a HGBPBMY1 (AK096141), HGBPBMY2 (4843 30 1 1; 4843 1), HGBPBMY3 (4843 30 2 1; 4843 2), HGBPBMY4 (FLJ10961), MGBPBMY1 (LOC229900), MGBPBMY2 (LOC229902), MGBPBMY3 (BC031475) and/or MGBPBMY4 (BC007143) Polypeptide Ligand binding assays provide a direct method for ascertaining protein pharmacology and are adaptable to a high throughput format. A panel of known GBP purified ligands can be radiolabeled to high specific activity (50–2000 Ci/mmol) for binding studies. A determination is then made that the process of radiolabeling does not diminish the activity of the ligand towards its cognate protein. Assay conditions for buffers, ions, pH and other modulators such as nucleotides are optimized to establish a workable signal to noise ratio. For these assays, specific protein binding is defined as total associated radioactivity minus the radioactivity measured in the presence of an excess of unlabeled competing ligand. Where possible, more than one competing ligand is used to define residual nonspecific binding.

A number of GBP ligands are known in the art and are encompassed by the present invention.

Alternatively, a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide of the present invention can also be functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated identified using methods well known in the art, some of which are described herein.

Example 10

Method of Identifying Compounds that Interfere with HGBPBMY1 (AK096141). HGBPBMY2 (4843 30 1 1.4843 1), HGBPBMY3 (4843 30 2; 14843 2), HGBPBMY4 (FLJ10961), MGBPBMY1 (LOC229900). MGBPBMY2 (LOC229902), MGBPBMY3 (BC031475) and/or MGBPBMY4 (BC007143) Polypeptide/Cellular Product Interaction A HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide of the present invention can, in vivo, interact with one or more cellular or extracellular macromolecules, such as proteins. Such macromolecules include, but are not limited to, polypeptides, particularly GBP ligands, and those products identified via screening methods described, elsewhere herein. For the purposes of this discussion, such cellular and extracellular macromolecules are referred to herein as "binding partner(s)". For the purpose of the present invention, the term "binding partner" can also encompass polypeptides, small molecule compounds, polysaccharides, lipids, and any other molecule or molecule type referenced herein. Compounds that disrupt such interactions can be useful in regulating the activity of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide, especially a mutant HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide. Such compounds can include, but are not limited to molecules such as antibodies, peptides, and the like described in elsewhere herein.

The basic principle of the assay systems used to identify compounds that interfere with the interaction between a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and its cellular or extracellular binding partner or partners involves preparing a reaction mixture containing a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and the binding partner under conditions and for a time sufficient to allow the two products to interact and bind, thus forming a complex.

In order to test a compound for inhibitory activity, the reaction mixture is prepared in the presence and absence of the test compound. The test compound can be initially included in the reaction mixture, or can be added at a time subsequent to the addition of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and its cellular or extracellular binding partner. Control reaction mixtures are incubated without the test compound or with a placebo. The formation of any complexes between a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and the cellular or extracellular binding partner is then detected. The formation of a complex in the control reaction, but not in the reaction mixture containing the test compound, indicates that the compound interferes with the interaction of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and the interactive binding partner. Additionally, complex formation within reaction mixtures containing the test compound and a normal HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide can also be compared to complex formation within reaction mixtures containing the test compound and a mutant a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2. (LOC229902), MGBPBMY3 (BC031475) and/or MGBPBMY4 (BC007143) polypeptide. This comparison can be important in those cases in which it is desirable to identify compounds that disrupt interactions of a mutant but not a normal HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide.

The assay for compounds that interfere with the interaction of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and binding partners can be conducted in a heterogeneous or homogeneous format. Heterogeneous assays involve anchoring either a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or the binding partner onto a solid phase and detecting complexes anchored on the solid phase at the end of the reaction.

In homogeneous assays, the entire reaction is carried out in a liquid phase. In either approach, the order of addition of reactants can be varied to obtain different information about the compounds being tested. For example, test compounds that interfere with the interaction between a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and its binding partners, e.g., by competition, can be identified by conducting the reaction in the presence of the test substance; i.e., by adding the test substance to the reaction mixture prior to or simultaneously with a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or the interactive cellular or extracellular binding partner, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with a solution of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the present invention, a homogeneous assay can be used. In this approach, a preformed complex comprising a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and an interactive cellular or extracellular binding partner product is prepared in which either the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide or its binding partners are labeled, but the signal generated by the label is quenched due to complex formation (see, e.g., U.S. Pat. No. 4,109,496 which describes this approach for immunoassays). The addition of a test substance that competes with and displaces one of the species from the preformed complex will result in the generation of a signal above background. In this way, test substances that disrupt HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide/ cellular or extracellular binding partner interaction can be identified.

In a particular embodiment, a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide can be prepared for immobilization using recombinant DNA techniques known in the art. For example, a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope, $^{125}$I, for example, by methods known to those of ordinary skill in the art. In a heterogeneous assay, a GST-HGBPBMY1 (AK096141), GST-HGBPBMY2 (4843 30 1 1; 4843_1), GST-HGBPBMY3 (4843 30 2 1; 4843_2), GST-HGBPBMY4 (FLJ10961), GST-MGBPBMY1 (LOC229900), GST-MGBPBMY2 (LOC229902), GST-MGBPBMY3 (BC031475) and/or GST-MGBPBMY4 (BC007143) polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-HGBPBMY1 (AK096141), GST-HGBPBMY2 (4843 30 1 1; 4843_1), GST-HGBPBMY3 (4843 30 2 1; 4843_2), GST-HGBPBMY4 (FLJ10961), GST-MGBPBMY1 (LOC229900), GST-MGBPBMY2 (LOC229902), GST-MGBPBMY3 (BC031475) and/or GST-MGBPBMY4 (BC007143) polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the present invention, these same techniques can be employed using peptide fragments that correspond to the binding domains of a HGBPBMY1 (AK096141), HGBPBMY2 (4843 30 1 1; 4843_1), HGBPBMY3 (4843 30 2 1; 4843_2), HGBPBMY4 (FLJ-10961), MGBPBMY1 (LOC229900), MGBPBMY2 (LOC229902), MGBPBMY3 (BC031475) and/or MGBPBMY4 (BC007143) polypeptide product and the interactive cellular or extracellular binding partner (in case where the binding partner is a product), in place of one or both of the full length products.

Any number of methods known to those of ordinary skill in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described herein, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 11

Isolation of a Specific Clone from a Deposited Sample

The deposited material in a sample assigned a ATCC Deposit Number cited in Table I for any given cDNA clone also can contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1–10 plasmid DNAs, each containing a different cDNA clone and/or partial cDNA clone; but such a deposit sample can include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:X.

Particularly, a specific polynucleotide with 30–40 nucleotides is synthesized using an DNA synthesizer (e.g., such as those avaiable from Applied Biosystems, Foster City, Calif., USA) according to the sequence reported. The oligonucleotide is labeled, for instance, with $^{32}$P-labled ATP using T4 polynucleotide kinase and purified according to routine methods. (see, e.g., Sambrook et al., *Molecular Cloning: A Laboratory Manual*, (3rd ed.) Cold Spring Harbor Laboratory Press, Cold Spring Harbor, N.Y., USA (2001)). The plasmid mixture is transformed into a suitable host, as indicated above (such as XL-1 Blue (Stratagene, La Jolla, Calif., USA)) using techniques known to those of skill in the art, such as those provided by the vector supplier or in related publications or patents cited herein. The transformants are plated on 1.5% agar plates (containing the appropriate selection agent, e.g., ampicillin) to a density of about 150 transformants (colonies) per plate. These plates are screened using nylon membranes according to routine methods for bacterial colony screening (e.g., Sambrook et al., *Molecular Cloning: A Laboratory Manual*, (3d ed.) Cold Spring Harbor Laboratory Press, Cold Spring Harbor, N.Y., USA (2001)), or other techniques known to those of ordinary skill in the art.

Alternatively, two primers of 17–20 nucleotides derived from both ends of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16 (i.e., within the region of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16 bounded by the 5' NT and the 3' NT of the clone defined in Table I; SEQ ID NO:X) are synthesized and used to amplify the desired cDNA using the deposited cDNA plasmid as a template. The polymerase chain reaction is carried out under routine conditions, for instance, in 25 µl of reaction mixture with 0.5 µg of the above cDNA template. A convenient reaction mixture is 1.5–5 mM MgCl$_2$, 0.01% (w/v) gelatin, 20 µM each of dATP, dCTP, dGTP, dTTP, 25 pmol of each primer and 0.25 Unit of Taq polymerase. Thirty five cycles of PCR (e.g., denaturation at 94 degree C. for 1 min; annealing at 55 degree C. for 1 min; elongation at 72 degree C. for 1 min) are performed with an automated thermal cycler (e.g., a Perkin-Elmer Cetus 9600 Cycler, Wellesley, Mass., USA). The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding a polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene that may not be present in the deposited clone. The methods that follow are exemplary and should not be construed as limiting the scope of the present invention. These methods include but are not limited to, filter probing, clone enrichment using specific probes, and protocols similar or identical to 5' and 3' "RACE" protocols that are known in the art. For instance, a method similar to 5' RACE is available for generating the missing 5' end of a desired full-length transcript. (Fromont-Racine et al., (1993) *Nucl. Acid Res.* 21(7): 1683–1684).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This method starts with total RNA isolated from the desired source, although poly-A+ RNA can also be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in Schaefer, (1995) *Anal. Biochem.* 227:255–273.

An alternative method for carrying out 5' or 3' RACE for the identification of coding or non-coding sequences is provided by Frohman et al., (1988) *Proc. Natl. Acad. Sci. U.S.A.* 85:8998–9002. Briefly, a cDNA clone missing either the 5' or 3' end can be reconstructed to include the absent base pairs extending to the translational start or stop codon, respectively. In some cases, cDNAs are missing the start translation codon.

The following briefly describes a modification of this original 5' RACE procedure. Poly A+ or total RNAs reverse transcribed with Superscript II (Gibco BRL) and an antisense or I complementary primer specific to the cDNA sequence. The primer is removed from the reaction with an Amicon Microcon Concentrator (Millipore, Bedford, Mass., USA). The first-strand cDNA is then tailed with dATP and terminal deoxynucleotide transferase (Gibco BRL). Thus, an anchor sequence is produced which is needed for PCR amplification. The second strand is synthesized from the dA-tail in PCR buffer, Taq DNA polymerase (Perkin-Elmer Cetus, Wellesley, Mass., USA), an oligo-dT primer containing three adjacent restriction sites (XhoI, SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed cDNA is purified from the agarose with the Magic PCR Prep kit (Promega, Madison, Wis., USA), restriction digested with XhoI or SalI, and ligated to a plasmid such as pBluescript SKII (Stratagene, La Jolla, Calif., USA) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco BRL for both 5' and 3' RACE for recovery of full length genes. A second kit is available from Clontech (Palo Alto, Calif., USA) which is a modification of a related technique, SLIC (single-stranded ligation to single-stranded cDNA), developed by Dumas et al., (Dumas et al., (1991) *Nucl. Acid Res.* 19:5227–32). The differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3' RACE. While the full-length gene may be present in the library and can be identified by probing, a useful method for generating the 5' or 3' end is to use the existing sequence information from the original cDNA to generate the missing information. A method similar to 5' RACE is available for generating the missing 5' end of a desired full-length gene. (This method was published by Fromont-Racine et al., (1993) *Nucl. Acid Res.* 21(7):1683–1684). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used, but is not a prerequisite for this procedure. The RNA preparation may then be treated with phosphatase if necessary to eliminate 5' phosphate groups on degraded or damaged RNA that may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 12

Tissue Distribution of a Polypeptide of the Present Invention

Tissue distribution of mRNA expression of polynucleotides of the present invention is determined using protocols for Northern blot analysis, described by, among others, Sambrook et al., *Molecular Cloning: A Laboratory Manual*, ($3^{rd}$ ed.) Cold Spring Harbor Laboratory Press, Cold Spring Harbor, N.Y., USA (2001). For example, a cDNA probe produced by a method described herein is labeled with $^{32}P$ using the REDIPRIME® DNA labeling system (Amersham Life Science, Arlington Heights, Ill., USA), according to manufacturer's instructions. After labeling, the probe is purified using a CHROMA SPIN0–100 column (Clontech Laboratories, Inc., Palo Alto, Calif., USA) according to the manufacturer's protocol. The purified, labeled probe is then used to examine various tissues for mRNA expression.

Tissue northern blots containing the bound mRNA of various tissues are examined with the labeled probe using EXPRESSHYB® hybridization solution (Clonetech, Palo Alto, Calif., USA) according to the manufacturer's protocol. Northern blots can be produced using various protocols known in the art (e.g., Sambrook et al., *Molecular Cloning: A Laboratory Manual*, (3rd ed.) Cold Spring Harbor Laboratory Press, Cold Spring Harbor, N.Y., USA (2001)). Following hybridization and washing, the blots are mounted and exposed to film at −70° C. overnight, and the films developed according to standard procedures.

Example 13

Chromosomal Mapping of a Polynucleotide of the Present Invention

An oligonucleotide primer set is designed according to the sequence at the 5' end of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16. In one embodiment, this primer spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios Laboratories, Inc., New Haven, Conn., USA). The reactions are analyzed on either 8% polyacrylamide gels or 3.5% agarose gels. Chromosome mapping is determined by the presence of an approximately 100 bp PCR fragment in the particular somatic cell hybrid.

Example 14

Bacterial Expression of a Polypeptide of the Present Invention

A polynucleotide encoding a polypeptide of the present invention is amplified using PCR oligonucleotide primers corresponding to the 5' and 3' ends of the DNA sequence, as outlined herein, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform E. coli strain M15/rep4 (Qiagen, Inc.) which contains multiple copies of the plasmid pREP4, that expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 μg/mil) and Kan (25 μg/ml). The O/N culture is used to inoculate a large culture at a ratio of 1:100 to 1:250. The cells are grown to an optical density 600 (O.D.600) of between 0.4 and 0.6. IPTG (isopropyl-B-D-thiogalacto pyranoside) is then added to a final concentration of 1 mM. IPTG induces by inactivating the lacI repressor, clearing the P/O leading to increased gene expression.

Cells are grown for another 3 to 4 hours. Cells are then harvested by centrifugation (20 mins at 6000×g). The cell pellet is solubilized in the chaotropic agent 6 molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc.). Proteins with a 6×His tag bind to the Ni-NTA resin with high affinity and can be purified in a simple one-step procedure (for details see: *The QIAexpressionist* (1995) published by QIAGEN, Inc.).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 15

Purification of a Polypeptide of the Present Invention from an Inclusion Body The following alternative method can be used to purify a polypeptide expressed in E coli when it is present in the form of inclusion bodies. Unless otherwise specified, all of the following steps are conducted at 4–10 degree C.

Upon completion of the production phase of the E. coli fermentation, the cell culture is cooled to 4–10° C. and the cells harvested by continuous centrifugation at 15,000 rpm (Heraeus Sepatech, Osterode, Germany). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (e.g., such as those available from Microfluidics Corp., Newton, Mass., USA or APV Systems, Wilmington, Mass., USA) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems, Foster City Calif., USA). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-500, Perceptive Biosystems, Foster City, Calif., USA) and weak anion (Poros CM-200, Perceptive Biosystems, Foster City, Calif., USA) exchange resins. The columns are equilibrated with 40 mM sodium acetate, pH 6.0. Both columns are washed with 40 mM sodium acetate, pH 6.0, 200 mM NaCl. The CM-20® column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 51g of purified protein is loaded. The purified protein can also be tested for endotoxin/LPS contamination, and typically the LPS content is less than 0.1 ng/ml according to LAL assays.

Example 16

Cloning and Expression of a Polypeptide of the Present Invention in a Baculovirus Expression System In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIMI, as one skilled in the art would readily appreciate, as long as the construct provides appropriately located signals for transcription, translation, secretion and the like, including a signal peptide and an in-frame AUG as required. Such vectors are described, for instance, in Luckow et al., (1989) *Virology* 170:31–39.

A polynucleotide encoding a polypeptide of the present invention is amplified using PCR oligonucleotide primers corresponding to the 5' and 3' ends of the DNA sequence, as outlined herein, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described herein. If the naturally occurring signal sequence is used to produce the protein, the vector used does not need a second signal peptide. Alternatively, the vector can be modified to include a baculovirus leader sequence, using the standard methods described by Summers et al. (Summers et al., (1987) "A Manual of Methods for Baculovirus Vectors and Insect Cell Culture Procedures," Texas Agricultural Experimental Station Bulletin No. 1555).

The amplified fragment is isolated from a 1% agarose gel using a commercially available kit (GENECLEAN®, BIO 101 Inc., La Jolla, Calif., USA). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit (GENECLEAN®, BIO 101 Inc., La Jolla, Calif., USA).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif., USA) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five µg of a plasmid containing the polynucleotide is co-transformed with 1.0 µg of a commercially available linearized baculovirus DNA (e.g., BACULOGOLD® baculovirus DNA, Pharmingen, San Diego, Calif., USA), using the lipofection method described by Felgner et al. (Felgner et al., (1987) *Proc. Natl. Acad. Sci. U.S.A.* 84:7413–7417). One µg of BACULOGOLD® virus DNA and 5 µg of the plasmid are mixed in a sterile well of a microtiter plate containing 50 µl of serum-free Grace's medium (Life Technologies Inc., Rockville, Md., USA). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added.

Cultivation is then continued at 27° C. for four days.

After four days the supernatant is collected and a plaque assay is performed, as described by Summers & Smith, (Summers et al., (1987) "A Manual of Methods for Baculovirus Vectors and Insect Cell Culture Procedures," Texas Agricultural Experimental Station Bulletin No. 1555). An agarose gel with BLUE GAL (Life Technologies Inc., Rockville, Md., USA) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Rockville, Md., USA, pp. 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md., USA). After 42 hours, 5 µCi of $^{35}$S-methionine and 5 RCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 17

Expression of a Polypeptide of the Present Invention in Mammalian Cells

A polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail $QC_{1-3}$ cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest (see, e.g., Alt et al., (1978) *J. Biol. Chem.* 253:1357–1370; Hamlin & Ma, (1990) *Biochim. Biophys. Acta* 1097:107–143; Page & Sydenham, (1991) *Biotechnol.* 9:64–68). Another useful selection marker is the enzyme glutamine synthase (GS) (Murphy et al., (1991) *Biochem J.* 227:277–279; Bebbington et al., (1992) *Bio/Technology* 10:169–175). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence (see, e.g., PCT Publication WO 96/34891). The amplified fragment is isolated from a 1% agarose gel using a commercially available kit (GENECLEAN®, BIO 101 Inc., La Jolla, Calif., USA). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB11 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using lipofectin (Felgner et al., (1987) *Proc. Natl. Acad. Sci. USA* 84:7413–7417). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (available from Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and western blot or by reversed phase HPLC analysis.

Example 18

Method of Creating N- and C-terminal Deletion Mutants Corresponding to a HGBPBMY1 (AK096141), HGBPBMY2 (4843 30 1 1; 4843_1), HGBPBMY3 (4843 30 2 1:4843_2), HGBPBMY4 (FLJ10961), MGBPBMY1 (LOC229900), MGBPBMY2 (LOC229902), MGBPBMY3 (BC031475) and/or MGBPBMY4 (BC007143) Polypeptide of the Present Invention As described elsewhere herein, the present invention encompasses the creation of N- and C-terminal deletion mutants, in addition to any combination of N- and C-terminal deletions thereof, corresponding to a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide of the present invention. A number of methods are available to one of ordinary skill in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding a full-length HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143) polypeptide sequence (as described in herein, for example, in SEQ ID NO:Y), appropriate primers of about 15–25 nucleotides derived from the desired 5' and 3' positions of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16 (SEQ ID NO:X) may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, FLAG® (Sigma, St. Louis, Mo., USA) tag sequences, kozac sequences, or other sequences discussed and/or referenced herein.

Representative PCR amplification conditions are provided below, although the skilled artisan would appreciate that other conditions may be required for efficient amplification. A 100 µl PCR reaction mixture may be prepared using 10 ng of the template DNA (cDNA clone of HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143)), 200 µM 4dNTPs, 1 µM primers, 0.25U Taq DNA polymerase (PE), and standard Taq DNA polymerase buffer. Representative PCR cycling condition are as follows:

| 20–25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SaiII restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula: $(S+(X*3))$ to $((S+(X*3))+25)$, wherein 'S' is equal to the nucleotide position of the initiating start codon of a HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBM3 and/or MGBPBMY4 (BC007143) gene (i.e., SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: $(S+(X*3))$ to $((S+(X*3))-25)$, wherein 'S' is equal to the nucleotide position of the initiating start codon of the HGBPBMY1 (AK096141), HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBM3 and/or MGBPBMY4 (BC007143) gene (SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention.

expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence (see, e.g., PCT Publication WO 96/34891 and/or U.S. Pat. No. 6,066,781).

Human IgG Fc region:

```
gggatccggagcccaaatcttctgacaaaactcacacatgcccaccgtgcccagcacctgaattcgagggtgcaccgtca         (SEQ ID NO: 59)

gtcttcctcttccccccaaaacccaaggacaccctcatgatctcccggactcctgaggtcacatgcgtggtggtggacgtaa gccacgaagaccctgaggtcaagttcaactggtacgtggacggcgtggaggtgcataatgccaagacaaagccgcggg aggagcagtacaacagcacgtaccgtgtggtcagcgtcctcaccgtcctgcaccaggactggctgaatggcaaggagta caagtgcaaggtctccaacaaagccctcccaacccccatcgagaaaaccatctccaaagccaaagggcagccccgaga accacaggtgtacaccctgcccccatcccgggatgagctgaccaagaaccaggtcagcctgacctgcctggtcaaaggc ttctatcccagcgacatcgccgtggagtgggagagcaatgggcagccggagaacaactacaagaccacgcctcccgtgc tggactccgacggctccttcttcctctacagcaagctcaccgtggacaagagcaggtggcagcaggggaacgtcttctcat gctccgtgatgcatgaggctctgcacaaccactacacgcagaagagcctctccctgtctccgggtaaatgagtgcgacgg ccgcgactctagaggat
```

Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 19

Protein Fusions Comprising a Polypeptide of the Present Invention

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification (see the Examples described herein; see also EP A 394,827; Traunecker et al., (1988) Nature 331:84–86). Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian Example 20

Production of an Antibody from a Polypeptide of the Present Invention

Antibodies of the present invention can be prepared by a variety of methods. As one example of such methods, cells expressing a polypeptide of the present invention are administered to an animal to induce the production of sera containing polyclonal antibodies. In a representative method, a preparation of the polypeptide is prepared and purified to render it substantially free of natural contaminants. Such a preparation is then introduced into an animal in order to produce polyclonal antisera of greater specific activity.

In another representative method, the antibodies of the present invention are monoclonal antibodies (or protein binding fragments thereof). Such monoclonal antibodies can be prepared using hybridoma technology (Köhler et al., (1975) Nature 256:495; Köhler et al., (1976) Eur. J. Immunol. 6:511; Köhler et al., (1976) Eur. J. Immunol. 6:292; Hammerling et al., in: Monoclonal Antibodies and T-Cell Hybridomas, Elsevier, New York, N.Y., USA, pp. 563–681 (1981)). In general, such procedures involve immunizing an animal (e.g., a mouse or rabbit) with polypeptide or, alternatively, with a polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 ug/ml of streptomycin.

The splenocytes of such animals are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Wands et al., (1981) *Gastroenterology* 80:225–232). The hybridoma cells obtained through such a selection are then assayed to identify clones that secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, for example a mouse or rabbit. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described herein. Methods for producing chimeric antibodies are known in the art (see, for a review, Morrison, (1985) *Science* 229:1202; Oi et al., (1986) *BioTechniques* 4:214; U.S. Pat. No. 4,816,567; EP 171496; EP 173494; PCT Publications WO 8601533 and WO 8702671; Boulianne et al., (1984) *Nature* 312:643; Neuberger et al., (1985) *Nature* 314:268).

Moreover, in another representative method, antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 21

Regulation of Protein Expression via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, e.g., Gossen et al., (1992) *Proc. Natl. Acad. Sci. USA*. 89:5547; Wang et al., (1994) *Proc. Natl. Acad. Sci. USA* 91:8180; No. et al., (1996) *Proc. Natl. Acad. Sci. U.S.A.* 93:3346; and Rivera et al., (1996) *Nature Med.* 2:1028; in addition to additional examples disclosed elsewhere herein). In one example, the gene for erthropoietin (epo) was transferred into mice and primates under the control of a small molecule inducer for expression (e.g., tetracycline or rapamycin) (see, Bohl et al., (1998) *Blood* 92:1512; Rendahl et al., (1998) *Nat. Biotech.* 16:757; Rivera et al., (1999) *Proc. Natl. Acad. Sci. USA* 96:8657; and Ye et al., (1999) *Science* 283:88). Although such systems enable efficient induction of the gene of interest in the organism upon addition of the inducing agent (i.e., tetracycline, rapamycin, etc.), the levels of expression tend to peak at 24 hours and trail off to background levels after 4 to 14 days. Thus, controlled transient expression is difficult to attain using these systems, though such control would be desirable.

An alternative method of controlling gene expression levels of a protein from a transgene (i.e., including stable and transient transformants) has recently been elucidated (Rivera et al., (2000) *Science* 287:826–830). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in de-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in Rivera et al., (2000) *Science* 287:826–830). Briefly, fusion protein constructs are created using polynucleotide sequences of the present invention with one or more copies (for example, at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain can be, for example, the mutant domain isolated from the human FKBP12 (Phe$^{36}$ to Met) protein (as disclosed in Rivera et al., (2000) *Science* 287:826–830), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from a polypeptide of the present invention subsequent to secretion from the ER and upon entry into the trans-Golgi (Denault et al., (1996) *FEBS Lett.* 379:113). Alternatively, those of ordinary skill in the art would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)$_x$ domains, the furin sequence (or other proteolytic sequence), and the coding sequence of a polypeptide of the present invention. Those of ordinary skill in the art will appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 22

Alteration of Protein Glycosylation Sites to Enhance Characteristics of a Polypeptide of the Present Invention Many eukaryotic cell surface proteins are post-translationally processed to incorporate N-linked and O-linked carbohydrates (Kornfeld & Kornfeld, (1985) Ann. Rev. Biochem. 54:631–64; Rademacher et al., (1988) Ann. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler & Simons, (1995) Cell 81:309–312; Helenius, (1994) Mol. Biol. Cell 5:253–265; Olden et al., (1978) Cell 13:461–473; Caton et al., (1982) Cell 37:417–427; Alexander & Elder, (1984) Science 226:1328–1330; and Flack et al., (1994) J. Biol. Chem. 269:14015–14020). In higher organisms, the nature and extent of glycosylation can markedly affect the circulating half-life and bio-availability of proteins by mechanisms involving receptor mediated uptake and clearance (Ashwell & Morrell, (1974) Adv. Enzymol. 41:99–128; Ashwell & Harford, (1982) Ann. Rev. Biochem. 51:531–54). Receptor systems have been identified that are thought to play a major role in the clearance of serum proteins through recognition of various carbohydrate structures on the glycoproteins (Stockert, (1995) Physiol. Rev. 75:591–609; Kery et al., (1992) Arch. Biochem. Biophys. 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoprotein's primary structure (Berman & Lasky, (1985) Trends Biotechnol. 3:51–53). However, studies have reported that the deletion of N-linked glycosylation sites often impairs intracellular transport and results in the intracellular accumulation of glycosylation site variants (Machamer & Rose, (1988) J. Biol. Chem. 263:5955–5960; Gallagher et al., (1992) J. Virology. 66:7136–7145; Collier et al., (1993) Biochem. 32:7818–7823; Claffey et al., (1995) Biochim. Biophys. Acta 1246:1–9; Dube et al., (1988) J. Biol. Chem. 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a protein's ability to be expressed, either endogenously or recombinately, in another organism (i.e., expressing a human protein in E. coli, yeast, or viral organisms; or an E. coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to those of ordinary skill in the art, for example using PCR-directed mutagenesis (see, e.g., Sambrook et al., Molecular Cloning: A Laboratory Manual, (3rd ed.) Cold Spring Harbor Laboratory Press, Cold Spring Harbor, N.Y., USA (2001)). Similarly, glycosylation sites could be added, or modified at the level of the DNA using similar methods, for example PCR (see Sambrook et al., Molecular Cloning: A Laboratory Manual, (3d ed.) Cold Spring Harbor Laboratory Press, Cold Spring Harbor, N.Y., USA (2001)). The results of modifying the glycosylation sites for a particular protein (e.g., solubility, secretion potential, activity, aggregation, proteolytic resistance, etc.) could then be analyzed using methods know in the art.

Those of ordinary skill in the art will acknowledge the existence of other computer algorithms capable of predicting the location of glycosylation sites within a protein. For example, the MOTIF computer program (Genetics Computer Group suite of programs) provides this function as well.

Example 23

Method of Enhancing the Biological Activity/Functional Characteristics of a Polypeptide of the Present Invention through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for proteins used in gene therapy, transgenic animal production, the bioprocess production and purification of the protein, and use of the protein as a chemical modulator among others. Therefore, there is a need to identify novel variants of isolated proteins possessing characteristics that enhance their application as a therapeutic for treating diseases of animal origin, in addition to the protein's applicability to common industrial and pharmaceutical applications.

Thus, one aspect of the present invention relates to the ability to enhance specific characteristics of a polypeptide of the present invention through directed molecular evolution. Such an enhancement may, in a non-limiting example, (a) provide an additional utility for a polypeptide and/or polynucleotide of the present invention, for example as a component in a kit, (b) impart a desirable physical property to a polypeptide of the present invention, such as an enhancement in solubility, structure, or codon optimization, (c) impart an enhanced biological activity, including any associated enzymatic activity, which encompasses a polypeptide's enzyme kinetics, (e.g., Ki, Kcat, Km, Vmax, Kd), protein-protein activity, protein-DNA binding activity, antagonist/inhibitory activity (including direct or indirect interaction), agonist activity (including direct or indirect interaction), (d) a polypeptide's antigenicity (e.g., where it would be desirable to either increase or decrease the antigenic potential of the protein), (e) the immunogenicity of the protein, (f) the ability of a polypeptide to form dimers, trimers, or multimers with either itself or other proteins, (g) the antigenic efficacy of the present invention, including its subsequent use a preventative treatment for disease or disease states, or (h) as an effector for targeting diseased genes, to name just a few examples. Moreover, the ability to enhance specific characteristics of a protein may also be applicable to changing the characterized activity of an enzyme to an activity completely unrelated to its initially characterized activity. Other desirable enhancements of the present invention would be specific to each individual protein, and would thus be well known in the art and contemplated by the present invention.

Directed evolution is comprised of several steps. In one embodiment, a first step is to establish a library of variants for the gene or protein of interest. The next step is to then select for those variants that entail the activity it is desired to identify. The design of the screen is essential since the screen should be selective enough to eliminate non-useful variants, but not so stringent as to eliminate all variants. The last step is then to repeat the above steps using the best variant from the previous screen. Each successive cycle, can then be tailored as necessary, such as by increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Sambrook et al., *Molecular Cloning: A Laboratory Manual*, (3rd ed.) Cold Spring Harbor Laboratory Press, Cold Spring Harbor, N.Y., USA (2001)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore et al., (1996) *Nature Biotechnol.* 14:458), or through the application of randomized synthetic oligonucleotides corresponding to specific regions of interest (as described by Derbyshire et al., (1986) *Gene* 46:145–152; and Hill et al., (1987) *Method Enzymol.* 55:559–568). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (Stemmer, (1994) *Proc. Natl. Acad. Sci. USA* 91:10747) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the present invention. This new, and often preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, the process begins with a randomly digested pool of small fragments of a target gene, created by DNase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments, further diversifying the potential hybridization sites during the annealing step of the reaction.

A variety of reaction conditions could be utilized to carry-out the DNA shuffling reaction. However, specific reaction conditions for DNA shuffling are provided, for example, in Stemmer, (1994) *Proc. Natl. Acad. Sci. U.S.A.* 91:10747.

Briefly:

In one embodiment, the DNA substrate to be subjected to the DNA shuffling reaction is prepared. Preparation may be in the form of simply purifying the DNA from contaminating cellular material, chemicals, buffers, oligonucleotide primers, deoxynucleotides, RNAs, etc., and may entail the use of DNA purification kits as those commerically available (e.g., from Qiagen, Inc., or from Promega, Corp., Madison, Wis., USA for example).

Once the DNA substrate has been purified, it would be subjected to Dnase I digestion. About 2–4 µg of the DNA substrate(s) would be digested with 0.0015 units of Dnase I (Sigma, St. Louis, Mo., USA) per µl in 100 µl of 50 mM Tris-HCL, pH 7.4/lniM $MgCl_2$ for 10–20 min. at room temperature. The resulting fragments of 10–50 bp could then be purified by running them through a 2% low-melting point agarose gel by electrophoresis onto DE81 ion-exchange paper (Whatman) or could be purified using Microcon concentrators (Amicon, Millipore, Wellesley, Mass., USA) of the appropriate molecular weight cutoff, or could use oligonucleotide purification columns (Qiagen, Inc.), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM $MgCl_2$, 50 mM KCl, 10 mM Tris.HCL, pH 9.0, and 0.1% Triton X-100, at a final fragment concentration of 10–30ng/μl. No primers are added at this point. Taq DNA polymerase (Promega, Madison, Wis., USA) would be used at 2.5 units per 100 μl of reaction mixture. A PCR program of 94 C for 60 seconds; 94 C for 30 seconds, 50–55 C for 30 seconds, and 72 C for 30 seconds using 30–45 cycles, followed by 72 C for 5 min using an MJ Research (Cambridge, Mass., USA) PTC-150 thermocycler. After the assembly reaction is completed, a 1:40 dilution of the resulting primeness product would then be introduced into a PCR mixture (using the same buffer mixture used for the assembly reaction) containing 0.8 μm of each primer and subjecting this mixture to 15 cycles of PCR (using 94 C for 30 seconds, 50 C for 30 seconds, and 72 C for 30 seconds). Representative primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the present invention. The DNA shuffling method can also be tailored to the desired level of mutagenesis using the methods described by Zhao et al. (Zhao et al., (1997) *Nucl Acid Res.* 25(6): 1307–1308).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: Moore et al., (1997) *J. Mol. Biol.* 272:336–347; Cross et al., (1998) *Mol. Cell. Biol.* 18:2923–2931; and Crameri et al., (1997) *Nat. Biotech.* 15:436–438).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000-fold increase over the wild-type form of the enzyme. In essence, the background mutagenesis yielded the genetic variability on which recombination acted to enhance the activity.

A third feature of recombination is that it can be used to remove deleterious mutations. As discussed herein, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the present invention encompasses the application of DNA shuffling technology to the evolution of polynucleotides and polypeptides of the present invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT Publications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the present invention as described in PCT Publications WO 98/13485, WO 98/13487, WO 98/27230, WO 98/31837, and Crameri et al., (1997) *Nat. Biotech.* 15:436–438, respectively.

Additional methods of applying "DNA Shuffling" technology to the polynucleotides and polypeptides of the present invention, including their proposed applications, can be found in U.S. Pat. No. 5,605,793; PCT Publications WO 95/22625; WO 97/20078; WO 97/35966; and WO 98/42832; WO 00/09727 specifically provides methods for applying DNA shuffling to the identification of herbicide selective crops which could be applied to the polynucleotides and polypeptides of the present invention; additionally, PCT Publication WO 00/12680 provides methods and compositions for generating, modifying, adapting, and optimizing polynucleotide sequences that confer detectable phenotypic properties on plant species; each of the above are hereby incorporated in their entirety herein for all purposes.

Example 24

Method of Determining Alterations in a Gene Corresponding to a Polynucleotide of the Present Invention RNA isolated from entire families or individual subjects presenting with a phenotype of interest (such as a disease) is be isolated cDNA is then generated from these RNA samples using protocols known in the art. The cDNA is then used as a template for PCR, employing primers surrounding regions of interest in SEQ ID NO:2, SEQ ID NO:4, SEQ ID NO:6, SEQ ID NO:8, SEQ ID NO:10, SEQ ID NO:12, SEQ ID NO:14, and/or SEQ ID NO:16. Representative PCR conditions consist of 35 cycles at 95 degrees C. for 30 seconds; 60–120 seconds at 52–58° C.; and 60–120 seconds at 70 degrees C., using buffer solutions described in Sidransky et al. (Sidransky et al., (1991) *Science* 252:706).

PCR products are then sequenced using primers labeled at their 5' end with T4 polynucleotide kinase, employing SEQUITHERM Polymerase. (Epicentre Technologies, Madison, Wis., USA). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., (Holton et al., (1991) *Nucl. Acid Research* 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to the methods described herein are nick-translated with digoxigenindeoxy-uridine 5'-triphosphate (Boehringer Manheim), and FISH performed as described in Johnson et al. (Johnson et al., (1991) *Method Cell Biol.* 35:73–99). Hybridization with the labeled probe is carried out using a vast excess of human cot-i DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt., USA) in combination with a cooled charge-coupled device camera (Photometrics, Tucson, Ariz., USA) and variable excitation wavelength filters (Johnson et al., (1991) *Genet. Anal. Tech. Appl.* 8:75). Image collection, analysis and chromosomal fractional length measurements are performed using the ISee Graphical Program System. (Inovision Corporation, Durham, N.C., USA). Chromosome alterations of the genomic region hybridized by the probe are identified as insertions, deletions, and translocations. These alterations are used as a diagnostic marker for an associated disease.

Example 25

Method of Detecting Abnormal Levels of a Polypeptide of the Present Invention in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. The wells of a microtiter plate are coated with specific antibodies, at a final concentration of 0.2 to 10 µg/ml. The antibodies are either monoclonal or polyclonal and are produced by the method described elsewhere herein. The wells are blocked so that non-specific binding of the polypeptide to the well is reduced.

The coated wells are then incubated for greater than about 2 hours at room temperature with a sample containing the polypeptide. Preferably, serial dilutions of the sample should be used to validate results. The plates are then washed three times with deionized or distilled water to remove unbounded polypeptide.

Next, 50 µl of specific antibody-alkaline phosphatase conjugate, at a concentration of 25–400 ng, is added and incubated for 2 hours at room temperature. The plates are again washed three times with deionized or distilled water to remove unbounded conjugate.

Add 75 µl of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Since the polypeptides of the present invention exhibit GTPase activity, a GTPase activity assay can also be employed to determine the concentration of polypeptide in the sample.

Example 26

Formulations

The present invention also provides methods of treatment and/or prevention diseases, disorders, and/or conditions (such as, for example, any one or more of the diseases or disorders disclosed herein) by administration to a subject of an effective amount of a therapeutic. The term "therapeutic" includes polynucleotides and/or polypeptides of the present invention (including fragments and variants), agonists or antagonists thereof, and/or antibodies thereto, in combination with a pharmaceutically acceptable carrier type (e.g., a sterile carrier).

A therapeutic may be formulated and dosed in a fashion consistent with good medical practice, taking into account the clinical condition of the individual subject (especially the side effects of treatment with the therapeutic alone), the site of delivery, the method of administration, the scheduling of administration, and other factors known to practitioners. The "effective amount" for purposes herein is thus determined by such considerations.

As a general proposition, the total pharmaceutically effective amount of the therapeutic administered parenterally per dose will be in the range of about 1 µg/kg/day to 10 mg/kg/day of subject body weight, although, as noted above, this will be subject to therapeutic discretion. More preferably, this dose is at least 0.01 mg/kg/day, and most preferably for humans between about 0.01 and 1 mg/kg/day for the hormone. If given continuously, the therapeutic is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration, which include intravenous, intramuscular, intraperitoneal, intrasternal, subcutaneous and intraarticular injection and infusion.

Therapeutics of the present invention are also suitably administered by sustained-release systems. Suitable examples of sustained-release therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type.

A therapeutic of the present invention may also be suitably administered by sustained-release systems. Suitable examples of sustained-release therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., (1983) *Biopolymers* 22:547–556), poly (2-hydroxyethyl methacrylate) (Langer et al., (1981) *J. Biomed. Mater. Res.* 15:167–277, and Langer, (1982) *Chem. Tech.* 12:98–10), ethylene vinyl acetate (Langer et al., (1981) *J. Biomed. Mater. Res.* 15:167–277) or poly-D-(-)-3-hydroxybutyric acid (EP 133,988).

Sustained-release therapeutics also include liposomally entrapped therapeutics of the present invention (see, generally, Langer, (1990) *Science* 249:1527–1533; Treat et al., in *Liposomes in the Therapy of Infectious Disease and Cancer*, (Lopez-Berestein and Fidler, eds.), Albert R. Liss, New York, N.Y., USA, pp. 317–327 and 353–365 (1989)). Liposomes containing the therapeutic are prepared by methods known per se: DE 3,218,121; Epstein et al., (1985) *Proc. Natl. Acad. Sci. U.S.A.* 82:3688–3692; Hwang et al., (1980) *Proc. Natl. Acad. Sci. U.S.A.* 77:4030–4034; EP 52,322; EP 36,676; EP 88,046; EP 143,949; EP 142,641; Japanese Patent Application 83-118008; U.S. Pat. Nos. 4,485,045 and 4,544,545; and EP 102,324). Ordinarily, the liposomes are of the small (about 200–800 Angstroms) unilamellar type in which the lipid content is greater than about 30 mol. percent cholesterol, the selected proportion being adjusted for the optimal therapeutic.

In yet an additional embodiment, a therapeutics of the present invention are delivered by way of a pump (see Langer, (1990) *Science* 249:1527–1533; Sefton, (1987) *CRC Crit. Ref. Biomed. Eng.* 14:201; Buchwald et al., (1980) *Surgery* 88:507; Saudek et al., (1989) *N. Engl. J. Med.* 321:574).

Other controlled release systems are discussed in the review by Langer (Langer, (1990) *Science* 249:1527–1533).

For parenteral administration, in one embodiment, the therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the therapeutic.

Generally, the formulations are prepared by contacting the therapeutic uniformly and intimately with liquid carriers or finely divided solid carriers or both. Then, if necessary, the product is shaped into the desired formulation. For example, the carrier can be a parenteral carrier, or can be a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

A therapeutic will typically be formulated in such vehicles at a concentration of about 0.1 mg/ml to 100 mg/ml, or 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-mil vials are filled with 5 mil of sterile-filtered 1% (w/v) aqueous therapeutic solution, and the resulting mixture is lyophilized. The infusion solution is prepared by reconstituting the lyophilized therapeutic using bacteriostatic "Water-for-Injection."

The present invention also provides a pharmaceutical pack or kit comprising one or more containers filled with one or more of the ingredients of the therapeutics of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the therapeutics may be employed in conjunction with other therapeutic compounds.

The therapeutics of the present invention may be administered alone or in combination with adjuvants. Adjuvants that may be administered with the therapeutics of the present invention include, but are not limited to, alum, alum plus deoxycholate (ImmunoAg, Vienna, Austria), MTP-PE (Biocine Corp., Emeryville, Calif., USA), QS21 (Genentech, Inc., South San Francisco, Calif., USA), BCG, and MPL. In a specific embodiment, therapeutics of the present invention are administered in combination with alum. In another specific embodiment, a therapeutic of the present invention is administered in combination with QS-21. Further adjuvants that may be administered with the therapeutics of the present invention include, but are not limited to, Monophosphoryl lipid immunomodulator, ADJUVAX 100a, QS-21, QS-18, CRL1005, Aluminum salts, MF-59, and Virosomal adjuvant technology. Vaccines that may be administered with the therapeutics of the present invention include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

A therapeutic of the present invention may be administered alone or in combination with other therapeutic agents. Therapeutic agents that may be administered in combination with the therapeutics of the present invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the therapeutics (which include the polypeptides, polynucleotides of the present invention, and fragments thereof) of the present invention are administered in combination with members of the TNF family. TNF, TNF-related or TNF-like molecules that may be administered with the therapeutics of the present invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (PCT Publication WO 96/14328), AIM-I (PCT Publication WO 97/33899), endokine-alpha (PCT Publication WO 98/07880), TR6 (PCT Publication WO 98/30694), OPG, and neutrokine-alpha (PCT Publication WO 98/18921, OX40, and nerve growth factor (NGF), and soluble forms of Fas, CD30, CD27, CD40 and 4-IBB, TR2 (PCT Publication WO 96/34095), DR3 (PCT Publication WO 97/33904), DR4 (PCT Publication WO 98/32856), TR5 (PCT Publication WO 98/30693), TR6 (PCT Publication WO 98/30694), TR7 (PCT Publication WO 98/41629), TRANK, TR9 (PCT Publication WO 98/56892),TR10 (PCT Publication WO 98/54202), 312C2 (PCT Publication WO 98/06842), and TR12, and soluble forms CD154, CD70, and CD153.

In certain embodiments, a therapeutic of the present invention is administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with a therapeutic of the present invention, include, but are not limited to, RETROVIR® (zidovudine/AZT), VIDEX® (didanosine/ddI), HIVID® (zalcitabine/ddC), ZERIT® (stavudine/d4T), EPIVIR® (lamivudine/3TC), and COMBIVIR® (zidovudine/lamivudine). Non-nucleoside reverse transcriptase inhibitors that may be administered in combination with a therapeutics of the present invention, include, but are not limited to, VIRAMUNE® (nevirapine), RESCRIPTOR® (delavirdine), and SUSTIVA® (efavirenz). Protease inhibitors that may be administered in combination with a therapeutic of the present invention, include, but are not limited to, CRIXIVAN® (indinavir), NORVIR® (ritonavir), INVIRASE® (saquinavir), and VIRACEPT® (nelfinavir). In a specific embodiment, antiretroviral agents, nucleoside reverse transcriptase inhibitors, non-nucleoside reverse transcriptase inhibitors, and/or protease inhibitors may be used in any combination with a therapeutic of the present invention to treat AIDS and/or to prevent or treat HIV infection.

In other embodiments, a therapeutic of the present invention may be administered in combination with anti-opportunistic infection agents. Anti-opportunistic agents that may be administered in combination with a therapeutic of the present invention, include, but are not limited to, TRIMETHOPRIM-SULFAMETHOXAZOLE®, DAPSONE®, PENTAMIDINE®, ATOVAQUONE®, ISONIAZID®, RIFAMPIN®, PYRAZINAMIDE®, ETHAMBUTOL®, RIFABUTIN®, CLARITHROMYCIN®, AZITHROMYCIN®, GANCICLOVIR®, FOSCARNET®, CIDOFOVIR®, FLUCONAZOLE®, ITRACONAZOLE®, KETOCONAZOLE®, ACYCLOVIR®, FAMCICOLVIR®, PYRIMETHAMINE®, LEUCOVORIN®, NEUPOGEN® (filgrastim/G-CSF), and LEUKINE® (sargramostim/GM-CSF). In a specific embodiment, a therapeutic of the present invention is used in any combination with TRIMETHOPRIM-SULFAMETHOXAZOLE®, DAPSONE®, PENTAMIDINE®, and/or ATOVAQUONE® to prophylactically treat or prevent an opportunistic *Pneumocystis carinii* pneumonia infection. In another specific embodiment, a therapeutic of the present invention is used in any combination with ISONIAZID®, RIFAMPIN®, PYRAZINAMIDE®, and/or ETHAMBUTOL® to prophylactically treat or prevent an opportunistic *Mycobacterium avium* complex infection. In another specific embodiment, a therapeutic of the present invention is used in any combination with RIFABUTIN®, CLARITHROMYCIN®, and/or AZITHROMYCIN® to prophylactically treat or prevent an opportunistic *Mycobacterium tuberculosis* infection. In another specific embodiment, a therapeutic of the present invention is used in any combination with GANCICLOVIR®, FOSCARNET®, and/or CIDOFOVIR® to prophylactically treat or prevent an opportunistic cytomegalovirus infection. In another specific embodiment, a therapeutic of the present invention is used in any combination with FLUCONAZOLE®, ITRACONAZOLE®, and/or KETOCONAZOLE® to prophylactically treat or prevent an opportunistic fungal infection. In another specific embodiment, a therapeutic of the present invention is used in any combination with ACYCLOVIR® and/or FAMCICOLVIR® to prophylactically treat or prevent an opportunistic herpes simplex virus type I and/or type II infection. In another specific embodiment, a therapeutic of the present invention is used in any combination with PYRIMETHAMINE® and/or LEUCOVORIN® to prophylactically treat or prevent an opportunistic *Toxoplasma gondii* infection. In another specific embodiment, a therapeutic of the present invention is used in any combination with LEUCOVORIN® and/or NEUPOGEN® to prophylactically treat or prevent an opportunistic bacterial infection.

In a further embodiment, a therapeutic of the present invention is administered in combination with an antiviral agent. Antiviral agents that may be administered with the Therapeutics of the present invention include, but are not limited to, acyclovir, ribavirin, amantadine, and remantidine.

In a further embodiment, a therapeutic of the present invention is administered in combination with an antibiotic agent. Antibiotic agents that may be administered with a therapeutic of the present invention include, but are not limited to, amoxicillin, beta-lactamases, aminoglycosides, beta-lactam (glycopeptide), beta-lactamases, clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with a therapeutic of the present invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, a therapeutic of the present invention is administered in combination with immunosuppressants. Immunosuppressants preparations that may be administered with a therapeutic of the present invention include, but are not limited to, ORTHOCLONE® (OKT3), SANDIMMUNE/NEORAL/SANGDYA® (cyclosporin), PROGRAF® (tacrolimus), CELLCEPT® (mycophenolate), Azathioprine, glucorticosteroids, and RAPAMUNE® (sirolimus). In a specific embodiment, immunosuppressants may be used to prevent rejection of organ or bone marrow transplantation.

In an additional embodiment, a therapeutic of the present invention is administered alone or in combination with one or more intravenous immune globulin preparations. Intravenous immune globulin preparations that may be administered with a therapeutic of the present invention include, but are not limited to, GAMMAR®, IVEEGAM®, SANDOGLOBULIN®, GAMMAGARD S/D®, and GAMIMUNE®. In a specific embodiment, a therapeutic of the present invention is administered in combination with intravenous immune globulin preparations in transplantation therapy (e.g., bone marrow transplant).

In an additional embodiment, a therapeutic of the present invention is administered alone or in combination with an anti-inflammatory agent. Anti-inflammatory agents that may be administered with a therapeutic of the present invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the present invention are administered in combination with a chemotherapeutic agent. Chemotherapeutic agents that may be administered with a therapeutic of the present invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, a therapeutic of the present invention is administered in combination with CHOP (cyclophosphamide, doxorubicin, vincristine, and prednisone) or any combination of the components of CHOP. In another embodiment, a therapeutic of the present invention is administered in combination with RITUXIMAB®. In a further embodiment, a therapeutic of the present invention is administered with RITUXIMAB® and CHOP, or RITUXIMAB® and any combination of the components of CHOP.

In an additional embodiment, a therapeutic of the present invention is administered in combination with cytokines. Cytokines that may be administered with a therapeutic of the present invention include, but are not limited to, IL2, IL3, IL-4, IL5, IL6, IL7, IL10, IL12, IL13, IL15, anti-CD40, CD40L, IFN-gamma and TNF-alpha. In another embodiment, a therapeutic of the present invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, a therapeutic of the present invention is administered in combination with angiogenic proteins. Angiogenic proteins that may be administered with a therapeutic of the present invention includes, but are not limited to, Glioma Derived Growth Factor (GDGF), as disclosed in EP 399816; Platelet Derived Growth Factor-A (PDGF-A), as disclosed in EP 682110; Platelet Derived Growth Factor-B (PDGF-B), as disclosed in EP 282317; Placental Growth Factor (PlGF), as disclosed in PCT Publication WO 92/06194; Placental Growth Factor-2 (PlGF-2), as disclosed in Hauser et al., (1993) *Growth Factors* 4:259–268; Vascular Endothelial Growth Factor (VEGF), as disclosed in PCT Publication WO 90/13649; Vascular Endothelial Growth Factor-A (VEGF-A), as disclosed in EP 506477; Vascular Endothelial Growth Factor-2 (VEGF-2), as disclosed in PCT Publication WO 96/39515; Vascular Endothelial Growth Factor B (VEGF-3); Vascular Endothelial Growth Factor B-186 (VEGF-B186), as disclosed in PCT Publication WO 96/26736; Vascular Endothelial Growth Factor-D (VEGF-D), as disclosed in PCT Publication WO 98/02543; Vascular Endothelial Growth Factor-D (VEGF-D), as disclosed in PCT Publication WO 98/07832; and Vascular Endothelial Growth Factor-E (VEGF-E), as disclosed in German Patent Number DE19639601. The above mentioned references are incorporated herein by reference.

In an additional embodiment, a therapeutic of the present invention is administered in combination with hematopoietic growth factors. Hematopoietic growth factors that may be administered with a therapeutic of the present invention include, but are not limited to, LEUKINE® (SARGRAMOSTIM) and NEUPOGEN® (FILGRASTIM).

In an additional embodiment, a therapeutic of the present invention is administered in combination with Fibroblast Growth Factors. Fibroblast Growth Factors that may be administered with a therapeutic of the present invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of therapeutic (e.g., those from african descent). Conversly, certain ethnic populations, particularly those having increased frequency of the mutated PGP (e.g., of caucasian descent, or non-african descent) may require less pharmaceutical compositions in the formulation due to an effective increase in efficacy of such compositions as a result of the increased effective absorption (e.g., less PGP activity) of said composition.

In additional embodiments, a therapeutic of the present invention is administered in combination with other therapeutic or prophylactic regimens, such as, for example, radiation therapy, KINERET therapy or anti-TNF therapy.

Example 27

Method of Treating Decreased Levels of a Polypeptide of the Present Invention

The present invention relates to a method for treating an individual in need of an increased level of a polypeptide of the present invention comprising administering to such an individual a composition comprising a therapeutically effective amount of an agonist of the present invention (including polypeptides of the present invention). Moreover, it will be appreciated that conditions caused by a decrease in the standard or normal expression level of a secreted protein in an individual can be treated by administering a polypeptide of the present invention, preferably in the secreted form.

Thus, the present invention also provides a method of treatment of an individual in need of an increased level of a polypeptide of the present invention comprising administering to such an individual a therapeutic comprising an amount of the polypeptide to increase the activity level of the polypeptide in such an individual. This therapy can be employed alone or in combination with another therapy.

For example, a subject with decreased levels of a polypeptide of the present invention receives a daily dose 0.1–100 µg/kg of the polypeptide for six consecutive days. The polypeptide can be, for example, in the secreted form. A representative dosing scheme, based on administration and formulation, is provided herein.

In another method, the in vivo level of a polypeptide of the present invention is elevated by increasing the transcription of the polynucleotide encoding the polypeptide. As described furthere herein, this method can include introducing a nucleic acid sequence encoding the polypeptide having decreased or undesirably low levels.

Example 28

Method of Treating Increased Levels of a Polypeptide of the Present Invention

The present invention also relates to a method of treating an individual in need of a decreased level of a polypeptide of the present invention in the body comprising administering to such an individual a composition comprising a therapeutically effective amount of an antagonist of the present invention (including polypeptides and antibodies of the present invention). This therapy can be employed alone or in combination with another therapy.

In one example, antisense technology is used to inhibit production of a polypeptide of the present invention. This technology is one example of a method of decreasing levels of a polypeptide, preferably a secreted form, due to a variety of etiologies, such as cancer. For example, a subject diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 29

Method of Treatment Using Gene Therapy-Ex Vivo

In one embodiment of the present invention, ex vivo gene therapy is employed to treat a condition. One method of gene therapy transplants fibroblasts, which are capable of expressing a polypeptide, onto a subject. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerges. The monolayer is trypsinized and scaled into larger flasks.

pMV-7 (Kirschmeier et al., (1988) *DNA* 7:219–25), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers that correspond to the 5' and 3' end sequences respectively as set forth herein using primers and having appropriate restriction sites and initiation/stop codons, if necessary. In one embodiment, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced (e.g., by employing a GTPase activity assay).

The engineered fibroblasts are then transplanted onto the host, either alone or after having been grown to confluence on CYTODEX 3 microcarrier beads.

Example 30

Gene Therapy Using an Endogenous Polynucleotide of the Present Invention

Another method of gene therapy according to the present invention involves operably associating an endogenous polynucleotide sequence of the present invention with a promoter via homologous recombination as described, for example, in U.S. Pat. No. 5,641,670; PCT Publication WO 96/29411; PCT Publication WO 94/12650; Koller et al., (1989) *Proc. Natl. Acad. Sci. U.S.A.* 86:8932–8935; and Zijlstra et al., (1989) *Nature* 342:435–438. This method involves the activation of a gene which is present in the target cells, but which is not expressed in the cells, or is expressed at a lower level than desired. This therapy can be employed alone or in combination with another therapy.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. The amplified promoter can contain distinct restriction enzyme sites on the 5' and 3' ends. For example, the 3' end of the first targeting sequence can contain the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place that results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the locus corresponding to a polynucleotide of the present invention, plasmid pUC18 (MBI Fermentas, Amherst, N.Y., USA) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter-XbaI and BamHI; fragment 1-XbaI; fragment 2-BamHI) and ligated together. The resulting ligation product is digested with HindIII, and ligated with the HindIII-digested pUC18 plasmid.

Plasmid DNA is added to a sterile cuvette with about a 0.4 cm electrode gap (Bio-Rad, Hercules, Calif., USA). The final DNA concentration is generally at least about 120μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad, Hercules, Calif., USA). Capacitance and voltage are set at about 960 μF and about 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to about 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on CYTODEX 3 microcarrier beads. The fibroblasts now produce the protein product. The fibroblasts can then be introduced into a subject as described above.

Example 31

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of a polypeptide of the present invention. A polynucleotide of the present invention may be operatively linked to a promoter or any other genetic elements necessary for the expression of the polypeptide by the target tissue. Such gene therapy and delivery techniques and methods are known in the art, see, for example, PCT Publications WO 90/11092 and WO 98/11779; U.S. Pat. Nos. 5,693,622, 5,705,151, 5,580,859; Tabata et al., (1997) Cardiovasc. Res. 35(3):470–479; Chao et al., (1997) Pharmacol. Res. 35(6): 517–522; Wolff, (1997) Neuromuscul. Disord. 7(5):314–318; Schwartz et al., (1996) Gene Ther. 3(5): 405–411; Tsurumi et al., (1996) Circulation 94(12):3281–3290 (1996) (all incorporated herein by reference). This therapy can be employed alone or in combination with another therapy, such as a KINERET or anti-TNF therapy.

A polynucleotide construct may be delivered by any method that delivers injectable materials to the cells of an animal, such as, injection into the interstitial space of tissues (heart, muscle, skin, lung, liver, intestine and the like). A polynucleotide construct can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, a polynucleotide of the present invention may also be delivered in liposome formulations (such as those taught in Felgner et al., (1995) Ann. N.Y. Acad. Sci. 772:126–139 and Abdallah et al., (1995) Biol. Cell 85(1):1–7), which can be prepared by methods known to those of ordinary skill in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is often desirable for the reasons discussed herein. The construct may be conveniently delivered by injection into the tissues comprising these cells. In one embodiment, the construct is delivered to, and expressed in, persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For a naked polynucleotide injection, an effective dosage amount of DNA or RNA will be in the range of from about 0.05 g/kg body weight to about 50 mg/kg body weight. In one embodiment, the dosage will be from about 0.005 mg/kg to about 20 mg/kg and in another embodiment from about 0.05 mg/kg to about 5 mg/kg. Of course, as those of ordinary skill in the art will appreciate, this dosage will vary according to the tissue site of injection. The appropriate and effective dosage of nucleic acid sequence can readily be determined by those of ordinary skill in the art and may depend on the condition being treated and the route of administration. The representative route of administration is by the parenteral route of injection into the interstitial space of tissues. However, other parenteral routes may also be used, such as inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 µm cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 32

Transgenic Animals

The polypeptides of the present invention can also be expressed in transgenic animals. Animals of any species, including, but not limited to, mice, rats, rabbits, hamsters, guinea pigs, pigs, goats, sheep, cows and non-human primates, e.g., baboons, monkeys, and chimpanzees may be used to generate transgenic animals. In a specific embodiment, techniques described herein or otherwise known in the art, are used to express polypeptides of the present invention in humans, as part of a gene therapy protocol.

Any technique known in the art may be used to introduce the transgene (i.e., polynucleotides of the present invention) into animals to produce the founder lines of transgenic animals. Such techniques include, but are not limited to, pronuclear microinjection (Paterson et al., (1994) *Appl. Microbiol. Biotechnol.* 40:691–698; Carver et al., (1993) *Biotechnology* 11:1263–1270; Wright et al., (1991) *Biotechnology* 9:830–834; and U.S. Pat. No. 4,873,191); retrovirus mediated gene transfer into germ lines (Van der Putten et al., (1985) *Proc. Natl. Acad. Sci. U.S.A.* 82:6148–6152), blastocysts or embryos; gene targeting in embryonic stem cells (Thompson et al., (1989) *Cell* 56:313–321); electroporation of cells or embryos (Lo, (1983) *Mol Cell. Biol.* 3:1803–1814); introduction of the polynucleotides of the present invention using a gene gun (see, e.g., Ulmer et al., (1993) *Science* 259:1745; introducing nucleic acid constructs into embryonic pleuripotent stem cells and transferring the stem cells back into the blastocyst; and spermmediated gene transfer (Lavitrano et al., (1989) *Cell* 57:717–723; etc. For a review of such techniques, see Gordon, (1989) *Intl. Rev. Cytol.* 115:171–229, which is incorporated by reference herein in its entirety.

Any technique known in the art may be used to produce transgenic clones containing polynucleotides of the present invention, for example, nuclear transfer into enucleated oocytes of nuclei from cultured embryonic, fetal, or adult cells induced to quiescence (Campell et al., (1996) *Nature* 380:64–66; Wilmut et al., (1997) *Nature* 385:810–813).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., (1992) *Proc. Natl. Acad. Sci. U.S.A.* 89:6232–6236). The regulatory sequences required for such a cell-type specific activation will depend upon the particular cell type of interest, and will be apparent to those of skill in the art.

When it is desired that the polynucleotide transgene be integrated into the chromosomal site of the endogenous gene, gene targeting is sometimes desirable. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., (1994) *Science* 265:103–106). The regulatory sequences required for such a cell-type specific inactivation will depend upon the particular cell type of interest, and will be apparent to those of ordinary skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the present invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 33

Knock-Out Animals

Endogenous gene expression can also be reduced by inactivating or "knocking out" the gene and/or its promoter using targeted homologous recombination. (see, e.g., Smithies et al., (1985) *Nature* 317:230–234; Thomas & Capecchi, (1987) *Cell* 51:503–512; Thompson et al., (1989) *Cell* 5:313–321; each of which is incorporated by reference herein in its entirety) or another method. For example, a mutant, non-functional polynucleotide of the present invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the present invention in vivo.

In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (see, e.g., Thomas & Capecchi, (1987) *Cell* 51:503–512; Thompson et al., (1989) *Cell* 5:313–321). However, this approach can be routinely adapted for use in humans provided the recombinant DNA constructs are directly administered or targeted to the required site in vivo using appropriate viral vectors that will be apparent to those of ordinary skill in the art.

In further embodiments of the present invention, cells that are genetically engineered to express the polypeptides of the present invention, or alternatively, that are genetically engineered not to express the polypeptides of the present invention (e.g., knockouts) are administered to a subject in vivo.

Such cells may be obtained from the subject (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the present invention into the cells, or alternatively, to disrupt the coding sequence and/or endogenous regulatory sequence associated with the polypeptides of the present invention, e.g., by transduction (using viral vectors, and preferably vectors that integrate a transgene, such as neo, into the cell genome) or transfection procedures, including, but not limited to, the use of plasmids, cosmids, YACs, naked DNA, electroporation, liposomes, etc. The coding sequence of the polypeptides of the present invention can be placed under the control of a strong constitutive or inducible promoter or promoter/enhancer to achieve expression, and preferably secretion, of the polypeptides of the present invention. The engineered cells that express and, in some cases, secrete the polypeptides of the present invention can be introduced into the subject systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft (see, for example, U.S. Pat. No. 5,399,349; and U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form, which, while allowing for an exchange of components with the immediate extracellular environment, does not allow the introduced cells to be recognized by the host immune system.

Transgenic and "knock-out" animals of the present invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 34

Method of Isolating Antibody Fragments Directed against HGBPBMY1 (AK096141). HGPBMY2, HGBPBMY3 (4843 30 2 1; 4843 2). HGBPBMY4 (FLJ10961). MGPBMY1, MGBPBMY2 (LOC229902). MGBPBMY and/or MGBPBMY4 (BC007143) from a Library of scFvs Naturally occurring V-genes isolated from human PBLs can be constructed into a library of antibody fragments that contain reactivities against HGBPBMY1, HGBPBMY2 (4843 30 1 1; 4843_1), HGBPBMY3 (4843 30 2 1; 4843_2), HGBPBMY4 (FLJ10961), MGBPBMY1 (LOC229900), MGBPBMY2 (LOC229902), MGBPBMY3 (BC031475) and/or MGBPBMY4 (BC007143), to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT Publication WO 92/01047. To rescue phage displaying antibody fragments, approximately $10^9$ E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to inoculate 50 ml of 2×TY-AMP-GLU, 2×10$^8$ TU of delta gene 3 helper (M13 delta gene III, see PCT Publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 µg/ml kanamycin and grown overnight. Phage are prepared using known techniques, such as those described in PCT Publication WO 92/01047.

In one embodiment, M13 delta gene II is emplpoyed and is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 ug kanamycin/ml (2×TY-AMP-KAN) and grown overnight, shaking at 37° C. Phage particles are purified and concentrated from the culture medium by two PEG-precipitations, resuspended in 2 ml PBS and passed through a 0.45 µm filter (Minisart NML; Sartorius Corp., Edgewood, N.Y., USA) to give a final concentration of approximately 1013 transducing units/ml (ampicillin-resistant clones).

Panning of the Library

Immunotubes (Nunc, Roskilde, Denmark) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS, 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced from single colonies for assay. ELISAs are performed with microtitre plates coated with either 10 pg/ml of a polypeptide of the present invention in 50 mM bicarbonate pH 9.6. Clones positive in ELISA are further characterized by PCR fingerprinting (see, e.g., PCT Publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 35

Biological Effects of HGBPBMY1 (AK096141), HGBPBMY2 (4843 30 1 1, 4843 1), HGBPBMY3 (4843 30 2 1; 4843 2), HGBPBMY4 (FLJ10961), MGBPBMY1 (LOC229900), MGBBMY2, MGB-PBMY3 (BC031475) and/or MGBPBMY4 (BC007143) Polypeptides of the Present Invention

Astrocyte and Neuronal Assays

Recombinant polypeptides of the present invention, expressed in E. coli and purified as described herein, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the present invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., (1986) Proc. Natl. Acad. Sci. U.S.A. 83:3012–3016, assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the present invention to induce neurite outgrowth can be compared to the response achieved with FGF-2 using, for example, a thymidine incorporation assay.

Fibroblast and Endothelial Cell Assays

In one emobidment, human lung fibroblasts are obtained from Clonetics (San Diego, Calif., USA) and maintained in growth media from Clonetics. Dermal microvascular endothelial cells are obtained from Cell Applications (San Diego, Calif., USA). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CYTOFLUOR fluorescence reader (Applied Biosystems, Foster City, Calif., USA). For the PGE2 assays, the human lung fibroblasts are cultured at 5,000 cells/well in a 96-well plate for one day. After a medium change to 0.1% BSA basal medium, the cells are incubated with FGF-2 or polypeptides of the present invention with or without IL-1 for 24 hours. The supernatants are collected and assayed for PGE2 by EIA kit (Cayman, Ann Arbor, Mich., USA). For the 1L-6 assays, the human lung fibroblasts are cultured at 5,000 cells/well in a 96-well plate for one day. After a medium change to 0.1% BSA basal medium, the cells are incubated with FGF-2 or with or without polypeptides of the present invention for 24 hours. The supernatants are collected and assayed for 1L-6 by ELISA kit (Endogen, Cambridge, Mass., USA).

Human lung fibroblasts are cultured with FGF-2 or polypeptides of the present invention for 3 days in basal medium before the addition of Alamar Blue to assess effects on growth of the fibroblasts. FGF-2 should show a stimulation at 10–2500 ng/ml which can be used to compare stimulation with polypeptides of the present invention.

Example 36

Method of Assessing the Expression Profile of a HGBPBMY1 Polypeptide of the Present Invention Using mRNA Tissue and Cell Sources Total RNA from tissues was isolated using the TriZol protocol (Invitrogen) and quantified by determining its absorbance at 260 nm. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGBPBMY1, the primer probe sequences were as follows:

```
Forward Primer
5'- AGTGCCCAGAAAAGGAGTTAAGG -3'      (SEQ ID NO: 61)

Reverse Primer
5'- GCAGGATGGATTCCTCTATAACCA -3'    (SEQ ID NO: 62)

TAQMAN Probe
5'- AGACGAGGTCCTCCAGAGCTTCCTGC -3'  (SEQ ID NO: 63)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM magnesium chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TAQMAN probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ A tissue expression profile of the HGBPBMY1 polypeptide is provided in FIG. 43 and described herein.

Example 37

Method of Assessing the Expression Profile of a HGBPBMY2 Polypeptide of the Present Invention Using mRNA Tissue and Cell Sources Total RNA from tissues was isolated using the TriZol protocol (Invitrogen) and quantified by determining its absorbance at 260 nm. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGBPBMY2, the primer probe sequences were as follows:

```
Forward Primer
5'- TGGAGCCCCTGCCTCAA -3'          (SEQ ID NO: 64)

Reverse Primer
5'- CAGAAATGATGGACCTCCTCACT -3'    (SEQ ID NO: 65)

TAQMAN Probe
5'- ACACACATTGCTCCAACACTGAGGCC -3' (SEQ ID NO: 66)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM magnesium chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TAQMAN probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ A tissue expression profile of the HGBPBMY2 polypeptide is provided in FIG. 44 and described elsewhre herein.

Example 38

Method of Assessing the Expression Profile of a HGBPBMY3 Polypeptide of the Present Invention Using mRNA Tissue and Cell Sources Total RNA from tissues was isolated using the TriZol protocol (Invitrogen) and quantified by determining its absorbance at 260 nm. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGBPBMY3, the primer probe sequences were as follows:

```
Forward Primer 5'- GGATGGCAGGAAGACAAACAG -3'              (SEQ ID NO: 67)

Reverse Primer 5'- GCCTTAGGACCCAGAGAACACA -3'             (SEQ ID NO: 68)

TAQMAN Probe   5'- CACCTGCTTACAGCCGTCTCCTACTTCTCACT -3'   (SEQ ID NO: 69)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM magnesium chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TAQMAN probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta ct)}$ The tissue expression profile of the HGBPBMY3 polypeptide is provided in FIG. 45 and described herein.

Example 39

Method of Assessing the Expression Profile of a HGBPBMY4 Polypeptide of the Present Invention Using mRNA Tissue and Cell Sources Total RNA from tissues was isolated using the TriZol protocol (Invitrogen) and quantified by determining its absorbance at 260 nm. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGBPBMY4, the primer probe sequences were as follows

```
Forward Primer 5'- AAGATGCATTTACCTCTGTACCAACA -3'   (SEQ ID NO: 70)

Reverse Primer 5'- CCACTGGTCGTCTGGAAGAATAA -3'      (SEQ ID NO: 71)

TAQMAN Probe   5'- AGGAGGGATCATGAGTTGCCACCACTC -3'  (SEQ ID NO: 72)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM magnesium chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TAQMAN probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The tissue expression profile of the HGBPBMY4 polypeptide is provided in FIG. 46 and described herein.

Example 40

Method of Assessing the Expression Profile of a GBP1 Polypeptide of the Present Invention Using mRNA Tissue and Cell Sources Total RNA from tissues was isolated using the TriZol protocol (Invitrogen) and quantified by determining its absorbance at 260 nm. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For GBP1, the primer probe sequences were as follows

```
Forward Primer 5'- AATGTTGCAGGAAATGCAAAGA -3'         (SEQ ID NO: 73)

Reverse Primer 5'- AGCAACTGGACCCTGTCGTT -3'          (SEQ ID NO: 74)

TAQMAN Probe   5'- CAGGAACACTTGAAACAACTGACTGAGAAGATGG -3' (SEQ ID NO: 75)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM magnesium chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TAQMAN probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The tissue expression profile of the GBP1 polypeptide is provided in FIG. 47 and described herein.

Example 41

Method of Assessing the Expression Profile of a GBP5 Polypeptide of the Present Invention Using mRNA Tissue and Cell Sources Total RNA from tissues was isolated using the TriZol protocol (Invitrogen) and quantified by determining its absorbance at 260 nm. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For GBP5, the primer probe sequences were as follows

```
Forward Primer
5'- GGCACAAGTGAAAGCAGAAGCT -3'    (SEQ ID NO: 76)

Reverse Primer
5'- TTGCTCGTTCTGCCTTTGAA -3'      (SEQ ID NO: 77)

TAQMAN Probe
5'- TGAAGCGCAAAGGTTGGCGGC -3'     (SEQ ID NO: 78)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM magnesium chloride by heating the sample to 72° C. for 2 min and then cooling to 55° C. for 30 min. 1.25 U/l of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 2.0 µM of the TAQMAN probe, 500 µM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The tissue expression profile of the GBP5 polypeptide is provided in FIG. 48 and described herein.

One of ordinary skill in the art could readily modify the exemplified studies to test the activity of polynucleotides of the present invention (e.g., gene therapy), agonists, and/or antagonists of polynucleotides or polypeptides of the present invention.

Example 42 siRNA Studies

Guanine Nucleotide Binding

Genes encoding different GBP family members were cloned into the vector pcDNA3.1mychis (Invitrogen) for expression in mammalian cells. Cos-7 cells were transfected with 5 µg of DNA per group using lipofectamine 2000 (Invitrogen) according to manufacturer's instructions. Approximately 18 hours after transfection, the cells were harvested using trypsin and lysed in RIPA buffer (10 mM sodium phosphate pH 7.2, 0.25 M sodium chloride, 0.1% SDS, 1% NP40, 1% sodium deoxycholate, 2 mM EDTA, protease inhibitor cocktail). An aliquot of the lysate was reserved for the whole cell lysate sample. The remainder was divided in thirds, and incubated for three hours at 4° C. with agarose coated with either GTP, GDP, or GMP (Sigma Chemical Company). The beads were pelleted, washed with buffer (0.1% NP40, 150 mM NaCl, 50 mM Tris pH7.5), and resuspended in SDS sample buffer. Samples were electrophoresed through 4–20% tris-glycine gels, transferred to nitrocellulose, blocked overnight with 5% non-fat dry milk and 0.3% BSA in Tris-buffered saline, and probed with a mouse monoclonal antibody specific for the myc epitope tag (Invitrogen).

siRNA Studies

To test for knockdown of protein expression using siRNAs, Cos-7 cells were transfected as described herein with expression vectors encoding either GBP-1 or GBP-2 in the presence and absence of 40 nM siRNA duplex specific for either GBP-1 ("1–3", GCUCGAGAAACUACAAGAUTT, (SEQ ID NO:79), Qiagen, Inc.) or GBP-2 ("582", UUUGUAUUUCCUCCAACAUTT (SEQ ID NO:80), Sequitur Inc., Natick, Mass.). Approximately 18 hours following transfection, cells were harvested using trypsin, and lysed in RIPA buffer as described previously. Lysates were electrophoresed through 4–20% tris-glycine gels, transferred to nitrocellulose, blocked overnight with 5% non-fat dry milk and 0.3% BSA in Tris-buffered saline, and probed with a mouse monoclonal antibody specific for the myc epitope tag.

In some experiments, human umbilical vein endothelial cells (HUVECs, Clonetics Corp., San Diego, Calif., USA) were transfected using lipofectamine 2000 with 100 nM siRNA duplexes. Cells were cultured overnight, and then stimulated for 6 hours with 10 ng/ml TNFα. Supernatants were analyzed for MCP-1 and IL-8 levels by ELISA (Pharmingen, San Diego, Calif., USA). Cytokine levels were corrected for cell number using the CELL TITER kit (Promega).

RESULTS

One of the hallmarks of the GBP family is the ability to bind guanine nucleotides. To test whether the novel GBP family members were also able to bind guanine nucleotides, the GBP family members were expressed in Cos-7 cells and the lysates batched onto agarose beads coated with either GTP, GDP, or GMP. Bound proteins were eluted from the beads and analyzed with whole cell lysates (WL) in a myc western blot (see FIG. 49). As expected, GBP-1 and GBP-2 bound well to all three beads. GBP-5 and FLJ10961 bound well to GDP and GMP, and weakly to GTP. Family member AK096141 bound weakly to GDP and GMP, and not at all to GTP. Lastly, family member 4843__1 did not bind to any of the beads.

To more fully elucidate the function of GBP family members, siRNA experiments were initiated. Co-expression of GBP-1 and GBP-2 expression vectors with siRNAs targeting these genes (indicated as 1–3 and 582 in FIG. 50A) resulted in specific knockdown of protein expression (FIG. 50A). When transfected into human umbilical vein endothelial cells, the GBP-1 specific siRNA (1–3) inhibited TNFα-induced MCP-1 expression by 70% (FIG. 50B). The GBP-2 specific siRNA (582) inhibited MCP-1 expression by approximately 40%. These siRNAs failed to inhibit IL-8 secretion, indicating that they were not toxic. The degree of inhibition observed was comparable to, or greater than, that observed with siRNAs targeting known components of the signal transduction pathway such as NF-κB p65 (40% inhibition) and Stat1 (20% inhibition). These data indicate that members of the GBP family may play roles in TNFα-induced inflammatory responses.

It will be clear that the present invention may be practiced otherwise than as particularly described in the foregoing description and Examples. Numerous modifications and variations of the present invention are possible in light of the above teachings and, therefore, are within the scope of the appended claims.

REFERENCES CITED HEREIN

The entire disclosure of each document cited (including patents, patent applications, journal articles, abstracts, laboratory manuals, books, or other disclosures) in the Background of the present invention, Detailed Description, and Examples is hereby incorporated herein by reference. Further, the hard copy of the Sequence Listing submitted herewith and the corresponding computer readable form are both incorporated herein by reference in their entireties.

TABLE I

| Gene No. | cDNA CloneID | ATCC Deposit No. Z and Date | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|
| 1 | HGBPBMY1 (AK096141) | | 2 | 2454 | 140 | 2053 | 3 | 635 |
| 2 | HGBPBMY2 (4843 301 1; 4843_1) | PTA-6007 05/20/04 | 4 | 2367 | 1 | 2364 | 5 | 788 |
| 3 | HGBPBMY3 (4843 302 1; 4843_2) | | 6 | 1392 | 1 | 1392 | 7 | 464 |
| 4 | HGBPBMY4 (FLJ10961) | | 8 | 2952 | 200 | 1889 | 9 | 563 |
| 5 | MGBPBMY1 (LOC229900) | | 10 | 2484 | 93 | 1989 | 11 | 632 |
| 6 | MGBPBMY2 (LOC229902) | | 12 | 1818 | 1 | 1815 | 13 | 605 |
| 7 | MGBPBMY3 (BC031475) | | 14 | 3387 | 80 | 1235 | 15 | 385 |
| 8 | MGBPBMY4 (BC007143) | | 16 | 4193 | 321 | 1770 | 17 | 483 |

What is claimed is:

1. An isolated nucleic acid molecule comprising a polynucleotide sequence selected from the group consisting of:
   (a) an isolated polynucleotide encoding a polypeptide comprising amino acids 1–668 of SEQ ID NO: 5;
   (b) an isolated polynucleotide encoding a polypeptide comprising amino acids 2–668 of SEQ ID NO: 5;
   (c) an isolated polynucleotide comprising nucleotides 88 to 2109 of SEQ ID NO: 4, wherein said nucleotides encode a polypeptide corresponding to amino acids 1 to 668 of SEQ ID NO: 5;
   (d) an isolated polynucleotide comprising nucleotides 91 to 2091 of SEQ ID NO: 4, wherein said nucleotides encode a polypeptide corresponding to amino acids 2 to 668 of SEQ ID NO: 5;
   (e) ATCC Deposit No: PTA-6007; and
   (f) an isolated polynucleotide that hybridizes under stringent hybridization conditions to a polynucleotide sequence provided in (a)–(e), wherein said polynucleotide encodes a polypeptide that has guanylate binding activity wherein such stringent hybridization conditions are selected from the group consisting of (A) 7% SDS, 0.5 M NaPO$_4$, 1 mM EDTA at 50° C. followed by washing in 0.1×SSC, 0.1% SDS at 65° C. and (B) 4×SSC at 65° C., followed by washing in 0.1×SSC at 65° C. for one hour.

2. The isolated nucleic acid molecule of claim 1, wherein said polynucleotide is (a).

3. The isolated nucleic acid molecule of claim 1, wherein said polynucleotide is (b).

4. The isolated nucleic acid molecule of claim 1, wherein said polynucleotide is (c).

5. The isolated nucleic acid molecule of claim 1, wherein said polynucleotide is (d).

6. The isolated nucleic acid molecule of claim 1, wherein said polynucleotide is (e).

7. The isolated nucleic acid molecule of claim 1, wherein said polynucleotide is (f).

8. An isolated nucleic acid molecule comprising a polynucleotide having a nucleotide sequence that is at least 95% identical to a polynucleotide sequence provided in claim 2, wherein percent identity is calculated using a CLUSTALW global sequence alignment using default parameters, wherein said polynucleotide encodes a polypeptide that has guanylate binding activity.

9. An isolated nucleic acid molecule comprising a polynucleotide having a nucleotide sequence that is at least 95% identical to a polynucleotide sequence provided in claim 3, wherein percent identity is calculated using a CLUSTALW global sequence alignment using default parameters, wherein said polynucleotide encodes a polypeptide that has guanylate binding activity.

10. An isolated nucleic acid molecule comprising a polynucleotide having a nucleotide sequence that is at least 95% identical to a polynucleotide sequence provided in claim 4, wherein percent identity is calculated using a CLUSTALW global sequence alignment using default parameters, wherein said polynucleotide encodes a polypeptide that has guanylate binding activity.

11. An isolated nucleic acid molecule comprising a polynucleotide having a nucleotide sequence that is at least 95% identical to a polynucleotide sequence provided in claim 5, wherein percent identity is calculated using a CLUSTALW global sequence alignment using default parameters, wherein said polynucleotide encodes a polypeptide that has guanylate binding activity.

12. An isolated nucleic acid molecule comprising a polynucleotide having a nucleotide sequence that is at least 95% identical to a polynucleotide sequence provided in claim 6, wherein percent identity is calculated using a CLUSTALW global sequence alignment using default parameters, wherein said polynucleotide encodes a polypeptide that has guanylate binding activity.

13. A recombinant vector comprising the isolated nucleic acid molecule of claim 1.

14. An isolated recombinant host cell comprising the vector sequence of claim 13.

15. A method of making an isolated polypeptide comprising:
(a) culturing the isolated recombinant host cell of claim 14 under conditions such that said polypeptide is expressed; and
(b) recovering said polypeptide.

* * * * *

SEQUENCE LISTING

<160> NUMBER OF SEQ ID NOS: 80

<210> SEQ ID NO 1
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: X at positions 2 and 3 are aliphatic; X at
      position 4 is any amino acid

<400> SEQUENCE: 1

Cys Xaa Xaa Xaa
1

<210> SEQ ID NO 2
<211> LENGTH: 2454
<212> TYPE: DNA
<213> ORGANISM: Homo sapiens
<220> FEATURE:
<221> NAME/KEY: CDS
<222> LOCATION: (140)..(2053)

<400> SEQUENCE: 2

```
aagaaaaaaa gtgggagaaa tcagtgcagc caaattcaga actaaagaga agagaataaa      60
gactcataac tttctcattg aagctgcctt cttaccaagt ccagaggatc tctactctgg     120
acagaggaac gccctgaac atg gca tca gag atc cac atg cca ggc cca gtg     172
                       Met Ala Ser Glu Ile His Met Pro Gly Pro Val
                         1               5                  10 tgc ctc att gag aac act aaa ggg cat ctg gtg gtg aat tca gaa gct     220
Cys Leu Ile Glu Asn Thr Lys Gly His Leu Val Val Asn Ser Glu Ala
         15                  20                  25 ctg gaa atc ctg tct gcc att aca cag cct gta gta gtg gtg gca att     268
Leu Glu Ile Leu Ser Ala Ile Thr Gln Pro Val Val Val Val Ala Ile
     30                  35                  40 gtg ggc ctc tac cgc aca ggc aaa tcc tac cta atg aac aag ctg gct     316
Val Gly Leu Tyr Arg Thr Gly Lys Ser Tyr Leu Met Asn Lys Leu Ala
 45                  50                  55
```

-continued

| | | |
|---|---|---|
| ggg aag aac aaa ggc ttc cct ctg ggc tgc aca gtg aag tct gaa acc<br>Gly Lys Asn Lys Gly Phe Pro Leu Gly Cys Thr Val Lys Ser Glu Thr<br>60                    65                    70                    75 | 364 |
| aaa ggc atc tgg atg tgg tgt gtg ccc cac ccc tcc aag cca aac cac<br>Lys Gly Ile Trp Met Trp Cys Val Pro His Pro Ser Lys Pro Asn His<br>                    80                    85                    90 | 412 |
| acc ctg atc ctt ctg gac acg gag ggc ctg ggt gat atg gaa aag agt<br>Thr Leu Ile Leu Leu Asp Thr Glu Gly Leu Gly Asp Met Glu Lys Ser<br>              95                    100                  105 | 460 |
| gac cct aag agt gac tcg tgg atc ttt gcc ctg gct gtg ctt cta agc<br>Asp Pro Lys Ser Asp Ser Trp Ile Phe Ala Leu Ala Val Leu Leu Ser<br>           110                    115                  120 | 508 |
| agc agc ttt gtc tac aac agc atg ggc acc atc aac cac cag gcc ctg<br>Ser Ser Phe Val Tyr Asn Ser Met Gly Thr Ile Asn His Gln Ala Leu<br>125                    130                    135 | 556 |
| gag cag ctg cac tac gtg act gag cta aca gag cta atc agg gca aaa<br>Glu Gln Leu His Tyr Val Thr Glu Leu Thr Glu Leu Ile Arg Ala Lys<br>140                    145                    150                  155 | 604 |
| tcg tgc ccc aga cct gat gaa gtt gag gac tcc agc gag ttt gtg agt<br>Ser Cys Pro Arg Pro Asp Glu Val Glu Asp Ser Ser Glu Phe Val Ser<br>                    160                    165                  170 | 652 |
| ttc ttt cca gac ttt att tgg act gtt cga gat ttt acc ctg gag ctg<br>Phe Phe Pro Asp Phe Ile Trp Thr Val Arg Asp Phe Thr Leu Glu Leu<br>              175                    180                  185 | 700 |
| aag tta gat gga cac ccc atc aca gaa gat gag tac ctg gag aat gcc<br>Lys Leu Asp Gly His Pro Ile Thr Glu Asp Glu Tyr Leu Glu Asn Ala<br>190                    195                    200 | 748 |
| ttg aag ctg att tca ggc aag aat ccc caa atc caa aat tct aac aag<br>Leu Lys Leu Ile Ser Gly Lys Asn Pro Gln Ile Gln Asn Ser Asn Lys<br>205                    210                    215 | 796 |
| ccc agg gag tgg atc agg cat ttc ttt cca aaa cag aag tgc ttt gtc<br>Pro Arg Glu Trp Ile Arg His Phe Phe Pro Lys Gln Lys Cys Phe Val<br>220                    225                    230                  235 | 844 |
| ttt gac cgg cca ata aat gac aaa aaa ctc tta ctc cat gtt gaa gaa<br>Phe Asp Arg Pro Ile Asn Asp Lys Lys Leu Leu Leu His Val Glu Glu<br>                    240                    245                  250 | 892 |
| gta cga gaa gac caa ctg gat agt aat ttc cag atg caa tca gaa aat<br>Val Arg Glu Asp Gln Leu Asp Ser Asn Phe Gln Met Gln Ser Glu Asn<br>              255                    260                    265 | 940 |
| ttc tgt tct tat atc ttc acc cat gca aag acc aag acc ctg aga gag<br>Phe Cys Ser Tyr Ile Phe Thr His Ala Lys Thr Lys Thr Leu Arg Glu<br>270                    275                    280 | 988 |
| gga atc ctt gtc act gga aac cgg ctg ggg atg ctg gtg gag acc tac<br>Gly Ile Leu Val Thr Gly Asn Arg Leu Gly Met Leu Val Glu Thr Tyr<br>285                    290                    295 | 1036 |
| ctg gat gcc atc aac agt gga gcg act cct tgt ctg gag aat gca atg<br>Leu Asp Ala Ile Asn Ser Gly Ala Thr Pro Cys Leu Glu Asn Ala Met<br>300                    305                    310                  315 | 1084 |
| gca gtt ctg gcc cag tgt gag aac tca gca gcc gtg cag agg gca gcc<br>Ala Val Leu Ala Gln Cys Glu Asn Ser Ala Ala Val Gln Arg Ala Ala<br>                    320                    325                  330 | 1132 |
| aac cac tac agc cag cag atg gcc cag caa gtg aga ttc ccc aca gac<br>Asn His Tyr Ser Gln Gln Met Ala Gln Gln Val Arg Phe Pro Thr Asp<br>              335                    340                    345 | 1180 |
| aca ctc cag gag ctg ctg gac gtg cat gca gtt tgt gag agg gaa gcc<br>Thr Leu Gln Glu Leu Leu Asp Val His Ala Val Cys Glu Arg Glu Ala<br>              350                    355                  360 | 1228 |
| att gca gtc ttc atg gag tac tcc ttc aaa gat aaa agc cag gaa ttt<br>Ile Ala Val Phe Met Glu Tyr Ser Phe Lys Asp Lys Ser Gln Glu Phe<br>365                    370                    375 | 1276 |

-continued

```
cag aag aag ctt gtg gac acc atg gag aaa aag aag gaa gac ttt gtg      1324
Gln Lys Lys Leu Val Asp Thr Met Glu Lys Lys Lys Glu Asp Phe Val
380                 385                 390                 395 ctg cag aat gaa gag gca tct gcc aaa tat tgt cag gct gag ctt aag      1372
Leu Gln Asn Glu Glu Ala Ser Ala Lys Tyr Cys Gln Ala Glu Leu Lys
                400                 405                 410 cgg ctt tca gag ctc ttg aca gaa agt att tca aga gga act ttc ttt      1420
Arg Leu Ser Glu Leu Leu Thr Glu Ser Ile Ser Arg Gly Thr Phe Phe
            415                 420                 425 gtt ccg ggg ggg cac aat atc tac tta gaa gca aaa aag aag att gaa      1468
Val Pro Gly Gly His Asn Ile Tyr Leu Glu Ala Lys Lys Lys Ile Glu
        430                 435                 440 cag gac tat aca cta gtg ccc aga aaa gga gtt aag gca gac gag gtc      1516
Gln Asp Tyr Thr Leu Val Pro Arg Lys Gly Val Lys Ala Asp Glu Val
    445                 450                 455 ctc cag agc ttc ctg cag tca cag gtg gtt ata gag gaa tcc atc ctg      1564
Leu Gln Ser Phe Leu Gln Ser Gln Val Val Ile Glu Glu Ser Ile Leu
460                 465                 470                 475 cag tca gac aaa gcc ctc act gct gga gag aag gcc ata gca gct aag      1612
Gln Ser Asp Lys Ala Leu Thr Ala Gly Glu Lys Ala Ile Ala Ala Lys
                480                 485                 490 cag gct aag aag gag gca gct gaa aag gaa cag gag ctg cta aga caa      1660
Gln Ala Lys Lys Glu Ala Ala Glu Lys Glu Gln Glu Leu Leu Arg Gln
            495                 500                 505 aaa cag aag gaa cag cag caa atg atg gag gct caa gag aga agt ttc      1708
Lys Gln Lys Glu Gln Gln Gln Met Met Glu Ala Gln Glu Arg Ser Phe
        510                 515                 520 cag gaa aac ata gct caa ctc aag aag aag atg gag agg gaa agg gaa      1756
Gln Glu Asn Ile Ala Gln Leu Lys Lys Lys Met Glu Arg Glu Arg Glu
    525                 530                 535 aac tat atg aga gaa ctg aga aag atg ttg agt cac aag atg aag gtc      1804
Asn Tyr Met Arg Glu Leu Arg Lys Met Leu Ser His Lys Met Lys Val
540                 545                 550                 555 cta gaa gaa ctg ctt act gaa gga ttt aaa gag ata ttt gag tcg tta      1852
Leu Glu Glu Leu Leu Thr Glu Gly Phe Lys Glu Ile Phe Glu Ser Leu
                560                 565                 570 aat gaa gag att aat cga ctg aaa gaa caa att gaa gca gct gaa aat      1900
Asn Glu Glu Ile Asn Arg Leu Lys Glu Gln Ile Glu Ala Ala Glu Asn
            575                 580                 585 gaa gag ccc tca gtg ttt tca cag att ctt gat gtg gct ggc agt ata      1948
Glu Glu Pro Ser Val Phe Ser Gln Ile Leu Asp Val Ala Gly Ser Ile
        590                 595                 600 ttt att gca gca cta cct ggg gct gct aag cta gtt gat tta gga atg      1996
Phe Ile Ala Ala Leu Pro Gly Ala Ala Lys Leu Val Asp Leu Gly Met
    605                 610                 615 aaa att ctt agc tca tta tgt aat agg ctg aga aat cct ggt aag aaa      2044
Lys Ile Leu Ser Ser Leu Cys Asn Arg Leu Arg Asn Pro Gly Lys Lys
620                 625                 630                 635 att ata agc tgaggtttct tttgttaaaa tggtataacg ctgttgctca              2093
Ile Ile Ser ttttaaaagt atatgtgtta ttgcagtttc atttaagaag agtttaaaat taaaaagcaa    2153
atttcaaaga atattatggc ctgaagttca taaaaacaaa cttaattttg actaaagtaa    2213
taattaatag aaatggggaa caagttagaa gataaaatta ttcctagaaa agatttaagt   2273
aaagcaaaag gacaaatggt aatataaaga aattattttc aattaatgtt atagtcacag    2333
agataattta agttataatt agctcttgca aatcagtgag aagagagtaa cgccacatat    2393
tttaaacagg caaaaatatg ataataaaaa tgtttaattt tactgacaat aaaagttgtg    2453
```

-continued c                                                                                   2454

<210> SEQ ID NO 3
<211> LENGTH: 638
<212> TYPE: PRT
<213> ORGANISM: Homo sapiens

<400> SEQUENCE: 3

```
Met Ala Ser Glu Ile His Met Pro Gly Pro Val Cys Leu Ile Glu Asn
1               5                   10                  15

Thr Lys Gly His Leu Val Val Asn Ser Glu Ala Leu Glu Ile Leu Ser
            20                  25                  30

Ala Ile Thr Gln Pro Val Val Val Ala Ile Val Gly Leu Tyr Arg
        35                  40                  45

Thr Gly Lys Ser Tyr Leu Met Asn Lys Leu Ala Gly Lys Asn Lys Gly
    50                  55                  60

Phe Pro Leu Gly Cys Thr Val Lys Ser Glu Thr Lys Gly Ile Trp Met
65                  70                  75                  80

Trp Cys Val Pro His Pro Ser Lys Pro Asn His Thr Leu Ile Leu Leu
                85                  90                  95

Asp Thr Glu Gly Leu Gly Asp Met Glu Lys Ser Asp Pro Lys Ser Asp
            100                 105                 110

Ser Trp Ile Phe Ala Leu Ala Val Leu Leu Ser Ser Ser Phe Val Tyr
        115                 120                 125

Asn Ser Met Gly Thr Ile Asn His Gln Ala Leu Glu Gln Leu His Tyr
    130                 135                 140

Val Thr Glu Leu Thr Glu Leu Ile Arg Ala Lys Ser Cys Pro Arg Pro
145                 150                 155                 160

Asp Glu Val Glu Asp Ser Ser Glu Phe Val Ser Phe Pro Asp Phe
                165                 170                 175

Ile Trp Thr Val Arg Asp Phe Thr Leu Glu Leu Lys Leu Asp Gly His
            180                 185                 190

Pro Ile Thr Glu Asp Glu Tyr Leu Glu Asn Ala Leu Lys Leu Ile Ser
        195                 200                 205

Gly Lys Asn Pro Gln Ile Gln Asn Ser Asn Lys Pro Arg Glu Trp Ile
    210                 215                 220

Arg His Phe Phe Pro Lys Gln Lys Cys Phe Val Phe Asp Arg Pro Ile
225                 230                 235                 240

Asn Asp Lys Lys Leu Leu Leu His Val Glu Glu Val Arg Glu Asp Gln
                245                 250                 255

Leu Asp Ser Asn Phe Gln Met Gln Ser Glu Asn Phe Cys Ser Tyr Ile
            260                 265                 270

Phe Thr His Ala Lys Thr Lys Thr Leu Arg Glu Gly Ile Leu Val Thr
        275                 280                 285

Gly Asn Arg Leu Gly Met Leu Val Glu Thr Tyr Leu Asp Ala Ile Asn
    290                 295                 300

Ser Gly Ala Thr Pro Cys Leu Glu Asn Ala Met Ala Val Leu Ala Gln
305                 310                 315                 320

Cys Glu Asn Ser Ala Ala Val Gln Arg Ala Ala Asn His Tyr Ser Gln
                325                 330                 335

Gln Met Ala Gln Gln Val Arg Phe Pro Thr Asp Thr Leu Gln Glu Leu
            340                 345                 350

Leu Asp Val His Ala Val Cys Glu Arg Glu Ala Ile Ala Val Phe Met
        355                 360                 365
```

-continued

```
Glu Tyr Ser Phe Lys Asp Lys Ser Gln Glu Phe Gln Lys Lys Leu Val
    370                 375                 380

Asp Thr Met Glu Lys Lys Lys Glu Asp Phe Val Leu Gln Asn Glu Glu
385                 390                 395                 400

Ala Ser Ala Lys Tyr Cys Gln Ala Glu Leu Lys Arg Leu Ser Glu Leu
                405                 410                 415

Leu Thr Glu Ser Ile Ser Arg Gly Thr Phe Phe Val Pro Gly Gly His
            420                 425                 430

Asn Ile Tyr Leu Glu Ala Lys Lys Ile Glu Gln Asp Tyr Thr Leu
                435                 440                 445

Val Pro Arg Lys Gly Val Lys Ala Asp Glu Val Leu Gln Ser Phe Leu
    450                 455                 460

Gln Ser Gln Val Val Ile Glu Glu Ser Ile Leu Gln Ser Asp Lys Ala
465                 470                 475                 480

Leu Thr Ala Gly Glu Lys Ala Ile Ala Ala Lys Gln Ala Lys Lys Glu
                485                 490                 495

Ala Ala Glu Lys Glu Gln Glu Leu Leu Arg Gln Lys Gln Lys Glu Gln
            500                 505                 510

Gln Gln Met Met Glu Ala Gln Glu Arg Ser Phe Gln Glu Asn Ile Ala
        515                 520                 525

Gln Leu Lys Lys Lys Met Glu Arg Glu Arg Glu Asn Tyr Met Arg Glu
    530                 535                 540

Leu Arg Lys Met Leu Ser His Lys Met Lys Val Leu Glu Glu Leu Leu
545                 550                 555                 560

Thr Glu Gly Phe Lys Glu Ile Phe Glu Ser Leu Asn Glu Glu Ile Asn
                565                 570                 575

Arg Leu Lys Glu Gln Ile Glu Ala Ala Glu Asn Glu Glu Pro Ser Val
            580                 585                 590

Phe Ser Gln Ile Leu Asp Val Ala Gly Ser Ile Phe Ile Ala Ala Leu
        595                 600                 605

Pro Gly Ala Ala Lys Leu Val Asp Leu Gly Met Lys Ile Leu Ser Ser
    610                 615                 620

Leu Cys Asn Arg Leu Arg Asn Pro Gly Lys Lys Ile Ile Ser
625                 630                 635
```

<210> SEQ ID NO 4
<211> LENGTH: 2130
<212> TYPE: DNA
<213> ORGANISM: Homo sapiens
<220> FEATURE:
<221> NAME/KEY: CDS
<222> LOCATION: (88)..(2109)

<400> SEQUENCE: 4

```
aagcttggta ccgagctcgg atcatcaaca agtttgtaca aaaaagcagg ctccgcggcc      60 gccccttca ccagatctgc agttgcc atg gaa tct gga ccc aaa atg ttg gcc     114
                            Met Glu Ser Gly Pro Lys Met Leu Ala
                              1               5 ccc gtt tgc ctg gtg gaa aat aac aat gag cag cta ttg gtg aac cag     162
Pro Val Cys Leu Val Glu Asn Asn Asn Glu Gln Leu Leu Val Asn Gln
 10              15                  20                  25 caa gct ata cag att ctt gaa aag att tct cag cca gtg gtg gtg gcc     210
Gln Ala Ile Gln Ile Leu Glu Lys Ile Ser Gln Pro Val Val Val Ala
             30                  35                  40 att gta gga ctg tac cgt aca ggg aaa tcc tac ttg atg aac cat ctg     258
Ile Val Gly Leu Tyr Arg Thr Gly Lys Ser Tyr Leu Met Asn His Leu
```

-continued

|  | 45 | 50 | 55 |  |
|---|---|---|---|---|
| gca gga cag aat cat ggc ttc cct ctg ggc tcc acg gtg cag tct gaa<br>Ala Gly Gln Asn His Gly Phe Pro Leu Gly Ser Thr Val Gln Ser Glu<br>60 65 70 | | | | 306 |
| acc aag ggc atc tgg atg tgg tgc gtg ccc cac cca tcc aag cca aac<br>Thr Lys Gly Ile Trp Met Trp Cys Val Pro His Pro Ser Lys Pro Asn<br>75 80 85 | | | | 354 |
| cac acc ctg gtc ctt ctg gac acc gaa ggt ctg ggc gat gtg gaa aag<br>His Thr Leu Val Leu Leu Asp Thr Glu Gly Leu Gly Asp Val Glu Lys<br>90 95 100 105 | | | | 402 |
| ggt gac cct aag aat gac tcc tgg atc ttt gcc ctg gct gtg ctc ctg<br>Gly Asp Pro Lys Asn Asp Ser Trp Ile Phe Ala Leu Ala Val Leu Leu<br>110 115 120 | | | | 450 |
| tgc agc acc ttt gtc tac aac agc atg agc acc atc aac cac cag gcc<br>Cys Ser Thr Phe Val Tyr Asn Ser Met Ser Thr Ile Asn His Gln Ala<br>125 130 135 | | | | 498 |
| ctg gag cag ctg cat tat gtg acg gag ctc aca gaa cta att aag gca<br>Leu Glu Gln Leu His Tyr Val Thr Glu Leu Thr Glu Leu Ile Lys Ala<br>140 145 150 | | | | 546 |
| aag tcc tcc cca agg cct gat gga gta gaa gat tcc aca gag ttt gtg<br>Lys Ser Ser Pro Arg Pro Asp Gly Val Glu Asp Ser Thr Glu Phe Val<br>155 160 165 | | | | 594 |
| agt ttc ttc cca gac ttt ctt tgg aca gta cgg gat ttc act ctg gag<br>Ser Phe Phe Pro Asp Phe Leu Trp Thr Val Arg Asp Phe Thr Leu Glu<br>170 175 180 185 | | | | 642 |
| ctg aag ttg aac ggt cac cct atc aca gaa gat gaa tac ctg gag aat<br>Leu Lys Leu Asn Gly His Pro Ile Thr Glu Asp Glu Tyr Leu Glu Asn<br>190 195 200 | | | | 690 |
| gcc ttg aag ctg att caa ggc aat aat ccc aga gtt caa aca tcc aat<br>Ala Leu Lys Leu Ile Gln Gly Asn Asn Pro Arg Val Gln Thr Ser Asn<br>205 210 215 | | | | 738 |
| ttt ccc agg gag tgc atc agg cgt ttc tta cca aaa cgg aag tgt ttc<br>Phe Pro Arg Glu Cys Ile Arg Arg Phe Leu Pro Lys Arg Lys Cys Phe<br>220 225 230 | | | | 786 |
| gtc ttt gac cgg cca aca aat gac aaa gac ctt cta gcc aat att gag<br>Val Phe Asp Arg Pro Thr Asn Asp Lys Asp Leu Leu Ala Asn Ile Glu<br>235 240 245 | | | | 834 |
| aag gtg tca gaa aag caa ctg gat ccc aaa ttc cag gaa caa aca aac<br>Lys Val Ser Glu Lys Gln Leu Asp Pro Lys Phe Gln Glu Gln Thr Asn<br>250 255 260 265 | | | | 882 |
| att ttc tgt tct tac atc ttc act cat gca aga acc aag acc ctc agg<br>Ile Phe Cys Ser Tyr Ile Phe Thr His Ala Arg Thr Lys Thr Leu Arg<br>270 275 280 | | | | 930 |
| gag gga atc aca gtc act ggg aat cgt ctg gga act ctg gca gtg act<br>Glu Gly Ile Thr Val Thr Gly Asn Arg Leu Gly Thr Leu Ala Val Thr<br>285 290 295 | | | | 978 |
| tat gta gag gcc atc aac agt gga gca gtg cct tgt ctg gag aat gca<br>Tyr Val Glu Ala Ile Asn Ser Gly Ala Val Pro Cys Leu Glu Asn Ala<br>300 305 310 | | | | 1026 |
| gtg ata act ctg gcc cag cgt gag aac tca gcg gcc gtg cag agg gca<br>Val Ile Thr Leu Ala Gln Arg Glu Asn Ser Ala Ala Val Gln Arg Ala<br>315 320 325 | | | | 1074 |
| tct gac tac tac agc cag cag atg gcc cag cga gtg aag ttc ccc aca<br>Ser Asp Tyr Tyr Ser Gln Gln Met Ala Gln Arg Val Lys Phe Pro Thr<br>330 335 340 345 | | | | 1122 |
| gac acg ctc cag gag ctg ctg gac gtg cat gcg gcc tgt gag agg gaa<br>Asp Thr Leu Gln Glu Leu Leu Asp Val His Ala Ala Cys Glu Arg Glu<br>350 355 360 | | | | 1170 |
| gcc att gca atc ttc atg gag cac tcc ttc aag gat gaa aat cag gaa | | | | 1218 |

-continued

| | | |
|---|---|---|
| Ala Ile Ala Ile Phe Met Glu His Ser Phe Lys Asp Glu Asn Gln Glu<br>365 370 375 | | |
| ttc cag aag aag ttc atg gaa acc aca atg aat aag aag ggg gat ttc<br>Phe Gln Lys Lys Phe Met Glu Thr Thr Met Asn Lys Lys Gly Asp Phe<br>380 385 390 | 1266 | |
| ttg ctg cag aat gaa gag tca tct gtt caa tac tgc cag gct aaa ctc<br>Leu Leu Gln Asn Glu Glu Ser Ser Val Gln Tyr Cys Gln Ala Lys Leu<br>395 400 405 | 1314 | |
| aat gag ctc tca aag gga cta atg gaa agt atc tca gca gga agt ttc<br>Asn Glu Leu Ser Lys Gly Leu Met Glu Ser Ile Ser Ala Gly Ser Phe<br>410 415 420 425 | 1362 | |
| tct gtt cct gga ggg cac aag ctc tac atg gaa aca aag gaa agg att<br>Ser Val Pro Gly Gly His Lys Leu Tyr Met Glu Thr Lys Glu Arg Ile<br>430 435 440 | 1410 | |
| gaa cag gac tat tgg caa gtt ccc agg aaa gga gta aag gca aaa gag<br>Glu Gln Asp Tyr Trp Gln Val Pro Arg Lys Gly Val Lys Ala Lys Glu<br>445 450 455 | 1458 | |
| gtc ttc cag agg ttc ctg gag tca cag atg gtg ata gag gaa tcc atc<br>Val Phe Gln Arg Phe Leu Glu Ser Gln Met Val Ile Glu Glu Ser Ile<br>460 465 470 | 1506 | |
| ttg cag tca gat aaa gcc ctc act gat aga gag aag gca gta gca gtg<br>Leu Gln Ser Asp Lys Ala Leu Thr Asp Arg Glu Lys Ala Val Ala Val<br>475 480 485 | 1554 | |
| gat cgg gcc aag aag gag gca gct gag aag gaa cag gaa ctt tta aaa<br>Asp Arg Ala Lys Lys Glu Ala Ala Glu Lys Glu Gln Glu Leu Leu Lys<br>490 495 500 505 | 1602 | |
| cag aaa tta cag gag cag cag caa cag atg gag gct caa gtt aag agt<br>Gln Lys Leu Gln Glu Gln Gln Gln Gln Met Glu Ala Gln Val Lys Ser<br>510 515 520 | 1650 | |
| cgc aag gaa aac ata gcc caa ctg aag gag aag ctg cag atg gag aga<br>Arg Lys Glu Asn Ile Ala Gln Leu Lys Glu Lys Leu Gln Met Glu Arg<br>525 530 535 | 1698 | |
| gaa cac cta ctg aga gag cag att atg atg ttg gag cac acg cag aag<br>Glu His Leu Leu Arg Glu Gln Ile Met Met Leu Glu His Thr Gln Lys<br>540 545 550 | 1746 | |
| gtc caa aat gat tgg ctt cat gaa gga ttt aag aag aag tat gag gag<br>Val Gln Asn Asp Trp Leu His Glu Gly Phe Lys Lys Lys Tyr Glu Glu<br>555 560 565 | 1794 | |
| atg aat gca gag ata agt caa ttt aaa cgt atg att gat act aca aaa<br>Met Asn Ala Glu Ile Ser Gln Phe Lys Arg Met Ile Asp Thr Thr Lys<br>570 575 580 585 | 1842 | |
| aat gat gat act ccc tgg att gca cga acc ttg gac aac ctt gcc gat<br>Asn Asp Asp Thr Pro Trp Ile Ala Arg Thr Leu Asp Asn Leu Ala Asp<br>590 595 600 | 1890 | |
| gag cta act gca ata ttg tct gct cct gct aaa tta att ggt cat ggt<br>Glu Leu Thr Ala Ile Leu Ser Ala Pro Ala Lys Leu Ile Gly His Gly<br>605 610 615 | 1938 | |
| gtc aaa ggt gtg agc tca ctc ttt aaa aag cat aag ctc ccc ttt aag<br>Val Lys Gly Val Ser Ser Leu Phe Lys Lys His Lys Leu Pro Phe Lys<br>620 625 630 | 1986 | |
| ggt ggg cgc gcc gac cca gct ttc ttg tac aaa gtg gtt gat cta gag<br>Gly Gly Arg Ala Asp Pro Ala Phe Leu Tyr Lys Val Val Asp Leu Glu<br>635 640 645 | 2034 | |
| ggc ccg cgg ttc gaa caa aaa ctc atc tca gaa gag gat ctg aat atg<br>Gly Pro Arg Phe Glu Gln Lys Leu Ile Ser Glu Glu Asp Leu Asn Met<br>650 655 660 665 | 2082 | |
| cat acc ggt cat cat cac cat cac cat tgagtttaaa cccgctgatc a<br>His Thr Gly His His His His His His<br>670 | 2130 | |

<210> SEQ ID NO 5
<211> LENGTH: 674
<212> TYPE: PRT
<213> ORGANISM: Homo sapiens

<400> SEQUENCE: 5

```
Met Glu Ser Gly Pro Lys Met Leu Ala Pro Val Cys Leu Val Glu Asn
1               5                   10                  15

Asn Asn Glu Gln Leu Leu Val Asn Gln Gln Ala Ile Gln Ile Leu Glu
            20                  25                  30

Lys Ile Ser Gln Pro Val Val Ala Ile Val Gly Leu Tyr Arg Thr
        35                  40                  45

Gly Lys Ser Tyr Leu Met Asn His Leu Ala Gly Gln Asn His Gly Phe
    50                  55                  60

Pro Leu Gly Ser Thr Val Gln Ser Glu Thr Lys Gly Ile Trp Met Trp
65                  70                  75                  80

Cys Val Pro His Pro Ser Lys Pro Asn His Thr Leu Val Leu Leu Asp
                85                  90                  95

Thr Glu Gly Leu Gly Asp Val Glu Lys Gly Asp Pro Lys Asn Asp Ser
            100                 105                 110

Trp Ile Phe Ala Leu Ala Val Leu Leu Cys Ser Thr Phe Val Tyr Asn
        115                 120                 125

Ser Met Ser Thr Ile Asn His Gln Ala Leu Glu Gln Leu His Tyr Val
    130                 135                 140

Thr Glu Leu Thr Glu Leu Ile Lys Ala Lys Ser Ser Pro Arg Pro Asp
145                 150                 155                 160

Gly Val Glu Asp Ser Thr Glu Phe Val Ser Phe Phe Pro Asp Phe Leu
                165                 170                 175

Trp Thr Val Arg Asp Phe Thr Leu Glu Leu Lys Leu Asn Gly His Pro
            180                 185                 190

Ile Thr Glu Asp Glu Tyr Leu Glu Asn Ala Leu Lys Leu Ile Gln Gly
        195                 200                 205

Asn Asn Pro Arg Val Gln Thr Ser Asn Phe Pro Arg Glu Cys Ile Arg
    210                 215                 220

Arg Phe Leu Pro Lys Arg Lys Cys Phe Val Phe Asp Arg Pro Thr Asn
225                 230                 235                 240

Asp Lys Asp Leu Leu Ala Asn Ile Glu Lys Val Ser Glu Lys Gln Leu
                245                 250                 255

Asp Pro Lys Phe Gln Glu Gln Thr Asn Ile Phe Cys Ser Tyr Ile Phe
            260                 265                 270

Thr His Ala Arg Thr Lys Thr Leu Arg Glu Gly Ile Thr Val Thr Gly
        275                 280                 285

Asn Arg Leu Gly Thr Leu Ala Val Thr Tyr Val Glu Ala Ile Asn Ser
    290                 295                 300

Gly Ala Val Pro Cys Leu Glu Asn Ala Val Ile Thr Leu Ala Gln Arg
305                 310                 315                 320

Glu Asn Ser Ala Ala Val Gln Arg Ala Ser Asp Tyr Tyr Ser Gln Gln
                325                 330                 335

Met Ala Gln Arg Val Lys Phe Pro Thr Asp Thr Leu Gln Glu Leu Leu
            340                 345                 350

Asp Val His Ala Ala Cys Glu Arg Glu Ala Ile Ala Ile Phe Met Glu
        355                 360                 365

His Ser Phe Lys Asp Glu Asn Gln Glu Phe Gln Lys Lys Phe Met Glu
    370                 375                 380
```

```
Thr Thr Met Asn Lys Lys Gly Asp Phe Leu Leu Gln Asn Glu Glu Ser
385                 390                 395                 400

Ser Val Gln Tyr Cys Gln Ala Lys Leu Asn Glu Leu Ser Lys Gly Leu
            405                 410                 415

Met Glu Ser Ile Ser Ala Gly Ser Phe Ser Val Pro Gly Gly His Lys
            420                 425                 430

Leu Tyr Met Glu Thr Lys Glu Arg Ile Glu Gln Asp Tyr Trp Gln Val
        435                 440                 445

Pro Arg Lys Gly Val Lys Ala Lys Glu Val Phe Gln Arg Phe Leu Glu
450                 455                 460

Ser Gln Met Val Ile Glu Glu Ser Ile Leu Gln Ser Asp Lys Ala Leu
465                 470                 475                 480

Thr Asp Arg Glu Lys Ala Val Ala Val Asp Arg Ala Lys Lys Glu Ala
            485                 490                 495

Ala Glu Lys Glu Gln Glu Leu Leu Lys Gln Lys Leu Gln Glu Gln Gln
            500                 505                 510

Gln Gln Met Glu Ala Gln Val Lys Ser Arg Lys Glu Asn Ile Ala Gln
    515                 520                 525

Leu Lys Glu Lys Leu Gln Met Glu Arg Glu His Leu Leu Arg Glu Gln
530                 535                 540

Ile Met Met Leu Glu His Thr Gln Lys Val Gln Asn Asp Trp Leu His
545                 550                 555                 560

Glu Gly Phe Lys Lys Lys Tyr Glu Glu Met Asn Ala Glu Ile Ser Gln
                565                 570                 575

Phe Lys Arg Met Ile Asp Thr Thr Lys Asn Asp Asp Thr Pro Trp Ile
            580                 585                 590

Ala Arg Thr Leu Asp Asn Leu Ala Asp Glu Leu Thr Ala Ile Leu Ser
        595                 600                 605

Ala Pro Ala Lys Leu Ile Gly His Gly Val Lys Gly Val Ser Ser Leu
610                 615                 620

Phe Lys Lys His Lys Leu Pro Phe Lys Gly Gly Arg Ala Asp Pro Ala
625                 630                 635                 640

Phe Leu Tyr Lys Val Val Asp Leu Glu Gly Pro Arg Phe Glu Gln Lys
                645                 650                 655

Leu Ile Ser Glu Glu Asp Leu Asn Met His Thr Gly His His His His
            660                 665                 670

His His

<210> SEQ ID NO 6
<211> LENGTH: 1392
<212> TYPE: DNA
<213> ORGANISM: Homo sapiens
<220> FEATURE:
<221> NAME/KEY: CDS
<222> LOCATION: (1)..(1392)

<400> SEQUENCE: 6 atg gta tca gag atc cac atg aca ggc cca atg tgc ctc att gag aac      48
Met Val Ser Glu Ile His Met Thr Gly Pro Met Cys Leu Ile Glu Asn
1               5                   10                  15 act aat ggg cga ctg atg gcg aat cca gaa gct ctg aag atc ctt tct      96
Thr Asn Gly Arg Leu Met Ala Asn Pro Glu Ala Leu Lys Ile Leu Ser
            20                  25                  30 gcc att acg cag cct gtg gtg gtg gtg gcg act cgc aca gga aaa tcc     144
Ala Ile Thr Gln Pro Val Val Val Val Ala Thr Arg Thr Gly Lys Ser
        35                  40                  45
```

```
tac ctg att aac aag ctg gct cag aag aaa aag ggc ttc tct ctg ggc      192
Tyr Leu Ile Asn Lys Leu Ala Gln Lys Lys Lys Gly Phe Ser Leu Gly
     50                  55                  60 tcc aca gtg cag tct cac act aaa gga atc tgg atg tgg tgt atg ccc      240
Ser Thr Val Gln Ser His Thr Lys Gly Ile Trp Met Trp Cys Met Pro
 65                  70                  75                  80 cat ccc aag aag cca ggc cac atc cta gtt ctg ctg gac acc gag ggt      288
His Pro Lys Lys Pro Gly His Ile Leu Val Leu Leu Asp Thr Glu Gly
                 85                  90                  95 ctg gga gat gta gag aag ggt gac aac cag aat gac tcc tgg atc ttc      336
Leu Gly Asp Val Glu Lys Gly Asp Asn Gln Asn Asp Ser Trp Ile Phe
            100                 105                 110 gcc ctg gcc gtc ctc ctg aac agc act tcc atg tac aat agc ata gga      384
Ala Leu Ala Val Leu Leu Asn Ser Thr Ser Met Tyr Asn Ser Ile Gly
        115                 120                 125 acc att aac cag cag gcc atg gac caa ctg cac tat gtg aca gag ctg      432
Thr Ile Asn Gln Gln Ala Met Asp Gln Leu His Tyr Val Thr Glu Leu
    130                 135                 140 aca cat cga gtc caa cca aaa tct tca cct gat gag aat gag aat gag      480
Thr His Arg Val Gln Pro Lys Ser Ser Pro Asp Glu Asn Glu Asn Glu
145                 150                 155                 160 gat tca gct gac ttt gag agc ttc ttc cca gac ttt gca ggt cta gag      528
Asp Ser Ala Asp Phe Glu Ser Phe Phe Pro Asp Phe Ala Gly Leu Glu
                165                 170                 175 agc ctg gtg ctg acc tat gtc aat gcc atc agc agt ggg gat cta ccc      576
Ser Leu Val Leu Thr Tyr Val Asn Ala Ile Ser Ser Gly Asp Leu Pro
            180                 185                 190 tgc atg gag aac gca gtc ctg gcc ttg gcc cag ata gag aac tca gcc      624
Cys Met Glu Asn Ala Val Leu Ala Leu Ala Gln Ile Glu Asn Ser Ala
        195                 200                 205 gca gtg caa aag gct att gcc cac tat gaa aag cag atg ggc cag aag      672
Ala Val Gln Lys Ala Ile Ala His Tyr Glu Lys Gln Met Gly Gln Lys
    210                 215                 220 gtg cag ctg ccc aca gaa acc ctc cag gag ctg ctg gac ctg cac agg      720
Val Gln Leu Pro Thr Glu Thr Leu Gln Glu Leu Leu Asp Leu His Arg
225                 230                 235                 240 gac agt gag agc aag gcc act gaa gtt ttc atc agg tcc tcc ttc aaa      768
Asp Ser Glu Ser Lys Ala Thr Glu Val Phe Ile Arg Ser Ser Phe Lys
                245                 250                 255 gat gtg gac cat cta ttt caa aag gag tta gcg gcc cag cta gac aaa      816
Asp Val Asp His Leu Phe Gln Lys Glu Leu Ala Ala Gln Leu Asp Lys
            260                 265                 270 aag cgg gat gac ttt tgt aaa cag aat cag gaa gca tca tca gat cgt      864
Lys Arg Asp Asp Phe Cys Lys Gln Asn Gln Glu Ala Ser Ser Asp Arg
        275                 280                 285 tgc tca gct tta ctt cag gtc att ttc agt cct cta gaa gaa gaa gtg      912
Cys Ser Ala Leu Leu Gln Val Ile Phe Ser Pro Leu Glu Glu Glu Val
    290                 295                 300 aag gcg gga att tat tcg aaa cca ggg ggc tat cgt ctc ttt att cag      960
Lys Ala Gly Ile Tyr Ser Lys Pro Gly Gly Tyr Arg Leu Phe Ile Gln
305                 310                 315                 320 aag tta caa gac ctg gag aaa aag tac tat gag gaa ccg agg aag ggg     1008
Lys Leu Gln Asp Leu Glu Lys Lys Tyr Tyr Glu Glu Pro Arg Lys Gly
                325                 330                 335 ata cag gga att tca cca cca agg aca aca ggg caa agg aaa gaa ttc     1056
Ile Gln Gly Ile Ser Pro Pro Arg Thr Thr Gly Gln Arg Lys Glu Phe
            340                 345                 350 cca gag gaa agg atg gca gga aga caa aca gga aca cct gct tac agc     1104
Pro Glu Glu Arg Met Ala Gly Arg Gln Thr Gly Thr Pro Ala Tyr Ser
```

|  |  |  |  |  |  |  |  |  |  |  |  |
|---|---|---|---|---|---|---|---|---|---|---|---|
| | | 355 | | | | 360 | | | | 365 | |
| cgt | ctc | cta | ctt | ctc | act | ttg | tgt | tct | ctg | ggt | cct | aag | gct | gaa | gag | 1152 |
| Arg | Leu | Leu | Leu | Leu | Thr | Leu | Cys | Ser | Leu | Gly | Pro | Lys | Ala | Glu | Glu |
| | 370 | | | | | 375 | | | | | 380 |

```
                355                 360                 365
cgt ctc cta ctt ctc act ttg tgt tct ctg ggt cct aag gct gaa gag   1152
Arg Leu Leu Leu Leu Thr Leu Cys Ser Leu Gly Pro Lys Ala Glu Glu
    370                 375                 380 att ctg cag aca tac ttg aaa tcc aag gag tct atg act gat gca att   1200
Ile Leu Gln Thr Tyr Leu Lys Ser Lys Glu Ser Met Thr Asp Ala Ile
385                 390                 395                 400 ctc cag aca gac cag act ctc aca gaa aaa gaa aag gag att gaa gtg   1248
Leu Gln Thr Asp Gln Thr Leu Thr Glu Lys Glu Lys Glu Ile Glu Val
            405                 410                 415 gaa cgt gtg aaa gct gag tct gca cag gct tca gca aaa atg ttg cag   1296
Glu Arg Val Lys Ala Glu Ser Ala Gln Ala Ser Ala Lys Met Leu Gln
        420                 425                 430 caa atg caa aga aag aat gag cag atg atg gaa cag aag gag agg agt   1344
Gln Met Gln Arg Lys Asn Glu Gln Met Met Glu Gln Lys Glu Arg Ser
            435                 440                 445 tat cag gaa cac ttg aaa caa ctg act gag aag atg gag agc gac agg   1392
Tyr Gln Glu His Leu Lys Gln Leu Thr Glu Lys Met Glu Ser Asp Arg
450                 455                 460
```

<210> SEQ ID NO 7
<211> LENGTH: 464
<212> TYPE: PRT
<213> ORGANISM: Homo sapiens

<400> SEQUENCE: 7

```
Met Val Ser Glu Ile His Met Thr Gly Pro Met Cys Leu Ile Glu Asn
1               5                   10                  15

Thr Asn Gly Arg Leu Met Ala Asn Pro Glu Ala Leu Lys Ile Leu Ser
            20                  25                  30

Ala Ile Thr Gln Pro Val Val Val Ala Thr Arg Thr Gly Lys Ser
        35                  40                  45

Tyr Leu Ile Asn Lys Leu Ala Gln Lys Lys Gly Phe Ser Leu Gly
    50                  55                  60

Ser Thr Val Gln Ser His Thr Lys Gly Ile Trp Met Trp Cys Met Pro
65                  70                  75                  80

His Pro Lys Lys Pro Gly His Ile Leu Val Leu Leu Asp Thr Glu Gly
                85                  90                  95

Leu Gly Asp Val Glu Lys Gly Asp Asn Gln Asn Asp Ser Trp Ile Phe
            100                 105                 110

Ala Leu Ala Val Leu Leu Asn Ser Thr Ser Met Tyr Asn Ser Ile Gly
        115                 120                 125

Thr Ile Asn Gln Gln Ala Met Asp Gln Leu His Tyr Val Thr Glu Leu
    130                 135                 140

Thr His Arg Val Gln Pro Lys Ser Ser Pro Asp Glu Asn Glu Asn Glu
145                 150                 155                 160

Asp Ser Ala Asp Phe Glu Ser Phe Phe Pro Asp Phe Ala Gly Leu Glu
                165                 170                 175

Ser Leu Val Leu Thr Tyr Val Asn Ala Ile Ser Ser Gly Asp Leu Pro
            180                 185                 190

Cys Met Glu Asn Ala Val Leu Ala Leu Ala Gln Ile Glu Asn Ser Ala
        195                 200                 205

Ala Val Gln Lys Ala Ile Ala His Tyr Glu Lys Gln Met Gly Gln Lys
    210                 215                 220

Val Gln Leu Pro Thr Glu Thr Leu Gln Glu Leu Leu Asp Leu His Arg
225                 230                 235                 240
```

-continued

```
Asp Ser Glu Ser Lys Ala Thr Glu Val Phe Ile Arg Ser Ser Phe Lys
                245                 250                 255

Asp Val Asp His Leu Phe Gln Lys Glu Leu Ala Ala Gln Leu Asp Lys
            260                 265                 270

Lys Arg Asp Asp Phe Cys Lys Gln Asn Gln Glu Ala Ser Ser Asp Arg
        275                 280                 285

Cys Ser Ala Leu Leu Gln Val Ile Phe Ser Pro Leu Glu Glu Glu Val
    290                 295                 300

Lys Ala Gly Ile Tyr Ser Lys Pro Gly Gly Tyr Arg Leu Phe Ile Gln
305                 310                 315                 320

Lys Leu Gln Asp Leu Glu Lys Lys Tyr Tyr Glu Glu Pro Arg Lys Gly
                325                 330                 335

Ile Gln Gly Ile Ser Pro Pro Arg Thr Thr Gly Gln Arg Lys Glu Phe
            340                 345                 350

Pro Glu Glu Arg Met Ala Gly Arg Gln Thr Gly Thr Pro Ala Tyr Ser
        355                 360                 365

Arg Leu Leu Leu Thr Leu Cys Ser Leu Gly Pro Lys Ala Glu Glu
    370                 375                 380

Ile Leu Gln Thr Tyr Leu Lys Ser Lys Glu Ser Met Thr Asp Ala Ile
385                 390                 395                 400

Leu Gln Thr Asp Gln Thr Leu Thr Glu Lys Glu Lys Glu Ile Glu Val
                405                 410                 415

Glu Arg Val Lys Ala Glu Ser Ala Gln Ala Ser Ala Lys Met Leu Gln
            420                 425                 430

Gln Met Gln Arg Lys Asn Glu Gln Met Met Glu Gln Lys Glu Arg Ser
        435                 440                 445

Tyr Gln Glu His Leu Lys Gln Leu Thr Glu Lys Met Glu Ser Asp Arg
    450                 455                 460
```

<210> SEQ ID NO 8
<211> LENGTH: 2952
<212> TYPE: DNA
<213> ORGANISM: Homo sapiens
<220> FEATURE:
<221> NAME/KEY: CDS
<222> LOCATION: (201)..(1889)

<400> SEQUENCE: 8

```
cagtttcatt aggctctgaa gccattacaa aggttgctta acttctaatt atttgatcac    60
tgaggaaaat ccagaaagct acacaacact gaagggtgaa ataaaagtc cagcgatcca   120 gcgaaagaaa agagaagtga cagaaacaac tttacctgga ctgaagataa aagcacagac   180
aagagaacaa tgccctggac atg gct cca gag atc cac atg aca ggc cca atg   233
                      Met Ala Pro Glu Ile His Met Thr Gly Pro Met
                        1               5                  10 tgc ctc att gag aac act aat ggg gaa ctg gtg gcg aat cca gaa gct    281
Cys Leu Ile Glu Asn Thr Asn Gly Glu Leu Val Ala Asn Pro Glu Ala
             15                  20                  25 ctg aaa atc ctg tct gcc att aca cag cct gtg gtg gtg gtg gca att    329
Leu Lys Ile Leu Ser Ala Ile Thr Gln Pro Val Val Val Val Ala Ile
         30                  35                  40 gtg ggc ctc tac cgc aca gga aaa tcc tac ctg atg aac aag cta gct    377
Val Gly Leu Tyr Arg Thr Gly Lys Ser Tyr Leu Met Asn Lys Leu Ala
     45                  50                  55 ggg aag aat aag ggc ttc tct ctg ggc tcc aca gtg aaa tct cac acc    425
Gly Lys Asn Lys Gly Phe Ser Leu Gly Ser Thr Val Lys Ser His Thr
 60                  65                  70                  75
```

```
aaa gga atc tgg atg tgg tgt gtg cct cac ccc aaa aag cca gaa cac      473
Lys Gly Ile Trp Met Trp Cys Val Pro His Pro Lys Lys Pro Glu His
            80                  85                  90 acc tta gtc ctg ctt gac act gag ggc ctg gga gat gta aag aag ggt      521
Thr Leu Val Leu Leu Asp Thr Glu Gly Leu Gly Asp Val Lys Lys Gly
 95                 100                 105 gac aac cag aat gac tcc tgg atc ttc acc ctg gcc gtc ctc ctg agc      569
Asp Asn Gln Asn Asp Ser Trp Ile Phe Thr Leu Ala Val Leu Leu Ser
        110                 115                 120 agc act ctc gtg tac aat agc atg gga acc atc aac cag cag gct atg      617
Ser Thr Leu Val Tyr Asn Ser Met Gly Thr Ile Asn Gln Gln Ala Met
125                 130                 135 gac caa ctg tac tat gtg aca gag ctg aca cat cga atc cga tca aaa      665
Asp Gln Leu Tyr Tyr Val Thr Glu Leu Thr His Arg Ile Arg Ser Lys
140                 145                 150                 155 tcc tca cct gat gag aat gag aat gag gat tca gct gac ttt gtg agc      713
Ser Ser Pro Asp Glu Asn Glu Asn Glu Asp Ser Ala Asp Phe Val Ser
            160                 165                 170 ttc ttc cca gat ttt gtg tgg aca ctg aga gat ttc tcc ctg gac ttg      761
Phe Phe Pro Asp Phe Val Trp Thr Leu Arg Asp Phe Ser Leu Asp Leu
        175                 180                 185 gaa gca gat gga caa ccc ctc aca cca gat gag tac ctg gag tat tcc      809
Glu Ala Asp Gly Gln Pro Leu Thr Pro Asp Glu Tyr Leu Glu Tyr Ser
    190                 195                 200 ctg aag cta acg caa ggt aac agg aag ctt gcc cag ctt gag aaa cta      857
Leu Lys Leu Thr Gln Gly Asn Arg Lys Leu Ala Gln Leu Glu Lys Leu
205                 210                 215 caa gat gaa gag ctg gac cct gaa ttt gtg caa caa gta gca gac ttc      905
Gln Asp Glu Glu Leu Asp Pro Glu Phe Val Gln Gln Val Ala Asp Phe
220                 225                 230                 235 tgt tcc tac atc ttt agc aat tcc aaa act aaa act ctt tca gga ggc      953
Cys Ser Tyr Ile Phe Ser Asn Ser Lys Thr Lys Thr Leu Ser Gly Gly
            240                 245                 250 atc aag gtc aat ggg cct tgt cta gag agc cta gtg ctg acc tat atc     1001
Ile Lys Val Asn Gly Pro Cys Leu Glu Ser Leu Val Leu Thr Tyr Ile
        255                 260                 265 aat gct atc agc aga ggg gat ctg ccc tgc atg gag aac gca gtc ctg     1049
Asn Ala Ile Ser Arg Gly Asp Leu Pro Cys Met Glu Asn Ala Val Leu
    270                 275                 280 gcc ttg gcc cag ata gag aac tca gcc gca gtg caa aag gct att gcc     1097
Ala Leu Ala Gln Ile Glu Asn Ser Ala Ala Val Gln Lys Ala Ile Ala
285                 290                 295 cac tat gac cag cag atg ggc cag aag gtg cag ctg ccc gca gaa acc     1145
His Tyr Asp Gln Gln Met Gly Gln Lys Val Gln Leu Pro Ala Glu Thr
300                 305                 310                 315 ctc cag gag ctg ctg gac ctg cac agg gtt agt gag agg gag gcc act     1193
Leu Gln Glu Leu Leu Asp Leu His Arg Val Ser Glu Arg Glu Ala Thr
            320                 325                 330 gaa gtc tat atg aag aac tct ttc aag gat gtg gac cat ctg ttt caa     1241
Glu Val Tyr Met Lys Asn Ser Phe Lys Asp Val Asp His Leu Phe Gln
        335                 340                 345 aag aaa tta gcg gcc cag cta gac aaa aag cgg gat gac ttt tgt aaa     1289
Lys Lys Leu Ala Ala Gln Leu Asp Lys Lys Arg Asp Asp Phe Cys Lys
    350                 355                 360 cag aat caa gaa gca tca tca gat cgt tgc tca gct tta ctt cag gtc     1337
Gln Asn Gln Glu Ala Ser Ser Asp Arg Cys Ser Ala Leu Leu Gln Val
365                 370                 375 att ttc agt cct cta gaa gaa gaa gtg aag gcg gga att tat tcg aaa     1385
Ile Phe Ser Pro Leu Glu Glu Glu Val Lys Ala Gly Ile Tyr Ser Lys
380                 385                 390                 395
```

-continued

```
cca ggg ggc tat tgt ctc ttt att cag aag cta caa gac ctg gag aaa      1433
Pro Gly Gly Tyr Cys Leu Phe Ile Gln Lys Leu Gln Asp Leu Glu Lys
            400                 405                 410 aag tac tat gag gaa cca agg aag ggg ata cag gct gaa gag att ctg      1481
Lys Tyr Tyr Glu Glu Pro Arg Lys Gly Ile Gln Ala Glu Glu Ile Leu
        415                 420                 425 cag aca tac ttg aaa tcc aag gag tct gtg acc gat gca att cta cag      1529
Gln Thr Tyr Leu Lys Ser Lys Glu Ser Val Thr Asp Ala Ile Leu Gln
        430                 435                 440 aca gac cag att ctc aca gaa aag gaa aag gag att gaa gtg gaa tgt      1577
Thr Asp Gln Ile Leu Thr Glu Lys Glu Lys Glu Ile Glu Val Glu Cys
    445                 450                 455 gta aaa gct gaa tct gca cag gct tca gca aaa atg gtg gag gaa atg      1625
Val Lys Ala Glu Ser Ala Gln Ala Ser Ala Lys Met Val Glu Glu Met
460                 465                 470                 475 caa ata aag tat cag cag atg atg gaa gag aaa gag aag agt tat caa      1673
Gln Ile Lys Tyr Gln Gln Met Met Glu Glu Lys Glu Lys Ser Tyr Gln
            480                 485                 490 gaa cat gtg aaa caa ttg act gag aag atg gag agg gag agg gcc cag      1721
Glu His Val Lys Gln Leu Thr Glu Lys Met Glu Arg Glu Arg Ala Gln
        495                 500                 505 ttg ctg gaa gag caa gag aag acc ctc act agt aaa ctt cag gaa cag      1769
Leu Leu Glu Glu Gln Glu Lys Thr Leu Thr Ser Lys Leu Gln Glu Gln
        510                 515                 520 gcc cga gta cta aag gag aga tgc caa ggt gaa agt acc caa ctt caa      1817
Ala Arg Val Leu Lys Glu Arg Cys Gln Gly Glu Ser Thr Gln Leu Gln
    525                 530                 535 aat gag ata caa aag cta cag aag acc ctg aaa aaa aaa acc aag aga      1865
Asn Glu Ile Gln Lys Leu Gln Lys Thr Leu Lys Lys Lys Thr Lys Arg
540                 545                 550                 555 tat atg tcg cat aag cta aag atc taaacaacag agcttttctg tcatcctaac    1919
Tyr Met Ser His Lys Leu Lys Ile
                560 ccaaggcata actgaaacaa ttttagaatt tggaacaagt gtcactatat tgataataa    1979
ttagatcttg catcataaca ctaaaagttt acaagaacat gcagttcaat gatcaaaatc  2039
atgtttttc cttaaaaaga ttgtaaattg tgcaacaaag atgcatttac ctctgtacca   2099
acagaggagg gatcatgagt tgccaccact cagaagttta ttcttccaga cgaccagtgg  2159
atactgagga aagtcttagg taaaaatctt gggacatatt tgggcactgg tttggccaag  2219
tgtacaatag gtcccaatat cagaaacaac catcctagct tcctagggaa gacagtgtac  2279
agttctccat tatatcaagg ctacaaggtc tatgagcaat aatgtgattt ctggacattg  2339
cccatggata attctcactg atggatctca agctaaagca aaccatctta tacagagatc  2399
tagaatctta tattttccat aggaaggtaa agaaatcatt agcaagagta ggaattgaat  2459
cataaacaaa ttggctaatg aagaaatctt ttctttcttg ttcaattcat ctagattata  2519
accttaatgt gacacctgag acctttagac agttgaccct gaattaaata gtcacatggt  2579
aacaattatg cactgtgtaa ttttagtaat gtataacatg caatgatgca ctttaactga  2639
agatagagac tatgttagaa aattgaacta atttaattat ttgattgttt taatcctaaa  2699
gcataagtta gtcttttcct gattcttaaa ggtcatactt gaatcctgc caattttccc   2759
caaagggaat atggaatttt ttttgacttt cttttgagca ataaaataat tgtcttgcca  2819
ttacttagta tatgtagact tcatcccaat tgtcaaacat cctaggtaag tggttgacat  2879
ttcttacagc aattacagat tatttttgaa ctagaaataa actaaactag aaacaaaaaa  2939
```
aaaaaaaaaa aaa                                                                2952

<210> SEQ ID NO 9
<211> LENGTH: 563
<212> TYPE: PRT
<213> ORGANISM: Homo sapiens

<400> SEQUENCE: 9

Met Ala Pro Glu Ile His Met Thr Gly Pro Met Cys Leu Ile Glu Asn
1               5                   10                  15

Thr Asn Gly Glu Leu Val Ala Asn Pro Glu Ala Leu Lys Ile Leu Ser
            20                  25                  30

Ala Ile Thr Gln Pro Val Val Val Ala Ile Val Gly Leu Tyr Arg
        35                  40                  45

Thr Gly Lys Ser Tyr Leu Met Asn Lys Leu Ala Gly Lys Asn Lys Gly
50                  55                  60

Phe Ser Leu Gly Ser Thr Val Lys Ser His Thr Lys Gly Ile Trp Met
65                  70                  75                  80

Trp Cys Val Pro His Pro Lys Lys Pro Glu His Thr Leu Val Leu Leu
                85                  90                  95

Asp Thr Glu Gly Leu Gly Asp Val Lys Lys Gly Asp Asn Gln Asn Asp
            100                 105                 110

Ser Trp Ile Phe Thr Leu Ala Val Leu Leu Ser Ser Thr Leu Val Tyr
        115                 120                 125

Asn Ser Met Gly Thr Ile Asn Gln Gln Ala Met Asp Gln Leu Tyr Tyr
130                 135                 140

Val Thr Glu Leu Thr His Arg Ile Arg Ser Lys Ser Ser Pro Asp Glu
145                 150                 155                 160

Asn Glu Asn Glu Asp Ser Ala Asp Phe Val Ser Phe Phe Pro Asp Phe
                165                 170                 175

Val Trp Thr Leu Arg Asp Phe Ser Leu Asp Leu Glu Ala Asp Gly Gln
            180                 185                 190

Pro Leu Thr Pro Asp Glu Tyr Leu Glu Tyr Ser Leu Lys Leu Thr Gln
        195                 200                 205

Gly Asn Arg Lys Leu Ala Gln Leu Glu Lys Leu Gln Asp Glu Glu Leu
210                 215                 220

Asp Pro Glu Phe Val Gln Gln Val Ala Asp Phe Cys Ser Tyr Ile Phe
225                 230                 235                 240

Ser Asn Ser Lys Thr Lys Thr Leu Ser Gly Gly Ile Lys Val Asn Gly
                245                 250                 255

Pro Cys Leu Glu Ser Leu Val Leu Thr Tyr Ile Asn Ala Ile Ser Arg
            260                 265                 270

Gly Asp Leu Pro Cys Met Glu Asn Ala Val Leu Ala Leu Ala Gln Ile
        275                 280                 285

Glu Asn Ser Ala Ala Val Gln Lys Ala Ile Ala His Tyr Asp Gln Gln
290                 295                 300

Met Gly Gln Lys Val Gln Leu Pro Ala Glu Thr Leu Gln Glu Leu Leu
305                 310                 315                 320

Asp Leu His Arg Val Ser Glu Arg Glu Ala Thr Glu Val Tyr Met Lys
                325                 330                 335

Asn Ser Phe Lys Asp Val Asp His Leu Phe Gln Lys Lys Leu Ala Ala
            340                 345                 350

Gln Leu Asp Lys Lys Arg Asp Asp Phe Cys Lys Gln Asn Gln Glu Ala
        355                 360                 365

```
Ser Ser Asp Arg Cys Ser Ala Leu Leu Gln Val Ile Phe Ser Pro Leu
    370                 375                 380

Glu Glu Glu Val Lys Ala Gly Ile Tyr Ser Lys Pro Gly Gly Tyr Cys
385                 390                 395                 400

Leu Phe Ile Gln Lys Leu Gln Asp Leu Glu Lys Lys Tyr Tyr Glu Glu
                405                 410                 415

Pro Arg Lys Gly Ile Gln Ala Glu Glu Ile Leu Gln Thr Tyr Leu Lys
            420                 425                 430

Ser Lys Glu Ser Val Thr Asp Ala Ile Leu Gln Thr Asp Gln Ile Leu
        435                 440                 445

Thr Glu Lys Glu Lys Glu Ile Glu Val Glu Cys Val Lys Ala Glu Ser
    450                 455                 460

Ala Gln Ala Ser Ala Lys Met Val Glu Met Gln Ile Lys Tyr Gln
465                 470                 475                 480

Gln Met Met Glu Glu Lys Glu Lys Ser Tyr Gln Glu His Val Lys Gln
                485                 490                 495

Leu Thr Glu Lys Met Glu Arg Glu Arg Ala Gln Leu Leu Glu Glu Gln
            500                 505                 510

Glu Lys Thr Leu Thr Ser Lys Leu Gln Glu Gln Ala Arg Val Leu Lys
        515                 520                 525

Glu Arg Cys Gln Gly Glu Ser Thr Gln Leu Gln Asn Glu Ile Gln Lys
    530                 535                 540

Leu Gln Lys Thr Leu Lys Lys Thr Lys Arg Tyr Met Ser His Lys
545                 550                 555                 560

Leu Lys Ile

<210> SEQ ID NO 10
<211> LENGTH: 2484
<212> TYPE: DNA
<213> ORGANISM: Mus musculus
<220> FEATURE:
<221> NAME/KEY: CDS
<222> LOCATION: (94)..(1989)

<400> SEQUENCE: 10
gaatcgggcg ggcgcagcag caagcctaaa ggtgctgaat ccaggtagca gagaatccgg      60
tgcaggctgg ttaccatggc atctggtccc aac atg gag gct cct gtg tgc cta     114
                                    Met Glu Ala Pro Val Cys Leu
                                      1               5 gtg gaa aat gag aat gaa gaa ctg agg gtg aac tcc aaa gca ata aac     162
Val Glu Asn Glu Asn Glu Glu Leu Arg Val Asn Ser Lys Ala Ile Asn
         10                  15                  20 att ctt gag agg atc act cag cct gta gtg gtg gtg gcc att gta gga     210
Ile Leu Glu Arg Ile Thr Gln Pro Val Val Val Val Ala Ile Val Gly
     25                  30                  35 cta tac cgt acg gga aaa tcc tac ttg atg aac cgc ttg gca gga cag     258
Leu Tyr Arg Thr Gly Lys Ser Tyr Leu Met Asn Arg Leu Ala Gly Gln
 40                  45                  50                  55 aac cat ggc ttc aat ctg ggc acc aca gtt agg tct gaa act aag ggc     306
Asn His Gly Phe Asn Leu Gly Thr Thr Val Arg Ser Glu Thr Lys Gly
                 60                  65                  70 atc tgg atg tgg tgt gtg cct cac ccc agc aag ccc aag ttc aca ctc     354
Ile Trp Met Trp Cys Val Pro His Pro Ser Lys Pro Lys Phe Thr Leu
             75                  80                  85 gtg ctt ctg gac acg gag ggc tta gga gat gtg gaa aag ggt gac cct     402
Val Leu Leu Asp Thr Glu Gly Leu Gly Asp Val Glu Lys Gly Asp Pro
         90                  95                 100
```

-continued

```
aag aat gac tcg tgg atc ttc gcc ctg gct gtg ctt ctg agc agc acc       450
Lys Asn Asp Ser Trp Ile Phe Ala Leu Ala Val Leu Leu Ser Ser Thr
    105                 110                 115 ttt gtc tac aac agc atg agc acc atc aac cac cag gcc ctg gag cag       498
Phe Val Tyr Asn Ser Met Ser Thr Ile Asn His Gln Ala Leu Glu Gln
120                 125                 130                 135 ctg cac tat gtc aca gaa ctg aca gag cgg atc agg gca aag tcc act       546
Leu His Tyr Val Thr Glu Leu Thr Glu Arg Ile Arg Ala Lys Ser Thr
                140                 145                 150 tca cgg tct gaa gaa gtg gat gac tct gat gag ttt gta agt ttc ttt       594
Ser Arg Ser Glu Glu Val Asp Asp Ser Asp Glu Phe Val Ser Phe Phe
            155                 160                 165 cca gat ttt atc tgg act gtt cga gat ttc gtt ctg gag ctg aag tta       642
Pro Asp Phe Ile Trp Thr Val Arg Asp Phe Val Leu Glu Leu Lys Leu
        170                 175                 180 gag gga cgt gtc atc aca gca gac gag tac cta gaa aat gcc ctg aag       690
Glu Gly Arg Val Ile Thr Ala Asp Glu Tyr Leu Glu Asn Ala Leu Lys
    185                 190                 195 ctg atc cca ggc atg agt atc aaa gcc cag aaa gct aac ttg cct agg       738
Leu Ile Pro Gly Met Ser Ile Lys Ala Gln Lys Ala Asn Leu Pro Arg
200                 205                 210                 215 gaa tgc atc agg cac ttc ttt cca aga cgg aag tgc ttt gtc ttt gat       786
Glu Cys Ile Arg His Phe Phe Pro Arg Arg Lys Cys Phe Val Phe Asp
                220                 225                 230 cga cct aca aaa gac aaa gaa ctt tta gtg cat gtt gag gaa atg cca       834
Arg Pro Thr Lys Asp Lys Glu Leu Leu Val His Val Glu Glu Met Pro
            235                 240                 245 gag gac cag ttg gat cac agt ttc caa gtg cag tca aaa gaa ttc tgt       882
Glu Asp Gln Leu Asp His Ser Phe Gln Val Gln Ser Lys Glu Phe Cys
        250                 255                 260 tcc tac atc ttc tcc aat tcg aag gcc aag acc ttg aaa gag gga atc       930
Ser Tyr Ile Phe Ser Asn Ser Lys Ala Lys Thr Leu Lys Glu Gly Ile
    265                 270                 275 gtt gtc aat gga aac cga ctg gcg act ctg gtg acg acc tac gtg gat       978
Val Val Asn Gly Asn Arg Leu Ala Thr Leu Val Thr Thr Tyr Val Asp
280                 285                 290                 295 gct atc aat agt gga gac gtg ccg tgt tta gag aac gca gta aca acc      1026
Ala Ile Asn Ser Gly Asp Val Pro Cys Leu Glu Asn Ala Val Thr Thr
                300                 305                 310 ctg gcc cag cgt gag aac tcc ata gct gtg cag aag gca gct gac cac      1074
Leu Ala Gln Arg Glu Asn Ser Ile Ala Val Gln Lys Ala Ala Asp His
            315                 320                 325 tac agt gag cag atg gcc cag cga atg agg ctc ccc aca gac acg ctc      1122
Tyr Ser Glu Gln Met Ala Gln Arg Met Arg Leu Pro Thr Asp Thr Leu
        330                 335                 340 cag gag ctg ctg act gtg cat aca gcc tgt gag aag gaa gcc att gct      1170
Gln Glu Leu Leu Thr Val His Thr Ala Cys Glu Lys Glu Ala Ile Ala
    345                 350                 355 gtc ttc atg gag cac tcc ttc aag gat gag aat cag caa ttc cag aag      1218
Val Phe Met Glu His Ser Phe Lys Asp Glu Asn Gln Gln Phe Gln Lys
360                 365                 370                 375 aac ttg gtg gtc acc ata gag gaa aaa aag gaa gat ttc ctg cga cag      1266
Asn Leu Val Val Thr Ile Glu Glu Lys Lys Glu Asp Phe Leu Arg Gln
                380                 385                 390 aat gaa gca gcg tct ctc agt cac tgc cag gct gag ctg gac aag ctc      1314
Asn Glu Ala Ala Ser Leu Ser His Cys Gln Ala Glu Leu Asp Lys Leu
            395                 400                 405 tca gag tcc ctg agg gag agc atc tca cgt gga gtt ttc tct gtt cct      1362
Ser Glu Ser Leu Arg Glu Ser Ile Ser Arg Gly Val Phe Ser Val Pro
        410                 415                 420
```

-continued

```
ggg ggt cac agg ctc tac tta gag gcc agg aag aag gtt gaa cag gac      1410
Gly Gly His Arg Leu Tyr Leu Glu Ala Arg Lys Lys Val Glu Gln Asp
        425                 430                 435 tat gag cga gtg ccc agg aag gga gtg aag gca aat cat gtc ctt cag      1458
Tyr Glu Arg Val Pro Arg Lys Gly Val Lys Ala Asn His Val Leu Gln
440                 445                 450                 455 agc ttc cta cag tca cag att tcc att gag gac tcc att atg cag tca      1506
Ser Phe Leu Gln Ser Gln Ile Ser Ile Glu Asp Ser Ile Met Gln Ser
                460                 465                 470 gac aaa gcc ctc act gat ggc cag aag gcc atg gaa gct gag cga gct      1554
Asp Lys Ala Leu Thr Asp Gly Gln Lys Ala Met Glu Ala Glu Arg Ala
            475                 480                 485 cag aag gag gca gct gag aag gag cag gag cta cta aga cag aaa cag      1602
Gln Lys Glu Ala Ala Glu Lys Glu Gln Glu Leu Leu Arg Gln Lys Gln
        490                 495                 500 aag gag ctg cag cag gtg atg gaa gct caa gag aga agc tac aag gaa      1650
Lys Glu Leu Gln Gln Val Met Glu Ala Gln Glu Arg Ser Tyr Lys Glu
505                 510                 515 aat gtg gcc cag ctg cac gag aag atg gag aca gaa agg aag aac atc      1698
Asn Val Ala Gln Leu His Glu Lys Met Glu Thr Glu Arg Lys Asn Ile
520                 525                 530                 535 ctg aga gag caa gag gtg aag ctg gaa cac aag ttg aag att caa aaa      1746
Leu Arg Glu Gln Glu Val Lys Leu Glu His Lys Leu Lys Ile Gln Lys
                540                 545                 550 gac atg ctt aat gag gga ttt aaa agg aaa tgt gaa gca atg gat ttg      1794
Asp Met Leu Asn Glu Gly Phe Lys Arg Lys Cys Glu Ala Met Asp Leu
            555                 560                 565 gag ata agt caa cta caa aaa gag att caa cta aat aag gag aag aat      1842
Glu Ile Ser Gln Leu Gln Lys Glu Ile Gln Leu Asn Lys Glu Lys Asn
        570                 575                 580 agc tca ttg ggt gca aaa atc ctt gat ggg ttt gga gat gta tta att      1890
Ser Ser Leu Gly Ala Lys Ile Leu Asp Gly Phe Gly Asp Val Leu Ile
585                 590                 595 tca gta gtg cct ggt tct ggt aag tac ttt ggt cta ggg ttg aaa ata      1938
Ser Val Val Pro Gly Ser Gly Lys Tyr Phe Gly Leu Gly Leu Lys Ile
600                 605                 610                 615 tta agc agc caa atg aat cag aca cag aat tca gac aaa gtt aga aaa      1986
Leu Ser Ser Gln Met Asn Gln Thr Gln Asn Ser Asp Lys Val Arg Lys
                620                 625                 630 ctc taagtatagc tttccccccac ctccctgaga cttactttg aagtccatct           2039
Leu cactttaatt tcatttatca aatttcaaaa accaagaata taggtcactc tctataaatt    2099
aatggcaaga ccccattgct gaaaacaaat gtatacaact cattgattga tggagaactc    2159
aagctggtgc ccatagatcc ttctccttat atgcggacat ctttggcaca gaatgacact    2219
ctgcatgcta ccaaaggaaa aacacaaatg ccagcccagc cacaagccct ttgatctaca    2279
atggcatcct gcctgcaaaa tatgcaaatg cagtggtggc acaaactgtg ggagtaacta    2339
accaatatct gatttgattt aaggccaact tcacgggatg aaacccatgc ctacactgcc    2399
tgggtgatcc agaacctaga tcagatagcc cagcgaacct tgagtaaaac caaatactat    2459
tgttgtatta aaaaaaaaa aaaaa                                           2484

<210> SEQ ID NO 11
<211> LENGTH: 632
<212> TYPE: PRT
<213> ORGANISM: Mus musculus

<400> SEQUENCE: 11
```

```
Met Glu Ala Pro Val Cys Leu Val Asn Glu Asn Glu Leu Arg
1               5                   10                  15

Val Asn Ser Lys Ala Ile Asn Ile Leu Glu Arg Ile Thr Gln Pro Val
            20                  25                  30

Val Val Val Ala Ile Val Gly Leu Tyr Arg Thr Gly Lys Ser Tyr Leu
            35                  40                  45

Met Asn Arg Leu Ala Gly Gln Asn His Gly Phe Asn Leu Gly Thr Thr
50                      55                  60

Val Arg Ser Glu Thr Lys Gly Ile Trp Met Trp Cys Val Pro His Pro
65                  70                  75                  80

Ser Lys Pro Lys Phe Thr Leu Val Leu Leu Asp Thr Glu Gly Leu Gly
                85                  90                  95

Asp Val Glu Lys Gly Asp Pro Lys Asn Asp Ser Trp Ile Phe Ala Leu
                100                 105                 110

Ala Val Leu Leu Ser Ser Thr Phe Val Tyr Asn Ser Met Ser Thr Ile
            115                 120                 125

Asn His Gln Ala Leu Glu Gln Leu His Tyr Val Thr Glu Leu Thr Glu
130                 135                 140

Arg Ile Arg Ala Lys Ser Thr Ser Arg Ser Glu Glu Val Asp Asp Ser
145                 150                 155                 160

Asp Glu Phe Val Ser Phe Phe Pro Asp Phe Ile Trp Thr Val Arg Asp
                165                 170                 175

Phe Val Leu Glu Leu Lys Leu Glu Gly Arg Val Ile Thr Ala Asp Glu
                180                 185                 190

Tyr Leu Glu Asn Ala Leu Lys Leu Ile Pro Gly Met Ser Ile Lys Ala
            195                 200                 205

Gln Lys Ala Asn Leu Pro Arg Glu Cys Ile Arg His Phe Phe Pro Arg
            210                 215                 220

Arg Lys Cys Phe Val Phe Asp Arg Pro Thr Lys Asp Lys Glu Leu Leu
225                 230                 235                 240

Val His Val Glu Glu Met Pro Glu Asp Gln Leu Asp His Ser Phe Gln
                245                 250                 255

Val Gln Ser Lys Glu Phe Cys Ser Tyr Ile Phe Ser Asn Ser Lys Ala
                260                 265                 270

Lys Thr Leu Lys Glu Gly Ile Val Val Asn Gly Asn Arg Leu Ala Thr
            275                 280                 285

Leu Val Thr Thr Tyr Val Asp Ala Ile Asn Ser Gly Asp Val Pro Cys
            290                 295                 300

Leu Glu Asn Ala Val Thr Thr Leu Ala Gln Arg Glu Asn Ser Ile Ala
305                 310                 315                 320

Val Gln Lys Ala Ala Asp His Tyr Ser Glu Gln Met Ala Gln Arg Met
                325                 330                 335

Arg Leu Pro Thr Asp Thr Leu Gln Glu Leu Leu Thr Val His Thr Ala
            340                 345                 350

Cys Glu Lys Glu Ala Ile Ala Val Phe Met Glu His Ser Phe Lys Asp
            355                 360                 365

Glu Asn Gln Gln Phe Gln Lys Asn Leu Val Val Thr Ile Glu Glu Lys
            370                 375                 380

Lys Glu Asp Phe Leu Arg Gln Asn Glu Ala Ala Ser Leu Ser His Cys
385                 390                 395                 400

Gln Ala Glu Leu Asp Lys Leu Ser Glu Ser Leu Arg Glu Ser Ile Ser
                405                 410                 415
```

```
Arg Gly Val Phe Ser Val Pro Gly Gly His Arg Leu Tyr Leu Glu Ala
            420                 425                 430

Arg Lys Lys Val Glu Gln Asp Tyr Glu Arg Val Pro Arg Lys Gly Val
            435                 440                 445

Lys Ala Asn His Val Leu Gln Ser Phe Leu Gln Ser Gln Ile Ser Ile
            450                 455                 460

Glu Asp Ser Ile Met Gln Ser Asp Lys Ala Leu Thr Asp Gly Gln Lys
465                 470                 475                 480

Ala Met Glu Ala Glu Arg Ala Gln Lys Glu Ala Glu Lys Glu Gln
                485                 490                 495

Glu Leu Leu Arg Gln Lys Gln Lys Glu Leu Gln Gln Val Met Glu Ala
            500                 505                 510

Gln Glu Arg Ser Tyr Lys Glu Asn Val Ala Gln Leu His Glu Lys Met
            515                 520                 525

Glu Thr Glu Arg Lys Asn Ile Leu Arg Glu Gln Glu Val Lys Leu Glu
530                 535                 540

His Lys Leu Lys Ile Gln Lys Asp Met Leu Asn Glu Gly Phe Lys Arg
545                 550                 555                 560

Lys Cys Glu Ala Met Asp Leu Glu Ile Ser Gln Leu Lys Glu Ile
                565                 570                 575

Gln Leu Asn Lys Glu Lys Asn Ser Ser Leu Gly Ala Lys Ile Leu Asp
            580                 585                 590

Gly Phe Gly Asp Val Leu Ile Ser Val Val Pro Gly Ser Gly Lys Tyr
            595                 600                 605

Phe Gly Leu Gly Leu Lys Ile Leu Ser Ser Gln Met Asn Gln Thr Gln
            610                 615                 620

Asn Ser Asp Lys Val Arg Lys Leu
625                 630

<210> SEQ ID NO 12
<211> LENGTH: 1818
<212> TYPE: DNA
<213> ORGANISM: Mus musculus
<220> FEATURE:
<221> NAME/KEY: CDS
<222> LOCATION: (1)..(1815)

<400> SEQUENCE: 12 atg gaa gga aaa gta tta cag tgg aac tcg tac ctg tct gaa ttc cat      48
Met Glu Gly Lys Val Leu Gln Trp Asn Ser Tyr Leu Ser Glu Phe His
1               5                   10                  15 tgt gac cag gat gtg gta aca aag gtg tct gtg cct tct ggc acc aag      96
Cys Asp Gln Asp Val Val Thr Lys Val Ser Val Pro Ser Gly Thr Lys
                20                  25                  30 gaa ata gct caa ttg cct cta acc ccc atc cct aac cca ctc atc act     144
Glu Ile Ala Gln Leu Pro Leu Thr Pro Ile Pro Asn Pro Leu Ile Thr
            35                  40                  45 tcc cca aag aag tac cca ttg aac tgt gga gac caa cgg aat ggt cac     192
Ser Pro Lys Lys Tyr Pro Leu Asn Cys Gly Asp Gln Arg Asn Gly His
        50                  55                  60 aag agt tgg tta atg cat ggt tta ctg atg gtt cat caa cca ctg atg     240
Lys Ser Trp Leu Met His Gly Leu Leu Met Val His Gln Pro Leu Met
65                  70                  75                  80 gag gca aaa cta atg gaa agc cag agc cta gag aca tgg gga tgg aat     288
Glu Ala Lys Leu Met Glu Ser Gln Ser Leu Glu Thr Trp Gly Trp Asn
                85                  90                  95 ggc caa cac caa gga agg aac cac aag atc agc ata gca cta ttg gct     336
Gly Gln His Gln Gly Arg Asn His Lys Ile Ser Ile Ala Leu Leu Ala
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 100 |     |     |     |     | 105 |     |     |     |     | 110 |     |     |     |     |
| ata | aaa | caa | aca | act | agg | aaa | aca | aaa | agt | ttt | tcc | atg | ggc | tcc | act | 384 |
| Ile | Lys | Gln | Thr | Thr | Arg | Lys | Thr | Lys | Ser | Phe | Ser | Met | Gly | Ser | Thr |     |
|     |     | 115 |     |     |     |     | 120 |     |     |     |     | 125 |     |     |     |     |
| gtg | cag | tct | caa | acc | agg | ggc | atc | tgg | atg | tgg | tgt | gtg | cct | cat | ccc | 432 |
| Val | Gln | Ser | Gln | Thr | Arg | Gly | Ile | Trp | Met | Trp | Cys | Val | Pro | His | Pro |     |
| 130 |     |     |     |     |     | 135 |     |     |     |     | 140 |     |     |     |     |     |
| gag | aaa | cct | gac | cac | acc | cta | gtt | ctg | gat | gac | acc | gag | ggc | cta | gga | 480 |
| Glu | Lys | Pro | Asp | His | Thr | Leu | Val | Leu | Asp | Asp | Thr | Glu | Gly | Leu | Gly |     |
| 145 |     |     |     | 150 |     |     |     |     | 155 |     |     |     |     | 160 |     |     |
| gat | gtt | gag | aaa | ggt | gac | aac | cag | aac | gac | tgc | tgg | atc | ttt | gcc | ctg | 528 |
| Asp | Val | Glu | Lys | Gly | Asp | Asn | Gln | Asn | Asp | Cys | Trp | Ile | Phe | Ala | Leu |     |
|     |     |     |     | 165 |     |     |     |     | 170 |     |     |     |     | 175 |     |     |
| gct | ata | ctt | cta | agc | agc | acc | ttt | gtc | tac | aac | agc | atc | ggg | gcc | atc | 576 |
| Ala | Ile | Leu | Leu | Ser | Ser | Thr | Phe | Val | Tyr | Asn | Ser | Ile | Gly | Ala | Ile |     |
|     |     |     | 180 |     |     |     |     | 185 |     |     |     |     | 190 |     |     |     |
| aac | cag | cag | gcc | atg | gac | cag | ctg | cac | ttt | ttc | tta | atg | caa | cat | gaa | 624 |
| Asn | Gln | Gln | Ala | Met | Asp | Gln | Leu | His | Phe | Phe | Leu | Met | Gln | His | Glu |     |
|     |     | 195 |     |     |     |     | 200 |     |     |     |     | 205 |     |     |     |     |
| atg | atg | ctg | atc | agc | tat | gtg | aca | gag | ctg | act | gac | aga | atc | aga | aca | 672 |
| Met | Met | Leu | Ile | Ser | Tyr | Val | Thr | Glu | Leu | Thr | Asp | Arg | Ile | Arg | Thr |     |
| 210 |     |     |     |     | 215 |     |     |     |     | 220 |     |     |     |     |     |     |
| aga | cgc | tcc | cct | gac | cat | caa | gct | ttg | gag | gac | tca | gat | gaa | tat | gtg | 720 |
| Arg | Arg | Ser | Pro | Asp | His | Gln | Ala | Leu | Glu | Asp | Ser | Asp | Glu | Tyr | Val |     |
| 225 |     |     |     |     | 230 |     |     |     |     | 235 |     |     |     |     | 240 |     |
| agc | ttc | ttc | cca | gac | ttt | gta | tgg | acc | ccg | aga | gac | ttc | tgt | ctt | gag | 768 |
| Ser | Phe | Phe | Pro | Asp | Phe | Val | Trp | Thr | Pro | Arg | Asp | Phe | Cys | Leu | Glu |     |
|     |     |     |     | 245 |     |     |     |     | 250 |     |     |     |     | 255 |     |     |
| ctg | aaa | aca | aat | gga | caa | ccc | ctc | tca | gca | gac | gaa | tac | cta | ggg | aat | 816 |
| Leu | Lys | Thr | Asn | Gly | Gln | Pro | Leu | Ser | Ala | Asp | Glu | Tyr | Leu | Gly | Asn |     |
|     |     |     | 260 |     |     |     |     | 265 |     |     |     |     | 270 |     |     |     |
| tcc | ctg | aag | ctt | ctt | caa | ggt | tgt | agt | caa | aaa | gaa | aaa | gag | tta | aat | 864 |
| Ser | Leu | Lys | Leu | Leu | Gln | Gly | Cys | Ser | Gln | Lys | Glu | Lys | Glu | Leu | Asn |     |
|     | 275 |     |     |     |     | 280 |     |     |     |     | 285 |     |     |     |     |     |
| ctg | tct | cag | ctc | tgt | atc | cgt | aaa | ttc | ttc | cca | act | aag | aaa | tgc | ttt | 912 |
| Leu | Ser | Gln | Leu | Cys | Ile | Arg | Lys | Phe | Phe | Pro | Thr | Lys | Lys | Cys | Phe |     |
|     | 290 |     |     |     |     | 295 |     |     |     |     | 300 |     |     |     |     |     |
| gtc | ttt | gag | cgc | cca | gca | ccc | ggg | aag | aag | att | ggc | cag | ctg | gaa | tca | 960 |
| Val | Phe | Glu | Arg | Pro | Ala | Pro | Gly | Lys | Lys | Ile | Gly | Gln | Leu | Glu | Ser |     |
| 305 |     |     |     |     | 310 |     |     |     |     | 315 |     |     |     |     | 320 |     |
| cta | cag | gat | aaa | gac | ctg | gac | tct | gac | ttc | gtg | aaa | caa | gtg | gca | gag | 1008 |
| Leu | Gln | Asp | Lys | Asp | Leu | Asp | Ser | Asp | Phe | Val | Lys | Gln | Val | Ala | Glu |     |
|     |     |     |     | 325 |     |     |     |     | 330 |     |     |     |     | 335 |     |     |
| ttc | tct | tcc | tat | gtt | ttc | agg | tct | tcc | aag | att | aaa | aaa | att | cca | gga | 1056 |
| Phe | Ser | Ser | Tyr | Val | Phe | Arg | Ser | Ser | Lys | Ile | Lys | Lys | Ile | Pro | Gly |     |
|     |     |     | 340 |     |     |     |     | 345 |     |     |     |     | 350 |     |     |     |
| gac | ctc | aag | gtc | aat | gga | ccg | cga | cta | aag | aat | ttg | gtg | aca | acc | tat | 1104 |
| Asp | Leu | Lys | Val | Asn | Gly | Pro | Arg | Leu | Lys | Asn | Leu | Val | Thr | Thr | Tyr |     |
|     |     | 355 |     |     |     |     | 360 |     |     |     |     | 365 |     |     |     |     |
| gtg | aac | acc | atc | agc | aat | ggg | tct | ctg | ccc | tgc | atg | gag | agt | gct | gtc | 1152 |
| Val | Asn | Thr | Ile | Ser | Asn | Gly | Ser | Leu | Pro | Cys | Met | Glu | Ser | Ala | Val |     |
|     | 370 |     |     |     |     | 375 |     |     |     |     | 380 |     |     |     |     |     |
| ctg | gct | ctg | tca | gaa | aca | gag | aac | tca | gca | gca | gtg | cga | aag | gcc | att | 1200 |
| Leu | Ala | Leu | Ser | Glu | Thr | Glu | Asn | Ser | Ala | Ala | Val | Arg | Lys | Ala | Ile |     |
| 385 |     |     |     |     | 390 |     |     |     |     | 395 |     |     |     |     | 400 |     |
| gcc | cac | tat | gac | cag | cag | atg | agc | cag | agt | ctg | aag | ctg | ccc | aca | gag | 1248 |
| Ala | His | Tyr | Asp | Gln | Gln | Met | Ser | Gln | Ser | Leu | Lys | Leu | Pro | Thr | Glu |     |
|     |     |     |     | 405 |     |     |     |     | 410 |     |     |     |     | 415 |     |     |
| acc | ctc | cag | gag | ctg | ctg | gac | ctg | cac | agg | agc | agt | gag | aaa | gaa | gcc | 1296 |

|     |     |     |     |     |     |     |     |     |     |     |     |     |     | |
|---|---|---|---|---|---|---|---|---|---|---|---|---|---|---|
| Thr | Leu | Gln | Glu | Leu | Leu | Asp | Leu | His | Arg | Ser | Ser | Glu | Lys | Glu Ala |
|     |     |     | 420 |     |     |     | 425 |     |     |     | 430 |     |     | |

```
atc aag att ttc atg gaa aat tcc ttc aaa gat gtt gac caa gtg ttc      1344
Ile Lys Ile Phe Met Glu Asn Ser Phe Lys Asp Val Asp Gln Val Phe
            435                 440                 445 cta aca aaa tta gag aaa gaa ggc aag caa agg gaa ttc tgt aag aag      1392
Leu Thr Lys Leu Glu Lys Glu Gly Lys Gln Arg Glu Phe Cys Lys Lys
450                 455                 460 aat caa gag gca tcc tca gat cgc tgt tca gtt ctg ctt cgg gat att      1440
Asn Gln Glu Ala Ser Ser Asp Arg Cys Ser Val Leu Leu Arg Asp Ile
465                 470                 475                 480 ttt ggt cca cta gaa gaa gac ttg aag cag ggt gtt ttt tac aaa cca      1488
Phe Gly Pro Leu Glu Glu Asp Leu Lys Gln Gly Val Phe Tyr Lys Pro
                485                 490                 495 acg ggt tgc tgt ctt ttc agc cag aag ata cag ggg ttg aag aga aag      1536
Thr Gly Cys Cys Leu Phe Ser Gln Lys Ile Gln Gly Leu Lys Arg Lys
            500                 505                 510 tat gag gaa cct ggg aag ggc gca ggt aac caa ggt aac caa ggt tcc      1584
Tyr Glu Glu Pro Gly Lys Gly Ala Gly Asn Gln Gly Asn Gln Gly Ser
        515                 520                 525 gca tgc cct ggg aag ttt ctt acc atc agg ctg cag tgt ccc cag gca      1632
Ala Cys Pro Gly Lys Phe Leu Thr Ile Arg Leu Gln Cys Pro Gln Ala
530                 535                 540 tca ctg ggg aac gcc agc tta tgc tgt tcg tgt atc aca tac ctg aag      1680
Ser Leu Gly Asn Ala Ser Leu Cys Cys Ser Cys Ile Thr Tyr Leu Lys
545                 550                 555                 560 gtc ttc ata ctg gat att tcc tgc tca ccc atc aga gac agt cac tca      1728
Val Phe Ile Leu Asp Ile Ser Cys Ser Pro Ile Arg Asp Ser His Ser
                565                 570                 575 ctt aac agt cag aca gtc act cgc tta aca act gag ctc aaa ctg acc      1776
Leu Asn Ser Gln Thr Val Thr Arg Leu Thr Thr Glu Leu Lys Leu Thr
            580                 585                 590 acc tta gcc acc agt ggg act gtc acc ctc tgt ttc agc tag              1818
Thr Leu Ala Thr Ser Gly Thr Val Thr Leu Cys Phe Ser
        595                 600                 605

<210> SEQ ID NO 13
<211> LENGTH: 605
<212> TYPE: PRT
<213> ORGANISM: Mus musculus

<400> SEQUENCE: 13

Met Glu Gly Lys Val Leu Gln Trp Asn Ser Tyr Leu Ser Glu Phe His
1               5                   10                  15

Cys Asp Gln Asp Val Val Thr Lys Val Ser Val Pro Ser Gly Thr Lys
            20                  25                  30

Glu Ile Ala Gln Leu Pro Leu Thr Pro Ile Pro Asn Pro Leu Ile Thr
        35                  40                  45

Ser Pro Lys Lys Tyr Pro Leu Asn Cys Gly Asp Gln Arg Asn Gly His
    50                  55                  60

Lys Ser Trp Leu Met His Gly Leu Leu Met Val His Gln Pro Leu Met
65                  70                  75                  80

Glu Ala Lys Leu Met Glu Ser Gln Ser Leu Glu Thr Trp Gly Trp Asn
                85                  90                  95

Gly Gln His Gln Gly Arg Asn His Lys Ile Ser Ile Ala Leu Leu Ala
            100                 105                 110

Ile Lys Gln Thr Thr Arg Lys Thr Lys Ser Phe Ser Met Gly Ser Thr
        115                 120                 125
```

-continued

```
Val Gln Ser Gln Thr Arg Gly Ile Trp Met Trp Cys Val Pro His Pro
        130                 135                 140
Glu Lys Pro Asp His Thr Leu Val Leu Asp Asp Thr Glu Gly Leu Gly
145                 150                 155                 160
Asp Val Glu Lys Gly Asp Asn Gln Asn Asp Cys Trp Ile Phe Ala Leu
                165                 170                 175
Ala Ile Leu Leu Ser Ser Thr Phe Val Tyr Asn Ser Ile Gly Ala Ile
            180                 185                 190
Asn Gln Gln Ala Met Asp Gln Leu His Phe Phe Leu Met Gln His Glu
        195                 200                 205
Met Met Leu Ile Ser Tyr Val Thr Glu Leu Thr Asp Arg Ile Arg Thr
    210                 215                 220
Arg Arg Ser Pro Asp His Gln Ala Leu Glu Asp Ser Asp Glu Tyr Val
225                 230                 235                 240
Ser Phe Phe Pro Asp Phe Val Trp Thr Pro Arg Asp Phe Cys Leu Glu
                245                 250                 255
Leu Lys Thr Asn Gly Gln Pro Leu Ser Ala Asp Glu Tyr Leu Gly Asn
                260                 265                 270
Ser Leu Lys Leu Leu Gln Gly Cys Ser Gln Lys Glu Lys Glu Leu Asn
        275                 280                 285
Leu Ser Gln Leu Cys Ile Arg Lys Phe Phe Pro Thr Lys Lys Cys Phe
    290                 295                 300
Val Phe Glu Arg Pro Ala Pro Gly Lys Lys Ile Gly Gln Leu Glu Ser
305                 310                 315                 320
Leu Gln Asp Lys Asp Leu Asp Ser Asp Phe Val Lys Gln Val Ala Glu
                325                 330                 335
Phe Ser Ser Tyr Val Phe Arg Ser Ser Lys Ile Lys Lys Ile Pro Gly
                340                 345                 350
Asp Leu Lys Val Asn Gly Pro Arg Leu Lys Asn Leu Val Thr Thr Tyr
        355                 360                 365
Val Asn Thr Ile Ser Asn Gly Ser Leu Pro Cys Met Glu Ser Ala Val
    370                 375                 380
Leu Ala Leu Ser Glu Thr Glu Asn Ser Ala Ala Val Arg Lys Ala Ile
385                 390                 395                 400
Ala His Tyr Asp Gln Gln Met Ser Gln Ser Leu Lys Leu Pro Thr Glu
                405                 410                 415
Thr Leu Gln Glu Leu Leu Asp Leu His Arg Ser Ser Glu Lys Glu Ala
                420                 425                 430
Ile Lys Ile Phe Met Glu Asn Ser Phe Lys Asp Val Asp Gln Val Phe
        435                 440                 445
Leu Thr Lys Leu Glu Lys Glu Gly Lys Gln Arg Glu Phe Cys Lys Lys
    450                 455                 460
Asn Gln Glu Ala Ser Ser Asp Arg Cys Ser Val Leu Leu Arg Asp Ile
465                 470                 475                 480
Phe Gly Pro Leu Glu Glu Asp Leu Lys Gln Gly Val Phe Tyr Lys Pro
                485                 490                 495
Thr Gly Cys Cys Leu Phe Ser Gln Lys Ile Gln Gly Leu Lys Arg Lys
                500                 505                 510
Tyr Glu Glu Pro Gly Lys Gly Ala Gly Asn Gln Gly Asn Gln Gly Ser
        515                 520                 525
Ala Cys Pro Gly Lys Phe Leu Thr Ile Arg Leu Gln Cys Pro Gln Ala
    530                 535                 540
Ser Leu Gly Asn Ala Ser Leu Cys Cys Ser Cys Ile Thr Tyr Leu Lys
```

-continued

```
                545                 550                 555                 560
            Val Phe Ile Leu Asp Ile Ser Cys Ser Pro Ile Arg Asp Ser His Ser
                            565                 570                 575

Leu Asn Ser Gln Thr Val Thr Arg Leu Thr Thr Glu Leu Lys Leu Thr
                            580                 585                 590

Thr Leu Ala Thr Ser Gly Thr Val Thr Leu Cys Phe Ser
                            595                 600                 605

<210> SEQ ID NO 14
<211> LENGTH: 3387
<212> TYPE: DNA
<213> ORGANISM: Mus musculus
<220> FEATURE:
<221> NAME/KEY: CDS
<222> LOCATION: (81)..(1235)

<400> SEQUENCE: 14
gcctgaggag gcagcagcag ctgagaactg cacttggacc tgtgctgtgg gaccagattc        60
atctacgttg gcaggttgct atg acc caa cca caa atg gct ccc att tgt ctt      113
                      Met Thr Gln Pro Gln Met Ala Pro Ile Cys Leu
                        1               5                  10 gtg gaa aac cac aat gaa cat ctg tcc atg aac cat gaa gcc ata gag        161
Val Glu Asn His Asn Glu His Leu Ser Met Asn His Glu Ala Ile Glu
              15                  20                  25 att ctg gag aag att tct cag cca gtg gta gtc gtg gct att gtt gga        209
Ile Leu Glu Lys Ile Ser Gln Pro Val Val Val Val Ala Ile Val Gly
         30                  35                  40 ttg tac cgt aca ggg aag tcc tat ttg atg aac cgt ctg gca gga cag        257
Leu Tyr Arg Thr Gly Lys Ser Tyr Leu Met Asn Arg Leu Ala Gly Gln
     45                  50                  55 aat cac ggt ttc cct ctg ggc tcc act gtg caa tct cag acc aag ggc        305
Asn His Gly Phe Pro Leu Gly Ser Thr Val Gln Ser Gln Thr Lys Gly
 60                  65                  70                  75 atc tgg atg tgg tgc atg cca cac ccc act aaa cca gag cac acc ctg        353
Ile Trp Met Trp Cys Met Pro His Pro Thr Lys Pro Glu His Thr Leu
                 80                  85                  90 gtc ctc ctg gac acc gag ggc ctg ggg gat gtg gaa aag ggt gat cct        401
Val Leu Leu Asp Thr Glu Gly Leu Gly Asp Val Glu Lys Gly Asp Pro
             95                 100                 105 aag aac gac ttg tgg atc ttt gcc ctt ggc gtg ctt ctg agc agc acc        449
Lys Asn Asp Leu Trp Ile Phe Ala Leu Gly Val Leu Leu Ser Ser Thr
        110                 115                 120 ttc atc tac aac agc atg aac acc atc agc cat gat tcc ctg gag aaa        497
Phe Ile Tyr Asn Ser Met Asn Thr Ile Ser His Asp Ser Leu Glu Lys
    125                 130                 135 cta cat tat gtc aca gaa ctc act gag ctg atc aga gca aag tct tca        545
Leu His Tyr Val Thr Glu Leu Thr Glu Leu Ile Arg Ala Lys Ser Ser
140                 145                 150                 155 cca aat cct gat gga ata aag aat tcc aca gag ttt gtg agt ttc ttt        593
Pro Asn Pro Asp Gly Ile Lys Asn Ser Thr Glu Phe Val Ser Phe Phe
                160                 165                 170 cca gac ttt gtc tgg act gtt cgg gat ttc atg cta gag ctg aag tta        641
Pro Asp Phe Val Trp Thr Val Arg Asp Phe Met Leu Glu Leu Lys Leu
            175                 180                 185 aat ggg gaa gat atc aca agt gat gag tac ctg gag aat gcc ctg aag        689
Asn Gly Glu Asp Ile Thr Ser Asp Glu Tyr Leu Glu Asn Ala Leu Lys
        190                 195                 200 ctg atc cca ggt tac aat ccc aga gtg caa gca tcc aat tca gcc agg        737
Leu Ile Pro Gly Tyr Asn Pro Arg Val Gln Ala Ser Asn Ser Ala Arg
    205                 210                 215
```

```
gaa tgc atc aga tgt ttc ttt cct aac cgg aag tgt ttt gtc ttt gac      785
Glu Cys Ile Arg Cys Phe Phe Pro Asn Arg Lys Cys Phe Val Phe Asp
220                 225                 230                 235 cgg cca act cat gac aga gaa ctc tta caa aaa ctt gag act att tca      833
Arg Pro Thr His Asp Arg Glu Leu Leu Gln Lys Leu Glu Thr Ile Ser
                240                 245                 250 gaa gac caa ctg gat ctt aag ttc cgg gaa gaa aca aac gct ttt gtt      881
Glu Asp Gln Leu Asp Leu Lys Phe Arg Glu Glu Thr Asn Ala Phe Val
            255                 260                 265 tct tac atc ttc aat tat gcc aag att aag acc ctc aaa gag gga att      929
Ser Tyr Ile Phe Asn Tyr Ala Lys Ile Lys Thr Leu Lys Glu Gly Ile
        270                 275                 280 aag gtc act ggg aat gga ttg ggg att cta gtg aca acc tat gta gat      977
Lys Val Thr Gly Asn Gly Leu Gly Ile Leu Val Thr Thr Tyr Val Asp
    285                 290                 295 gcc atc aac agt gga gca gtg cct tgt gtg gat gat gct gtg aca act     1025
Ala Ile Asn Ser Gly Ala Val Pro Cys Val Asp Asp Ala Val Thr Thr
300                 305                 310                 315 ctg gcc cag cat gag aac tca gta gct gtg cag agg gca gct gac cac     1073
Leu Ala Gln His Glu Asn Ser Val Ala Val Gln Arg Ala Ala Asp His
                320                 325                 330 tac agt gag cag atg gtc cag cga ctg agc ctt ccc aca gac acg ctc     1121
Tyr Ser Glu Gln Met Val Gln Arg Leu Ser Leu Pro Thr Asp Thr Leu
            335                 340                 345 cag gag ctg ctg gat gtg cat gca gcc tgc gag aag gaa gcc atg gct     1169
Gln Glu Leu Leu Asp Val His Ala Ala Cys Glu Lys Glu Ala Met Ala
        350                 355                 360 gtc ttc atg gag cat tcc ttc aag gac gaa aat cag caa ttc ctg aag     1217
Val Phe Met Glu His Ser Phe Lys Asp Glu Asn Gln Gln Phe Leu Lys
    365                 370                 375 aag ctg gtg gta atc tgt tgatggcatt aactatcatg gctctacccc            1265
Lys Leu Val Val Ile Cys
380                 385 ttcaagactg tagtattgat gagccttcat tggccatatg tgcatttatt attcaaagat   1325
atgtgtttca gagtatcatg aataatacag ttatgaacga ctacatgtcc ccttccaaaa   1385
atttcaggtg ctttcagtct agtaatgtct aacagatgga ataatgagta tatagtgtcc   1445
taaatccttt acccagttaa tgtttgtgga ctgtgatcct gcccaggqca tctatagtgc   1505
atccttgaac ttgctatatt cttctgttcc taagaaactg tttctcactg gagtctcact   1565
acagcccagt gttcttctat tgccccttgt tatatcattg tgtccttgaa gatagaattc   1625
caggatgtga cacctacaaa gaaccagaga tggttggatg taccccatct cttttgcagaa  1685
ggtcttgaag accaggaaca ccaagaacat ttactgtggt cttccacagc tttttcagca   1745
tctgagttca ggttttagca cttcacattc ccatgagttc ttattacatt ggaatgcttt   1805
ctcatgagga ataggttggc cctttttataa tgtttcttgg aattttattc cttcttttcc  1865
ttcaattatg tcagatctct gtacacttcc tttgtaggaa ttaataggtg aggcgaaagt   1925
gcttttcctg ttgaagaatg aagaggcatc tgataaatac tgccaggaag aactggatcg   1985
actttcaaag gatttgatgg acaatatctc aacattttct gttcctgggg acacaggct    2045
ctacatggac atgagagaga agattgagca tgattactgg caagttccca ggaaggggt    2105
gaaggcaaga gaagtcttcc agagctttct tcagtcgcag gccatcattg agagttccat   2165
cctgcaggca gacacagccc tcactgctgg gcagaaggcc attgcagagg agcgcaccaa   2225
gaaggaggca gctgagaagg agcaggatct gctaagacag aagcagaagg agcagcagga   2285
```

-continued

```
gtatatggag gctcaagaga aaaggaacaa ggaaaacata gagcaactga gaaggaagct    2345
ggagcaggag agagagcagc tcatcaaaga ccataacatg atggtggaga agaagctgaa    2405
ggaacaaaag gctttgcttg aggaaggatt taagaagaaa gctgaagaaa tggacggaga    2465
gatacagcaa ctgaaacata acatcgagga tatgaaaaaa aacagtggtt ccattttcga    2525
tactattata agagaagttg cttcatttat ttttctccc atttcaatga ttgaaaaggg     2585
tataaggtcc cttttttagt aaaaatgata gactgtgata tacactttgt gttactttga    2645
cgctgcctgt tttccatttt cactccgcag agaagtttaa acataaaaag tgctgattag    2705
agggcatctg tgcccacac agaagacata gaacagctcc tacatgtctg cacagacaat     2765
gcttgccttt agaaacata ttttgaaacc attcctatga aagctatgca tttagtcatc     2825
agatgtgatc actgctggcc aatttaacta catatagaat ctgcatatag aatctgtact    2885
cctatgagga ccatgtagcc caggataggt tgtacgggat tctctcaggt taatatggta    2945
gggaacccat cctaagtgtg ggcagcacca ttcctgtgga ctgaagacac agtagaaaga    3005
tgaaagcaat ctccctacca cttgtggctt cgactgtgga tgccatacaa caagccagcc    3065
ttgacttctc tcagaatgca ttatccagcc ttgaccgaat gtatcatcat gatacatgga    3125
gctcaacaaa ccattcatta agttggtttt gtgagggtat ttcatcacag caagaggaag    3185
tcactgatat cataatagtg ataatcctgg aaactactta atcatccctg agttagattg    3245
gcaataaatt ttaatatgac ttgttcttgg agtactgtat agtcaagaaa caaatgtcag    3305
tcaaactatc tgtatagtga tctaaattga gctaaaatat atcttaaaaa taaagtcaaa    3365
acactataaa aaaaaaaaaa aa                                             3387
```

<210> SEQ ID NO 15
<211> LENGTH: 385
<212> TYPE: PRT
<213> ORGANISM: Mus musculus

<400> SEQUENCE: 15

```
Met Thr Gln Pro Gln Met Ala Pro Ile Cys Leu Val Glu Asn His Asn
1               5                   10                  15

Glu His Leu Ser Met Asn His Glu Ala Ile Glu Ile Leu Glu Lys Ile
            20                  25                  30

Ser Gln Pro Val Val Val Ala Ile Val Gly Leu Tyr Arg Thr Gly
        35                  40                  45

Lys Ser Tyr Leu Met Asn Arg Leu Ala Gly Gln Asn His Gly Phe Pro
    50                  55                  60

Leu Gly Ser Thr Val Gln Ser Gln Thr Lys Gly Ile Trp Met Trp Cys
65                  70                  75                  80

Met Pro His Pro Thr Lys Pro Glu His Thr Leu Val Leu Leu Asp Thr
                85                  90                  95

Glu Gly Leu Gly Asp Val Glu Lys Gly Asp Pro Lys Asn Asp Leu Trp
            100                 105                 110

Ile Phe Ala Leu Gly Val Leu Leu Ser Ser Thr Phe Ile Tyr Asn Ser
        115                 120                 125

Met Asn Thr Ile Ser His Asp Ser Leu Glu Lys Leu His Tyr Val Thr
    130                 135                 140

Glu Leu Thr Glu Leu Ile Arg Ala Lys Ser Ser Pro Asn Pro Asp Gly
145                 150                 155                 160

Ile Lys Asn Ser Thr Glu Phe Val Ser Phe Phe Pro Asp Phe Val Trp
                165                 170                 175
```

-continued

```
Thr Val Arg Asp Phe Met Leu Glu Leu Lys Leu Asn Gly Glu Asp Ile
            180                 185                 190

Thr Ser Asp Glu Tyr Leu Glu Asn Ala Leu Lys Leu Ile Pro Gly Tyr
        195                 200                 205

Asn Pro Arg Val Gln Ala Ser Asn Ser Ala Arg Glu Cys Ile Arg Cys
    210                 215                 220

Phe Phe Pro Asn Arg Lys Cys Phe Val Phe Asp Arg Pro Thr His Asp
225                 230                 235                 240

Arg Glu Leu Leu Gln Lys Leu Glu Thr Ile Ser Glu Asp Gln Leu Asp
                245                 250                 255

Leu Lys Phe Arg Glu Glu Thr Asn Ala Phe Val Ser Tyr Ile Phe Asn
            260                 265                 270

Tyr Ala Lys Ile Lys Thr Leu Lys Glu Gly Ile Lys Val Thr Gly Asn
        275                 280                 285

Gly Leu Gly Ile Leu Val Thr Thr Tyr Val Asp Ala Ile Asn Ser Gly
    290                 295                 300

Ala Val Pro Cys Val Asp Asp Ala Val Thr Thr Leu Ala Gln His Glu
305                 310                 315                 320

Asn Ser Val Ala Val Gln Arg Ala Ala Asp His Tyr Ser Glu Gln Met
                325                 330                 335

Val Gln Arg Leu Ser Leu Pro Thr Asp Thr Leu Gln Glu Leu Leu Asp
            340                 345                 350

Val His Ala Ala Cys Glu Lys Glu Ala Met Ala Val Phe Met Glu His
        355                 360                 365

Ser Phe Lys Asp Glu Asn Gln Gln Phe Leu Lys Lys Leu Val Val Ile
    370                 375                 380

Cys
385

<210> SEQ ID NO 16
<211> LENGTH: 4193
<212> TYPE: DNA
<213> ORGANISM: Mus musculus
<220> FEATURE:
<221> NAME/KEY: CDS
<222> LOCATION: (322)..(1770)

<400> SEQUENCE: 16
ggagcctgag gaggcagcag cagctgagaa ctgcacttgg acctgtgctg tgggaccagg     60
ttgctatgac ccaaccacaa atggctccca tttgccttgt ggaaaaccac aatgaacagc    120
tgtcagtgaa ccaggaagcc atagagattc tggacaagat ttctcagcca gtggtagtcg    180
tggctattgt tggattgtac cgtacaggga agtcctattt gatgaactgt ttggcgggac    240
agaatcacgg gtgatcctaa gaacgacttg tggatctttg ccctcagcgt gcttctgagc    300
agcaccttca tctacaacag c atg atc acc atc aac cac cag gcc ctg gag    351
                        Met Ile Thr Ile Asn His Gln Ala Leu Glu
                          1               5                  10 cag ctg cat tat gtc aca gaa ctc aca gag ctg atc aga gca aag tct    399
Gln Leu His Tyr Val Thr Glu Leu Thr Glu Leu Ile Arg Ala Lys Ser
                 15                  20                  25 tcc cca aat cct gct gga ata aag aat tcc aca gag ttt gtg agt ttc    447
Ser Pro Asn Pro Ala Gly Ile Lys Asn Ser Thr Glu Phe Val Ser Phe
             30                  35                  40 ttt cca gac ttt gtc tgg act gtt cgg gat ttc atg ctg gag ctg aag    495
Phe Pro Asp Phe Val Trp Thr Val Arg Asp Phe Met Leu Glu Leu Lys
         45                  50                  55
```

-continued

| | | |
|---|---|---|
| tta aat ggg gaa gac atc aca agt gat gac tac ctg gag aat gcc ttg<br>Leu Asn Gly Glu Asp Ile Thr Ser Asp Asp Tyr Leu Glu Asn Ala Leu<br>60                            65                        70 | | 543 |
| aag ctg atc cca ggt gac aaa ccc aga atg caa gca tcc aat tca tgc<br>Lys Leu Ile Pro Gly Asp Lys Pro Arg Met Gln Ala Ser Asn Ser Cys<br>75                          80                       85                        90 | | 591 |
| agg gaa tgc atc aga ctt ttc ttt cct aac cgg aag tgt ttt gtc ttt<br>Arg Glu Cys Ile Arg Leu Phe Phe Pro Asn Arg Lys Cys Phe Val Phe<br>                        95                        100                      105 | | 639 |
| gac cgg cca acg cat gac aaa gaa ctt tta caa aaa ctt gat tct atc<br>Asp Arg Pro Thr His Asp Lys Glu Leu Leu Gln Lys Leu Asp Ser Ile<br>            110                      115                      120 | | 687 |
| aca gaa gac caa ctg gat cct aag ttc cag gaa gta aca aag gct ttt<br>Thr Glu Asp Gln Leu Asp Pro Lys Phe Gln Glu Val Thr Lys Ala Phe<br>125                        130                      135 | | 735 |
| gtt tct tac atc ttc act tat gcc aag atc aag acc cta aaa gag gga<br>Val Ser Tyr Ile Phe Thr Tyr Ala Lys Ile Lys Thr Leu Lys Glu Gly<br>140                        145                      150 | | 783 |
| att aag gtc act ggg aat aga cta ggg att ctg gtg aca acc tat gtg<br>Ile Lys Val Thr Gly Asn Arg Leu Gly Ile Leu Val Thr Thr Tyr Val<br>155                        160                      165                      170 | | 831 |
| aat gcc atc aac agt gga gca gtg cct tgt ctg gat gat gct gtg aca<br>Asn Ala Ile Asn Ser Gly Ala Val Pro Cys Leu Asp Asp Ala Val Thr<br>                      175                      180                      185 | | 879 |
| act ctg gcc cag cgt gag aac tca gta gct gtg cag aaa gca gcc gac<br>Thr Leu Ala Gln Arg Glu Asn Ser Val Ala Val Gln Lys Ala Ala Asp<br>            190                      195                      200 | | 927 |
| cac tat agt gag cag atg gcc cag cga ctg agg ctt cct aca gaa acg<br>His Tyr Ser Glu Gln Met Ala Gln Arg Leu Arg Leu Pro Thr Glu Thr<br>205                        210                      215 | | 975 |
| ctc cag gag ctg ctg gat gtg cat gca gcc tgc gag aag gaa gcc atg<br>Leu Gln Glu Leu Leu Asp Val His Ala Ala Cys Glu Lys Glu Ala Met<br>220                        225                      230 | | 1023 |
| gct gtc ttc atg gag cat tcc ttc aag gac gaa aat cag caa ttc ctg<br>Ala Val Phe Met Glu His Ser Phe Lys Asp Glu Asn Gln Gln Phe Leu<br>235                        240                      245                      250 | | 1071 |
| aag aag ctg gtg gaa tta ata gga gag aac aaa gag ctt ttc ctg tcg<br>Lys Lys Leu Val Glu Leu Ile Gly Glu Asn Lys Glu Leu Phe Leu Ser<br>                      255                      260                      265 | | 1119 |
| aag aat gaa gag gca tca aat aaa tac tgt caa gaa gaa ctg gat cga<br>Lys Asn Glu Glu Ala Ser Asn Lys Tyr Cys Gln Glu Glu Leu Asp Arg<br>            270                      275                      280 | | 1167 |
| ctt tca aag gat ttt atg gaa aat att tca aca ttt ttt gtt cct tgt<br>Leu Ser Lys Asp Phe Met Glu Asn Ile Ser Thr Phe Phe Val Pro Cys<br>285                        290                      295 | | 1215 |
| gga cac aag ctt tac atg gac aag agg gag aag att gaa cat gac tac<br>Gly His Lys Leu Tyr Met Asp Lys Arg Glu Lys Ile Glu His Asp Tyr<br>300                        305                      310 | | 1263 |
| tgg cag gtt ccc agg aaa ggg gtg aag gca agt gaa gtc ttc cag agc<br>Trp Gln Val Pro Arg Lys Gly Val Lys Ala Ser Glu Val Phe Gln Ser<br>315                        320                      325                      330 | | 1311 |
| ttt ctg cag tca cag gcc ttc atc gag agt tcc atc ttg cag gca gat<br>Phe Leu Gln Ser Gln Ala Phe Ile Glu Ser Ser Ile Leu Gln Ala Asp<br>            335                      340                      345 | | 1359 |
| aca gcg ctc act gct ggg gag aag gcc att gca gag gag cgt gcc cag<br>Thr Ala Leu Thr Ala Gly Glu Lys Ala Ile Ala Glu Glu Arg Ala Gln<br>350                        355                      360 | | 1407 |
| aag gtg gcg gca gag aag gag caa gag ctg cta aga cag aag cag aag<br>Lys Val Ala Ala Glu Lys Glu Gln Glu Leu Leu Arg Gln Lys Gln Lys<br>365                        370                      375 | | 1455 |

```
gag cag cag gag tat atg gag gct caa gag aaa agt cac aag gaa aac     1503
Glu Gln Gln Glu Tyr Met Glu Ala Gln Glu Lys Ser His Lys Glu Asn
    380                 385                 390 cta gag caa ctg aga agg aag ctg gag cag gag aga gag cag gac atc     1551
Leu Glu Gln Leu Arg Arg Lys Leu Glu Gln Glu Arg Glu Gln Asp Ile
395                 400                 405                 410 aaa gac cat gat atg atg ctg aag aag cta atg aag gat caa aag gct     1599
Lys Asp His Asp Met Met Leu Lys Lys Leu Met Lys Asp Gln Lys Ala
                415                 420                 425 ttc ctt gag gaa gga ttt aag aag aaa gct gaa gaa atg aac aaa gag     1647
Phe Leu Glu Glu Gly Phe Lys Lys Lys Ala Glu Glu Met Asn Lys Glu
        430                 435                 440 ata cag caa ctg aga gat gtc atc aag gat aag aaa aga aac act gat     1695
Ile Gln Gln Leu Arg Asp Val Ile Lys Asp Lys Lys Arg Asn Thr Asp
    445                 450                 455 cga att aag gag gct ctc tta aat gga ttt tct aca gtt ctt ttt cat     1743
Arg Ile Lys Glu Ala Leu Leu Asn Gly Phe Ser Thr Val Leu Phe His
    460                 465                 470 tac ctt gtc cgt tat cta aag cat tta tgattgagtc cttcacattt          1790
Tyr Leu Val Arg Tyr Leu Lys His Leu
475                 480 gtggaaatga tagactgtga aatacacttt gtttcataca tgcctgcaaa gacaatgtta  1850
gcctttagag gacacatttt tgaaatgagt cctatggaag ctatgcaagt agtaattaca  1910
tgtgattact gttggccaat ttgactgcat agagaatcag caaggagaca aggttttctg  1970
tactcctatg aggaccatgt agcccaggtt agcttgtggg ggactgtctc aggttaatat  2030
tgtaggaaac acatcctacg ggtgggcagc actgttcctg tggactgaag aaacagagaa  2090
agatgaaaac aaatggccct accacttgtg gcttcctgac tgtggatgct atacaacaag  2150
ccaggctcaa cttctctcag aatgcattct ccagccttga cacaatgtat catcatgatt  2210
catagacccc aacaaaccct tcttaagtt ggttttgtga gggtatttca tctcagcaag  2270
aggaaaagtc attgatatca taatcgtgat aatcctggaa actacttaaa catcacttgt  2330
tagattggca atgaaattta atatgacttg atcttggcgt actatatagt caagaaacaa  2390
atgtcagtca agctatctgt aaaatgatct gaattgtact aaaatgtacc caaaagataa  2450
agtcaaaaca ccatacaact gtgtgattat tattagaaat gctactatcc catgcaaaca  2510
tacaagaaca caaatgaaat gccctctgga agattagtaa aaagcctggt ctactggctt  2570
catctagaga gattaagttg gagccaaaag ttgaagggat gtgtgcattc catgacgttc  2630
tcagtcttac acatttcatg aagagtgctg ggaaagtgac agtgatagtg acaataagtt  2690
aaaactcacc actgcatgat gaaacatctg cttctagaaa tggtataagc cactagaagt  2750
cacccaagaa caagacttga gtaccaggaa gcataacatt gcagcttaa tgatgttttc   2810
ctttaaggct ttccatttt aaaagtaatt taaatagtgc atttttgta aaaccacata    2870
tcaaaatgtt atttcaacag gcaatcaaaa taatttatgc atgcttttta catcaaattt  2930
atttatttgc aaagtaacag ggaaactgta ttaagagcca tatgataata tagagtataa  2990
gagaatacat ggggcacatg ggaggtggag agctcagaga tggctctggg tcaagaatgc  3050
acaatgctta tccagggtag ctcagttcct ggggcaggta acaactacct gtaaatctaa  3110
ctccaaggga cctgacttcc ttttctcaaa cccaagggtc actgttactt ccatcacata  3170
tcctcagctt acacatatac atacttacaa gtaagattta aaggaatata ctgttaacat  3230
tgataatgga ccatatgagt aaagacacaa ggacacttat tagtgcatta atgaatatga  3290
```

-continued

```
tttatttaag gtgtacccac cccagctcct ctaagacatc ctcaaattac cctcgcacct    3350
tcatgtcttc tcttccccca cctcttcctc tttcctcata ccctgaataa attaatgctg    3410
ccctcatgtc cctgggcatt agacaccatc taccagacca tggacaattg atcatgaccc    3470
aaaccctcat agaaaacaca ctccctctcc cagtcaccag atatcaactg ctagtagttc    3530
ctcagctagg ggtggggtct catgagctca ctgcctctcc acactggatg ttgactggct    3590
tcatagtatg tatcttgttt caacaaatat cactattgtc gtagcccat catatccaga    3650 aaatattatt ttagaacagt atggtcttat ttttatgctt aaattaatta tttcaaaatt    3710
aaaatgtaga cattcttaag atttctggaa tcttggagaa gcctacttcg tctctattaa    3770
tgcctgtgaa atgtcaagtt caaaagaatg aactgtgtaa aggagagaga gagatcttgg    3830
tgctgtttta ttgggagcca ttttgtttgc ttcagtgaaa gctgacctgc caggcacaat    3890
caagtcaggt tagggtctgc tggcagattt cctggcctac tgactcatgg aactacaaga    3950
ggaaatacac ttgaggctca aggcaagggg gtgaaagttc aattcatctt ggtggttgga    4010
acaggaaatc ctctggataa gaaaagatgt cctgtgtgta cattagccat tatttctgct    4070
accttgtgac attgtttctc atgatactga gagatataat aaagctaaga aaataaact    4130 tgaggttgat gtggtattca cctgcaacct tcccaattct aaaaaaaaaa aaaaaaaaa    4190 aaa                                                                 4193
```

<210> SEQ ID NO 17
<211> LENGTH: 483
<212> TYPE: PRT
<213> ORGANISM: Mus musculus

<400> SEQUENCE: 17

```
Met Ile Thr Ile Asn His Gln Ala Leu Glu Gln Leu His Tyr Val Thr
  1               5                  10                  15

Glu Leu Thr Glu Leu Ile Arg Ala Lys Ser Ser Pro Asn Pro Ala Gly
             20                  25                  30

Ile Lys Asn Ser Thr Glu Phe Val Ser Phe Pro Asp Phe Val Trp
         35                  40                  45

Thr Val Arg Asp Phe Met Leu Glu Leu Lys Leu Asn Gly Glu Asp Ile
     50                  55                  60

Thr Ser Asp Asp Tyr Leu Glu Asn Ala Leu Lys Leu Ile Pro Gly Asp
 65                  70                  75                  80

Lys Pro Arg Met Gln Ala Ser Asn Ser Cys Arg Glu Cys Ile Arg Leu
             85                  90                  95

Phe Phe Pro Asn Arg Lys Cys Phe Val Phe Asp Arg Pro Thr His Asp
            100                 105                 110

Lys Glu Leu Leu Gln Lys Leu Asp Ser Ile Thr Glu Asp Gln Leu Asp
        115                 120                 125

Pro Lys Phe Gln Glu Val Thr Lys Ala Phe Val Ser Tyr Ile Phe Thr
    130                 135                 140

Tyr Ala Lys Ile Lys Thr Leu Lys Glu Gly Ile Lys Val Thr Gly Asn
145                 150                 155                 160

Arg Leu Gly Ile Leu Val Thr Thr Tyr Val Asn Ala Ile Asn Ser Gly
                165                 170                 175

Ala Val Pro Cys Leu Asp Asp Ala Val Thr Thr Leu Ala Gln Arg Glu
            180                 185                 190

Asn Ser Val Ala Val Gln Lys Ala Ala Asp His Tyr Ser Glu Gln Met
        195                 200                 205
```

-continued

```
Ala Gln Arg Leu Arg Leu Pro Thr Glu Thr Leu Gln Glu Leu Leu Asp
    210                 215                 220

Val His Ala Ala Cys Glu Lys Glu Ala Met Ala Val Phe Met Glu His
225                 230                 235                 240

Ser Phe Lys Asp Glu Asn Gln Gln Phe Leu Lys Lys Leu Val Glu Leu
                245                 250                 255

Ile Gly Glu Asn Lys Glu Leu Phe Leu Ser Lys Asn Glu Glu Ala Ser
            260                 265                 270

Asn Lys Tyr Cys Gln Glu Glu Leu Asp Arg Leu Ser Lys Asp Phe Met
        275                 280                 285

Glu Asn Ile Ser Thr Phe Phe Val Pro Cys Gly His Lys Leu Tyr Met
    290                 295                 300

Asp Lys Arg Glu Lys Ile Glu His Asp Tyr Trp Gln Val Pro Arg Lys
305                 310                 315                 320

Gly Val Lys Ala Ser Glu Val Phe Gln Ser Phe Leu Gln Ser Gln Ala
                325                 330                 335

Phe Ile Glu Ser Ser Ile Leu Gln Ala Asp Thr Ala Leu Thr Ala Gly
            340                 345                 350

Glu Lys Ala Ile Ala Glu Arg Ala Gln Lys Val Ala Ala Glu Lys
        355                 360                 365

Glu Gln Glu Leu Leu Arg Gln Lys Gln Lys Glu Gln Gln Glu Tyr Met
    370                 375                 380

Glu Ala Gln Glu Lys Ser His Lys Glu Asn Leu Glu Gln Leu Arg Arg
385                 390                 395                 400

Lys Leu Glu Gln Glu Arg Glu Gln Asp Ile Lys Asp His Asp Met Met
                405                 410                 415

Leu Lys Lys Leu Met Lys Asp Gln Lys Ala Phe Leu Glu Glu Gly Phe
            420                 425                 430

Lys Lys Lys Ala Glu Glu Met Asn Lys Glu Ile Gln Gln Leu Arg Asp
        435                 440                 445

Val Ile Lys Asp Lys Lys Arg Asn Thr Asp Arg Ile Lys Glu Ala Leu
    450                 455                 460

Leu Asn Gly Phe Ser Thr Val Leu Phe His Tyr Leu Val Arg Tyr Leu
465                 470                 475                 480

Lys His Leu

<210> SEQ ID NO 18
<211> LENGTH: 8
<212> TYPE: PRT
<213> ORGANISM: Artificial
<220> FEATURE:
<223> OTHER INFORMATION: Commercially available purification tag

<400> SEQUENCE: 18

Asp Tyr Lys Asp Asp Asp Asp Lys
1               5

<210> SEQ ID NO 19
<211> LENGTH: 22
<212> TYPE: DNA
<213> ORGANISM: Artificial
<220> FEATURE:
<223> OTHER INFORMATION: Synthesized primer

<400> SEQUENCE: 19
cattggtctg gccaagtcta ca                                          22
```

```
<210> SEQ ID NO 20
<211> LENGTH: 25
<212> TYPE: DNA
<213> ORGANISM: Artificial
<220> FEATURE:
<223> OTHER INFORMATION: Synthesized Primer

<400> SEQUENCE: 20
ttcactaaga agctagggtg gttgt                                   25

<210> SEQ ID NO 21
<211> LENGTH: 22
<212> TYPE: DNA
<213> ORGANISM: Artificial
<220> FEATURE:
<223> OTHER INFORMATION: Synthesized Primer

<400> SEQUENCE: 21
ggaggaagag ctgaaccctg at                                      22

<210> SEQ ID NO 22
<211> LENGTH: 21
<212> TYPE: DNA
<213> ORGANISM: Artificial
<220> FEATURE:
<223> OTHER INFORMATION: Synthesized Primer

<400> SEQUENCE: 22
gactgcaatg ccacctgaaa g                                       21

<210> SEQ ID NO 23
<211> LENGTH: 27
<212> TYPE: DNA
<213> ORGANISM: Artificial
<220> FEATURE:
<223> OTHER INFORMATION: Synthesized primer

<400> SEQUENCE: 23
ggcattagag attcttgaca agatttc                                 27

<210> SEQ ID NO 24
<211> LENGTH: 24
<212> TYPE: DNA
<213> ORGANISM: Artificial
<220> FEATURE:
<223> OTHER INFORMATION: Synthesized Primer

<400> SEQUENCE: 24
cctgcaagac gattcatgag atag                                    24

<210> SEQ ID NO 25
<211> LENGTH: 22
<212> TYPE: DNA
<213> ORGANISM: Artificial
<220> FEATURE:
<223> OTHER INFORMATION: Synthesized Primer

<400> SEQUENCE: 25
cagcacaaca ttccaagctc aa                                      22

<210> SEQ ID NO 26
<211> LENGTH: 26
<212> TYPE: DNA
<213> ORGANISM: Artificial
<220> FEATURE:
<223> OTHER INFORMATION: Synthesized Primer
```

```
<400> SEQUENCE: 26
ggatcatcgt tattaacagt cctctg                                        26

<210> SEQ ID NO 27
<211> LENGTH: 21
<212> TYPE: DNA
<213> ORGANISM: Artificial
<220> FEATURE:
<223> OTHER INFORMATION: Synthesized Primer

<400> SEQUENCE: 27
gggagtggat caggcatttc t                                             21

<210> SEQ ID NO 28
<211> LENGTH: 27
<212> TYPE: DNA
<213> ORGANISM: Artificial
<220> FEATURE:
<223> OTHER INFORMATION: Synthesized Primer

<400> SEQUENCE: 28
actatccagt tggtcttctc gtacttc                                       27

<210> SEQ ID NO 29
<211> LENGTH: 20
<212> TYPE: DNA
<213> ORGANISM: Artificial
<220> FEATURE:
<223> OTHER INFORMATION: Synthesized Primer

<400> SEQUENCE: 29
ggagtgcatc aggcgtttct                                               20

<210> SEQ ID NO 30
<211> LENGTH: 24
<212> TYPE: DNA
<213> ORGANISM: Artificial
<220> FEATURE:
<223> OTHER INFORMATION: Synthesized Primer

<400> SEQUENCE: 30
ccagttgctt ttctgacacc ttct                                          24

<210> SEQ ID NO 31
<211> LENGTH: 21
<212> TYPE: DNA
<213> ORGANISM: Artificial
<220> FEATURE:
<223> OTHER INFORMATION: Synthesized Primer

<400> SEQUENCE: 31
aggatggcag gaagacaaac a                                             21

<210> SEQ ID NO 32
<211> LENGTH: 22
<212> TYPE: DNA
<213> ORGANISM: Artificial
<220> FEATURE:
<223> OTHER INFORMATION: Synthesized Primer

<400> SEQUENCE: 32
ctggtctgtc tggagaattg ca                                            22

<210> SEQ ID NO 33
<211> LENGTH: 22
```

```
<212> TYPE: DNA
<213> ORGANISM: Artificial
<220> FEATURE:
<223> OTHER INFORMATION: Synthesized Primer

<400> SEQUENCE: 33
gatcatgagt tgccaccact ca                                              22

<210> SEQ ID NO 34
<211> LENGTH: 21
<212> TYPE: DNA
<213> ORGANISM: Artificial
<220> FEATURE:
<223> OTHER INFORMATION: Synthesized Primer

<400> SEQUENCE: 34
gtgcccaaat atgtcccaag a                                               21

<210> SEQ ID NO 35
<211> LENGTH: 23
<212> TYPE: DNA
<213> ORGANISM: Mus musculus

<400> SEQUENCE: 35
gagatgctga tggaacagaa gga                                             23

<210> SEQ ID NO 36
<211> LENGTH: 22
<212> TYPE: DNA
<213> ORGANISM: Mus musculus

<400> SEQUENCE: 36
tcctgctcca tcttctcagt ca                                              22

<210> SEQ ID NO 37
<211> LENGTH: 24
<212> TYPE: DNA
<213> ORGANISM: Mus musculus

<400> SEQUENCE: 37
caggctttga aacaactgct atga                                            24

<210> SEQ ID NO 38
<211> LENGTH: 20
<212> TYPE: DNA
<213> ORGANISM: Mus musculus

<400> SEQUENCE: 38
cagtgcccag tggtcagaca                                                 20

<210> SEQ ID NO 39
<211> LENGTH: 22
<212> TYPE: DNA
<213> ORGANISM: Mus musculus

<400> SEQUENCE: 39
ggaaaccctc actgtttggt ca                                              22

<210> SEQ ID NO 40
<211> LENGTH: 23
<212> TYPE: DNA
<213> ORGANISM: Mus musculus

<400> SEQUENCE: 40
```
cttagtgagc cgaggaattt cag    23

<210> SEQ ID NO 41
<211> LENGTH: 19
<212> TYPE: DNA
<213> ORGANISM: Mus musculus

<400> SEQUENCE: 41
gtccatgtga ggcgaggaa    19

<210> SEQ ID NO 42
<211> LENGTH: 20
<212> TYPE: DNA
<213> ORGANISM: Mus musculus

<400> SEQUENCE: 42
aacgactcgg gcactgttgt    20

<210> SEQ ID NO 43
<211> LENGTH: 21
<212> TYPE: DNA
<213> ORGANISM: Mus musculus

<400> SEQUENCE: 43
gctgaagcaa ggtagcgatg a    21

<210> SEQ ID NO 44
<211> LENGTH: 20
<212> TYPE: DNA
<213> ORGANISM: Mus musculus

<400> SEQUENCE: 44
cctcgttgct gagtgttgga    20

<210> SEQ ID NO 45
<211> LENGTH: 20
<212> TYPE: DNA
<213> ORGANISM: Mus musculus

<400> SEQUENCE: 45
ctgagggtga actccaaagc    20

<210> SEQ ID NO 46
<211> LENGTH: 20
<212> TYPE: DNA
<213> ORGANISM: Mus musculus

<400> SEQUENCE: 46
cccagattga agccatggtt    20

<210> SEQ ID NO 47
<211> LENGTH: 21
<212> TYPE: DNA
<213> ORGANISM: Mus musculus

<400> SEQUENCE: 47
caccatcagc aatgggtctc t    21

<210> SEQ ID NO 48
<211> LENGTH: 23
<212> TYPE: DNA
<213> ORGANISM: Mus musculus

<400> SEQUENCE: 48

-continued ctggctcatc tgctggtcat agt                    23

<210> SEQ ID NO 49
<211> LENGTH: 26
<212> TYPE: DNA
<213> ORGANISM: Mus musculus

<400> SEQUENCE: 49
cacagcaaga ggaagtcact gatatc                 26

<210> SEQ ID NO 50
<211> LENGTH: 22
<212> TYPE: DNA
<213> ORGANISM: Mus musculus

<400> SEQUENCE: 50
tgccaatcta actcagggat ga                     22

<210> SEQ ID NO 51
<211> LENGTH: 23
<212> TYPE: DNA
<213> ORGANISM: Mus musculus

<400> SEQUENCE: 51
cacaatgctt atccaggta gct                     23

<210> SEQ ID NO 52
<211> LENGTH: 28
<212> TYPE: DNA
<213> ORGANISM: Mus musculus

<400> SEQUENCE: 52
gtcccttgga gttagattta caggtagt               28

<210> SEQ ID NO 53
<211> LENGTH: 20
<212> TYPE: DNA
<213> ORGANISM: Mus musculus

<400> SEQUENCE: 53
catggccttc cgtgttccta                        20

<210> SEQ ID NO 54
<211> LENGTH: 21
<212> TYPE: DNA
<213> ORGANISM: Mus musculus

<400> SEQUENCE: 54
cctgcttcac caccttcttg a                      21

<210> SEQ ID NO 55
<211> LENGTH: 17
<212> TYPE: DNA
<213> ORGANISM: Homo sapiens

<400> SEQUENCE: 55
agccgagcca catcgct                           17

<210> SEQ ID NO 56
<211> LENGTH: 19
<212> TYPE: DNA
<213> ORGANISM: Homo sapiens -continued
<210> SEQ ID NO 57
<211> LENGTH: 20
<212> TYPE: DNA
<213> ORGANISM: Artificial
<220> FEATURE:
<223> OTHER INFORMATION: Synthesized primer

<400> SEQUENCE: 57
taatacgact cactataggg                                              20

<210> SEQ ID NO 58
<211> LENGTH: 18
<212> TYPE: DNA
<213> ORGANISM: Artificial
<220> FEATURE:
<223> OTHER INFORMATION: Synthesized primer

<400> SEQUENCE: 58
atttaggtga cactatag                                                18

<210> SEQ ID NO 59
<211> LENGTH: 733
<212> TYPE: DNA
<213> ORGANISM: Homo sapiens

<400> SEQUENCE: 59
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca acccccatcg   360
agaaaaccat ctccaaagcc aaagggcagc ccgagaacc acaggtgtac accctgcccc    420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                     733

<210> SEQ ID NO 60
<211> LENGTH: 29
<212> TYPE: PRT
<213> ORGANISM: Artificial
<220> FEATURE:
<223> OTHER INFORMATION: Synthesized Peptide

<400> SEQUENCE: 60

Pro Lys Lys Lys Arg Lys Val Ala Ala Val Ala Leu Leu Pro Ala Val
1               5                   10                  15

Leu Leu Ala Leu Leu Ala Pro Lys Lys Arg Lys Val
            20                  25

```
<210> SEQ ID NO 61
<211> LENGTH: 23
<212> TYPE: DNA
<213> ORGANISM: Homo sapiens

<400> SEQUENCE: 61
agtgcccaga aaaggagtta agg                                          23

<210> SEQ ID NO 62
<211> LENGTH: 24
<212> TYPE: DNA
<213> ORGANISM: Homo sapiens

<400> SEQUENCE: 62
gcaggatgga ttcctctata acca                                         24

<210> SEQ ID NO 63
<211> LENGTH: 26
<212> TYPE: DNA
<213> ORGANISM: Homo sapiens

<400> SEQUENCE: 63
agacgaggtc ctccagagct tcctgc                                       26

<210> SEQ ID NO 64
<211> LENGTH: 17
<212> TYPE: DNA
<213> ORGANISM: Homo sapiens

<400> SEQUENCE: 64
tggagcccct gcctcaa                                                 17

<210> SEQ ID NO 65
<211> LENGTH: 23
<212> TYPE: DNA
<213> ORGANISM: Homo sapiens

<400> SEQUENCE: 65
cagaaatgat ggacctcctc act                                          23

<210> SEQ ID NO 66
<211> LENGTH: 26
<212> TYPE: DNA
<213> ORGANISM: Homo sapiens

<400> SEQUENCE: 66
acacacattg ctccaacact gaggcc                                       26

<210> SEQ ID NO 67
<211> LENGTH: 21
<212> TYPE: DNA
<213> ORGANISM: Homo sapiens

<400> SEQUENCE: 67
ggatggcagg aagacaaaca g                                            21

<210> SEQ ID NO 68
<211> LENGTH: 22
<212> TYPE: DNA
<213> ORGANISM: Homo sapiens

<400> SEQUENCE: 68
gccttaggac ccagagaaca ca                                           22
```

```
<210> SEQ ID NO 69
<211> LENGTH: 32
<212> TYPE: DNA
<213> ORGANISM: Homo sapiens

<400> SEQUENCE: 69
cacctgctta cagccgtctc ctacttctca ct                              32

<210> SEQ ID NO 70
<211> LENGTH: 26
<212> TYPE: DNA
<213> ORGANISM: Homo sapiens

<400> SEQUENCE: 70
aagatgcatt tacctctgta ccaaca                                     26

<210> SEQ ID NO 71
<211> LENGTH: 23
<212> TYPE: DNA
<213> ORGANISM: Homo sapiens

<400> SEQUENCE: 71
ccactggtcg tctggaagaa taa                                        23

<210> SEQ ID NO 72
<211> LENGTH: 27
<212> TYPE: DNA
<213> ORGANISM: Homo sapiens

<400> SEQUENCE: 72
aggagggatc atgagttgcc accactc                                    27

<210> SEQ ID NO 73
<211> LENGTH: 22
<212> TYPE: DNA
<213> ORGANISM: Homo sapiens

<400> SEQUENCE: 73
aatgttgcag gaaatgcaaa ga                                         22

<210> SEQ ID NO 74
<211> LENGTH: 20
<212> TYPE: DNA
<213> ORGANISM: Homo sapiens

<400> SEQUENCE: 74
agcaactgga ccctgtcgtt                                            20

<210> SEQ ID NO 75
<211> LENGTH: 34
<212> TYPE: DNA
<213> ORGANISM: Homo sapiens

<400> SEQUENCE: 75
caggaacact tgaaacaact gactgagaag atgg                            34

<210> SEQ ID NO 76
<211> LENGTH: 22
<212> TYPE: DNA
<213> ORGANISM: Homo sapiens

<400> SEQUENCE: 76
ggcacaagtg aaagcagaag ct                                         22
```

```
<210> SEQ ID NO 77
<211> LENGTH: 20
<212> TYPE: DNA
<213> ORGANISM: Homo sapiens

<400> SEQUENCE: 77
ttgctcgttc tgcctttgaa                                               20

<210> SEQ ID NO 78
<211> LENGTH: 21
<212> TYPE: DNA
<213> ORGANISM: Homo sapiens

<400> SEQUENCE: 78
tgaagcgcaa aggttggcgg c                                             21

<210> SEQ ID NO 79
<211> LENGTH: 21
<212> TYPE: DNA
<213> ORGANISM: Homo sapiens

<400> SEQUENCE: 79
gcucgagaaa cuacaagaut t                                             21

<210> SEQ ID NO 80
<211> LENGTH: 21
<212> TYPE: DNA
<213> ORGANISM: Homo sapiens

<400> SEQUENCE: 80
uuuguauuuc cuccaacaut t                                             21
```